(12) United States Patent
Higuchi

(10) Patent No.: US 11,773,101 B2
(45) Date of Patent: Oct. 3, 2023

(54) GPR35 MODULATORS

(71) Applicant: Prometheus Biosciences, Inc., San Diego, CA (US)

(72) Inventor: Robert Higuchi, Solana Beach, CA (US)

(73) Assignee: Prometheus Biosciences, Inc., San Diego, CA (US)

(*) Notice: Subject to any disclaimer, the term of this patent is extended or adjusted under 35 U.S.C. 154(b) by 186 days.

(21) Appl. No.: 17/323,979

(22) Filed: May 18, 2021

(65) Prior Publication Data

US 2021/0380590 A1    Dec. 9, 2021

Related U.S. Application Data

(62) Division of application No. 16/751,092, filed on Jan. 23, 2020, now Pat. No. 11,053,251.

(60) Provisional application No. 62/928,223, filed on Oct. 30, 2019, provisional application No. 62/873,703, filed on Jul. 12, 2019, provisional application No. 62/796,459, filed on Jan. 24, 2019.

(51) Int. Cl.
*C07D 487/04* (2006.01)
*A61P 1/00* (2006.01)

(52) U.S. Cl.
CPC ............ *C07D 487/04* (2013.01); *A61P 1/00* (2018.01)

(58) Field of Classification Search
CPC ................................. C07D 487/04; A61P 1/00
See application file for complete search history.

(56) References Cited

U.S. PATENT DOCUMENTS

| | | | | |
|---|---|---|---|---|
| 3,933,822 A | * | 1/1976 | Broughton | C07D 471/04 544/298 |
| 3,987,160 A | | 10/1976 | Broughton et al. | |
| 4,052,390 A | * | 10/1977 | Broughton | C07D 487/04 544/254 |
| 4,167,568 A | | 9/1979 | Knowles et al. | |
| 4,923,874 A | | 5/1990 | McMahom et al. | |
| 5,474,796 A | | 12/1995 | Brennan | |
| 8,819,989 B2 | | 9/2014 | Paternoster et al. | |
| 9,353,115 B2 | | 5/2016 | Lipford et al. | |
| 10,519,373 B2 | | 12/2019 | Spittle et al. | |
| 11,053,251 B2 | | 7/2021 | Higuchi | |
| 2015/0273088 A1 | | 10/2015 | Piwnica-Worms et al. | |
| 2018/0305459 A1 | | 10/2018 | McGovern et al. | |
| 2020/0362025 A1 | | 11/2020 | Kruidenier et al. | |
| 2021/0395827 A1 | | 12/2021 | Bilsborough et al. | |
| 2022/0056106 A1 | | 2/2022 | Bilsborough et al. | |
| 2022/0290241 A1 | | 9/2022 | McGovern et al. | |

FOREIGN PATENT DOCUMENTS

| | | |
|---|---|---|
| WO | WO-2004035584 A1 | 4/2004 |
| WO | WO-2015021080 A2 | 2/2015 |
| WO | WO-2019210203 A1 | 10/2019 |
| WO | WO-2020154492 A1 | 7/2020 |
| WO | WO-2022020617 A1 | 1/2022 |
| WO | WO-2022103961 A1 | 5/2022 |
| WO | WO-2022140283 A1 | 6/2022 |

OTHER PUBLICATIONS

Berge et al. Pharmaceutical Salts. Journal of Pharmaceutical Sciences 66(1):1-19 (Jan. 1977).
PCT/US2021/042813 International Preliminary Report on Patentability dated Feb. 2, 2023.
PCT/US2021/042813 International Search Report and Written Opinion dated Nov. 15, 2021.
PubChem CID 137173496 (2019).
6-(4-Chlorophenyl)-5-(4-pyrazin-2-ylphenyl)-3-(3-sulfanylphenyl)triazolo[4,5-d]pyrimidin-7-one. PubCham-CID-70962124. 7 pages (2013).
Berge S.M. et al., "Pharmaceutical Salts," Journal of Pharmaceutical Science, 66:1-19, 1997.
Broughton et al.: Antiallergic Activity of 2-Pehnyl-8-azapurin-6-ones.J. Med. Chem. 18:1117-1122 (1975).
Jenkins et al.: Antagonists of GPR35 display high species ortholog selectivity and varying modes of action. J Pharmacol Exp Ther. 343(3):683-695 (2012).
MacKenzie et al.: "GPR35 as a novel therapeutic target" Review Article Nov. 9, 2011, vol. 2, Article 68 (pp. 1-10).
PCT/US2020/014777 International Search Report and Written Opinion dated Apr. 16, 2020.
Prometheus Biosciences, Inc. Form S-1 Registration Statement as filed with the Securities and Exchange Commission on Feb. 19, 2021 (246 pages).
U.S. Appl. No. 16/751,092 Office Action dated Dec. 7, 2020.

* cited by examiner

*Primary Examiner* — Erich A Leeser
(74) *Attorney, Agent, or Firm* — Wilson Sonsini Goodrich & Rosati

(57) ABSTRACT

Described herein are GPR35 modulators and methods of using these compounds in the treatment of diseases, disorders or conditions. Also described herein are pharmaceutical compositions containing such compounds.

19 Claims, No Drawings

GPR35 MODULATORS

CROSS REFERENCE

This application is a divisional application of U.S. application Ser. No. 16/751,092, filed Jan. 23, 2020, now U.S. Pat. No. 11,053,251, which claims benefit of U.S. Provisional Application No. 62/796,459, filed on Jan. 24, 2019, U.S. Provisional Application No. 62/873,703, filed on Jul. 12, 2019, and U.S. Provisional Application No. 62/928,223, filed on Oct. 30, 2019, all of which are herein incorporated by reference in their entirety.

BACKGROUND OF THE INVENTION

Millions of people are affected by inflammatory disease or conditions. A prominent inflammatory disease is inflammatory bowel disease (IBD). IBD has two common forms, Crohn's disease (CD) and ulcerative colitis (UC), which are chronic, relapsing inflammatory disorders of the gastrointestinal tract. Each of these forms has various sub-conditions that are present in sub-populations of CD and UC patients. Some CD and UC patients experience a rapid onset of sub-conditions, while others experience a relative delay.

Few treatment options are available to patients that suffer from IBD. Further, selecting a therapy that is appropriate for any individual patient at any given stage of their disease is complicated by the unpredictability of each individual's prognosis. Current therapeutic regimens include one or more of anti-inflammatory medication (e.g., corticosteroids) and immunomodulatory therapy (e.g., anti-TNF therapy). However, nearly half of all patients treated with an anti-TNF therapy do not respond to the induction of the therapy, or experience a loss of response to the treatment after a period of time, during which, disease severity has progressed significantly. Therefore, there remains a significant need for targeted and effective treatment options that respond to the underlying immunopathogenesis of IBD.

SUMMARY OF THE INVENTION

In one aspect, provided herein are compounds of Formula (I"):

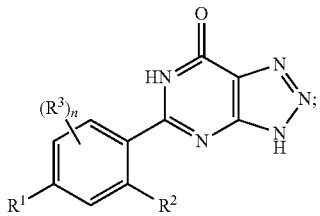

Formula (I")

wherein:

$R^1$ is —$CH_2R^4$, —CN, —$B(OH)_2$, —$N(R^{10})_2$, —$NR^{10}C(O)R^9$, —C(O)OH, —$CH_2C(O)OH$, —$C(O)N(R^{10})_2$, —$C(O)NHS(O)_2N(R^{10})_2$, —$C_{1-6}$alkyl-OH, $C_{3-8}$cycloalkyl,

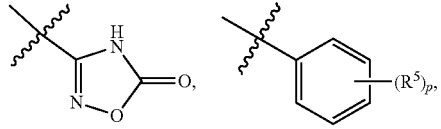

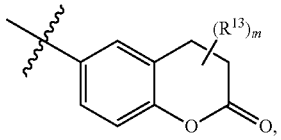

or a 5- or 6-membered heteroaryl optionally substituted with one, two, or three $R^8$ groups;

$R^2$ is H, —OH, —$N(R^{10})_2$, —$NHS(O)_2R^9$, —$S(O)_2N(R^{10})_2$, —$C(O)N(R^{10})_2$, —$OC(O)N(R^{10})_2$, —O—$C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl;

each $R^3$ is independently selected from halogen, —CN, —OH, —$OR^9$, —$SR^9$, —$N(R^{10})_2$, —$NO_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

$R^4$ is

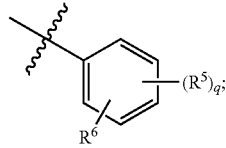

each $R^5$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-$R^9$, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{2-6}$alkenyl, —$C_{2-6}$alkenyl-$C(O)OR^{10}$, $C_{2-6}$alkynyl, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, and $C_{1-9}$heteroaryl; wherein $C_{3-8}$cycloalkyl, —$C_{1-6}$alkyl-$C_{3-8}$cycloalkyl, phenyl, —$C_{1-6}$alkyl-phenyl, and $C_{1-9}$heteroaryl are optionally substituted with one, two, or three groups independently selected from halogen, —$C(O)OR^{10}$, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl and —$C_{1-6}$alkyl-$C_{2-9}$heterocycloalkyl are optionally substituted with one, two, or three groups independently selected from halogen, —$C(O)OR^{10}$, $C_{1-6}$alkyl, $C_{1-6}$haloalkyl, and oxo;

$R^6$ is —$C(O)OR^7$, —$C(O)NHS(O)_2N(R^{10})_2$,

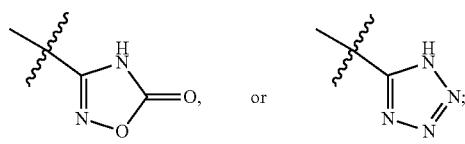 [SMILES: *c1noc(=O)[nH]1 ; *c1nnn[nH]1]

$R^7$ is independently selected from H and $C_{1-6}$alkyl;

each $R^8$ is independently selected from halogen, —OH, —$OR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo; each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —$OR^{11}$, —$N(R^{11})_2$, $C_{1-6}$alkyl, $C_{3-8}$cycloalkyl, —$N(R^{11})C(O)R^{12}$, —$C(O)R^{12}$, and —$C(O)OR^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —$N(R^{11})_2$, and —$C(O)OR^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —$C(O)OH$;

each $R^{11}$ is independently selected from H and $C_{1-6}$alkyl;
each $R^{12}$ is independently selected from H and $C_{1-6}$alkyl;
each $R^{13}$ is independently selected from $C_{1-6}$alkyl;
m is 1, 2, 3, or 4;
n is 0, 1, 2, or 3;
p is 0, 1, 2, 3, 4, or 5; and
q is 0, 1, 2, 3, or 4;
or a pharmaceutically acceptable salt or solvate thereof.

In another aspect, provided herein are compounds of Formula (I'):

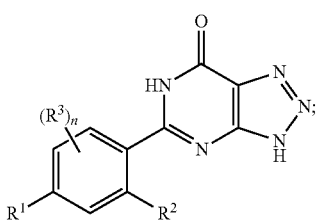

Formula (I')

wherein.

$R^1$ is —$CH_2R^4$, —CN, —$B(OH)_2$, —$N(R^{10})_2$, —$NR^{10}C(O)R^9$, —$C(O)OH$, —$CH_2C(O)OH$, —$C(O)N(R^{10})_2$, —$C(O)NHS(O)_2N(R^{10})_2$, —$C_{1-6}$alkyl-OH, $C_{3-8}$cycloalkyl,

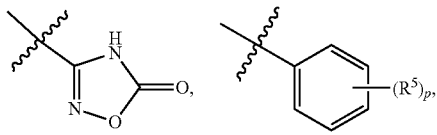

or a 5- or 6-membered heteroaryl optionally substituted with one, two, or three $R^8$ groups;

$R^2$ is H, —OH, —$N(R^{10})_2$, —$NHS(O)_2R^9$, —$S(O)_2N(R^{10})_2$, —$C(O)N(R^{10})_2$, —$OC(O)N(R^{10})_2$, —O—$C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl;

each $R^3$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

$R^4$ is

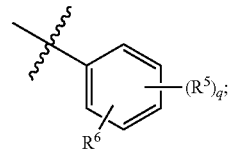

each $R^5$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, $NR^{10}C(O)N(R^{10})_2$, —$NR^{10}C(O)(R^9$, —$NR^{10}C(O)OR^9$, $C_{1-6}$alkyl, —$C_{1-6}$alkyl-$R^9$, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{2-6}$alkenyl, —$C_{2-6}$alkenyl-$C(O)OR^{10}$, $C_{2-6}$alkynyl, $C_{1-6}$haloalkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;

$R^6$ is —$C(O)OR^7$, —$C(O)NHS(O)_2N(R^{10})_2$,

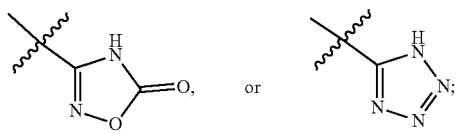 [SMILES: *c1noc(=O)[nH]1 ; *c1nnn[nH]1]

each $R^7$ is independently selected from H and $C_{1-6}$alkyl;
each $R^8$ is independently selected from halogen, —OH, —$OR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;
each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —$OR^{11}$, —$N(R^{11})_2$, $C_{1-6}$alkyl, $C_{3-8}$cycloalkyl, —$N(R^{11})C(O)R^{12}$, —$C(O)R^{12}$, and —$C(O)OR^{12}$;
each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —$N(R^{11})_2$, and —$C(O)OR^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;
each $R^{11}$ is independently selected from H and $C_{1-6}$alkyl;
$R^{12}$ is independently selected from H and $C_{1-6}$alkyl;
n is 0, 1, 2, or 3;
p is 0, 1, 2, 3, 4, or 5;
q is 0, 1, 2, 3, or 4;
or a pharmaceutically acceptable salt or solvate thereof.

In another aspect, provided herein are compounds of Formula (I):

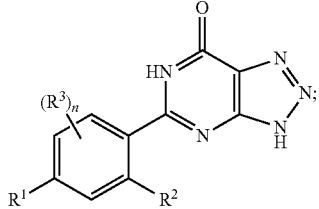

Formula (I)

wherein:
$R^1$ is —$CH_2R^4$, —CN, —$B(OH)_2$, —$N(R^{10})_2$, —$NR^{10}C(O)R^9$, —C(O)OH, —$CH_2C(O)OH$, —$C(O)N(R^{10})_2$, —$C(O)NHS(O)_2N(R^{10})_2$, —$C_{1-6}$alkyl-OH, $C_{3-8}$cycloalkyl,

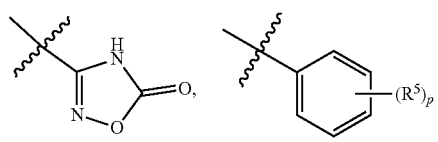

or a 5- or 6-membered heteroaryl optionally substituted with one, two, or three $R^8$ groups;
$R^2$ is H, —OH, —$N(R^{10})_2$, —$NHS(O)_2R^9$, —$S(O)_2N(R^{10})_2$, —$C(O)N(R^{10})_2$, —$OC(O)N(R^{10})_2$, —O—$C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl;
each $R^3$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
$R^4$ is

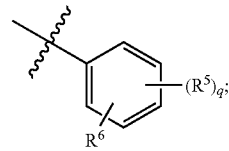

each $R^5$ is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{2-6}$alkenyl, $C_{2-6}$alkynyl, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;
$R^6$ is —$C(O)OR^7$, —$C(O)NHS(O)_2N(R^{10})_2$,

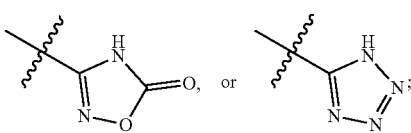 [SMILES: *c1noc(=O)[nH]1 ; "or" ; *c1nnn[nH]1 ; ";"]

each $R^7$ is independently selected from H and $C_{1-6}$alkyl;
each $R^8$ is independently selected from halogen, —OH, —$OR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —C(O)

N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{1-6}$haloalkyl, C$_{1-6}$haloalkyl-OH, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, and C$_{1-9}$heteroaryl; wherein phenyl, —C$_{1-6}$alkyl-phenyl, and C$_{1-9}$heteroaryl are optionally substituted with one, two, or three groups independently selected from halogen, C$_{1-6}$alkyl, C$_{1-6}$haloalkyl, C$_{3-8}$cycloalkyl, and C$_{2-9}$heterocycloalkyl; and wherein C$_{2-9}$heterocycloalkyl is optionally substituted with one, two, or three groups independently selected from halogen, C$_{1-6}$alkyl, C$_{1-6}$haloalkyl, and oxo;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, —N(R$^{11}$)$_2$, and —C(O)OR$^{12}$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;

R$^{12}$ is independently selected from H and C$_{1-6}$alkyl;

n is 0, 1, 2, or 3;

p is 0, 1, 2, 3, 4, or 5;

q is 0, 1, 2, 3, or 4;

or a pharmaceutically acceptable salt or solvate thereof.

In some embodiments is a compound of Formula (I), (I'), or (I"), or a pharmaceutically acceptable salt or solvate thereof, wherein R$^1$ is

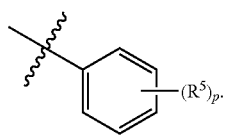

In some embodiments is a compound of Formula (I), (I'), or (I"), or a pharmaceutically acceptable salt or solvate thereof, wherein p is 0, 1, or 2. In some embodiments is a compound of Formula (I), (I'), or (I"), or a pharmaceutically acceptable salt or solvate thereof, wherein each R$^5$ is independently selected from halogen, —OH, —OR$^9$, —N(R$^{10}$)$_2$, —S(O)$_2$R$^9$, —NHS(O)$_2$R$^9$, —S(O)$_2$N(R$^{10}$)$_2$, —C(O)NHS(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, C$_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{1-6}$haloalkyl, C$_{1-6}$haloalkyl-OH, C$_{3-8}$cycloalkyl, C$_{2-9}$heterocycloalkyl, and C$_{1-9}$heteroaryl. In some embodiments is a compound of Formula (I), (I'), or (I"), or a pharmaceutically acceptable salt or solvate thereof, wherein each R$^5$ is independently selected from halogen, —OH, —OR$^9$, —N(R$^{10}$)$_2$, —C(O)NHS(O)$_2$N(R$^{10}$)$_2$, —C(O)OR$^{10}$, —C(O)N(R$^{10}$)$_2$, —NR$^{10}$C(O)R$^9$, C$_{1-6}$alkyl, —C$_{1-6}$alkyl-C(O)OR$^{10}$, and C$_{1-9}$heteroaryl. In some embodiments is a compound of Formula (I), (I'), or (I"), or a pharmaceutically acceptable salt or solvate thereof, wherein each R$^5$ is independently selected from —OR$^9$, —C(O)OR$^{10}$, —C(O)N(R$^{10}$)$_2$, C$_{1-6}$alkyl, —C$_{1-6}$alkyl-C(O)OR$^{10}$, and

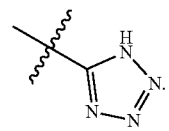 [SMILES: *c1nnn[nH]1]

In some embodiments is a compound of Formula (I), (I'), or (I"), or a pharmaceutically acceptable salt or solvate thereof, wherein each R$^5$ is independently selected from —C(O)OR$^{10}$. In some embodiments is a compound of Formula (I), (I'), or (I"), or a pharmaceutically acceptable salt or solvate thereof, wherein each R$^5$ is independently selected from —OH, —OR$^9$ and —C$_{1-6}$alkyl-C(O)OR$^{10}$. In some embodiments is a compound of Formula (I), (I'), or (I"), or a pharmaceutically acceptable salt or solvate thereof, wherein R$^9$ is C$_{1-6}$alkyl optionally substituted with —C(O)OR$^{12}$. In some embodiments is a compound of Formula (I), (I'), or (I"), or a pharmaceutically acceptable salt or solvate thereof, wherein each R$^{10}$ is independently selected from H and C$_{1-6}$alkyl. In some embodiments is a compound of Formula (I), (I'), or (I"), or a pharmaceutically acceptable salt or solvate thereof, wherein p is 1 or 2. In some embodiments is a compound of Formula (I), (I'), or (I"), or a pharmaceutically acceptable salt or solvate thereof, wherein p is 1. In some embodiments is a compound of Formula (I), (I'), or (I"), or a pharmaceutically acceptable salt or solvate thereof, wherein p is 2. In some embodiments is a compound of Formula (I), (I'), or (I"), or a pharmaceutically acceptable salt or solvate thereof, wherein p is 0. In some embodiments is a compound of Formula (I), (I'), or (I"), or a pharmaceutically acceptable salt or solvate thereof, wherein R$^1$ is a 5- or 6-membered heteroaryl optionally substituted with one, two, or three R$^8$ groups. In some embodiments is a compound of Formula (I), (I'), or (I"), or a pharmaceutically acceptable salt or solvate thereof, wherein R$^1$ is a 5-membered heteroaryl optionally substituted with one, two, or three R$^8$ groups. In some embodiments is a compound of Formula (I), (I'), or (I"), or a pharmaceutically acceptable salt or solvate thereof, wherein R$^1$ is a 5-membered heteroaryl optionally substituted with one, two, or three R$^8$ groups, wherein the 5-membered heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl. In some embodiments is a compound of Formula (I), (I'), or (I"), or a pharmaceutically acceptable salt or solvate thereof, wherein R$^1$ is a 5-membered heteroaryl optionally substituted with one or two R$^8$ groups, wherein the 5-membered heteroaryl is selected from oxazolyl, thiazolyl, pyrazolyl, furanyl, thienyl, pyrrolyl, tetrazolyl, and isoxazolyl. In some embodiments is a compound of Formula (I), (I'), or (I"), or a pharmaceutically acceptable salt or solvate thereof, wherein R$^1$ is a 6-membered heteroaryl optionally substituted with one, two, or three $R^8$ groups. In some embodiments is a compound of Formula (I), (I'), or (I"), or a pharmaceutically acceptable salt or solvate thereof, wherein $R^1$ is a 6-membered heteroaryl optionally substituted with one, two, or three $R^8$ groups, wherein the 6-membered heteroaryl is selected from pyridinyl, pyrimidinyl, pyrazinyl, pyridazinyl, and triazinyl. In some embodiments is a compound of Formula (I), (I'), or (I"), or a pharmaceutically acceptable salt or solvate thereof, wherein $R^1$ is a 6-membered heteroaryl optionally substituted with one or two $R^8$ groups, wherein the 6-membered heteroaryl is selected from pyridinyl and pyrimidinyl. In some embodiments is a compound of Formula (I), (I'), or (I"), or a pharmaceutically acceptable salt or solvate thereof, wherein each $R^8$ is independently selected from halogen, —C(O)OR$^{10}$, $C_{1-6}$alkyl, and —$C_{1-6}$alkyl-C(O)OR$^{10}$. In some embodiments is a compound of Formula (I), (I'), or (I"), or a pharmaceutically acceptable salt or solvate thereof, each $R^8$ is independently selected from —C(O)OR$^{10}$. In some embodiments is a compound of Formula (I), (I'), or (I"), or a pharmaceutically acceptable salt or solvate thereof, wherein $R^1$ is an unsubstituted 5-membered heteroaryl selected from oxazolyl, thiazolyl, pyrazolyl, furanyl, thienyl, pyrrolyl, tetrazolyl, and isoxazolyl. In some embodiments is a compound of Formula (I), (I'), or (I"), or a pharmaceutically acceptable salt or solvate thereof, wherein $R^1$ is an unsubstituted 6-membered heteroaryl selected from pyridinyl and pyrimidinyl. In some embodiments is a compound of Formula (I), (I'), or (I"), or a pharmaceutically acceptable salt or solvate thereof, wherein $R^1$ is —C(O)N(R$^{10}$)$_2$. In some embodiments is a compound of Formula (I), (I'), or (I"), or a pharmaceutically acceptable salt or solvate thereof, wherein $R^1$ is —N(R$^{10}$)$_2$. In some embodiments is a compound of Formula (I), (I'), or (I"), or a pharmaceutically acceptable salt or solvate thereof, wherein each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N(R$^{11}$)$_2$, and —C(O)OR$^{12}$. In some embodiments is a compound of Formula (I), (I'), or (I"), or a pharmaceutically acceptable salt or solvate thereof, wherein each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N(R$^{11}$)$_2$, and —C(O)OR$^{12}$. In some embodiments is a compound of Formula (I), (I'), or (I"), or a pharmaceutically acceptable salt or solvate thereof, wherein each $R^{10}$ is independently selected from H and $C_{1-6}$alkyl optionally substituted with —C(O)OR$^{12}$. In some embodiments is a compound of Formula (I), (I'), or (I"), or a pharmaceutically acceptable salt or solvate thereof, wherein the two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (I), (I'), or (I"), or a pharmaceutically acceptable salt or solvate thereof, wherein the two $R^{10}$ and the nitrogen atom to which they are attached are combined to form a 5-membered heterocycloalkyl ring substituted with —C(O)OH. In some embodiments is a compound of Formula (I), (I'), or (I"), or a pharmaceutically acceptable salt or solvate thereof, wherein the two $R^{10}$ and the nitrogen atom to which they are attached are combined to form a 6-membered heterocycloalkyl ring substituted with —C(O)OH. In some embodiments is a compound of Formula (I), (I'), or (I"), or a pharmaceutically acceptable salt or solvate thereof, wherein $R^1$ is —C(O)OH. In some embodiments is a compound of Formula (I), (I'), or (I"), or a pharmaceutically acceptable salt or solvate thereof, wherein $R^1$ is

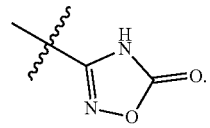 [SMILES: *c1noc(=O)[nH]1]

In some embodiments is a compound of Formula (I), (I'), or (I"), or a pharmaceutically acceptable salt or solvate thereof, wherein $R^2$ is H, —OH, —N(R$^{10}$)$_2$, or —O—$C_{1-6}$alkyl. In some embodiments is a compound of Formula (I), (I'), or (I"), or a pharmaceutically acceptable salt or solvate thereof, wherein $R^2$ is —O—$C_{1-6}$alkyl. In some embodiments is a compound of Formula (I), (I'), or (I"), or a pharmaceutically acceptable salt or solvate thereof, wherein $R^2$ is —OCH$_2$CH$_3$. In some embodiments is a compound of Formula (I), (I'), or (I"), or a pharmaceutically acceptable salt or solvate thereof, wherein $R^2$ is H. In some embodiments is a compound of Formula (I), (I'), or (I"), or a pharmaceutically acceptable salt or solvate thereof, wherein n is 1. In some embodiments is a compound of Formula (I), (I'), or (I"), or a pharmaceutically acceptable salt or solvate thereof, wherein each $R^3$ is independently selected from halogen, —OH, —OR$^9$, —N(R$^{10}$)$_2$, $C_{1-6}$alkyl, —$C_{1-6}$alkyl-OH, —$C_{1-6}$alkyl-OR$^9$, and $C_{1-6}$haloalkyl. In some embodiments is a compound of Formula (I), (I'), or (I"), or a pharmaceutically acceptable salt or solvate thereof, wherein each $R^3$ is independently selected from halogen, —OR$^9$, and $C_{1-6}$alkyl. In some embodiments is a compound of Formula (I), (I'), or (I"), or a pharmaceutically acceptable salt or solvate thereof, wherein each $R^3$ is —OR$^9$ and $R^9$ is $C_{3-8}$cycloalkyl. In some embodiments is a compound of Formula (I), (I'), or (I"), or a pharmaceutically acceptable salt or solvate thereof, wherein n is 0.

In another aspect described herein is a pharmaceutical composition comprising a compound of Formula (I), (I'), or (I"), or a pharmaceutically acceptable salt or solvate thereof, and a pharmaceutically acceptable excipient.

In another aspect described herein is a method of treating an inflammatory bowel disease in a patient in need thereof, comprising administering to the patient a therapeutically effective amount of a compound of Formula (I), (I'), or (I"), or a pharmaceutically acceptable salt or solvate thereof. In some embodiments is a method of treating an inflammatory bowel disease in a patient in need thereof, comprising administering to the patient a therapeutically effective amount of a compound of Formula (I), (I'), or (I"), or a pharmaceutically acceptable salt or solvate thereof, wherein the inflammatory bowel disease is selected from Crohn's disease, ulcerative colitis, and perianal Crohn's disease. In some cases, the ulcerative colitis is a severe form of ulcerative colitis. In some cases, the severe form of ulcerative colitis is medically refractory ulcerative colitis.

In another aspect described herein is a method of modulating GPR35 activity comprising contacting GPR35, or portion thereof, with a compound of Formula (I), (I'), or (I"), or a pharmaceutically acceptable salt or solvate thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, C1-Cx includes C1-C2, C1-C3 ... C1-Cx. C1-Cx refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)xHy group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

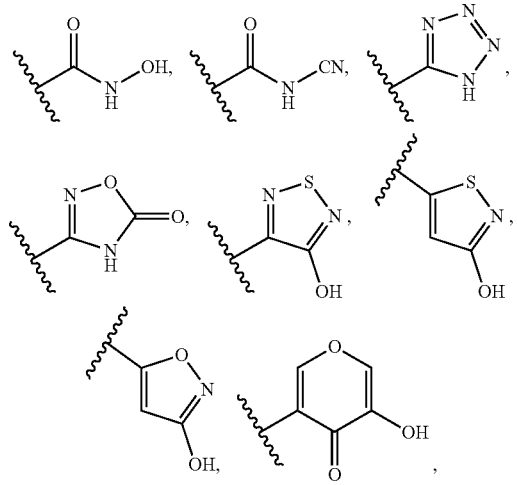

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may be the same or they may be different. Non-limiting examples of haloalkyls include —CH$_2$Cl, —CF$_3$, —CHF$_2$, —CH$_2$CF$_3$, —CF$_2$CF$_3$, and the like.

The terms "fluoroalkyl" and "fluoroalkoxy" include alkyl and alkoxy groups, respectively, that are substituted with one or more fluorine atoms. Non-limiting examples of fluoroalkyls include —CF$_3$, —CHF$_2$, —CH$_2$F, —CH$_2$CF$_3$, —CF$_2$CF$_3$, —CF$_2$CF$_2$CF$_3$, —CF(CH$_3$)$_2$, and the like. Non-limiting examples of fluoroalkoxy groups, include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH$_2$—NH—OCH$_3$, —CH$_2$—O—Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2$H, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

As used herein, the term "about" or "approximately" means within 20%, preferably within 10%, and more preferably within 5% of a given value or range.

The term a "therapeutically effective amount" as used herein refers to the amount of a compound of Formula (I), (I'), (I"), (Ia), (Ib), (Ic), or (Id) that, when administered to a mammal in need, is effective to at least partially treat the conditions described herein.

The term "modulate" encompasses either a decrease or an increase in activity depending on the target molecule.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "patient" or "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

As used herein, "medically refractory," or "refractory," as used herein, refers to the failure of a standard treatment to induce remission of a disease. In some embodiments, the disease comprises an inflammatory disease disclosed herein. A non-limiting example of refractory inflammatory disease includes refractory Crohn's disease, and refractory ulcerative colitis (e.g., medically refractory UC, or mrUC). Non-limiting examples of standard treatment include glucocorticosteriods, anti-TNFalpha therapy, anti-a4-b7 therapy (vedolizumab), anti-IL12p40 therapy (ustekinumab), Thalidomide, and Cytoxin.

G Protein-Coupled Receptor 35 (GPR35)

G Protein-Coupled Receptor 35 (GPR35) is a receptor for kynurenic acid, an intermediate in the tryptophan metabolic pathway. GPR35 mediates calcium mobilization and inositol phosphate production. GPR35, and nucleic acids encoding GPR35, are characterized by NCBI Entrez Gene ID 2859. Studies show that GPR35 is linked to inflammatory regulation, either by the presence of the receptor at the surface of immune specific cells, or by agonists activation leading to changes in immune response. Accordingly, it is hypothesized that GPR35, and nucleic acids encoding GPR35, play a role is inflammatory disease pathology making GPR35 an attractive therapeutic target to treat inflammatory diseases or conditions.

The compounds of Formula (I), (I'), or (I") described herein are GPR35 modulators. In some embodiments, compounds of Formula (I), (I'), or (I") described herein are GPR35 agonists. In some embodiments, compounds of Formula (I), (I'), or (I") described herein are GPR35 inverse agonists. In some embodiments, compounds of Formula (I), (I'), or (I") described herein are GPR35 antagonists. The compounds of Formula (I), (I'), or (I") described herein, and compositions comprising these compounds, are useful for the treatment of an inflammatory bowel disease.

In some embodiments, provided herein is a compound of Formula (I"), or a pharmaceutically acceptable salt or solvate thereof:

Formula (I")

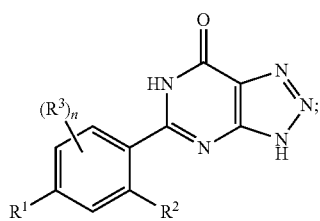

wherein:

$R^1$ is $-CH_2R^4$, $-CN$, $-B(OH)_2$, $-N(R^{10})_2$, $-NR^{10}C(O)R^9$, $-C(O)OH$, $-CH_2C(O)OH$, $-C(O)N(R^{10})_2$, $-C(O)NHS(O)_2N(R^{10})_2$, $-C_{1-6}$alkyl-OH, $C_{3-8}$cycloalkyl,

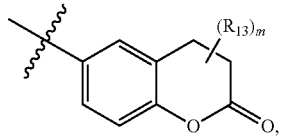

or a 5- or 6-membered heteroaryl optionally substituted with one, two, or three $R^8$ groups;

$R^2$ is H, $-OH$, $-N(R^{10})_2$, $-NHS(O)_2R^9$, $-S(O)_2N(R^{10})_2$, $-C(O)N(R^{10})_2$, $-OC(O)N(R^{10})_2$, $-O-C_{1-6}$alkyl, $-C_{1-6}$alkyl-OH, $-C_{1-6}$alkyl-OR$^9$, $-C_{1-6}$alkyl-N(R$^{10})_2$, $C_{2-6}$alkenyl, $C_{2-6}$alkynyl, $C_{1-6}$haloalkyl, $C_{3-8}$cycloalkyl;

each $R^3$ is independently selected from halogen, $-CN$, $-OH$, $-OR^9$, $-SR^9$, $-N(R^{10})_2$, $-NO_2$, $-S(O)R^9$, $-S(O)_2R^9$, $-NHS(O)_2R^9$, $-S(O)_2N(R^{10})_2$, $-C(O)R^9$, $-C(O)OR^{10}$, $-OC(O)R^9$, $-C(O)N(R^{10})_2$, $-OC(O)N(R^{10})_2$, $-NR^{10}C(O)N(R^{10})_2$, $-NR^{10}C(O)R^9$, $-NR^{10}C(O)OR^9$, $C_{1-6}$alkyl, $-C_{1-6}$alkyl-OH, $-C_{1-6}$alkyl-OR$^9$, $-C_{1-6}$alkyl-N(R$^{10})_2$, $C_{2-6}$alkenyl, $C_{2-6}$alkynyl, $C_{1-6}$haloalkyl, $C_{3-8}$cycloalkyl, and $-C_{1-6}$alkyl-$C_{3-8}$cycloalkyl;

$R^4$ is

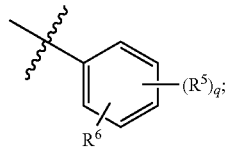

each $R^5$ is independently selected from halogen, $-CN$, $-OH$, $-OR^9$, $-SR^9$, $-N(R^{10})_2$, $-S(O)R^9$, $-S(O)_2R^9$, $-NHS(O)_2R^9$, $-S(O)_2N(R^{10})_2$, $-C(O)NHS(O)_2N(R^{10})_2$, $-C(O)R^9$, $-C(O)OR^{10}$, $-OC(O)R^9$, $-C(O)N(R^{10})_2$, $-OC(O)N(R^{10})_2$, $-NR^{10}C(O)N(R^{10})_2$, $-NR^{10}C(O)R^9$, $-NR^{10}C(O)OR^9$, $C_{1-6}$alkyl, $-C_{1-6}$alkyl-R$^9$, $-C_{1-6}$alkyl-OH, $-C_{1-6}$alkyl-OR$^9$, $-C_{1-6}$alkyl-N(R$^{10})_2$, $-C_{1-6}$alkyl-C(O)OR$^{10}$, $C_{2-6}$alkenyl, $-C_{2-6}$alkenyl-C(O)OR$^{10}$, $C_{2-6}$alkynyl, $C_{1-6}$haloalkyl, $C_{1-6}$haloalkyl-OH, $C_{3-8}$cycloalkyl, $-C_{1-6}$alkyl-$C_{3-8}$cycloalkyl, phenyl, $-C_{1-6}$alkyl-phenyl, $C_{2-9}$heterocycloalkyl, $-C_{1-6}$alkyl-$C_{2-9}$heterocycloalkyl, and $C_{1-9}$heteroaryl; wherein $C_{3-8}$cycloalkyl, $-C_{1-6}$alkyl-$C_{3-8}$cycloalkyl, phenyl, $-C_{1-6}$alkyl-phenyl, and $C_{1-9}$heteroaryl are optionally substituted with one, two, or three groups independently selected from halogen, $-C(O)OR^{10}$, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl and $-C_{1-6}$alkyl-$C_{2-9}$heterocycloalkyl are optionally substituted with one, two, or three groups independently selected from halogen, $-C(O)OR^{10}$, $C_{1-6}$alkyl, $C_{1-6}$haloalkyl, and oxo;

$R^6$ is $-C(O)OR^7$, $-C(O)NHS(O)_2N(R^{10})_2$,

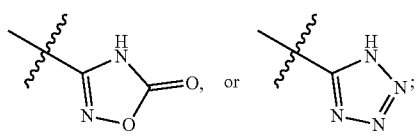 [SMILES: *c1noc(=O)[nH]1 ; "or" ; *c1nnn[nH]1 ; ";"]

R⁷ is independently selected from H and $C_{1-6}$alkyl;

each R⁸ is independently selected from halogen, —OH, —OR⁹, —N(R¹⁰)₂, —S(O)R⁹, —S(O)₂R⁹, —NHS(O)₂R⁹, —S(O)₂N(R¹⁰)₂, —C(O)NHS(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-OH, —$C_{1-6}$alkyl-OR⁹, —$C_{1-6}$alkyl-N(R¹⁰)₂, —$C_{1-6}$alkyl-C(O)OR¹⁰, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;

each R⁹ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —OR¹¹, —N(R¹¹)₂, $C_{1-6}$alkyl, $C_{3-8}$cycloalkyl, —N(R¹¹)C(O)R¹², —C(O)R¹², and —C(O)OR¹²;

each R¹⁰ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N(R¹¹)₂, and —C(O)OR¹²; or two R¹⁰ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each R¹¹ is independently selected from H and $C_{1-6}$alkyl;

each R¹² is independently selected from H and $C_{1-6}$alkyl;

each R¹³ is independently selected from $C_{1-6}$alkyl;

m is 1, 2, 3, or 4;

n is 0, 1, 2, or 3;

p is 0, 1, 2, 3, 4, or 5; and q is 0, 1, 2, 3, or 4;

or a pharmaceutically acceptable salt or solvate thereof.

In some embodiments is a compound of Formula (I"), or a pharmaceutically acceptable salt or solvate thereof, wherein R¹ is

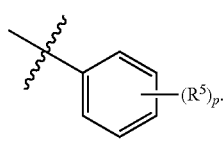

In some embodiments is a compound of Formula (I"), or a pharmaceutically acceptable salt or solvate thereof, wherein R¹ is

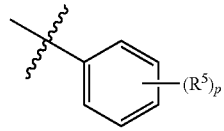

and p is 0, 1, or 2. In some embodiments is a compound of Formula (I"), or a pharmaceutically acceptable salt or solvate thereof, wherein R¹ is

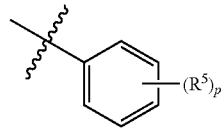

and p is 0. In some embodiments is a compound of Formula (I"), or a pharmaceutically acceptable salt or solvate thereof, wherein R¹ is

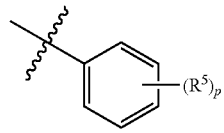

and p is 1. In some embodiments is a compound of Formula (I"), or a pharmaceutically acceptable salt or solvate thereof, wherein R¹ is

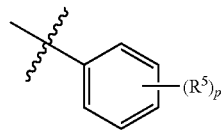

and p is 2. In some embodiments is a compound of Formula (I"), or a pharmaceutically acceptable salt or solvate (RE) thereof, wherein R¹ is

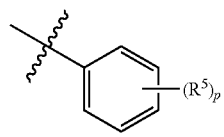

and p is 1 or 2. In some embodiments is a compound of Formula (I"), or a pharmaceutically acceptable salt or solvate thereof, wherein $R^1$ is

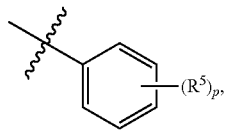

p is 1 or 2, and each $R^5$ is independently selected from halogen, —OH, —$OR^9$, —$N(R^{10})_2$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, $C_{1-6}$alkyl, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{1-6}$haloalkyl, $C_{1-6}$haloalkyl-OH, $C_{3-8}$cycloalkyl, $C_{2-9}$heterocycloalkyl, and $C_{1-9}$heteroaryl. In some embodiments is a compound of Formula (I"), or a pharmaceutically acceptable salt or solvate thereof, wherein $R^1$ is

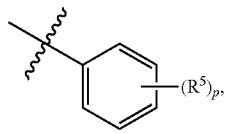

p is 1 or 2, each $R^5$ is independently selected from halogen, —OH, —$OR^9$, —$N(R^{10})_2$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, $C_{1-6}$alkyl, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{1-6}$haloalkyl, $C_{1-6}$haloalkyl-OH, $C_{3-8}$cycloalkyl, $C_{2-9}$heterocycloalkyl, and $C_{1-9}$heteroaryl, and each $R^{10}$ is independently selected from H and $C_{1-6}$alkyl. In some embodiments is a compound of Formula (I"), or a pharmaceutically acceptable salt or solvate thereof, wherein $R^1$ is

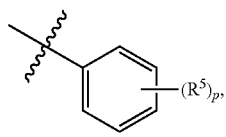

p is 1 or 2, and each $R^5$ is independently selected from halogen, —OH, —$OR^9$, —$N(R^{10})_2$, —$C(O)NHS(O)_2N(R^{10})_2$, —$C(O)OR^{10}$, —$C(O)N(R^{10})_2$, —$NR^{10}C(O)R^9$, $C_{1-6}$alkyl, —$C_{1-6}$alkyl-$C(O)OR^{10}$, and $C_{1-9}$heteroaryl. In some embodiments is a compound of Formula (I"), or a pharmaceutically acceptable salt or solvate thereof, wherein $R^1$ is

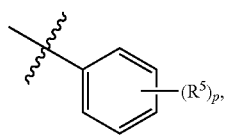

p is 1 or 2, each $R^5$ is independently selected from halogen, —OH, —$OR^9$, —$N(R^{10})_2$, —$C(O)NHS(O)_2N(R^{10})_2$, —$C(O)OR^{10}$, —$C(O)N(R^{10})_2$, —$NR^{10}C(O)R^9$, $C_{1-6}$alkyl, —$C_{1-6}$alkyl-$C(O)OR^{10}$, and $C_{1-9}$heteroaryl, and each $R^{10}$ is independently selected from H and $C_{1-6}$alkyl. In some embodiments is a compound of Formula (I"), or a pharmaceutically acceptable salt or solvate thereof, wherein $R^1$ is

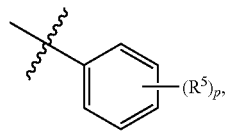

p is 1 or 2, and each $R^5$ is independently selected from —$OR^9$, —$C(O)OR^{10}$, —$C(O)N(R^{10})_2$, $C_{1-6}$alkyl, —$C_{1-6}$alkyl-$C(O)OR^{10}$. In some embodiments is a compound of Formula (I"), or a pharmaceutically acceptable salt or solvate thereof, wherein $R^1$ is

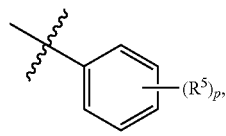

p is 1 or 2, each $R^5$ is independently selected from —$OR^9$, —$C(O)OR^{10}$, —$C(O)N(R^{10})_2$, $C_{1-6}$alkyl, —$C_{1-6}$alkyl-$C(O)OR^{10}$, and each $R^{10}$ is independently selected from H and $C_{1-6}$alkyl. In some embodiments is a compound of Formula (I"), or a pharmaceutically acceptable

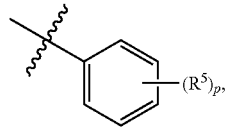

salt or solvate thereof, wherein $R^1$ is, p is 1 or 2, and each $R^5$ is independently selected from —$C(O)OR^{10}$. In some embodiments is a compound of Formula (I"), or a pharmaceutically acceptable salt or solvate thereof, wherein $R^1$ is

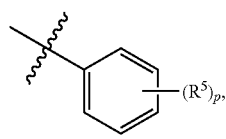

p is 1 or 2, each $R^5$ is independently selected from —$C(O)OR^{10}$, and each $R^{10}$ is independently selected from H and $C_{1-6}$alkyl. In some embodiments is a compound of Formula (I"), or a pharmaceutically acceptable salt or solvate thereof, wherein $R^1$ is

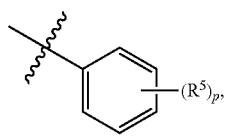

p is 1 or 2, and each $R^5$ is independently selected from —OH, —$OR^9$ and —$C_{1-6}$alkyl-C(O)$OR^{10}$. In some embodiments is a compound of Formula (I"), or a pharmaceutically acceptable salt or solvate thereof, wherein $R^1$ is

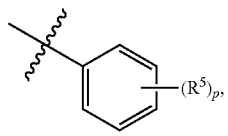

p is 1 or 2, and each $R^5$ is independently selected from —OH, —$OR^9$ and —$C_{1-6}$alkyl-C(O)$OR^{10}$, and $R^9$ is $C_{1-6}$alkyl optionally substituted with —C(O)$OR^{12}$. In some embodiments is a compound of Formula (I"), or a pharmaceutically acceptable salt or solvate thereof, wherein $R^1$ is

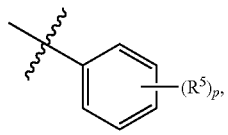

p is 1, and $R^5$ is independently selected from —C(O)OH.

In some embodiments is a compound of Formula (I"), or a pharmaceutically acceptable salt or solvate thereof, wherein $R^1$ is a 5- or 6-membered heteroaryl optionally substituted with one, two, or three $R^8$ groups. In some embodiments is a compound of Formula (I"), or a pharmaceutically acceptable salt or solvate thereof, wherein $R^1$ is a 5-membered heteroaryl optionally substituted with one, two, or three $R^8$ groups. In some embodiments is a compound of Formula (I"), or a pharmaceutically acceptable salt or solvate thereof, wherein $R^1$ is a 5-membered heteroaryl optionally substituted with one, two, or three $R^8$ groups, wherein the 5-membered heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl. In some embodiments is a compound of Formula (I"), or a pharmaceutically acceptable salt or solvate thereof, wherein $R^1$ is a 5-membered heteroaryl optionally substituted with one or two $R^8$ groups, wherein the 5-membered heteroaryl is selected from oxazolyl, thiazolyl, pyrazolyl, furanyl, thienyl, pyrrolyl, tetrazolyl, and isoxazolyl. In some embodiments is a compound of Formula (I"), or a pharmaceutically acceptable salt or solvate thereof, wherein $R^1$ is oxazolyl optionally substituted with one or two $R^8$ groups. In some embodiments is a compound of Formula (I"), or a pharmaceutically acceptable salt or solvate thereof, wherein $R^1$ is thiazolyl optionally substituted with one or two $R^8$ groups. In some embodiments is a compound of Formula (I"), or a pharmaceutically acceptable salt or solvate thereof, wherein $R^1$ is pyrazolyl optionally substituted with one or two $R^8$ groups. In some embodiments is a compound of Formula (I"), or a pharmaceutically acceptable salt or solvate thereof, wherein $R^1$ is furanyl optionally substituted with one or two $R^8$ groups. In some embodiments is a compound of Formula (I"), or a pharmaceutically acceptable salt or solvate thereof, wherein $R^1$ is thienyl optionally substituted with one or two $R^8$ groups. In some embodiments is a compound of Formula (I"), or a pharmaceutically acceptable salt or solvate thereof, wherein $R^1$ is pyrrolyl optionally substituted with one or two $R^8$ groups. In some embodiments is a compound of Formula (I"), or a pharmaceutically acceptable salt or solvate thereof, wherein $R^1$ is tetrazolyl optionally substituted with one or two $R^8$ groups. In some embodiments is a compound of Formula (I"), or a pharmaceutically acceptable salt or solvate thereof, wherein $R^1$ is isoxazolyl optionally substituted with one or two $R^8$ groups. In some embodiments is a compound of Formula (I"), or a pharmaceutically acceptable salt or solvate thereof, wherein $R^1$ is a 6-membered heteroaryl optionally substituted with one, two, or three $R^8$ groups. In some embodiments is a compound of Formula (I"), or a pharmaceutically acceptable salt or solvate thereof, wherein $R^1$ is a 6-membered heteroaryl optionally substituted with one, two, or three $R^8$ groups, wherein the 6-membered heteroaryl is selected from pyridinyl, pyrimidinyl, pyrazinyl, pyridazinyl, and triazinyl. In some embodiments is a compound of Formula (I"), or a pharmaceutically acceptable salt or solvate thereof, wherein $R^1$ is a 6-membered heteroaryl optionally substituted with one or two $R^8$ groups, wherein the 6-membered heteroaryl is selected from pyridinyl and pyrimidinyl. In some embodiments is a compound of Formula (I"), or a pharmaceutically acceptable salt or solvate thereof, wherein $R^1$ is pyridinyl optionally substituted with one or two $R^8$ groups. In some embodiments is a compound of Formula (I"), or a pharmaceutically acceptable salt or solvate thereof, wherein $R^1$ is pyrimidinyl optionally substituted with one or two $R^8$ groups. In some embodiments is a compound of Formula (I"), or a pharmaceutically acceptable salt or solvate thereof, wherein each $R^8$ is independently selected from halogen, —C(O)$OR^{10}$, $C_{1-6}$alkyl, and —$C_{1-6}$alkyl-C(O)$OR^{10}$. In some embodiments is a compound of Formula (I"), or a pharmaceutically acceptable salt or solvate thereof, wherein each $R^8$ is independently selected from —C(O)$OR^{10}$. In some embodiments is a compound of Formula (I"), or a pharmaceutically acceptable salt or solvate thereof, wherein $R^1$ is an unsubstituted 5-membered heteroaryl selected from oxazolyl, thiazolyl, pyrazolyl, furanyl, thienyl, pyrrolyl, tetrazolyl, and isoxazolyl. In some embodiments is a compound of Formula (I"), or a pharmaceutically acceptable salt or solvate thereof, wherein $R^1$ is an unsubstituted 6-membered heteroaryl selected from pyridinyl and pyrimidinyl.

In some embodiments is a compound of Formula (I"), or a pharmaceutically acceptable salt or solvate thereof, wherein $R^1$ is —C(O)N($R^{10}$)$_2$. In some embodiments is a compound of Formula (I"), or a pharmaceutically acceptable salt or solvate thereof, wherein $R^1$ is —C(O)N($R^{10}$)$_2$ and each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N($R^{11}$)$_2$, and —C(O)$OR^{12}$. In some embodiments is a compound of Formula (I"), or a pharmaceutically acceptable salt or solvate thereof, wherein $R^1$ is —C(O)N($R^{10}$)$_2$ and each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N($R^{11}$)$_2$, and —C(O)O$R^{12}$. In some embodiments is a compound of Formula (I"), or a pharmaceutically acceptable salt or solvate thereof, wherein $R^1$ is —C(O)N($R^{10}$)$_2$ and each $R^{10}$ is independently selected from H and $C_{1-6}$alkyl optionally substituted with —C(O)O$R^{12}$. In some embodiments is a compound of Formula (I"), or a pharmaceutically acceptable salt or solvate thereof, wherein $R^1$ is —C(O)N($R^{10}$)$_2$ and each $R^{10}$ is independently selected from H and $C_{1-6}$alkyl optionally substituted with —C(O)OH. In some embodiments is a compound of Formula (I"), or a pharmaceutically acceptable salt or solvate thereof, wherein $R^1$ is —C(O)N($R^{10}$)$_2$ and the two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (I"), or a pharmaceutically acceptable salt or solvate thereof, wherein $R^1$ is —C(O)N($R^{10}$)$_2$ and the two $R^{10}$ and the nitrogen atom to which they are attached are combined to form a 5-membered heterocycloalkyl ring substituted with —C(O)OH. In some embodiments is a compound of Formula (I"), or a pharmaceutically acceptable salt or solvate thereof, wherein $R^1$ is —C(O)N($R^{10}$)$_2$ and the two $R^{10}$ and the nitrogen atom to which they are attached are combined to form a 6-membered heterocycloalkyl ring substituted with —C(O)OH.

In some embodiments is a compound of Formula (I"), or a pharmaceutically acceptable salt or solvate thereof, wherein $R^1$ is —N($R^{10}$)$_2$. In some embodiments is a compound of Formula (I"), or a pharmaceutically acceptable salt or solvate thereof, wherein $R^1$ is —N($R^{10}$)$_2$ and each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N($R^{11}$)$_2$, and —C(O)O$R^{12}$. In some embodiments is a compound of Formula (I"), or a pharmaceutically acceptable salt or solvate thereof, wherein $R^1$ is —N($R^{10}$)$_2$ and each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N($R^{11}$)$_2$, and —C(O)O$R^{12}$. In some embodiments is a compound of Formula (I"), or a pharmaceutically acceptable salt or solvate thereof, wherein $R^1$ is —N($R^{10}$)$_2$ and each $R^{10}$ is independently selected from H and $C_{1-6}$alkyl optionally substituted with —C(O)O$R^{12}$. In some embodiments is a compound of Formula (I"), or a pharmaceutically acceptable salt or solvate thereof, wherein $R^1$ is —N($R^{10}$)$_2$ and each $R^{10}$ is independently selected from H and $C_{1-6}$alkyl optionally substituted with —C(O)OH. In some embodiments is a compound of Formula (I"), or a pharmaceutically acceptable salt or solvate thereof, wherein $R^1$ is —N($R^{10}$)$_2$ and the two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (I"), or a pharmaceutically acceptable salt or solvate thereof, wherein $R^1$ is —N($R^{10}$)$_2$ and the two $R^{10}$ and the nitrogen atom to which they are attached are combined to form a 5-membered heterocycloalkyl ring substituted with —C(O)OH. In some embodiments is a compound of Formula (I"), or a pharmaceutically acceptable salt or solvate thereof, wherein $R^1$ is —N($R^{10}$)$_2$ and the two $R^{10}$ and the nitrogen atom to which they are attached are combined to form a 6-membered heterocycloalkyl ring substituted with —C(O)OH.

In some embodiments is a compound of Formula (I"), or a pharmaceutically acceptable salt or solvate thereof, wherein $R^1$ is —C(O)OH.

In some embodiments is a compound of Formula (I"), or a pharmaceutically acceptable salt or solvate thereof, wherein $R^1$ is —CH$_2$C(O)OH.

In some embodiments is a compound of Formula (I"), or a pharmaceutically acceptable salt or solvate thereof, wherein $R^1$ is —C(O)NHS(O)$_2$N($R^{10}$)$_2$.

In some embodiments is a compound of Formula (I"), or a pharmaceutically acceptable salt or solvate thereof, wherein $R^1$ is

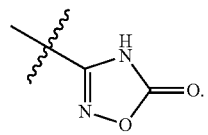 [SMILES: *c1noc(=O)[nH]1]

In some embodiments is a compound of Formula (I"), or a pharmaceutically acceptable salt or solvate thereof, wherein $R^1$ is

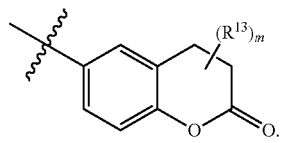

In some embodiments is a compound of Formula (I"), or a pharmaceutically acceptable salt or solvate thereof, wherein $R^1$ is

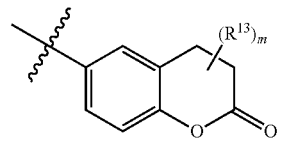

and m is 2. In some embodiments is a compound of Formula (I"), or a pharmaceutically acceptable salt or solvate thereof, wherein $R^1$ is

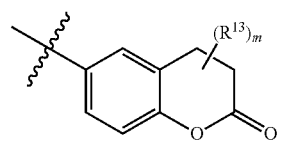

and m is 1.

In some embodiments is a compound of Formula (I″), or a pharmaceutically acceptable salt or solvate thereof, wherein R¹ is —CH₂R⁴ and R⁴ is

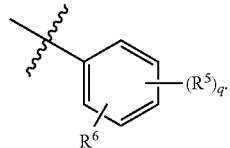

In some embodiments is a compound of Formula (I″), or a pharmaceutically acceptable salt or solvate thereof, wherein R¹ is —CH₂R⁴, R⁴ is

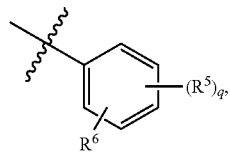

and q is 0. In some embodiments is a compound of Formula (I″), or a pharmaceutically acceptable salt or solvate thereof, wherein R¹ is —CH₂R⁴, R⁴ is

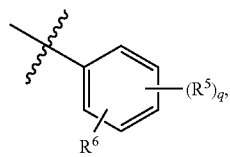

q is 0, and R⁶ is —C(O)OR⁷. In some embodiments is a compound of Formula (I″), or a pharmaceutically acceptable salt or solvate thereof, wherein R¹ is —CH₂R⁴, R⁴ is

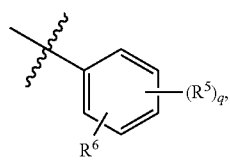

q is 0, and R⁶ is —C(O)OH. In some embodiments is a compound of Formula (I″), or a pharmaceutically acceptable salt or solvate thereof, wherein R¹ is —CH₂R⁴, R⁴ is

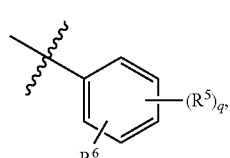

q is 0, and R⁶ is —C(O)NHS(O)₂N(R¹⁰)₂. In some embodiments is a compound of Formula (I″), or a pharmaceutically acceptable salt or solvate thereof, wherein R¹ is —CH₂R⁴, R⁴ is

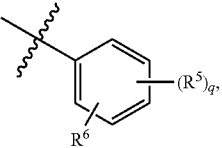

q is 0, and R⁶ is

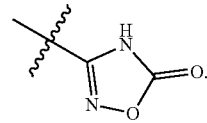 [SMILES: *c1noc(=O)[nH]1]

In some embodiments is a compound of Formula (I″), or a pharmaceutically acceptable salt or solvate thereof, wherein R¹ is —CH₂R⁴, R⁴ is

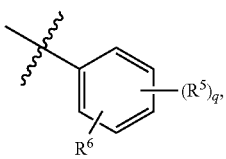

q is 0, and R⁶ is

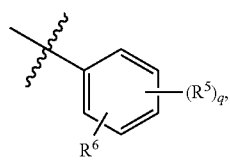

In some embodiments is a compound of Formula (I″), or a pharmaceutically acceptable salt or solvate thereof, wherein R² is H, —OH, —N(R¹⁰)₂, or —O—C₁₋₆alkyl. In some embodiments is a compound of Formula (I″), or a pharmaceutically acceptable salt or solvate thereof, wherein R² is —O—C₁₋₆alkyl. In some embodiments is a compound of Formula (I″), or a pharmaceutically acceptable salt or solvate thereof, wherein R² is —OCH₂CH₃. In some embodiments is a compound of Formula (I″), or a pharmaceutically acceptable salt or solvate thereof, wherein R² is H. In some embodiments is a compound of Formula (I″), or a pharmaceutically acceptable salt or solvate thereof, wherein R² is —OH. In some embodiments is a compound of Formula (I″), or a pharmaceutically acceptable salt or solvate thereof, wherein R² is —N(R¹⁰)₂.

In some embodiments is a compound of Formula (I″), or a pharmaceutically acceptable salt or solvate thereof, wherein n is 0.

In some embodiments is a compound of Formula (I″), or a pharmaceutically acceptable salt or solvate thereof, wherein n is 1, 2, or 3. In some embodiments is a compound of Formula (I″), or a pharmaceutically acceptable salt or solvate thereof, wherein n is 1, 2, or 3 and each R³ is independently selected from halogen, —CN, —OR⁹, —N(R¹⁰)₂, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —NR¹⁰C(O)N(R¹⁰)₂, —NR¹⁰C(O)R⁹, C₁₋₆alkyl, —C₁₋₆alkyl-OH, —C₁₋₆alkyl-OR⁹, —C₁₋₆alkyl-N(R¹⁰)₂, C₁₋₆haloalkyl, $C_{3-8}$cycloalkyl, and —$C_{1-6}$alkyl-$C_{3-8}$cycloalkyl. In some embodiments is a compound of Formula (I"), or a pharmaceutically acceptable salt or solvate thereof, wherein n is 1, 2, or 3 and each R³ is independently selected from halogen, —OR⁹, —N(R¹⁰)₂, —C(O)OR¹⁰, —C(O)N(R¹⁰)₂, and $C_{1-6}$alkyl. In some embodiments is a compound of Formula (I"), or a pharmaceutically acceptable salt or solvate thereof, wherein n is 1, 2, or 3 and each R³ is independently selected from halogen and $C_{1-6}$alkyl. In some embodiments is a compound of Formula (I"), or a pharmaceutically acceptable salt or solvate thereof, wherein n is 1. In some embodiments is a compound of Formula (I"), or a pharmaceutically acceptable salt or solvate thereof, wherein n is 1 and R³ is selected from halogen, —OH, —OR⁹, —N(R¹⁰)₂, $C_{1-6}$alkyl, —$C_{1-6}$alkyl-OH, —$C_{1-6}$alkyl-OR⁹, and $C_{1-6}$haloalkyl. In some embodiments is a compound of Formula (I"), or a pharmaceutically acceptable salt or solvate thereof, wherein n is 1 and R³ is selected from halogen, —OR⁹, and $C_{1-6}$alkyl. In some embodiments is a compound of Formula (I"), or a pharmaceutically acceptable salt or solvate thereof, wherein n is 1 and R³ is selected from halogen, —OR⁹, and $C_{1-6}$alkyl. In some embodiments is a compound of Formula (I"), or a pharmaceutically acceptable salt or solvate thereof, wherein n is 1 and R³ is —OR⁹. In some embodiments is a compound of Formula (I"), or a pharmaceutically acceptable salt or solvate thereof, wherein n is 1, R³ is —OR⁹, and R⁹ is $C_{3-8}$cycloalkyl. In some embodiments is a compound of Formula (I"), or a pharmaceutically acceptable salt or solvate thereof, wherein n is 1, R³ is —OR⁹, and R⁹ is cyclopentyl.

In some embodiments, provided herein is a compound of Formula (I'), or a pharmaceutically acceptable salt or solvate thereof:

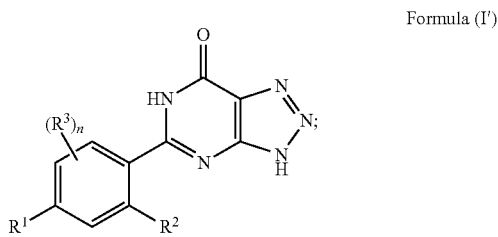

Formula (I')

wherein:
R¹ is —CH₂R⁴, —CN, —B(OH)₂, —N(R¹⁰)₂, —NR¹⁰C(O)R⁹, —C(O)OH, —CH₂C(O)OH, —C(O)N(R¹⁰)₂, —C(O)NHS(O)₂N(R¹⁰)₂, —$C_{1-6}$alkyl-OH, $C_{3-8}$cycloalkyl,

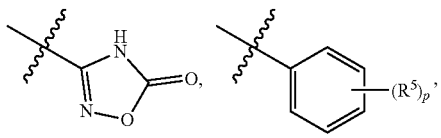

or a 5- or 6-membered heteroaryl optionally substituted with one, two, or three R⁸ groups;
R² is H, —OH, —N(R¹⁰)₂, —NHS(O)₂R⁹, —S(O)₂N(R¹⁰)₂, —C(O)N(R¹⁰)₂, —OC(O)N(R¹⁰)₂, —O—$C_{1-6}$alkyl, —$C_{1-6}$alkyl-OH, —$C_{1-6}$alkyl-OR⁹, —$C_{1-6}$alkyl-N(R¹⁰)₂, $C_{2-6}$alkenyl, $C_{2-6}$alkynyl, $C_{1-6}$haloalkyl, $C_{3-8}$cycloalkyl;

each R³ is independently selected from halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-OH, —$C_{1-6}$alkyl-OR⁹, —$C_{1-6}$alkyl-N(R¹⁰)₂, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
R⁴ is

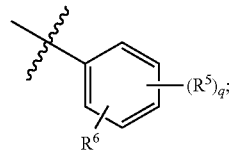

each R⁵ is independently selected from halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)NHS(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-R⁹, —$C_{1-6}$alkyl-OH, —$C_{1-6}$alkyl-OR⁹, —$C_{1-6}$alkyl-N(R¹⁰)₂, —$C_{1-6}$alkyl-C(O)OR¹⁰, $C_{2-6}$alkenyl, —$C_{2-6}$alkenyl-C(O)OR¹⁰, $C_{2-6}$alkynyl, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;
R⁶ is —C(O)OR⁷, —C(O)NHS(O)₂N(R¹⁰)₂,

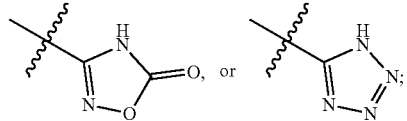 [SMILES: *c1noc(=O)[nH]1 ; "or" ; *c1nnn[nH]1]

each R⁷ is independently selected from H and $C_{1-6}$alkyl;
each R⁸ is independently selected from halogen, —OH, —OR⁹, —N(R¹⁰)₂, —S(O)R⁹, —S(O)₂R⁹, —NHS(O)₂R⁹, —S(O)₂N(R¹⁰)₂, —C(O)NHS(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-OH, —$C_{1-6}$alkyl-OR⁹, —$C_{1-6}$alkyl-N(R¹⁰)₂, —$C_{1-6}$alkyl-C(O)OR¹⁰, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —$OR^{11}$, —$N(R^{11})_2$, $C_{1-6}$alkyl, $C_{3-8}$cycloalkyl, —$N(R^{11})C(O)R^{12}$, —$C(O)R^{12}$, and —$C(O)OR^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —$N(R^{11})_2$, and —$C(O)OR^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —$C(O)OH$;

each $R^{11}$ is independently selected from H and $C_{1-6}$alkyl;

$R^{12}$ is independently selected from H and $C_{1-6}$alkyl;

n is 0, 1, 2, or 3;

p is 0, 1, 2, 3, 4, or 5; and q is 0, 1, 2, 3, or 4.

In some embodiments is a compound of Formula (I'), or a pharmaceutically acceptable salt or solvate thereof, wherein $R^1$ is

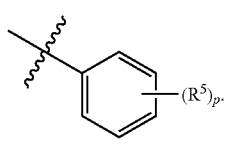

In some embodiments is a compound of Formula (I'), or a pharmaceutically acceptable salt or solvate thereof, wherein $R^1$ is

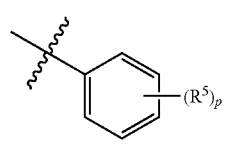

and p is 0, 1, or 2. In some embodiments is a compound of Formula (I'), or a pharmaceutically acceptable salt or solvate thereof, wherein $R^1$ is

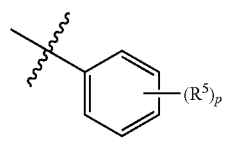

and p is 0. In some embodiments is a compound of Formula (I'), or a pharmaceutically acceptable salt or solvate thereof, wherein $R^1$ is

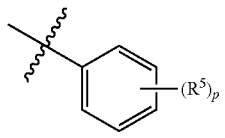

and p is 1. In some embodiments is a compound of Formula (I'), or a pharmaceutically acceptable salt or solvate thereof, wherein $R^1$ is

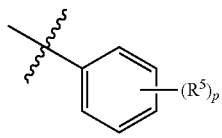

and p is 2. In some embodiments is a compound of Formula (I'), or a pharmaceutically acceptable salt or solvate thereof, wherein $R^1$ is

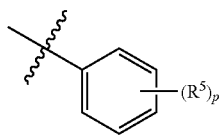

and p is 1 or 2. In some embodiments is a compound of Formula (I'), or a pharmaceutically acceptable salt or solvate thereof, wherein $R^1$ is

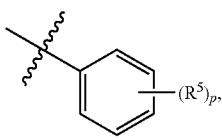

p is 1 or 2, and each $R^5$ is independently selected from halogen, —OH, —$OR^9$, —$N(R^{10})_2$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, $C_{1-6}$alkyl, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{1-6}$haloalkyl, $C_{1-6}$haloalkyl-OH, $C_{3-8}$cycloalkyl, $C_{2-9}$heterocycloalkyl, and $C_{1-9}$heteroaryl. In some embodiments is a compound of Formula (I'), or a pharmaceutically acceptable salt or solvate thereof, wherein $R^1$ is p is 1 or 2, each $R^5$ is independently selected from halogen, —OH, —$OR^9$, —$N(R^{10})_2$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, $C_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{1-6}$haloalkyl, C$_{1-6}$haloalkyl-OH, C$_{3-8}$cycloalkyl, C$_{2-9}$heterocycloalkyl, and C$_{1-9}$heteroaryl, and each R$^{10}$ is independently selected from H and C$_{1-6}$alkyl. In some embodiments is a compound of Formula (I'), or a pharmaceutically acceptable salt or solvate thereof, wherein R$^1$ is

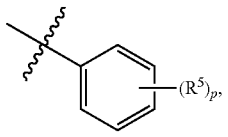

p is 1 or 2, and each R$^5$ is independently selected from halogen, —OH, —OR$^9$, —N(R$^{10}$)$_2$, —C(O)NHS(O)$_2$N(R$^{10}$)$_2$, —C(O)OR$^{10}$, —C(O)N(R$^{10}$)$_2$, —NR$^{10}$C(O)R$^9$, C$_{1-6}$alkyl, —C$_{1-6}$alkyl-C(O)OR$^{10}$, and C$_{1-9}$heteroaryl. In some embodiments is a compound of Formula (I'), or a pharmaceutically acceptable salt or solvate thereof, wherein R$^1$ is

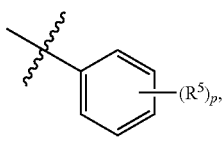

p is 1 or 2, each R$^5$ is independently selected from halogen, —OH, —OR$^9$, —N(R$^{10}$)$_2$, —C(O)NHS(O)$_2$N(R$^{10}$)$_2$, —C(O)OR$^{10}$, —C(O)N(R$^{10}$)$_2$, —NR$^{10}$C(O)R$^9$, C$_{1-6}$alkyl, —C$_{1-6}$alkyl-C(O)OR$^{10}$, and C$_{1-9}$heteroaryl, and each R$^{10}$ is independently selected from H and C$_{1-6}$alkyl. In some embodiments is a compound of Formula (I'), or a pharmaceutically acceptable salt or solvate thereof, wherein R$^1$ is

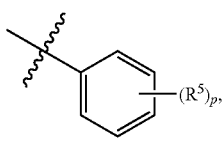

p is 1 or 2, and each R$^5$ is independently selected from —OR$^9$, —C(O)OR$^{10}$, —C(O)N(R$^{10}$)$_2$, C$_{1-6}$alkyl, —C$_{1-6}$alkyl-C(O)OR$^{10}$. In some embodiments is a compound of Formula (I'), or a pharmaceutically acceptable salt or solvate thereof, wherein R$^1$ is

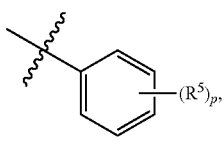

p is 1 or 2, each R$^5$ is independently selected from —OR$^9$, —C(O)OR$^{10}$, —C(O)N(R$^{10}$)$_2$, C$_{1-6}$alkyl, —C$_{1-6}$alkyl-C(O)OR$^{10}$, and each R$^{10}$ is independently selected from H and C$_{1-6}$alkyl. In some embodiments is a compound of Formula (I'), or a pharmaceutically acceptable salt or solvate thereof, wherein R$^1$ is

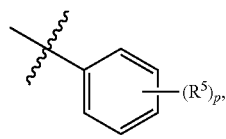

p is 1 or 2, and each R$^5$ is independently selected from —C(O)OR$^{10}$. In some embodiments is a compound of Formula (I'), or a pharmaceutically acceptable salt or solvate thereof, wherein R$^1$ is

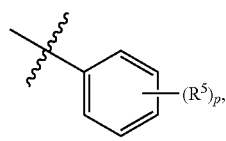

p is 1 or 2, each R$^5$ is independently selected from —C(O)OR$^{10}$, and each R$^{10}$ is independently selected from H and C$_{1-6}$alkyl. In some embodiments is a compound of Formula (I'), or a pharmaceutically acceptable salt or solvate thereof, wherein R$^1$ is

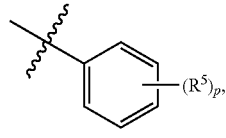

p is 1 or 2, and each R$^5$ is independently selected from —OH, —OR$^9$ and —C$_{1-6}$alkyl-C(O)OR$^{10}$. In some embodiments is a compound of Formula (I'), or a pharmaceutically acceptable salt or solvate thereof, wherein R$^1$ is

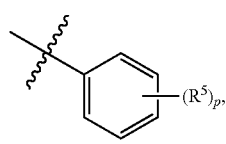

p is 1 or 2, and each R$^5$ is independently selected from —OH, —OR$^9$ and —C$_{1-6}$alkyl-C(O)OR$^{10}$, and R$^9$ is C$_{1-6}$alkyl optionally substituted with —C(O)OR$^{12}$. In some embodiments is a compound of Formula (I'), or a pharmaceutically acceptable salt or solvate thereof, wherein R$^1$ is

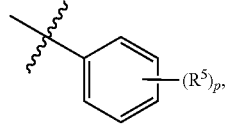

p is 1, and R$^5$ is independently selected from —C(O)OH.

In some embodiments is a compound of Formula (I'), or a pharmaceutically acceptable salt or solvate thereof, wherein R$^1$ is a 5- or 6-membered heteroaryl optionally substituted with one, two, or three R$^8$ groups. In some embodiments is a compound of Formula (I'), or a pharmaceutically acceptable salt or solvate thereof, wherein R$^1$ is a 5-membered heteroaryl optionally substituted with one, two, or three $R^8$ groups. In some embodiments is a compound of Formula (I'), or a pharmaceutically acceptable salt or solvate thereof, wherein $R^1$ is a 5-membered heteroaryl optionally substituted with one, two, or three $R^8$ groups, wherein the 5-membered heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl. In some embodiments is a compound of Formula (I'), or a pharmaceutically acceptable salt or solvate thereof, wherein $R^1$ is a 5-membered heteroaryl optionally substituted with one or two $R^8$ groups, wherein the 5-membered heteroaryl is selected from oxazolyl, thiazolyl, pyrazolyl, furanyl, thienyl, pyrrolyl, tetrazolyl, and isoxazolyl. In some embodiments is a compound of Formula (I'), or a pharmaceutically acceptable salt or solvate thereof, wherein $R^1$ is oxazolyl optionally substituted with one or two $R^8$ groups. In some embodiments is a compound of Formula (I'), or a pharmaceutically acceptable salt or solvate thereof, wherein $R^1$ is thiazolyl optionally substituted with one or two $R^8$ groups. In some embodiments is a compound of Formula (I'), or a pharmaceutically acceptable salt or solvate thereof, wherein $R^1$ is pyrazolyl optionally substituted with one or two $R^8$ groups. In some embodiments is a compound of Formula (I'), or a pharmaceutically acceptable salt or solvate thereof, wherein $R^1$ is furanyl optionally substituted with one or two $R^8$ groups. In some embodiments is a compound of Formula (I'), or a pharmaceutically acceptable salt or solvate thereof, wherein $R^1$ is thienyl optionally substituted with one or two $R^8$ groups. In some embodiments is a compound of Formula (I'), or a pharmaceutically acceptable salt or solvate thereof, wherein $R^1$ is pyrrolyl optionally substituted with one or two $R^8$ groups. In some embodiments is a compound of Formula (I'), or a pharmaceutically acceptable salt or solvate thereof, wherein $R^1$ is tetrazolyl optionally substituted with one or two $R^8$ groups. In some embodiments is a compound of Formula (I'), or a pharmaceutically acceptable salt or solvate thereof, wherein $R^1$ is isoxazolyl optionally substituted with one or two $R^8$ groups. In some embodiments is a compound of Formula (I'), or a pharmaceutically acceptable salt or solvate thereof, wherein $R^1$ is a 6-membered heteroaryl optionally substituted with one, two, or three $R^8$ groups. In some embodiments is a compound of Formula (I'), or a pharmaceutically acceptable salt or solvate thereof, wherein $R^1$ is a 6-membered heteroaryl optionally substituted with one, two, or three $R^8$ groups, wherein the 6-membered heteroaryl is selected from pyridinyl, pyrimidinyl, pyrazinyl, pyridazinyl, and triazinyl. In some embodiments is a compound of Formula (I'), or a pharmaceutically acceptable salt or solvate thereof, wherein $R^1$ is a 6-membered heteroaryl optionally substituted with one or two $R^8$ groups, wherein the 6-membered heteroaryl is selected from pyridinyl and pyrimidinyl. In some embodiments is a compound of Formula (I'), or a pharmaceutically acceptable salt or solvate thereof, wherein $R^1$ is pyridinyl optionally substituted with one or two $R^8$ groups. In some embodiments is a compound of Formula (I'), or a pharmaceutically acceptable salt or solvate thereof, wherein $R^1$ is pyrimidinyl optionally substituted with one or two $R^8$ groups. In some embodiments is a compound of Formula (I'), or a pharmaceutically acceptable salt or solvate thereof, wherein each $R^8$ is independently selected from halogen, —C(O)OR$^{10}$, $C_{1-6}$alkyl, and —C$_{1-6}$alkyl-C(O)OR$^{10}$. In some embodiments is a compound of Formula (I'), or a pharmaceutically acceptable salt or solvate thereof, wherein each $R^8$ is independently selected from —C(O)OR$^{10}$. In some embodiments is a compound of Formula (I'), or a pharmaceutically acceptable salt or solvate thereof, wherein $R^1$ is an unsubstituted 5-membered heteroaryl selected from oxazolyl, thiazolyl, pyrazolyl, furanyl, thienyl, pyrrolyl, tetrazolyl, and isoxazolyl. In some embodiments is a compound of Formula (I'), or a pharmaceutically acceptable salt or solvate thereof, wherein $R^1$ is an unsubstituted 6-membered heteroaryl selected from pyridinyl and pyrimidinyl.

In some embodiments is a compound of Formula (I'), or a pharmaceutically acceptable salt or solvate thereof, wherein $R^1$ is —C(O)N($R^{10}$)$_2$. In some embodiments is a compound of Formula (I'), or a pharmaceutically acceptable salt or solvate thereof, wherein $R^1$ is —C(O)N($R^{10}$)$_2$ and each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N($R^{11}$)$_2$, and —C(O)OR$^{12}$. In some embodiments is a compound of Formula (I'), or a pharmaceutically acceptable salt or solvate thereof, wherein $R^1$ is —C(O)N($R^{10}$)$_2$ and each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N($R^{11}$)$_2$, and —C(O)OR$^{12}$. In some embodiments is a compound of Formula (I'), or a pharmaceutically acceptable salt or solvate thereof, wherein $R^1$ is —C(O)N($R^{10}$)$_2$ and each $R^{10}$ is independently selected from H and $C_{1-6}$alkyl optionally substituted with —C(O)OR$^{12}$. In some embodiments is a compound of Formula (I'), or a pharmaceutically acceptable salt or solvate thereof, wherein $R^1$ is —C(O)N($R^{10}$)$_2$ and each $R^{10}$ is independently selected from H and $C_{1-6}$alkyl optionally substituted with —C(O)OH. In some embodiments is a compound of Formula (I'), or a pharmaceutically acceptable salt or solvate thereof, wherein $R^1$ is —C(O)N($R^{10}$)$_2$ and the two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (I'), or a pharmaceutically acceptable salt or solvate thereof, wherein $R^1$ is —C(O)N($R^{10}$)$_2$ and the two $R^{10}$ and the nitrogen atom to which they are attached are combined to form a 5-membered heterocycloalkyl ring substituted with —C(O)OH. In some embodiments is a compound of Formula (I'), or a pharmaceutically acceptable salt or solvate thereof, wherein $R^1$ is —C(O)N($R^{10}$)$_2$ and the two $R^{10}$ and the nitrogen atom to which they are attached are combined to form a 6-membered heterocycloalkyl ring substituted with —C(O)OH.

In some embodiments is a compound of Formula (I'), or a pharmaceutically acceptable salt or solvate thereof, wherein $R^1$ is —N($R^{10}$)$_2$. In some embodiments is a compound of Formula (I'), or a pharmaceutically acceptable salt or solvate thereof, wherein $R^1$ is —N($R^{10}$)$_2$ and each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N($R^{11}$)$_2$, and —C(O)OR$^{12}$. In some embodiments is a compound of Formula (I'), or a pharmaceutically acceptable salt or solvate thereof, wherein $R^1$ is —N($R^{10}$)$_2$ and each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N(R$^{11}$)$_2$, and —C(O)OR$^{12}$. In some embodiments is a compound of Formula (I'), or a pharmaceutically acceptable salt or solvate thereof, wherein R$^1$ is —N(R$^{10}$)$_2$ and each R$^{10}$ is independently selected from H and $C_{1-6}$alkyl optionally substituted with —C(O)OR$^{12}$. In some embodiments is a compound of Formula (I'), or a pharmaceutically acceptable salt or solvate thereof, wherein R$^1$ is —N(R$^{10}$)$_2$ and each R$^{10}$ is independently selected from H and $C_{1-6}$alkyl optionally substituted with —C(O)OH. In some embodiments is a compound of Formula (I'), or a pharmaceutically acceptable salt or solvate thereof, wherein R$^1$ is —N(R$^{10}$)$_2$ and the two R$^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (I'), or a pharmaceutically acceptable salt or solvate thereof, wherein R$^1$ is —N(R$^{10}$)$_2$ and the two R$^{10}$ and the nitrogen atom to which they are attached are combined to form a 5-membered heterocycloalkyl ring substituted with —C(O)OH. In some embodiments is a compound of Formula (I'), or a pharmaceutically acceptable salt or solvate thereof, wherein R$^1$ is —N(R$^{10}$)$_2$ and the two R$^{10}$ and the nitrogen atom to which they are attached are combined to form a 6-membered heterocycloalkyl ring substituted with —C(O)OH.

In some embodiments is a compound of Formula (I'), or a pharmaceutically acceptable salt or solvate thereof, wherein R$^1$ is —C(O)OH.

In some embodiments is a compound of Formula (I'), or a pharmaceutically acceptable salt or solvate thereof, wherein R$^1$ is —CH$_2$C(O)OH.

In some embodiments is a compound of Formula (I'), or a pharmaceutically acceptable salt or solvate thereof, wherein R$^1$ is —C(O)NHS(O)$_2$N(R$^{10}$)$_2$.

In some embodiments is a compound of Formula (I'), or a pharmaceutically acceptable salt or solvate thereof, wherein R$^1$ is

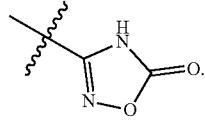 [SMILES: *c1noc(=O)[nH]1]

In some embodiments is a compound of Formula (I'), or a pharmaceutically acceptable salt or solvate thereof, wherein R$^1$ is —CH$_2$R$^4$ and R$^4$ is

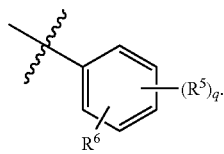

In some embodiments is a compound of Formula (I'), or a pharmaceutically acceptable salt or solvate thereof, wherein R$^1$ is —CH$_2$R$^4$, R$^4$ is

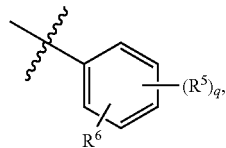

and q is 0. In some embodiments is a compound of Formula (I'), or a pharmaceutically acceptable salt or solvate thereof, wherein R$^1$ is —CH$_2$R$^4$, R$^4$ is

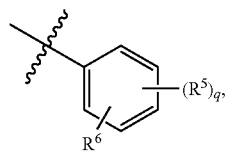

q is 0, and R$^6$ is —C(O)OR$^7$. In some embodiments is a compound of Formula (I'), or a pharmaceutically acceptable salt or solvate thereof, wherein R$^1$ is —CH$_2$R$^4$, R$^4$ is

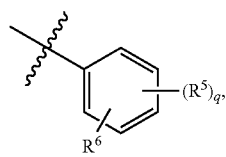

q is 0, and R$^6$ is —C(O)OH. In some embodiments is a compound of Formula (I'), or a pharmaceutically acceptable salt or solvate thereof, wherein R$^1$ is —CH$_2$R$^4$, R$^4$ is

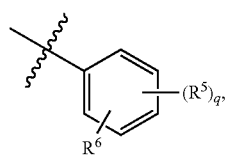

q is 0, and R$^6$ is —C(O)NHS(O)$_2$N(R$^{10}$)$_2$. In some embodiments is a compound of Formula (I'), or a pharmaceutically acceptable salt or solvate thereof, wherein R$^1$ is —CH$_2$R$^4$, R$^4$ is

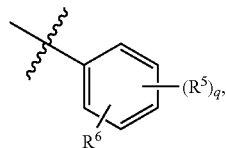

q is 0, and $R^6$ is

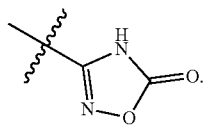 [SMILES: *c1noc(=O)[nH]1]

In some embodiments is a compound of Formula (I'), or a pharmaceutically acceptable salt or solvate thereof, wherein $R^1$ is —$CH_2R^4$, $R^4$ is

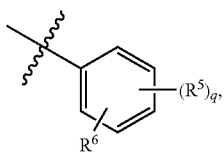

q is 0, and $R^6$ is

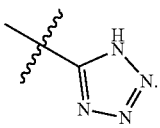 [SMILES: *c1nnn[nH]1]

In some embodiments is a compound of Formula (I'), or a pharmaceutically acceptable salt or solvate thereof, wherein $R^2$ is H, —OH, —$N(R^{10})_2$, or —O—$C_{1-6}$alkyl. In some embodiments is a compound of Formula (I'), or a pharmaceutically acceptable salt or solvate thereof, wherein $R^2$ is —O—$C_{1-6}$alkyl. In some embodiments is a compound of Formula (I'), or a pharmaceutically acceptable salt or solvate thereof, wherein $R^2$ is —$OCH_2CH_3$. In some embodiments is a compound of Formula (I'), or a pharmaceutically acceptable salt or solvate thereof, wherein $R^2$ is H. In some embodiments is a compound of Formula (I'), or a pharmaceutically acceptable salt or solvate thereof, wherein $R^2$ is —OH. In some embodiments is a compound of Formula (I'), or a pharmaceutically acceptable salt or solvate thereof, wherein $R^2$ is —$N(R^{10})_2$.

In some embodiments is a compound of Formula (I'), or a pharmaceutically acceptable salt or solvate thereof, wherein n is 0.

In some embodiments is a compound of Formula (I'), or a pharmaceutically acceptable salt or solvate thereof, wherein n is 1, 2, or 3. In some embodiments is a compound of Formula (I'), or a pharmaceutically acceptable salt or solvate thereof, wherein n is 1, 2, or 3 and each $R^3$ is independently selected from halogen, —CN, —$OR^9$, —$N(R^{10})_2$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$NR^{10}C(O)N(R^{10})_2$, —$NR^{10}C(O)R^9$, $C_{1-6}$alkyl, —$C_{1-6}$alkyl-OH, —$C_{1-6}$alkyl-$OR^9$, —$C_{1-6}$alkyl-$N(R^{10})_2$, $C_{1-6}$haloalkyl, $C_{3-8}$cycloalkyl, and —$C_{1-6}$alkyl-$C_{3-8}$cycloalkyl. In some embodiments is a compound of Formula (I'), or a pharmaceutically acceptable salt or solvate thereof, wherein n is 1, 2, or 3 and each $R^3$ is independently selected from halogen, —$OR^9$, —$N(R^{10})_2$, —$C(O)OR^{10}$, —$C(O)N(R^{10})_2$, and $C_{1-6}$alkyl. In some embodiments is a compound of Formula (I'), or a pharmaceutically acceptable salt or solvate thereof, wherein n is 1, 2, or 3 and each $R^3$ is independently selected from halogen and $C_{1-6}$alkyl. In some embodiments is a compound of Formula (I'), or a pharmaceutically acceptable salt or solvate thereof, wherein n is 1. In some embodiments is a compound of Formula (I'), or a pharmaceutically acceptable salt or solvate thereof, wherein n is 1 and $R^3$ is selected from halogen, —OH, —$OR^9$, —$N(R^{10})_2$, $C_{1-6}$alkyl, —$C_{1-6}$alkyl-OH, —$C_{1-6}$alkyl-$OR^9$, and $C_{1-6}$haloalkyl. In some embodiments is a compound of Formula (I'), or a pharmaceutically acceptable salt or solvate thereof, wherein n is 1 and $R^3$ is selected from halogen, —$OR^9$, and $C_{1-6}$alkyl. In some embodiments is a compound of Formula (I'), or a pharmaceutically acceptable salt or solvate thereof, wherein n is 1 and $R^3$ is selected from halogen, —$OR^9$, and $C_{1-6}$alkyl. In some embodiments is a compound of Formula (I'), or a pharmaceutically acceptable salt or solvate thereof, wherein n is 1 and $R^3$ is —$OR^9$. In some embodiments is a compound of Formula (I'), or a pharmaceutically acceptable salt or solvate thereof, wherein n is 1, $R^3$ is —$OR^9$, and $R^9$ is $C_{3-8}$cycloalkyl. In some embodiments is a compound of Formula (I'), or a pharmaceutically acceptable salt or solvate thereof, wherein n is 1, $R^3$ is —$OR^9$, and $R^9$ is cyclopentyl.

In some embodiments, provided herein is a compound of Formula (I), or a pharmaceutically acceptable salt or solvate thereof:

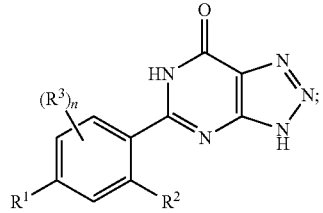

Formula (I)

wherein.

$R^1$ is —$CH_2R^4$, —CN, —$B(OH)_2$, —$N(R^{10})_2$, —$NR^{10}C(O)R^9$, —C(O)OH, —$CH_2C(O)OH$, —$C(O)N(R^{10})_2$, —$C(O)NHS(O)_2N(R^{10})_2$, —$C_{1-6}$alkyl-OH, $C_{3-8}$cycloalkyl,

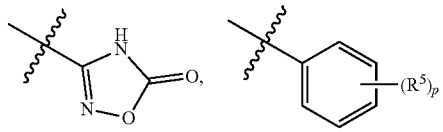

or a 5- or 6-membered heteroaryl optionally substituted with one, two, or three $R^8$ groups;

$R^2$ is H, —OH, —$N(R^{10})_2$, —$NHS(O)_2R^9$, —$S(O)_2N(R^{10})_2$, —$C(O)N(R^{10})_2$, —$OC(O)N(R^{10})_2$, —O—$C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl;

each $R^3$ is independently selected from halogen, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

R⁴ is

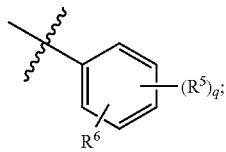

each R⁵ is independently selected from halogen, —CN, —OH, —OR⁹, —SR⁹, —N(R¹⁰)₂, —S(O)R⁹, —S(O)₂R⁹, —NHS(O)₂R⁹, —S(O)₂N(R¹⁰)₂, —C(O)NHS(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-OH, —$C_{1-6}$alkyl-OR⁹, —$C_{1-6}$alkyl-N(R¹⁰)₂, —$C_{1-6}$alkyl-C(O)OR¹⁰, $C_{2-6}$alkenyl, $C_{2-6}$alkynyl, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;

R⁶ is —C(O)OR⁷, —C(O)NHS(O)₂N(R¹⁰)₂,

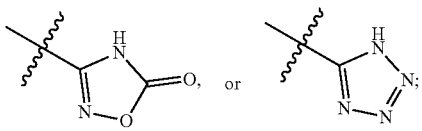 [SMILES: *c1noc(=O)[nH]1 ; *c1nnn[nH]1]

each R⁷ is independently selected from H and $C_{1-6}$alkyl;
each R⁸ is independently selected from halogen, —OH, —OR⁹, —N(R¹⁰)₂, —S(O)R⁹, —S(O)₂R⁹, —NHS(O)₂R⁹, —S(O)₂N(R¹⁰)₂, —C(O)NHS(O)₂N(R¹⁰)₂, —C(O)R⁹, —C(O)OR¹⁰, —OC(O)R⁹, —C(O)N(R¹⁰)₂, —OC(O)N(R¹⁰)₂, —NR¹⁰C(O)N(R¹⁰)₂, —NR¹⁰C(O)R⁹, —NR¹⁰C(O)OR⁹, $C_{1-6}$alkyl, —$C_{1-6}$alkyl-OH, —$C_{1-6}$alkyl-OR⁹, —$C_{1-6}$alkyl-N(R¹⁰)₂, —$C_{1-6}$alkyl-C(O)OR¹⁰, $C_{1-6}$haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, and $C_{1-9}$heteroaryl; wherein phenyl, —$C_{1-6}$alkyl-phenyl, and $C_{1-9}$heteroaryl are optionally substituted with one, two, or three groups independently selected from halogen, $C_{1-6}$alkyl, $C_{1-6}$haloalkyl, $C_{3-8}$cycloalkyl, and $C_{2-9}$heterocycloalkyl; and wherein $C_{2-9}$heterocycloalkyl is optionally substituted with one, two, or three groups independently selected from halogen, $C_{1-6}$alkyl, $C_{1-6}$haloalkyl, and oxo;

each R⁹ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —OR¹¹, —N(R¹¹)₂, $C_{1-6}$alkyl, $C_{3-8}$cycloalkyl, —C(O)R¹², and —C(O)OR¹²;

each R¹⁰ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N(R¹¹)₂, and —C(O)OR¹²; or two R¹⁰ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each R¹¹ is independently selected from H and $C_{1-6}$alkyl;
R¹² is independently selected from H and $C_{1-6}$alkyl;
n is 0, 1, 2, or 3;
p is 0, 1, 2, 3, 4, or 5; and
q is 0, 1, 2, 3, or 4.

In some embodiments is a compound of Formula (I), or a pharmaceutically acceptable salt or solvate thereof, wherein R¹ is

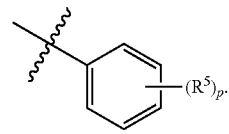

In some embodiments is a compound of Formula (I), or a pharmaceutically acceptable salt or solvate thereof, wherein R¹ is

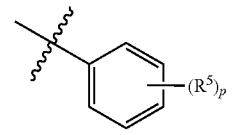

and p is 0, 1, or 2. In some embodiments is a compound of Formula (I), or a pharmaceutically acceptable salt or solvate thereof, wherein R¹ is

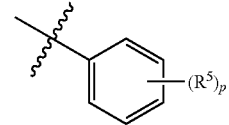

and p is 0. In some embodiments is a compound of Formula (I), or a pharmaceutically acceptable salt or solvate thereof, wherein R¹ is

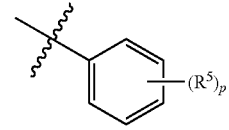

and p is 1. In some embodiments is a compound of Formula (I), or a pharmaceutically acceptable salt or solvate thereof, wherein $R^1$ is

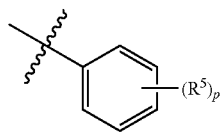

and p is 2. In some embodiments is a compound of Formula (I), or a pharmaceutically acceptable salt or solvate thereof, wherein $R^1$ is

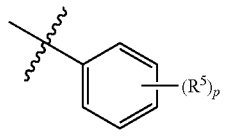

and p is 1 or 2. In some embodiments is a compound of Formula (I), or a pharmaceutically acceptable salt or solvate thereof, wherein $R^1$ is

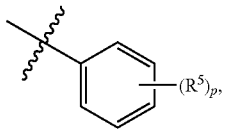

p is 1 or 2, and each $R^5$ is independently selected from halogen, —OH, —OR$^9$, —N(R$^{10}$)$_2$, —S(O)$_2$R$^9$, —NHS(O)$_2$R$^9$, —S(O)$_2$N(R$^{10}$)$_2$, —C(O)NHS(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, $C_{1-6}$alkyl, —$C_{1-6}$alkyl-OH, —$C_{1-6}$alkyl-OR$^9$, —$C_{1-6}$alkyl-N(R$^{10}$)$_2$, —$C_{1-6}$alkyl-C(O)OR$^{10}$, $C_{1-6}$haloalkyl, $C_{1-6}$haloalkyl-OH, $C_{3-8}$cycloalkyl, $C_{2-9}$heterocycloalkyl, and $C_{1-9}$heteroaryl. In some embodiments is a compound of Formula (I), or a pharmaceutically acceptable salt or solvate thereof, wherein $R^1$ is

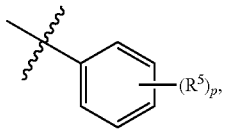

p is 1 or 2, each $R^5$ is independently selected from halogen, —OH, —OR$^9$, —N(R$^{10}$)$_2$, —S(O)$_2$R$^9$, —NHS(O)$_2$R$^9$, —S(O)$_2$N(R$^{10}$)$_2$, —C(O)NHS(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, $C_{1-6}$alkyl, —$C_{1-6}$alkyl-OH, —$C_{1-6}$alkyl-OR$^9$, —$C_{1-6}$alkyl-N(R$^{10}$)$_2$, —$C_{1-6}$alkyl-C(O)OR$^{10}$, $C_{1-6}$haloalkyl, $C_{1-6}$haloalkyl-OH, $C_{3-8}$cycloalkyl, $C_{2-9}$heterocycloalkyl, and $C_{1-9}$heteroaryl, and each $R^{10}$ is independently selected from H and $C_{1-6}$alkyl. In some embodiments is a compound of Formula (I), or a pharmaceutically acceptable salt or solvate thereof, wherein $R^1$ is

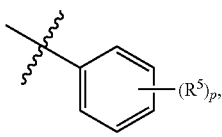

p is 1 or 2, and each $R^5$ is independently selected from halogen, —OH, —OR$^9$, —N(R$^{10}$)$_2$, —C(O)NHS(O)$_2$N(R$^{10}$)$_2$, —C(O)OR$^{10}$, —C(O)N(R$^{10}$)$_2$, —NR$^{10}$C(O)R$^9$, $C_{1-6}$alkyl, —$C_{1-6}$alkyl-C(O)OR$^{10}$, and $C_{1-9}$heteroaryl. In some embodiments is a compound of Formula (I), or a pharmaceutically acceptable salt or solvate thereof, wherein $R^1$ is

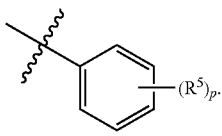

p is 1 or 2, each $R^5$ is independently selected from halogen, —OH, —OR$^9$, —N(R$^{10}$)$_2$, —C(O)NHS(O)$_2$N(R$^{10}$)$_2$, —C(O)OR$^{10}$, —C(O)N(R$^{10}$)$_2$, —NR$^{10}$C(O)R$^9$, $C_{1-6}$alkyl, —$C_{1-6}$alkyl-C(O)OR$^{10}$, and $C_{1-9}$heteroaryl, and each $R^{10}$ is independently selected from H and $C_{1-6}$alkyl. In some embodiments is a compound of Formula (I), or a pharmaceutically acceptable salt or solvate thereof, wherein $R^1$ is

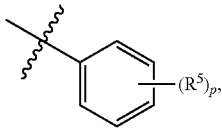

p is 1 or 2, and each $R^5$ is independently selected from —OR$^9$, —C(O)OR$^{10}$, —C(O)N(R$^{10}$)$_2$, $C_{1-6}$alkyl, —$C_{1-6}$alkyl-C(O)OR$^{10}$. In some embodiments is a compound of Formula (I), or a pharmaceutically acceptable salt or solvate thereof, wherein $R^1$ is

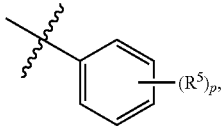

p is 1 or 2, each $R^5$ is independently selected from —OR$^9$, —C(O)OR$^{10}$, —C(O)N(R$^{10}$)$_2$, $C_{1-6}$alkyl, —$C_{1-6}$alkyl-C(O)OR$^{10}$, and each $R^{10}$ is independently selected from H and $C_{1-6}$alkyl. In some embodiments is a compound of Formula (I), or a pharmaceutically acceptable salt or solvate thereof, wherein $R^1$ is

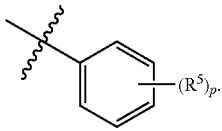

p is 1 or 2, and each R⁵ is independently selected from —C(O)OR¹⁰. In some embodiments is a compound of Formula (I), or a pharmaceutically acceptable salt or solvate thereof, wherein R¹ is

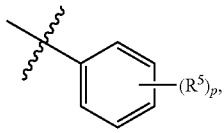

p is 1 or 2, each R⁵ is independently selected from —C(O)OR¹⁰, and each R¹⁰ is independently selected from H and $C_{1-6}$alkyl. In some embodiments is a compound of Formula (I), or a pharmaceutically acceptable salt or solvate thereof, wherein R¹ is

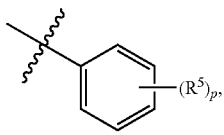

p is 1 or 2, and each R⁵ is independently selected from —OH, —OR⁹ and —$C_{1-6}$alkyl-C(O)OR¹⁰. In some embodiments is a compound of Formula (I″), or a pharmaceutically acceptable salt or solvate thereof, wherein R¹ is

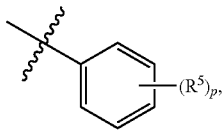

p is 1 or 2, and each R⁵ is independently selected from —OH, —OR⁹ and —$C_{1-6}$alkyl-C(O)OR¹⁰, and R⁹ is $C_{1-6}$alkyl optionally substituted with —C(O)OR¹². In some embodiments is a compound of Formula (I), or a pharmaceutically acceptable salt or solvate thereof, wherein R¹ is

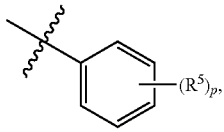

p is 1, and R⁵ is independently selected from —C(O)OH.

In some embodiments is a compound of Formula (I), or a pharmaceutically acceptable salt or solvate thereof, wherein R¹ is a 5- or 6-membered heteroaryl optionally substituted with one, two, or three R⁸ groups. In some embodiments is a compound of Formula (I), or a pharmaceutically acceptable salt or solvate thereof, wherein R¹ is a 5-membered heteroaryl optionally substituted with one, two, or three R⁸ groups. In some embodiments is a compound of Formula (I), or a pharmaceutically acceptable salt or solvate thereof, wherein R¹ is a 5-membered heteroaryl optionally substituted with one, two, or three R⁸ groups, wherein the 5-membered heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl. In some embodiments is a compound of Formula (I), or a pharmaceutically acceptable salt or solvate thereof, wherein R¹ is a 5-membered heteroaryl optionally substituted with one or two R⁸ groups, wherein the 5-membered heteroaryl is selected from oxazolyl, thiazolyl, pyrazolyl, furanyl, thienyl, pyrrolyl, tetrazolyl, and isoxazolyl. In some embodiments is a compound of Formula (I), or a pharmaceutically acceptable salt or solvate thereof, wherein R¹ is oxazolyl optionally substituted with one or two R⁸ groups. In some embodiments is a compound of Formula (I), or a pharmaceutically acceptable salt or solvate thereof, wherein R¹ is thiazolyl optionally substituted with one or two R⁸ groups. In some embodiments is a compound of Formula (I), or a pharmaceutically acceptable salt or solvate thereof, wherein R¹ is pyrazolyl optionally substituted with one or two R⁸ groups. In some embodiments is a compound of Formula (I), or a pharmaceutically acceptable salt or solvate thereof, wherein R¹ is furanyl optionally substituted with one or two R⁸ groups. In some embodiments is a compound of Formula (I), or a pharmaceutically acceptable salt or solvate thereof, wherein R¹ is thienyl optionally substituted with one or two R⁸ groups. In some embodiments is a compound of Formula (I), or a pharmaceutically acceptable salt or solvate thereof, wherein R¹ is pyrrolyl optionally substituted with one or two R⁸ groups. In some embodiments is a compound of Formula (I), or a pharmaceutically acceptable salt or solvate thereof, wherein R¹ is tetrazolyl optionally substituted with one or two R⁸ groups. In some embodiments is a compound of Formula (I), or a pharmaceutically acceptable salt or solvate thereof, wherein R¹ is isoxazolyl optionally substituted with one or two R⁸ groups. In some embodiments is a compound of Formula (I), or a pharmaceutically acceptable salt or solvate thereof, wherein R¹ is a 6-membered heteroaryl optionally substituted with one, two, or three R⁸ groups. In some embodiments is a compound of Formula (I), or a pharmaceutically acceptable salt or solvate thereof, wherein R¹ is a 6-membered heteroaryl optionally substituted with one, two, or three R⁸ groups, wherein the 6-membered heteroaryl is selected from pyridinyl, pyrimidinyl, pyrazinyl, pyridazinyl, and triazinyl. In some embodiments is a compound of Formula (I), or a pharmaceutically acceptable salt or solvate thereof, wherein R¹ is a 6-membered heteroaryl optionally substituted with one or two R⁸ groups, wherein the 6-membered heteroaryl is selected from pyridinyl and pyrimidinyl. In some embodiments is a compound of Formula (I), or a pharmaceutically acceptable salt or solvate thereof, wherein R¹ is pyridinyl optionally substituted with one or two R⁸ groups. In some embodiments is a compound of Formula (I), or a pharmaceutically acceptable salt or solvate thereof, wherein R¹ is pyrimidinyl optionally substituted with one or two R⁸ groups. In some embodiments is a compound of Formula (I), or a pharmaceutically acceptable salt or solvate thereof, wherein each R⁸ is independently selected from halogen, —C(O)OR¹⁰, $C_{1-6}$alkyl, and —$C_{1-6}$alkyl-C(O)OR¹⁰. In some embodiments is a compound of Formula (I), or a pharmaceutically acceptable salt or solvate thereof, wherein each R⁸ is independently selected from —C(O)OR¹⁰. In some embodiments is a compound of Formula (I), or a pharmaceutically acceptable salt or solvate thereof, wherein R¹ is an unsubstituted 5-membered heteroaryl selected from oxazolyl, thiazolyl, pyrazolyl, furanyl, thienyl, pyrrolyl, tetrazolyl, and isoxazolyl. In some embodiments is a compound of Formula (I), or a pharmaceutically acceptable salt or solvate thereof, wherein R¹ is an unsubstituted 6-membered heteroaryl selected from pyridinyl and pyrimidinyl.

In some embodiments is a compound of Formula (I), or a pharmaceutically acceptable salt or solvate thereof, wherein $R^1$ is —C(O)N($R^{10}$)$_2$. In some embodiments is a compound of Formula (I), or a pharmaceutically acceptable salt or solvate thereof, wherein $R^1$ is —C(O)N($R^{10}$)$_2$ and each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N($R^{11}$)$_2$, and —C(O)O$R^{12}$. In some embodiments is a compound of Formula (I), or a pharmaceutically acceptable salt or solvate thereof, wherein $R^1$ is —C(O)N($R^{10}$)$_2$ and each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N($R^{11}$)$_2$, and —C(O)O$R^{12}$. In some embodiments is a compound of Formula (I), or a pharmaceutically acceptable salt or solvate thereof, wherein $R^1$ is —C(O)N($R^{10}$)$_2$ and each $R^{10}$ is independently selected from H and $C_{1-6}$alkyl optionally substituted with —C(O)O$R^{12}$. In some embodiments is a compound of Formula (I), or a pharmaceutically acceptable salt or solvate thereof, wherein $R^1$ is —C(O)N($R^{10}$)$_2$ and each $R^{10}$ is independently selected from H and $C_{1-6}$alkyl optionally substituted with —C(O)OH. In some embodiments is a compound of Formula (I), or a pharmaceutically acceptable salt or solvate thereof, wherein $R^1$ is —C(O)N($R^{10}$)$_2$ and the two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (I), or a pharmaceutically acceptable salt or solvate thereof, wherein $R^1$ is —C(O)N($R^{10}$)$_2$ and the two $R^{10}$ and the nitrogen atom to which they are attached are combined to form a 5-membered heterocycloalkyl ring substituted with —C(O)OH. In some embodiments is a compound of Formula (I), or a pharmaceutically acceptable salt or solvate thereof, wherein $R^1$ is —C(O)N($R^{10}$)$_2$ and the two $R^{10}$ and the nitrogen atom to which they are attached are combined to form a 6-membered heterocycloalkyl ring substituted with —C(O)OH.

In some embodiments is a compound of Formula (I), or a pharmaceutically acceptable salt or solvate thereof, wherein $R^1$ is —N($R^{10}$)$_2$. In some embodiments is a compound of Formula (I), or a pharmaceutically acceptable salt or solvate thereof, wherein $R^1$ is —N($R^{10}$)$_2$ and each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N($R^{11}$)$_2$, and —C(O)O$R^{12}$. In some embodiments is a compound of Formula (I), or a pharmaceutically acceptable salt or solvate thereof, wherein $R^1$ is —N($R^{10}$)$_2$ and each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N($R^{11}$)$_2$, and —C(O)O$R^{12}$. In some embodiments is a compound of Formula (I), or a pharmaceutically acceptable salt or solvate thereof, wherein $R^1$ is —N($R^{10}$)$_2$ and each $R^{10}$ is independently selected from H and $C_{1-6}$alkyl optionally substituted with —C(O)O$R^{12}$. In some embodiments is a compound of Formula (I), or a pharmaceutically acceptable salt or solvate thereof, wherein $R^1$ is —N($R^{10}$)$_2$ and each $R^{10}$ is independently selected from H and $C_{1-6}$alkyl optionally substituted with —C(O)OH. In some embodiments is a compound of Formula (I), or a pharmaceutically acceptable salt or solvate thereof, wherein $R^1$ is —N($R^{10}$)$_2$ and the two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (I), or a pharmaceutically acceptable salt or solvate thereof, wherein $R^1$ is —N($R^{10}$)$_2$ and the two $R^{10}$ and the nitrogen atom to which they are attached are combined to form a 5-membered heterocycloalkyl ring substituted with —C(O)OH. In some embodiments is a compound of Formula (I), or a pharmaceutically acceptable salt or solvate thereof, wherein $R^1$ is —N($R^{10}$)$_2$ and the two $R^{10}$ and the nitrogen atom to which they are attached are combined to form a 6-membered heterocycloalkyl ring substituted with —C(O)OH.

In some embodiments is a compound of Formula (I), or a pharmaceutically acceptable salt or solvate thereof, wherein $R^1$ is —C(O)OH.

In some embodiments is a compound of Formula (I), or a pharmaceutically acceptable salt or solvate thereof, wherein $R^1$ is —CH$_2$C(O)OH.

In some embodiments is a compound of Formula (I), or a pharmaceutically acceptable salt or solvate thereof, wherein $R^1$ is —C(O)NHS(O)$_2$N($R^{10}$)$_2$.

In some embodiments is a compound of Formula (I), or a pharmaceutically acceptable salt or solvate thereof, $R^1$ is

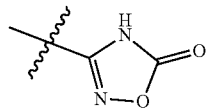

In some embodiments is a compound of Formula (I), or a pharmaceutically acceptable salt or solvate thereof, wherein $R^1$ is —CH$_2$$R^4$ and $R^4$ is

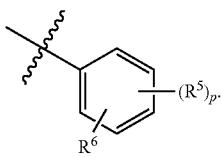

In some embodiments is a compound of Formula (I), or a pharmaceutically acceptable salt or solvate thereof, wherein $R^1$ is —CH$_2$$R^4$, $R^4$ is

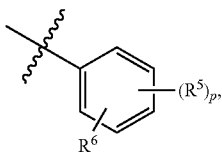

and q is 0. In some embodiments is a compound of Formula (I), or a pharmaceutically acceptable salt or solvate thereof, wherein $R^1$ is —CH$_2$$R^4$, $R^4$ is

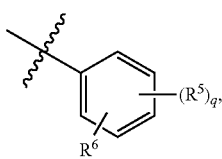

q is 0, and R⁶ is —C(O)OR⁷. In some embodiments is a compound of Formula (I), or a pharmaceutically acceptable salt or solvate thereof, wherein R¹ is —CH₂R⁴, R⁴ is

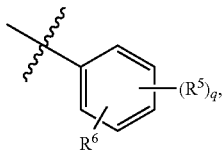

q is 0, and R⁶ is —C(O)OH. In some embodiments is a compound of Formula (I), or a pharmaceutically acceptable salt or solvate thereof, wherein R¹ is —CH₂R⁴, R⁴ is

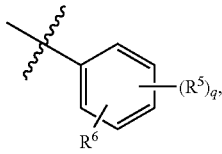

q is 0, and R⁶ is —C(O)NHS(O)₂N(R¹⁰)₂. In some embodiments is a compound of Formula (I), or a pharmaceutically acceptable salt or solvate thereof, wherein R¹ is —CH₂R⁴, R⁴ is

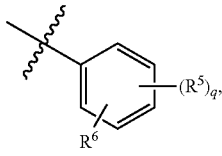

q is 0, and R⁶ is

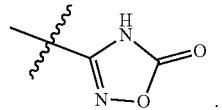 [SMILES: *c1noc(=O)[nH]1]

In some embodiments is a compound of Formula (I), or a pharmaceutically acceptable salt or solvate thereof, wherein R¹ is —CH₂R⁴, R⁴ is

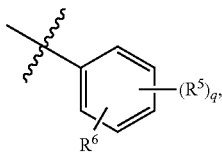

q is 0, and R⁶ is

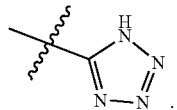

In some embodiments is a compound of Formula (I), or a pharmaceutically acceptable salt or solvate thereof, wherein R² is H, —OH, —N(R¹⁰)₂, or —O—C₁₋₆alkyl. In some embodiments is a compound of Formula (I), or a pharmaceutically acceptable salt or solvate thereof, wherein R² is —O—C₁₋₆alkyl. In some embodiments is a compound of Formula (I), or a pharmaceutically acceptable salt or solvate thereof, wherein R² is —OCH₂CH₃. In some embodiments is a compound of Formula (I), or a pharmaceutically acceptable salt or solvate thereof, wherein R² is H. In some embodiments is a compound of Formula (I), or a pharmaceutically acceptable salt or solvate thereof, wherein R² is —OH. In some embodiments is a compound of Formula (I), or a pharmaceutically acceptable salt or solvate thereof, wherein R² is —N(R¹⁰)₂.

In some embodiments is a compound of Formula (I), or a pharmaceutically acceptable salt or solvate thereof, wherein n is 0.

In some embodiments is a compound of Formula (I), or a pharmaceutically acceptable salt or solvate thereof, wherein n is 1, 2, or 3. In some embodiments is a compound of Formula (I), or a pharmaceutically acceptable salt or solvate thereof, wherein n is 1, 2, or 3 and each R³ is independently selected from halogen, —CN, —OR⁹, —N(R¹⁰)₂, —S(O)₂R⁹, —NHS(O)₂R⁹, —S(O)₂N(R¹⁰)₂, —C(O)R⁹, —C(O)OR¹⁰, —OC(O)R⁹, —C(O)N(R¹⁰)₂, —NR¹⁰C(O)N(R¹⁰)₂, —NR¹⁰C(O)R⁹, C₁₋₆alkyl, —C₁₋₆alkyl-OH, —C₁₋₆alkyl-OR⁹, —C₁₋₆alkyl-N(R¹⁰)₂, C₁₋₆haloalkyl, C₃₋₈cycloalkyl, and —C₁₋₆alkyl-C₃₋₈cycloalkyl. In some embodiments is a compound of Formula (I), or a pharmaceutically acceptable salt or solvate thereof, wherein n is 1, 2, or 3 and each R³ is independently selected from halogen, —OR⁹, —N(R¹⁰)₂, —C(O)OR¹⁰, —C(O)N(R¹⁰)₂, and C₁₋₆alkyl. In some embodiments is a compound of Formula (I), or a pharmaceutically acceptable salt or solvate thereof, wherein n is 1, 2, or 3 and each R³ is independently selected from halogen and C₁₋₆alkyl. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein n is 1 and R³ is selected from halogen, —OH, —OR⁹, —N(R¹⁰)₂, C₁₋₆alkyl, —C₁₋₆alkyl-OH, —C₁₋₆alkyl-OR⁹, and C₁₋₆haloalkyl. In some embodiments is a compound of Formula (I), or a pharmaceutically acceptable salt or solvate thereof, wherein n is 1 and R³ is selected from halogen, —OR⁹, and C₁₋₆alkyl. In some embodiments is a compound of Formula (I), or a pharmaceutically acceptable salt or solvate thereof, wherein n is 1 and R³ is selected from halogen, —OR⁹, and C₁₋₆alkyl. In some embodiments is a compound of Formula (I), or a pharmaceutically acceptable salt or solvate thereof, wherein n is 1 and R³ is —OR⁹. In some embodiments is a compound of Formula (I), or a pharmaceutically acceptable salt or solvate thereof, wherein n is 1, R³ is —OR⁹, and R⁹ is C₃₋₈cycloalkyl. In some embodiments is a compound of Formula (I), or a pharmaceutically acceptable salt or solvate thereof, wherein n is 1, R³ is —OR⁹, and R⁹ is cyclopentyl.

In some embodiments, provided herein is a compound of Formula (Ia), or a pharmaceutically acceptable salt or solvate thereof:

Formula (Ia)

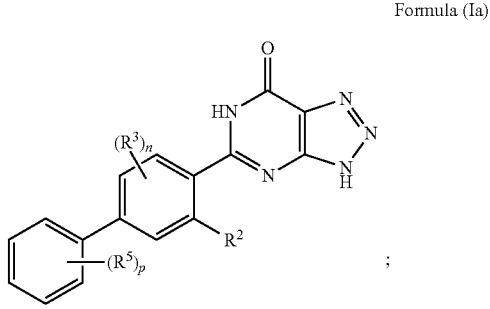

wherein:
R$^2$ is H, —OH, —N(R$^{10}$)$_2$, —NHS(O)$_2$R$^9$, —S(O)$_2$N(R$^{10}$)$_2$, —C(O)N(R$^{10}$)$_2$, —OC(O)N(R$^{10}$)$_2$, —O—C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl;

each R$^3$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, C$_{2-6}$alkenyl, C$_{2-6}$alkynyl, C$_{1-6}$haloalkyl, C$_{3-8}$cycloalkyl, and —C$_{1-6}$alkyl-C$_{3-8}$cycloalkyl;

each R$^5$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)NHS(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{2-6}$alkenyl, C$_{2-6}$alkynyl, C$_{1-6}$haloalkyl, C$_{1-6}$haloalkyl-OH, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, and C$_{1-9}$heteroaryl; wherein phenyl, —C$_{1-6}$alkyl-phenyl, and C$_{1-9}$heteroaryl are optionally substituted with one, two, or three groups independently selected from halogen, C$_{1-6}$alkyl, C$_{1-6}$haloalkyl, C$_{3-8}$cycloalkyl, and C$_{2-9}$heterocycloalkyl; and wherein C$_{2-9}$heterocycloalkyl is optionally substituted with one, two, or three groups independently selected from halogen, C$_{1-6}$alkyl, C$_{1-6}$haloalkyl, and oxo;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, —N(R$^{11}$)$_2$, and —C(O)OR$^{12}$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl;
R$^{12}$ is independently selected from H and C$_{1-6}$alkyl;
n is 0, 1, 2, or 3; and
p is 0, 1, 2, 3, 4, or 5.

In some embodiments is a compound of Formula (Ia), or a pharmaceutically acceptable salt or solvate thereof, wherein p is 0, 1, or 2. In some embodiments is a compound of Formula (Ia), or a pharmaceutically acceptable salt or solvate thereof, wherein p is 0. In some embodiments is a compound of Formula (Ia), or a pharmaceutically acceptable salt or solvate thereof, wherein p is 1. In some embodiments is a compound of Formula (Ia), or a pharmaceutically acceptable salt or solvate thereof, wherein p is 2. In some embodiments is a compound of Formula (Ia), or a pharmaceutically acceptable salt or solvate thereof, wherein p is 1 or 2. In some embodiments is a compound of Formula (Ia), or a pharmaceutically acceptable salt or solvate thereof, wherein p is 1 or 2, and each R$^5$ is independently selected from halogen, —OH, —OR$^9$, —N(R$^{10}$)$_2$, —S(O)$_2$R$^9$, —NHS(O)$_2$R$^9$, —S(O)$_2$N(R$^{10}$)$_2$, —C(O)NHS(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, C$_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{1-6}$haloalkyl, C$_{1-6}$haloalkyl-OH, C$_{3-8}$cycloalkyl, C$_{2-9}$heterocycloalkyl, and C$_{1-9}$heteroaryl. In some embodiments is a compound of Formula (Ia), or a pharmaceutically acceptable salt or solvate thereof, wherein p is 1 or 2, each R$^5$ is independently selected from halogen, —OH, —OR$^9$, —N(R$^{10}$)$_2$, —S(O)$_2$R$^9$, —NHS(O)$_2$R$^9$, —S(O)$_2$N(R$^{10}$)$_2$, —C(O)NHS(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, C$_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{1-6}$haloalkyl, C$_{1-6}$haloalkyl-OH, C$_{3-8}$cycloalkyl, C$_{2-9}$heterocycloalkyl, and C$_{1-9}$heteroaryl, and each R$^{10}$ is independently selected from H and C$_{1-6}$alkyl. In some embodiments is a compound of Formula (Ia), or a pharmaceutically acceptable salt or solvate thereof, wherein p is 1 or 2, and each R$^5$ is independently selected from halogen, —OH, —OR$^9$, —N(R$^{10}$)$_2$, —C(O)NHS(O)$_2$N(R$^{10}$)$_2$, —C(O)OR$^{10}$, —C(O)N(R$^{10}$)$_2$, —NR$^{10}$C(O)R$^9$, C$_{1-6}$alkyl, —C$_{1-6}$alkyl-C(O)OR$^{10}$, and C$_{1-9}$heteroaryl. In some embodiments is a compound of Formula (Ia), or a pharmaceutically acceptable salt or solvate thereof, wherein p is 1 or 2, each R$^5$ is independently selected from halogen, —OH, —OR$^9$, —N(R$^{10}$)$_2$, —C(O)NHS(O)$_2$N(R$^{10}$)$_2$, —C(O)OR$^{10}$, —C(O)N(R$^{10}$)$_2$, —NR$^{10}$C(O)R$^9$, C$_{1-6}$alkyl, —C$_{1-6}$alkyl-C(O)OR$^{10}$, and C$_{1-9}$heteroaryl, and each R$^{10}$ is independently selected from H and C$_{1-6}$alkyl. In some embodiments is a compound of Formula (Ia), or a pharmaceutically acceptable salt or solvate thereof, wherein p is 1 or 2, and each R$^5$ is independently selected from —OR$^9$, —C(O)OR$^{10}$, —C(O)N(R$^{10}$)$_2$, C$_{1-6}$alkyl, —C$_{1-6}$alkyl-C(O)OR$^{10}$. In some embodiments is a compound of Formula (Ia), or a pharmaceutically acceptable salt or solvate thereof, wherein p is 1 or 2, each R$^5$ is independently selected from —OR$^9$, —C(O)OR$^{10}$, —C(O)N(R$^{10}$)$_2$, C$_{1-6}$alkyl, —C$_{1-6}$alkyl-C(O)OR$^{10}$, and each R$^{10}$ is independently selected from H and $C_{1-6}$alkyl. In some embodiments is a compound of Formula (Ia), or a pharmaceutically acceptable salt or solvate thereof, wherein p is 1 or 2, and each $R^5$ is independently selected from —C(O)O$R^{10}$. In some embodiments is a compound of Formula (Ia), or a pharmaceutically acceptable salt or solvate thereof, wherein p is 1 or 2, each $R^5$ is independently selected from —C(O)O$R^{10}$, and each $R^{10}$ is independently selected from H and $C_{1-6}$alkyl. In some embodiments is a compound of Formula (Ia), or a pharmaceutically acceptable salt or solvate thereof, wherein $R^1$ is

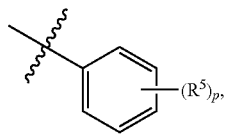

p is 1 or 2, and each $R^5$ is independently selected from —OH, —O$R^9$ and —$C_{1-6}$alkyl-C(O)O$R^{10}$. In some embodiments is a compound of Formula (Ia), or a pharmaceutically acceptable salt or solvate thereof, wherein $R^1$ is

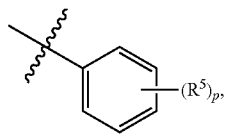

p is 1 or 2, and each $R^5$ is independently selected from —OH, —O$R^9$ and —$C_{1-6}$alkyl-C(O)O$R^{10}$, and $R^9$ is $C_{1-6}$alkyl optionally substituted with —C(O)O$R^{12}$. In some embodiments is a compound of Formula (Ia), or a pharmaceutically acceptable salt or solvate thereof, wherein p is 1, and $R^5$ is independently selected from —C(O)OH.

In some embodiments is a compound of Formula (Ia), or a pharmaceutically acceptable salt or solvate thereof, wherein $R^2$ is H, —OH, —N($R^{10}$)$_2$, or —O—$C_{1-6}$alkyl. In some embodiments is a compound of Formula (Ia), or a pharmaceutically acceptable salt or solvate thereof, wherein $R^2$ is —O—$C_{1-6}$alkyl. In some embodiments is a compound of Formula (Ia), or a pharmaceutically acceptable salt or solvate thereof, wherein $R^2$ is —OCH$_2$CH$_3$. In some embodiments is a compound of Formula (Ia), or a pharmaceutically acceptable salt or solvate thereof, wherein $R^2$ is H. In some embodiments is a compound of Formula (Ia), or a pharmaceutically acceptable salt or solvate thereof, wherein $R^2$ is —OH. In some embodiments is a compound of Formula (Ia), or a pharmaceutically acceptable salt or solvate thereof, wherein $R^2$ is —N($R^{10}$)$_2$.

In some embodiments is a compound of Formula (Ia), or a pharmaceutically acceptable salt or solvate thereof, wherein n is 0.

In some embodiments is a compound of Formula (Ia), or a pharmaceutically acceptable salt or solvate thereof, wherein n is 1, 2, or 3. In some embodiments is a compound of Formula (Ia), or a pharmaceutically acceptable salt or solvate thereof, wherein n is 1, 2, or 3 and each $R^3$ is independently selected from halogen, —CN, —O$R^9$, —N($R^{10}$)$_2$, —S(O)$_2$$R^9$, —NHS(O)$_2$$R^9$, —S(O)$_2$N($R^{10}$)$_2$, —C(O)$R^9$, —C(O)O$R^{10}$, —OC(O)$R^9$, —C(O)N($R^{10}$)$_2$, —N$R^{10}$C(O)N($R^{10}$)$_2$, —N$R^{10}$C(O)$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{1-6}$haloalkyl, $C_{3-8}$cycloalkyl, and —$C_{1-6}$alkyl-$C_{3-8}$cycloalkyl. In some embodiments is a compound of Formula (Ia), or a pharmaceutically acceptable salt or solvate thereof, wherein n is 1, 2, or 3 and each $R^3$ is independently selected from halogen, —O$R^9$, —N($R^{10}$)$_2$, —C(O)O$R^{10}$, —C(O)N($R^{10}$)$_2$, and $C_{1-6}$alkyl. In some embodiments is a compound of Formula (Ia), or a pharmaceutically acceptable salt or solvate thereof, wherein n is 1, 2, or 3 and each $R^3$ is independently selected from halogen and $C_{1-6}$alkyl. In some embodiments is a compound of Formula (Ia), or a pharmaceutically acceptable salt or solvate thereof, wherein n is 1. In some embodiments is a compound of Formula (Ia), or a pharmaceutically acceptable salt or solvate thereof, wherein n is 1 and $R^3$ is selected from halogen, —OH, —O$R^9$, —N($R^{10}$)$_2$, $C_{1-6}$alkyl, —$C_{1-6}$alkyl-OH, —$C_{1-6}$alkyl-O$R^9$, and $C_{1-6}$haloalkyl. In some embodiments is a compound of Formula (Ia), or a pharmaceutically acceptable salt or solvate thereof, wherein n is 1 and $R^3$ is selected from halogen, —O$R^9$, and $C_{1-6}$alkyl. In some embodiments is a compound of Formula (Ia), or a pharmaceutically acceptable salt or solvate thereof, wherein n is 1 and $R^3$ is selected from halogen, —O$R^9$, and $C_{1-6}$alkyl. In some embodiments is a compound of Formula (Ia), or a pharmaceutically acceptable salt or solvate thereof, wherein n is 1 and $R^3$ is —O$R^9$. In some embodiments is a compound of Formula (Ia), or a pharmaceutically acceptable salt or solvate thereof, wherein n is 1, $R^3$ is —O$R^9$, and $R^9$ is $C_{3-8}$cycloalkyl. In some embodiments is a compound of Formula (Ia), or a pharmaceutically acceptable salt or solvate thereof, wherein n is 1, $R^3$ is —O$R^9$, and $R^9$ is cyclopentyl.

In some embodiments, provided herein is a compound of Formula (Ib), or a pharmaceutically acceptable salt or solvate thereof:

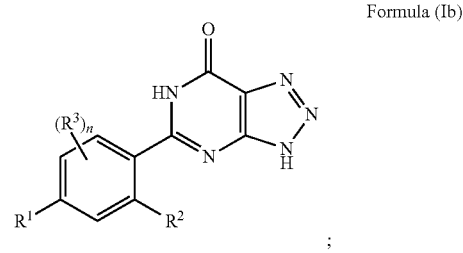

Formula (Ib)

wherein:
$R^1$ is a 5- or 6-membered heteroaryl optionally substituted with one, two, or three $R^8$ groups;
$R^2$ is H, —OH, —N($R^{10}$)$_2$, —NHS(O)$_2$$R^9$, —S(O)$_2$N($R^{10}$)$_2$, —C(O)N($R^{10}$)$_2$, —OC(O)N($R^{10}$)$_2$, —O—$C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl;
each $R^3$ is independently selected from halogen, —CN, —OH, —O$R^9$, —S$R^9$, —N($R^{10}$)$_2$, —S(O)$R^9$, —S(O)$_2$$R^9$, —NHS(O)$_2$$R^9$, —S(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
each $R^8$ is independently selected from halogen, —OH, —O$R^9$, —N($R^{10}$)$_2$, —S(O)$R^9$, —S(O)$_2$$R^9$, —NHS(O)$_2$$R^9$, —S(O)$_2$N($R^{10}$)$_2$, —C(O)NHS(O)$_2$N($R^{10}$)$_2$, —C(O)$R^9$, —C(O)O$R^{10}$, —OC(O)$R^9$, —C(O)N($R^{10}$)$_2$, —OC(O)N($R^{10}$)$_2$, —N$R^{10}$C(O)N($R^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{1-6}$haloalkyl, C$_{1-6}$haloalkyl-OH, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, and C$_{1-9}$heteroaryl; wherein phenyl, —C$_{1-6}$alkyl-phenyl, and C$_{1-9}$heteroaryl are optionally substituted with one, two, or three groups independently selected from halogen, C$_{1-6}$alkyl, C$_{1-6}$haloalkyl, C$_{3-8}$cycloalkyl, and C$_{2-9}$heterocycloalkyl; and wherein C$_{2-9}$heterocycloalkyl is optionally substituted with one, two, or three groups independently selected from halogen, C$_{1-6}$alkyl, C$_{1-6}$haloalkyl, and oxo;

each R$^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —C(O)R$^{12}$, and —C(O)OR$^{12}$;

each R$^{10}$ is independently selected from H, C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, and C$_{2-9}$heteroaryl, wherein C$_{1-6}$alkyl, phenyl, —C$_{1-6}$alkyl-phenyl, and C$_{2-9}$heteroaryl are optionally substituted with one or two groups independently selected from halogen, C$_{1-6}$alkyl, —N(R$^{11}$)$_2$, and —C(O)OR$^{12}$; or two R$^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;

each R$^{11}$ is independently selected from H and C$_{1-6}$alkyl; R$^{12}$ is independently selected from H and C$_{1-6}$alkyl; and n is 0, 1, 2, or 3.

In some embodiments is a compound of Formula (Ib), or a pharmaceutically acceptable salt or solvate thereof, wherein R$^1$ is a 5-membered heteroaryl optionally substituted with one, two, or three R$^8$ groups. In some embodiments is a compound of Formula (Ib), or a pharmaceutically acceptable salt or solvate thereof, wherein R$^1$ is a 5-membered heteroaryl optionally substituted with one, two, or three R$^8$ groups, wherein the 5-membered heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl. In some embodiments is a compound of Formula (Ib), or a pharmaceutically acceptable salt or solvate thereof, wherein R$^1$ is a 5-membered heteroaryl optionally substituted with one or two R$^8$ groups, wherein the 5-membered heteroaryl is selected from oxazolyl, thiazolyl, pyrazolyl, furanyl, thienyl, pyrrolyl, tetrazolyl, and isoxazolyl. In some embodiments is a compound of Formula (Ib), or a pharmaceutically acceptable salt or solvate thereof, wherein R$^1$ is oxazolyl optionally substituted with one or two R$^8$ groups. In some embodiments is a compound of Formula (Ib), or a pharmaceutically acceptable salt or solvate thereof, wherein R$^1$ is thiazolyl optionally substituted with one or two R$^8$ groups. In some embodiments is a compound of Formula (Ib), or a pharmaceutically acceptable salt or solvate thereof, wherein R$^1$ is pyrazolyl optionally substituted with one or two R$^8$ groups. In some embodiments is a compound of Formula (Ib), or a pharmaceutically acceptable salt or solvate thereof, wherein R$^1$ is furanyl optionally substituted with one or two R$^8$ groups. In some embodiments is a compound of Formula (Ib), or a pharmaceutically acceptable salt or solvate thereof, wherein R$^1$ is thienyl optionally substituted with one or two R$^8$ groups. In some embodiments is a compound of Formula (Ib), or a pharmaceutically acceptable salt or solvate thereof, wherein R$^1$ is pyrrolyl optionally substituted with one or two R$^8$ groups. In some embodiments is a compound of Formula (Ib), or a pharmaceutically acceptable salt or solvate thereof, wherein R$^1$ is tetrazolyl optionally substituted with one or two R$^8$ groups. In some embodiments is a compound of Formula (Ib), or a pharmaceutically acceptable salt or solvate thereof, wherein R$^1$ is isoxazolyl optionally substituted with one or two R$^8$ groups. In some embodiments is a compound of Formula (Ib), or a pharmaceutically acceptable salt or solvate thereof, wherein R$^1$ is a 6-membered heteroaryl optionally substituted with one, two, or three R$^8$ groups. In some embodiments is a compound of Formula (Ib), or a pharmaceutically acceptable salt or solvate thereof, wherein R$^1$ is a 6-membered heteroaryl optionally substituted with one, two, or three R$^8$ groups, wherein the 6-membered heteroaryl is selected from pyridinyl, pyrimidinyl, pyrazinyl, pyridazinyl, and triazinyl. In some embodiments is a compound of Formula (Ib), or a pharmaceutically acceptable salt or solvate thereof, wherein R$^1$ is a 6-membered heteroaryl optionally substituted with one or two R$^8$ groups, wherein the 6-membered heteroaryl is selected from pyridinyl and pyrimidinyl. In some embodiments is a compound of Formula (Ib), or a pharmaceutically acceptable salt or solvate thereof, wherein R$^1$ is pyridinyl optionally substituted with one or two R$^8$ groups. In some embodiments is a compound of Formula (Ib), or a pharmaceutically acceptable salt or solvate thereof, wherein R$^1$ is pyrimidinyl optionally substituted with one or two R$^8$ groups. In some embodiments is a compound of Formula (Ib), or a pharmaceutically acceptable salt or solvate thereof, wherein each R$^8$ is independently selected from halogen, —C(O)OR$^{10}$, C$_{1-6}$alkyl, and —C$_{1-6}$alkyl-C(O)OR$^{10}$. In some embodiments is a compound of Formula (Ib), or a pharmaceutically acceptable salt or solvate thereof, wherein each R$^8$ is independently selected from —C(O)OR$^{10}$. In some embodiments is a compound of Formula (Ib), or a pharmaceutically acceptable salt or solvate thereof, wherein R$^1$ is an unsubstituted 5-membered heteroaryl selected from oxazolyl, thiazolyl, pyrazolyl, furanyl, thienyl, pyrrolyl, tetrazolyl, and isoxazolyl. In some embodiments is a compound of Formula (Ib), or a pharmaceutically acceptable salt or solvate thereof, wherein R$^1$ is an unsubstituted 6-membered heteroaryl selected from pyridinyl and pyrimidinyl.

In some embodiments is a compound of Formula (Ib), or a pharmaceutically acceptable salt or solvate thereof, wherein R$^2$ is H, —OH, —N(R$^{10}$)$_2$, or —O—C$_{1-6}$alkyl. In some embodiments is a compound of Formula (Ib), or a pharmaceutically acceptable salt or solvate thereof, wherein R$^2$ is —O—C$_{1-6}$alkyl. In some embodiments is a compound of Formula (Ib), or a pharmaceutically acceptable salt or solvate thereof, wherein R$^2$ is —OCH$_2$CH$_3$. In some embodiments is a compound of Formula (Ib), or a pharmaceutically acceptable salt or solvate thereof, wherein R$^2$ is H. In some embodiments is a compound of Formula (Ib), or a pharmaceutically acceptable salt or solvate thereof, wherein R$^2$ is —OH. In some embodiments is a compound of Formula (Ib), or a pharmaceutically acceptable salt or solvate thereof, wherein R$^2$ is —N(R$^{10}$)$_2$.

In some embodiments is a compound of Formula (Ib), or a pharmaceutically acceptable salt or solvate thereof, wherein n is 0.

In some embodiments is a compound of Formula (Ib), or a pharmaceutically acceptable salt or solvate thereof, wherein n is 1, 2, or 3. In some embodiments is a compound of Formula (Ib), or a pharmaceutically acceptable salt or solvate thereof, wherein n is 1, 2, or 3 and each $R^3$ is independently selected from halogen, —CN, —OR$^9$, —N(R$^{10}$)$_2$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —NR$^{10}$C(O)N(R$^{10}$)$_2$, —NR$^{10}$C(O)R$^9$, $C_{1-6}$alkyl, —$C_{1-6}$alkyl-OH, —$C_{1-6}$alkyl-OR$^9$, —$C_{1-6}$alkyl-N(R$^{10}$)$_2$, $C_{1-6}$haloalkyl, $C_{3-8}$cycloalkyl, and —$C_{1-6}$alkyl-$C_{3-8}$cycloalkyl. In some embodiments is a compound of Formula (Ib), or a pharmaceutically acceptable salt or solvate thereof, wherein n is 1, 2, or 3 and each $R^3$ is independently selected from halogen, —OR$^9$, —N(R$^{10}$)$_2$, —C(O)OR$^{10}$, —C(O)N(R$^{10}$)$_2$, and $C_{1-6}$alkyl. In some embodiments is a compound of Formula (Ib), or a pharmaceutically acceptable salt or solvate thereof, wherein n is 1, 2, or 3 and each $R^3$ is independently selected from halogen and $C_{1-6}$alkyl. In some embodiments is a compound of Formula (Ib), or a pharmaceutically acceptable salt or solvate thereof, wherein n is 1. In some embodiments is a compound of Formula (Ib), or a pharmaceutically acceptable salt or solvate thereof, wherein n is 1 and $R^3$ is selected from halogen, —OH, —OR$^9$, —N(R$^{10}$)$_2$, $C_{1-6}$alkyl, —$C_{1-6}$alkyl-OH, —$C_{1-6}$alkyl-OR$^9$, and $C_{1-6}$haloalkyl. In some embodiments is a compound of Formula (Ib), or a pharmaceutically acceptable salt or solvate thereof, wherein n is 1 and $R^3$ is selected from halogen, —OR$^9$, and $C_{1-6}$alkyl. In some embodiments is a compound of Formula (Ib), or a pharmaceutically acceptable salt or solvate thereof, wherein n is 1 and $R^3$ is selected from halogen, —OR$^9$, and $C_{1-6}$alkyl. In some embodiments is a compound of Formula (Ib), or a pharmaceutically acceptable salt or solvate thereof, wherein n is 1 and $R^3$ is —OR$^9$. In some embodiments is a compound of Formula (Ib), or a pharmaceutically acceptable salt or solvate thereof, wherein n is 1, $R^3$ is —OR$^9$, and $R^9$ is $C_{3-8}$cycloalkyl. In some embodiments is a compound of Formula (Ib), or a pharmaceutically acceptable salt or solvate thereof, wherein n is 1, $R^3$ is —OR$^9$, and $R^9$ is cyclopentyl.

In some embodiments, provided herein is a compound of Formula (Ic), or a pharmaceutically acceptable salt or solvate thereof:

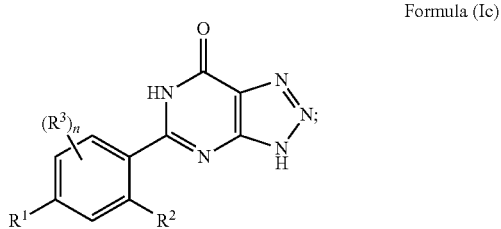

Formula (Ic)

wherein:
$R^1$ is —C(O)N(R$^{10}$)$_2$;
$R^2$ is H, —OH, —N(R$^{10}$)$_2$, —NHS(O)$_2$R$^9$, —S(O)$_2$N(R$^{10}$)$_2$, —C(O)N(R$^{10}$)$_2$, —OC(O)N(R$^{10}$)$_2$, —O—$C_{1-6}$alkyl, —$C_{1-6}$alkyl-OH, —$C_{1-6}$alkyl-OR$^9$, —$C_{1-6}$alkyl-N(R$^{10}$)$_2$, $C_{2-6}$alkenyl, $C_{2-6}$alkynyl, $C_{1-6}$haloalkyl, $C_{3-8}$cycloalkyl;
each $R^3$ is independently selected from halogen, —CN, —OH, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^{10}$C(O)OR$^9$, $C_{1-6}$alkyl, —$C_{1-6}$alkyl-OH, —$C_{1-6}$alkyl-OR$^9$, —$C_{1-6}$alkyl-N(R$^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;

each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —OR$^{11}$, —N(R$^{11}$)$_2$, $C_{1-6}$alkyl, $C_{3-8}$cycloalkyl, —C(O)R$^{12}$, and —C(O)OR$^{12}$;

each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N(R$^{11}$)$_2$, and —C(O)OR$^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;

each $R^{11}$ is independently selected from H and $C_{1-6}$alkyl;
$R^{12}$ is independently selected from H and $C_{1-6}$alkyl; and
n is 0, 1, 2, or 3.

In some embodiments is a compound of Formula (Ic), or a pharmaceutically acceptable salt or solvate thereof, wherein each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N(R$^{11}$)$_2$, and —C(O)OR$^{12}$. In some embodiments is a compound of Formula (Ic), or a pharmaceutically acceptable salt or solvate thereof, wherein each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N(R$^{11}$)$_2$, and —C(O)OR$^{12}$. In some embodiments is a compound of Formula (Ic), or a pharmaceutically acceptable salt or solvate thereof, wherein each $R^{10}$ is independently selected from H and $C_{1-6}$alkyl optionally substituted with —C(O)OR$^{12}$. In some embodiments is a compound of Formula (Ic), or a pharmaceutically acceptable salt or solvate thereof, wherein each $R^{10}$ is independently selected from H and $C_{1-6}$alkyl optionally substituted with —C(O)OH. In some embodiments is a compound of Formula (Ic), or a pharmaceutically acceptable salt or solvate thereof, wherein $R^1$ is —C(O)N(R$^{10}$)$_2$ and the two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (Ic), or a pharmaceutically acceptable salt or solvate thereof, wherein $R^1$ is —C(O)N(R$^{10}$)$_2$ and the two $R^{10}$ and the nitrogen atom to which they are attached are combined to form a 5-membered heterocycloalkyl ring substituted with —C(O)OH. In some embodiments is a compound of Formula (Ic), or a pharmaceutically acceptable salt or solvate thereof, wherein $R^1$ is —C(O)N($R^{10}$)$_2$ and the two $R^{10}$ and the nitrogen atom to which they are attached are combined to form a 6-membered heterocycloalkyl ring substituted with —C(O)OH.

In some embodiments is a compound of Formula (Ic), or a pharmaceutically acceptable salt or solvate thereof, wherein $R^2$ is H, —OH, —N($R^{10}$)$_2$, or —O—$C_{1-6}$alkyl. In some embodiments is a compound of Formula (Ic), or a pharmaceutically acceptable salt or solvate thereof, wherein $R^2$ is —O—$C_{1-6}$alkyl. In some embodiments is a compound of Formula (Ic), or a pharmaceutically acceptable salt or solvate thereof, wherein $R^2$ is —OCH$_2$CH$_3$. In some embodiments is a compound of Formula (Ic), or a pharmaceutically acceptable salt or solvate thereof, wherein $R^2$ is H. In some embodiments is a compound of Formula (Ic), or a pharmaceutically acceptable salt or solvate thereof, wherein $R^2$ is —OH. In some embodiments is a compound of Formula (Ic), or a pharmaceutically acceptable salt or solvate thereof, wherein $R^2$ is —N($R^{10}$)$_2$.

In some embodiments is a compound of Formula (Ic), or a pharmaceutically acceptable salt or solvate thereof, wherein n is 0.

In some embodiments is a compound of Formula (Ic), or a pharmaceutically acceptable salt or solvate thereof, wherein n is 1, 2, or 3. In some embodiments is a compound of Formula (Ic), or a pharmaceutically acceptable salt or solvate thereof, wherein n is 1, 2, or 3 and each $R^3$ is independently selected from halogen, —CN, —OR$^9$, —N($R^{10}$)$_2$, —S(O)$_2$R$^9$, —NHS(O)$_2$R$^9$, —S(O)$_2$N($R^{10}$)$_2$, —C(O)R$^9$, —C(O)OR$^{10}$, —OC(O)R$^9$, —C(O)N($R^{10}$)$_2$, —NR$^{10}$C(O)N($R^{10}$)$_2$, —NR$^{10}$C(O)R$^9$, $C_{1-6}$alkyl, —$C_{1-6}$alkyl-OH, —$C_{1-6}$alkyl-OR$^9$, —$C_{1-6}$alkyl-N($R^{10}$)$_2$, $C_{1-6}$haloalkyl, $C_{3-8}$cycloalkyl, and —$C_{1-6}$alkyl-$C_{3-8}$cycloalkyl. In some embodiments is a compound of Formula (Ic), or a pharmaceutically acceptable salt or solvate thereof, wherein n is 1, 2, or 3 and each $R^3$ is independently selected from halogen, —OR$^9$, —N($R^{10}$)$_2$, —C(O)OR$^{10}$, —C(O)N($R^{10}$)$_2$, and $C_{1-6}$alkyl. In some embodiments is a compound of Formula (Ic), or a pharmaceutically acceptable salt or solvate thereof, wherein n is 1, 2, or 3 and each $R^3$ is independently selected from halogen and $C_{1-6}$alkyl. In some embodiments is a compound of Formula (Ic), or a pharmaceutically acceptable salt or solvate thereof, wherein n is 1. In some embodiments is a compound of Formula (Ic), or a pharmaceutically acceptable salt or solvate thereof, wherein n is 1 and $R^3$ is selected from halogen, —OH, —OR$^9$, —N($R^{10}$)$_2$, $C_{1-6}$alkyl, —$C_{1-6}$alkyl-OH, —$C_{1-6}$alkyl-OR$^9$, and $C_{1-6}$haloalkyl. In some embodiments is a compound of Formula (Ic), or a pharmaceutically acceptable salt or solvate thereof, wherein n is 1 and $R^3$ is selected from halogen, —OR$^9$, and $C_{1-6}$alkyl. In some embodiments is a compound of Formula (Ic), or a pharmaceutically acceptable salt or solvate thereof, wherein n is 1 and $R^3$ is selected from halogen, —OR$^9$, and $C_{1-6}$alkyl. In some embodiments is a compound of Formula (Ic), or a pharmaceutically acceptable salt or solvate thereof, wherein n is 1 and $R^3$ is —OR$^9$. In some embodiments is a compound of Formula (Ic), or a pharmaceutically acceptable salt or solvate thereof, wherein n is 1, $R^3$ is —OR$^9$, and $R^9$ is $C_{3-8}$cycloalkyl. In some embodiments is a compound of Formula (Ic), or a pharmaceutically acceptable salt or solvate thereof, wherein n is 1, $R^3$ is —OR$^9$, and $R^9$ is cyclopentyl.

In some embodiments, provided herein is a compound of Formula (Id), or a pharmaceutically acceptable salt or solvate thereof:

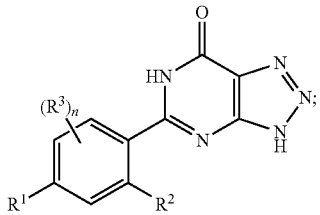

Formula (Id)

wherein.
$R^1$ is —N($R^{10}$)$_2$;
$R^2$ is H, —OH, —N($R^{10}$)$_2$, —NHS(O)$_2$R$^9$, —S(O)$_2$N($R^{10}$)$_2$, —C(O)N($R^{10}$)$_2$, —OC(O)N($R^{10}$)$_2$, —O—$C_{1-6}$alkyl, —$C_{1-6}$alkyl-OH, —$C_{1-6}$alkyl-OR$^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl;
each $R^3$ is independently selected from halogen, —CN, —OH, —OR$^9$, —SR$^9$, —N($R^{10}$)$_2$, —S(O)R$^9$, —S(O)$_2$R$^9$, —NHS(O)$_2$R$^9$, —S(O)$_2$N($R^{10}$)$_2$, —C(O)R$^9$, —C(O)OR$^{10}$, —OC(O)R$^9$, —C(O)N($R^{10}$)$_2$, —OC(O)N($R^{10}$)$_2$, —NR$^{10}$C(O)N($R^{10}$)$_2$, —NR$^{10}$C(O)R$^9$, —NR$^{10}$C(O)OR$^9$, $C_{1-6}$alkyl, —$C_{1-6}$alkyl-OH, —$C_{1-6}$alkyl-OR$^9$, —$C_{1-6}$alkyl-N($R^{10}$)$_2$, $C_{2-6}$alkenyl, $C_{2-6}$alkynyl, $C_{1-6}$haloalkyl, $C_{3-8}$cycloalkyl, and —$C_{1-6}$alkyl-$C_{3-8}$cycloalkyl;
each $R^9$ is independently selected from $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, and —$C_{1-6}$alkyl-$C_{2-9}$heteroaryl, wherein $C_{1-6}$alkyl, phenyl, —$C_{1-6}$alkyl-phenyl, —$C_{1-6}$alkyl-$C_{2-9}$heterocycloalkyl, $C_{2-9}$heteroaryl, and —$C_{1-6}$alkyl-$C_{2-9}$heteroaryl are optionally substituted with one or two groups independently selected from $C_{1-6}$alkyl, —OR$^{11}$, —N(R$^{D1}$)$_2$, $C_{1-6}$alkyl, $C_{3-8}$cycloalkyl, —C(O)R$^{12}$, and —C(O)OR$^{12}$;
each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N(R$^{D1}$)$_2$, and —C(O)OR$^{12}$; or two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH;
each $R^{11}$ is independently selected from H and $C_{1-6}$alkyl;
$R^{12}$ is independently selected from H and $C_{1-6}$alkyl; and
n is 0, 1, 2, or 3.

In some embodiments is a compound of Formula (Id), or a pharmaceutically acceptable salt or solvate thereof, wherein each $R^{10}$ is independently selected from H, $C_{1-6}$alkyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, and $C_{2-9}$heteroaryl, wherein $C_{1-6}$alkyl, phenyl, —$C_{1-6}$alkyl-phenyl, and $C_{2-9}$heteroaryl are optionally substituted with one or two groups independently selected from halogen, $C_{1-6}$alkyl, —N(R$^{11}$)$_2$, and —C(O)OR$^{12}$. In some embodiments is a compound of Formula (Id), or a pharmaceutically acceptable salt or solvate thereof, wherein each $R^{10}$ is independently selected from H, $C_{1-6}$alkyl, $C_{3-8}$cycloalkyl, phenyl, and $C_{2-9}$heteroaryl, wherein $C_{1-6}$alkyl, phenyl, and $C_{2-9}$heteroaryl are optionally substituted with one or two groups independently selected from halogen, $C_{1-6}$alkyl, —N($R^{11}$)$_2$, and —C(O)O$R^{12}$. In some embodiments is a compound of Formula (Id), or a pharmaceutically acceptable salt or solvate thereof, wherein each $R^{10}$ is independently selected from H and $C_{1-6}$alkyl optionally substituted with —C(O)O$R^{12}$. In some embodiments is a compound of Formula (Id), or a pharmaceutically acceptable salt or solvate thereof, wherein each $R^{10}$ is independently selected from H and $C_{1-6}$alkyl optionally substituted with —C(O)OH. In some embodiments is a compound of Formula (Id), or a pharmaceutically acceptable salt or solvate thereof, wherein $R^1$ is —N($R^{10}$)$_2$ and the two $R^{10}$ and the nitrogen atom to which they are attached are combined to form a 5- or 6-membered heterocycloalkyl ring optionally substituted with one, two, or three groups independently selected from $C_{1-6}$alkyl, oxo, and —C(O)OH. In some embodiments is a compound of Formula (Id), or a pharmaceutically acceptable salt or solvate thereof, wherein $R^1$ is —N($R^{10}$)$_2$ and the two $R^{10}$ and the nitrogen atom to which they are attached are combined to form a 5-membered heterocycloalkyl ring substituted with —C(O)OH. In some embodiments is a compound of Formula (Id), or a pharmaceutically acceptable salt or solvate thereof, wherein $R^1$ is —N($R^{10}$)$_2$ and the two $R^{10}$ and the nitrogen atom to which they are attached are combined to form a 6-membered heterocycloalkyl ring substituted with —C(O)OH.

In some embodiments is a compound of Formula (Id), or a pharmaceutically acceptable salt or solvate thereof, wherein $R^2$ is H, —OH, —N($R^{10}$)$_2$, or —O—$C_{1-6}$alkyl. In some embodiments is a compound of Formula (Id), or a pharmaceutically acceptable salt or solvate thereof, wherein $R^2$ is —O—$C_{1-6}$alkyl. In some embodiments is a compound of Formula (Id), or a pharmaceutically acceptable salt or solvate thereof, wherein $R^2$ is —OCH$_2$CH$_3$. In some embodiments is a compound of Formula (Id), or a pharmaceutically acceptable salt or solvate thereof, wherein $R^2$ is H. In some embodiments is a compound of Formula (Id), or a pharmaceutically acceptable salt or solvate thereof, wherein $R^2$ is —OH. In some embodiments is a compound of Formula (Id), or a pharmaceutically acceptable salt or solvate thereof, wherein $R^2$ is —N($R^{10}$)$_2$.

In some embodiments is a compound of Formula (Id), or a pharmaceutically acceptable salt or solvate thereof, wherein n is 0.

In some embodiments is a compound of Formula (Id), or a pharmaceutically acceptable salt or solvate thereof, wherein n is 1, 2, or 3. In some embodiments is a compound of Formula (Id), or a pharmaceutically acceptable salt or solvate thereof, wherein n is 1, 2, or 3 and each $R^3$ is independently selected from halogen, —CN, —O$R^9$, —N($R^{10}$)$_2$, —S(O)$_2R^9$, —NHS(O)$_2R^9$, —S(O)$_2$N($R^{10}$)$_2$, —C(O)$R^9$, —C(O)O$R^{10}$, —OC(O)$R^9$, —C(O)N($R^{10}$)$_2$, —N$R^{10}$C(O)N($R^{10}$)$_2$, —N$R^{10}$C(O)$R^9$, $C_{1-6}$alkyl, —$C_{1-6}$alkyl-OH, —$C_{1-6}$alkyl-O$R^9$, —$C_{1-6}$alkyl-N($R^{10}$)$_2$, $C_{1-6}$haloalkyl, $C_{3-8}$cycloalkyl, and —$C_{1-6}$alkyl-$C_{3-8}$cycloalkyl. In some embodiments is a compound of Formula (Id), or a pharmaceutically acceptable salt or solvate thereof, wherein n is 1, 2, or 3 and each $R^3$ is independently selected from halogen, —O$R^9$, —N($R^{10}$)$_2$, —C(O)O$R^{10}$, —C(O)N($R^{10}$)$_2$, and $C_{1-6}$alkyl. In some embodiments is a compound of Formula (Id), or a pharmaceutically acceptable salt or solvate thereof, wherein n is 1, 2, or 3 and each $R^3$ is independently selected from halogen and $C_{1-6}$alkyl. In some embodiments is a compound of Formula (Id), or a pharmaceutically acceptable salt or solvate thereof, wherein n is 1. In some embodiments is a compound of Formula (Id), or a pharmaceutically acceptable salt or solvate thereof, wherein n is 1 and $R^3$ is selected from halogen, —OH, —O$R^9$, —N($R^{10}$)$_2$, $C_{1-6}$alkyl, —$C_{1-6}$alkyl-OH, —$C_{1-6}$alkyl-O$R^9$, and $C_{1-6}$haloalkyl. In some embodiments is a compound of Formula (Id), or a pharmaceutically acceptable salt or solvate thereof, wherein n is 1 and $R^3$ is selected from halogen, —O$R^9$, and $C_{1-6}$alkyl. In some embodiments is a compound of Formula (Id), or a pharmaceutically acceptable salt or solvate thereof, wherein n is 1 and $R^3$ is selected from halogen, —O$R^9$, and $C_{1-6}$alkyl. In some embodiments is a compound of Formula (Id), or a pharmaceutically acceptable salt or solvate thereof, wherein n is 1 and $R^3$ is —O$R^9$. In some embodiments is a compound of Formula (Id), or a pharmaceutically acceptable salt or solvate thereof, wherein n is 1, $R^3$ is —O$R^9$, and $R^9$ is $C_{3-8}$cycloalkyl. In some embodiments is a compound of Formula (Id), or a pharmaceutically acceptable salt or solvate thereof, wherein n is 1, $R^3$ is —O$R^9$, and $R^9$ is cyclopentyl.

In some embodiments, provided herein is a compound selected from:

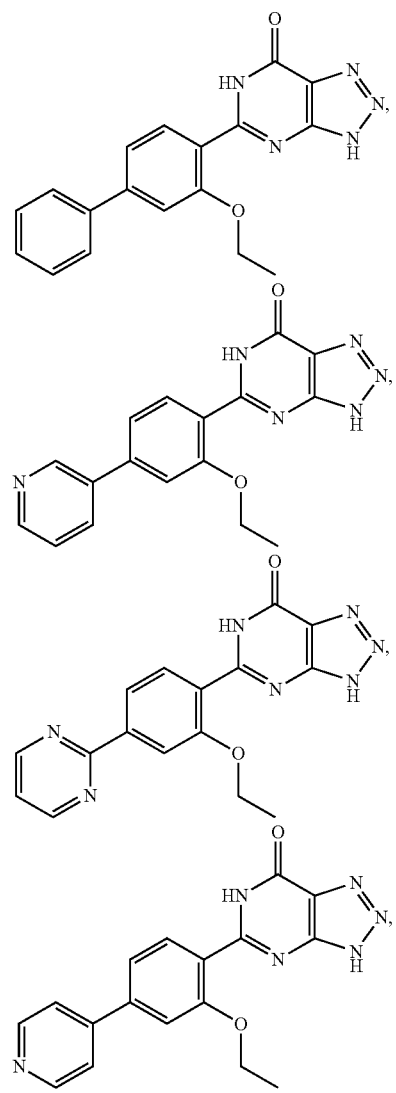

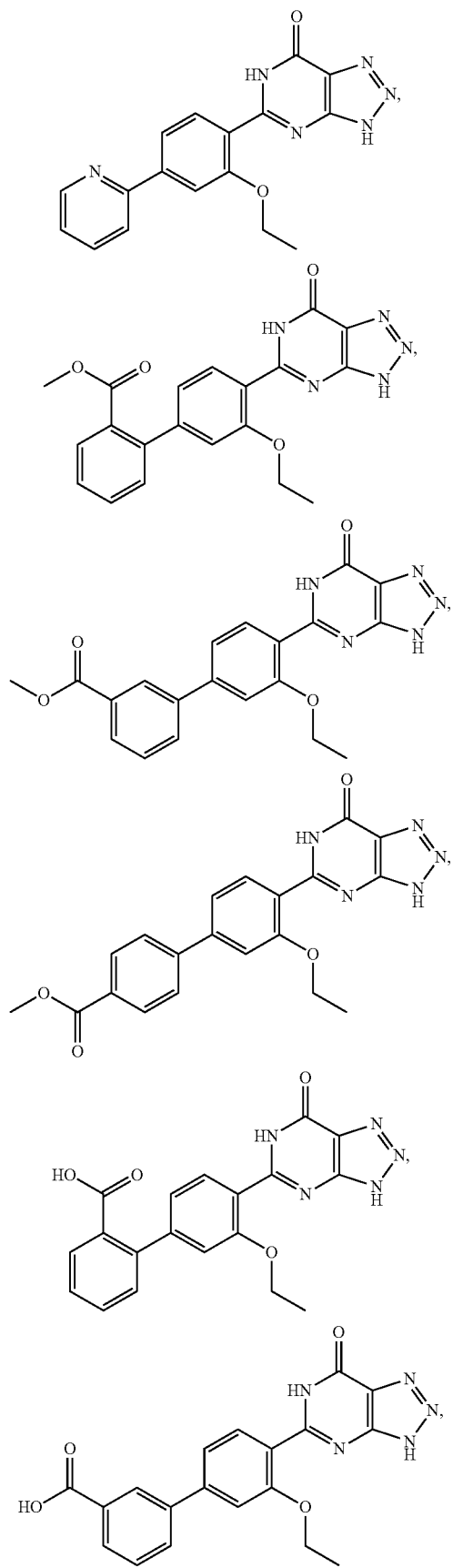
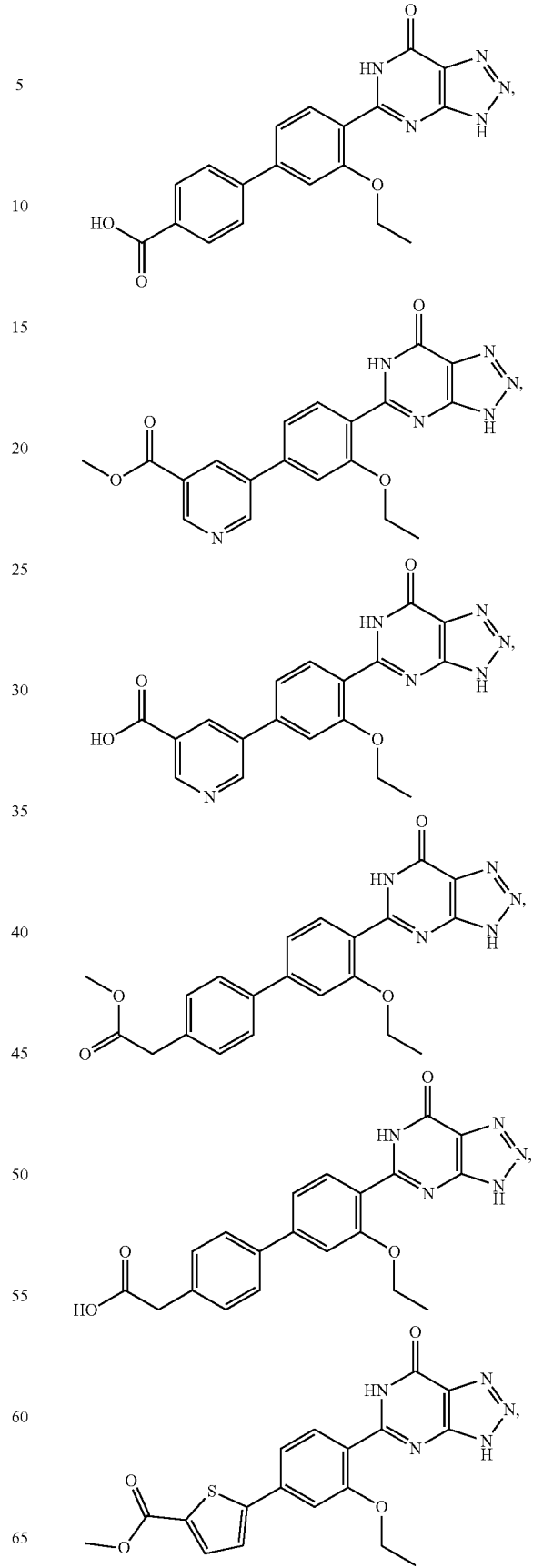

65
-continued
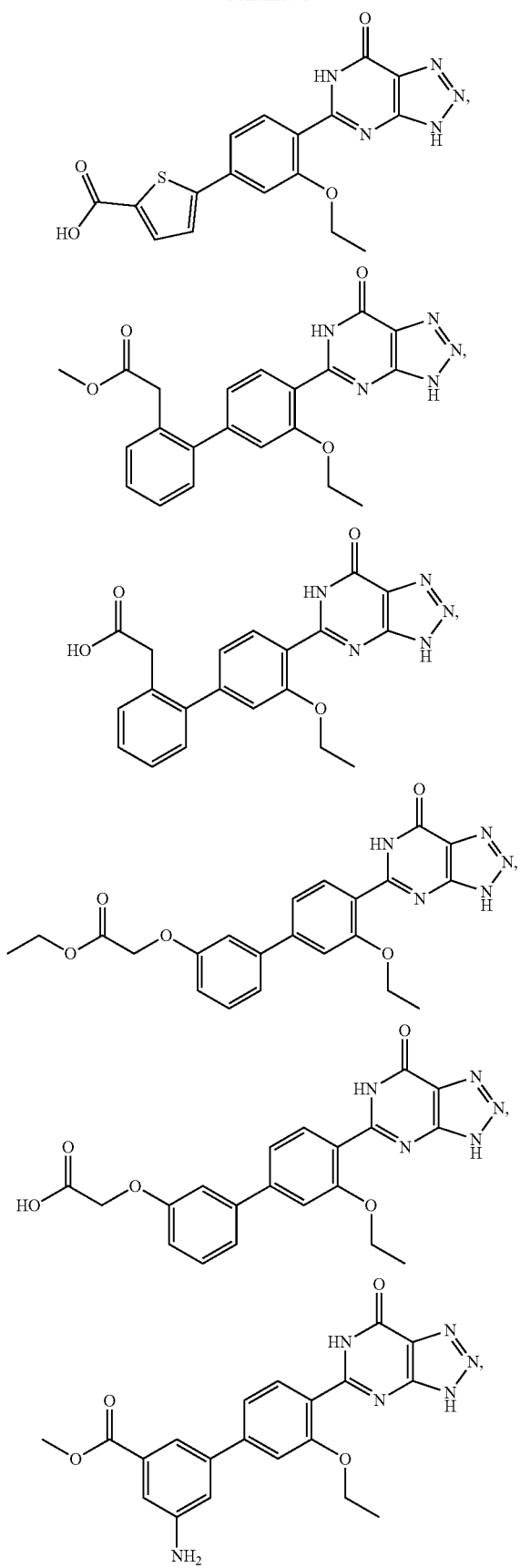
66
-continued
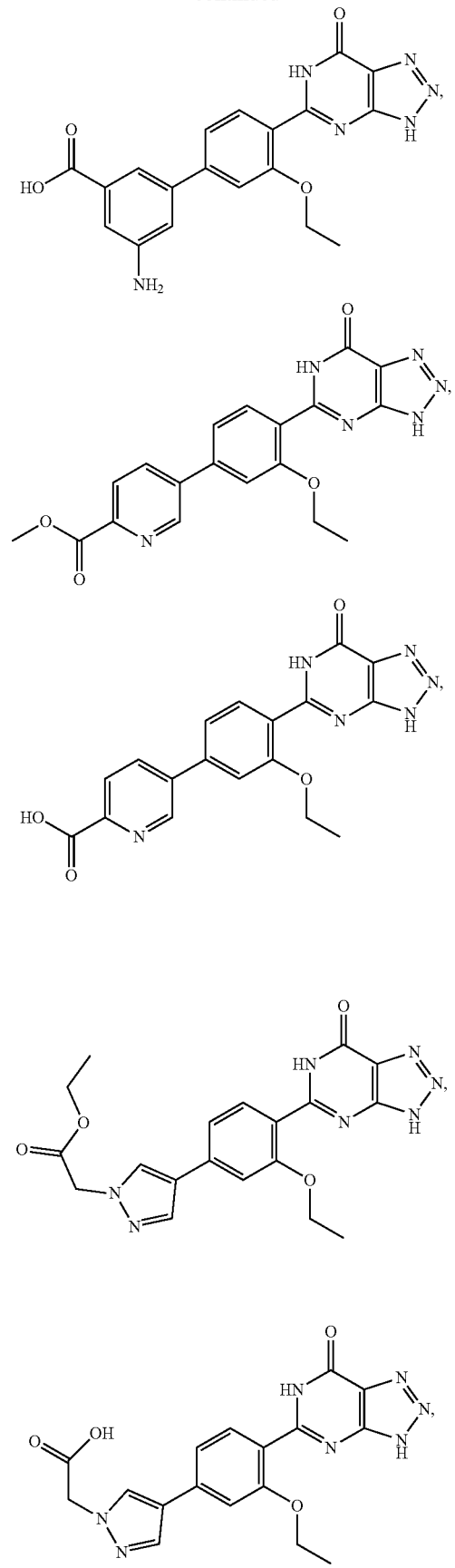

-continued
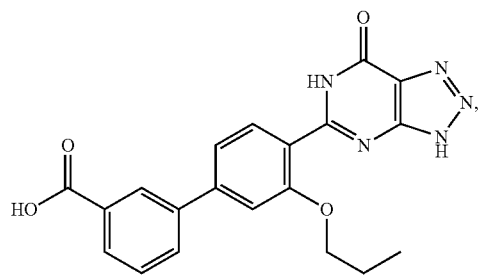
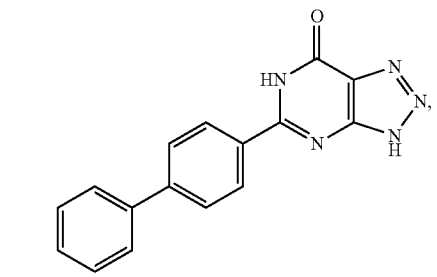
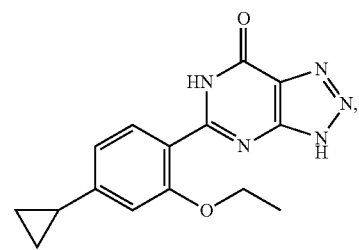
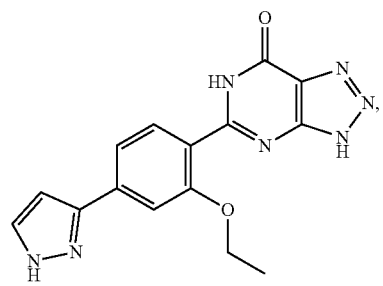
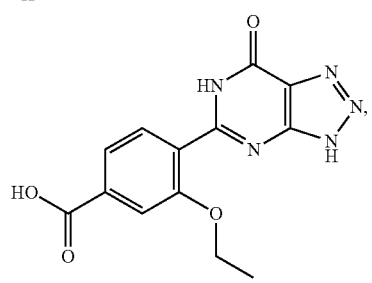
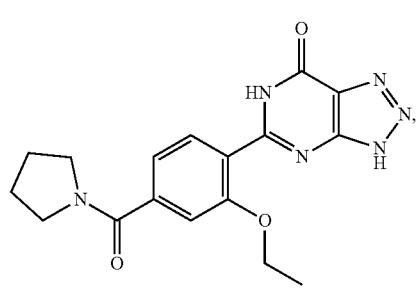
-continued
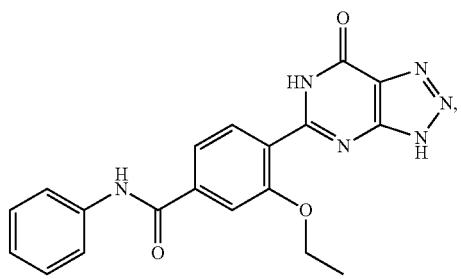
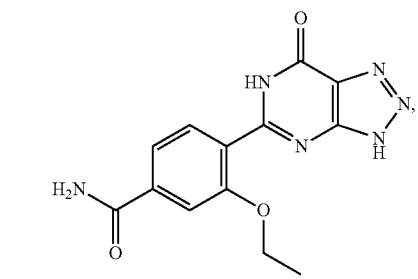
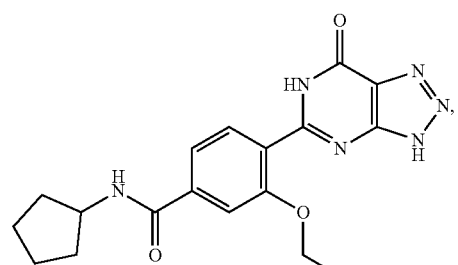
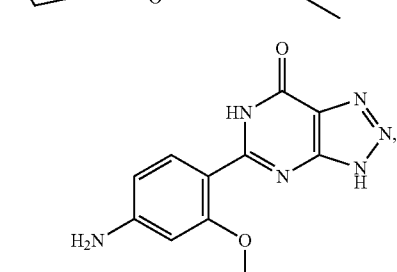
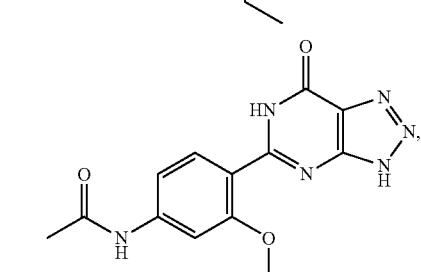
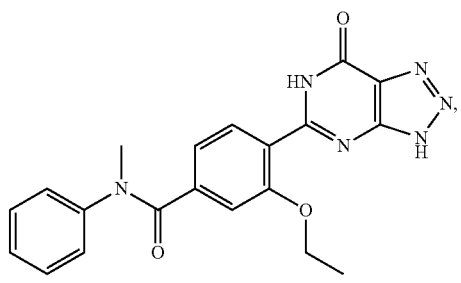

-continued
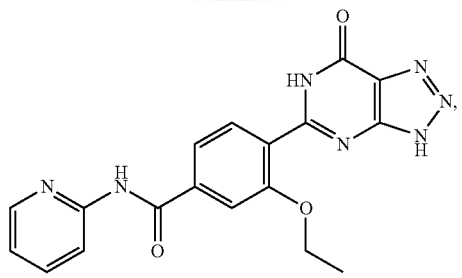
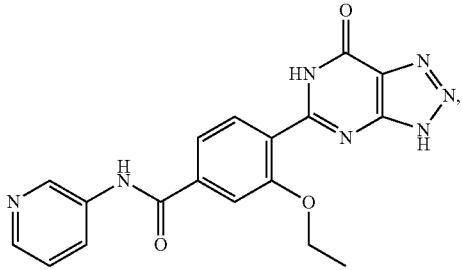
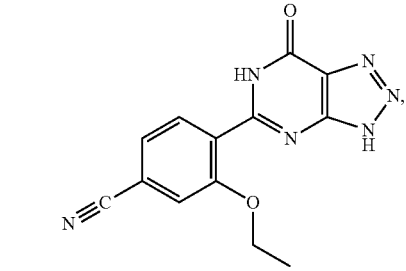
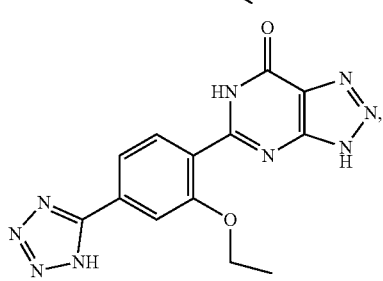
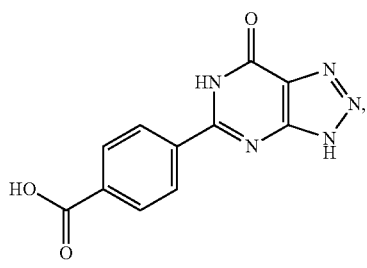
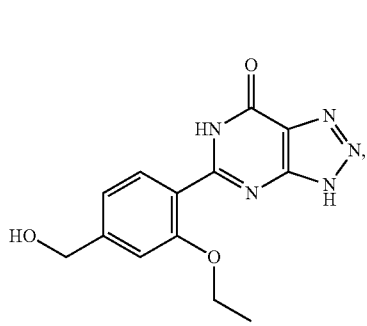
-continued
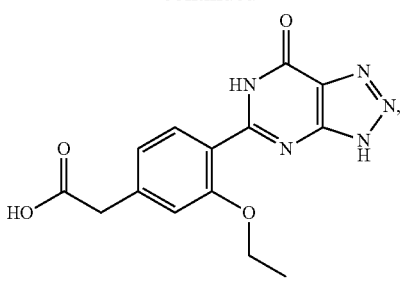
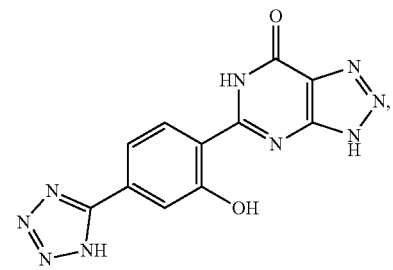
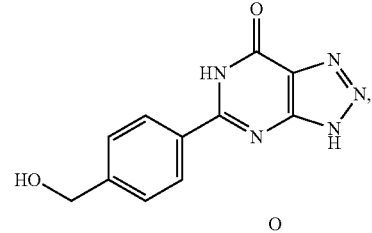
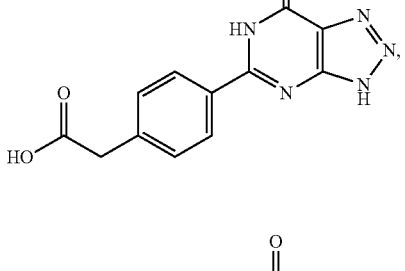
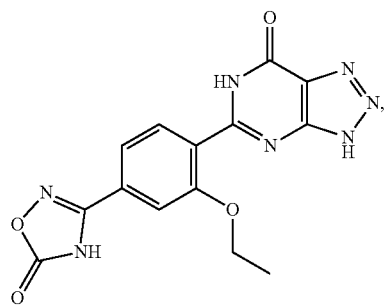
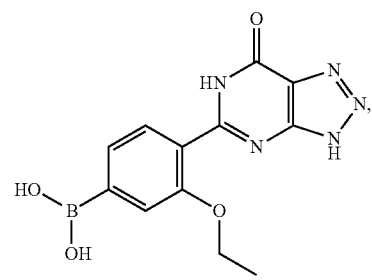

| 71 -continued | 72 -continued |
|---|---|
| 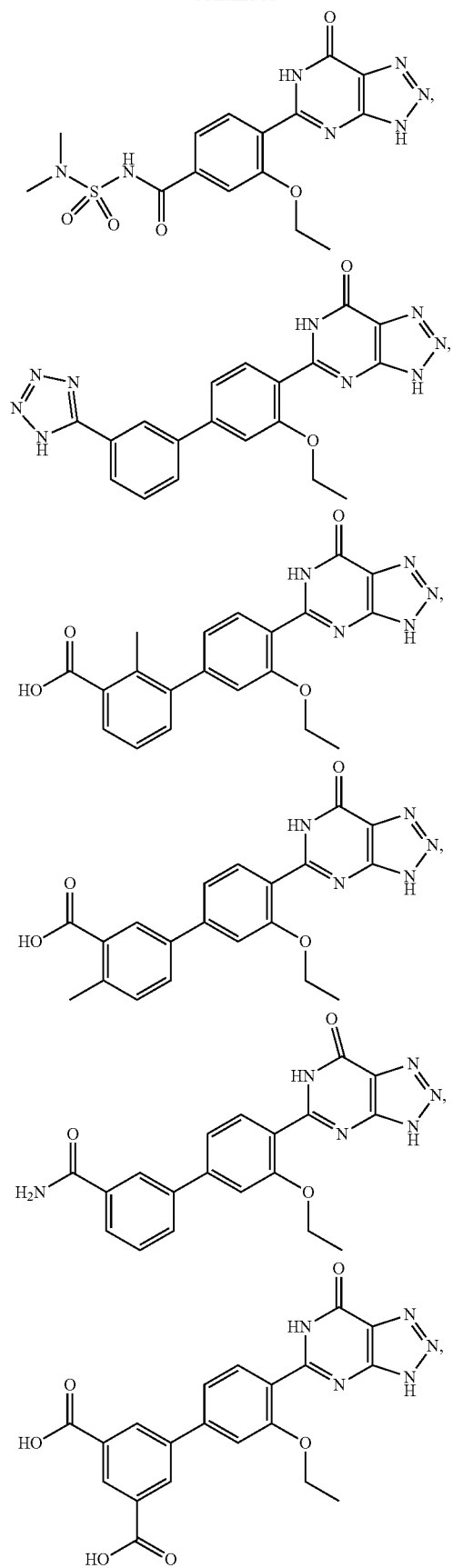 | 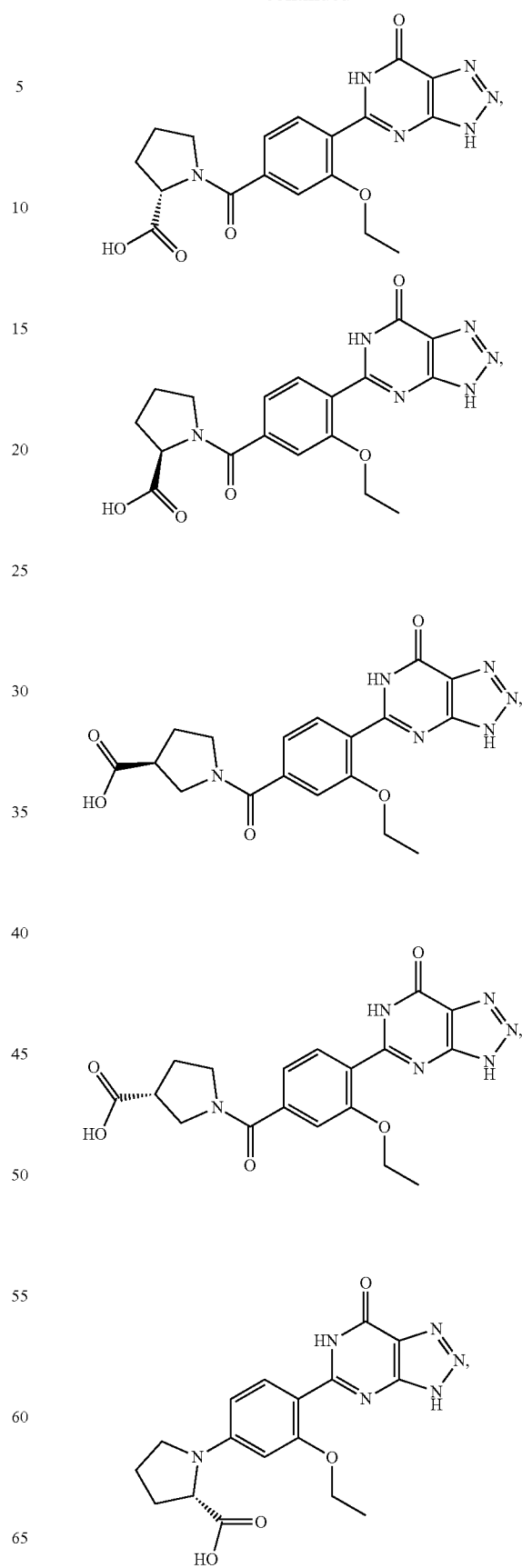 |

73
-continued
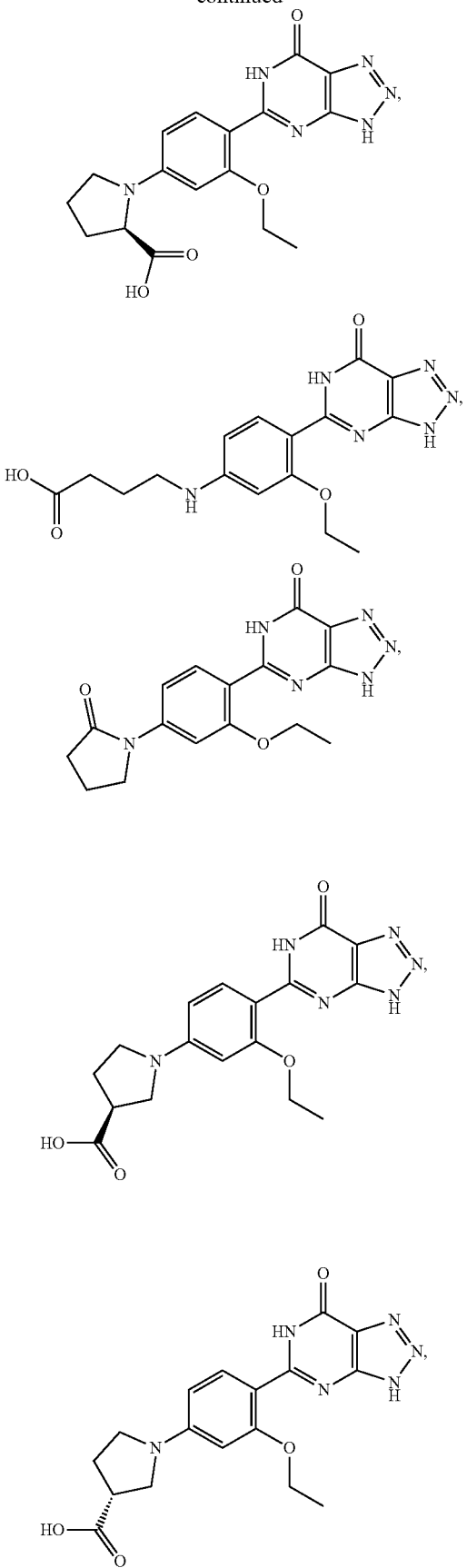
74
-continued
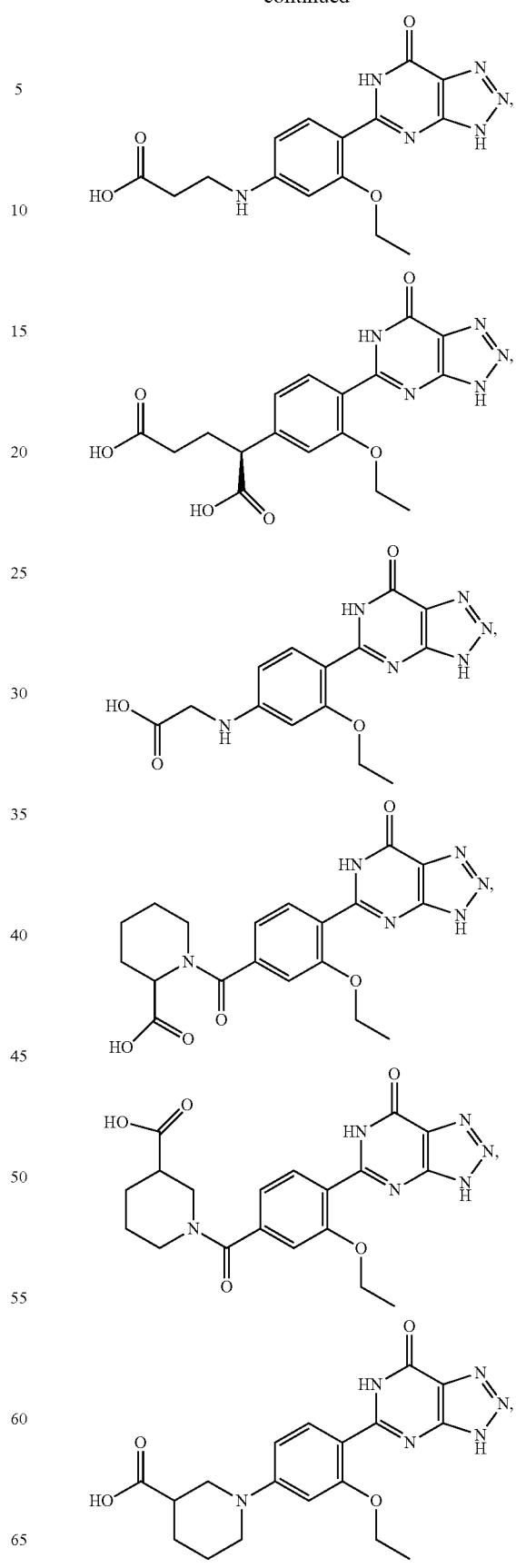

75
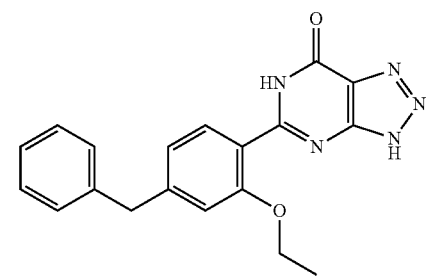
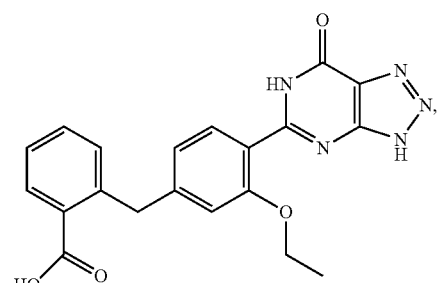
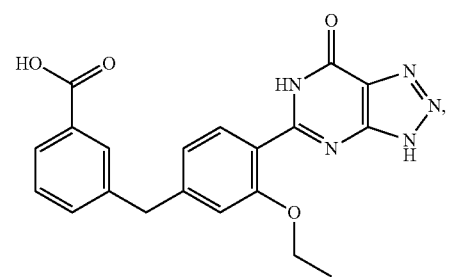
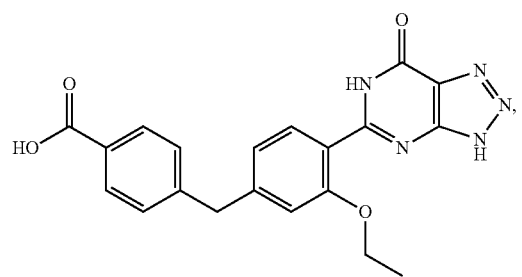
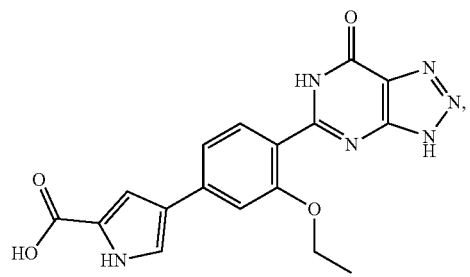
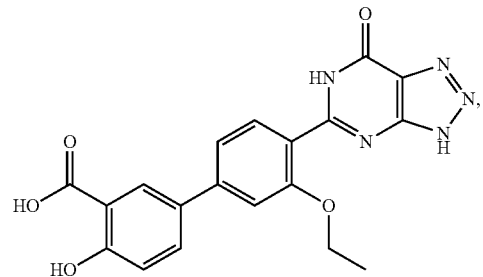
76
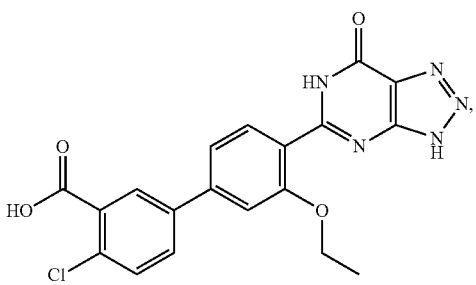
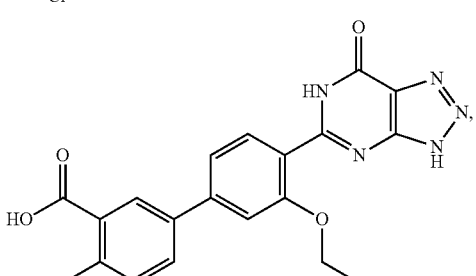
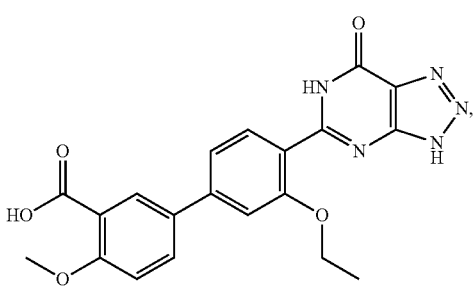
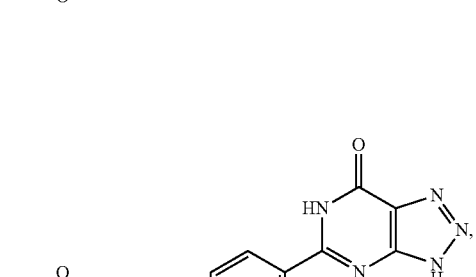
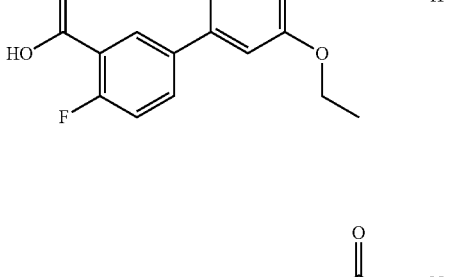
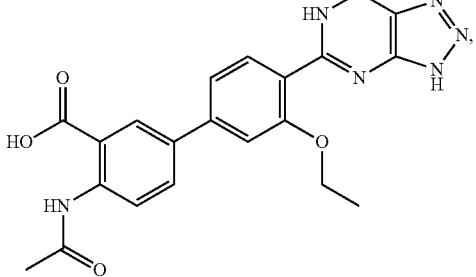

77
-continued
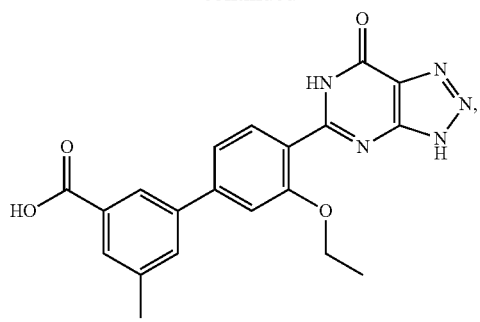
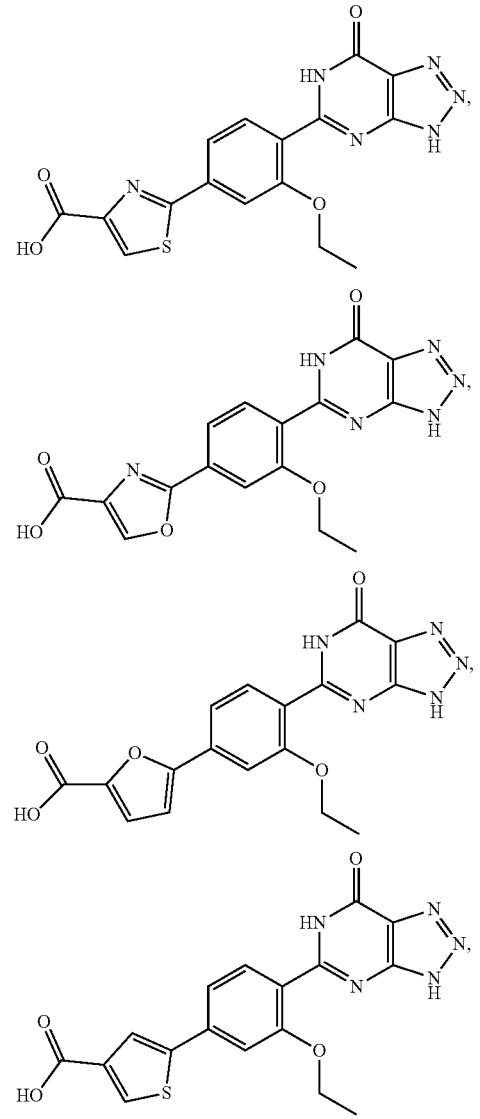
78
-continued
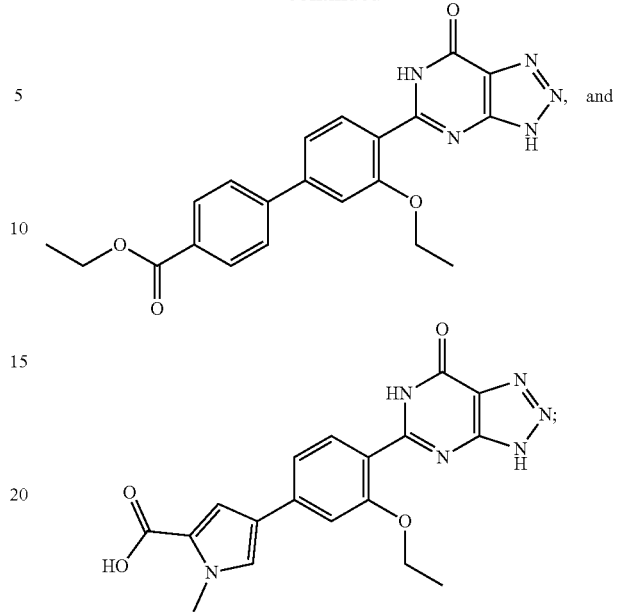
pharmaceutically acceptable salt or solvate thereof.
In some embodiments, provided herein is a compound selected from:
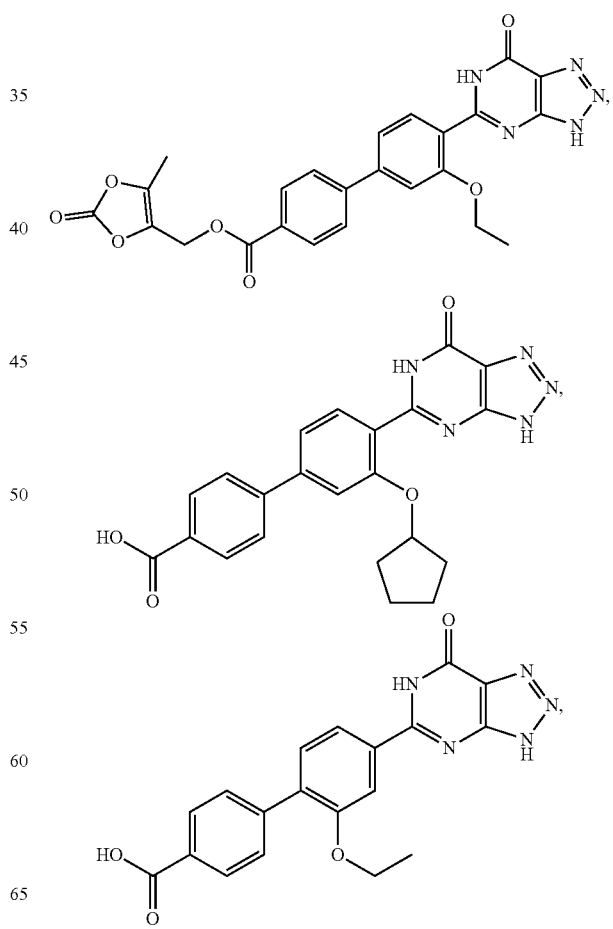

-continued
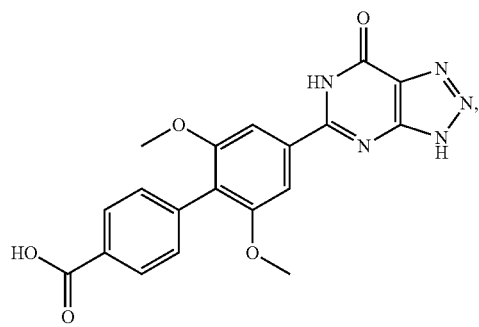
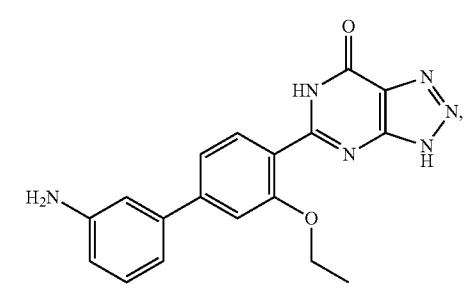
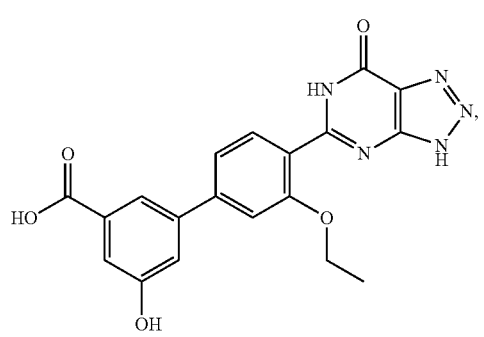
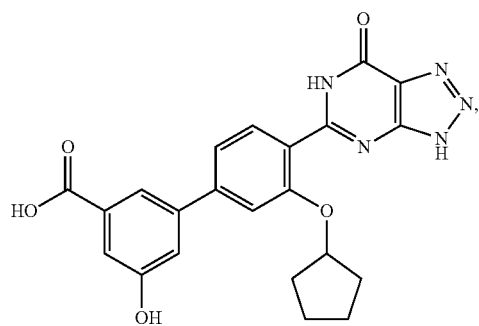
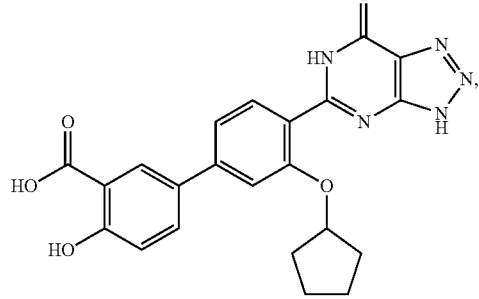
-continued
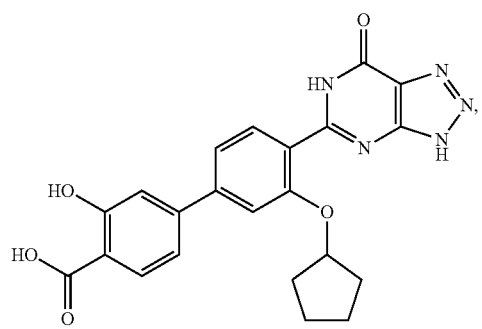
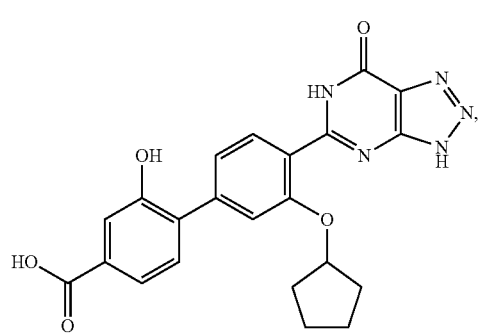
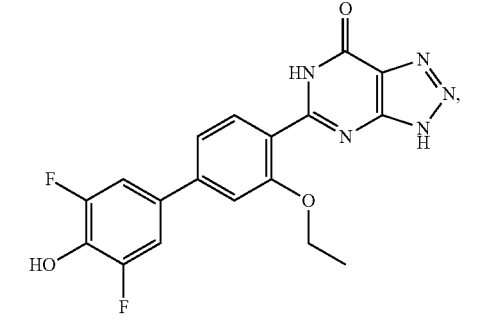
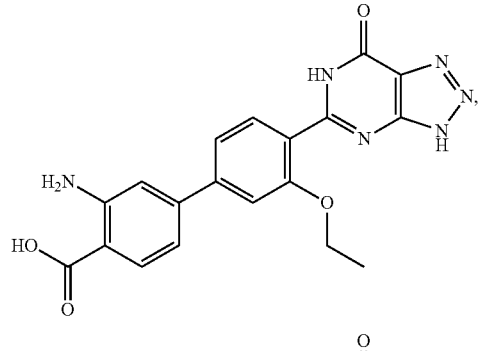
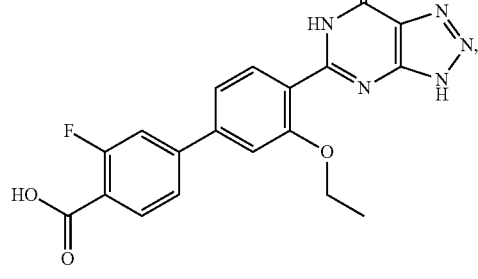

81
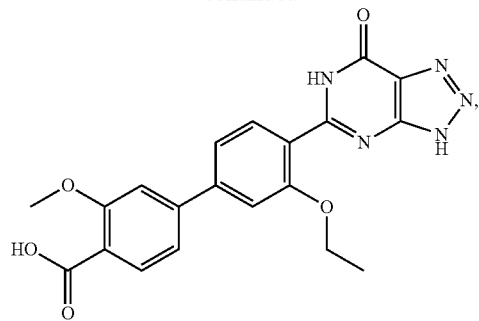
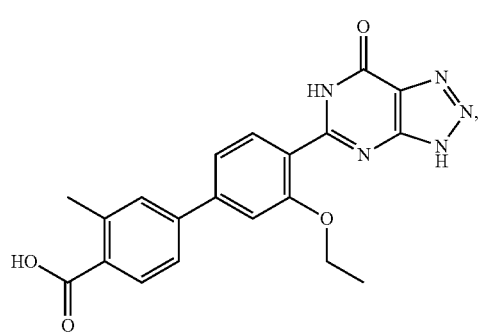
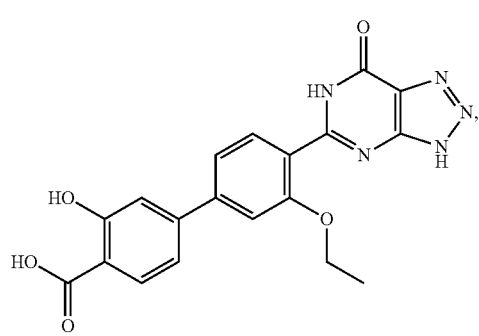
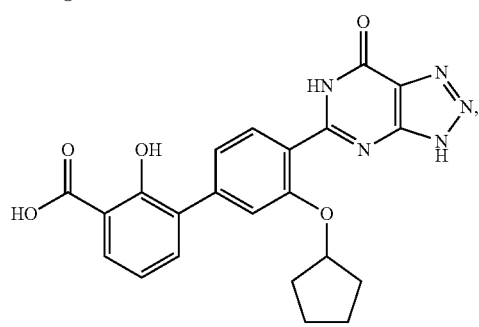
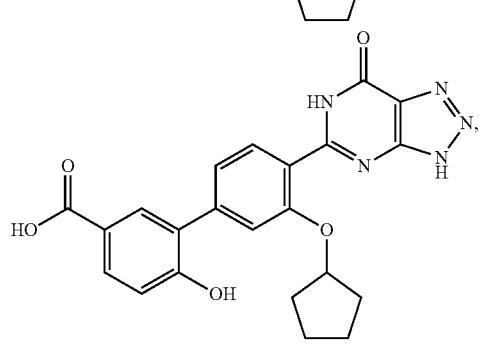
82
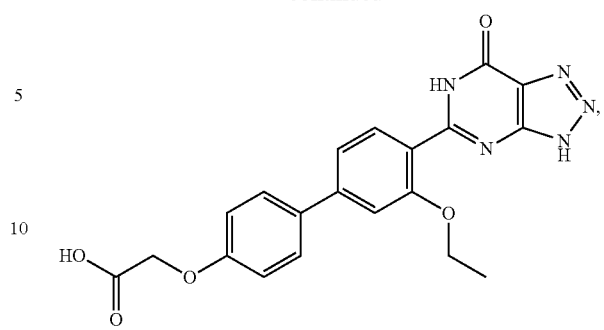
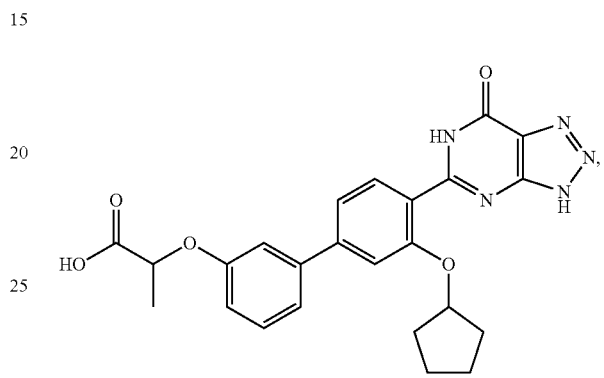
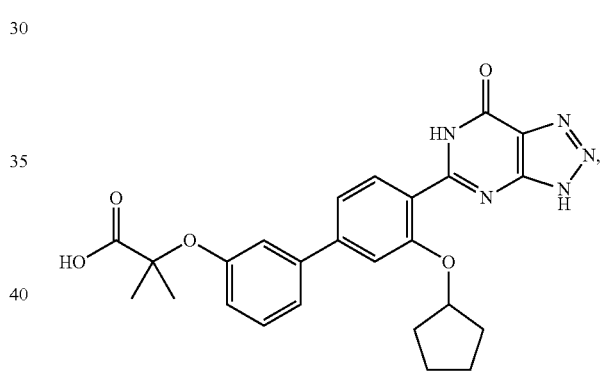
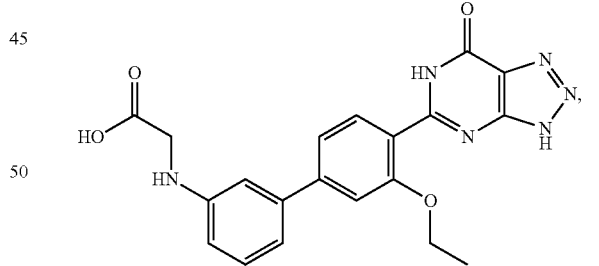
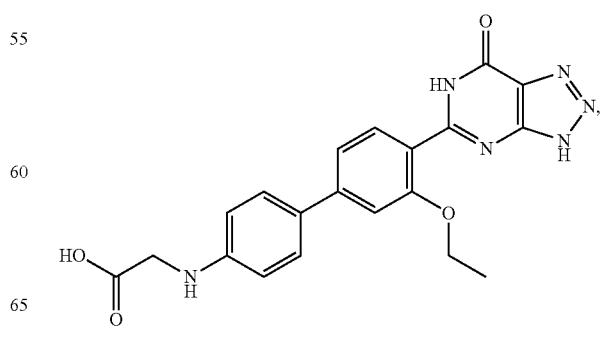

83
-continued
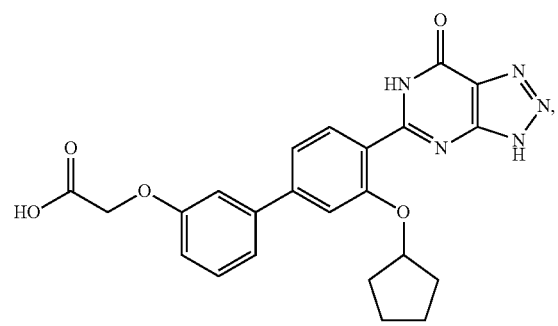
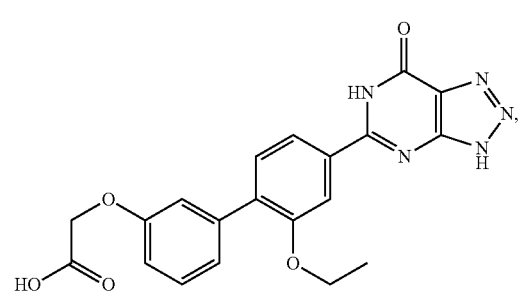
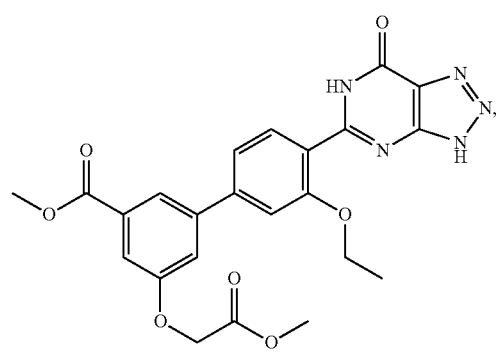
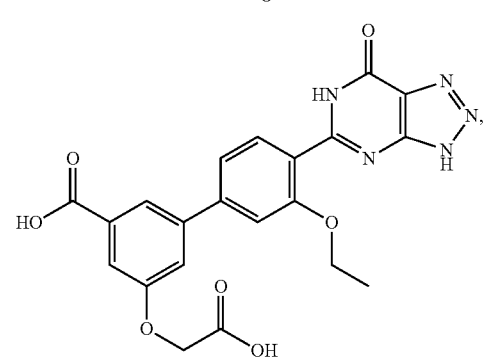
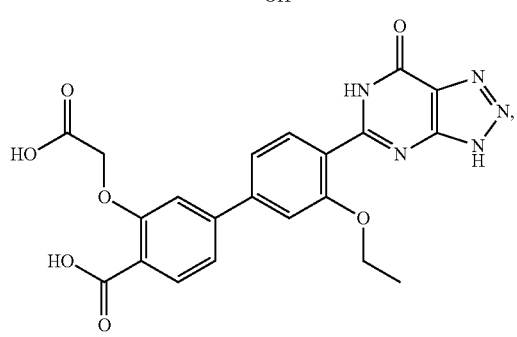
84
-continued
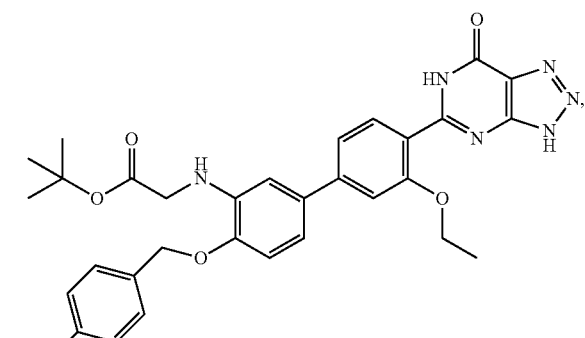
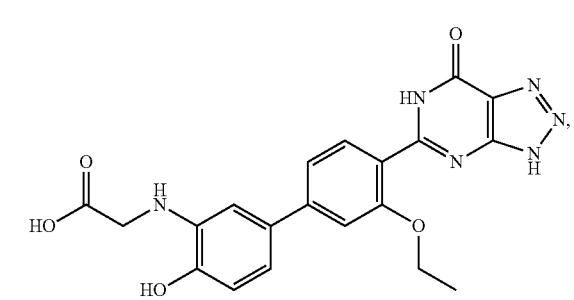
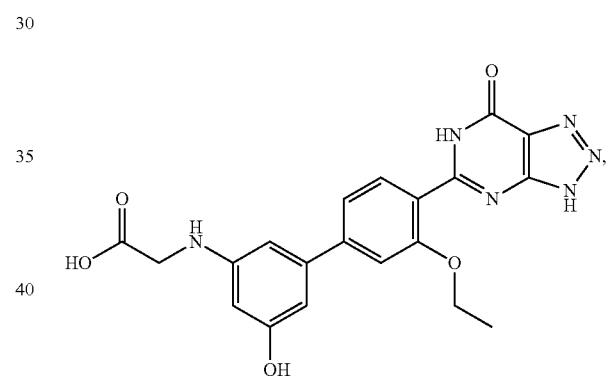
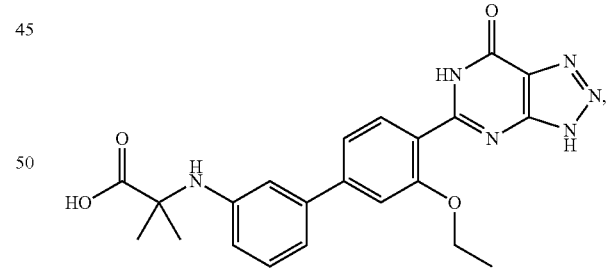
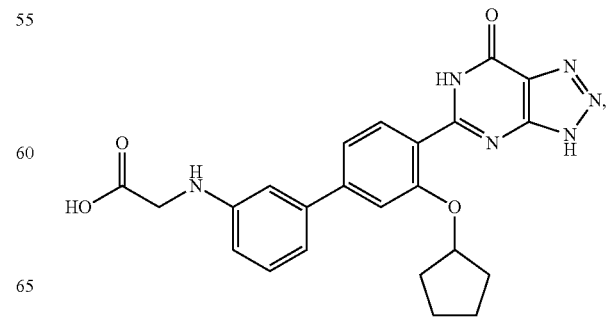

85
-continued
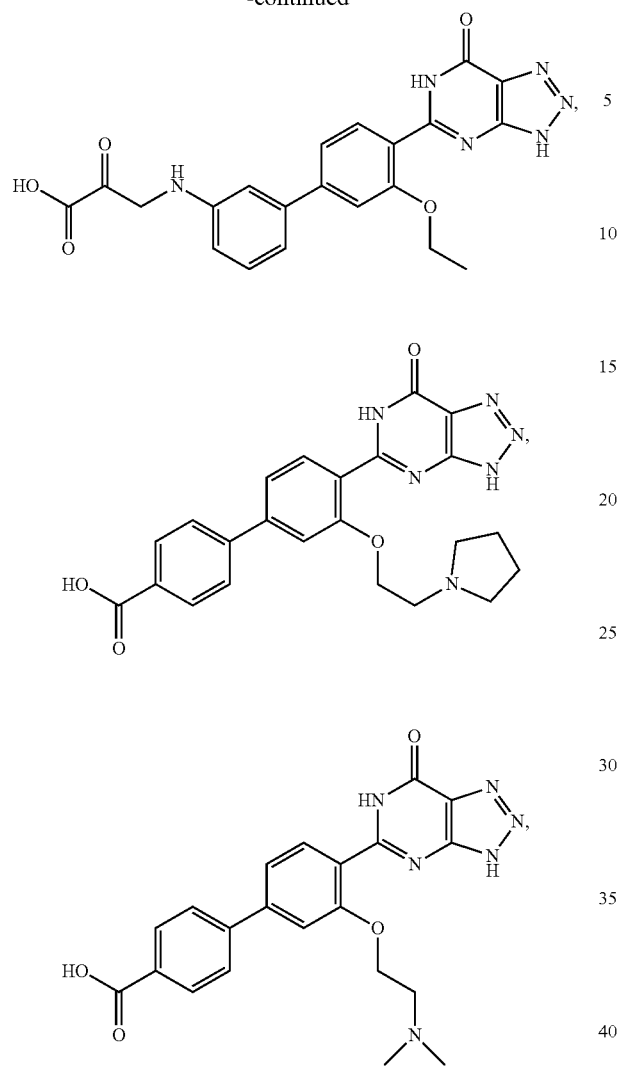
86
-continued
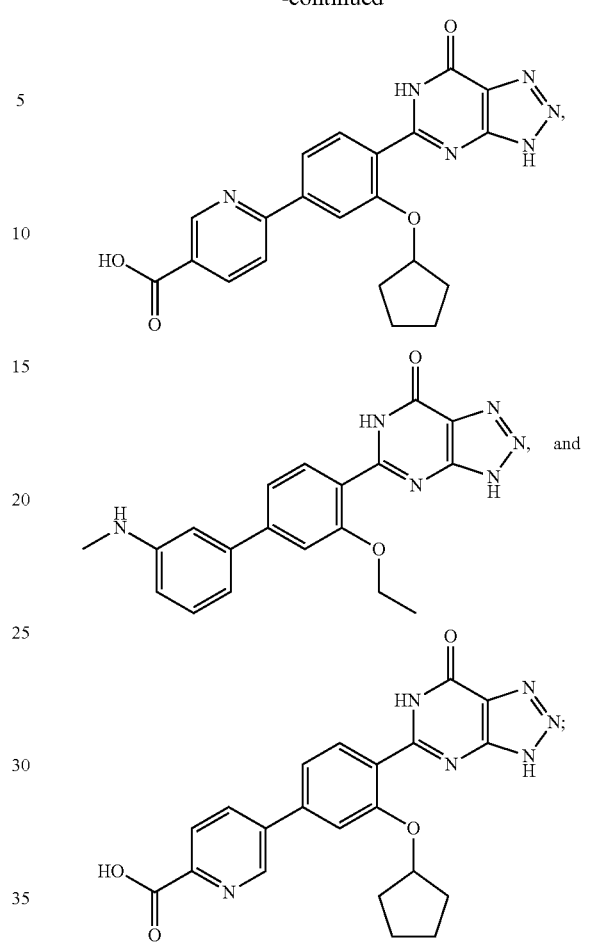
or a pharmaceutically acceptable salt or solvate thereof.
In some embodiments, provided herein is a compound selected from:
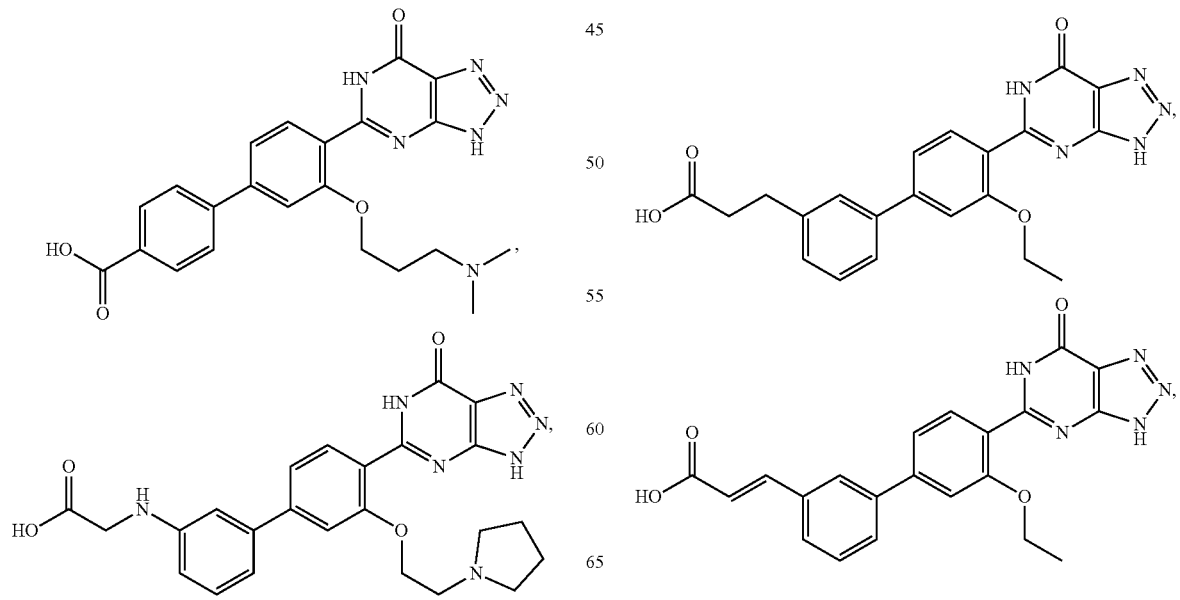

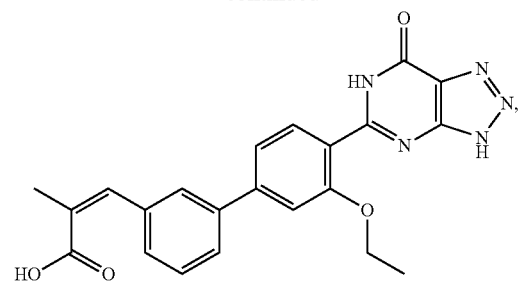
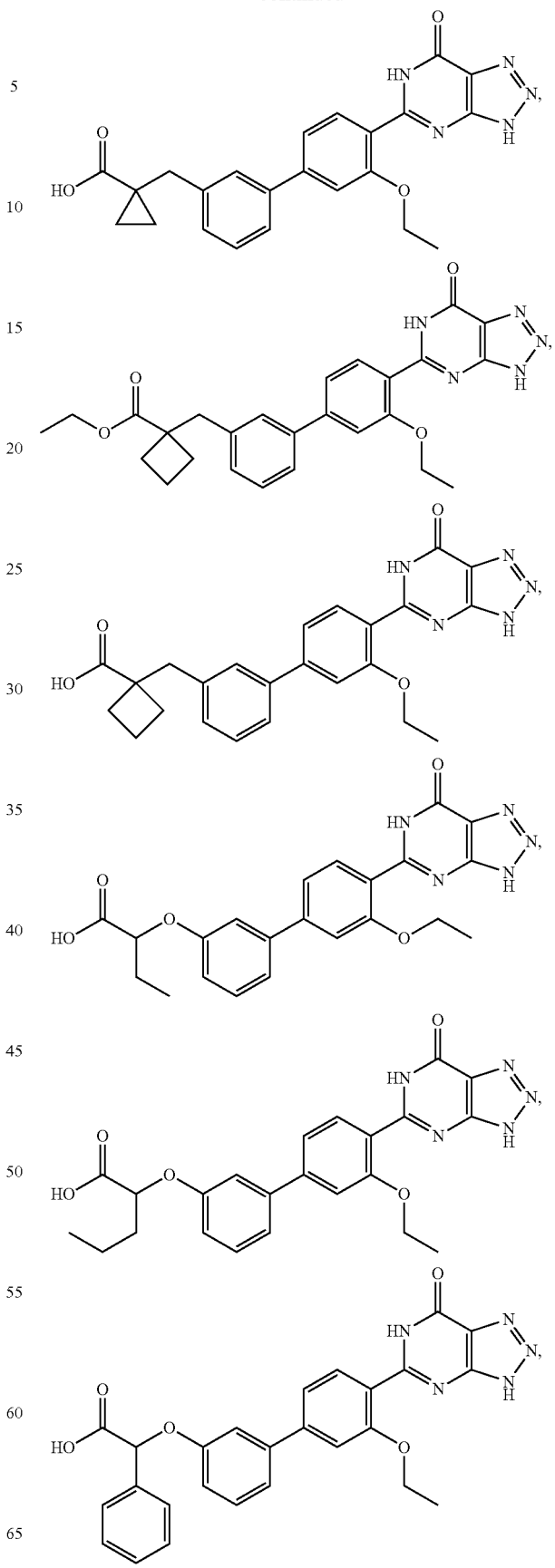

89
-continued
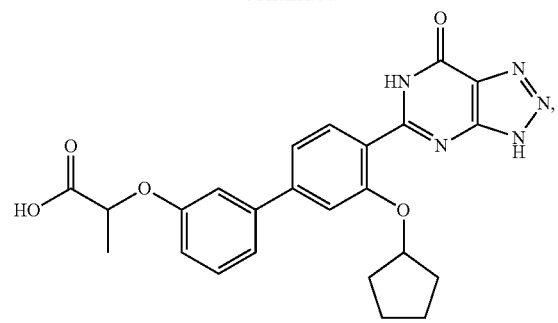
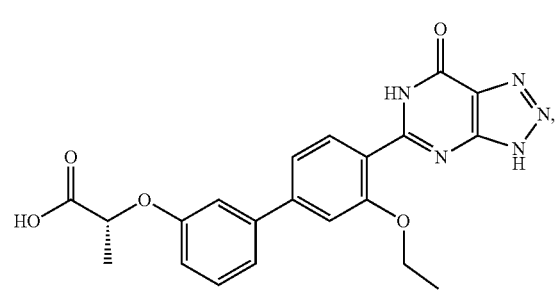
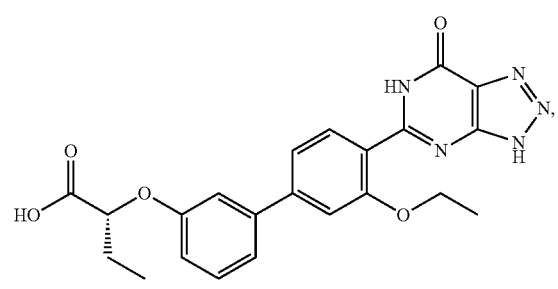
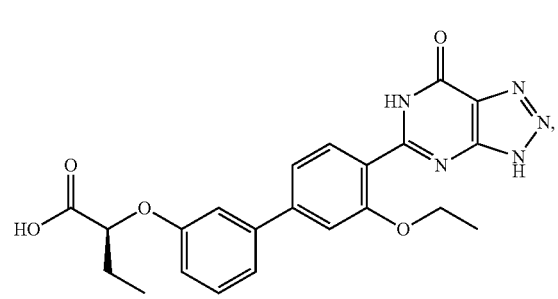
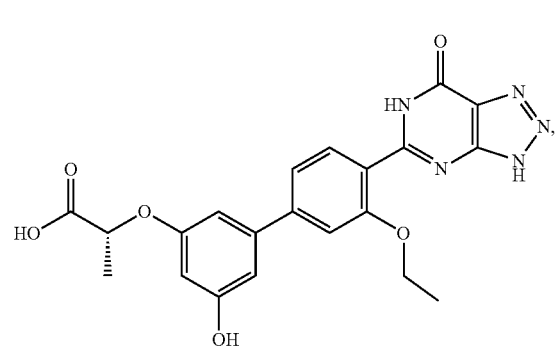
90
-continued
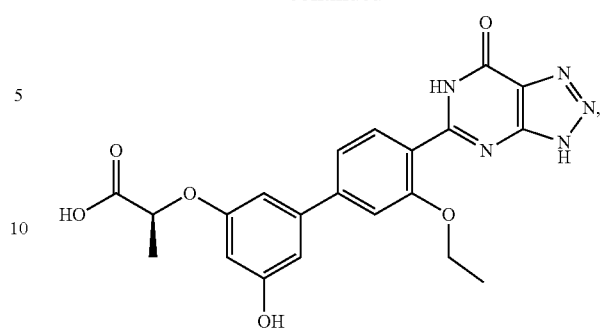
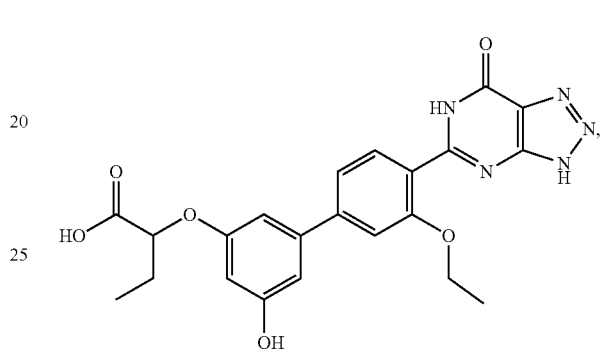
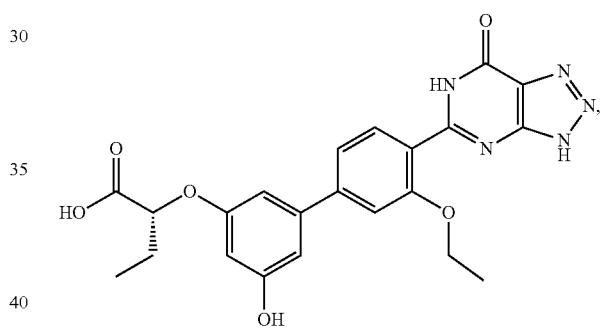
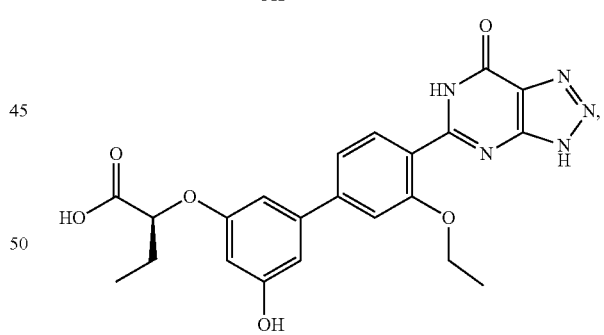
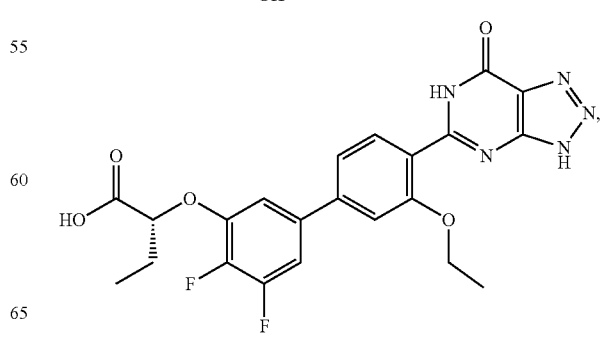

91
-continued
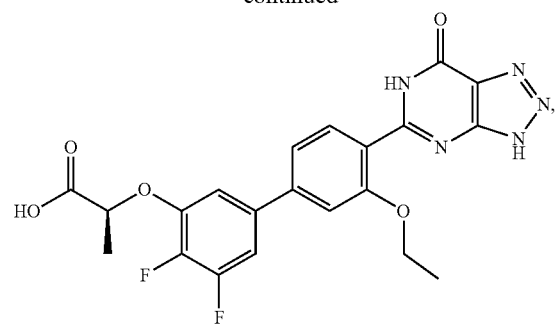
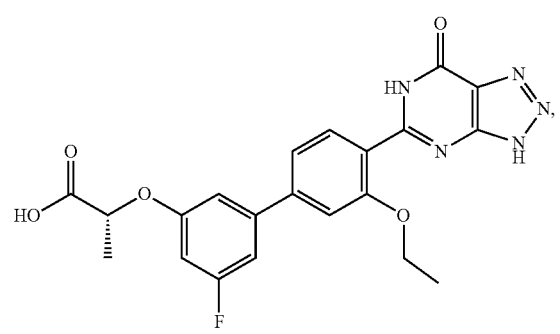
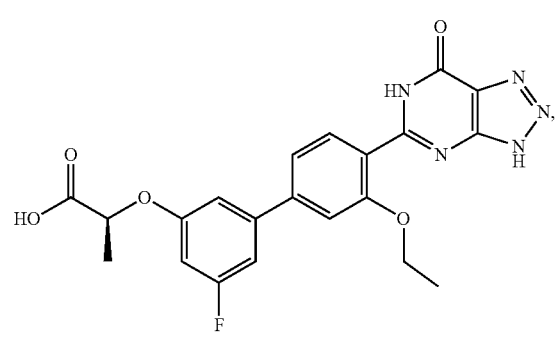
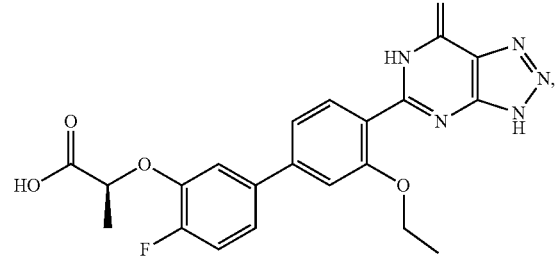
92
-continued
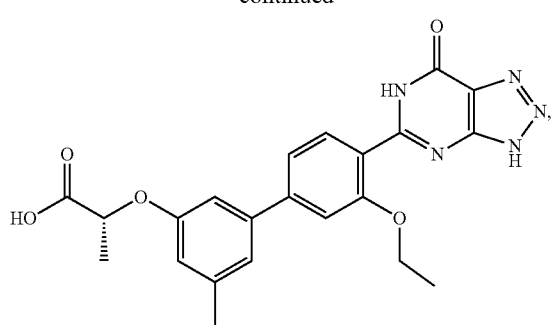
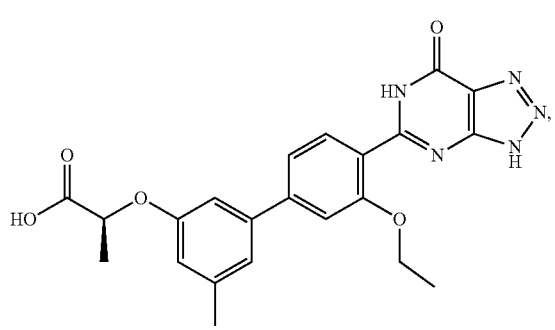
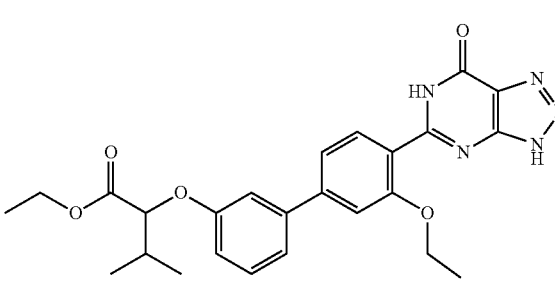
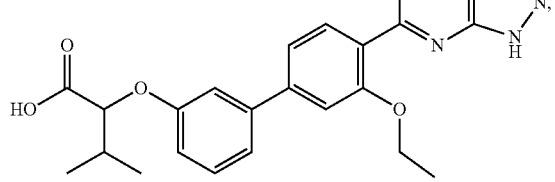
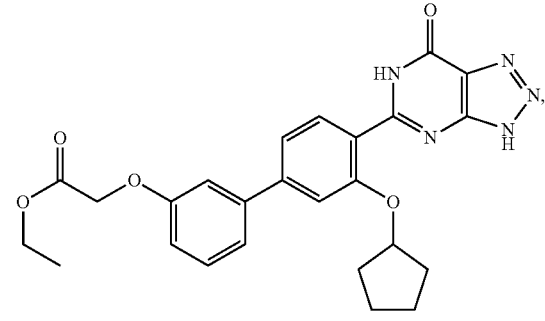

93
-continued
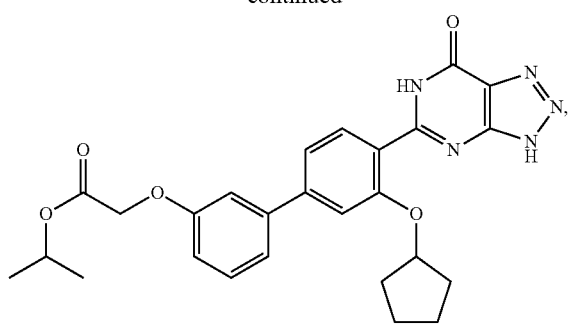
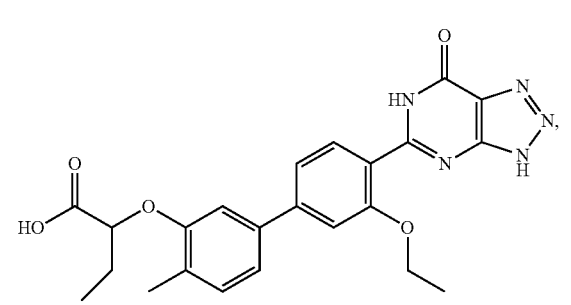
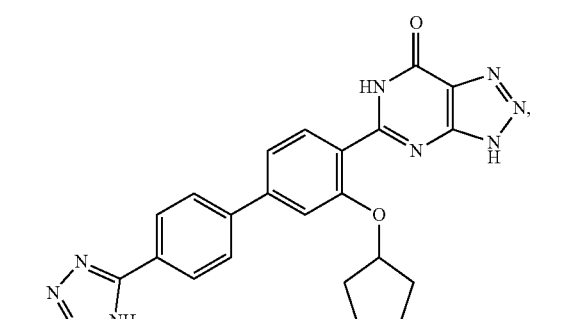
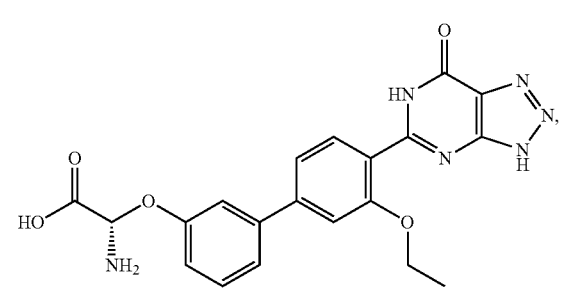
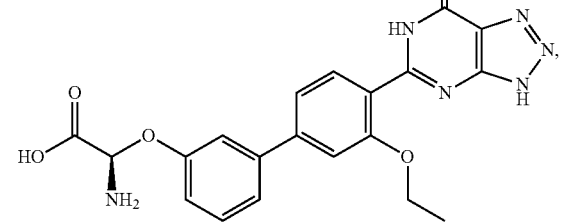
94
-continued
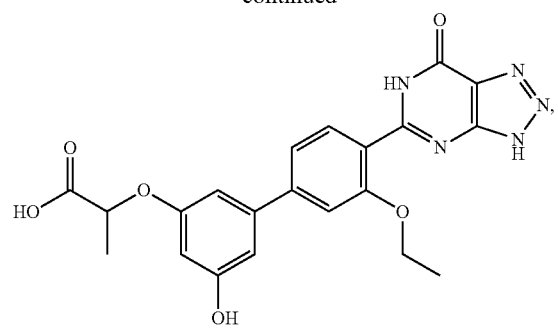
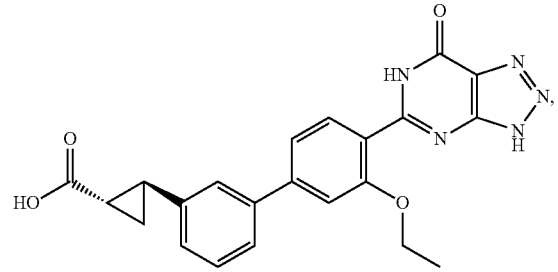
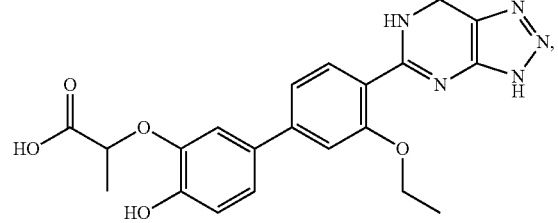
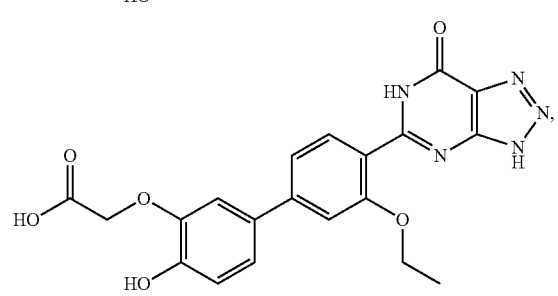
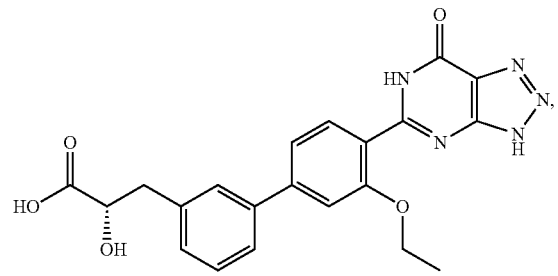
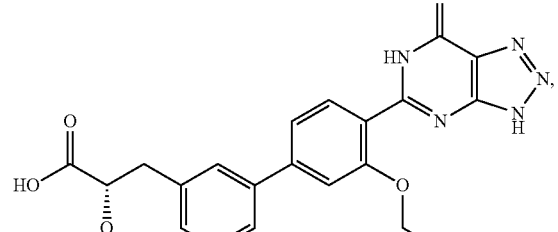

95
-continued
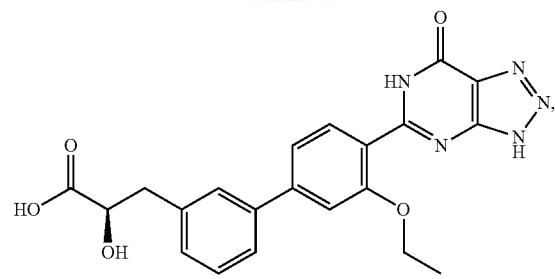
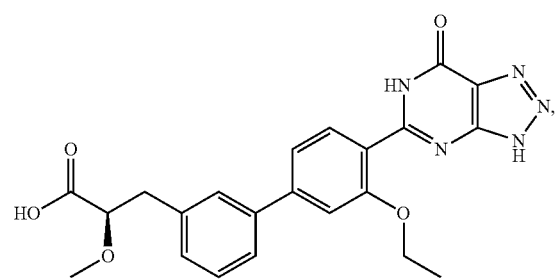
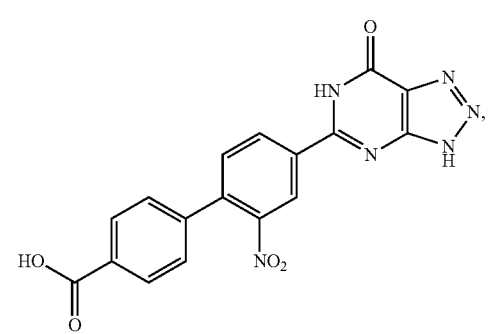
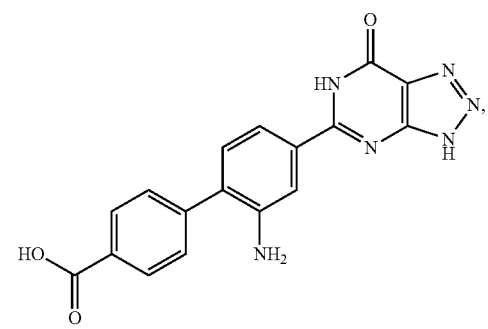
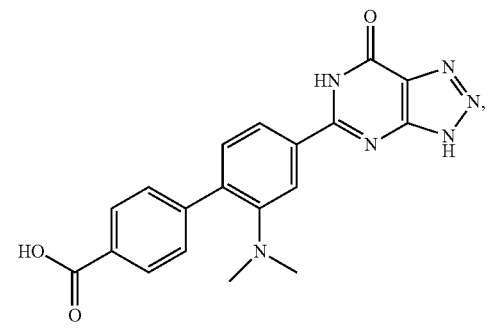
96
-continued
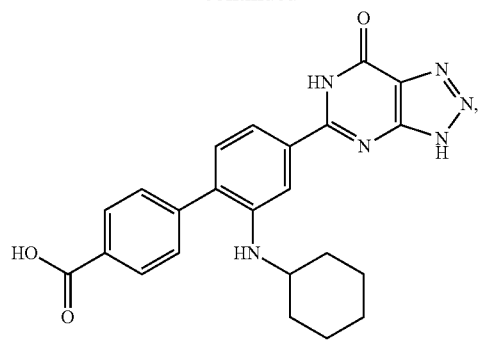
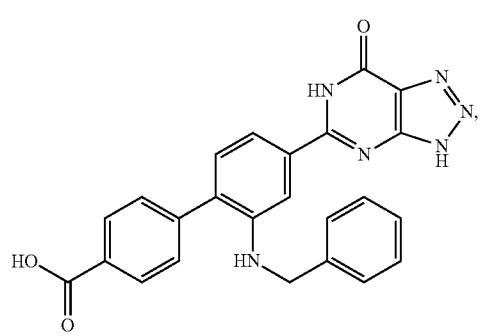
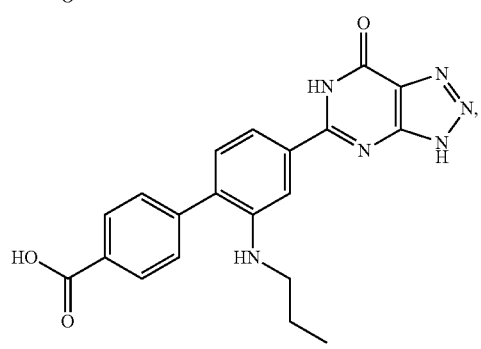
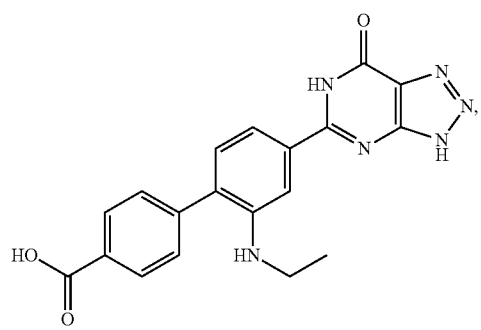
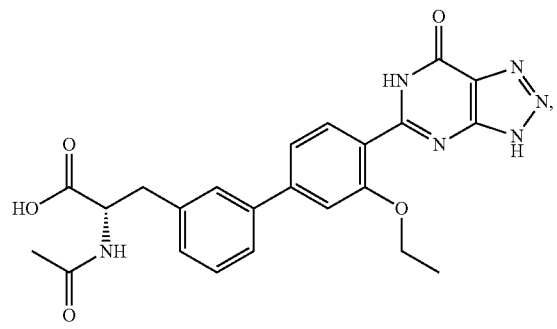

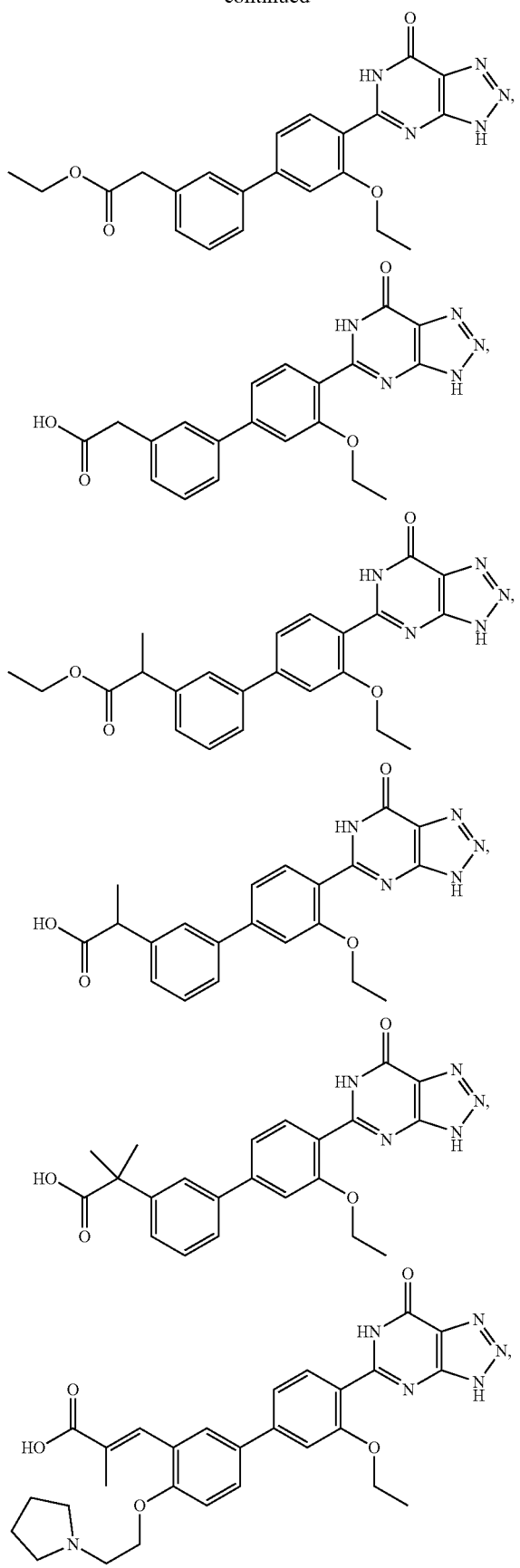
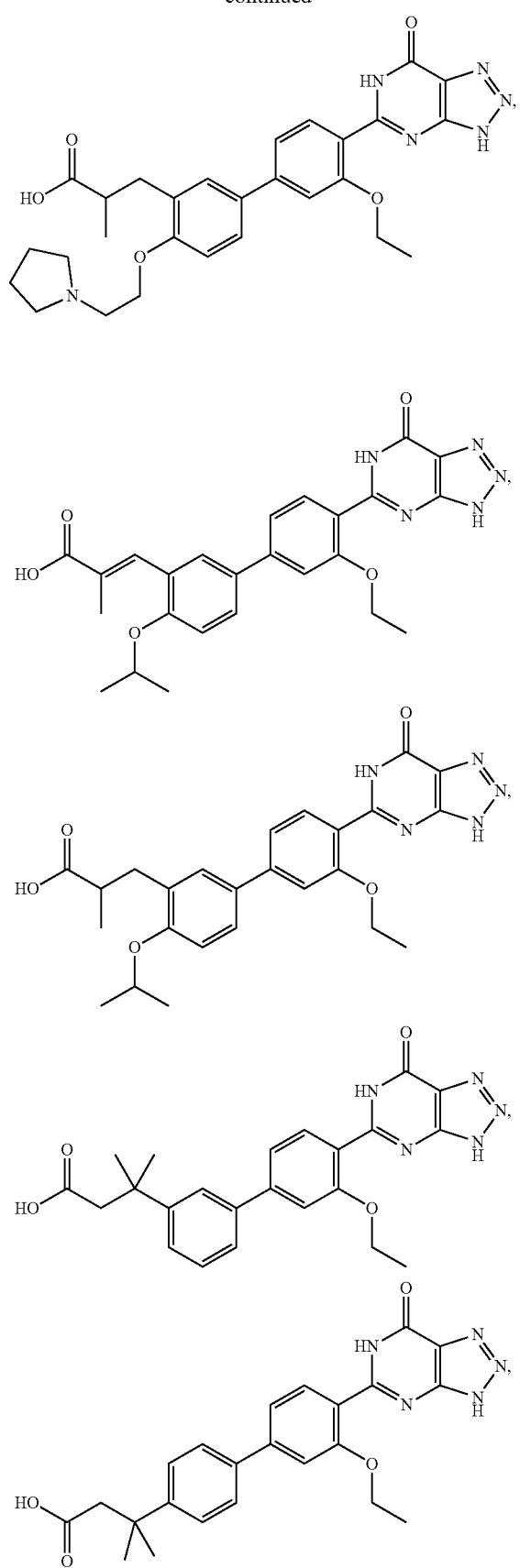

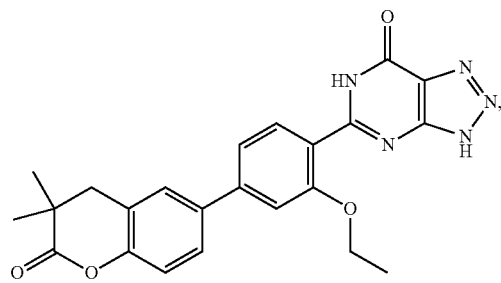

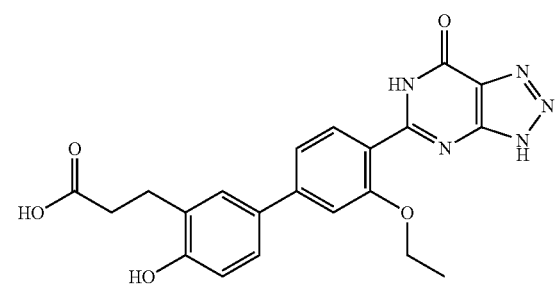
and

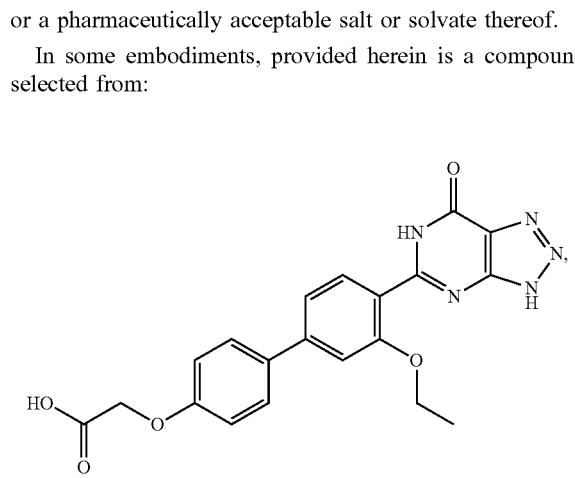

or a pharmaceutically acceptable salt or solvate thereof.

In some embodiments, provided herein is a compound selected from:

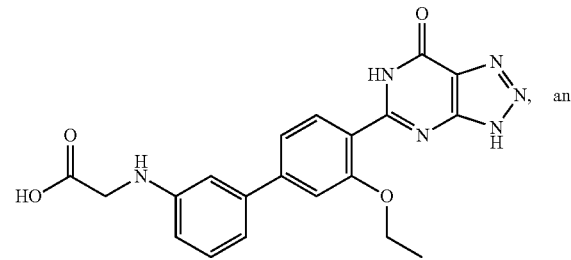

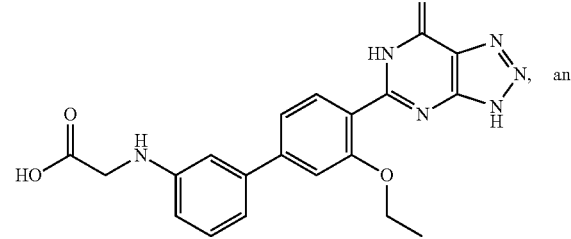
and

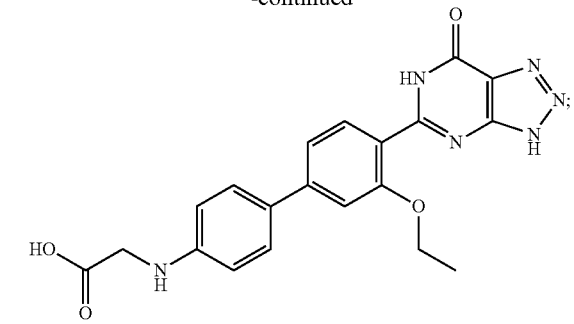

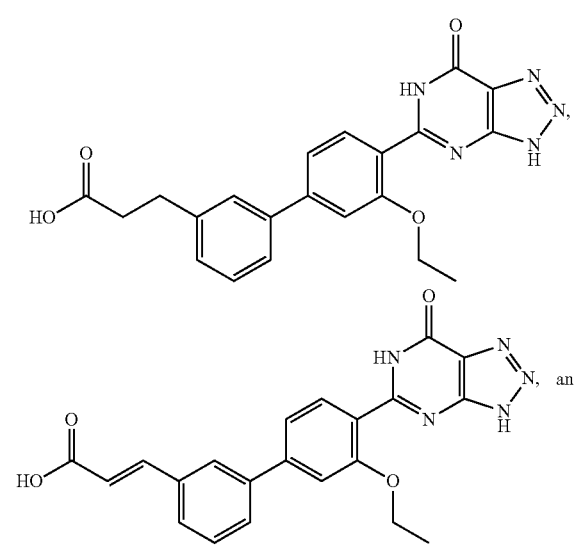

or a pharmaceutically acceptable salt or solvate thereof.

In some embodiments, provided herein is a compound selected from:

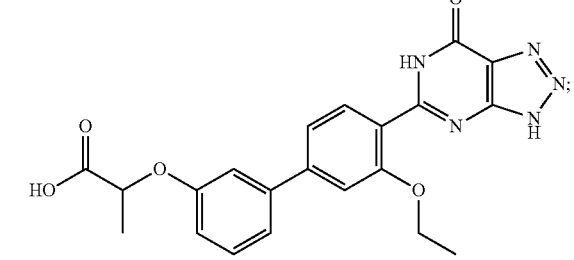

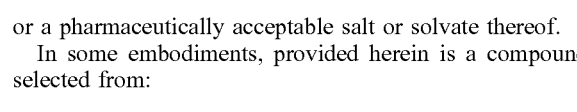
and

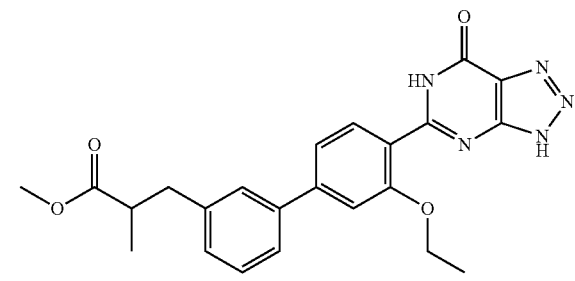

or a pharmaceutically acceptable salt or solvate thereof.

In some embodiments, provided herein is a compound selected from:

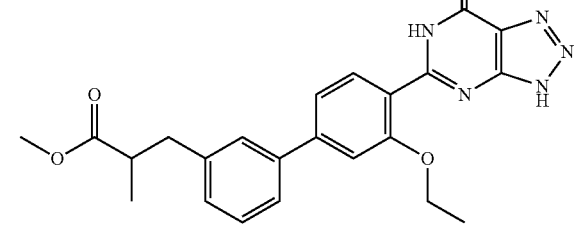

101
-continued
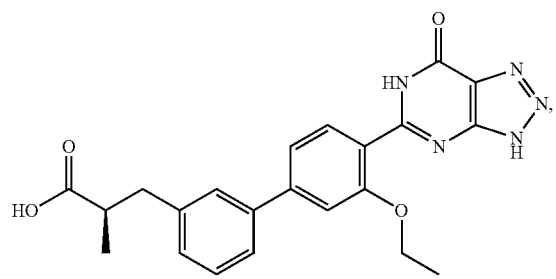
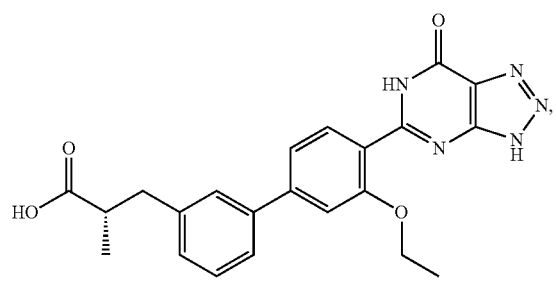
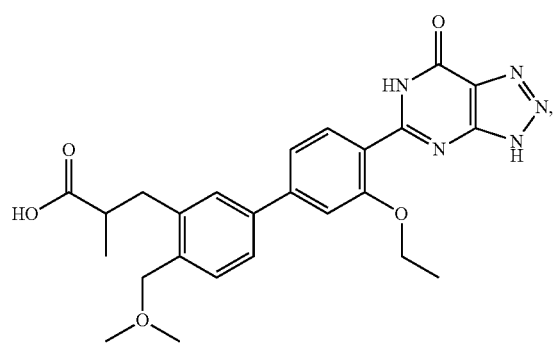
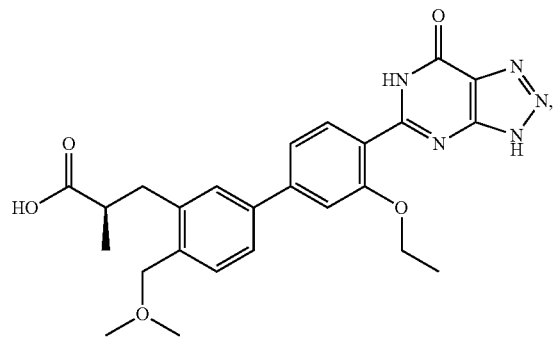
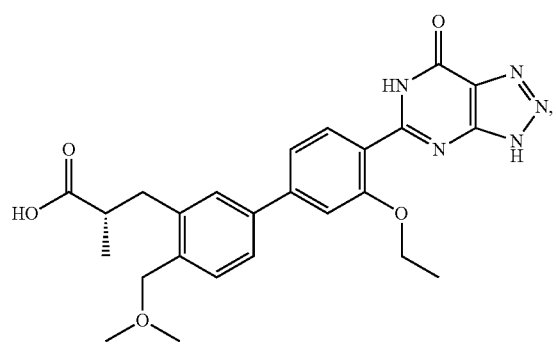
102
-continued
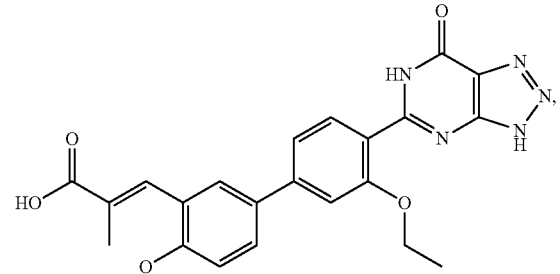
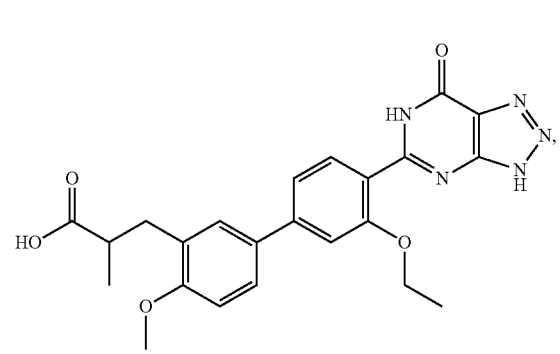
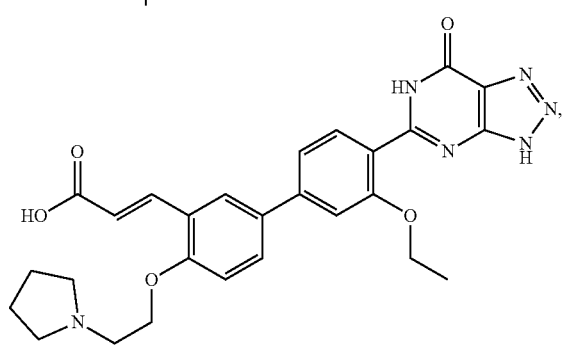
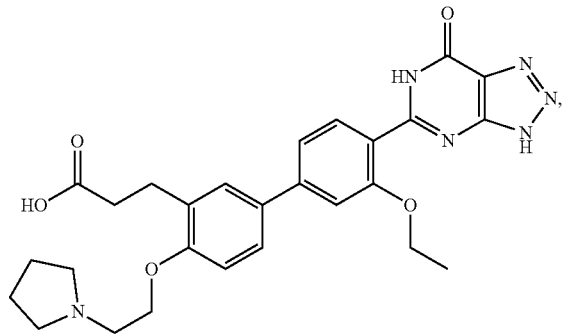
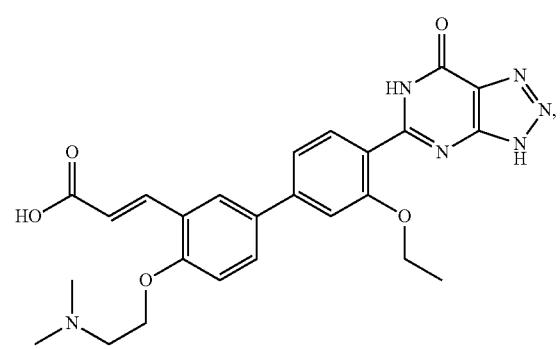

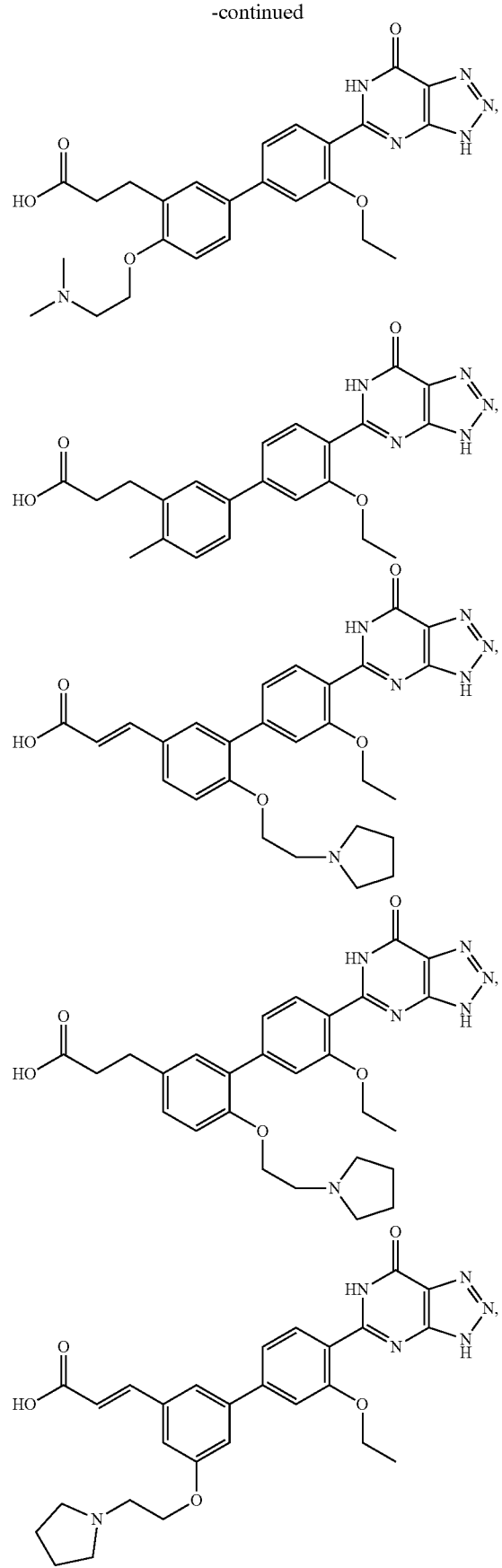
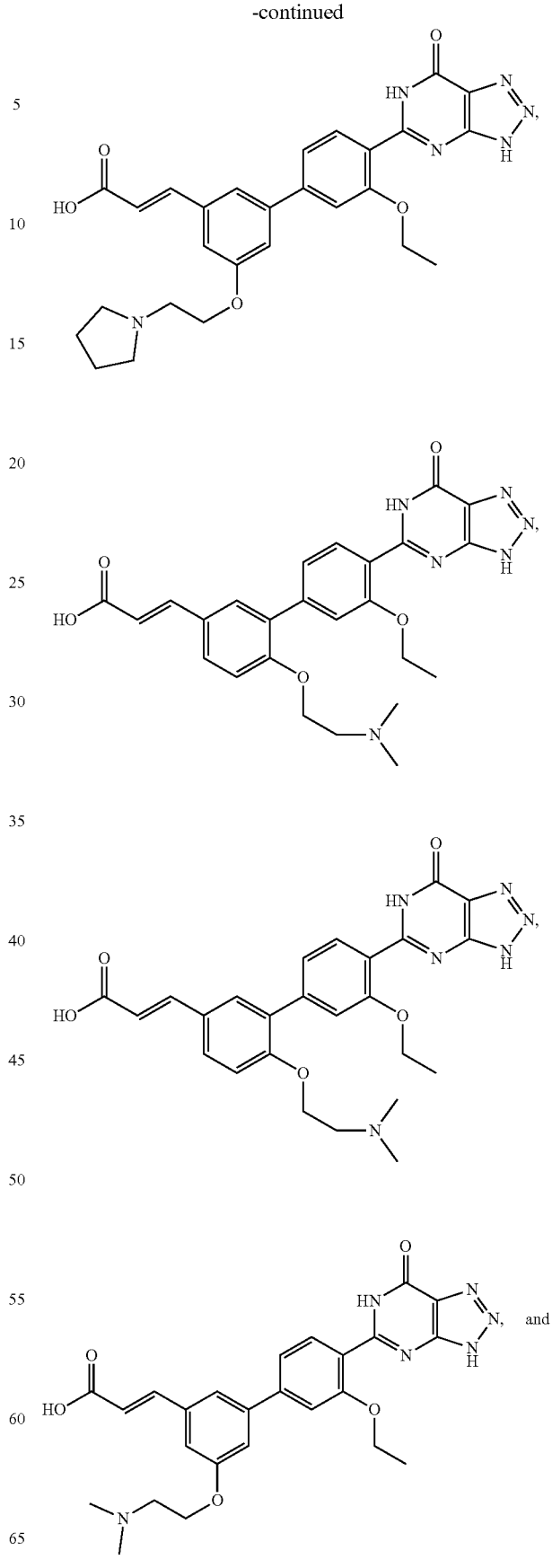

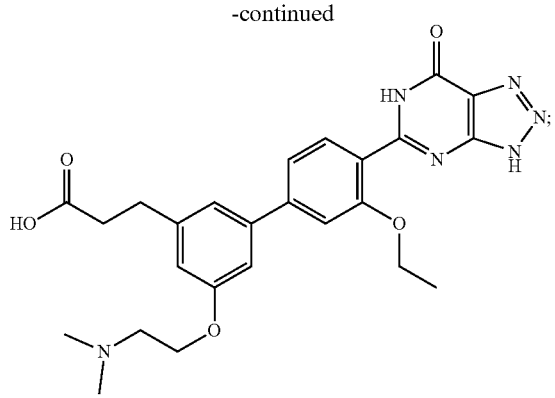

or a pharmaceutically acceptable salt or solvate thereof.

Any combination of the groups described above for the various variables is contemplated herein. Throughout the specification, groups and substituents thereof can be chosen by one skilled in the field to provide stable moieties and compounds.

In some embodiments, the therapeutic agent(s) (e.g. compound of Formula (I), (I'), (I"), (Ia), (Ib), (Ic), or (Id)) is present in the pharmaceutical composition as a pharmaceutically acceptable salt. In some embodiments, any compound described above is suitable for any method or composition described herein.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^{2}H$, $^{3}H$, $^{13}C$, $^{14}C$, $^{5}N$, $^{17}O$, $^{18}O$, $^{31}P$, $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd$^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

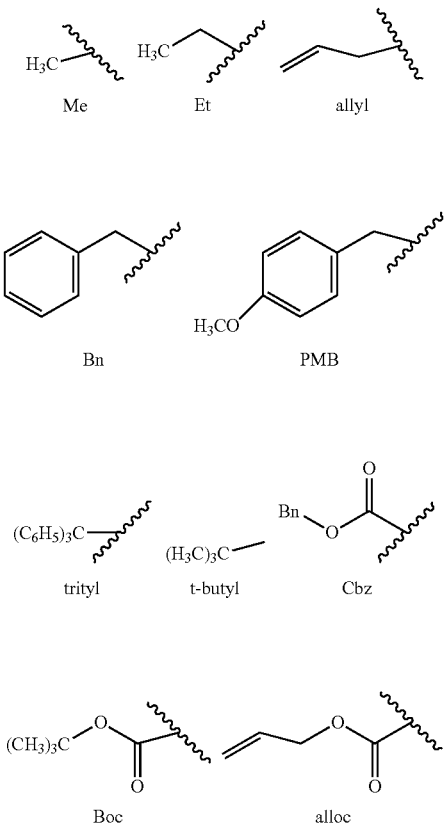

-continued

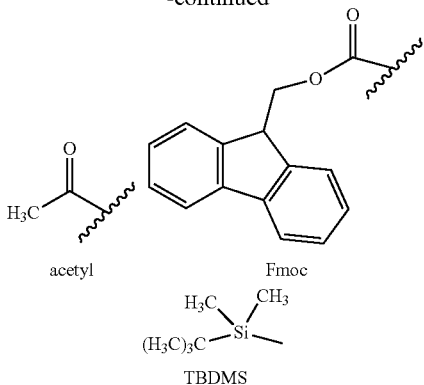

acetyl        Fmoc

TBDMS

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Methods of Treatment and Prevention

In some embodiments is a method of treating an inflammatory bowel disease in a patient in need thereof, comprising administering to the patient a therapeutically effective amount of a compound of Formula (I), (I'), (I"), (Ia), (Ib), (Ic), or (Id), or a pharmaceutically acceptable salt or solvate thereof. In some embodiments is a method of treating an inflammatory bowel disease in a patient in need thereof, comprising administering to the patient a therapeutically effective amount of a compound of Formula (I), (I'), (I"), (Ia), (Ib), (Ic), or (Id), or a pharmaceutically acceptable salt or solvate thereof, wherein the inflammatory bowel disease is selected from Crohn's disease, ulcerative colitis, and perianal Crohn's disease. In some embodiments is a method of treating an inflammatory bowel disease in a patient in need thereof, comprising administering to the patient a therapeutically effective amount of a compound of Formula (I), (I'), (I"), (Ia), (Ib), (Ic), or (Id), or a pharmaceutically acceptable salt or solvate thereof, wherein the inflammatory bowel disease is Crohn's disease. In some embodiments is a method of treating an inflammatory bowel disease in a patient in need thereof, comprising administering to the patient a therapeutically effective amount of a compound of Formula (I), (I'), (I"), (Ia), (Ib), (Ic), or (Id), or a pharmaceutically acceptable salt or solvate thereof, wherein the inflammatory bowel disease is ulcerative colitis. In some cases, the ulcerative colitis is a severe form of ulcerative colitis. In some cases, the severe form of ulcerative colitis is medically refractory ulcerative colitis. In some embodiments is a method of treating an inflammatory bowel disease in a patient in need thereof, comprising administering to the patient a therapeutically effective amount of a compound of Formula (I), (I'), (I"), (Ia), (Ib), (Ic), or (Id), or a pharmaceutically acceptable salt or solvate thereof, wherein the inflammatory bowel disease is perianal Crohn's disease.

Pharmaceutical Compositions and Methods of Administration

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some embodiments is a pharmaceutical composition comprising a pharmaceutically acceptable carrier and a compound of Formula (I), (I'), (I"), (Ia), (Ib), (Ic), or (Id), or a pharmaceutically acceptable salt or solvate thereof. In some embodiments is a pharmaceutical composition comprising a pharmaceutically acceptable carrier and a compound of Formula (I), or a pharmaceutically acceptable salt or solvate thereof. In some embodiments is a pharmaceutical composition comprising a pharmaceutically acceptable carrier and a compound of Formula (I'), or a pharmaceutically acceptable salt or solvate thereof. In some embodiments is a pharmaceutical composition comprising a pharmaceutically acceptable carrier and a compound of Formula (I"), or a pharmaceutically acceptable salt or solvate thereof. In some embodiments is a pharmaceutical composition comprising a pharmaceutically acceptable carrier and a compound of Formula (Ia), or a pharmaceutically acceptable salt or solvate thereof. In some embodiments is a pharmaceutical composition comprising a pharmaceutically acceptable carrier and a compound of Formula (Ib), or a pharmaceutically acceptable salt or solvate thereof. In some embodiments is a pharmaceutical composition comprising a pharmaceutically acceptable carrier and a compound of Formula (Ic), or a pharmaceutically acceptable salt or solvate thereof. In some embodiments is a pharmaceutical composition comprising a pharmaceutically acceptable carrier and a compound of Formula (Id), or a pharmaceutically acceptable salt or solvate thereof.

Another embodiment provides a pharmaceutical composition consisting essentially of a pharmaceutically acceptable carrier and a compound of Formula (I), (I'), (I"), (Ia), (Ib), (Ic), or (Id), or a pharmaceutically acceptable salt or solvate thereof. In some embodiments is a pharmaceutical composition consisting essentially of a pharmaceutically acceptable carrier and a compound of Formula (I), or a pharmaceutically acceptable salt or solvate thereof. In some embodiments is a pharmaceutical composition consisting essentially of a pharmaceutically acceptable carrier and a compound of Formula (I'), or a pharmaceutically acceptable salt or solvate thereof. In some embodiments is a pharmaceutical composition consisting essentially of a pharmaceutically acceptable carrier and a compound of Formula (I"), or a pharmaceutically acceptable salt or solvate thereof. In some embodiments is a pharmaceutical composition consisting essentially of a pharmaceutically acceptable carrier and a compound of Formula (Ia), or a pharmaceutically acceptable salt or solvate thereof. In some embodiments is a pharmaceutical composition consisting essentially of a pharmaceutically acceptable carrier and a compound of Formula (Ib), or a pharmaceutically acceptable salt or solvate thereof. In some embodiments is a pharmaceutical composition consisting essentially of a pharmaceutically acceptable carrier and a compound of Formula (Ic), or a pharmaceutically acceptable salt or solvate thereof. In some embodiments is a pharmaceutical composition consisting essentially of a pharmaceutically acceptable carrier and a compound of Formula (Id), or a pharmaceutically acceptable salt or solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

In some embodiments, compositions and compounds described herein are administered to subjects in a biologically compatible form suitable for topical administration. Topical administration may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the compound of Formula (I), (I'), (I''), (Ia), (Ib), (Ic), or (Id) and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of a compound of Formula (I), (I'), (I''), (Ia), (Ib), (Ic), or (Id) can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

EXAMPLES

The following examples are offered for purposes of illustration and are not intended to limit the scope of the claims provided herein.

As used above, and throughout the description of the invention, the following abbreviations, unless otherwise indicated, shall be understood to have the following meanings:

ACN or MeCN acetonitrile
AcOH acetic acid
$AlMe_3$ trimethylaluminum
Bn benzyl
BOC or Boc t-butyl carbamate
CDI 1,1'-carbonyldiimidazole
$Cy_3P\ BF_4$ tricyclohexylphosphonium tetrafluoroborate
DCE dichloroethane
DCM dichloromethane
DDQ 2,3-dichloro-5,6-dicyano-p-benzoquinone DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EA or EtOAc ethyl acetate
HPLC high performance liquid chromatography
LAH lithium aluminum hydride
Me methyl
MeOH methanol
MS mass spectroscopy
NMM N-methylmorpholine
NMR nuclear magnetic resonance
Pd(dppf)Cl₂ [1,1'-bis(diphenylphosphino)ferrocene]dichloropalladium(II)
Pd(DTBPF)Cl₂ [1,1'-bis(di-tert-butylphosphino)ferrocene]dichloropalladium(II)
Pd(OAc)₂ palladium(II) acetate
PMB para-methoxybenzyl
TEA triethylamine
TFA trifluoroacetic acid
THF tetrahydrofuran Example 1: Synthesis of 5-(3-Ethoxy-[1,1'-biphenyl]-4-yl)-3,6-dihydro-7H-[1,2,3]triazolo[4,5-d]pyrimidin-7-one (Compound 101)

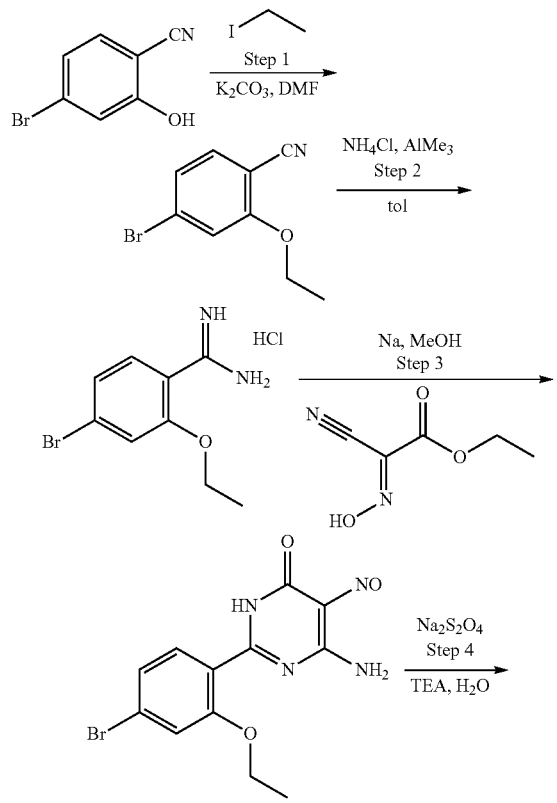

-continued

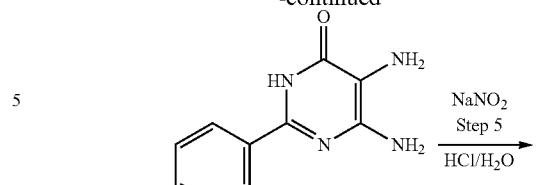

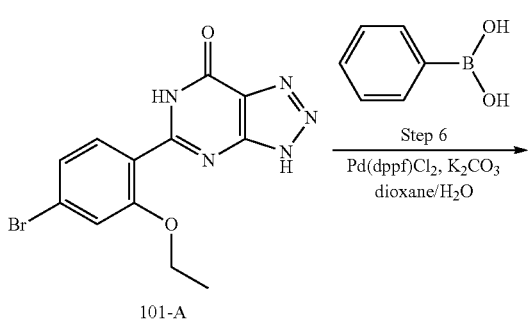

101-A

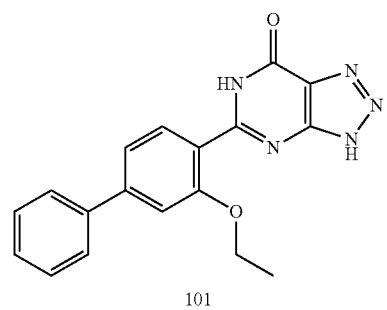

101

Step 1: To a stirred solution of 4-bromo-2-hydroxybenzonitrile (3.00 g, 15.2 mmol, 1.00 equiv) and K₂CO₃ (4.19 g, 30.3 mmol, 2.00 equiv) in DMF (30.0 mL) was added ethyl iodide (3.07 g, 19.7 mmol, 1.30 equiv) at room temperature. The resulting mixture was stirred overnight. The resulting mixture was diluted with water (100 mL). The precipitated solids were collected by filtration and washed with water (2×20 mL). The resulting solid was dried under infrared lamp. This resulted in 4-bromo-2-ethoxybenzonitrile (3 g, 88%) as an off-white solid.

To Step 2: To a stirred mixture of NH₄Cl (2.37 g, 44.2 mmol, 4.00 equiv) in toluene (20.0 mL) was added AlMe₃ (22.1 mL, 44.2 mmol, 4.00 equiv) dropwise at room temperature under N₂ atmosphere. The resulting mixture was stirred for 30 min at room temperature. To the above mixture was added 4-bromo-2-ethoxybenzonitrile (2.50 g, 11.1 mmol, 1.00 equiv). The resulting mixture was stirred for additional 16 h at 110° C. The mixture was allowed to cool down to 0° C. The reaction was quenched by the addition of methanol (50 mL) dropwise. The solid was filtered out and the filter cake was washed with methanol (3×30 mL) and DCM (3×30 mL). The filtrate was concentrated under reduced pressure till a small amount of solvent remained. The residue was diluted with EA (30 mL) and the precipitated solids were collected by filtration and washed with EA (2×20 mL). The resulting solid was dried with infrared lamp. This resulted in 4-bromo-2-ethoxybenzenecarboximidamide hydrochloride (3 g, 97%) as a white solid. LCMS (ESI)=243.1, 245.1 [M+H]$^+$.

Step 3: To a stirred solution of MeOH (30 mL) was added Na (0.99 g, 42.9 mmol, 4.00 equiv) in portions at room temperature under N$_2$ atmosphere. The resulting mixture was stirred until the solid was dissolved completely at room temperature. To the above mixture was added 4-bromo-2-ethoxybenzenecarboximidamide hydrochloride (3.00 g, 10.7 mmol, 1.00 equiv) and (E)-(ethyl cyano(hydroxyimino)formate) (3.05 g, 21.5 mmol, 2.00 equiv). The resulting mixture was refluxed overnight. The mixture was allowed to cool down to room temperature. The reaction was quenched by the addition of water (100 mL). The mixture was acidified to pH 5.0 with AcOH. The precipitated solids were collected by filtration and washed with water (3×20 mL). The resulting solid was dried with an infrared light. This resulted in 6-amino-2-(4-bromo-2-ethoxyphenyl)-5-nitroso-3H-pyrimidin-4-one (3 g, 82%) as a green solid. LCMS (ESI)=338.8, 340.8 [M+H]$^+$.

Step 4: To a stirred solution of 6-amino-2-(4-bromo-2-ethoxyphenyl)-5-nitroso-3H-pyrimidin-4-one (2.00 g, 5.90 mmol, 1.00 equiv) in water (20.0 mL) and TEA (4.00 mL) was added Na$_2$S$_2$O$_4$ (3.08 g, 17.7 mmol, 3.00 equiv) at room temperature. The resulting mixture was stirred for 30 min at room temperature. The resulting mixture was diluted with water (20 mL). The mixture was acidified to pH 5.0 with AcOH. The precipitated solids were collected by filtration and washed with water (2×10 mL). The resulting solid was dried with an infrared light. This resulted in 5,6-diamino-2-(4-bromo-2-ethoxyphenyl)-3H-pyrimidin-4-one (1 g, 52%) as a green solid. LCMS (ESI)=325.1, 327.1 [M+H]$^+$.

Step 5: To a stirred solution of 5,6-diamino-2-(4-bromo-2-ethoxyphenyl)-3H-pyrimidin-4-one) in HCl (6M) (10.0 mL) was added sodium nitrite (0.42 g, 6.15 mmol, 2.00 equiv) in portions at 0° C. The resulting mixture was stirred for 1 h at room temperature. The resulting mixture was diluted with water (30 mL). The precipitated solids were collected by filtration and washed with water (2×10 mL). The crude product was purified by preparative HPLC to afford 5-(4-bromo-2-ethoxyphenyl)-3,6-dihydro-7H-[1,2,3]triazolo[4,5-d]pyrimidin-7-one (600 mg, 58%) as a white solid. LCMS (ESI)=336.0, 337.9 [M+H]+. 1H NMR (300 MHz, DMSO-d$_6$) δ 12.26 (s, 1H), 7.63 (d, J=8.2 Hz, 1H), 7.41 (d, J=1.7 Hz, 1H), 7.30 (dd, J=8.3, 1.7 Hz, 1H), 4.17 (q, J=6.9 Hz, 2H), 1.32 (t, J=6.9 Hz, 3H).

Step 6: Into an 8-mL sealed tube purged and maintained with an inert atmosphere of nitrogen, was placed 5-(4-bromo-2-ethoxyphenyl)-3,6-dihydro-7H-[1,2,3]triazolo[4,5-d]pyrimidin-7-one (30 mg, 1 equiv), phenylboronic acid (21.7 mg, 2 equiv), dioxane (0.5 mL), H$_2$O (0.1 mL), K$_2$CO$_3$ (36.9 mg, 3 equiv), Pd(dppf)Cl$_2$ (6.5 mg, 0.1 equiv). The resulting solution was stirred for 2 h at 100° C. in an oil bath. The solids were filtered out. The resulting mixture was concentrated under vacuum. The crude product was purified by preparative HPLC to afford 5-(3-ethoxy-[1,1'-biphenyl]-4-yl)-3,6-dihydro-7H-[1,2,3]triazolo[4,5-d]pyrimidin-7-one (Compound 101) (12 mg, 40%) as a light yellow solid. LCMS (ESI)=334 [M+H]$^+$. $^1$H NMR (300 MHz, DMSO-d6) δ 12.24 (s, 1H), 7.87 (d, J=8.0 Hz, 1H), 7.79 (d, J=7.1 Hz, 2H), 7.52 (t, J=7.3 Hz, 2H), 7.44 (q, J=7.5 Hz, 3H), 4.31 (q, J=6.9 Hz, 2H), 1.40 (t, J=6.9 Hz, 3H)

Example 2: Synthesis of 5-(2-Ethoxy-4-(pyridin-3-yl)phenyl)-3,6-dihydro-7H-[1,2,3]triazolo[4,5-d]pyrimidin-7-one (Compound 102)

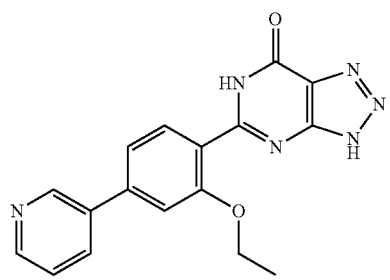

5-(2-Ethoxy-4-(pyridin-3-yl)phenyl)-3,6-dihydro-7H-[1,2,3]triazolo[4,5-d]pyrimidin-7-one (Compound 102) was prepared using the procedure of Step 6, Example 1 from 5-(4-bromo-2-ethoxyphenyl)-3,6-dihydro-7H-[1,2,3]triazolo[4,5-d]pyrimidin-7-one and pyridin-3-ylboronic acid. LCMS (ESI)=335.1 [M+H]$^+$. $^1$H NMR (300 MHz, DMSO-d$_6$) δ 12.34 (s, 1H), 9.23 (d, J=1.8 Hz, 1H), 8.81 (dd, J=5.2, 1.3 Hz, 1H), 8.64 (d, J=8.0 Hz, 1H), 7.88 (dd, J=8.0, 3.6 Hz, 2H), 7.61 (s, 1H), 7.55 (dd, J=8.0, 1.5 Hz, 1H), 4.32 (q, J=7.0 Hz, 2H), 1.39 (t, J=6.9 Hz, 3H).

Example 3: Synthesis of 5-(2-Ethoxy-4-(pyrimidin-2-yl)phenyl)-3,6-dihydro-7H-[1,2,3]triazolo[4,5-d]pyrimidin-7-one (Compound 103)

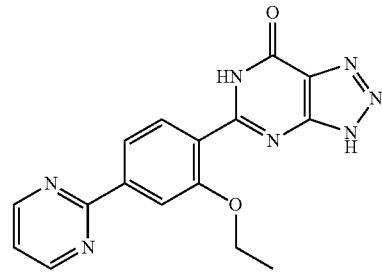

5-(2-Ethoxy-4-(pyrimidin-2-yl)phenyl)-3,6-dihydro-7H-[1,2,3]triazolo[4,5-d]pyrimidin-7-one was prepared using the procedure of Step 6, Example 1 from 5-(4-bromo-2-ethoxyphenyl)-3,6-dihydro-7H-[1,2,3]triazolo[4,5-d]pyrimidin-7-one and 2-(tributylstannyl)pyrimidine. LCMS (ESI)=336.1 [M+H]$^+$.

Example 4: Synthesis of 5-(2-Ethoxy-4-(pyridin-4-yl)phenyl)-3,6-dihydro-7H-[1,2,3]triazolo[4,5-d]pyrimidin-7-one (Compound 104)

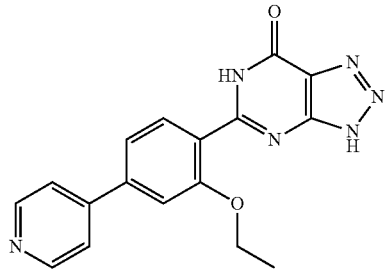

5-(2-Ethoxy-4-(pyridin-4-yl)phenyl)-3,6-dihydro-7H-[1,2,3]triazolo[4,5-d]pyrimidin-7-one was prepared using the procedure of Step 6, Example 1 from 5-(4-bromo-2-ethoxyphenyl)-3,6-dihydro-7H-[1,2,3]triazolo[4,5-d]pyrimidin-7-one and pyridin-4-ylboronic acid. LCMS (ESI)=335.1 [M+H]$^+$.

Example 5: Synthesis of 5-(2-Ethoxy-4-(pyridin-2-yl)phenyl)-3,6-dihydro-7H-[1,2,3]triazolo[4,5-d]pyrimidin-7-one (Compound 105)

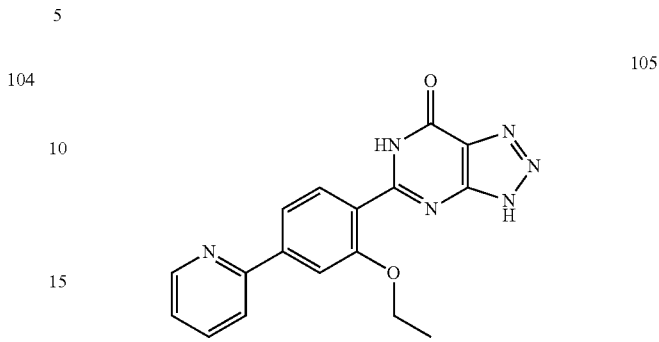

5-(2-Ethoxy-4-(pyridin-2-yl)phenyl)-3,6-dihydro-7H-[1,2,3]triazolo[4,5-d]pyrimidin-7-one was prepared using the procedure of Step 6, Example 1 from 5-(4-bromo-2-ethoxyphenyl)-3,6-dihydro-7H-[1,2,3]triazolo[4,5-d]pyrimidin-7-one and 2-(tributylstannyl)pyridine. LCMS (ESI)=335.1 [M+H]$^+$.

Example 6: Synthesis of Methyl 3'-ethoxy-4'-(7-oxo-6,7-dihydro-3H-[1,2,3]triazolo[4,5-d]pyrimidin-5-yl)-[1,1'-biphenyl]-2-carboxylate (Compound 106)

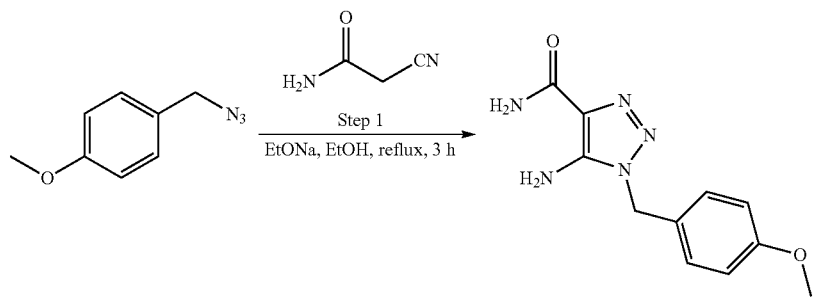

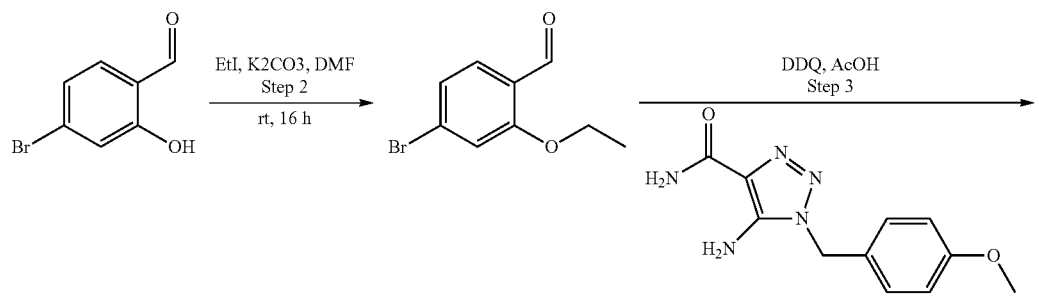

-continued

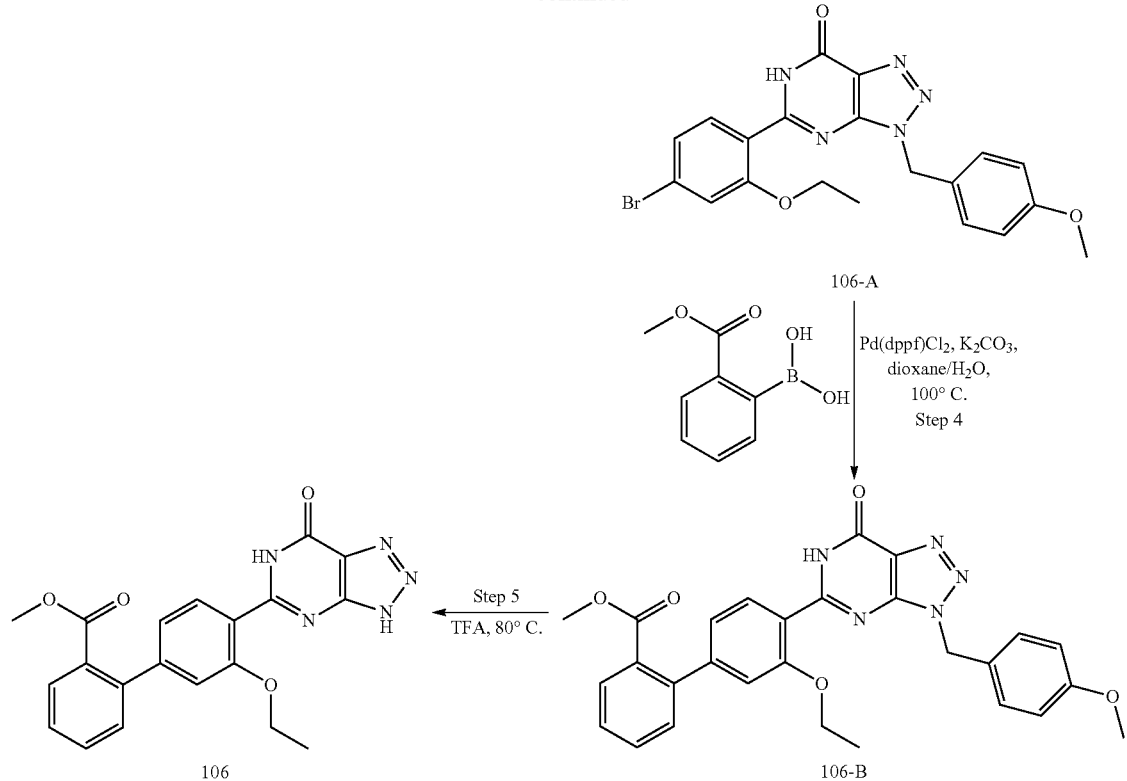

Step 1: To a stirred solution of 1-(azidomethyl)-4-methoxybenzene (5.00 g, 30.6 mmol, 1.00 equiv) and cyanoacetamide (2.58 g, 30.6 mmol, 1.00 equiv) in EtOH (50.0 mL) was added EtONa (6.26 g, 91.9 mmol, 3.00 equiv) at room temperature under $N_2$ atmosphere. The resulting mixture was stirred for 3 h at 78° C. under $N_2$ atmosphere. The mixture was allowed to cool down to room temperature. The precipitated solids were collected by filtration and washed with EtOH (2×10 mL). The resulting solid was dried under an infrared lamp. This resulted in 5-amino-1-[(4-methoxyphenyl)methyl]-1,2,3-triazole-4-carboxamide (3 g, 40%) as a grey solid.

Step 2: To a stirred solution of 4-bromo-2-hydroxybenzaldehyde (2.00 g, 9.949 mmol, 1.00 equiv) and K2CO3 (2.75 g, 19.9 mmol, 2.00 equiv) in DMF (20.0 mL) was added ethyl iodide (1.86 g, 11.9 mmol, 1.20 equiv) at room temperature. The resulting mixture was stirred overnight at room temperature. The resulting mixture was diluted with water (100 mL). The precipitated solids were collected by filtration and washed with water (2×20 mL). The resulting solid was dried under an infrared lamp. This resulted in 4-bromo-2-ethoxybenzaldehyde (1.9 g, 83%) as a white solid.

Step 3: To a stirred solution of 5-amino-1-[(4-methoxyphenyl)methyl]-1,2,3-triazole-4-carboxamide (1.50 g, 6.07 mmol, 1.00 equiv) and 4-bromo-2-ethoxybenzaldehyde (2.08 g, 9.10 mmol, 1.50 equiv) in AcOH (20.0 mL) was added DDQ (2.75 g, 12.1 mmol, 2.00 equiv) at room temperature. The resulting mixture was stirred for 24 h at 80° C. The mixture was allowed to cool to room temperature. The resulting mixture was diluted with water (50 mL). The precipitated solids were collected by filtration and washed with water (2×10 mL). The residue was re-dissolved with sodium bicarbonate aqueous solution (50 mL). The precipitated solids were collected by filtration and washed with sodium bicarbonate aqueous solution (2×10 mL) and water (2×10 mL). The resulting solid was dried under an infrared lamp. This resulted in 5-(4-bromo-2-ethoxyphenyl)-3-(4-methoxybenzyl)-3,6-dihydro-7H-[1,2,3]triazolo[4,5-d]pyrimidin-7-one (Compound 106-A) (1.5 g, crude) as a grey solid. The crude product (30 mg) was purified by preparative HPLC to afford 5-(4-bromo-2-ethoxyphenyl)-3-(4-methoxybenzyl)-3,6-dihydro-7H-[1,2,3]triazolo[4,5-d]pyrimidin-7-one (7 mg) as a white solid. LCMS (ESI)=456 [M+H]+. $^1$H NMR (300 MHz, DMSO-$d_6$) δ 12.44 (s, 1H), 7.68 (d, J=8.3 Hz, 1H), 7.43 (d, J=1.5 Hz, 1H), 7.35 (d, J=8.4 Hz, 3H), 6.92 (d, J=8.7 Hz, 2H), 5.69 (s, 2H), 4.18 (q, J=6.9 Hz, 2H), 3.73 (s, 3H), 1.32 (t, J=6.9 Hz, 3H).

Step 4: To a stirred solution of 5-(4-bromo-2-ethoxyphenyl)-3-(4-methoxybenzyl)-3,6-dihydro-7H-[1,2,3]triazolo[4,5-d]pyrimidin-7-one (100 mg, 0.219 mmol, 1.00 equiv), 2-(methoxycarbonyl)phenylboronic acid (78.9 mg, 0.438 mmol, 2.00 equiv) and K2CO3 (90.86 mg, 0.657 mmol, 3.00 equiv) in dioxane/H2O (2/0.20 mL) was added Pd(dppf)Cl2 CH2Cl2 (17.9 mg, 0.022 mmol, 0.10 equiv) at room temperature under $N_2$ atmosphere. The resulting mixture was stirred overnight at 100° C. The mixture was allowed to cool down to room temperature. The resulting mixture was concentrated under reduced pressure. The resulting mixture was diluted with water (2 mL). The precipitated solids were collected by filtration and washed with water (2×2 mL). The resulting solid was dried under an infrared lamp. This resulted in methyl 3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-2-carboxylate (100 mg, 89%) as a grey solid.

Step 5: A solution of methyl 3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-2-carboxylate (100 mg, 0.195 mmol, 1 equiv) in 2,2,2-trifluoroacetaldehyde (1 mL) was stirred for 2 h at 80° C. The mixture was allowed to cool down to room temperature. The resulting mixture was diluted with water (5 mL). The precipitated solids were collected by filtration and washed with water (2×1 mL). The resulting solid was dried by infrared light. This resulted in methyl 3'-ethoxy-4'-(7-oxo-6,7-dihydro-3H-[1,2,3]triazolo[4,5-d]pyrimidin-5-yl)-[1,1'-biphenyl]-2-carboxylate (90 mg, crude) as a gray solid. The crude product (20 mg) was purified by preparative HPLC to afford methyl 3'-ethoxy-4'-(7-oxo-6,7-dihydro-3H-[1,2,3]triazolo[4,5-d]pyrimidin-5-yl)-[1,1'-biphenyl]-2-carboxylate (5 mg, 6%) as a white solid. LCMS (ESI)=392.1 [M+H]+. $^1$H NMR (300 MHz, DMSO-$d_6$) δ 12.03 (s, 1H), 8.14 (s, 1H), 7.85 (d, J=7.9 Hz, 1H), 7.79 (d, J=7.7 Hz, 1H), 7.68 (t, J=7.6 Hz, 1H), 7.55 (t, J=7.4 Hz, 2H), 7.09 (s, 1H), 7.02 (d, J=8.0 Hz, 1H), 4.20 (q, J=6.7 Hz, 2H), 3.66 (s, 3H), 1.38 (t, J=6.9 Hz, 3H).

Example 7: Synthesis of Methyl 3'-ethoxy-4'-(7-oxo-6,7-dihydro-3H-[1,2,3]triazolo[4,5-d]pyrimidin-5-yl)-[1,1'-biphenyl]-3-carboxylate (Compound 107)

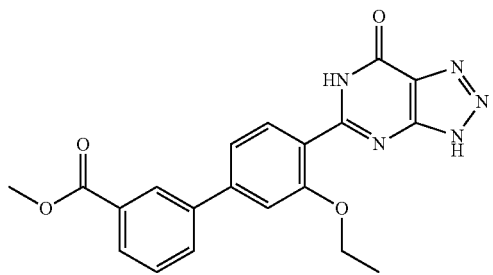

107

Methyl 3'-ethoxy-4'-(7-oxo-6,7-dihydro-3H-[1,2,3]triazolo[4,5-d]pyrimidin-5-yl)-[1,1'-biphenyl]-3-carboxylate was prepared using the procedure of Steps 4 and 5, Example 6, except that (3-(methoxycarbonyl)phenyl)boronic acid was used in Step 4. LCMS (ESI)=392.1 [M+H]+. $^1$H NMR (300 MHz, DMSO-$d_6$) δ 12.22 (s, 1H), 8.28 (s, 1H), 8.06 (dd, J=17.6, 7.8 Hz, 2H), 7.90 (d, J=7.9 Hz, 1H), 7.69 (t, J=7.8 Hz, 1H), 7.52-7.41 (m, 1.8 Hz, 2H), 4.32 (q, J=6.9 Hz, 2H), 3.92 (s, 3H), 1.40 (t, J=6.9 Hz, 3H).

Example 8: Synthesis of Methyl 3'-ethoxy-4'-(7-oxo-6,7-dihydro-3H-[1,2,3]triazolo[4,5-d]pyrimidin-5-yl)-[1,1'-biphenyl]-4-carboxylate (Compound 108)

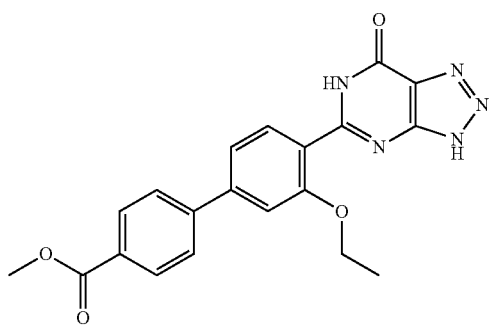

108

Methyl 3'-ethoxy-4'-(7-oxo-6,7-dihydro-3H-[1,2,3]triazolo[4,5-d]pyrimidin-5-yl)-[1,1'-biphenyl]-4-carboxylate was prepared using the procedure of Steps 4 and 5, Example 6, except that (4-(methoxycarbonyl)phenyl)boronic acid was used in Step 4. LCMS (ESI)=392.1 [M+H]+. $^1$H NMR (300 MHz, DMSO-$d_6$) δ 12.26 (s, 1H), 8.09 (d, J=8.5 Hz, 2H), 7.96 (d, J=8.5 Hz, 2H), 7.89 (d, J=7.9 Hz, 1H), 7.56-7.45 (m, 2H), 4.32 (q, J=7.1 Hz, 2H), 3.90 (s, 3H), 1.40 (t, J=6.9 Hz, 3H).

Example 9: Synthesis of 3'-Ethoxy-4'-(7-oxo-6,7-dihydro-3H-[1,2,3]triazolo[4,5-d]pyrimidin-5-yl)-[1,1'-biphenyl]-2-carboxylic Acid (Compound 109)

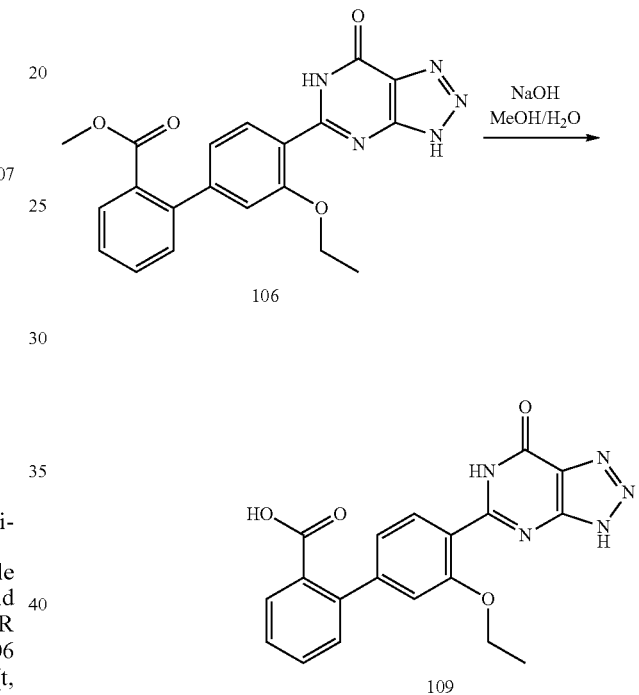

To a stirred solution of methyl 3'-ethoxy-4'-(7-oxo-6,7-dihydro-3H-[1,2,3]triazolo[4,5-d]pyrimidin-5-yl)-[1,1'-biphenyl]-2-carboxylate (70.0 mg, 0.179 mmol, 1.00 equiv) in MeOH/H$_2$O (2/0.4 mL) was added NaOH (35.8 mg, 0.894 mmol, 5.00 equiv) at room temperature under. The resulting mixture was stirred overnight at. The resulting mixture was diluted with water (10 mL). The aqueous layer was extracted with EA (2×5 mL). The mixture was acidified to pH 3-4 with conc.HCl. The resulting mixture was extracted with EA (3×5 mL). The combined organic layers were washed with brine (1×10 mL), dried over anhydrous Na$_2$SO$_4$. After filtration, the filtrate was concentrated under reduced pressure. The crude product was purified by preparative HPLC to afford 3'-ethoxy-4'-(7-oxo-6,7-dihydro-3H-[1,2,3]triazolo[4,5-d]pyrimidin-5-yl)-[1,1'-biphenyl]-2-carboxylic acid (Compound 109) (20.5 mg, 30%) as a white solid. LCMS (ESI)=378.1 [M+H]+. $^1$H NMR (300 MHz, DMSO-$d_6$) δ 12.23 (s, 1H), 7.90-7.73 (m, J=13.7, 4.6 Hz, 2H), 7.69-7.57 (m, J=7.5, 1.4 Hz, 1H), 7.57-7.42 (m, 2H), 7.15 (d, J=1.2 Hz, 1H), 7.07 (dd, J=8.0, 1.4 Hz, 1H), 4.21 (q, J=6.9 Hz, 2H), 1.37 (t, J=6.9 Hz, 3H).

Example 10: Synthesis of 3'-Ethoxy-4'-(7-oxo-6,7-dihydro-3H-[1,2,3]triazolo[4,5-d]pyrimidin-5-yl)-[1,1'-biphenyl]-3-carboxylic Acid (Compound 110)

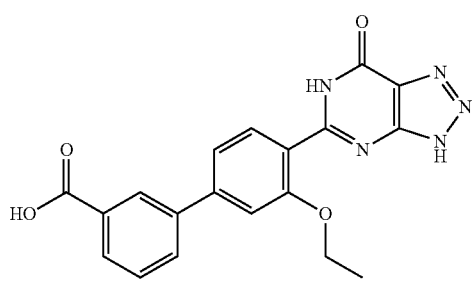

110

3'-Ethoxy-4'-(7-oxo-6,7-dihydro-3H-[1,2,3]triazolo[4,5-d]pyrimidin-5-yl)-[1,1'-biphenyl]-3-carboxylic acid (Compound 110) was prepared from Compound 107 using the procedure of Example 9. LCMS (ESI)=378.1 [M+H]$^+$. $^1$H NMR (300 MHz, DMSO-d$_6$) δ 12.20 (s, 1H), 8.27 (s, 1H), 8.09-7.97 (m, 2H), 7.90 (d, J=7.9 Hz, 1H), 7.66 (t, J=7.8 Hz, 1H), 7.52-7.40 (m, 2H), 4.33 (q, J=6.9 Hz, 2H), 1.40 (t, J=6.9 Hz, 3H).

Example 11: Synthesis of 3'-Ethoxy-4'-(7-oxo-6,7-dihydro-3H-[1,2,3]triazolo[4,5-d]pyrimidin-5-yl)-[1,1'-biphenyl]-4-carboxylic Acid (Compound 111 Palladium(II) Acetate)

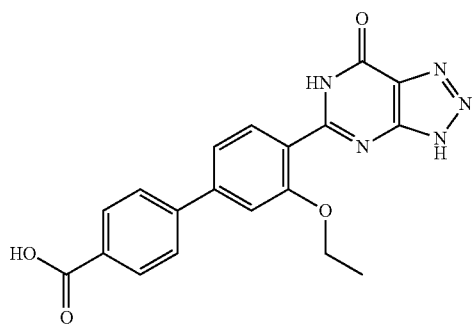

111

3'-Ethoxy-4'-(7-oxo-6,7-dihydro-3H-[1,2,3]triazolo[4,5-d]pyrimidin-5-yl)-[1,1'-biphenyl]-4-carboxylic acid (Compound 111) was prepared from Compound 108 using the procedure of Example 9. LCMS (ESI)=378.1 [M+H]$^+$. $^1$H NMR (300 MHz, DMSO-d$_6$) δ 12.04 (s, 1H), 8.06 (d, J=8.4 Hz, 2H), 7.99-7.87 (m, 3H), 7.56-7.43 (m, 2H), 4.32 (q, J=6.8 Hz, 2H), 1.40 (t, J=6.9 Hz, 3H).

Example 12: Synthesis of Methyl 5-(3-ethoxy-4-(7-oxo-6,7-dihydro-3H-[1,2,3]triazolo[4,5-d]pyrimidin-5-yl)phenyl)nicotinate (Compound 112)

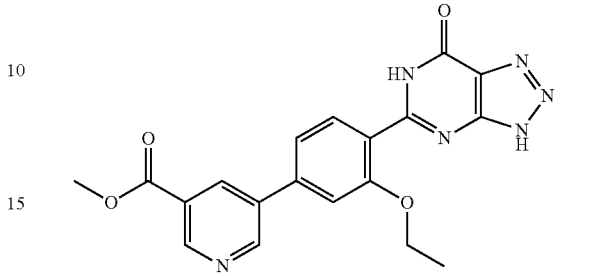

112

Methyl 5-(3-ethoxy-4-(7-oxo-6,7-dihydro-3H-[1,2,3]triazolo[4,5-d]pyrimidin-5-yl)phenyl)nicotinate (Compound 112) was prepared using the procedure of Steps 4 and 5, Example 6, except that (5-(methoxycarbonyl)pyridin-3-yl)boronic acid was used in Step 4. LCMS (ESI)=393.2 [M+H]$^+$.

Example 13: Synthesis of 5-(3-Ethoxy-4-(7-oxo-6,7-dihydro-3H-[1,2,3]triazolo[4,5-d]pyrimidin-5-yl)phenyl)nicotinic Acid (Compound 113)

113

5-(3-Ethoxy-4-(7-oxo-6,7-dihydro-3H-[1,2,3]triazolo[4,5-d]pyrimidin-5-yl)phenyl)nicotinic acid (Compound 113) was prepared from Compound 112 using the procedure of Example 9.

Example 14: Synthesis of Methyl 2-(3'-ethoxy-4'-(7-oxo-6,7-dihydro-3H-[1,2,3]triazolo[4,5-d]pyrimidin-5-yl)-[1,1'-biphenyl]-4-yl)acetate (Compound 114)

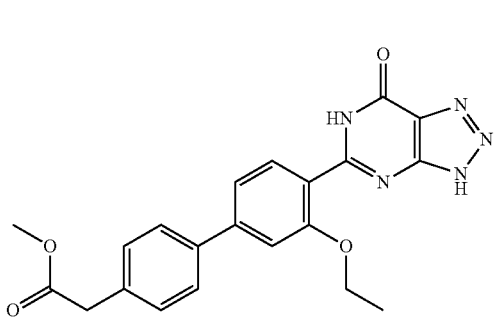

114

Methyl 2-(3'-ethoxy-4'-(7-oxo-6,7-dihydro-3H-[1,2,3]triazolo[4,5-d]pyrimidin-5-yl)-[1,1'-biphenyl]-4-yl)acetate (Compound 114) was prepared using the procedure of Steps 4 and 5, Example 6, except that (4-(2-methoxy-2-oxoethyl)phenyl)boronic acid was used in Step 4. LCMS (ESI)=406.2 [M+H]$^+$.

Example 16: Synthesis of Methyl 5-(3-ethoxy-4-(7-oxo-6,7-dihydro-3H-[1,2,3]triazolo[4,5-d]pyrimidin-5-yl)phenyl)thiophene-2-carboxylate (Compound 116)

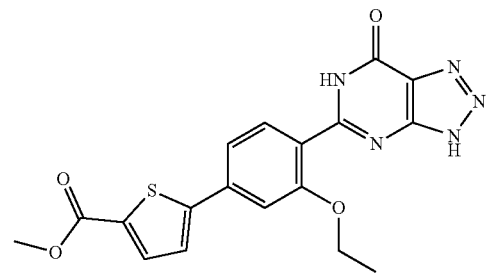

116

Methyl 5-(3-ethoxy-4-(7-oxo-6,7-dihydro-3H-[1,2,3]triazolo[4,5-d]pyrimidin-5-yl)phenyl)thiophene-2-carboxylate (Compound 116) was prepared using the procedure of Steps 4 and 5, Example 6, except that methyl 5-(4,4,5,5-tetramethyl-1,3,2-dioxaborolan-2-yl)thiophene-2-carboxylate was used in Step 4. LCMS (ESI)=398.1 [M+H]$^+$.

Example 15: Synthesis of 2-(3'-Ethoxy-4'-(7-oxo-6,7-dihydro-3H-[1,2,3]triazolo[4,5-d]pyrimidin-5-yl)-[1,1'-biphenyl]-4-yl)acetic Acid (Compound 115)

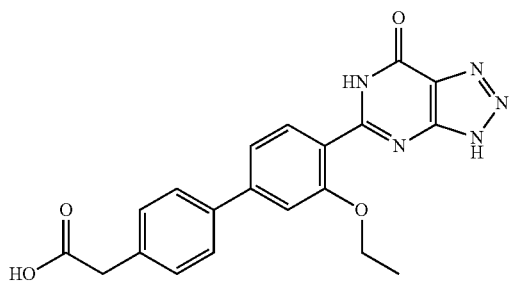

115

2-(3'-Ethoxy-4'-(7-oxo-6,7-dihydro-3H-[1,2,3]triazolo[4,5-d]pyrimidin-5-yl)-[1,1'-biphenyl]-4-yl)acetic acid (Compound 115) was prepared from Compound 114 using the procedure of Example 9. LCMS (ESI)=392.1 [M+H]$^+$.

Example 17: Synthesis of 5-(3-Ethoxy-4-(7-oxo-6,7-dihydro-3H-[1,2,3]triazolo[4,5-d]pyrimidin-5-yl)phenyl)thiophene-2-carboxylic Acid (Compound 117)

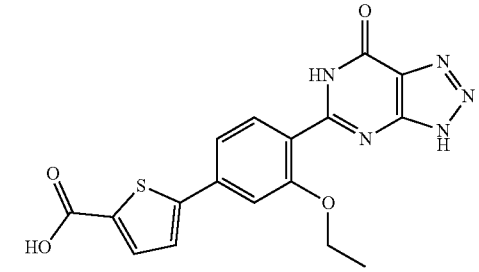

117

5-(3-Ethoxy-4-(7-oxo-6,7-dihydro-3H-[1,2,3]triazolo[4,5-d]pyrimidin-5-yl)phenyl)thiophene-2-carboxylic acid (Compound 117) was prepared from Compound 116 using the procedure of Example 9. LCMS (ESI)=384.1 [M+H]$^+$.

Example 18: Synthesis of Methyl 2-(3'-ethoxy-4'-(7-oxo-6,7-dihydro-3H-[1,2,3]triazolo[4,5-d]pyrimidin-5-yl)-[1,1'-biphenyl]-2-yl)acetate (Compound 118)

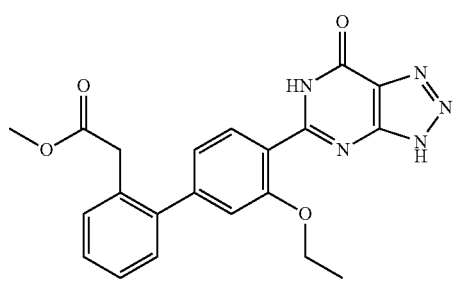

118

Methyl 2-(3'-ethoxy-4'-(7-oxo-6,7-dihydro-3H-[1,2,3]triazolo[4,5-d]pyrimidin-5-yl)-[1,1'-biphenyl]-2-yl)acetate (Compound 118) was prepared using the procedure of Steps 4 and 5, Example 6, except that (2-(2-methoxy-2-oxoethyl)phenyl)boronic acid was used in Step 4. LCMS (ESI)=406.2 [M+H]$^+$.

Example 20: Synthesis of Ethyl 2-((3'-ethoxy-4'-(7-oxo-6,7-dihydro-3H-[1,2,3]triazolo[4,5-d]pyrimidin-5-yl)-[1,1'-biphenyl]-3-yl)oxy)acetate (Compound 120)

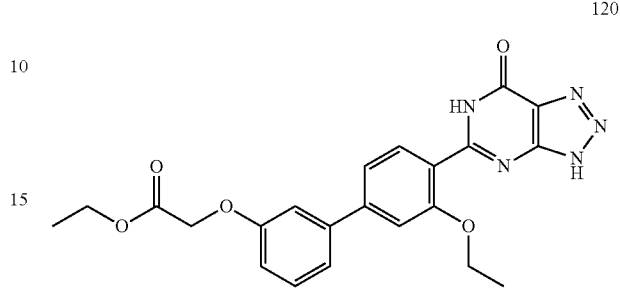

120

Ethyl 2-((3'-ethoxy-4'-(7-oxo-6,7-dihydro-3H-[1,2,3]triazolo[4,5-d]pyrimidin-5-yl)-[1,1'-biphenyl]-3-yl)oxy)acetate (Compound 120) was prepared using the procedure of Steps 4 and 5, Example 6, except that ethyl 2-(3-(4,4,5,5-tetramethyl-1,3,2-dioxaborolan-2-yl)phenoxy)acetate was used in Step 4. LCMS (ESI)=436.2 [M+H]$^+$.

Example 19: Synthesis of 2-(3'-Ethoxy-4'-(7-oxo-6,7-dihydro-3H-[1,2,3]triazolo[4,5-d]pyrimidin-5-yl)-[1,1'-biphenyl]-2-yl)acetic Acid (Compound 119)

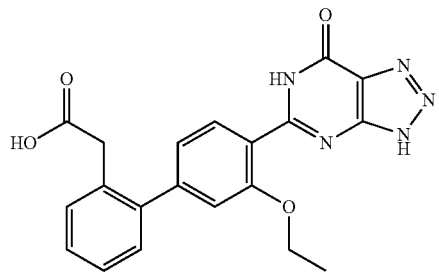

119

2-(3'-Ethoxy-4'-(7-oxo-6,7-dihydro-3H-[1,2,3]triazolo[4,5-d]pyrimidin-5-yl)-[1,1'-biphenyl]-2-yl)acetic acid (Compound 119) was prepared from Compound 118 using the procedure of Example 9. LCMS (ESI)=392.2 [M+H]$^+$.

Example 21: Synthesis of 2-((3'-Ethoxy-4'-(7-oxo-6,7-dihydro-3H-[1,2,3]triazolo[4,5-d]pyrimidin-5-yl)-[1,1'-biphenyl]-3-yl)oxy)acetic Acid (Compound 121)

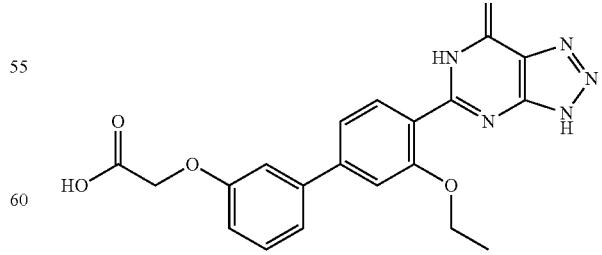

121

2-((3'-Ethoxy-4'-(7-oxo-6,7-dihydro-3H-[1,2,3]triazolo[4,5-d]pyrimidin-5-yl)-[1,1'-biphenyl]-3-yl)oxy)acetic acid (Compound 121) was prepared from Compound 120 using the procedure of Example 9. LCMS (ESI)=408.2 [M+H]$^+$.

Example 22: Synthesis of Methyl 5-amino-3'-ethoxy-4'-(7-oxo-6,7-dihydro-3H-[1,2,3]triazolo[4,5-d]pyrimidin-5-yl)-[1,1'-biphenyl]-3-carboxylate (Compound 122)

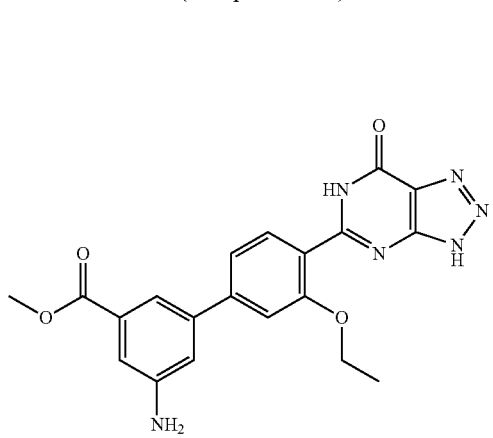

Methyl 5-amino-3'-ethoxy-4'-(7-oxo-6,7-dihydro-3H-[1,2,3]triazolo[4,5-d]pyrimidin-5-yl)-[1,1'-biphenyl]-3-carboxylate was prepared using the procedure of Steps 4 and 5, Example 6, except that (3-amino-5-(methoxycarbonyl)phenyl)boronic acid hydrochloride salt was used in Step 4. LCMS (ESI)=407.2 [M+H]$^+$.

Example 23: Synthesis of 5-amino-3'-ethoxy-4'-(7-oxo-6,7-dihydro-3H-[1,2,3]triazolo[4,5-d]pyrimidin-5-yl)-[1,1'-biphenyl]-3-carboxylic Acid (Compound 123)

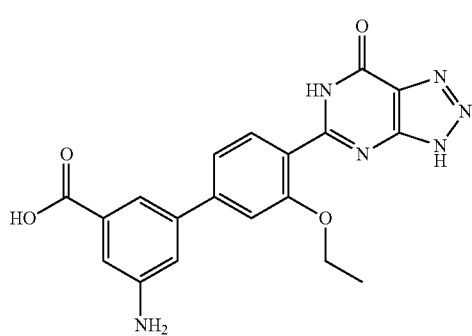

5-Amino-3'-ethoxy-4'-(7-oxo-6,7-dihydro-3H-[1,2,3]triazolo[4,5-d]pyrimidin-5-yl)-[1,1'-biphenyl]-3-carboxylic acid (Compound 123) was prepared from Compound 122 using the procedure of Example 9. LCMS (ESI)=393.1 [M+H]$^+$.

Example 24: Synthesis of Methyl 5-(3-ethoxy-4-(7-oxo-6,7-dihydro-3H-[1,2,3]triazolo[4,5-d]pyrimidin-5-yl)phenyl)picolinate (Compound 124)

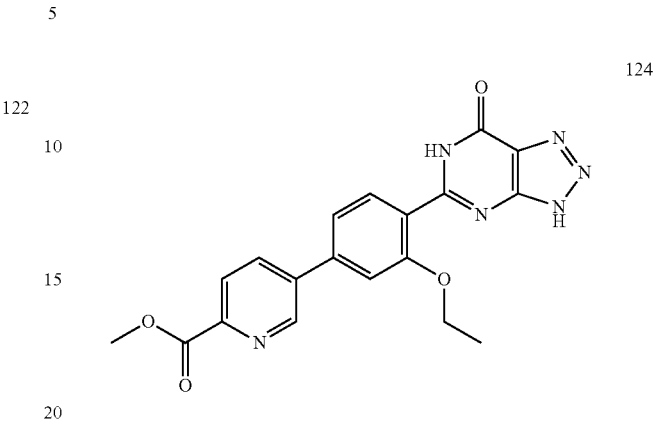

Methyl 5-(3-ethoxy-4-(7-oxo-6,7-dihydro-3H-[1,2,3]triazolo[4,5-d]pyrimidin-5-yl)phenyl)picolinate (Compound 124) was prepared using the procedure of Steps 4 and 5, Example 6, except that (6-(methoxycarbonyl)pyridin-3-yl)boronic acid was used in Step 4. LCMS (ESI)=393.1 [M+H]$^+$.

Example 25: Synthesis of 5-(3-Ethoxy-4-(7-oxo-6,7-dihydro-3H-[1,2,3]triazolo[4,5-d]pyrimidin-5-yl)phenyl)picolinic Acid (Compound 125)

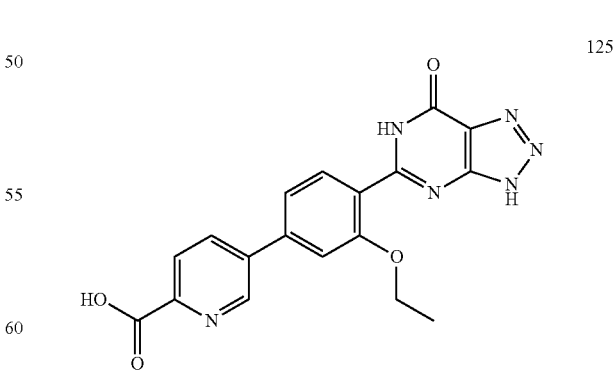

5-(3-Ethoxy-4-(7-oxo-6,7-dihydro-3H-[1,2,3]triazolo[4,5-d]pyrimidin-5-yl)phenyl)picolinic acid (Compound 125) was prepared from Compound 124 using the procedure of Example 9. LCMS (ESI)=379.1 [M+H]$^+$.

Example 26: Synthesis of Ethyl 2-(4-(3-ethoxy-4-(7-oxo-6,7-dihydro-3H-[1,2,3]triazolo[4,5-d]pyrimidin-5-yl)phenyl)-1H-pyrazol-1-yl)acetate (Compound 126)

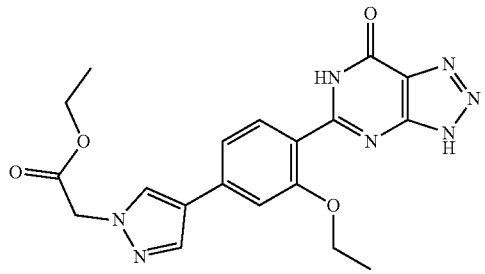

126

Ethyl 2-(4-(3-ethoxy-4-(7-oxo-6,7-dihydro-3H-[1,2,3]triazolo[4,5-d]pyrimidin-5-yl)phenyl)-1H-pyrazol-1-yl)acetate (Compound 126) was prepared using the procedure of Steps 4 and 5, Example 6, except that ethyl 2-(4-(4,4,5,5-tetramethyl-1,3,2-dioxaborolan-2-yl)-1H-pyrazol-1-yl)acetate was used in Step 4. LCMS (ESI)=410.2 [M+H]⁺.

Example 27: Synthesis of 2-(4-(3-Ethoxy-4-(7-oxo-6,7-dihydro-3H-[1,2,3]triazolo[4,5-d]pyrimidin-5-yl)phenyl)-1H-pyrazol-1-yl)acetic Acid (Compound 127)

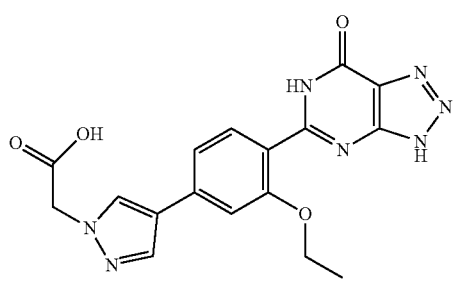

127

2-(4-(3-Ethoxy-4-(7-oxo-6,7-dihydro-3H-[1,2,3]triazolo[4,5-d]pyrimidin-5-yl)phenyl)-1H-pyrazol-1-yl)acetic acid was prepared from Compound 126 using the procedure of Example 9. LCMS (ESI)=382.2 [M+H]⁺.

Example 28: Synthesis of 4'-(7-Oxo-6,7-dihydro-3H-[1,2,3]triazolo[4,5-d]pyrimidin-5-yl)-3'-propoxy-[1,1'-biphenyl]-3-carboxylic Acid (Compound 128)

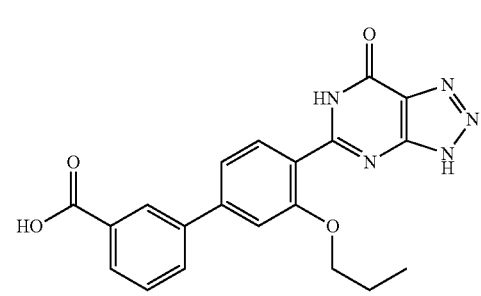

128

4'-(7-Oxo-6,7-dihydro-3H-[1,2,3]triazolo[4,5-d]pyrimidin-5-yl)-3'-propoxy-[1,1'-biphenyl]-3-carboxylic acid was prepared using the procedures in Example 6, except that 1-iodopropane was used in Step 2. LCMS (ESI)=392.1 [M+H]⁺.

Example 29: Synthesis of 5-([1,1'-biphenyl]-4-yl)-3,6-dihydro-7H-[1,2,3]triazolo[4,5-d]pyrimidin-7-one (Compound 129)

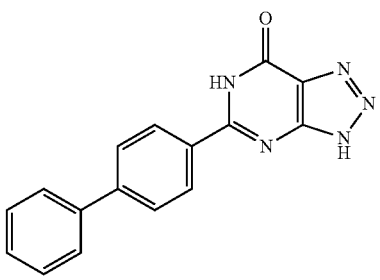

129

5-([1,1'-Biphenyl]-4-yl)-3,6-dihydro-7H-[1,2,3]triazolo[4,5-d]pyrimidin-7-one was prepared using the procedures in Example 6, except that 4-bromobenzaldehyde was used in Step 3. LCMS (ESI)=290.1 [M+H]⁺.

Example 30: Synthesis of 5-(4-cyclopropyl-2-ethoxyphenyl)-3,6-dihydro-7H-[1,2,3]triazolo[4,5-d]pyrimidin-7-one (Compound 130)

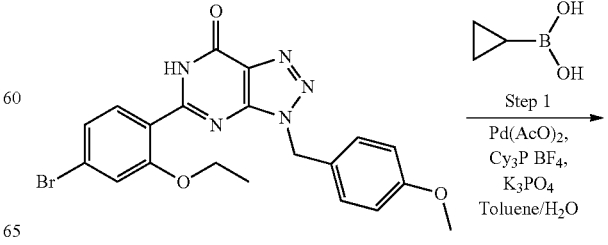

106-A

-continued

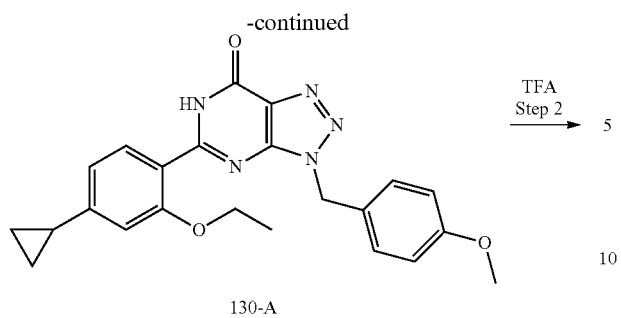

130-A

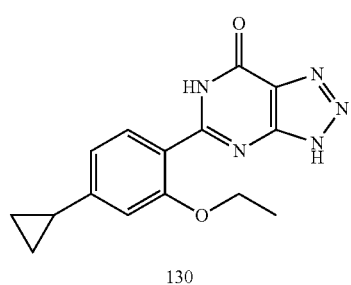

130

Step 1: To a stirred solution of 5-(4-bromo-2-ethoxyphenyl)-3-(4-methoxybenzyl)-3,6-dihydro-7H-[1,2,3]triazolo[4,5-d]pyrimidin-7-one (Compound 106-A) (50.0 mg, 0.110 mmol, 1.00 equiv), $K_3PO_4$ (69.8 mg, 0.329 mmol, 3.00 equiv) and cyclopropylboronic acid (18.8 mg, 0.219 mmol, 2.00 equiv) in Toluene/water (1/0.10 mL) were added tricyclohexylphosphonium tetrafluoroborate (8.07 mg, 0.022 mmol, 0.20 equiv) and Pd(OAc)$_2$ (2.46 mg, 0.011 mmol, 0.10 equiv) at room temperature under $N_2$ atmosphere. The resulting mixture was stirred overnight at 100° C. The mixture was allowed to cool down to room temperature. The residue was purified by silica gel column chromatography to afford 5-(4-cyclopropyl-2-ethoxyphenyl)-3-(4-methoxybenzyl)-3,6-dihydro-7H-[1,2,3]triazolo[4,5-d]pyrimidin-7-one (36 mg, 79%) as an off-white solid. LCMS (ESI)=418.2 [M+H]$^+$.

Step 2: Into an 8 mL vessel were added 5-(4-cyclopropyl-2-ethoxyphenyl)-3-(4-methoxybenzyl)-3,6-dihydro-7H-[1,2,3]triazolo[4,5-d]pyrimidin-7-one (36.00 mg, 0.086 mmol, 1.00 equiv) and 2,2,2-trifluoroacetaldehyde (1.00 mL) at room temperature. The resulting mixture was stirred for 1.5 h at 80° C. The resulting mixture was concentrated under reduced pressure. The crude product was purified by preparative HPLC to afford 5-(4-cyclopropyl-2-ethoxyphenyl)-3,6-dihydro-7H-[1,2,3]triazolo[4,5-d]pyrimidin-7-one (Compound 130) (9.5 mg, 32%) as a white solid. LCMS (ESI)=298.1 [M+H]$^+$. $^1$H NMR (300 MHz, DMSO-d$_6$): δ 11.12 (s, 1H), 8.22 (s, 1H), 7.84 (d, J=8.1 Hz, 1H), 6.88 (d, J=1.2 Hz, 1H), 6.78 (dd, J=8.1, 1.4 Hz, 1H), 4.20 (q, J=7.0 Hz, 2H), 2.06-1.92 (m, 1H), 1.39 (t, J=6.9 Hz, 3H), 1.09-0.93 (m, 2H), 0.86-0.71 (m, 2H).

Example 31: Synthesis of 5-(2-Ethoxy-4-(1H-pyrazol-3-yl)phenyl)-1,6-dihydro-7H-[1,2,3]triazolo[4,5-d]pyrimidin-7-one (Compound 131)

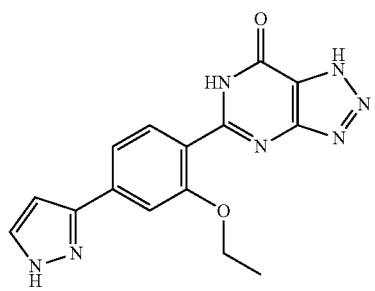

131

5-(2-Ethoxy-4-(1H-pyrazol-3-yl)phenyl)-1,6-dihydro-7H-[1,2,3]triazolo[4,5-d]pyrimidin-7-one was prepared using the procedure of Steps 4 and 5, Example 6, except that (1H-pyrazol-3-yl)boronic acid was used in Step 4. LCMS (ESI)=324.1 [M+H]$^+$.

Example 32: Synthesis of 3-Ethoxy-4-(7-oxo-6,7-dihydro-3H-[1,2,3]triazolo[4,5-d]pyrimidin-5-yl)benzoic Acid (Compound 132)

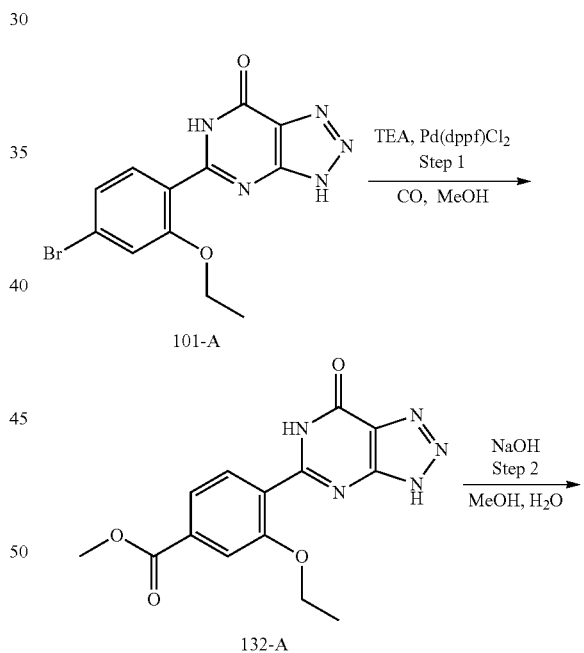

Step 1: To a 30 mL pressure tank reactor were added 5-(4-bromo-2-ethoxyphenyl)-3,6-dihydro-7H-[1,2,3]triazolo[4,5-d]pyrimidin-7-one (Compound 101-A) (50 mg, 0.149 mmol, 1 equiv), Pd(dppf)Cl$_2$ (10.9 mg, 0.015 mmol, 0.1 equiv), and triethylamine (45.2 mg, 0.446 mmol, 3 equiv) in MeOH at room temperature. The mixture was stirred for 3 h at 120° C. under CO atmosphere 10 atm. The resulting mixture was concentrated under reduced pressure. The crude product (40 mg) was used in the next step directly without further purification. To obtain an analytical sample, the crude product (20 mg) was purified by preparative HPLC to afford methyl 3-ethoxy-4-(7-oxo-6,7-dihydro-3H-[1,2,3]triazolo[4,5-d]pyrimidin-5-yl)benzoate (Compound 132-A) (14.1 mg, 26%) as a white solid. LCMS (ESI)=316.2 [M+H]$^+$. $^1$H NMR (300 MHz, DMSO-d$_6$) δ 12.47 (s, 1H), 7.81 (d, J=8.0 Hz, 1H), 7.76-7.55 (m, 2H), 4.21 (q, J=6.9 Hz, 2H), 3.91 (s, 3H), 1.34 (t, J=6.9 Hz, 3H).

Step 2: To an 8 mL vial was added methyl 3-ethoxy-4-(7-oxo-6,7-dihydro-3H-[1,2,3]triazolo[4,5-d]pyrimidin-5-yl)benzoate (30 mg, 0.09 mmol, 1 equiv) and NaOH (11.4 mg, 0.28 mmol, 3 equiv) in MeOH/H$_2$O (1 mL/0.2 mL), and the solution was stirred for 2 h at room temperature. The resulting mixture was filtered and the filter cake was washed with EtOAc (3×5 mL). The filtrate was concentrated under reduced pressure. The residue was dissolved in DMSO (3 mL) and purified by preparative to afford 3-ethoxy-4-(7-oxo-6,7-dihydro-3H-[1,2,3]triazolo[4,5-d]pyrimidin-5-yl)benzoic acid (Compound 132) (8.5 mg) as an off-white solid. LCMS (ESI)=302.1 [M+H]$^+$. $^1$H NMR (300 MHz, DMSO-d$_6$) δ 12.00 (s, 1H), 7.83 (d, J=7.8 Hz, 1H), 7.64 (d, J=10.4 Hz, 2H), 4.21 (q, J=6.9 Hz, 2H), 1.36 (t, J=6.9 Hz, 3H).

Example 33: Synthesis of 5-(2-Ethoxy-4-(pyrrolidine-1-carbonyl)phenyl)-3,6-dihydro-7H-[1,2,3]triazolo[4,5-d]pyrimidin-7-one (Compound 133)

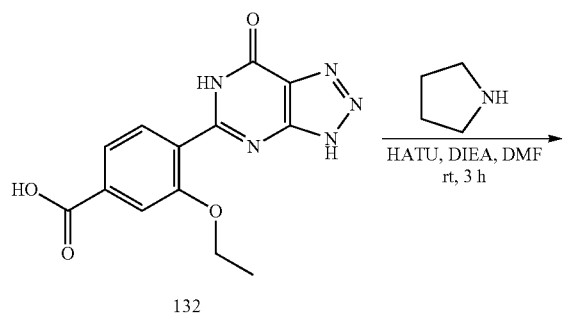

To a stirred solution of 3-ethoxy-4-(7-oxo-6,7-dihydro-3H-[1,2,3]triazolo[4,5-d]pyrimidin-5-yl)benzoic acid (50 mg, 0.166 mmol, 1 equiv) and DIEA (64.4 mg, 0.498 mmol, 3.0 equiv) in DMF (1 mL) was added HATU (75.7 mg, 0.199 mmol, 1.2 equiv) at room temperature. To the above mixture was added pyrrolidine (23.6 mg, 0.332 mmol, 2 equiv) at room temperature. The resulting mixture was stirred overnight at room temperature. The crude product was purified by preparative HPLC to afford 5-(2-ethoxy-4-(pyrrolidine-1-carbonyl)phenyl)-3,6-dihydro-7H-[1,2,3]triazolo[4,5-d]pyrimidin-7-one (5.1 mg, 8%) as a white solid. LCMS (ESI)=355.4 [M+H]$^+$. $^1$H NMR (300 MHz, DMSO-d$_6$) δ 12.32 (s, 1H), 7.75 (d, J=7.8 Hz, 1H), 7.26 (s, 1H), 7.20 (d, J=7.9 Hz, 1H), 4.24-4.12 (m, 2H), 3.49 (t, J=6.0 Hz, 2H), 3.41 (t, J=5.8 Hz, 2H), 1.95-1.79 (m, 4H), 1.34 (t, J=6.9 Hz, 3H).

Example 34: Synthesis of 3-Ethoxy-4-(7-oxo-6,7-dihydro-3H-[1,2,3]triazolo[4,5-d]pyrimidin-5-yl)-N-phenylbenzamide (Compound 134)

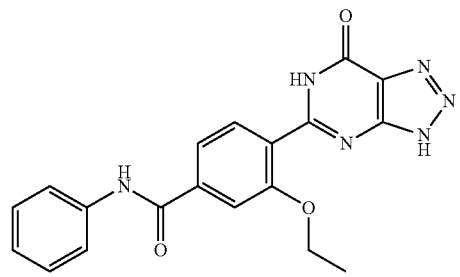

3-Ethoxy-4-(7-oxo-6,7-dihydro-3H-[1,2,3]triazolo[4,5-d]pyrimidin-5-yl)-N-phenylbenzamide (Compound 134) was prepared using the procedure in Example 33, except that aniline was used in the amide coupling step. LCMS (ESI)=377.1 [M+H]$^+$. $^1$H NMR (300 MHz, DMSO-d$_6$) δ 12.30 (s, 1H), 10.37 (s, 1H), 7.86 (d, J=7.5 Hz, 1H), 7.79 (d, J=7.7 Hz, 2H), 7.73-7.65 (m, 2H), 7.39 (t, J=7.9 Hz, 2H), 7.14 (t, J=7.4 Hz, 1H), 4.27 (q, J=6.9 Hz, 2H), 1.38 (t, J=6.8 Hz, 3H).

Example 35: Synthesis of 3-Ethoxy-4-(7-oxo-6,7-dihydro-3H-[1,2,3]triazolo[4,5-d]pyrimidin-5-yl)benzamide (Compound 135)

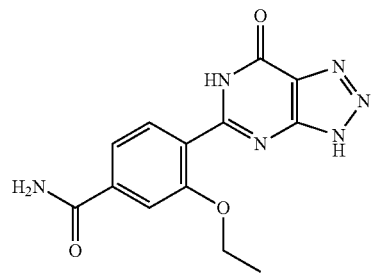

3-Ethoxy-4-(7-oxo-6,7-dihydro-1H-[1,2,3]triazolo[4,5-d]pyrimidin-5-yl)benzamide (Compound 135) was prepared using the procedure in Example 33, except that ammonium carbonate was used in the amide coupling step. LCMS (ESI)=301.1 [M+H]$^+$. $^1$H NMR (300 MHz, DMSO-d$_6$) δ 12.33 (s, 1H), 8.15 (s, 1H), 7.76 (d, J=7.8 Hz, 1H), 7.66-7.50 (m, 3H), 4.21 (q, J=7.1 Hz, 2H), 1.36 (t, J=6.9 Hz, 3H).

Example 36: Synthesis of N-Cyclopentyl-3-ethoxy-4-(7-oxo-6,7-dihydro-3H-[1,2,3]triazolo[4,5-d]pyrimidin-5-yl)benzamide (Compound 136)

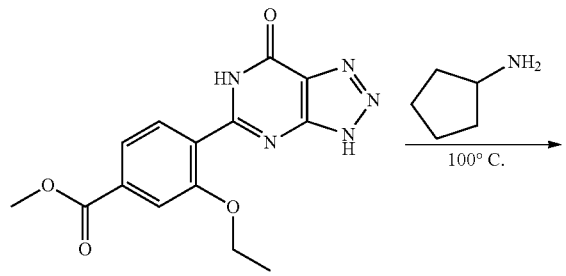

To an 8 mL vial was added methyl 3-ethoxy-4-(7-oxo-6,7-dihydro-3H-[1,2,3]triazolo[4,5-d]pyrimidin-5-yl)benzoate (50.0 mg, 0.159 mmol, 1.00 equiv) and cyclopentanamine (67.5 mg, 0.793 mmol, 5.00 equiv) at room temperature. The resulting mixture was stirred overnight at 100° C. The mixture was allowed to cool down to room temperature. The resulting mixture was diluted with DMSO (3 mL). The mixture was purified by preparative HPLC to afford N-cyclopentyl-3-ethoxy-4-(7-oxo-6,7-dihydro-3H-[1,2,3]triazolo[4,5-d]pyrimidin-5-yl)benzamide (9.7 mg, 17%) as a white solid. LCMS (ESI)=369.2 [M+H]$^+$. $^1$H NMR (300 MHz, DMSO-$d_6$): δ 12.26 (s, 1H), 8.43 (d, J=7.1 Hz, 1H), 7.79 (d, J=8.4 Hz, 1H), 7.64-7.52 (m, 2H), 4.34-4.14 (m, 3H), 2.03-1.84 (m, 2H), 1.82-1.47 (m, 6H), 1.37 (t, J=6.9 Hz, 3H).

The following compounds (Compounds 137-192) were prepared using similar methods as described in Examples 1-36.

| Cmpd | Structure | Chemical Name | m/z (M + H)$^+$ |
|---|---|---|---|
| 137 | 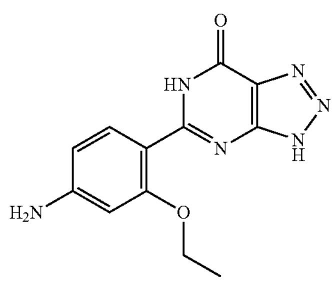 [SMILES: CCOc1cc(N)ccc1-c1nc2[nH]nnc2c(=O)[nH]1] | 5-(4-amino-2-ethoxyphenyl)-3,6-dihydro-7H-[1,2,3]triazolo[4,5-d]pyrimidin-7-one | 273.1 |
| 138 | 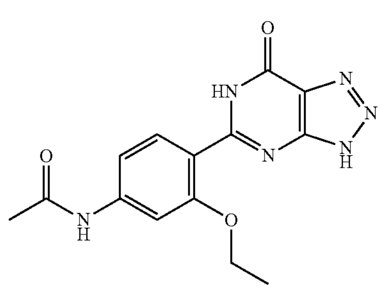 [SMILES: CCOc1cc(NC(C)=O)ccc1-c1nc2[nH]nnc2c(=O)[nH]1] | N-(3-ethoxy-4-(7-oxo-6,7-dihydro-3H-[1,2,3]triazolo[4,5-d]pyrimidin-5-yl)phenyl)acetamide | 315.1 |

-continued

| Cmpd | Structure | Chemical Name | m/z (M + H)+ |
|---|---|---|---|
| 139 | 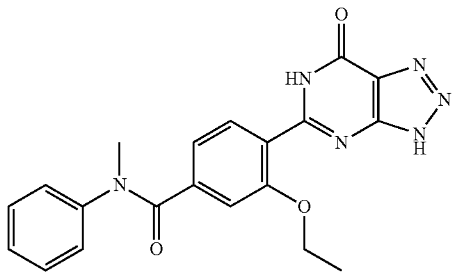 [SMILES: CCOc1cc(C(=O)N(C)c2ccccc2)ccc1-c1nc2[nH]nnc2c(=O)[nH]1] | 3-ethoxy-N-methyl-4-(7-oxo-6,7-dihydro-3H-[1,2,3]triazolo[4,5-d]pyrimidin-5-yl)-N-phenylbenzamide | 391.1 |
| 140 | 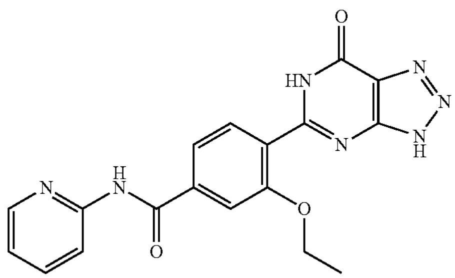 [SMILES: CCOc1cc(C(=O)Nc2ccccn2)ccc1-c1nc2[nH]nnc2c(=O)[nH]1] | 3-ethoxy-4-(7-oxo-6,7-dihydro-3H-[1,2,3]triazolo[4,5-d]pyrimidin-5-yl)-N-(pyridin-2-yl)benzamide | 378.1 |
| 141 | 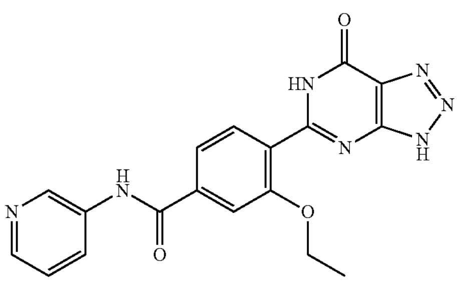 [SMILES: CCOc1cc(C(=O)Nc2cccnc2)ccc1-c1nc2[nH]nnc2c(=O)[nH]1] | 3-ethoxy-4-(7-oxo-6,7-dihydro-3H-[1,2,3]triazolo[4,5-d]pyrimidin-5-yl)-N-(pyridin-3-yl)benzamide | 378.1 |
| 142 | 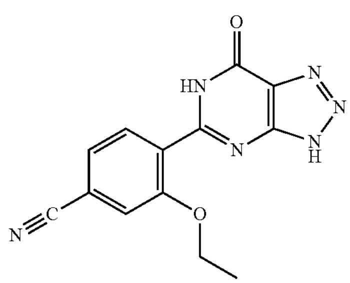 [SMILES: CCOc1cc(C#N)ccc1-c1nc2[nH]nnc2c(=O)[nH]1] | 3-ethoxy-4-(7-oxo-6,7-dihydro-3H-[1,2,3]triazolo[4,5-d]pyrimidin-5-yl)benzonitrile | 283.1 |
| 143 | 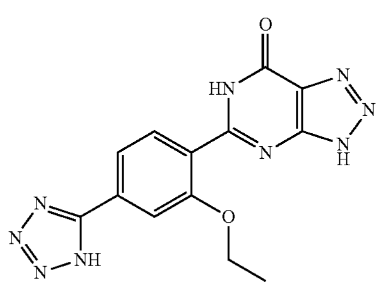 [SMILES: CCOc1cc(-c2nnn[nH]2)ccc1-c1nc2[nH]nnc2c(=O)[nH]1] | 5-(2-ethoxy-4-(1H-tetrazol-5-yl)phenyl)-3,6-dihydro-7H-[1,2,3]triazolo[4,5-d]pyrimidin-7-one | 326.1 |

-continued

| Cmpd | Structure | Chemical Name | m/z (M + H)+ |
|---|---|---|---|
| 144 | 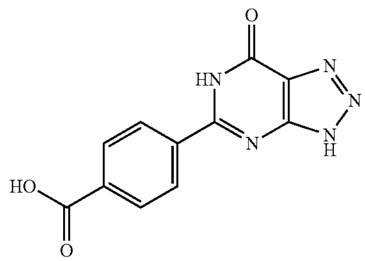 [SMILES: O=C(O)c1ccc(-c2nc3[nH]nnc3c(=O)[nH]2)cc1] | 4-(7-oxo-6,7-dihydro-3H-[1,2,3]triazolo[4,5-d]pyrimidin-5-yl)benzoic acid | 258.1 |
| 145 | 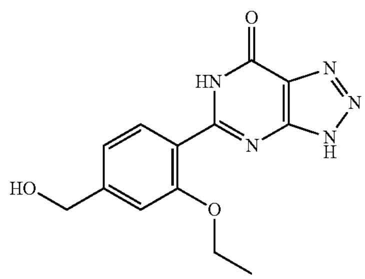 [SMILES: CCOc1cc(CO)ccc1-c1nc2[nH]nnc2c(=O)[nH]1] | 5-(2-ethoxy-4-(hydroxymethyl)phenyl)-3,6-dihydro-7H-[1,2,3]triazolo[4,5-d]pyrimidin-7-one | 288.1 |
| 146 | 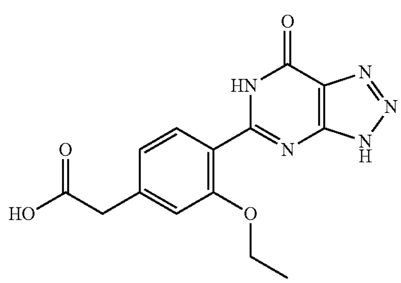 [SMILES: CCOc1cc(CC(=O)O)ccc1-c1nc2[nH]nnc2c(=O)[nH]1] | 2-(3-ethoxy-4-(7-oxo-6,7-dihydro-3H-[1,2,3]triazolo[4,5-d]pyrimidin-5-yl)phenyl)acetic acid | 316.1 |
| 147 | 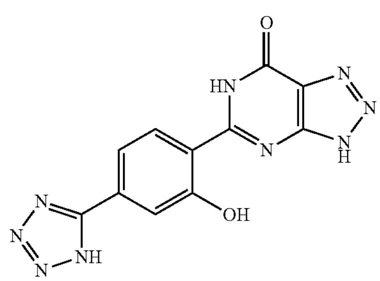 [SMILES: O=c1[nH]c(-c2ccc(-c3nnn[nH]3)cc2O)nc2[nH]nnc12] | 5-(2-hydroxy-4-(1H-tetrazol-5-yl)phenyl)-3,6-dihydro-7H-[1,2,3]triazolo[4,5-d]pyrimidin-7-one | 296.1 (M − H) |
| 148 | 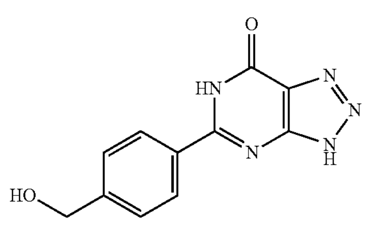 [SMILES: O=c1[nH]c(-c2ccc(CO)cc2)nc2[nH]nnc12] | 5-(4-(hydroxymethyl)phenyl)-3,6-dihydro-7H-[1,2,3]triazolo[4,5-d]pyrimidin-7-one | 244.1 |
| 149 | 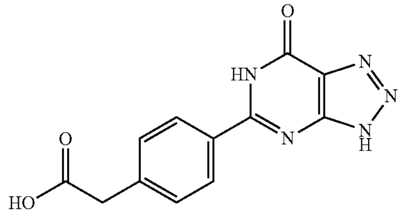 [SMILES: O=C(O)Cc1ccc(-c2nc3[nH]nnc3c(=O)[nH]2)cc1] | 2-(4-(7-oxo-6,7-dihydro-3H-[1,2,3]triazolo[4,5-d]pyrimidin-5-yl)phenyl)acetic acid | 272.1 |

-continued

| Cmpd | Structure | Chemical Name | m/z (M + H)+ |
|---|---|---|---|
| 150 | 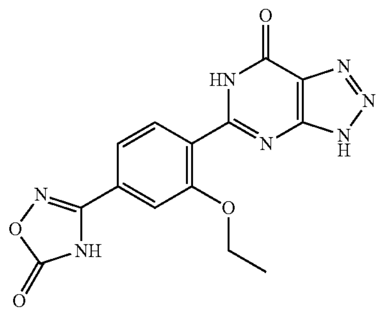 [SMILES: CCOc1cc(-c2noc(=O)[nH]2)ccc1-c1nc2[nH]nnc2c(=O)[nH]1] | 3-(3-ethoxy-4-(7-oxo-6,7-dihydro-3H-[1,2,3]triazolo[4,5-d]pyrimidin-5-yl)phenyl)-1,2,4-oxadiazol-5(4H)-one | 342 |
| 151 | 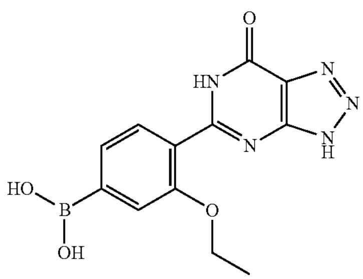 [SMILES: CCOc1cc(B(O)O)ccc1-c1nc2[nH]nnc2c(=O)[nH]1] | (3-ethoxy-4-(7-oxo-6,7-dihydro-3H-[1,2,3]triazolo[4,5-d]pyrimidin-5-yl)phenyl)boronic acid | 302.1 |
| 152 | 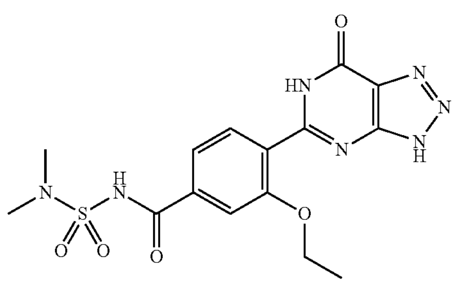 [SMILES: CCOc1cc(C(=O)NS(=O)(=O)N(C)C)ccc1-c1nc2[nH]nnc2c(=O)[nH]1] | N-(N,N-dimethylsulfamoyl)-3-ethoxy-4-(7-oxo-6,7-dihydro-3H-[1,2,3]triazolo[4,5-d]pyrimidin-5-yl)benzamide | 408.1 |
| 153 | 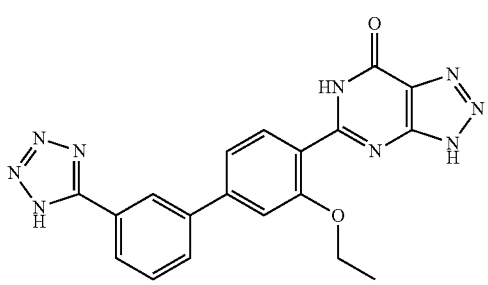 [SMILES: CCOc1cc(-c2cccc(-c3nnn[nH]3)c2)ccc1-c1nc2[nH]nnc2c(=O)[nH]1] | 5-(3-ethoxy-3'-(1H-tetrazol-5-yl)-[1,1'-biphenyl]-4-yl)-3,6-dihydro-7H-[1,2,3]triazolo[4,5-d]pyrimidin-7-one | 402.1 |
| 154 | 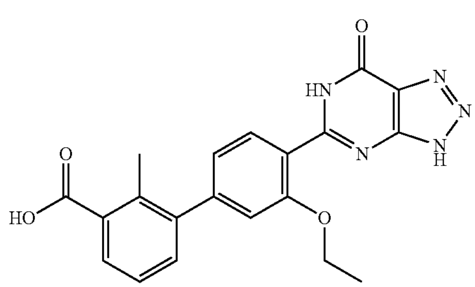 [SMILES: CCOc1cc(-c2cccc(C(=O)O)c2C)ccc1-c1nc2[nH]nnc2c(=O)[nH]1] | 3'-ethoxy-2-methyl-4'-(7-oxo-6,7-dihydro-3H-[1,2,3]triazolo[4,5-d]pyrimidin-5-yl)-[1,1'-biphenyl]-3-carboxylic acid | 392.1 |

-continued

| Cmpd | Structure | Chemical Name | m/z (M + H)+ |
|---|---|---|---|
| 155 | 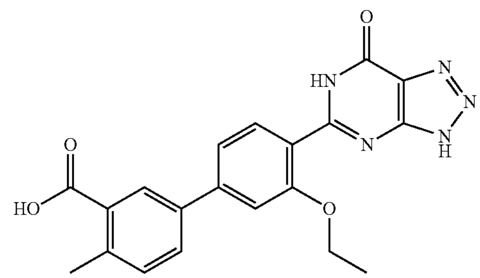 [SMILES: CCOc1cc(-c2ccc(C)c(C(=O)O)c2)ccc1-c1nc2[nH]nnc2c(=O)[nH]1] | 3'-ethoxy-4-methyl-4'-(7-oxo-6,7-dihydro-3H-[1,2,3]triazolo[4,5-d]pyrimidin-5-yl)-[1,1'-biphenyl]-3-carboxylic acid | 392.1 |
| 156 | 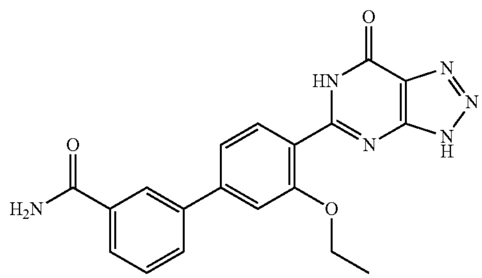 [SMILES: CCOc1cc(-c2cccc(C(N)=O)c2)ccc1-c1nc2[nH]nnc2c(=O)[nH]1] | 3'-ethoxy-4'-(7-oxo-6,7-dihydro-3H-[1,2,3]triazolo[4,5-d]pyrimidin-5-yl)-[1,1'-biphenyl]-3-carboxamide | 377.1 |
| 157 | 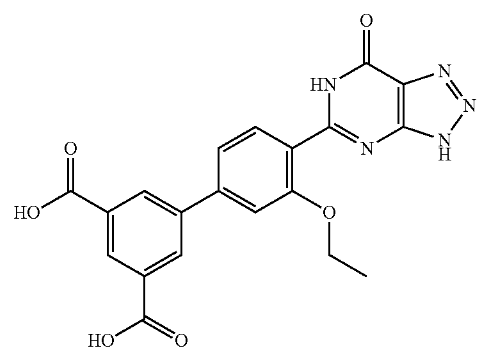 [SMILES: CCOc1cc(-c2cc(C(=O)O)cc(C(=O)O)c2)ccc1-c1nc2[nH]nnc2c(=O)[nH]1] | 3'-ethoxy-4'-(7-oxo-6,7-dihydro-3H-[1,2,3]triazolo[4,5-d]pyrimidin-5-yl)-[1,1'-biphenyl]-3,5-dicarboxylic acid | 422.1 |
| 158 | 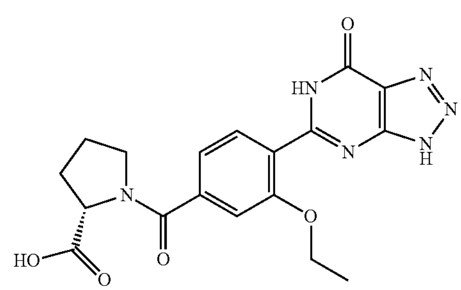 [SMILES: CCOc1cc(C(=O)N2CCC[C@H]2C(=O)O)ccc1-c1nc2[nH]nnc2c(=O)[nH]1] | (3-ethoxy-4-(7-oxo-6,7-dihydro-3H-[1,2,3]triazolo[4,5-d]pyrimidin-5-yl)benzoyl)-L-proline | 399.2 |
| 159 | 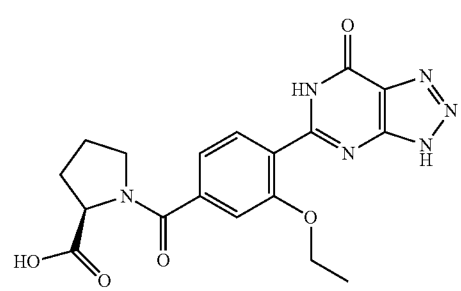 [SMILES: CCOc1cc(C(=O)N2CCC[C@@H]2C(=O)O)ccc1-c1nc2[nH]nnc2c(=O)[nH]1] | (3-ethoxy-4-(7-oxo-6,7-dihydro-3H-[1,2,3]triazolo[4,5-d]pyrimidin-5-yl)benzoyl)-D-proline | 399.1 |

| Cmpd | Structure | Chemical Name | m/z (M + H)+ |
|---|---|---|---|
| 160 | 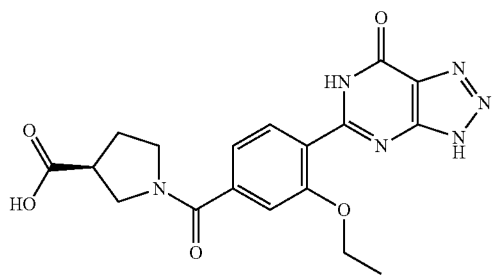 [SMILES: CCOc1cc(C(=O)N2CC[C@H](C(=O)O)C2)ccc1-c1nc2[nH]nnc2c(=O)[nH]1] | (S)-1-(3-ethoxy-4-(7-oxo-6,7-dihydro-3H-[1,2,3]triazolo[4,5-d]pyrimidin-5-yl)benzoyl)pyrrolidine-3-carboxylic acid | 399.2 |
| 161 | 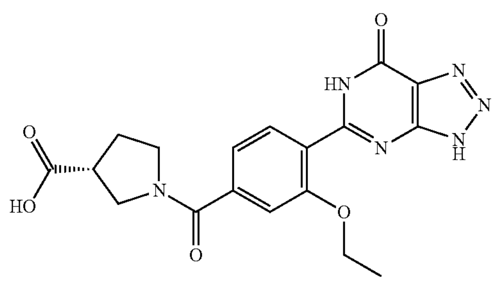 [SMILES: CCOc1cc(C(=O)N2CC[C@@H](C(=O)O)C2)ccc1-c1nc2[nH]nnc2c(=O)[nH]1] | (R)-1-(3-ethoxy-4-(7-oxo-6,7-dihydro-3H-[1,2,3]triazolo[4,5-d]pyrimidin-5-yl)benzoyl)pyrrolidine-3-carboxylic acid | 399.2 |
| 162 | 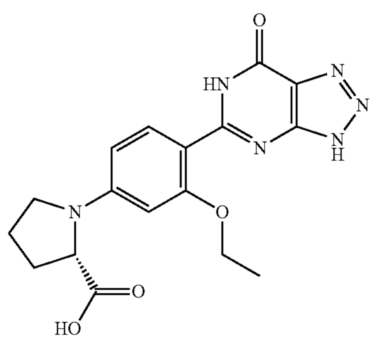 [SMILES: CCOc1cc(N2CCC[C@H]2C(=O)O)ccc1-c1nc2[nH]nnc2c(=O)[nH]1] | (3-ethoxy-4-(7-oxo-6,7-dihydro-3H-[1,2,3]triazolo[4,5-d]pyrimidin-5-yl)phenyl)-L-proline | 371.1 |
| 163 | 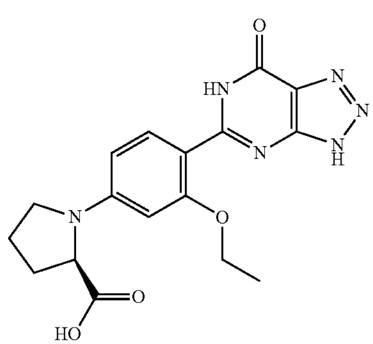 [SMILES: CCOc1cc(N2CCC[C@@H]2C(=O)O)ccc1-c1nc2[nH]nnc2c(=O)[nH]1] | (3-ethoxy-4-(7-oxo-6,7-dihydro-3H-[1,2,3]triazolo[4,5-d]pyrimidin-5-yl)phenyl)-D-proline | 371.2 |
| 164 | 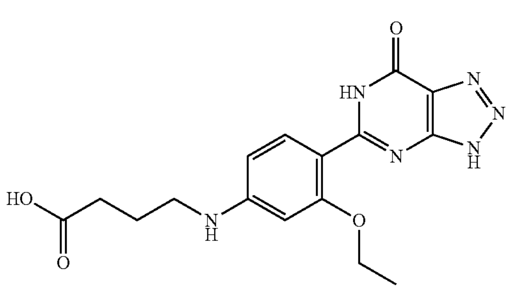 [SMILES: CCOc1cc(NCCCC(=O)O)ccc1-c1nc2[nH]nnc2c(=O)[nH]1] | 4-((3-ethoxy-4-(7-oxo-6,7-dihydro-3H-[1,2,3]triazolo[4,5-d]pyrimidin-5-yl)phenyl)amino)butanoic acid | 359.2 |

| Cmpd | Structure | Chemical Name | m/z (M + H)+ |
|---|---|---|---|
| 165 | 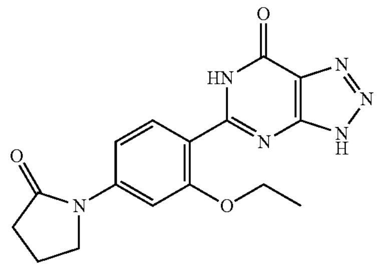 [SMILES: CCOc1cc(N2CCCC2=O)ccc1-c1nc2[nH]nnc2c(=O)[nH]1] | 5-(2-ethoxy-4-(2-oxopyrrolidin-1-yl)phenyl)-3,6-dihydro-7H-[1,2,3]triazolo[4,5-d]pyrimidin-7-one | 341.1 |
| 166 | 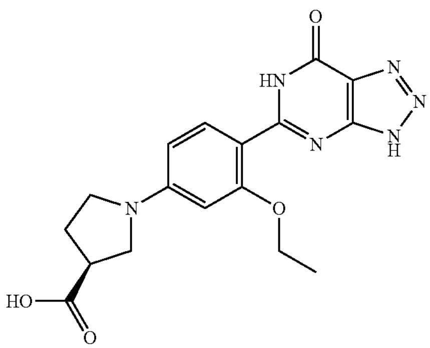 [SMILES: CCOc1cc(N2CC[C@H](C(=O)O)C2)ccc1-c1nc2[nH]nnc2c(=O)[nH]1] | (S)-1-(3-ethoxy-4-(7-oxo-6,7-dihydro-3H-[1,2,3]triazolo[4,5-d]pyrimidin-5-yl)phenyl)pyrrolidine-3-carboxylic acid | 371.2 |
| 167 | 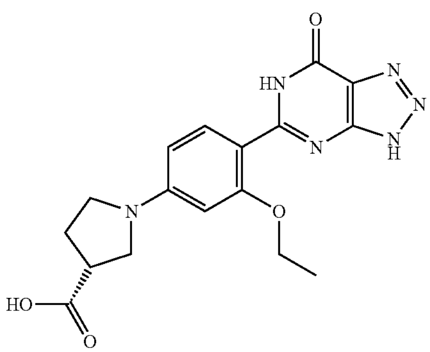 | (R)-1-(3-ethoxy-4-(7-oxo-6,7-dihydro-3H-[1,2,3]triazolo[4,5-d]pyrimidin-5-yl)phenyl)pyrrolidine-3-carboxylic acid | 371.1 |
| 168 | 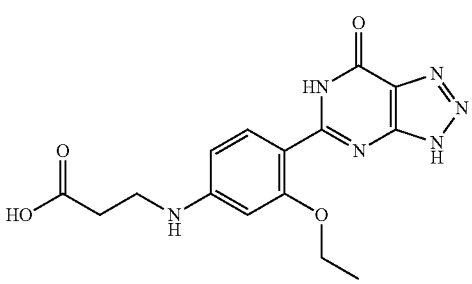 [SMILES: CCOc1cc(NCCC(=O)O)ccc1-c1nc2[nH]nnc2c(=O)[nH]1] | 3-((3-ethoxy-4-(7-oxo-6,7-dihydro-3H-[1,2,3]triazolo[4,5-d]pyrimidin-5-yl)phenyl)amino)propanoic acid | 345.1 |
| 169 | 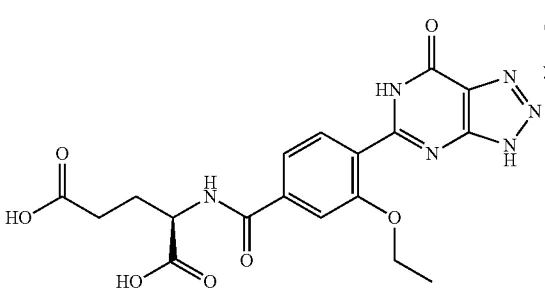 [SMILES: CCOc1cc(C(=O)N[C@H](CCC(=O)O)C(=O)O)ccc1-c1nc2[nH]nnc2c(=O)[nH]1] | (3-ethoxy-4-(7-oxo-6,7-dihydro-3H-[1,2,3]triazolo[4,5-d]pyrimidin-5-yl)benzoyl)-D-glutamic acid | 431.2 |

-continued

| Cmpd | Structure | Chemical Name | m/z (M + H)+ |
|---|---|---|---|
| 170 | 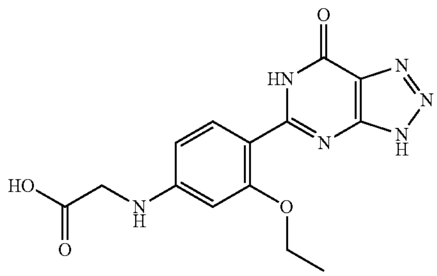 [SMILES: CCOc1cc(NCC(=O)O)ccc1-c1nc2[nH]nnc2c(=O)[nH]1] | (3-ethoxy-4-(7-oxo-6,7-dihydro-3H-[1,2,3]triazolo[4,5-d]pyrimidin-5-yl)phenyl)glycine | 331.1 |
| 171 | 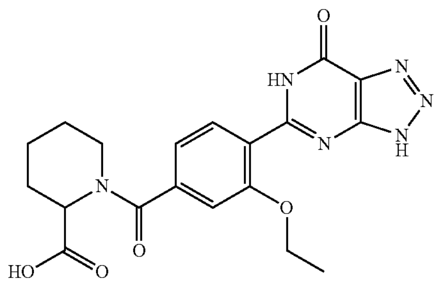 [SMILES: CCOc1cc(C(=O)N2CCCCC2C(=O)O)ccc1-c1nc2[nH]nnc2c(=O)[nH]1] | 1-(3-ethoxy-4-(7-oxo-6,7-dihydro-3H-[1,2,3]triazolo[4,5-d]pyrimidin-5-yl)benzoyl)piperidine-2-carboxylic acid | 413.1 |
| 172 | 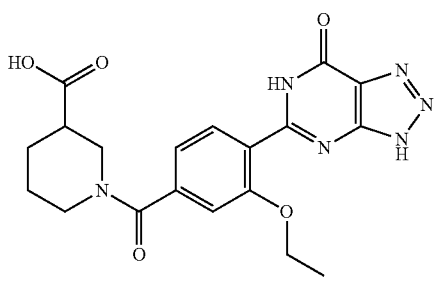 [SMILES: CCOc1cc(C(=O)N2CCCC(C(=O)O)C2)ccc1-c1nc2[nH]nnc2c(=O)[nH]1] | 1-(3-ethoxy-4-(7-oxo-6,7-dihydro-3H-[1,2,3]triazolo[4,5-d]pyrimidin-5-yl)benzoyl)piperidine-3-carboxylic acid | 413.1 |
| 173 | 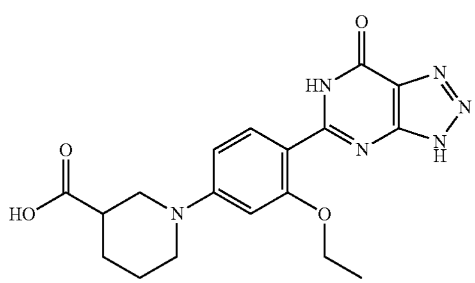 [SMILES: CCOc1cc(N2CCCC(C(=O)O)C2)ccc1-c1nc2[nH]nnc2c(=O)[nH]1] | 1-(3-ethoxy-4-(7-oxo-6,7-dihydro-3H-[1,2,3]triazolo[4,5-d]pyrimidin-5-yl)phenyl)piperidine-3-carboxylic acid | 385.1 |
| 174 | 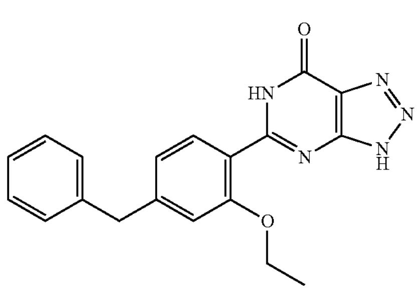 [SMILES: CCOc1cc(Cc2ccccc2)ccc1-c1nc2[nH]nnc2c(=O)[nH]1] | 5-(4-benzyl-2-ethoxyphenyl)-3,6-dihydro-7H-[1,2,3]triazolo[4,5-d]pyrimidin-7-one | 348.2 |

-continued

| Cmpd | Structure | Chemical Name | m/z (M + H)+ |
|---|---|---|---|
| 175 | 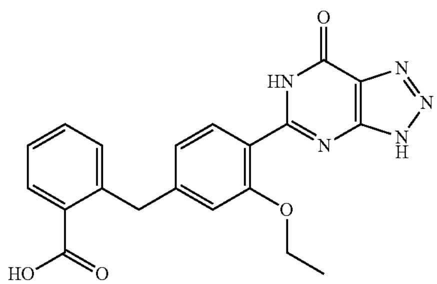 [SMILES: CCOc1cc(Cc2ccccc2C(=O)O)ccc1-c1nc2[nH]nnc2c(=O)[nH]1] | 2-(3-ethoxy-4-(7-oxo-6,7-dihydro-3H-[1,2,3]triazolo[4,5-d]pyrimidin-5-yl)benzyl)benzoic acid | 392.1 |
| 176 | 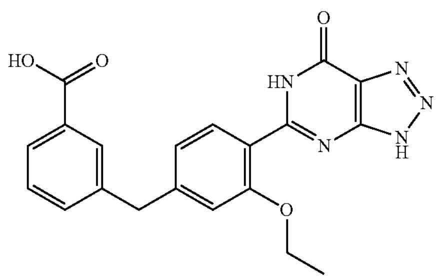 [SMILES: CCOc1cc(Cc2cccc(C(=O)O)c2)ccc1-c1nc2[nH]nnc2c(=O)[nH]1] | 3-(3-ethoxy-4-(7-oxo-6,7-dihydro-3H-[1,2,3]triazolo[4,5-d]pyrimidin-5-yl)benzyl)benzoic acid | 392.2 |
| 177 | 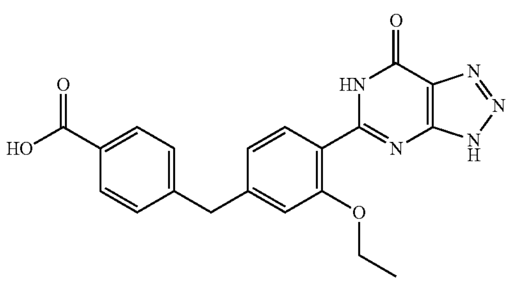 [SMILES: CCOc1cc(Cc2ccc(C(=O)O)cc2)ccc1-c1nc2[nH]nnc2c(=O)[nH]1] | 4-(3-ethoxy-4-(7-oxo-6,7-dihydro-3H-[1,2,3]triazolo[4,5-d]pyrimidin-5-yl)benzyl)benzoic acid | 392.2 |
| 178 | 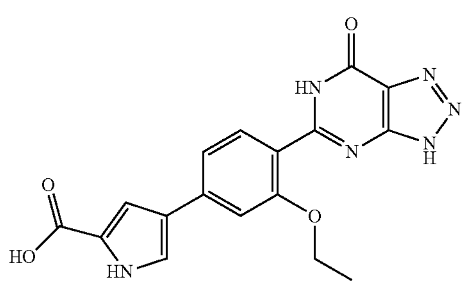 [SMILES: CCOc1cc(-c2c[nH]c(C(=O)O)c2)ccc1-c1nc2[nH]nnc2c(=O)[nH]1] | 4-(3-ethoxy-4-(7-oxo-6,7-dihydro-3H-[1,2,3]triazolo[4,5-d]pyrimidin-5-yl)phenyl)-1H-pyrrole-2-carboxylic acid | 367.1 |
| 179 | 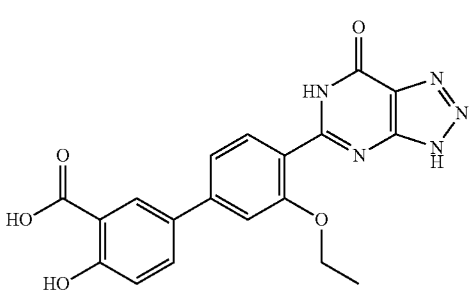 [SMILES: CCOc1cc(-c2ccc(O)c(C(=O)O)c2)ccc1-c1nc2[nH]nnc2c(=O)[nH]1] | 3'-ethoxy-4-hydroxy-4'-(7-oxo-6,7-dihydro-3H-[1,2,3]triazolo[4,5-d]pyrimidin-5-yl)-[1,1'-biphenyl]-3-carboxylic acid | 394.1 |

-continued

| Cmpd | Structure | Chemical Name | m/z (M + H)+ |
|---|---|---|---|
| 180 | 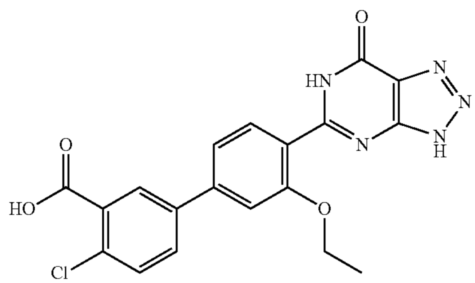 [SMILES: CCOc1cc(-c2ccc(Cl)c(C(=O)O)c2)ccc1-c1nc2[nH]nnc2c(=O)[nH]1] | 4-chloro-3'-ethoxy-4'-(7-oxo-6,7-dihydro-3H-[1,2,3]triazolo[4,5-d]pyrimidin-5-yl)-[1,1'-biphenyl]-3-carboxylic acid | 412.1 |
| 181 | 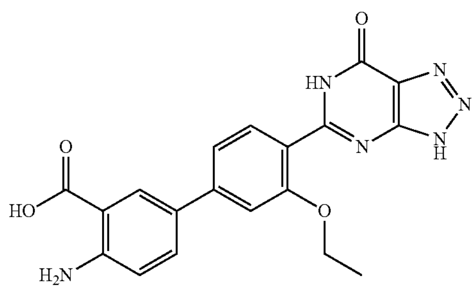 [SMILES: CCOc1cc(-c2ccc(N)c(C(=O)O)c2)ccc1-c1nc2[nH]nnc2c(=O)[nH]1] | 4-amino-3'-ethoxy-4'-(7-oxo-6,7-dihydro-3H-[1,2,3]triazolo[4,5-d]pyrimidin-5-yl)-[1,1'-biphenyl]-3-carboxylic acid | 393.1 |
| 182 | 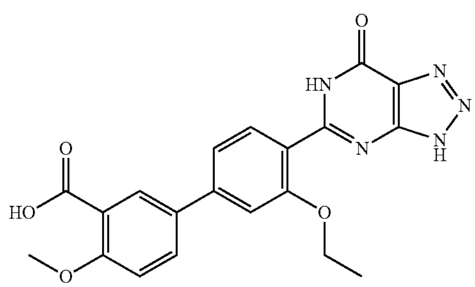 [SMILES: CCOc1cc(-c2ccc(OC)c(C(=O)O)c2)ccc1-c1nc2[nH]nnc2c(=O)[nH]1] | 3'-ethoxy-4-methoxy-4'-(7-oxo-6,7-dihydro-3H-[1,2,3]triazolo[4,5-d]pyrimidin-5-yl)-[1,1'-biphenyl]-3-carboxylic acid | 408.2 |
| 183 | 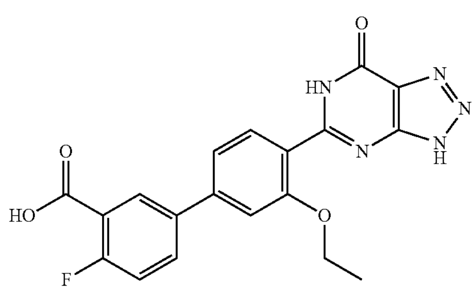 [SMILES: CCOc1cc(-c2ccc(F)c(C(=O)O)c2)ccc1-c1nc2[nH]nnc2c(=O)[nH]1] | 3'-ethoxy-4-fluoro-4'-(7-oxo-6,7-dihydro-3H-[1,2,3]triazolo[4,5-d]pyrimidin-5-yl)-[1,1'-biphenyl]-3-carboxylic acid | 396.1 |
| 184 | 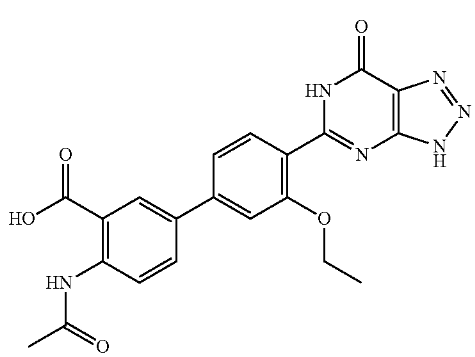 [SMILES: CCOc1cc(-c2ccc(NC(C)=O)c(C(=O)O)c2)ccc1-c1nc2[nH]nnc2c(=O)[nH]1] | 4-acetamido-3'-ethoxy-4'-(7-oxo-6,7-dihydro-3H-[1,2,3]triazolo[4,5-d]pyrimidin-5-yl)-[1,1'-biphenyl]-3-carboxylic acid | 435.2 |

-continued

| Cmpd | Structure | Chemical Name | m/z (M + H)+ |
|---|---|---|---|
| 185 | 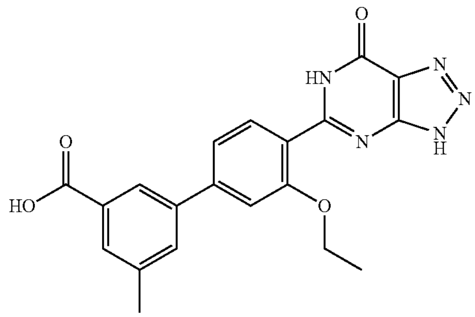 [SMILES: CCOc1cc(-c2cc(C)cc(C(=O)O)c2)ccc1-c1nc2[nH]nnc2c(=O)[nH]1] | 3'-ethoxy-5-methyl-4'-(7-oxo-6,7-dihydro-3H-[1,2,3]triazolo[4,5-d]pyrimidin-5-yl)-[1,1'-biphenyl]-3-carboxylic acid | 392.2 |
| 186 | 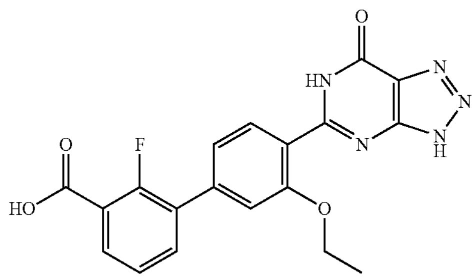 [SMILES: CCOc1cc(-c2cccc(C(=O)O)c2F)ccc1-c1nc2[nH]nnc2c(=O)[nH]1] | 3'-ethoxy-2-fluoro-4'-(7-oxo-6,7-dihydro-3H-[1,2,3]triazolo[4,5-d]pyrimidin-5-yl)-[1,1'-biphenyl]-3-carboxylic acid | 396.1 |
| 187 | 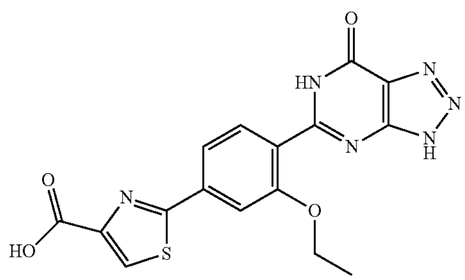 [SMILES: CCOc1cc(-c2nc(C(=O)O)co2)ccc1-c1nc2[nH]nnc2c(=O)[nH]1] | 2-(3-ethoxy-4-(7-oxo-6,7-dihydro-3H-[1,2,3]triazolo[4,5-d]pyrimidin-5-yl)phenyl)thiazole-4-carboxylic acid | 385.1 |
| 188 | 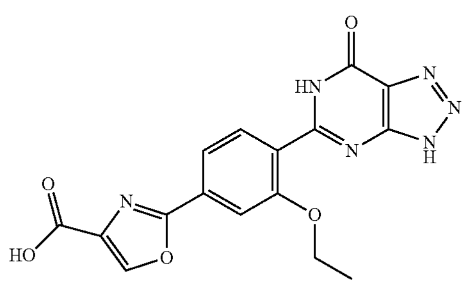 | 2-(3-ethoxy-4-(7-oxo-6,7-dihydro-3H-[1,2,3]triazolo[4,5-d]pyrimidin-5-yl)phenyl)oxazole-4-carboxylic acid | 369.1 |
| 189 | 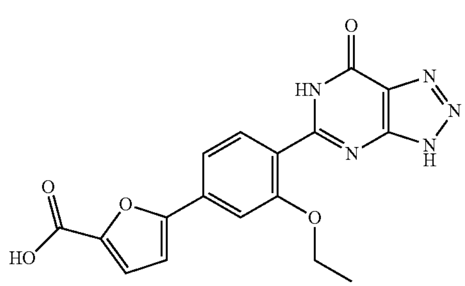 [SMILES: CCOc1cc(-c2ccc(C(=O)O)o2)ccc1-c1nc2[nH]nnc2c(=O)[nH]1] | 5-(3-ethoxy-4-(7-oxo-6,7-dihydro-3H-[1,2,3]triazolo[4,5-d]pyrimidin-5-yl)phenyl)furan-2-carboxylic acid | 368.1 |

-continued

| Cmpd | Structure | Chemical Name | m/z (M + H)+ |
|---|---|---|---|
| 190 | 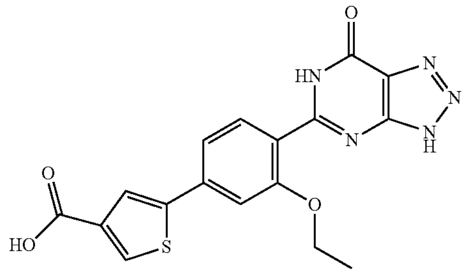 [SMILES: CCOc1cc(-c2cc(C(=O)O)cs2)ccc1-c1nc2[nH]nnc2c(=O)[nH]1] | 5-(3-ethoxy-4-(7-oxo-6,7-dihydro-3H-[1,2,3]triazolo[4,5-d]pyrimidin-5-yl)phenyl)thiophene-3-carboxylic acid | 384.1 |
| 191 | 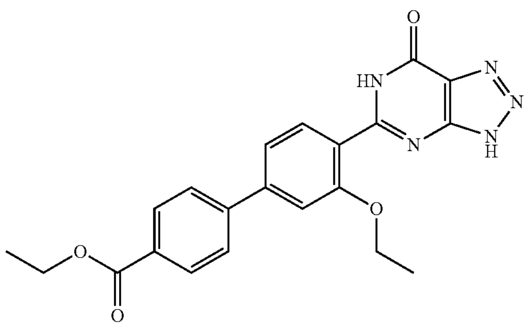 [SMILES: CCOC(=O)c1ccc(-c2ccc(-c3nc4[nH]nnc4c(=O)[nH]3)c(OCC)c2)cc1] | ethyl 3'-ethoxy-4'-(7-oxo-6,7-dihydro-3H-[1,2,3]triazolo[4,5-d]pyrimidin-5-yl)-[1,1'-biphenyl]-4-carboxylate | 406.2 |
| 192 | 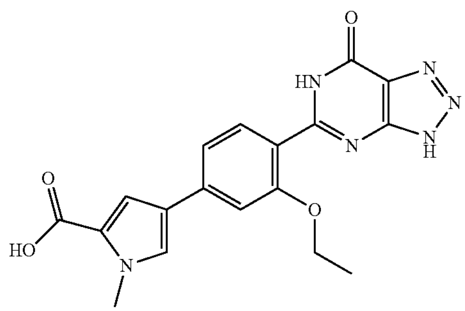 [SMILES: CCOc1cc(-c2cc(C(=O)O)n(C)c2)ccc1-c1nc2[nH]nnc2c(=O)[nH]1] | 4-(3-ethoxy-4-(7-oxo-6,7-dihydro-3H-[1,2,3]triazolo[4,5-d]pyrimidin-5-yl)phenyl)-1-methyl-1H-pyrrole-2-carboxylic acid | 381.1 |

Example 37: Synthesis of (5-Methyl-2-oxo-1,3-dioxol-4-yl)methyl 3'-ethoxy-4'-(7-oxo-6,7-dihydro-3H-[1,2,3]triazolo[4,5-d]pyrimidin-5-yl)-[1,1'-biphenyl]-4-carboxylate (Compound 193)

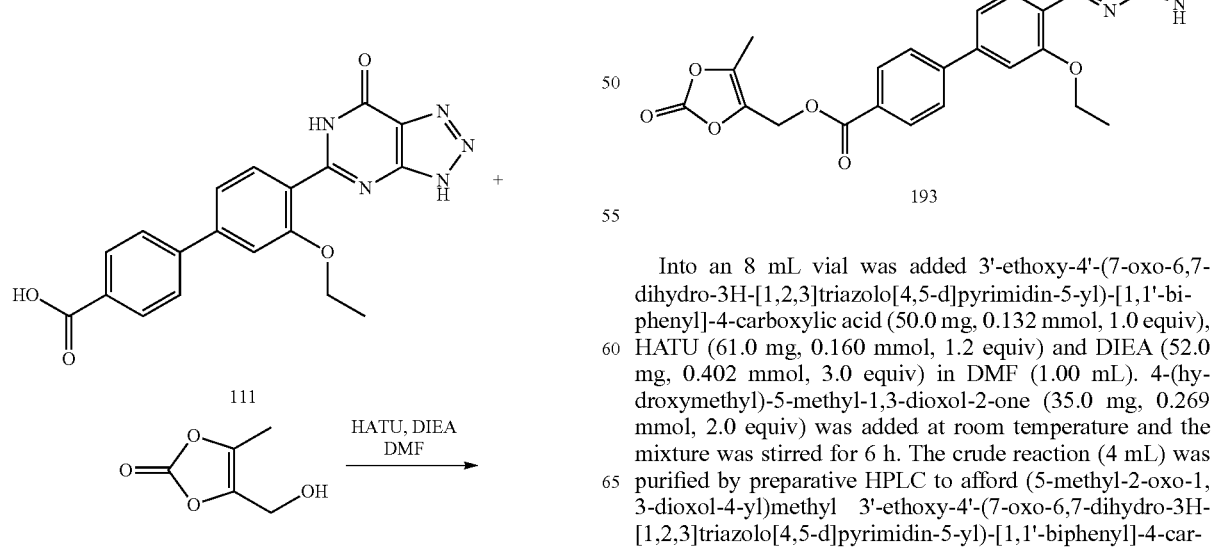

Into an 8 mL vial was added 3'-ethoxy-4'-(7-oxo-6,7-dihydro-3H-[1,2,3]triazolo[4,5-d]pyrimidin-5-yl)-[1,1'-biphenyl]-4-carboxylic acid (50.0 mg, 0.132 mmol, 1.0 equiv), HATU (61.0 mg, 0.160 mmol, 1.2 equiv) and DIEA (52.0 mg, 0.402 mmol, 3.0 equiv) in DMF (1.00 mL). 4-(hydroxymethyl)-5-methyl-1,3-dioxol-2-one (35.0 mg, 0.269 mmol, 2.0 equiv) was added at room temperature and the mixture was stirred for 6 h. The crude reaction (4 mL) was purified by preparative HPLC to afford (5-methyl-2-oxo-1,3-dioxol-4-yl)methyl 3'-ethoxy-4'-(7-oxo-6,7-dihydro-3H-[1,2,3]triazolo[4,5-d]pyrimidin-5-yl)-[1,1'-biphenyl]-4-carboxylate (25.1 mg, 370%) as an off-white solid. LCMS (ESI)=490.2 [M+H]+. $^1$H NMR (300 MHz, DMSO-d$_6$) δ 11.81 (s, 1H), 8.18-8.04 (m, 2H), 8.02-7.89 (m, 3H), 7.48 (d, J=7.2 Hz, 2H), 5.27 (s, 2H), 4.32 (q, J=6.9 Hz, 2H), 2.25 (s, 3H), 1.41 (t, J=6.9 Hz, 3H).

Example 38: Synthesis of 3'-(Cyclopentyloxy)-4'-(7-oxo-6,7-dihydro-3H-[1,2,3]triazolo[4,5-d]pyrimidin-5-yl)-[1,1'-biphenyl]-4-carboxylic Acid (Compound 194)

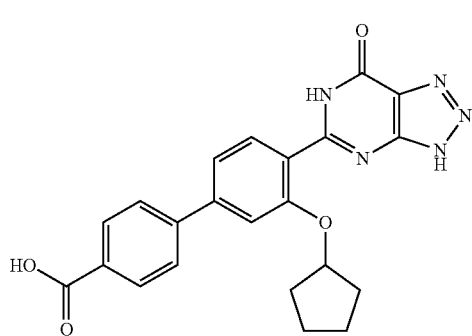

194

3'-(Cyclopentyloxy)-4'-(7-oxo-6,7-dihydro-3H-[1,2,3]triazolo[4,5-d]pyrimidin-5-yl)-[1,1'-biphenyl]-4-carboxylic acid was prepared using the procedures in Examples 6 and 9, except bromocyclopentane is used in Step 2, Example 6. LCMS (ESI)=418.1 [M+H]+. $^1$H NMR (300 MHz, DMSO-d$_6$) δ 8.08 (dd, J=12.9, 8.1 Hz, 3H), 7.89 (d, J=8.1 Hz, 2H), 7.46 (d, J=8.1 Hz, 2H), 5.28-5.19 (m, 1H), 2.09-1.82 (m, 4H), 1.82-1.53 (m, 4H).

Example 39: Synthesis of 2'-Ethoxy-4'-(7-oxo-6,7-dihydro-3H-[1,2,3]triazolo[4,5-d]pyrimidin-5-yl)-[1,1'-biphenyl]-4-carboxylic Acid (Compound 195)

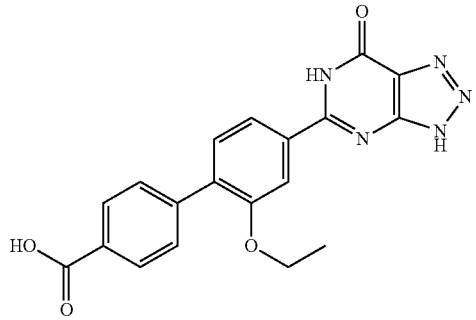

195

2'-Ethoxy-4'-(7-oxo-6,7-dihydro-3H-[1,2,3]triazolo[4,5-d]pyrimidin-5-yl)-[1,1'-biphenyl]-4-carboxylic acid was prepared using the procedures in Examples 6 and 9. LCMS (ESI)=378.1 [M+H]+. $^1$H NMR (300 MHz, DMSO-d$_6$) δ 7.98 (d, J=8.0 Hz, 2H), 7.84 (d, J=7.8 Hz, 2H), 7.66 (d, J=8.0 Hz, 2H), 7.46 (d, J=8.1 Hz, 1H), 4.23 (q, J=6.9 Hz, 2H), 1.34 (t, J=6.9 Hz, 3H).

Example 40: Synthesis of 2',6'-Dimethoxy-4'-(7-oxo-6,7-dihydro-3H-[1,2,3]triazolo[4,5-d]pyrimidin-5-yl)-[1,1'-biphenyl]-4-carboxylic Acid (Compound 196)

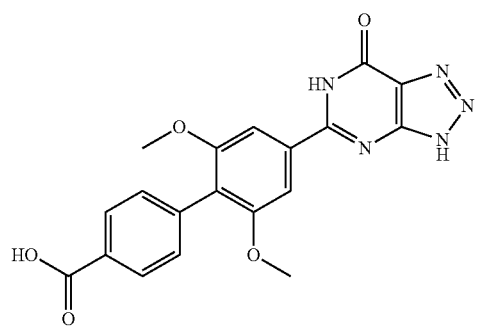

196

2',6'-Dimethoxy-4'-(7-oxo-6,7-dihydro-3H-[1,2,3]triazolo[4,5-d]pyrimidin-5-yl)-[1,1'-biphenyl]-4-carboxylic acid was prepared using the procedures in Examples 6 and 9. LCMS (ESI)=394.1 [M+H]+. $^1$H NMR (300 MHz, DMSO-d$_6$) δ 7.96 (d, J=8.2 Hz, 2H), 7.57 (s, 2H), 7.40 (d, J=8.3 Hz, 2H), 3.81 (s, 6H).

Example 41: Synthesis of 5-(3'-Amino-3-ethoxy-[1,1'-biphenyl]-4-yl)-3,6-dihydro-7H-[1,2,3]triazolo[4,5-d]pyrimidin-7-one (Compound 197)

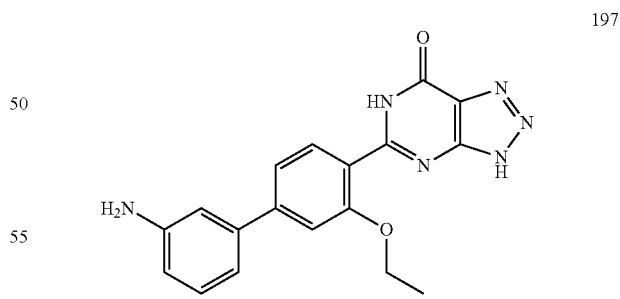

197

5-(3'-Amino-3-ethoxy-[1,1'-biphenyl]-4-yl)-3,6-dihydro-7H-[1,2,3]triazolo[4,5-d]pyrimidin-7-one was prepared using the procedures in Example 6. LCMS (ESI)=349.2 [M+H]+. $^1$H NMR (300 MHz, DMSO-d$_6$): δ 11.97 (s, 1H), 7.88 (d, J=8.5 Hz, 1H), 7.30 (d, J=6.6 Hz, 2H), 7.14 (t, J=7.8 Hz, 1H), 6.94 (t, J=1.9 Hz, 1H), 6.89 (d, J=7.6 Hz, 1H), 6.71-6.58 (m, 1H), 4.28 (q, J=6.9 Hz, 2H), 1.41 (t, J=6.9 Hz, 3H).

Example 42: Synthesis of 3'-Ethoxy-5-hydroxy-4'-(7-oxo-6,7-dihydro-3H-[1,2,3]triazolo[4,5-d]pyrimidin-5-yl)-[1,1'-biphenyl]-3-carboxylic Acid (Compound 198)

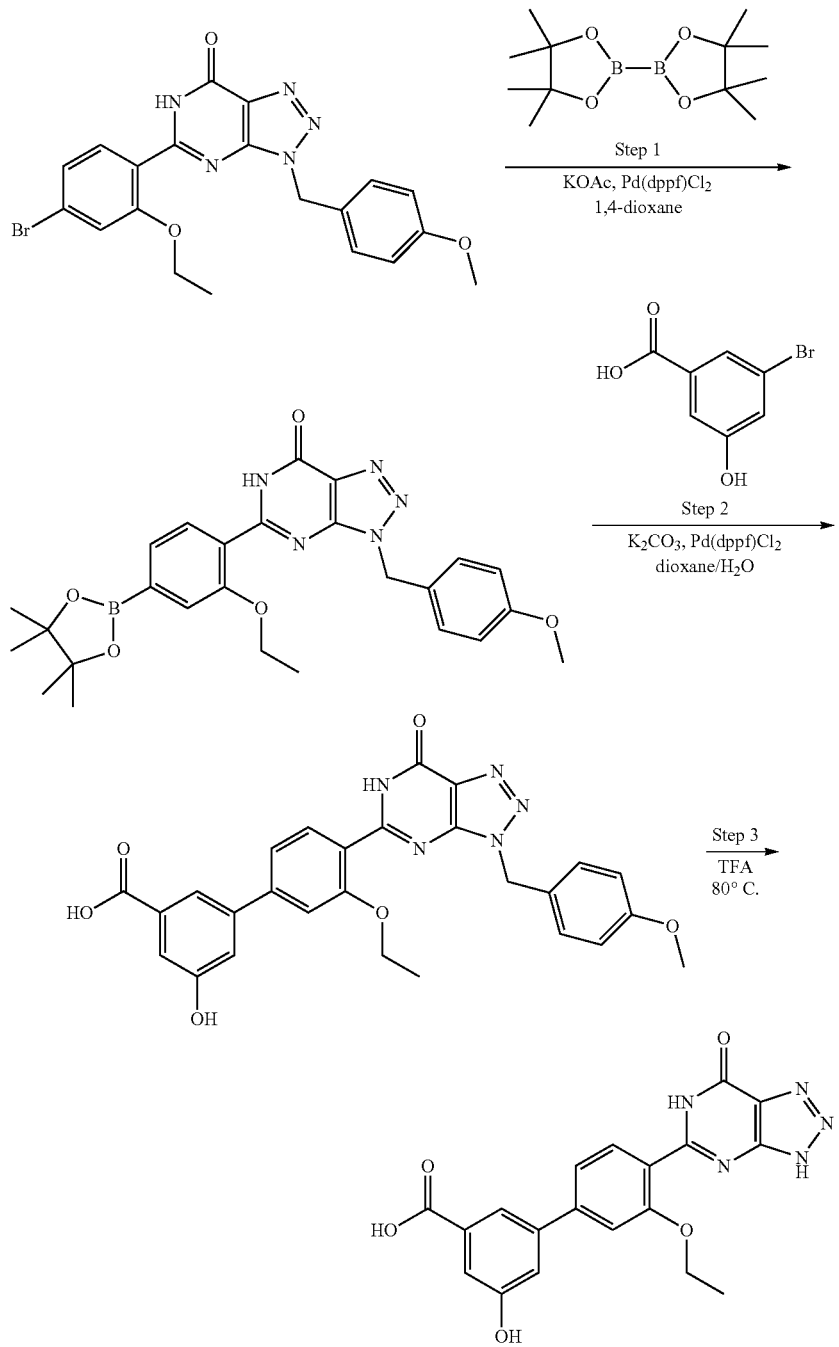

Step 1: Into a 40 mL vial was added 5-(4-bromo-2-ethoxyphenyl)-3-(4-methoxybenzyl)-3,6-dihydro-7H-[1,2,3]triazolo[4,5-d]pyrimidin-7-one (1.00 g, 2.19 mmol, 1.0 equiv) and 4,4,4',4',5,5,5',5'-octamethyl-2,2'-bi(1,3,2-dioxaborolane) (1.11 g, 4.37 mmol, 2.0 equiv) and KOAc (645 mg, 6.57 mmol, 3.0 equiv) and Pd(dppf)Cl$_2$ (160 mg, 0.219 mmol, 0.10 equi) in 1,4-dioxane (10 mL) at rt under N$_2$. The resulting mixture was stirred for 2 h at 100° C., then the reaction was quenched by the addition of water (100 mL) at rt. The precipitated solids were collected by filtration and washed with water (2×10 mL) and petroleum ether (2×10 mL) and dried to afford 5-(2-ethoxy-4-(4,4,5,5-tetramethyl- 1,3,2-dioxaborolan-2-yl)phenyl)-3-(4-methoxybenzyl)-3,6-dihydro-7H-[1,2,3]triazolo[4,5-d]pyrimidin-7-one (1.3 g, crude) as a brown solid. LCMS (ESI)=502.2 [M+H]$^+$.

Step 2: Into an 8 mL vial was added 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one (50.0 mg, 0.099 mmol, 1.0 equiv), 3-bromo-5-hydroxybenzoic acid (32.0 mg, 0.147 mmol, 1.5 equiv), $K_2CO_3$ (41.0 mg, 0.297 mmol, 3.0 equiv), Pd(dppf)Cl$_2$ (10 mg, 0.014 mmol, 0.14 equiv), dioxane (1.0 mL) and H$_2$O (0.10 mL). The resulting mixture was heated for 2 h at 80° C. under N$_2$, then allowed to cool to rt. The mixture was acidified to pH 4 with HCl (aq.), and the precipitated solids collected by filtration to afford 3'-ethoxy-5-hydroxy-4'-(3-(4-methoxybenzyl)-7-oxo-6,7-dihydro-3H-[1,2,3]triazolo[4,5-d]pyrimidin-5-yl)-[1,1'-biphenyl]-3-carboxylic acid (53 mg) as a brown solid. LCMS (ESI)=514.2 [M+H]$^+$.

Step 3: Into a vial was added 3'-ethoxy-5-hydroxy-4'-(3-(4-methoxybenzyl)-7-oxo-6,7-dihydro-3H-[1,2,3]triazolo[4,5-d]pyrimidin-5-yl)-[1,1'-biphenyl]-3-carboxylic acid (53.0 mg, 0.103 mmol, 1.0 equiv), trifluoroacetic acid (2.0 mL). The resulting mixture was stirred for 2 h at 80° C. The mixture was allowed to cool down to rt. The resulting mixture was concentrated under vacuum. The crude product was purified by preparative HPLC to afford 3'-ethoxy-5-hydroxy-4'-(7-oxo-6,7-dihydro-3H-[1,2,3]triazolo[4,5-d]pyrimidin-5-yl)-[1,1'-biphenyl]-3-carboxylic acid (6.3 mg, 16%) as an off-white solid. LCMS (ESI)=394.1 [M+H]$^+$. LCMS (ESI)=394.1 [M+H]$^+$. $^1$H NMR (300 MHz, DMSO-d$_6$) δ 12.00 (s, 1H), 10.00 (s, 1H), 7.90 (d, J=8.2 Hz, 1H), 7.71 (s, 1H), 7.44-7.33 (m, 4H), 4.31 (q, J=6.8 Hz, 2H).

Example 43: Synthesis of 3'-(Cyclopentyloxy)-5-hydroxy-4'-(7-oxo-6,7-dihydro-3H-[1,2,3]triazolo[4,5-d]pyrimidin-5-yl)-[1,1'-biphenyl]-3-carboxylic Acid (Compound 199)

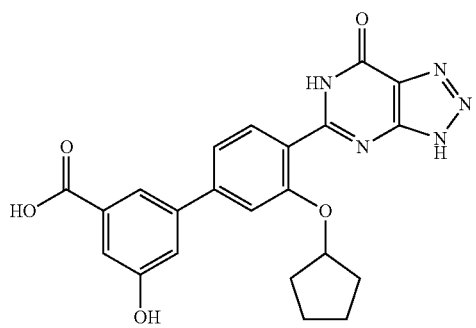

3'-(Cyclopentyloxy)-5-hydroxy-4'-(7-oxo-6,7-dihydro-3H-[1,2,3]triazolo[4,5-d]pyrimidin-5-yl)-[1,1'-biphenyl]-3-carboxylic acid was prepared using the procedures in Examples 6 and 42, except bromocyclopentane is used in Step 2, Example 6. LCMS (ESI)=434.2 [M+H]$^+$. $^1$H NMR (300 MHz, DMSO-d$_6$) δ 10.01 (s, 1H), 7.96 (d, J=8.2 Hz, 1H), 7.70 (s, 1H), 7.38 (t, J=7.5 Hz, 4H), 2.04-1.78 (m, 4H), 1.67-1.61 (m, 4H).

Example 44: Synthesis of 3'-(Cyclopentyloxy)-4-hydroxy-4'-(7-oxo-6,7-dihydro-3H-[1,2,3]triazolo[4,5-d]pyrimidin-5-yl)-[1,1'-biphenyl]-3-carboxylic Acid (Compound 200)

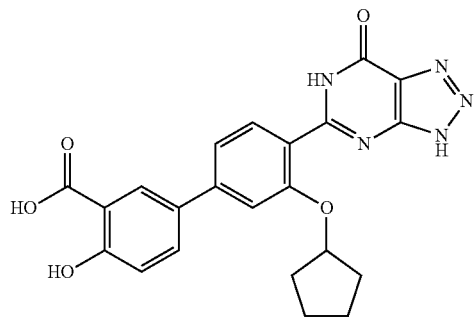

3'-(Cyclopentyloxy)-4-hydroxy-4'-(7-oxo-6,7-dihydro-3H-[1,2,3]triazolo[4,5-d]pyrimidin-5-yl)-[1,1'-biphenyl]-3-carboxylic acid was prepared using the procedures in Example 42. LCMS (ESI)=434.1 [M+H]$^+$. $^1$H NMR (300 MHz, DMSO-d$_6$) δ 12.02 (s, 1H), 8.12 (d, J=2.5 Hz, 1H), 8.00-7.86 (m, 2H), 7.46-7.33 (m, 2H), 7.08 (d, J=8.5 Hz, 1H), 5.22 (s, 1H), 2.16-1.74 (m, 4H), 1.76-1.47 (m, 4H).

Example 45: Synthesis of 3'-(Cyclopentyloxy)-3-hydroxy-4'-(7-oxo-6,7-dihydro-3H-[1,2,3]triazolo[4,5-d]pyrimidin-5-yl)-[1,1'-biphenyl]-4-carboxylic Acid (Compound 201)

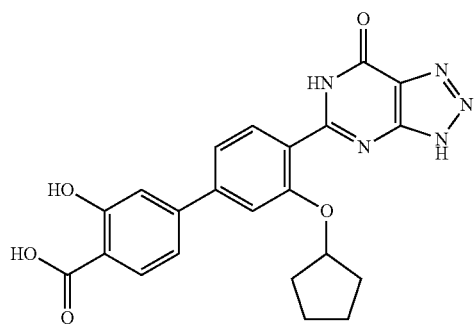

3'-(Cyclopentyloxy)-3-hydroxy-4'-(7-oxo-6,7-dihydro-3H-[1,2,3]triazolo[4,5-d]pyrimidin-5-yl)-[1,1'-biphenyl]-4-carboxylic acid was prepared using the procedures in Example 42. LCMS (ESI)=434.1 [M+H]$^+$. $^1$H NMR (300 MHz, DMSO-d$_6$) δ 7.99 (d, J=8.3 Hz, 1H), 7.80 (d, J=8.0 Hz, 1H), 7.43-7.33 (m, 2H), 7.12-7.01 (m, 2H), 5.18 (s, 1H), 1.97-1.91 (m, 2H), 1.87-1.81 (m, 2H), 1.67-1.61 (m, 4H).

Example 46: Synthesis of 3'-(Cyclopentyloxy)-2-hydroxy-4'-(7-oxo-6,7-dihydro-3H-[1,2,3]triazolo[4,5-d]pyrimidin-5-yl)-[1,1'-biphenyl]-4-carboxylic Acid (Compound 202)

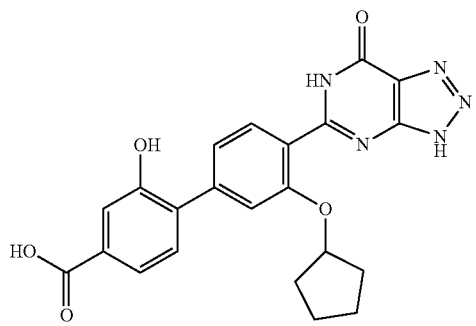

3'-(Cyclopentyloxy)-2-hydroxy-4'-(7-oxo-6,7-dihydro-3H-[1,2,3]triazolo[4,5-d]pyrimidin-5-yl)-[1,1'-biphenyl]-4-carboxylic acid was prepared using the procedures in Example 42. LCMS (ESI)=434.2 [M+H]$^+$. $^1$H NMR (300 MHz, DMSO-d$_6$) δ 12.10 (s, 1H), 7.91 (dd, J=8.2, 5.7 Hz, 2H), 7.47 (s, 2H), 7.38-7.26 (m, 2H), 5.23 (tt, J=5.7, 2.7 Hz, 1H), 2.04-1.77 (m, 4H), 1.75-1.55 (m, 4H).

Example 47: Synthesis of 5-(3-Ethoxy-3',5'-difluoro-4'-hydroxy-[1,1'-biphenyl]-4-yl)-3,6-dihydro-7H-[1,2,3]triazolo[4,5-d]pyrimidin-7-one (Compound 203)

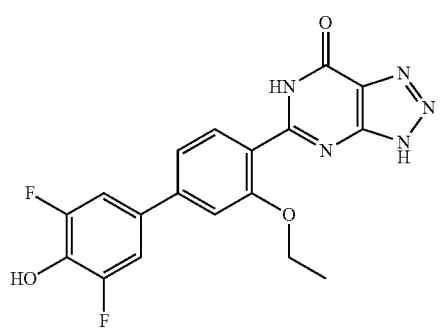

5-(3-Ethoxy-3',5'-difluoro-4'-hydroxy-[1,1'-biphenyl]-4-yl)-3,6-dihydro-7H-[1,2,3]triazolo[4,5-d]pyrimidin-7-one was prepared using the procedures in Example 42. LCMS (ESI)=386.2 [M+H]$^+$. $^1$H NMR (300 MHz, DMSO-d$_6$) δ 11.95 (s, 1H), 7.91-7.82 (m, 1H), 7.59 (dd, J=8.3, 1.7 Hz, 2H), 7.42 (d, J=6.8 Hz, 2H), 4.32 (q, J=6.9 Hz, 2H), 1.40 (t, J=6.9 Hz, 3H).

Example 48: Synthesis of 3-Amino-3'-ethoxy-4'-(7-oxo-6,7-dihydro-3H-[1,2,3]triazolo[4,5-d]pyrimidin-5-yl)-[1,1'-biphenyl]-4-carboxylic Acid (Compound 204)

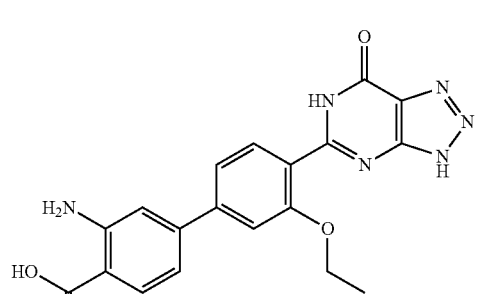

3-Amino-3'-ethoxy-4'-(7-oxo-6,7-dihydro-3H-[1,2,3]triazolo[4,5-d]pyrimidin-5-yl)-[1,1'-biphenyl]-4-carboxylic acid was prepared using the procedures in Example 42, except Pd(DTBPF)Cl$_2$ is used in Step 2. LCMS (ESI)=392.4 [M+H]$^+$. $^1$H NMR (300 MHz, DMSO-d$_6$) δ 7.92 (d, J=8.5 Hz, 1H), 7.81 (d, J=8.3 Hz, 1H), 7.35 (d, J=6.8 Hz, 2H), 7.14 (d, J=1.8 Hz, 1H), 6.92 (dd, J=8.4, 1.8 Hz, 1H), 4.29 (q, J=6.9 Hz, 2H), 1.41 (t, J=6.9 Hz, 3H).

Example 49: Synthesis of 3'-Ethoxy-3-fluoro-4'-(7-oxo-6,7-dihydro-3H-[1,2,3]triazolo[4,5-d]pyrimidin-5-yl)-[1,1'-biphenyl]-4-carboxylic Acid (Compound 205)

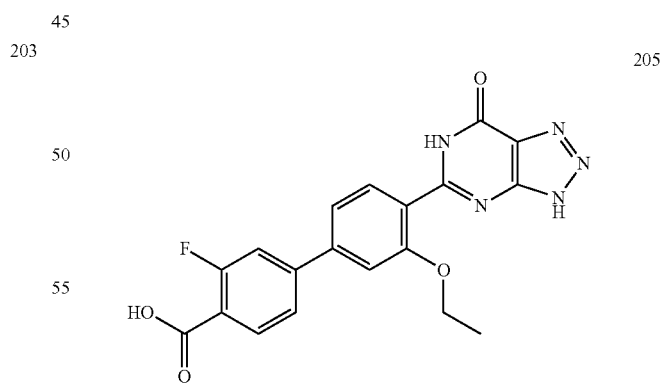

3'-Ethoxy-3-fluoro-4'-(7-oxo-6,7-dihydro-3H-[1,2,3]triazolo[4,5-d]pyrimidin-5-yl)-[1,1'-biphenyl]-4-carboxylic acid was prepared using the procedures in Example 48. LCMS (ESI)=396.1 [M+H]$^+$. $^1$H NMR (300 MHz, DMSO-d$_6$) δ 7.99 (d, J=8.5 Hz, 1H), 7.88 (t, J=8.1 Hz, 1H), 7.75-7.63 (m, 2H), 7.52-7.44 (m, 2H), 4.34 (q, J=6.9 Hz, 2H), 1.42 (t, J=6.9 Hz, 3H).

Example 50: Synthesis of 3'-Ethoxy-3-methoxy-4'-(7-oxo-6,7-dihydro-3H-[1,2,3]triazolo[4,5-d]pyrimidin-5-yl)-[1,1'-biphenyl]-4-carboxylic Acid (Compound 206)

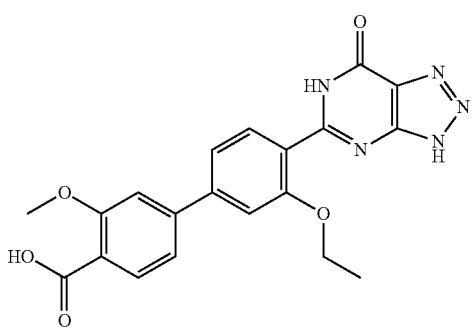

206

3'-Ethoxy-3-methoxy-4'-(7-oxo-6,7-dihydro-3H-[1,2,3]triazolo[4,5-d]pyrimidin-5-yl)-[1,1'-biphenyl]-4-carboxylic acid was prepared using the procedures in Example 48. LCMS (ESI)=408.2 [M+H]$^+$. $^1$H NMR (300 MHz, DMSO-d$_6$) δ 8.00 (d, J=8.0 Hz, 2H), 7.75 (d, J=7.8 Hz, 2H), 7.48 (dd, J=9.6, 1.5 Hz, 4H), 7.42 (s, 3H), 7.38 (d, J=1.5 Hz, 1H), 4.34 (q, J=6.9 Hz, 4H), 3.96 (s, 6H), 1.43 (t, J=6.9 Hz, 6H).

Example 52: Synthesis of 3'-Ethoxy-3-hydroxy-4'-(7-oxo-6,7-dihydro-3H-[1,2,3]triazolo[4,5-d]pyrimidin-5-yl)-[1,1'-biphenyl]-4-carboxylic Acid (Compound 208)

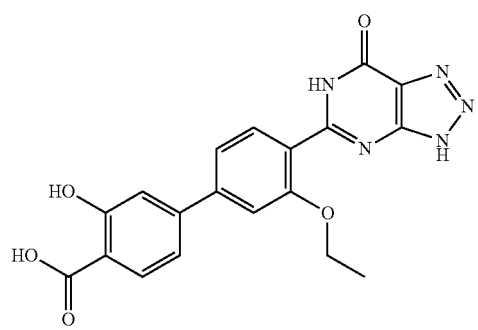

208

3'-Ethoxy-3-hydroxy-4'-(7-oxo-6,7-dihydro-3H-[1,2,3]triazolo[4,5-d]pyrimidin-5-yl)-[1,1'-biphenyl]-4-carboxylic was prepared from methyl 4-bromo-2-hydroxybenzoate using the procedures in Examples 48 and 9. LCMS (ESI)=394.01 [M+H]$^+$. $^1$H NMR (300 MHz, DMSO-d$_6$) δ 7.87 (d, J=8.4 Hz, 1H), 7.74 (d, J=7.8 Hz, 1H), 7.37 (d, J=6.5 Hz, 2H), 6.99 (d, J=10.9 Hz, 2H), 4.31 (q, J=6.9 Hz, 2H), 1.39 (t, J=6.9 Hz, 3H).

Example 51: Synthesis of 3'-Ethoxy-3-methyl-4'-(7-oxo-6,7-dihydro-3H-[1,2,3]triazolo[4,5-d]pyrimidin-5-yl)-[1,1'-biphenyl]-4-carboxylic Acid (Compound 207)

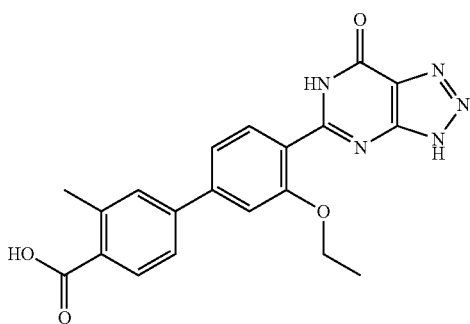

207

3'-Wthoxy-3-methyl-4'-(7-oxo-6,7-dihydro-3H-[1,2,3]triazolo[4,5-d]pyrimidin-5-yl)-[1,1'-biphenyl]-4-carboxylic acid was prepared using the procedures in Example 48. LCMS (ESI)=392.2 [M+H]$^+$. $^1$H NMR (300 MHz, DMSO-d$_6$) δ 12.89 (s, 1H), 7.95 (d, J=8.3 Hz, 1H), 7.87 (d, J=7.8 Hz, 1H), 7.78-7.67 (m, 2H), 7.47 (d, J=8.2 Hz, 2H), 4.31 (t, J=7.0 Hz, 2H), 2.64 (s, 3H), 1.40 (t, J=7.0 Hz, 3H).

Example 53: Synthesis of 3'-(Cyclopentyloxy)-2-hydroxy-4'-(7-oxo-6,7-dihydro-3H-[1,2,3]triazolo[4,5-d]pyrimidin-5-yl)-[1,1'-biphenyl]-3-carboxylic Acid (Compound 209)

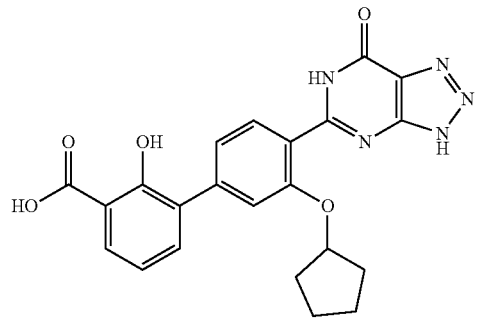

209

3'-(Cyclopentyloxy)-2-hydroxy-4'-(7-oxo-6,7-dihydro-3H-[1,2,3]triazolo[4,5-d]pyrimidin-5-yl)-[1,1'-biphenyl]-3-carboxylic acid was prepared from methyl 3-bromo-2-hydroxybenzoate using the procedures in Examples 42 and 9. LCMS (ESI)=434.1 [M+H]$^+$. $^1$H NMR (300 MHz, DMSO-d$_6$) δ 12.06 (s, 1H), 7.90 (t, J=9.2 Hz, 2H), 7.65 (d, J=7.6 Hz, 1H), 7.45 (s, 1H), 7.38-7.23 (m, 1H), 7.01 (t, J=7.8 Hz, 1H), 5.06 (s, 1H), 2.09-1.80 (m, 4H), 1.60-1.80 (m, 4H).

Example 54: Synthesis of 3'-(Cyclopentyloxy)-6-hydroxy-4'-(7-oxo-6,7-dihydro-3H-[1,2,3]triazolo[4,5-d]pyrimidin-5-yl)-[1,1'-biphenyl]-3-carboxylic Acid (Compound 210)

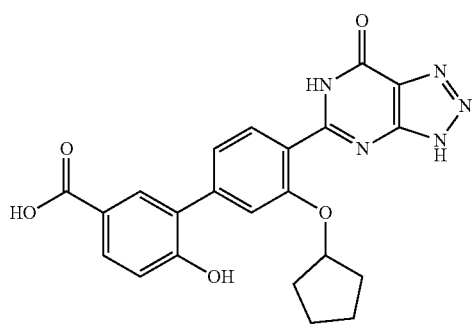

210

3'-(Cyclopentyloxy)-6-hydroxy-4'-(7-oxo-6,7-dihydro-3H-[1,2,3]triazolo[4,5-d]pyrimidin-5-yl)-[1,1'-biphenyl]-3-carboxylic acid was prepared from methyl 3-bromo-4-hydroxybenzoate using the procedures in Examples 42 and 9. LCMS (ESI)=434.2 [M+H]$^+$. $^1$H NMR (300 MHz, DMSO-$d_6$) δ 10.63 (s, 1H), 7.99 (d, J=8.2 Hz, 1H), 7.93 (d, J=2.2 Hz, 1H), 7.83 (dd, J=8.5, 2.2 Hz, 1H), 7.39 (d, J=1.6 Hz, 1H), 7.28 (dd, J=8.1, 1.5 Hz, 1H), 7.06 (d, J=8.4 Hz, 1H), 5.06 (d, J=3.5 Hz, 1H), 1.80-2.00 (m, 4H), 1.80-1.51 (m, 4H).

Example 55: Synthesis of 2-((3'-Ethoxy-4'-(7-oxo-6,7-dihydro-3H-[1,2,3]triazolo[4,5-d]pyrimidin-5-yl)-[1,1'-biphenyl]-4-yl)oxy)acetic Acid (Compound 211)

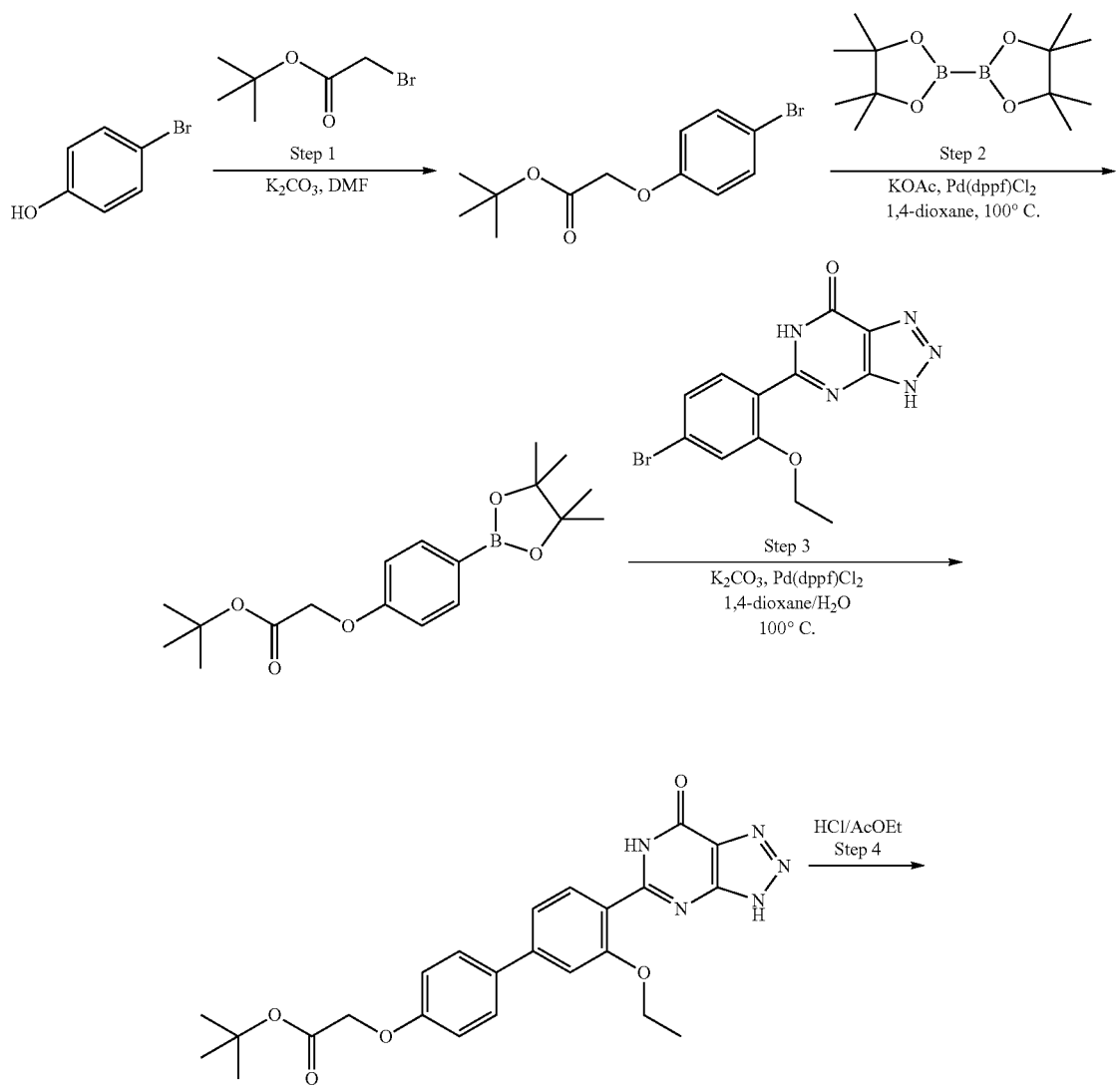

211-A

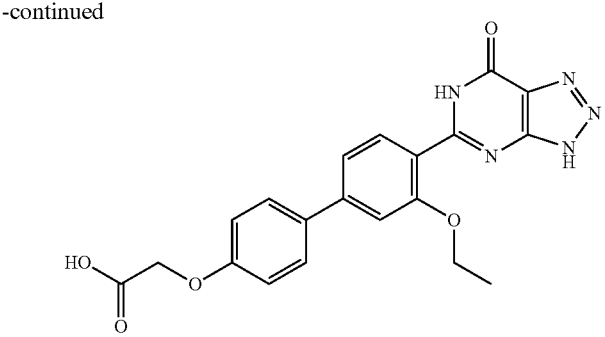

211

Step 1: Into a 40 mL vial was added 4-bromophenol (1.00 g, 5.78 mmol, 1.0 equiv), DMF (10 mL). To the above mixture was added potassium carbonate (420 mg, 17.5 mmol, 3.0 equiv) in portions at 0° C. The resulting mixture was stirred for additional 30 min at 0° C. To the above mixture was added tert-butyl 2-bromoacetate (1.40 g, 7.18 mmol, 1.24 equiv). The resulting mixture was stirred at rt until TLC analysis showed consumption of starting material. The resulting mixture was diluted with water (100 mL). The resulting mixture was extracted with EtOAc (3×100 mL). The combined organic layers were washed with brine (3×100 mL), dried over anhydrous $Na_2SO_4$, filtered and concentrated under reduced pressure. This afforded tert-butyl 2-(4-bromophenoxy)acetate (1.1 g, 66%) as a colorless oil.

Step 2: Into a 40 mL vial was added tert-butyl 2-(4-bromophenoxy)acetate (300 mg, 1.04 mmol, 1.0 equiv), bis(pinacolato)diboron (293 mg, 1.15 mmol, 1.1 equiv), $Pd(dppf)Cl_2$ (60.0 mg, 0.082 mmol, 0.08 equiv), KOAc (308 mg, 3.14 mmol, 3.0 equiv) and dioxane (5.0 mL). The resulting mixture was stirred for 4 h at 80° C. under $N_2$. The residue was purified by silica gel column chromatography to afford tert-butyl 2-(4-(4,4,5,5-tetramethyl-1,3,2-dioxaborolan-2-yl)phenoxy)acetate (240 mg, 69%) as a colorless oil. LCMS (ESI)=333.2 [M–H]$^+$.

Step 3: Into an 8 mL vial was added tert-butyl 2-(4-(4,4,5,5-tetramethyl-1,3,2-dioxaborolan-2-yl)phenoxy)acetate (80 mg, 0.239 mmol, 1.0 equiv), 5-(4-bromo-2-ethoxyphenyl)-3,6-dihydro-7H-[1,2,3]triazolo[4,5-d]pyrimidin-7-one (120 mg, 0.36 mmol, 1.5 equiv), $K_2CO_3$ (99.0 mg, 0.716 mmol, 3.0 equiv), $Pd(dppf)Cl_2$ (16.0 mg, 0.022 mmol, 0.09 equiv), dioxane (2.0 mL) and $H_2O$ (0.20 mL). The resulting mixture was stirred for 16 h at 100° C. under $N_2$. The resulting mixture was filtered, and the filtrate was concentrated under reduced pressure. The crude product was purified by preparative HPLC to afford tert-butyl 2-((3'-ethoxy-4'-(7-oxo-6,7-dihydro-3H-[1,2,3]triazolo[4,5-d]pyrimidin-5-yl)-[1,1'-biphenyl]-4-yl)oxy)acetate (75 mg, 68%) as an off-white solid.

Step 4: Into a 50 mL round-bottom flask was added tert-butyl 2-((3'-ethoxy-4'-(7-oxo-6,7-dihydro-3H-[1,2,3]triazolo[4,5-d]pyrimidin-5-yl)-[1,1'-biphenyl]-4-yl)oxy)acetate (75.0 mg, 0.162 mmol, 1.0 equiv) and 1M HCl/EtOAc (10 mL). The resulting mixture was stirred for 16 h at 50° C. The crude product was purified by preparative HPLC to afford 2-((3'-ethoxy-4'-(7-oxo-6,7-dihydro-3H-[1,2,3]triazolo[4,5-d]pyrimidin-5-yl)-[1,1'-biphenyl]-4-yl)oxy)acetic acid (19.6 mg, 30%) as an off-white solid. LCMS (ESI) =408.1 [M+H]$^+$. $^1$H NMR (300 MHz, DMSO-d$_6$) δ 12.06 (s, 1H), 7.88 (d, J=8.3 Hz, 1H), 7.74 (d, J=8.7 Hz, 2H), 7.38 (m, 2H), 7.05 (d, J=8.7 Hz, 2H), 4.75 (s, 2H), 4.31 (q, J=6.9 Hz, 2H), 1.40 (t, J=6.9 Hz, 3H).

Example 56: Synthesis of (±)-2-((3'-Ethoxy-4'-(7-oxo-6,7-dihydro-3H-[1,2,3]triazolo[4,5-d]pyrimidin-5-yl)-[1,1'-biphenyl]-3-yl)oxy)propanoic Acid (Compound 212)

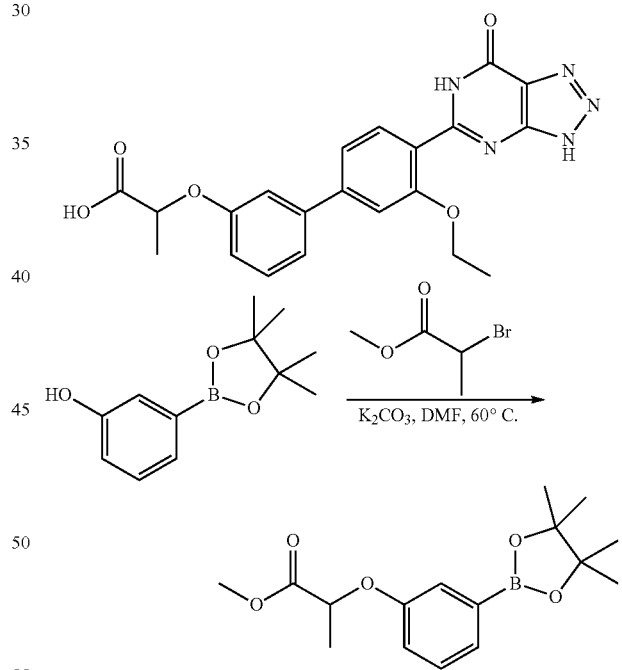

212

To a stirred solution of 3-(4,4,5,5-tetramethyl-1,3,2-dioxaborolan-2-yl)phenol (1.00 g, 4.54 mmol, 1.0 equiv) and methyl 2-bromopropanoate (1.14 g, 6.82 mmol, 1.5 equiv) in DMF (10.0 mL) was added $K_2CO_3$ (1.26 g, 9.09 mmol, 2.0 equiv) at rt. The resulting mixture was stirred for 16 h at 60° C., then the mixture was diluted with water (30 mL) and extracted with EtOAc (2×20 mL). The combined organic layers were washed with brine (20 mL), dried over anhydrous $Na_2SO_4$, filtered, and concentrated under reduced pressure. The residue was purified by silica gel column chromatography to afford methyl 2-[3-(4,4,5,5-tetramethyl- 1,3,2-dioxaborolan-2-yl)phenoxy]propanoate (520 mg, 37%) as a white solid. 2-((3'-Ethoxy-4'-(7-oxo-6,7-dihydro-3H-[1,2,3]triazolo[4,5-d]pyrimidin-5-yl)-[1,1'-biphenyl]-3-yl)oxy)propanoic acid was prepared using the procedures in Examples 1 and 9. LCMS (ESI)=422.1 [M+H]⁺. ¹H NMR (300 MHz, DMSO-d₆) δ 8.00 (d, J=8.5 Hz, 1H), 7.39-7.25 (m, 3H), 7.25-7.12 (m, 2H), 6.82 (d, J=8.0 Hz, 1H), 4.45-4.25 (m, 3H), 1.47-1.36 (m, 6H).

2-((3'-Ethoxy-4'-(7-oxo-6,7-dihydro-3H-[1,2,3]triazolo[4,5-d]pyrimidin-5-yl)-[1,1'-biphenyl]-3-yl)oxy)-2-methylpropanoic acid was prepared using the procedures in Examples 56, 1, and 9. LCMS (ESI)=436.2 [M+H]⁺. ¹H NMR (300 MHz, DMSO-d₆): δ 7.96 (d, J=8.5 Hz, 1H), 7.41-7.28 (m, 4H), 7.20 (s, 1H), 6.89 (d, J=7.1 Hz, 1H), 4.31 (q, J=6.9 Hz, 2H), 1.55 (s, 5H), 1.42 (t, J=6.9 Hz, 3H).

Example 57: Synthesis of 2-((3'-Ethoxy-4'-(7-oxo-6,7-dihydro-3H-[1,2,3]triazolo[4,5-d]pyrimidin-5-yl)-[1,1'-biphenyl]-3-yl)oxy)-2-methylpropanoic Acid (Compound 213)

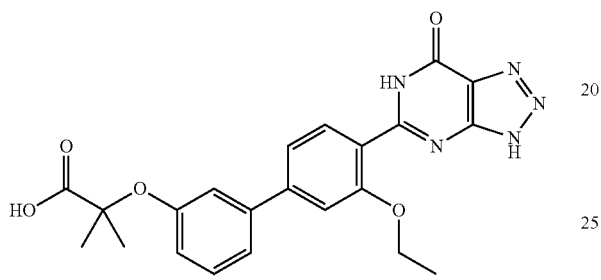

213

Example 58: Synthesis of (3'-Ethoxy-4'-(7-oxo-6,7-dihydro-3H-[1,2,3]triazolo[4,5-d]pyrimidin-5-yl)-[1,1'-biphenyl]-3-yl)glycine (Compound 214)

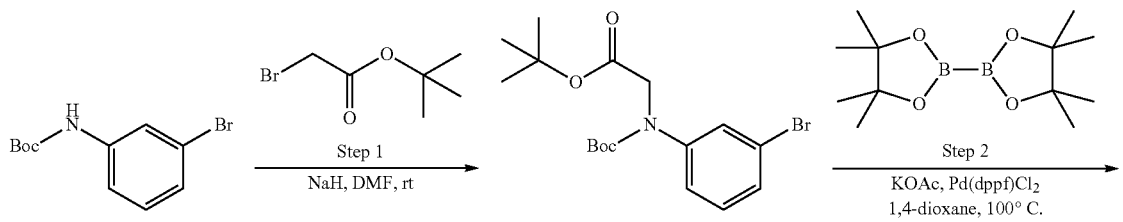

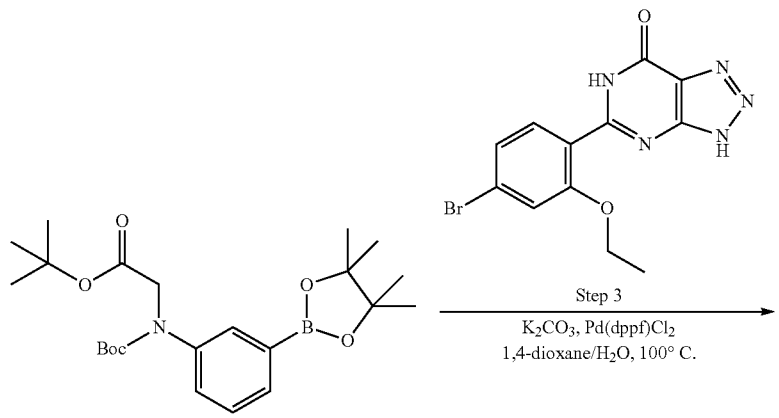

-continued

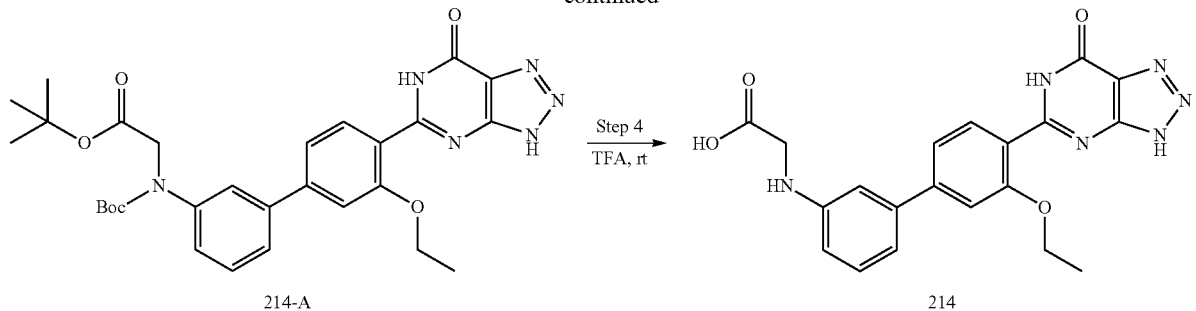

214-A

214

Step 1: Into a 40 mL vial was added tert-butyl N-(3-bromophenyl)carbamate (1.00 g, 3.68 mmol, 1.0 equiv), tert-butyl 2-bromoacetate (1.07 g, 5.51 mmol, 1.5 equiv), NaH (220 mg, 5.51 mmol, 1.5 equiv, 60%) and DMF (10.0 mL) at rt. The mixture was stirred for 1 h, then the reaction was quenched with ice water (50 mL). The resulting mixture was extracted with EtOAc (2×20 mL). The combined organic layers were washed with brine (1×20 mL), dried over anhydrous $Na_2SO_4$, filtered, and concentrated under reduced pressure. The residue was purified by silica gel column chromatography to afford tert-butyl N-(3-bromophenyl)-N-(tert-butoxycarbonyl)glycinate (800 mg, 56%) as a colorless oil. LCMS (ESI)=372 [M+H]⁺.

Step 2: Into an 8 mL of vial was added tert-butyl N-(3-bromophenyl)-N-(tert-butoxycarbonyl)glycinate (300 mg, 0.777 mmol, 1.0 equiv), bis(pinacolato)diboron (296 mg, 1.16 mmol, 1.5 equiv), Pd(dppf)$Cl_2$ (56.8 mg, 0.078 mmol, 0.10 equiv), KOAc (229 mg, 2.33 mmol, 3.0 equiv) and dioxane (5 mL). The mixture was stirred for 2 h at 100° C. The resulting mixture was cooled to rt, concentrated under reduced pressure, and the residue was purified by silica gel column chromatography to afford tert-butyl N-(tert-butoxycarbonyl)-N-(3-(4,4,5,5-tetramethyl-1,3,2-dioxaborolan-2-yl)phenyl)glycinate (270 mg, 80%) as a colorless oil.

Step 3: Into an 8 mL of vial was added 5-(4-bromo-2-ethoxyphenyl)-3,6-dihydro-7H-[1,2,3]triazolo[4,5-d]pyrimidin-7-one (70.0 mg, 0.208 mmol, 1.0 equiv), tert-butyl N-(tert-butoxycarbonyl)-N-(3-(4,4,5,5-tetramethyl-1,3,2-dioxaborolan-2-yl)phenyl)glycinate (135 mg, 0.312 mmol, 1.5 equiv), $K_2CO_3$ (57.6 mg, 0.416 mmol, 2.0 equiv), Pd(dppf)$Cl_2$ (15.2 mg, 0.021 mmol, 0.1 equiv), dioxane (1 mL) and $H_2O$ (0.3 mL). The resulting mixture was stirred for 16 h at 100° C. The mixture was allowed to cool to rt and was acidified to pH 6-7 with 2 M HCl. The mixture was purified by silica gel column chromatography to afford tert-butyl N-(tert-butoxycarbonyl)-N-(3'-ethoxy-4'-(7-oxo-6,7-dihydro-3H-[1,2,3]triazolo[4,5-d]pyrimidin-5-yl)-[1,1'-biphenyl]-3-yl)glycinate (50 mg, 43%) as an off-white solid.

Step 4: Into an 8 mL of vial was added tert-butyl N-(tert-butoxycarbonyl)-N-(3'-ethoxy-4'-(7-oxo-6,7-dihydro-3H-[1,2,3]triazolo[4,5-d]pyrimidin-5-yl)-[1,1'-biphenyl]-3-yl) glycinate (50.0 mg, 0.089 mmol, 1.0 equiv) and TFA (1.0 mL) at rt. The resulting mixture was stirred for 2 h at rt. The resulting mixture was concentrated under reduced pressure. The resulting mixture was diluted with DMSO (2 mL), then purified by preparative HPLC to afford (3'-ethoxy-4'-(7-oxo-6,7-dihydro-3H-[1,2,3]triazolo[4,5-d]pyrimidin-5-yl)-[1,1'-biphenyl]-3-yl)glycine (9.1 mg, 25%) as a white solid. LCMS (ESI)=407.1 [M+H]⁺. ¹H NMR (300 MHz, DMSO-$d_6$) δ 7.95 (d, J=8.4 Hz, 1H), 7.32 (dd, J=4.4, 2.8 Hz, 2H), 7.21 (t, J=7.8 Hz, 1H), 6.95 (d, J=9.1 Hz, 2H), 6.62 (d, J=8.5 Hz, 1H), 4.30 (q, J=6.8 Hz, 2H), 3.86 (s, 2H), 1.42 (t, J=6.9 Hz, 3H).

Example 59: Synthesis of (3'-Ethoxy-4'-(7-oxo-6,7-dihydro-3H-[1,2,3]triazolo[4,5-d]pyrimidin-5-yl)-[1,1'-biphenyl]-4-yl)glycine (Compound 215)

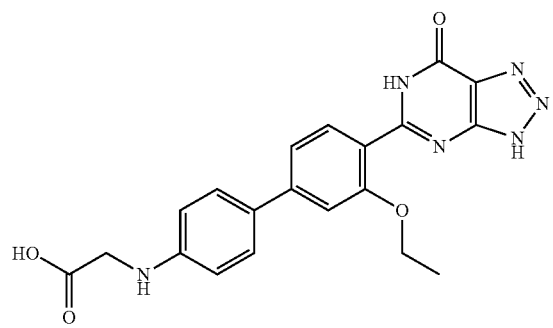

215

(3'-Ethoxy-4'-(7-oxo-6,7-dihydro-3H-[1,2,3]triazolo[4,5-d]pyrimidin-5-yl)-[1,1'-biphenyl]-4-yl)glycine was prepared using the procedures in Example 58. LCMS (ESI)=407.2 [M+H]⁺. ¹H NMR (300 MHz, DMSO-$d_6$) δ 7.95 (d, J=8.6 Hz, 1H), 7.56 (d, J=8.6 Hz, 2H), 7.36-7.27 (m, 2H), 6.68 (d, J=8.6 Hz, 2H), 4.31 (q, J=6.9 Hz, 2H), 3.82 (s, 2H), 1.43 (t, J=6.9 Hz, 3H).

Example 60: Synthesis of 2-((3'-(Cyclopentyloxy)-4'-(7-oxo-6,7-dihydro-3H-[1,2,3]triazolo[4,5-d]pyrimidin-5-yl)-[1,1'-biphenyl]-3-yl)oxy)acetic Acid (Compound 216)

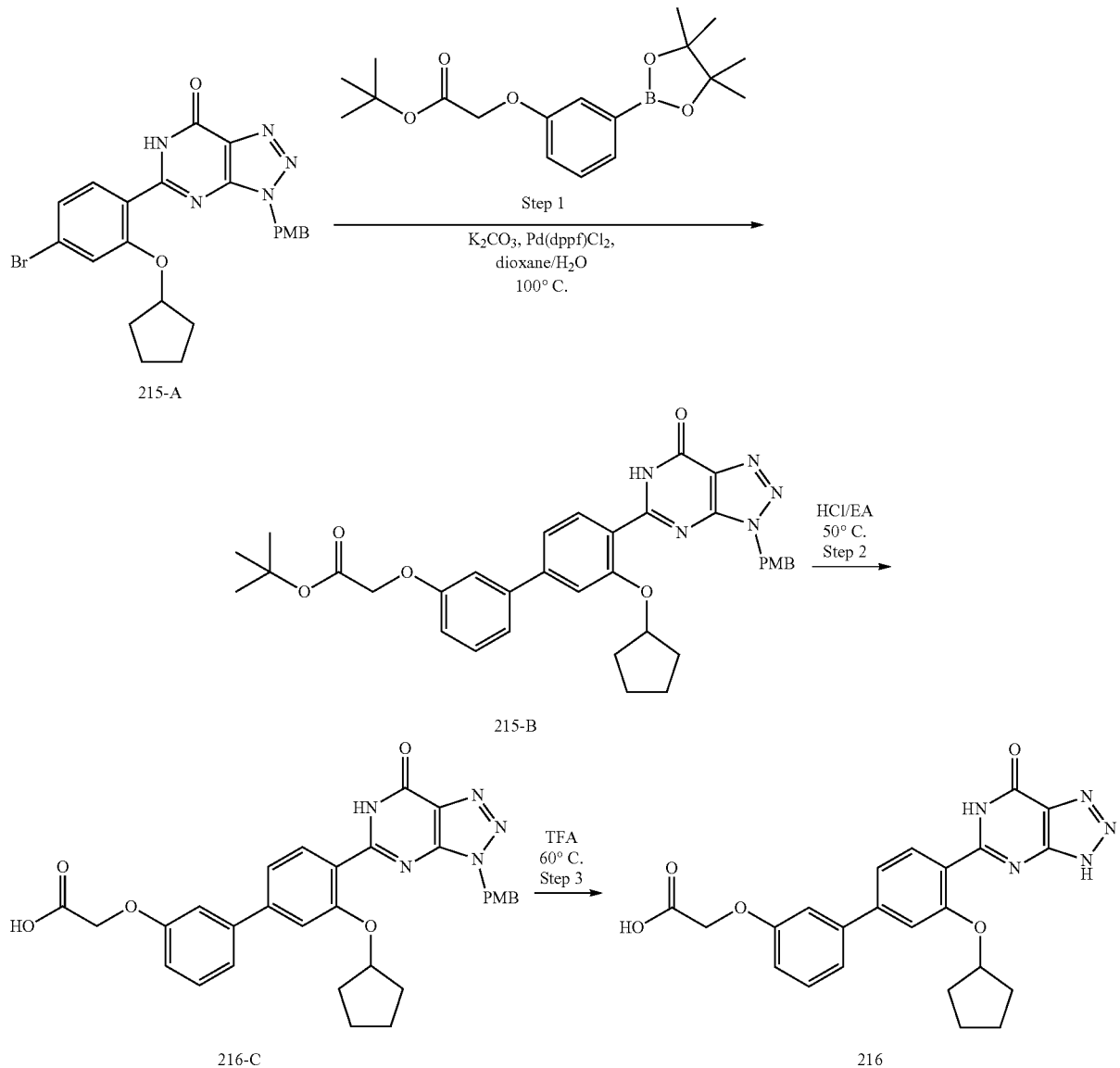

Step 1: Into an 8 mL of vial was added 5-(4-bromo-2-(cyclopentyloxy)phenyl)-3-(4-methoxybenzyl)-3,6-dihydro-7H-[1,2,3]triazolo[4,5-d]pyrimidin-7-one (200 mg, 0.403 mmol 10 equiv) and tert-butyl 2-(3-(4,4,5,5-tetramethyl-1,3,2-dioxaborolan-2-yl)phenoxy)acetate (202 mg, 0.604 mmol, 1.5 equiv), $K_2CO_3$ (167 mg, 1.21 mmol, 3.0 equiv), Pd(dppf)$Cl_2$ $CH_2Cl_2$ (32.9 mg, 0.040 mmol, 0.10 equiv), dioxane (3.0 me) and H2C (0.30 mL). The mixture was stirred for 2 h at 100° C. The mixture was allowed to cool down to rt, and the residue was purified by silica gel column chromatography to afford tert-butyl 2-((3'-(cyclopentyloxy)-4'-(3-(4-methoxybenzyl)-7-oxo-6,7-dihydro-3H-[1,2,3]triazolo[4,5-d]pyrimidin-5-yl)-[1,1'-biphenyl]-3-yl)oxy)acetate (250 mg) as an off-white solid.

Step 2: Into a 40 mL of vial was added tert-butyl 2-((3'-(cyclopentyloxy)-4'-(3-(4-methoxybenzyl)-7-oxo-6,7-dihydro-3H-[1,2,3]triazolo[4,5-d]pyrimidin-5-yl)-[1,1'-biphenyl]-3-yl)oxy)acetate (250 mg, 0.401 mmol, 1.0 equiv) and HCl (gas) in EA (5.0 mL saturated solution). The resulting mixture was stirred for 3 h at 50'° C. The resulting mixture was concentrated under reduced pressure to afford 2-((3'-(cyclopentyloxy)-4'-(3-(4-methoxybenzyl)-7-oxo-6,7-dihydro-3H-[1,2,3]triazolo[4,5-d]pyrimidin-5-yl)-[1,1'-biphenyl]-3-yl)oxy)acetic acid (200 mg), which was used in the next step without purification.

Step 3: Into an 8 mL vial was added 2-((3'-(cyclopentyloxy)-4'-(3-(4-methoxybenzyl)-7-oxo-6,7-dihydro-3H-[1,2,3]triazolo[4,5-d]pyrimidin-5-yl)-[1,1'-biphenyl]-3-yl)oxy)acetic acid (200 mg, 0.352 mmol, 1.0 equiv) and TFA (3.0 mL). The mixture was stirred for 2 h at 60° C. The mixture was concentrated under reduced pressure, and the crude residue was purified by preparative HPLC to afford 2-((3'-(cyclopentyloxy)-4'-(7-oxo-6,7-dihydro-3H-[1,2,3]triazolo[4,5-d]pyrimidin-5-yl)-[1,1'-biphenyl]-3-yl)oxy)acetic acid (19.6 mg, 12%) as a white solid. LCMS (ESI)=448.2 [M+H]$^+$. $^1$H NMR (300 MHz, DMSO-d$_6$) δ 8.05 (d, J=8.4 Hz, 1H), 7.46-7.36 (m, 3H), 7.33 (d, J=7.8 Hz, 1H), 7.24 (s, 1H), 6.96 (d, J=8.2 Hz, 1H), 5.23 (s, 1H), 4.68 (s, 2H), 2.02-1.86 (m, 4H), 1.81-1.51 (m, 4H).

Example 61: Synthesis of 2-((2'-Ethoxy-4'-(7-oxo-6,7-dihydro-3H-[1,2,3]triazolo[4,5-d]pyrimidin-5-yl)-[1,1'-biphenyl]-3-yl)oxy)acetic Acid (Compound 217)

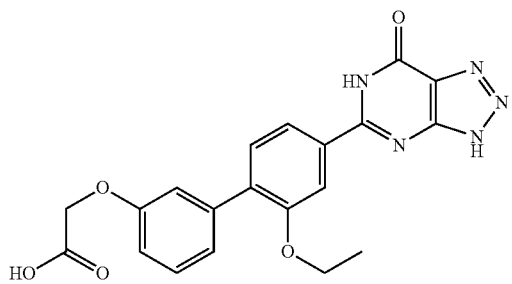

2-((2'-Ethoxy-4'-(7-oxo-6,7-dihydro-3H-[1,2,3]triazolo[4,5-d]pyrimidin-5-yl)-[1,1'-biphenyl]-3-yl)oxy)acetic acid was prepared using the procedures in Example 60. LCMS (ESI)=408.1 [M+H]$^+$. $^1$H NMR (300 MHz, DMSO-d$_6$) δ 12.68 (s, 1H), 7.88-7.79 (m, 2H), 7.50 (d, J=8.3 Hz, 1H), 7.36 (t, J=7.9 Hz, 1H), 7.23-7.09 (m, 2H), 6.92 (dd, J=8.7, 2.6 Hz, 1H), 4.72 (s, 2H), 4.22 (q, J=6.9 Hz, 2H), 1.35 (t, J=6.9 Hz, 3H).

Example 62: Synthesis of Methyl 3'-ethoxy-5-(2-methoxy-2-oxoethoxy)-4'-(7-oxo-6,7-dihydro-3H-[1,2,3]triazolo[4,5-d]pyrimidin-5-yl)-[1,1'-biphenyl]-3-carboxylate (Compound 218)

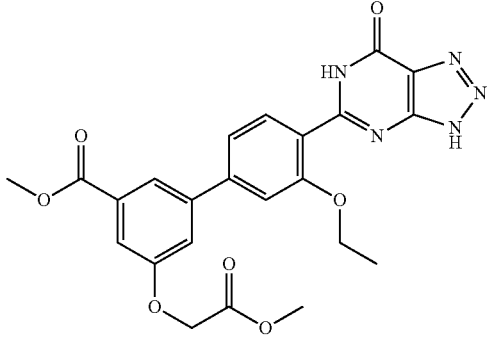

Methyl 3'-ethoxy-5-(2-methoxy-2-oxoethoxy)-4'-(7-oxo-6,7-dihydro-3H-[1,2,3]triazolo[4,5-d]pyrimidin-5-yl)-[1,1'-biphenyl]-3-carboxylate was prepared from methyl 3-bromo-5-hydroxybenzoate and methyl bromoacetate using the procedures in Example 55. LCMS (ESI)=480.2 [M+H]$^+$. $^1$H NMR (300 MHz, DMSO-d$_6$) δ 7.99 (d, J=8.5 Hz, 1H), 7.90 (s, 1H), 7.63 (s, 1H), 7.51-7.41 (m, 3H), 5.03 (s, 2H), 4.35 (t, J=6.9 Hz, 2H), 3.91 (s, 3H), 3.73 (s, 3H), 1.42 (t, J=6.9 Hz, 3H).

Example 63: Synthesis of 5-(Carboxymethoxy)-3'-ethoxy-4'-(7-oxo-6,7-dihydro-3H-[1,2,3]triazolo[4,5-d]pyrimidin-5-yl)-[1,1'-biphenyl]-3-carboxylic Acid (Compound 219)

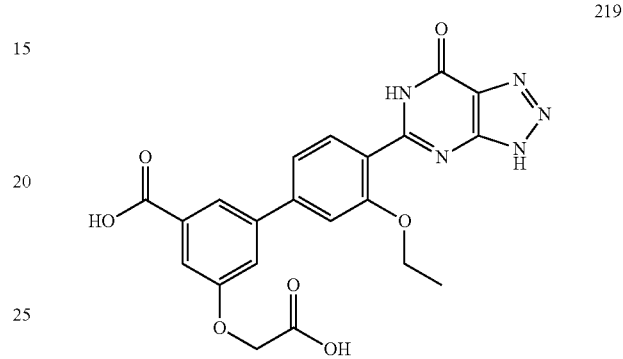

5-(Carboxymethoxy)-3'-ethoxy-4'-(7-oxo-6,7-dihydro-3H-[1,2,3]triazolo[4,5-d]pyrimidin-5-yl)-[1,1'-biphenyl]-3-carboxylic acid was synthesized from Compound 218 using the procedure in Example 9. LCMS (ESI)=452.1 [M+H]$^+$. $^1$H NMR (300 MHz, DMSO-d$_6$) δ 8.01 (d, J=8.1 Hz, 1H), 7.78 (s, 1H), 7.32 (m, 4H), 4.47-4.24 (m, 4H), 1.42 (t, J=7.0 Hz, 3H).

Example 64: Synthesis of 3-(Carboxymethoxy)-3'-ethoxy-4'-(7-oxo-6,7-dihydro-3H-[1,2,3]triazolo[4,5-d]pyrimidin-5-yl)-[1,1'-biphenyl]-4-carboxylic Acid (Compound 220)

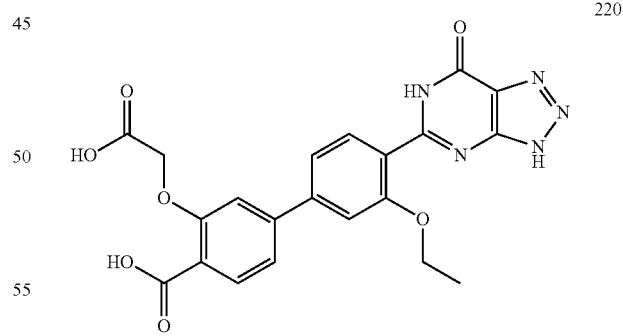

3-(Carboxymethoxy)-3'-ethoxy-4'-(7-oxo-6,7-dihydro-3H-[1,2,3]triazolo[4,5-d]pyrimidin-5-yl)-[1,1'-biphenyl]-4-carboxylic acid was synthesized from methyl 4-bromo-2-hydroxybenzoate and methyl bromoacetate using the procedures in Examples 55, 42, and 9. LCMS (ESI)=452.1 [M+H]$^+$. $^1$H NMR (300 MHz, DMSO-d$_6$) δ 12.25 (s, 1H), 7.86 (d, J=8.4 Hz, 1H), 7.67 (d, J=8.0 Hz, 1H), 7.57 (s, 1H), 7.46 (d, J=6.7 Hz, 3H), 4.79 (s, 2H), 4.32 (q, J=6.9 Hz, 2H), 1.39 (t, J=6.9 Hz, 3H).

Example 65: Synthesis of tert-butyl (3'-ethoxy-4-((4-methoxybenzyl)oxy)-4'-(7-oxo-6,7-dihydro-3H-[1,2,3]triazolo[4,5-d]pyrimidin-5-yl)-[1,1'-biphenyl]-3-yl)glycinate (Compound 221)

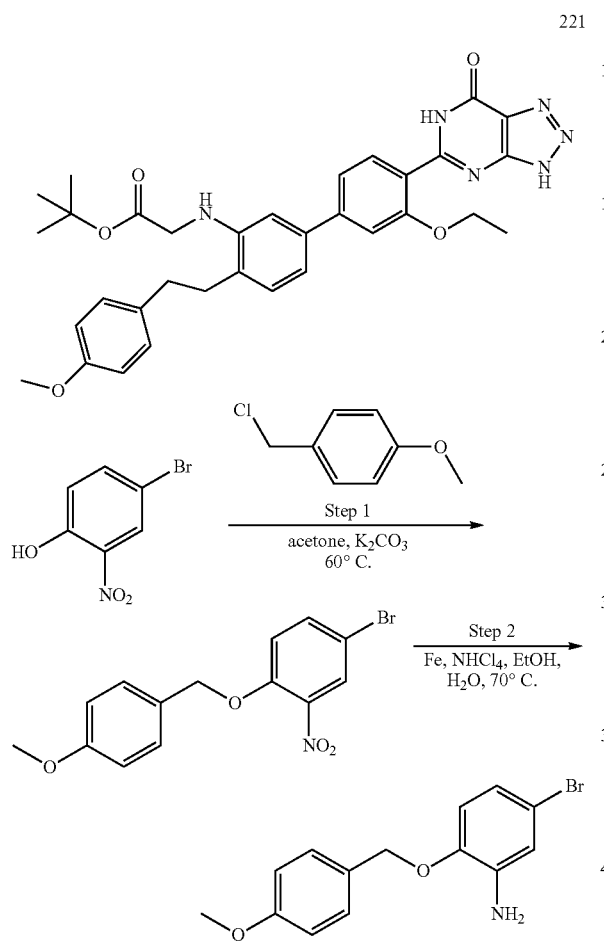

Step 1: Into a 100-mL round-bottom flask, was placed 4-bromo-2-nitrophenol (1.00 g, 4.59 mmol, 1.0 equiv), 4-chloroanisole (0.90 g, 6.31 mmol, 1.4 equiv), $K_2CO_3$ (1.90 g, 13.7 mmol, 3.0 equiv) and acetone (20 mL). The resulting solution was stirred overnight at 60° C. The resulting mixture was concentrated under vacuum, and the residue was purified by silica gel chromatography with ethyl acetate/petroleum ether (5/95) to afford 4-bromo-1-((4-methoxybenzyl)oxy)-2-nitrobenzene (850 mg, 57%) as a yellow oil. LCMS (ESI)=338.0 [M+H]⁺.

Step 2: Into a 100-mL round-bottom flask, was placed 4-bromo-1-((4-methoxybenzyl)oxy)-2-nitrobenzene (850 mg, 2.51 mmol, 1.0 equiv), $NH_4Cl$ (668 mg, 12.5 mmol, 5.0 equiv), Fe (420 mg, 7.52 mmol, 3.0 equiv) in EtOH (20 mL) and $H_2O$ (2 mL). The resulting solution was stirred for 20 min at 70° C. The solids were filtered, and the resulting mixture was concentrated under vacuum to afford 5-bromo-2-((4-methoxybenzyl)oxy)aniline (700 mg, 90%) as a brown solid. LCMS (ESI)=308.0 [M+H]⁺.

Tert-butyl (3'-ethoxy-4-((4-methoxybenzyl)oxy)-4'-(7-oxo-6,7-dihydro-3H-[1,2,3]triazolo[4,5-d]pyrimidin-5-yl)-[1,1'-biphenyl]-3-yl)glycinate (Compound 221) was prepared using procedures from Example 58. LCMS (ESI)=599.3 [M+H]⁺. ¹H NMR (300 MHz, DMSO-d₆) δ 12.14 (s, 1H), 7.84 (d, J=8.2 Hz, 1H), 7.49-7.40 (m, 2H), 7.34 (d, J=7.5 Hz, 2H), 7.09-6.95 (m, 3H), 6.97 (d, J=2.0 Hz, 1H), 6.79 (d, J=1.9 Hz, 1H), 5.26 (t, J=5.9 Hz, 1H), 5.13 (s, 2H), 4.29 (q, J=6.9 Hz, 2H), 3.98 (d, J=5.9 Hz, 2H), 3.78 (s, 3H), 1.43 (s, 9H), 1.39 (t, J=6.9 Hz, 3H).

Example 66: Synthesis of (3'-Ethoxy-4-hydroxy-4'-(7-oxo-6,7-dihydro-3H-[1,2,3]triazolo[4,5-d]pyrimidin-5-yl)-[1,1'-biphenyl]-3-yl)glycine (Compound 222)

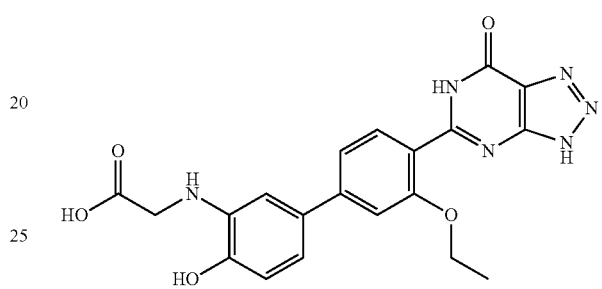

(3'-Ethoxy-4-hydroxy-4'-(7-oxo-6,7-dihydro-3H-[1,2,3]triazolo[4,5-d]pyrimidin-5-yl)-[1,1'-biphenyl]-3-yl)glycine was prepared from Compound 221 using the method in Step 4, Example 55. LCMS (ESI)=423.1 [M+H]⁺. ¹H NMR (300 MHz, DMSO-d₆) δ 8.01 (d, J=8.2 Hz, 1H), 7.29 (d, J=7.7 Hz, 2H), 6.84 (s, 1H), 6.81-6.70 (m, 2H), 4.30 (t, J=6.9 Hz, 2H), 3.71 (s, 2H), 1.44 (t, J=6.9 Hz, 3H).

Example 67: Synthesis of (3'-Ethoxy-5-hydroxy-4'-(7-oxo-6,7-dihydro-3H-[1,2,3]triazolo[4,5-d]pyrimidin-5-yl)-[1,1'-biphenyl]-3-yl)glycine (Compound 223)

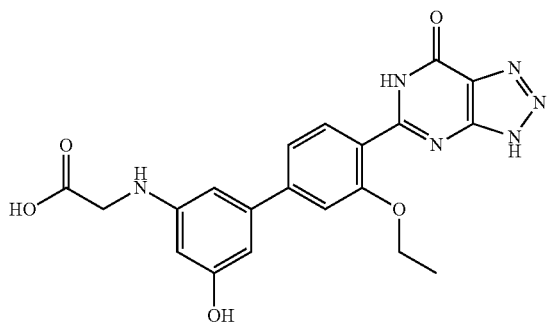

(3'-Ethoxy-5-hydroxy-4'-(7-oxo-6,7-dihydro-3H-[1,2,3]triazolo[4,5-d]pyrimidin-5-yl)-[1,1'-biphenyl]-3-yl)glycine was prepared from 3-bromo-5-nitrophenol and 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one using the procedures in Examples 65 and 60. LCMS (ESI)=423.2 [M+H]⁺. ¹H NMR (300 MHz, DMSO-d₆) δ 9.20 (s, 1H), 7.93 (d, J=8.4 Hz, 1H), 7.25 (dt, J=4.6, 2.3 Hz, 2H), 6.43-6.32 (m, 2H), 6.04 (d, J=2.1 Hz, 1H), 4.28 (q, J=6.8 Hz, 2H), 3.78 (s, 2H), 1.42 (t, J=6.9 Hz, 3H).

Example 68: Synthesis of 2-((3'-Ethoxy-4'-(7-oxo-6,7-dihydro-3H-[1,2,3]triazolo[4,5-d]pyrimidin-5-yl)-[1,1'-biphenyl]-3-yl)amino)-2-methylpropanoic Acid (Compound 224)

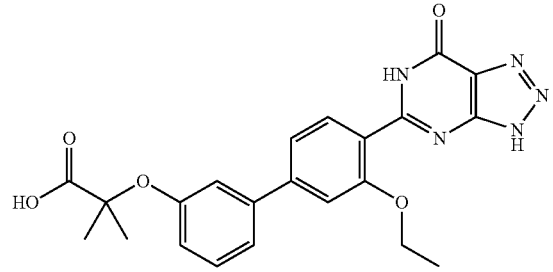

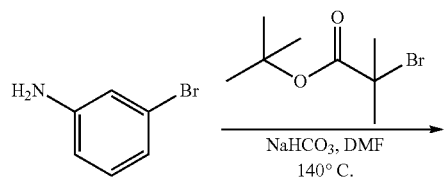

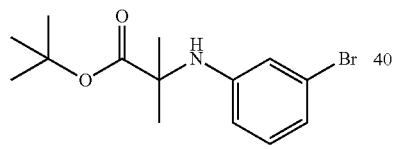

In a 40 mL vial, a mixture of 3-bromoaniline (1.00 g, 5.81 mmol, 1.0 equiv), tert-butyl 2-bromo-2-methylpropanoate (1.50 g, 6.72 mmol), NaHCO₃ (1.50 g, 17.9 mmol) in DMF (10 mL) was heated at 140° C. for 16 h. The mixture was allowed to cool down to rt and the residue was purified by silica gel column chromatography to afford tert-butyl 2-((3-bromophenyl)amino)-2-methylpropanoate (120 mg, 7%) as a brown oil. ¹H NMR (300 MHz, CDCl₃) δ 7.03 (t, J=8.0 Hz, 1H), 6.95-6.82 (m, 2H), 6.63 (d, J=8.0 Hz, 1H), 1.55 (s, 6H), 1.43 (s, 9H).

2-((3'-Ethoxy-4'-(7-oxo-6,7-dihydro-3H-[1,2,3]triazolo[4,5-d]pyrimidin-5-yl)-[1,1'-biphenyl]-3-yl)amino)-2-methylpropanoic acid was prepared from 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one using similar methods as described in Examples 42 and 60. ¹H NMR (300 MHz, DMSO-d₆) δ 11.94 (s, 1H), 7.87 (d, J=8.3 Hz, 1H), 7.30-7.13 (m, 3H), 6.93 (d, J=7.6 Hz, 1H), 6.86 (t, J=2.0 Hz, 1H), 6.59-6.50 (m, 1H), 4.27 (q, J=6.8 Hz, 2H), 1.48 (s, 6H), 1.41 (t, J=6.9 Hz, 3H).

Example 69: Synthesis of (3'-(Cyclopentyloxy)-4'-(7-oxo-6,7-dihydro-3H-[1,2,3]triazolo[4,5-d]pyrimidin-5-yl)-[1,1'-biphenyl]-3-yl)glycine (Compound 225)

(3'-(Cyclopentyloxy)-4'-(7-oxo-6,7-dihydro-3H-[1,2,3]triazolo[4,5-d]pyrimidin-5-yl)-[1,1'-biphenyl]-3-yl)glycine was prepared using the procedures in Example 58. LCMS (ESI)=447.2 [M+H]⁺. ¹H NMR (300 MHz, DMSO-d₆) δ 12.03 (s, 1H), 7.92 (d, J=8.4 Hz, 1H), 7.34 (dq, J=3.5, 1.6 Hz, 2H), 7.23 (t, J=7.8 Hz, 1H), 7.02-6.92 (m, 2H), 6.67 (dd, J=7.8, 2.2 Hz, 1H), 5.15 (dt, J=5.7, 3.0 Hz, 1H), 3.92 (s, 2H), 2.06-1.79 (m, 4H), 1.77-1.53 (m, 4H).

Example 70: Synthesis of 3-((3'-Ethoxy-4'-(7-oxo-6,7-dihydro-3H-[1,2,3]triazolo[4,5-d]pyrimidin-5-yl)-[1,1'-biphenyl]-3-yl)amino)propanoic Acid (Compound 226)

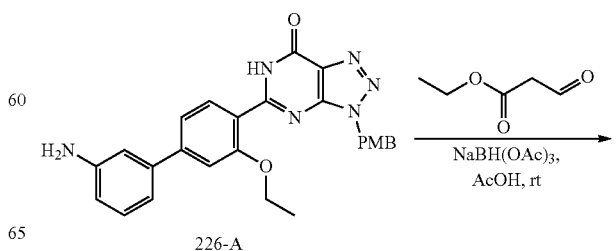

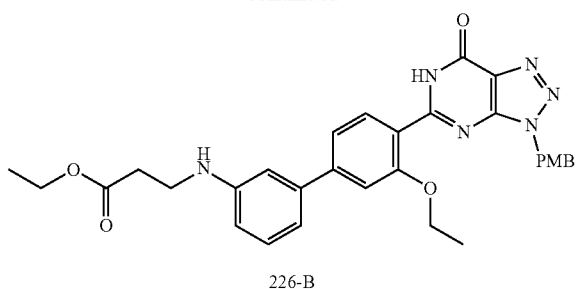

226-B 5-(3'-Amino-3-ethoxy-[1,1'-biphenyl]-4-yl)-3-(4-methoxybenzyl)-3,6-dihydro-7H-[1,2,3]triazolo[4,5-d]pyrimidin-7-one was prepared using the procedure in Example 1. Step 1: To a stirred solution of 5-(3'-amino-3-ethoxy-[1,1'-biphenyl]-4-yl)-3-(4-methoxybenzyl)-3,6-dihydro-7H-[1,2,3]triazolo[4,5-d]pyrimidin-7-one (80.0 mg, 0.171 mmol, 1.0 equiv) and ethyl 3-oxopropanoate (0.50 mL) in AcOH (1.0 mL) was added NaBH(OAc)$_3$ (362 mg, 1.71 mmol, 10 equiv) in portions at rt. The resulting mixture was stirred for 10 min, then the resulting mixture was diluted with water (10 mL). The mixture was basified to pH 8 with NaHCO$_3$, and the resulting mixture was extracted with EA (3×10 mL). The combined organic layers were washed with brine (20 mL), dried over anhydrous Na$_2$SO$_4$, filtered, and concentrated under reduced pressure. The residue was purified by silica gel column chromatography to afford ethyl 3-((3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)amino)propanoate (65 mg, 40%) as a light yellow solid.

3-((3'-Ethoxy-4'-(7-oxo-6,7-dihydro-3H-[1,2,3]triazolo[4,5-d]pyrimidin-5-yl)-[1,1'-biphenyl]-3-yl)amino)propanoic acid was prepared using the procedures in Example 6 and 9. LCMS (ESI)=421.2 [M+H]$^+$. $^1$H NMR (300 MHz, DMSO-d$_6$) δ 7.91 (d, J=8.3 Hz, 1H), 7.33 (d, J=7.4 Hz, 2H), 7.21 (t, J=7.9 Hz, 1H), 6.97-6.88 (m, 2H), 6.64 (dd, J=7.3, 1.9 Hz, 1H), 4.29 (q, J=6.9 Hz, 2H), 3.33 (t, J=6.7 Hz, 2H), 2.58-2.50 (m, 2H), 1.40 (t, J=6.9 Hz, 3H).

Example 71: Synthesis of 4'-(7-Oxo-6,7-dihydro-3H-[1,2,3]triazolo[4,5-d]pyrimidin-5-yl)-3'-(2-(pyrrolidin-1-yl)ethoxy)-[1,1'-biphenyl]-4-carboxylic Acid (Compound 227)

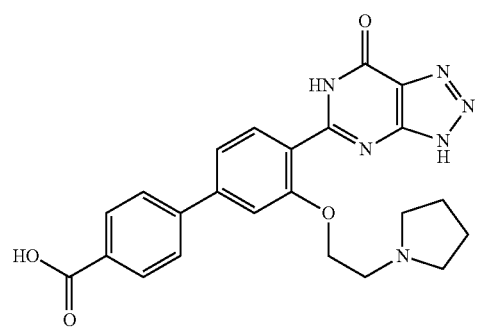

227

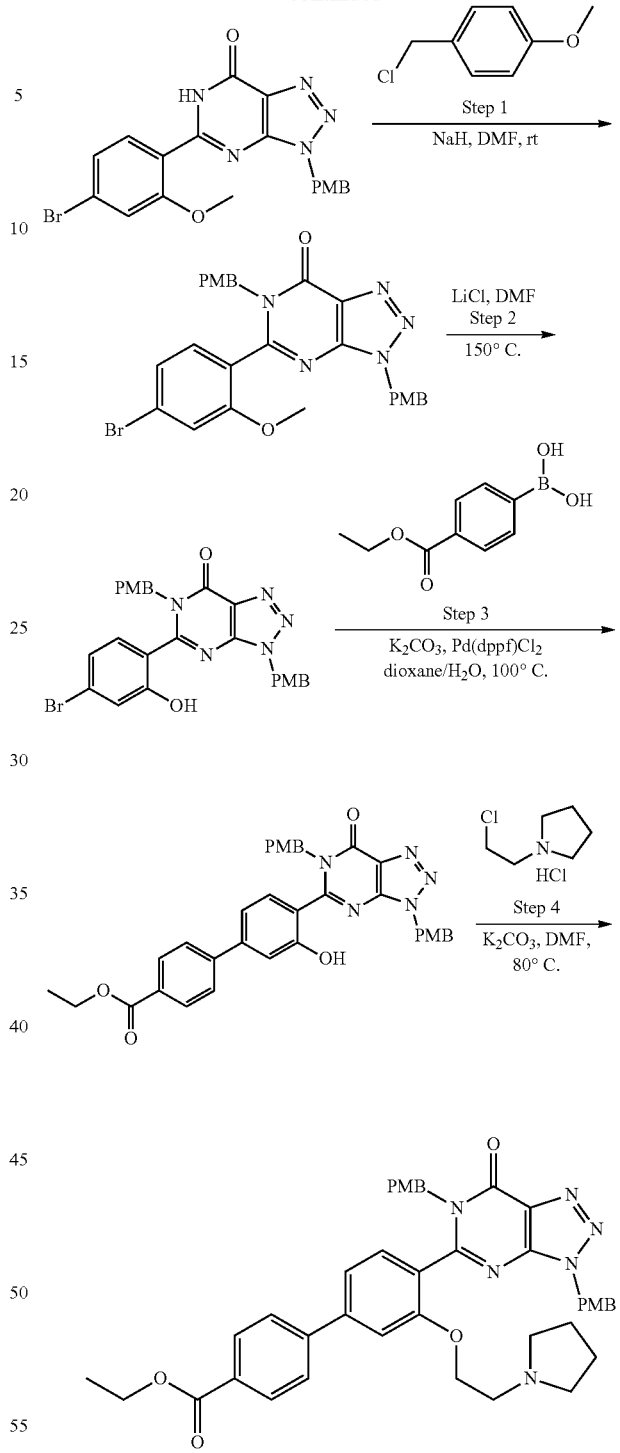

5-(4-Bromo-2-methoxyphenyl)-3-(4-methoxybenzyl)-3,6-dihydro-7H-[1,2,3]triazolo[4,5-d]pyrimidin-7-one was prepared using the procedures in Example 6.

Step 1: To a stirred solution of 5-(4-bromo-2-methoxyphenyl)-3-(4-methoxybenzyl)-3,6-dihydro-7H-[1,2,3]triazolo[4,5-d]pyrimidin-7-one (500 mg, 1.13 mmol, 1.0 equiv) in DMF (5.0 mL) was added NaH (90.4 mg, 2.26 mmol, 2.0 equiv, 60%) in portions at rt under N$_2$. The resulting mixture was stirred for 30 min at rt, then 4-methoxybenzyl chloride (212 mg, 1.36 mmol, 1.2 equiv)

was added dropwise. The resulting mixture was stirred for 24 h, then was quenched by the addition of water (20 mL). The mixture was extracted with EA (2×20 mL), and the combined organic layers were washed with brine (20 mL), dried over anhydrous $Na_2SO_4$, filtered, and concentrated under reduced pressure. The residue was purified by silica gel column chromatography to afford 5-(4-bromo-2-methoxyphenyl)-3,6-bis(4-methoxybenzyl)-3,6-dihydro-7H-[1,2,3]triazolo[4,5-d]pyrimidin-7-one (370 mg, 58%) as a yellow solid.

Step 2: To a stirred solution of 5-(4-bromo-2-methoxyphenyl)-3,6-bis(4-methoxybenzyl)-3,6-dihydro-7H-[1,2,3]triazolo[4,5-d]pyrimidin-7-one (250 mg, 0.445 mmol, 1.0 equiv) in DMF (5.0 mL) was added LiCl (188 mg, 4.44 mmol, 10 equiv). The resulting mixture was stirred for 9 h at 150° C., then allowed to cool down to rt. The reaction was quenched by the addition of water (20 mL) and acidified to pH 3-4 with conc. HCl. The mixture was extracted with EA (3×10 mL), and the combined organic layers were washed with brine (20 mL), dried over anhydrous $Na_2SO_4$, filtered, and concentrated under reduced pressure. The residue was purified by silica gel column chromatography to afford 5-(4-bromo-2-hydroxyphenyl)-3,6-bis(4-methoxybenzyl)-3,6-dihydro-7H-[1,2,3]triazolo[4,5-d]pyrimidin-7-one (230 mg, 55%) as a grey solid.

Step 3: To a solution of 5-(4-bromo-2-hydroxyphenyl)-3,6-bis(4-methoxybenzyl)-3,6-dihydro-7H-[1,2,3]triazolo[4,5-d]pyrimidin-7-one (200 mg, 0.212 mmol, 1.0 equiv) and 4-(ethoxycarbonyl)phenylboronic acid (61.6 mg, 0.317 mmol, 1.5 equiv) in dioxane (3.0 mL) and $H_2O$ (0.30 mL) was added $K_2CO_3$ (87.7 mg, 0.635 mmol, 3.0 equiv) and Pd(dppf)Cl$_2$ CH$_2$Cl$_2$ (15.5 mg, 0.021 mmol, 0.10 equiv). After stirring for 2 h at 100° C. under $N_2$, the mixture was concentrated under reduced pressure. The residue was purified by silica gel column chromatography to afford ethyl 4'-(3,6-bis(4-methoxybenzyl)-7-oxo-6,7-dihydro-3H-[1,2,3]triazolo[4,5-d]pyrimidin-5-yl)-3'-hydroxy-[1,1'-biphenyl]-4-carboxylate (150 mg, 34%) as a grey solid.

Step 4: To a stirred solution of ethyl 4'-(3,6-bis(4-methoxybenzyl)-7-oxo-6,7-dihydro-3H-[1,2,3]triazolo[4,5-d]pyrimidin-5-yl)-3'-hydroxy-[1,1'-biphenyl]-4-carboxylate (150 mg, 0.243 mmol, 1.0 equiv) and 1-(2-chloroethyl)pyrrolidine hydrochloride (12.4 mg, 0.073 mmol, 1.0 equiv) in DMF (2.0 mL) was added $K_2CO_3$ (30.2 mg, 0.219 mmol, 3.0 equiv) at rt. The resulting mixture was stirred for 2 h at 80° C. The resulting mixture was diluted with water (10 mL). The resulting mixture was extracted with EA (3×5 mL). The combined organic layers were washed with brine (10 mL), dried over anhydrous $Na_2SO_4$. After filtration, the filtrate was concentrated under reduced pressure. The residue was purified by silica gel column chromatography to afford ethyl 4'-(3,6-bis(4-methoxybenzyl)-7-oxo-6,7-dihydro-3H-[1,2,3]triazolo[4,5-d]pyrimidin-5-yl)-3'-(2-(pyrrolidin-1-yl)ethoxy)-[1,1'-biphenyl]-4-carboxylate (65 mg, 37%) as a yellow solid.

4'-(7-Oxo-6,7-dihydro-3H-[1,2,3]triazolo[4,5-d]pyrimidin-5-yl)-3'-(2-(pyrrolidin-1-yl)ethoxy)-[1,1'-biphenyl]-4-carboxylic acid was prepared using the procedures in Examples 6 and 9. LCMS (ESI)=447.2 [M+H]$^+$. $^1$H NMR (300 MHz, DMSO-d$_6$) δ 8.06 (d, J=8.3 Hz, 2H), 8.02-7.91 (m, 3H), 7.64 (d, J=1.7 Hz, 1H), 7.53 (dd, J=8.1, 1.6 Hz, 1H), 4.54 (s, 2H), 3.01 (s, 2H), 2.77 (s, 4H), 1.76 (s, 4H).

Example 72: Synthesis of 3'-(2-(Dimethylamino)ethoxy)-4'-(7-oxo-6,7-dihydro-3H-[1,2,3]triazolo[4,5-d]pyrimidin-5-yl)-[1,1'-biphenyl]-4-carboxylic Acid (Compound 228)

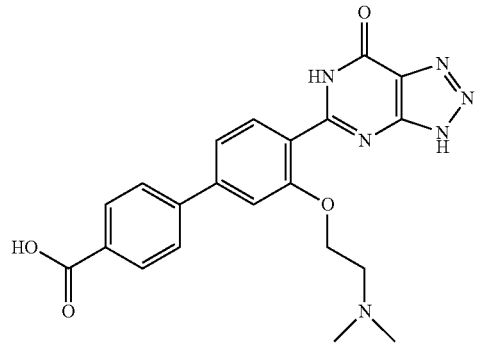

228

3'-(2-(Dimethylamino)ethoxy)-4'-(7-oxo-6,7-dihydro-3H-[1,2,3]triazolo[4,5-d]pyrimidin-5-yl)-[1,1'-biphenyl]-4-carboxylic acid was prepared using the procedures in Example 71. LCMS (ESI)=421.2 [M+H]$^+$. $^1$H NMR (300 MHz, DMSO-d$_6$) δ 8.13-8.04 (m, 2H), 8.00-7.91 (m, 2H), 7.81 (d, J=8.0 Hz, 1H), 7.62-7.50 (m, 2H), 4.62 (d, J=5.1 Hz, 2H), 3.53-3.45 (m, 2H), 2.82 (s, 6H).

Example 73: Synthesis of 3'-(3-(Dimethylamino)propoxy)-4'-(7-oxo-6,7-dihydro-3H-[1,2,3]triazolo[4,5-d]pyrimidin-5-yl)-[1,1'-biphenyl]-4-carboxylic Acid (Compound 229)

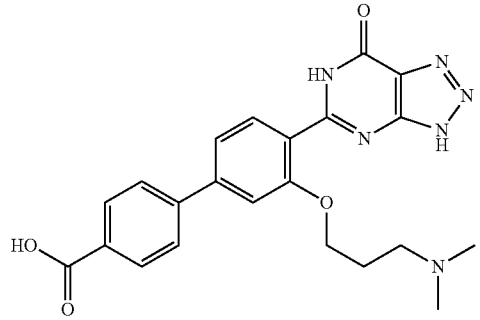

229

3'-(3-(Dimethylamino)propoxy)-4'-(7-oxo-6,7-dihydro-3H-[1,2,3]triazolo[4,5-d]pyrimidin-5-yl)-[1,1'-biphenyl]-4-carboxylic acid was prepared using the procedures in Example 71. LCMS (ESI)=435.2 [M+H]$^+$. $^1$H NMR (300 MHz, DMSO-d$_6$) δ 11.06 (s, 1H), 8.33 (s, 1H), 8.02-7.93 (m, 3H), 7.79 (d, J=8.1 Hz, 2H), 7.42 (d, J=8.9 Hz, 2H), 4.30 (t, J=6.1 Hz, 2H), 2.57 (t, J=7.0 Hz, 2H), 2.26 (s, 6H), 1.99 (q, J=6.6 Hz, 2H).

Example 74: Synthesis of (4'-(7-Oxo-6,7-dihydro-3H-[1,2,3]triazolo[4,5-d]pyrimidin-5-yl)-3'-(2-(pyrrolidin-1-yl)ethoxy)-[1,1'-biphenyl]-3-yl)glycine (Compound 230)

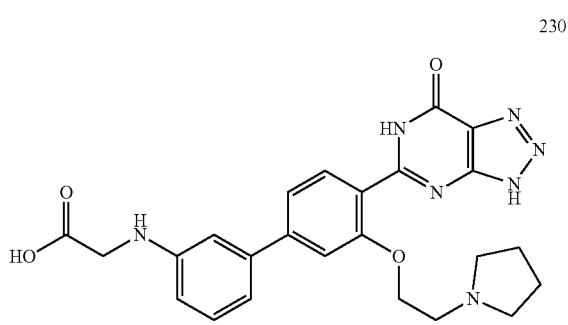 [SMILES: O=C(O)CNc1cccc(-c2ccc(-c3nc4[nH]nnc4c(=O)[nH]3)c(OCCN3CCCC3)c2)c1]

(4'-(7-Oxo-6,7-dihydro-3H-[1,2,3]triazolo[4,5-d]pyrimidin-5-yl)-3'-(2-(pyrrolidin-1-yl)ethoxy)-[1,1'-biphenyl]-3-yl)glycine was prepared using the procedures in Example 71, except the alkylation with 1-(2-chloroethyl)pyrrolidine hydrochloride was performed in Step 2, and the remaining steps performed as in Example 58. LCMS (ESI)=476.2 [M+H]$^+$. $^1$H NMR (300 MHz, DMSO-d$_6$) δ 7.93 (d, J=8.1 Hz, 1H), 7.46 (d, J=1.6 Hz, 1H), 7.38 (dd, J=8.0, 1.5 Hz, 1H), 7.21 (t, J=7.8 Hz, 1H), 7.02-6.91 (m, 2H), 6.64 (d, J=8.3 Hz, 1H), 4.51 (s, 2H), 3.90 (s, 2H), 3.03 (s, 2H), 2.79 (s, 4H), 1.77 (s, 4H).

Example 75: Synthesis of 6-(3-(Cyclopentyloxy)-4-(7-oxo-6,7-dihydro-3H-[1,2,3]triazolo[4,5-d]pyrimidin-5-yl)phenyl)nicotinic Acid (Compound 231)

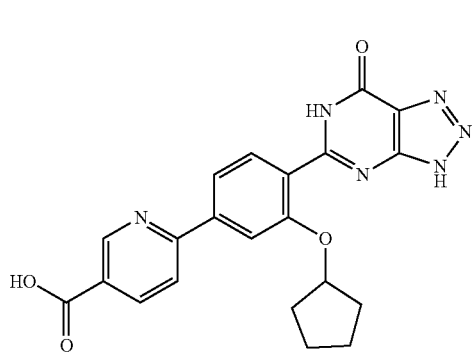

6-(3-(Cyclopentyloxy)-4-(7-oxo-6,7-dihydro-3H-[1,2,3] triazolo[4,5-d]pyrimidin-5-yl)phenyl)nicotinic acid was prepared from 6-bromonicotinic acid using the procedures in Example 42. LCMS (ESI)=419.1 [M+H]$^+$. $^1$H NMR (300 MHz, DMSO-d$_6$) δ 13.6 (broad s, 1H), 12.2 (broad s, 1H), 9.20 (s, 1H), 8.39 (dd, J=8.1, 2.1 Hz, 1H), 8.26 (d, J=8.4 Hz, 1H), 7.80-8.00 (m, 3H), 5.10-5.20 (m, 1H), 1.75-2.05 (m, 4H), 1.55-1.75 (m, 4H).

Example 76: Synthesis of 5-(3-Ethoxy-3'-(methylamino)-[1,1'-biphenyl]-4-yl)-3,6-dihydro-7H-[1,2,3] triazolo[4,5-d]pyrimidin-7-one (Compound 232)

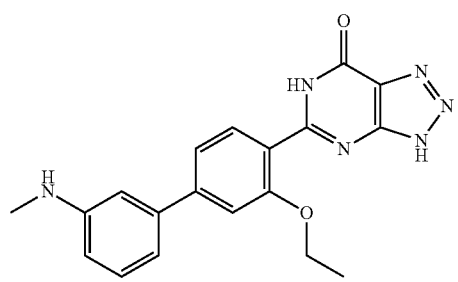

5-(3-Ethoxy-3'-(methylamino)-[1,1'-biphenyl]-4-yl)-3,6-dihydro-7H-[1,2,3]triazolo[4,5-d]pyrimidin-7-one was prepared from N-methyl-3-(4,4,5,5-tetramethyl-1,3,2-dioxaborolan-2-yl)aniline using the procedures in Example 6. LCMS (ESI)=363.2 [M+H]$^+$.

Example 77: Synthesis of 5-(3-(Cyclopentyloxy)-4-(7-oxo-6,7-dihydro-3H-[1,2,3]triazolo[4,5-d]pyrimidin-5-yl)phenyl)picolinic Acid (Compound 233)

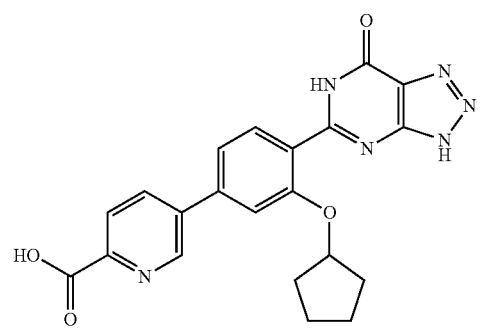

5-(3-(Cyclopentyloxy)-4-(7-oxo-6,7-dihydro-3H-[1,2,3] triazolo[4,5-d]pyrimidin-5-yl)phenyl)picolinic acid was prepared from methyl 5-bromopicolinate using the procedures in Examples 42 and 9. LCMS (ESI)=419.2 [M+H]$^+$. $^1$H NMR (300 MHz, DMSO-d$_6$) δ 11.7 (broad s, 1H), 9.11 (s, 1H), 8.38 (d, J=8.4 Hz, 1H), 8.10-8.18 (m, 1H), 8.14 (s, 1H), 8.03 (d, J=7.8, 1H), 7.50-7.60 (m, 2H), 5.18-5.28 (m, 1H), 1.80-2.00 (m, 4H), 1.55-1.75 (m, 4H).

Example 78: Synthesis of 3-(3'-ethoxy-4'-(7-oxo-6,7-dihydro-3H-[1,2,3]triazolo[4,5-d]pyrimidin-5-yl)-[1,1'-biphenyl]-3-yl)propanoic Acid (Compound 234)

Example 79: Synthesis of (E)-3-(3'-ethoxy-4'-(7-oxo-6,7-dihydro-3H-[1,2,3]triazolo[4,5-d]pyrimidin-5-yl)-[1,1'-biphenyl]-3-yl)acrylic Acid (Compound 235)

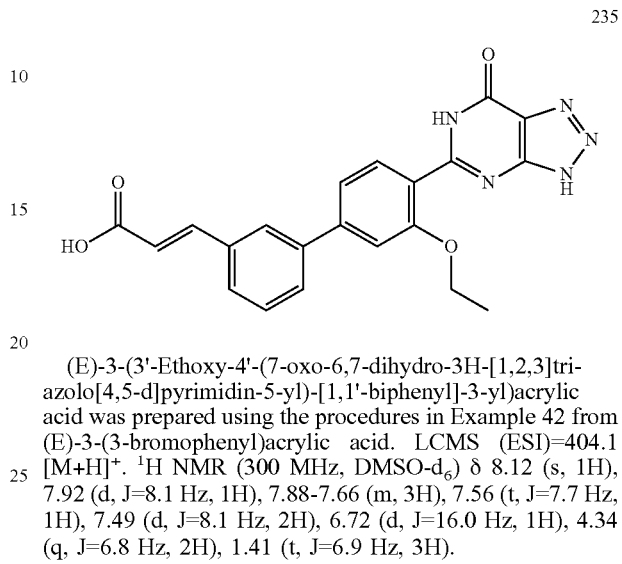

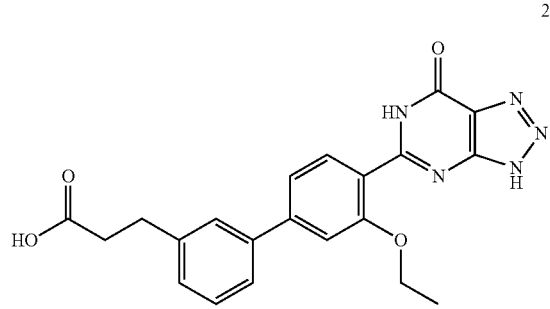

(E)-3-(3'-Ethoxy-4'-(7-oxo-6,7-dihydro-3H-[1,2,3]triazolo[4,5-d]pyrimidin-5-yl)-[1,1'-biphenyl]-3-yl)acrylic acid was prepared using the procedures in Example 42 from (E)-3-(3-bromophenyl)acrylic acid. LCMS (ESI)=404.1 [M+H]$^+$. $^1$H NMR (300 MHz, DMSO-d$_6$) δ 8.12 (s, 1H), 7.92 (d, J=8.1 Hz, 1H), 7.88-7.66 (m, 3H), 7.56 (t, J=7.7 Hz, 1H), 7.49 (d, J=8.1 Hz, 2H), 6.72 (d, J=16.0 Hz, 1H), 4.34 (q, J=6.8 Hz, 2H), 1.41 (t, J=6.9 Hz, 3H).

3-(3'-Ethoxy-4'-(7-oxo-6,7-dihydro-3H-[1,2,3]triazolo[4,5-d]pyrimidin-5-yl)-[1,1'-biphenyl]-3-yl)propanoic acid was prepared using the procedures in Example 42 from 3-(3-bromophenyl)propanoic acid. LCMS (ESI)=406.1 [M+H]$^+$. $^1$H NMR (300 MHz, DMSO-d$_6$) δ 12.17 (s, 2H), 7.87 (d, J=8.1 Hz, 1H), 7.69-7.56 (m, 2H), 7.41 (d, J=7.5 Hz, 3H), 7.35-7.26 (m, 1H), 4.31 (q, J=6.9 Hz, 2H), 2.93 (t, J=7.7 Hz, 2H), 2.68-2.52 (m, 2H), 1.40 (t, J=6.9 Hz, 3H).

Example 80: Synthesis of (Z)-3-(3'-ethoxy-4'-(7-oxo-6,7-dihydro-3H-[1,2,3]triazolo[4,5-d]pyrimidin-5-yl)-[1,1'-biphenyl]-3-yl)-2-methylacrylic Acid (Compound 236) and (E)-3-(3'-ethoxy-4'-(7-oxo-6,7-dihydro-3H-[1,2,3]triazolo[4,5-d]pyrimidin-5-yl)-[1,1'-biphenyl]-3-yl)-2-methylacrylic Acid (Compound 237)

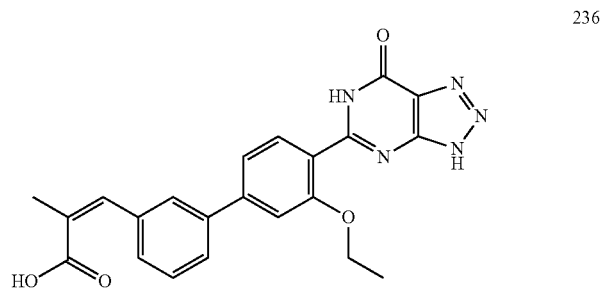

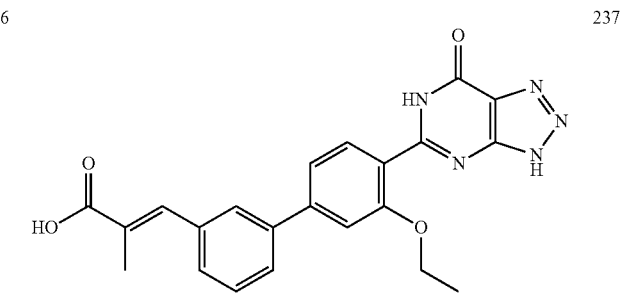

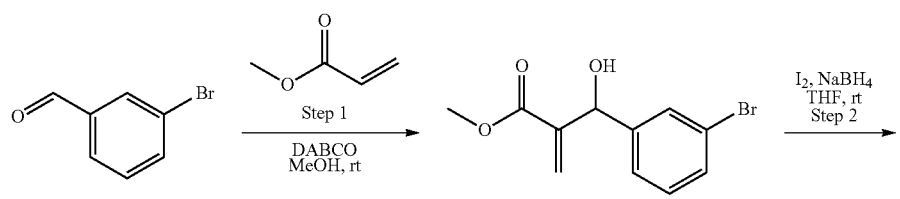

-continued
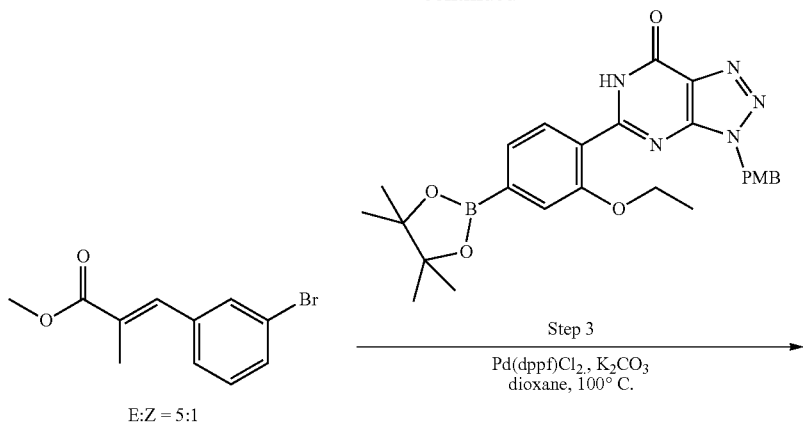
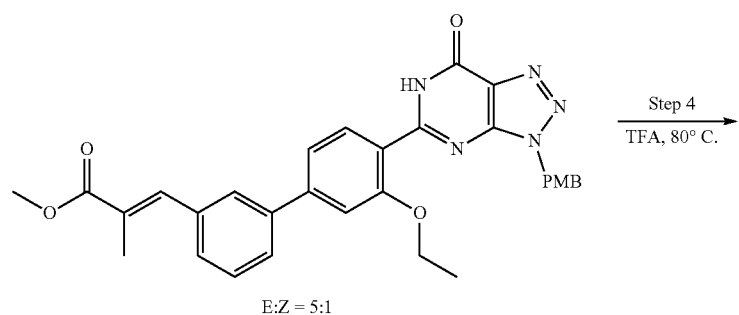
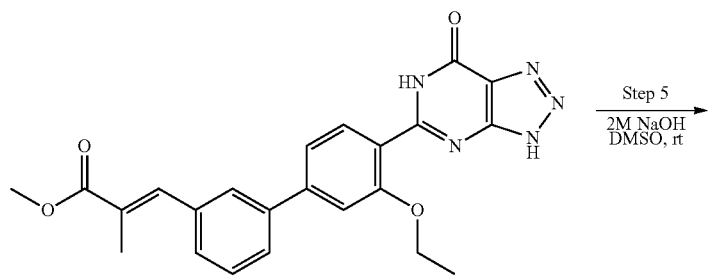
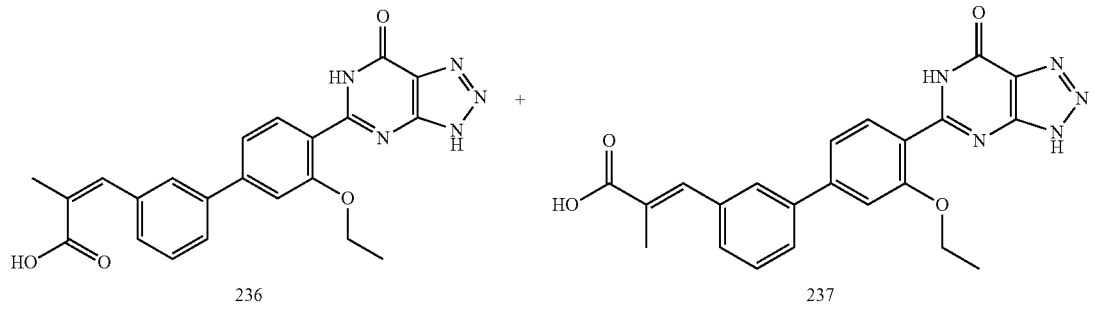

Step 1: Into a 50-mL round-bottom flask, was placed 3-bromobenzaldehyde (1.84 g, 9.94 mmol, 1.00 equiv) and methyl acrylate (2.57 g mg, 29.8 mmol, 3.00 equiv) in dioxane (0.50 mL) and H₂O (0.50 mL), DABCO (1.12 g, 9.94 mmol, 1.00 equiv) was added. The resulting solution was stirred for 14 hr at rt. The residue was applied onto a silica gel column with ethyl acetate/petroleum ether (1:10). This resulted in 2.5 g (93%) of methyl 2-((3-bromophenyl)(hydroxy)methyl)acrylate as a colorless oil. $^1$H NMR (300 MHz, DMSO-$d_6$) δ 7.78-7.35 (m, 2H), 6.24 (t, J=1.5 Hz, 2H), 6.20 (s, 1H), 6.02 (s, 1H), 5.88 (brs, 1H), 5.43 (d, J=1.5 Hz, 1H), 3.62 (s, 3H).

Step 2: To methyl 2-((3-bromophenyl)(hydroxy)methyl)acrylate (250 mg, 0.922 mmol, 1.00 equiv) was added THF (2.0 mL) and 12 (515 mg, 2.03 mmol, 2.20 equiv). The resulting brown solution was cooled to 0° C. NaBH₄ (69.8 mg, 1.84 mmol, 2.00 equiv) was added in small portions and the white suspension was allowed to stir for 17 h. The reaction was quenched by the addition of H₂O (5 ml) at 0° C. The resulting mixture was extracted with DCM (3×5 mL). The combined organic layers were washed with NaCl (5 mL), dried over anhydrous Na₂SO₄, filtered and concentrated under reduced pressure. The residue was purified by silica gel column chromatography to afford methyl (E)-3-(3-bromophenyl)-2-methylacrylate (40 mg, 17%) as a yellow oil. $^1$H NMR (300 MHz, CDCl₃) δ 7.63 (s, 1H), 7.55 (s, 1H), 7.48 (dt, J=7.3, 1.9 Hz, 1H), 7.41-7.23 (m, 2H), 3.85 (s, 3H), 2.13 (d, J=1.5 Hz, 3H).

Step 3: To a solution of 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one (94.7 mg, 0.188 mmol, 1.20 equiv) and methyl (2E)-3-(3-bromophenyl)-2-methylprop-2-enoate (40.0 mg, 0.157 mmol, 1.00 equiv) in dioxane (1.0 mL) and H₂O (0.1 mL) were added K₂CO₃ (65.0 mg, 0.470 mmol, 3.00 equiv) and Pd(dppf)Cl₂ (11.5 mg, 0.016 mmol, 0.10 equiv). After stirring for 2 h at 100° C. under a nitrogen atmosphere, the resulting mixture was concentrated under reduced pressure. The residue was purified by silica gel column chromatography to afford methyl (E)-3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)-2-methylacrylate (100 mg) as a white solid. LCMS (ESI)=552.2 [M+H]⁺.

Step 4: Into a 8-mL vial, was placed methyl (E)-3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)-2-methylacrylate (40.0 mg, 0.073 mmol, 1.00 equiv) in trifluoroacetic acid (1.0 mL). The resulting solution was stirred for 2 hr at 80° C., then concentrated under reduced pressure. This resulted in 40 mg of methyl (E)-3-(3'-ethoxy-4'-(7-oxo-6,7-dihydro-3H-[1,2,3]triazolo[4,5-d]pyrimidin-5-yl)-[1,1'-biphenyl]-3-yl)-2-methylacrylate as a yellow solid which was carried on without further purification. LCMS (ESI)=432.2 [M+H]⁺.

Step 5: Into a 8-mL vial, was placed methyl (E)-3-(3'-ethoxy-4'-(7-oxo-6,7-dihydro-3H-[1,2,3]triazolo[4,5-d]pyrimidin-5-yl)-[1,1'-biphenyl]-3-yl)-2-methylacrylate (40.0 mg) in DMSO (1.0 mL), then 2 N NaOH (1.0 mL) was added. The resulting solution was stirred for 2 hr at room temperature. The pH was adjusted to pH 6 by addition of AcOH. The crude product was purified by preparative HPLC to afford 1.6 mg (4.0%) of (Z)-3-(3'-ethoxy-4'-(7-oxo-6,7-dihydro-3H-[1,2,3]triazolo[4,5-d]pyrimidin-5-yl)-[1,1'-biphenyl]-3-yl)-2-methylacrylic acid (Peak 1) as a white solid, and 8.3 mg (21%) of (E)-3-(3'-ethoxy-4'-(7-oxo-6,7-dihydro-3H-[1,2,3]triazolo[4,5-d]pyrimidin-5-yl)-[1,1'-biphenyl]-3-yl)-2-methylacrylic acid (Peak 2) as a white solid.

Data for (Z)-3-(3'-ethoxy-4'-(7-oxo-6,7-dihydro-3H-[1,2,3]triazolo[4,5-d]pyrimidin-5-yl)-[1,1'-biphenyl]-3-yl)-2-methylacrylic acid: LCMS (ESI)=418.0 [M+H]⁺. $^1$H NMR (300 MHz, DMSO-$d_6$) δ 11.02 (brs, 1H) 8.01 (d, J=8.4 Hz, 1H), 7.81 (s, 1H), 7.59 (d, J=7.2 Hz, 1H), 7.48-7.36 (m, 4H), 4.35-4.28 (m, 2H), 2.03 (d, J=1.2 Hz, 3H), 1.44 (d, J=6.9 Hz, 3H).

Data for (E)-3-(3'-ethoxy-4'-(7-oxo-6,7-dihydro-3H-[1,2,3]triazolo[4,5-d]pyrimidin-5-yl)-[1,1'-biphenyl]-3-yl)-2-methylacrylic acid: LCMS (ESI)=418.0 [M+H]⁺. $^1$H NMR (300 MHz, DMSO-$d_6$) δ 8.00 (d, J=8.1 Hz, 1H), 7.84 (s, 1H), 7.77 (d, J=7.8 Hz, 1H), 7.72 (s, 1H), 7.60-7.51 (m, 2H), 7.44 (d, J=6.9 Hz, 2H), 4.33 (q, J=6.9 Hz, 2H), 2.10 (d, J=1.2 Hz, 3H), 1.43 (t, J=6.6 Hz, 3H).

Example 81: Synthesis of 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoic Acid (Compound 238)

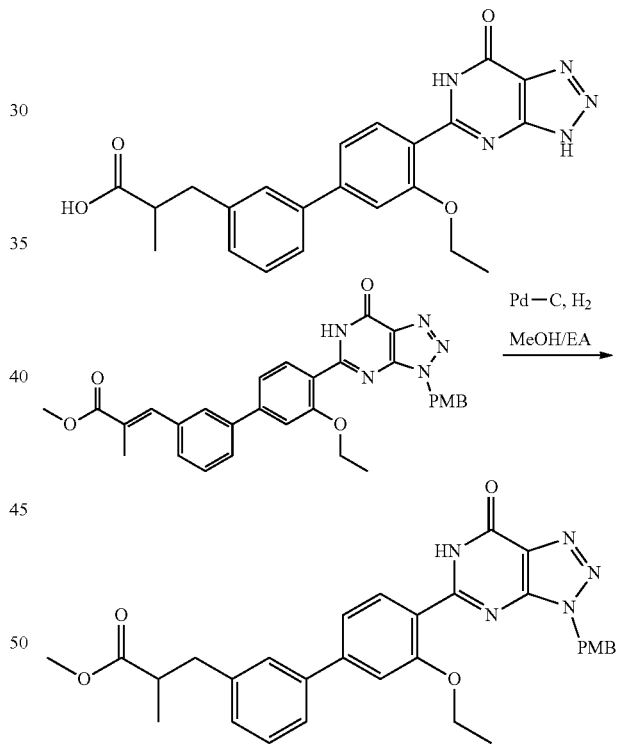

To a solution of methyl (E)-3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)-2-methylacrylate (60.0 mg, 0.109 mmol, 1.00 equiv) in MeOH (1.0 mL) was added Pd/C (10.0 mg). Hydrogen was introduced by hydrogen balloon and the mixture was stirred for 2 h at room temperature. The mixture was filtered through a Celite pad and concentrated under reduced pressure. This resulted in methyl 3-(3'-ethoxy-4'-(3-(4-methoxybenzyl)-7-oxo-6,7-dihydro-3H-[1,2,3]triazolo[4,5-d]pyrimidin-5-yl)-[1,1'-biphenyl]-3-yl)-2-methylpropanoate (40 mg, 66%) as a white solid. LCMS (ESI)=554.3 [M+H]⁺.

3-(3'-Ethoxy-4'-(7-oxo-6,7-dihydro-3H-[1,2,3]triazolo[4,5-d]pyrimidin-5-yl)-[1,1'-biphenyl]-3-yl)-2-methylpropanoic acid was prepared using the procedures in Examples 6 and 9. LCMS (ESI)=420.1 [M+H]+. 1H NMR (300 MHz, DMSO-d6) δ 8.00 (d, J=8.4 Hz, 1H), 7.61 (d, J=1.8 Hz, 2H), 7.44-7.37 (m, 3H), 7.24 (d, J=7.5 Hz, 1H), 4.33 (q, J=6.9 Hz, 2H), 3.05-2.96 (m, 1H), 2.77-2.70 (m, 2H), 1.43 (t, J=6.9 Hz, 3H), 1.10 (d, J=6.3 Hz, 3H).

Example 82: Synthesis of 2-((3'-ethoxy-4'-(7-oxo-6,7-dihydro-3H-[1,2,3]triazolo[4,5-d]pyrimidin-5-yl)-[1,1'-biphenyl]-3-yl)methyl)butanoic Acid (Compound 239)

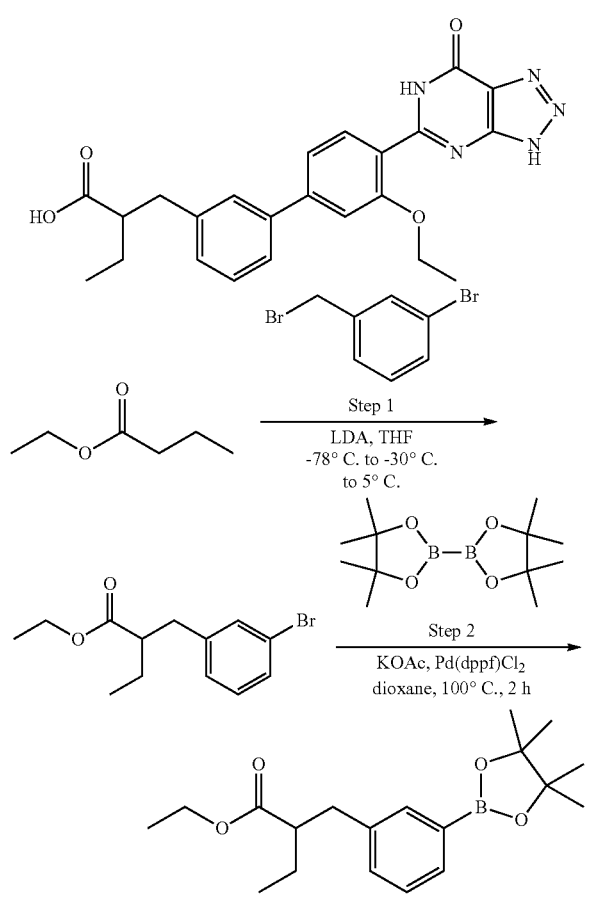

Step 1: To a stirred solution of ethyl butyrate (1.00 g, 8.61 mmol, 1.00 equiv) in THF (20 mL) was added LDA (2 M) (4.74 mL) dropwise at −78° C. under N2. The resulting mixture was stirred for 1.5 hr at −30° C. under N2. To the above mixture was added 1-bromo-3-(bromomethyl)benzene (2.37 g, 9.47 mmol, 1.1 equiv) dropwise over 15 min at −30° C. The resulting mixture was stirred for additional 3 hr at −30° C. The reaction was quenched by the addition of 1 M HCl (20 mL) at 5° C. The resulting mixture was extracted with Et2O (3×20 mL). The combined organic layers were washed with brine (2×20 ml), dried over anhydrous Na2SO4, filtered, and concentrated under reduced pressure. The residue was purified by silica gel column chromatography to afford ethyl 2-(3-bromobenzyl)butanoate (800 mg, 26.4%) as a white solid.

Step 2: Into a 20 ml vial were added ethyl 2-(3-bromobenzyl)butanoate (800 mg, 2.80 mmol, 1.00 equiv) and bis(pinacolato)diboron (1.42 g, 5.61 mmol, 2.0 equiv), KOAc (551 mg, 5.61 mmol, 2.0 equiv), dioxane (10.0 mL), Pd(dppf)Cl2 (205 mg, 0.281 mmol, 0.1 equiv) at rt. The resulting mixture was stirred for 2 hr at 100° C., then the resulting mixture was concentrated under reduced pressure. The residue was purified by silica gel column chromatography to afford ethyl 2-(3-(4,4,5,5-tetramethyl-1,3,2-dioxaborolan-2-yl)benzyl)butanoate (700 mg, 62%) as a white solid.

2-((3'-Ethoxy-4'-(7-oxo-6,7-dihydro-3H-[1,2,3]triazolo[4,5-d]pyrimidin-5-yl)-[1,1'-biphenyl]-3-yl)methyl)butanoic acid was prepared using the procedures in Examples 1 and 9. LCMS (ESI)=434.2 [M+H]+. 1H NMR (300 MHz, DMSO-d6) δ 8.23 (d, J=8.4 Hz, 1H), 7.55 (d, J=9.0 Hz, 2H), 7.46-7.35 (m, 1H), 7.40 (s, 2H), 7.28 (d, J=7.6 Hz, 1H), 4.41 (q, J=7.0 Hz, 2H), 3.02 (dd, J=13.6, 8.9 Hz, 1H), 2.86 (dd, J=13.6, 6.0 Hz, 1H), 2.71-2.55 (m, 1H), 1.78-1.53 (m, 4H), 1.00 (t, J=7.4 Hz, 3H).

Example 83: Separation of the enantiomers of 2-((3'-ethoxy-4'-(7-oxo-6,7-dihydro-3H-[1,2,3]triazolo[4,5-d]pyrimidin-5-yl)-[1,1'-biphenyl]-3-yl)methyl)butanoic Acid (Compound 240 and Compound 241)

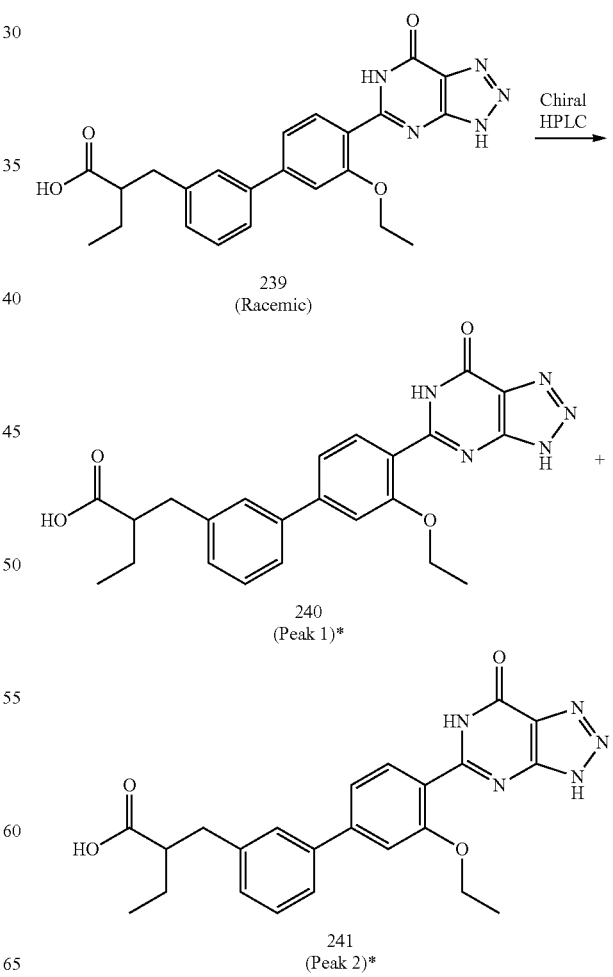

2-((3'-Ethoxy-4'-(7-oxo-6,7-dihydro-3H-[1,2,3]triazolo[4,5-d]pyrimidin-5-yl)-[1,1'-biphenyl]-3-yl)methyl)butanoic acid (racemic) (58 mg) was separated into the individual enantiomers by chiral preparative HPLC with CHIRALPAK IC-3 column, 20*250 mm, 5 um; mobile phase, 20 mL/min. Phase A: n-hexane/DCM=5/1, Phase B: Ethanol (0.1% TFA). This resulted in (S)-2-((3'-ethoxy-4'-(7-oxo-6,7-dihydro-3H-[1,2,3]triazolo[4,5-d]pyrimidin-5-yl)-[1,1'-biphenyl]-3-yl)methyl)butanoic acid (18 mg, 36%, ee %=99.5%) as a white solid and (R)-2-((3'-ethoxy-4'-(7-oxo-6,7-dihydro-3H-[1,2,3]triazolo[4,5-d]pyrimidin-5-yl)-[1,1'-biphenyl]-3-yl)methyl)butanoic acid (17.8 mg, 36%, ee %=99.2%) as a white solid.

Data for Compound 240 (Peak 1): LCMS (ESI)=434.2 [M+H]$^+$. HPLC (CHIRALPAK IC-3, 4.6×50 mm, 3 μm, 1.0 mL/min); A: n-hexane:DCM 5/1; B: EtOH w/0.1% TFA; 25% B): $t_R$=2.27 min. *Absolute stereochemistry for isolated single enantiomer not determined.

Data for Compound 241 (Peak 2): LCMS (ESI)=434.2 [M+H]$^+$. HPLC (CHIRALPAK IC-3, 4.6×50 mm, 3 μm, 1.0 mL/min; A: n-hexane/DCM, 5/1; B: EtOH w/0.1% TFA; 25% B): $t_R$=2.78 min. *Absolute stereochemistry for isolated single enantiomer not determined.

Example 84: Synthesis of ethyl 3-(3'-ethoxy-4'-(7-oxo-6,7-dihydro-3H-[1,2,3]triazolo[4,5-d]pyrimidin-5-yl)-[1,1'-biphenyl]-3-yl)-2,2-dimethylpropanoate (Compound 242)

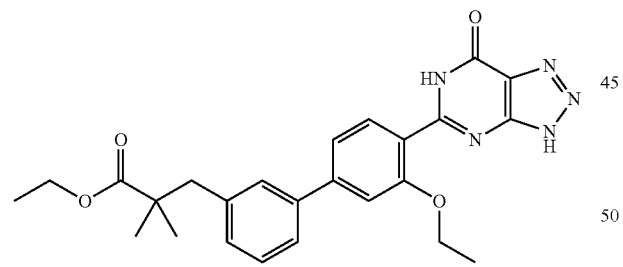

242

Ethyl 3-(3'-ethoxy-4'-(7-oxo-6,7-dihydro-3H-[1,2,3]triazolo[4,5-d]pyrimidin-5-yl)-[1,1'-biphenyl]-3-yl)-2,2-dimethylpropanoate was prepared using the procedures in Example 82 from ethyl isobutyrate. LCMS (ESI)=462.3 [M+H]$^+$. $^1$H NMR (300 MHz, DMSO-d$_6$) δ 11.68 (s, 1H), 7.93 (d, J=8.3 Hz, 1H), 7.63 (d, J=7.9 Hz, 1H), 7.51-7.31 (m, 4H), 7.17 (d, J=7.6 Hz, 1H), 4.30 (q, J=6.9 Hz, 2H), 4.07 (q, J=7.1 Hz, 2H), 2.92 (s, 2H), 1.41 (t, J=6.9 Hz, 3H), 1.18 (t, J=7.1 Hz, 3H), 1.16 (s, 6H).

Example 85: Synthesis of 3-(3'-ethoxy-4'-(7-oxo-6,7-dihydro-3H-[1,2,3]triazolo[4,5-d]pyrimidin-5-yl)-[1,1'-biphenyl]-3-yl)-2,2-dimethylpropanoic Acid (Compound 243)

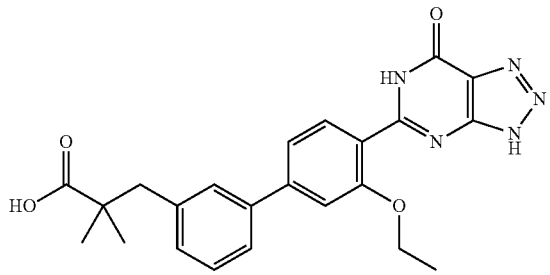

243

3-(3'-Ethoxy-4'-(7-oxo-6,7-dihydro-3H-[1,2,3]triazolo[4,5-d]pyrimidin-5-yl)-[1,1'-biphenyl]-3-yl)-2,2-dimethylpropanoic acid was prepared using the ester hydrolysis procedure in Example 9. LCMS (ESI)=434.2 [M+H]$^+$. $^1$H NMR (300 MHz, DMSO-d$_6$) δ 7.98 (d, J=8.4 Hz, 1H), 7.62 (d, J=7.7 Hz, 1H), 7.53 (s, 1H), 7.46-7.31 (m, 3H), 7.21 (d, J=7.5 Hz, 1H), 4.31 (q, J=6.8 Hz, 2H), 2.90 (s, 2H), 1.42 (t, J=6.9 Hz, 3H), 1.13 (s, 6H).

Example 86: Synthesis of 1-((3'-ethoxy-4'-(7-oxo-6,7-dihydro-3H-[1,2,3]triazolo[4,5-d]pyrimidin-5-yl)-[1,1'-biphenyl]-3-yl)methyl)cyclopropane-1-carboxylic Acid (Compound 244)

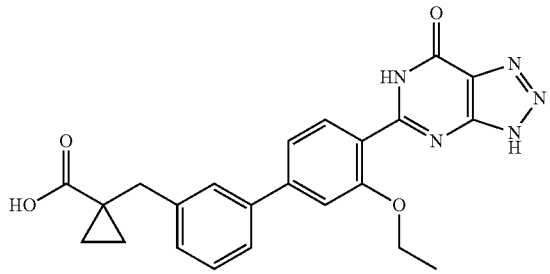

244

1-((3'-Ethoxy-4'-(7-oxo-6,7-dihydro-3H-[1,2,3]triazolo[4,5-d]pyrimidin-5-yl)-[1,1'-biphenyl]-3-yl)methyl)cyclopropane-1-carboxylic acid was prepared from tert-butyl cyclopropanecarboxylate using the procedures in Examples 82 and 58. LCMS (ESI)=433.2 [M+H]$^+$. $^1$H NMR (300 MHz, DMSO-d$_6$) δ 7.96 (d, J=8.5 Hz, 1H), 7.65 (t, J=1.7 Hz, 1H), 7.59 (dt, J=7.7, 1.6 Hz, 1H), 7.46-7.29 (m, 4H), 4.31 (q, J=6.9 Hz, 2H), 2.98 (s, 2H), 1.42 (t, J=6.9 Hz, 3H), 1.15 (q, J=3.7 Hz, 2H), 0.89 (q, J=3.9 Hz, 2H).

Example 87: Synthesis of ethyl 1-((3'-ethoxy-4'-(7-oxo-6,7-dihydro-3H-[1,2,3]triazolo[4,5-d]pyrimidin-5-yl)-[1,1'-biphenyl]-3-yl)methyl)cyclobutane-1-carboxylate (Compound 245)

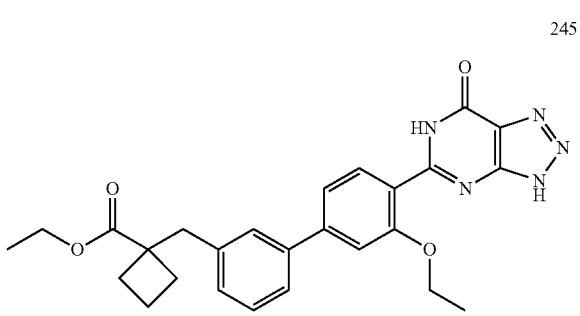 [SMILES: CCOC(=O)C1(Cc2cccc(-c3ccc(-c4nc5[nH]nnc5c(=O)[nH]4)c(OCC)c3)c2)CCC1]

245

Ethyl 1-((3'-ethoxy-4'-(7-oxo-6,7-dihydro-3H-[1,2,3]triazolo[4,5-d]pyrimidin-5-yl)-[1,1'-biphenyl]-3-yl)methyl)cyclobutane-1-carboxylate was prepared using the procedures in Example 82. LCMS (ESI)=474.3 [M+H]+. $^1$H NMR (300 MHz, DMSO-$d_6$) δ 12.07 (s, 1H), 7.89 (d, J=8.2 Hz, 1H), 7.63 (d, J=7.8 Hz, 1H), 7.50 (s, 1H), 7.47-7.32 (m, 3H), 7.19 (d, J=7.4 Hz, 1H), 4.30 (q, J=6.9 Hz, 2H), 4.08 (q, J=7.1 Hz, 2H), 3.17 (s, 2H), 2.40-2.28 (m, 2H), 2.16-2.02 (m, 2H), 1.99-1.72 (m, 2H), 1.41 (t, J=6.9 Hz, 3H), 1.15 (t, J=7.1 Hz, 3H).

Example 88: Synthesis of 1-((3'-ethoxy-4'-(7-oxo-6,7-dihydro-3H-[1,2,3]triazolo[4,5-d]pyrimidin-5-yl)-[1,1'-biphenyl]-3-yl)methyl)cyclobutane-1-carboxylic Acid (Compound 246)

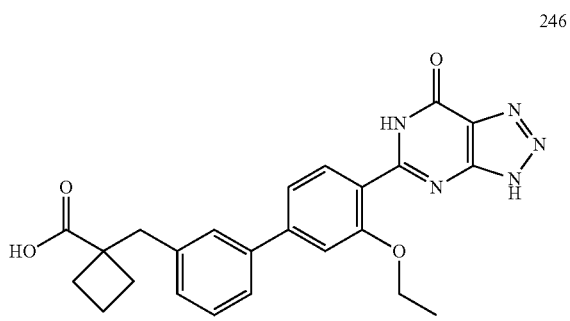 [SMILES: CCOc1cc(-c2cccc(CC3(C(=O)O)CCC3)c2)ccc1-c1nc2[nH]nnc2c(=O)[nH]1]

246

1-((3'-Ethoxy-4'-(7-oxo-6,7-dihydro-3H-[1,2,3]triazolo[4,5-d]pyrimidin-5-yl)-[1,1'-biphenyl]-3-yl)methyl)cyclobutane-1-carboxylic acid was prepared using the ester hydrolysis procedure in Example 9. LCMS (ESI)=446.2 [M+H]+. $^1$H NMR (300 MHz, DMSO-$d_6$) δ 7.93 (d, J=8.2 Hz, 1H), 7.61 (d, J=7.9 Hz, 1H), 7.54 (s, 1H), 7.46-7.32 (m, 3H), 7.24 (d, J=7.7 Hz, 1H), 4.31 (q, J=6.9 Hz, 2H), 3.15 (s, 2H), 2.39-2.22 (m, 2H), 2.12-1.97 (m, 2H), 1.96-1.71 (m, 2H), 1.42 (t, J=6.9 Hz, 3H).

Example 89: Synthesis of 2-((3'-ethoxy-4'-(7-oxo-6,7-dihydro-3H-[1,2,3]triazolo[4,5-d]pyrimidin-5-yl)-[1,1'-biphenyl]-3-yl)oxy)butanoic Acid (Compound 247)

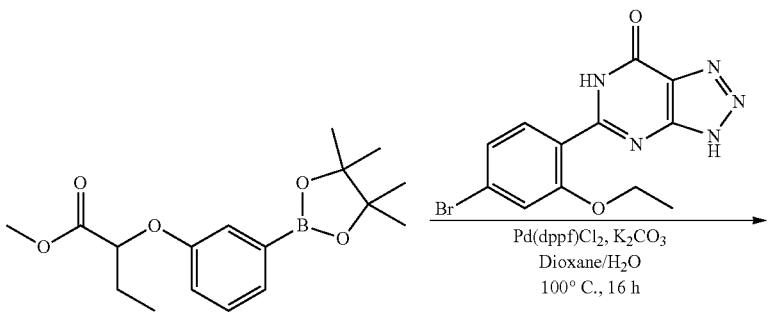

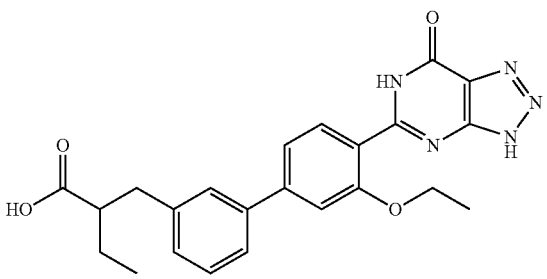

247

To a solution of methyl 2-(3-(4,4,5,5-tetramethyl-1,3,2-dioxaborolan-2-yl)phenoxy)butanoate (prepared from methyl 2-bromobutanoate using the methods in Example 56) (50.0 mg, 0.156 mmol, 1.00 equiv) and 5-(4-bromo-2-ethoxyphenyl)-3,6-dihydro-7H-[1,2,3]triazolo[4,5-d]pyrimidin-7-one (52.5 mg, 0.156 mmol, 1.00 equiv) in dioxane (0.50 mL) and H$_2$O (0.10 mL) were added K$_2$CO$_3$ (64.8 mg, 0.468 mmol, 3.00 equiv) and Pd(dppf)Cl$_2$ (11.4 mg, 0.011 mmol, 0.10 equiv). After stirring for 16 h at 100° C. under a nitrogen atmosphere, the resulting mixture was concentrated under reduced pressure. The crude product was purified by preparative HPLC to afford 2-((3'-ethoxy-4'-(7-oxo-6,7-dihydro-3H-[1,2,3]triazolo[4,5-d]pyrimidin-5-yl)-[1,1'-biphenyl]-3-yl)oxy)butanoic acid (15.7 mg, 23%) as an off-white solid. LCMS (ESI)=436.1 [M+H]$^+$. $^1$H NMR (300 MHz, DMSO-d$_6$) δ 12.05 (s, 1H), 7.88 (d, J=8.4 Hz, 1H), 7.38 (dt, J=11.0, 6.9 Hz, 4H), 7.26 (s, 1H), 6.95 (d, J=8.1 Hz, 1H), 4.83 (t, J=6.0 Hz, 1H), 4.31 (q, J=6.9 Hz, 2H), 2.00-1.85 (m, 2H), 1.40 (t, J=6.9 Hz, 3H), 1.05 (t, J=7.4 Hz, 3H).

Example 91: Synthesis of 2-((3'-ethoxy-4'-(7-oxo-6,7-dihydro-3H-[1,2,3]triazolo[4,5-d]pyrimidin-5-yl)-[1,1'-biphenyl]-3-yl)oxy)-2-phenylacetic Acid (Compound 249)

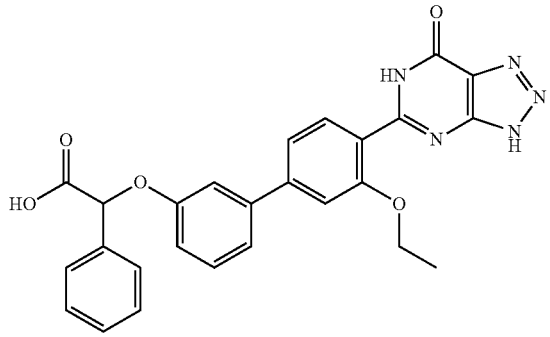

249

2-((3'-Ethoxy-4'-(7-oxo-6,7-dihydro-3H-[1,2,3]triazolo[4,5-d]pyrimidin-5-yl)-[1,1'-biphenyl]-3-yl)oxy)-2-phenylacetic acid was prepared from ethyl 2-bromo-2-phenylacetate using the procedures in Example 89. LCMS (ESI)=484.2 [M+H]$^+$. $^1$H NMR (300 MHz, DMSO-d$_6$) δ 7.93 (d, J=8.0 Hz, 1H), 7.66-7.57 (m, 2H), 7.47-7.29 (m, 8H), 7.05-6.96 (m, 1H), 5.82 (s, 1H), 4.31 (q, J=6.9 Hz, 2H), 1.41 (t, J=6.9 Hz, 3H).

Example 92: Synthesis of 2-((3'-(cyclopentyloxy)-4'-(7-oxo-6,7-dihydro-3H-[1,2,3]triazolo[4,5-d]pyrimidin-5-yl)-[1,1'-biphenyl]-3-yl)oxy)propanoic Acid (Compound 250)

Example 90: Synthesis of 2-((3'-ethoxy-4'-(7-oxo-6,7-dihydro-3H-[1,2,3]triazolo[4,5-d]pyrimidin-5-yl)-[1,1'-biphenyl]-3-yl)oxy)pentanoic Acid (Compound 248)

248

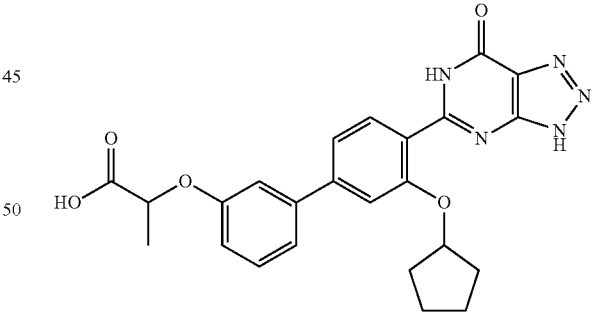

250

2-((3'-Ethoxy-4'-(7-oxo-6,7-dihydro-3H-[1,2,3]triazolo[4,5-d]pyrimidin-5-yl)-[1,1'-biphenyl]-3-yl)oxy)pentanoic acid was prepared using the procedures in Example 89. LCMS (ESI)=450.2 [M+H]$^+$. $^1$H NMR (300 MHz, DMSO-d$_6$) δ 12.20 (s, 1H), 7.86 (d, J=8.2 Hz, 1H), 7.48-7.31 (m, 4H), 7.26 (s, 1H), 6.94 (d, J=8.1 Hz, 1H), 4.87 (t, J=6.3 Hz, 1H), 4.31 (q, J=6.9 Hz, 2H), 1.89 (q, J=7.0 Hz, 2H), 1.52 (q, J=7.7 Hz, 2H), 1.40 (t, J=6.9 Hz, 3H), 0.96 (t, J=7.3 Hz, 3H).

2-((3'-(Cyclopentyloxy)-4'-(7-oxo-6,7-dihydro-3H-[1,2,3]triazolo[4,5-d]pyrimidin-5-yl)-[1,1'-biphenyl]-3-yl)oxy)propanoic acid was prepared using the procedures in Example 89. 462.2 [M+H]$^+$. $^1$H NMR (300 MHz, DMSO-d$_6$) δ 8.02 (d, J=8.4 Hz, 1H), 7.46-7.33 (m, 3H), 7.33 (d, J=7.7 Hz, 1H), 7.23 (t, J=2.1 Hz, 1H), 6.93 (ddd, J=8.1, 2.6, 1.1 Hz, 1H), 5.25-5.18 (m, 1H), 4.94 (d, J=7.5 Hz, 1H), 2.02-1.80 (m, 4H), 1.79-1.59 (m, 4H), 1.54 (d, J=6.7 Hz, 3H).

Example 93: Synthesis of (R)-2-((3'-ethoxy-4'-(7-oxo-6,7-dihydro-3H-[1,2,3]triazolo[4,5-d]pyrimidin-5-yl)-[1,1'-biphenyl]-3-yl)oxy)propanoic Acid (Compound 251)

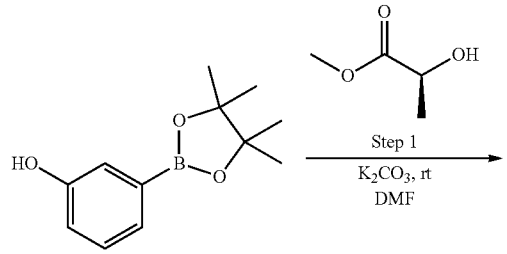

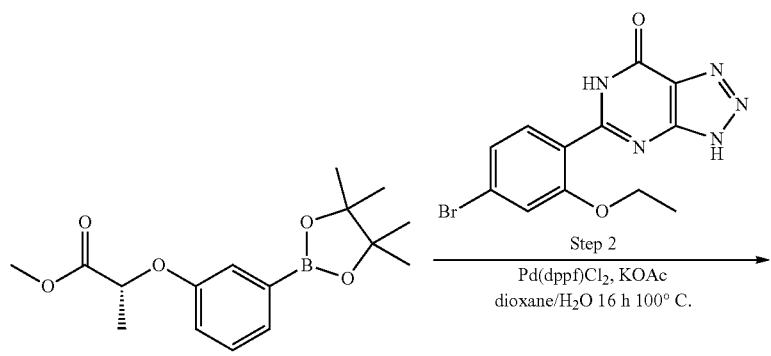

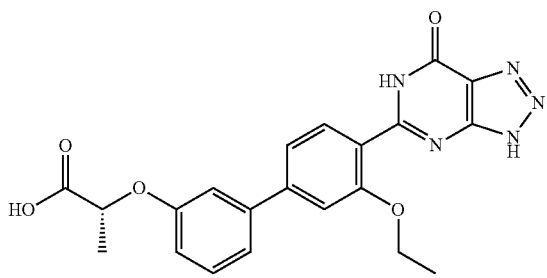

251

Step 1: To a stirred solution of 3-(4,4,5,5-tetramethyl-1,3,2-dioxaborolan-2-yl)phenol (1.00 g, 4.54 mmol, 1.00 equiv), methyl (S)-2-hydroxypropanoate (0.52 g, 5.00 mmol, 1.10 equiv) and PPh$_3$ (1.55 g, 5.90 mmol, 1.30 equiv) in THF (10 mL) was added DIAD (1.19 g, 5.91 mmol, 1.30 equiv) dropwise at 0° C. under N$_2$ atmosphere. The resulting mixture was stirred for 16 h at rt then concentrated under reduced pressure. The residue was purified by silica gel column chromatography to afford methyl (R)-2-(3-(4,4,5,5-tetramethyl-1,3,2-dioxaborolan-2-yl)phenoxy)propanoate (500 mg, 36%) as an off-white oil. LCMS (ESI)=307.2 [M+H]$^+$.

Step 2: To a solution of methyl (R)-2-(3-(4,4,5,5-tetramethyl-1,3,2-dioxaborolan-2-yl)phenoxy)propanoate (90.0 mg, 0.294 mmol, 1.00 equiv) and 5-(4-bromo-2-ethoxyphenyl)-3,6-dihydro-7H-[1,2,3]triazolo[4,5-d]pyrimidin-7-one (98.8 mg, 0.294 mmol, 1.0 equiv) in dioxane (1.0 mL) and H$_2$O (0.3 mL) was added K$_2$CO$_3$ (122 mg, 0.882 mmol, 3.00 equiv) and Pd(dppf)Cl$_2$ (21.5 mg, 0.029 mmol, 0.1 equiv). After stirring for 16 h at 100° C. under a nitrogen atmosphere, the resulting mixture was concentrated under reduced pressure. The residue was purified by preparative HPLC to afford (R)-2-((3'-ethoxy-4'-(7-oxo-6,7-dihydro-3H-[1,2,3]triazolo[4,5-d]pyrimidin-5-yl)-[1,1'-biphenyl]-3-yl)oxy)propanoic acid (15.7 mg, 13%) as an off-white solid. LCMS (ESI)=422.1 [M+H]$^+$. $^1$H NMR (300 MHz, DMSO-d$_6$) δ 7.97 (d, J=8.5 Hz, 1H), 7.40-7.25 (m, 4H), 7.21 (d, J=2.2 Hz, 1H), 6.89 (dd, J=8.7, 1.9 Hz, 1H), 4.77 (d, J=6.9 Hz, 1H), 4.31 (q, J=7.0 Hz, 2H), 1.49 (d, J=6.7 Hz, 3H), 1.42 (t, J=6.9 Hz, 3H). Analytical chiral HPLC: CHIRALPAK AD-3 column [100*3 mm, 3 μm, 1.5 mL/min, 50% hexanes: DCM (5:1)-100% EtOH (w/0.1% TFA)]: t$_R$ 2.01 min (Peak 1).

Example 94: Synthesis of (S)-2-((3'-ethoxy-4'-(7-oxo-6,7-dihydro-3H-[1,2,3]triazolo[4,5-d]pyrimidin-5-yl)-[1,1'-biphenyl]-3-yl)oxy)propanoic Acid (Compound 252)

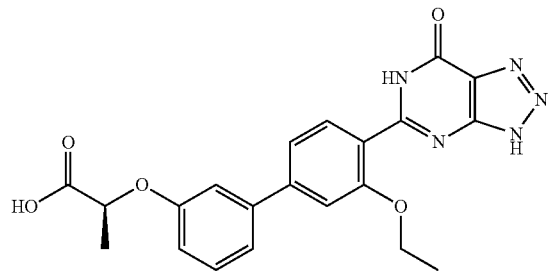

252

(S)-2-((3'-Ethoxy-4'-(7-oxo-6,7-dihydro-3H-[1,2,3]triazolo[4,5-d]pyrimidin-5-yl)-[1,1'-biphenyl]-3-yl)oxy)propanoic acid was prepared from methyl (R)-2-hydroxypropanoate using the procedures in Example 89. LCMS (ESI) =422.1 [M+H]⁺. Analytical chiral HPLC: CHIRALPAK AD-3 column [100*3 mm, 3 μm, 1.5 mL/min, 50% hexanes:DCM (5:1)-100% EtOH (w/0.1% TFA)] $t_R$ 3.48 min (Peak 2).

Example 95: Synthesis of (R)-2-((3'-ethoxy-4'-(7-oxo-6,7-dihydro-3H-[1,2,3]triazolo[4,5-d]pyrimidin-5-yl)-[1,1'-biphenyl]-3-yl)oxy)butanoic Acid (Compound 253) and (S)-2-((3'-ethoxy-4'-(7-oxo-6,7-dihydro-3H-[1,2,3]triazolo[4,5-d]pyrimidin-5-yl)-[1,1'-biphenyl]-3-yl)oxy)butanoic Acid (Compound 254)

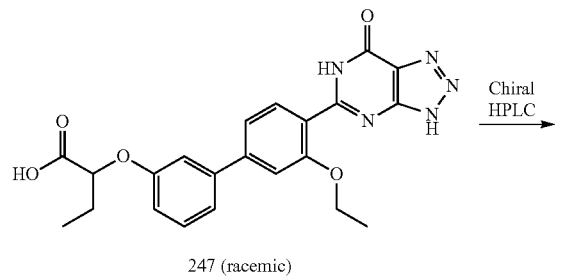

247 (racemic) → Chiral HPLC

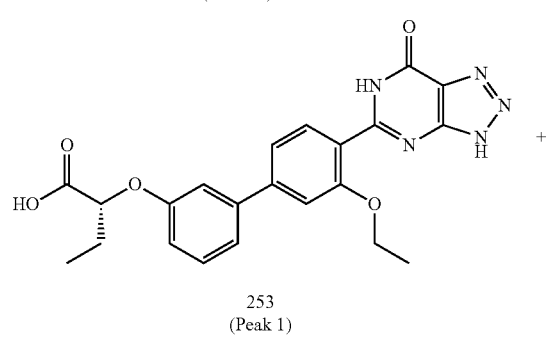

253 (Peak 1)

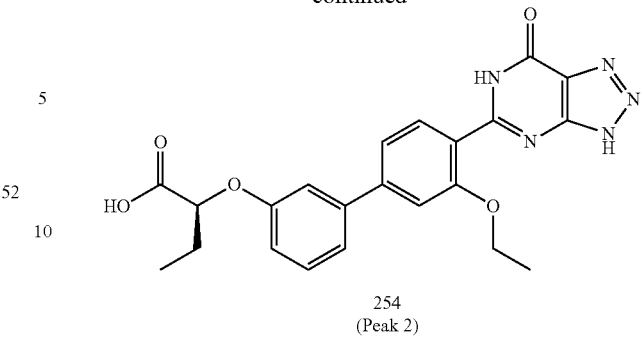

254 (Peak 2)

2-((3'-Ethoxy-4'-(7-oxo-6,7-dihydro-3H-[1,2,3]triazolo[4,5-d]pyrimidin-5-yl)-[1,1'-biphenyl]-3-yl)oxy)butanoic acid was purified into the individual enantiomers with a CHIRALPAK IC-3 column, 20*250 mm, 5 μM. A: n-hexane/DCM, 5/1. B: EtOH w/0.1% TFA, 20% B.

Data for (R)-2-((3'-ethoxy-4'-(7-oxo-6,7-dihydro-3H-[1,2,3]triazolo[4,5-d]pyrimidin-5-yl)-[1,1'-biphenyl]-3-yl)oxy)butanoic acid (Peak 1): LCMS (ESI)=436.1 [M+H]⁺. ¹H NMR (300 MHz, DMSO-d₆) δ 12.21 (s, 1H), 7.86 (d, J=8.5 Hz, 1H), 7.48-7.31 (m, 4H), 7.26 (t, J=2.1 Hz, 1H), 6.99-6.90 (m, 1H), 4.84 (dd, J=6.8, 5.2 Hz, 1H), 4.31 (q, J=7.0 Hz, 2H), 2.02-1.85 (m, 2H), 1.39 (t, J=6.9 Hz, 3H), 1.04 (t, J=7.4 Hz, 3H). Analytical chiral SFC: CHIRALPAK AD-3; 100*3.0 mm, 3 μm, EtOH (0.2% MSA), 1.5 mL/min; Pump B: 50.0%, $t_R$=1.51 min.

Data for (S)-2-((3'-ethoxy-4'-(7-oxo-6,7-dihydro-3H-[1,2,3]triazolo[4,5-d]pyrimidin-5-yl)-[1,1'-biphenyl]-3-yl)oxy)butanoic acid (Peak 2): LCMS (ESI)=436.1 [M+H]*. Chiral SFC: CHIRALPAK AD-3; 100*3.0 mm, 3 μm, EtOH (0.2% MSA), 1.5 mL/min; Pump B: 50.0%, $t_R$=3.94 min.

Example 96A: Synthesis of (R)-2-((3'-ethoxy-5-hydroxy-4'-(7-oxo-6,7-dihydro-3H-[1,2,3]triazolo[4,5-d]pyrimidin-5-yl)-[1,1'-biphenyl]-3-yl)oxy)propanoic Acid (Compound 255)

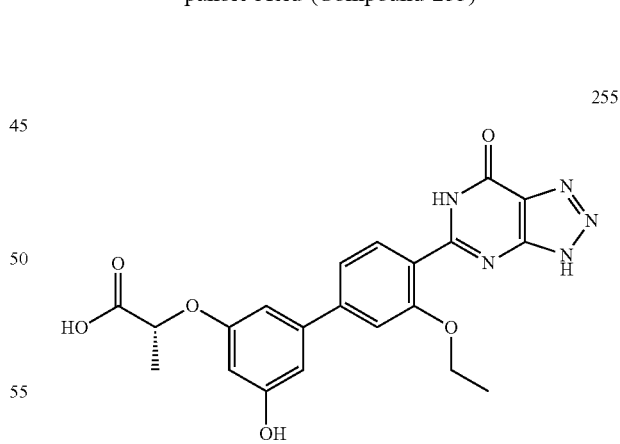

255

(R)-2-((3'-Ethoxy-5-hydroxy-4'-(7-oxo-6,7-dihydro-3H-[1,2,3]triazolo[4,5-d]pyrimidin-5-yl)-[1,1'-biphenyl]-3-yl)oxy)propanoic acid was prepared from methyl (R)-2-(3-bromo-5-hydroxyphenoxy)propanoate using the procedures in Examples 93, 42 and 9. LCMS (ESI)=438.1 [M+H]⁺. ¹H NMR (300 MHz, DMSO-d₆) δ 9.65 (s, 1H), 7.93 (d, J=8.2 Hz, 1H), 7.31-7.22 (m, 2H), 6.68 (d, J=7.7 Hz, 2H), 6.32 (s, 1H), 4.82-4.70 (m, 1H), 4.29 (q, J=6.8 Hz, 2H), 1.49 (d, J=6.7 Hz, 3H), 1.41 (t, J=6.9 Hz, 3H). Analytical chiral HPLC: CHIRALPAK AD-3 (100×3 mm, 3 μM, 1.5 mL/min; A: n-hexane/DCM, 5/1; B: EtOH w/0.1% TFA; 30% B): $t_R$=1.96 min (Peak 1).

Example 96B: Synthesis of (S)-2-((3'-ethoxy-5-hydroxy-4'-(7-oxo-6,7-dihydro-3H-[1,2,3]triazolo[4,5-d]pyrimidin-5-yl)-[1,1'-biphenyl]-3-yl)oxy)propanoic Acid (Compound 256)

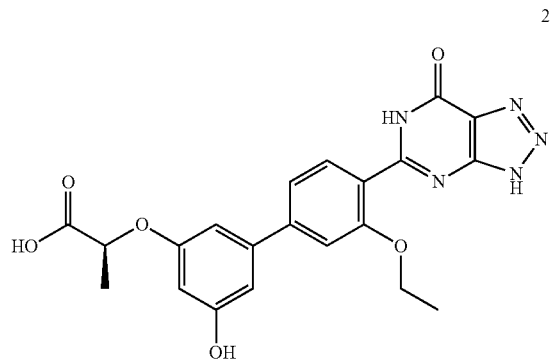

256

(S)-2-((3'-Ethoxy-5-hydroxy-4'-(7-oxo-6,7-dihydro-3H-[1,2,3]triazolo[4,5-d]pyrimidin-5-yl)-[1,1'-biphenyl]-3-yl)oxy)propanoic acid was prepared from methyl (S)-2-(3-bromo-5-hydroxyphenoxy)propanoate using the procedures in Example 96A. LCMS (ESI)=438.1 [M+H]⁺. ¹H NMR (300 MHz, DMSO-$d_6$) δ 9.65 (s, 1H), 7.93 (d, J=8.2 Hz, 1H), 7.31-7.22 (m, 2H), 6.68 (d, J=7.7 Hz, 2H), 6.32 (s, 1H), 4.82-4.70 (m, 1H), 4.29 (q, J=6.8 Hz, 2H), 1.49 (d, J=6.7 Hz, 3H), 1.41 (t, J=6.9 Hz, 3H). Analytical chiral HPLC: CHIRALPAK AD-3 (100×3 mm, 3 μM, 1.5 mL/min; A: n-hexane/DCM, 5/1; B: EtOH w/0.1% TFA; 30% B): $t_R$=2.68 min (Peak 2).

Example 97: Synthesis of 2-((3'-ethoxy-5-hydroxy-4'-(7-oxo-6,7-dihydro-3H-[1,2,3]triazolo[4,5-d]pyrimidin-5-yl)-[1,1'-biphenyl]-3-yl)oxy)butanoic Acid (Compound 257)

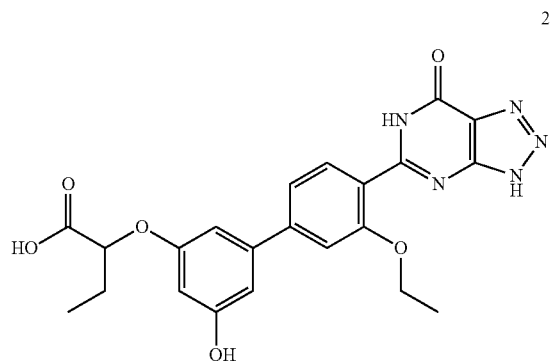

257

2-((3'-Ethoxy-5-hydroxy-4'-(7-oxo-6,7-dihydro-3H-[1,2,3]triazolo[4,5-d]pyrimidin-5-yl)-[1,1'-biphenyl]-3-yl)oxy)butanoic acid was prepared from methyl 2-bromobutanoate and 5-bromobenzene-1,3-diol using the procedures in Examples 42 and 9. LCMS (ESI)=452.1 [M+H]⁺. ¹H NMR (300 MHz, DMSO-$d_6$) δ 7.93 (d, J=8.4 Hz, 1H), 7.31-7.22 (m, 2H), 6.68 (dt, J=9.3, 1.8 Hz, 2H), 6.35 (t, J=2.1 Hz, 1H), 4.38 (dd, J=7.1, 5.1 Hz, 1H), 4.28 (q, J=6.9 Hz, 2H), 3.17 (s, 2H), 1.82 (dp, J=14.0, 7.1 Hz, 2H), 1.40 (t, J=6.9 Hz, 3H), 1.03 (d, J=24.0 Hz, 8H).

Example 98: Synthesis of (R)-2-((3'-ethoxy-5-hydroxy-4'-(7-oxo-6,7-dihydro-3H-[1,2,3]triazolo[4,5-d]pyrimidin-5-yl)-[1,1'-biphenyl]-3-yl)oxy)butanoic Acid (Compound 258)

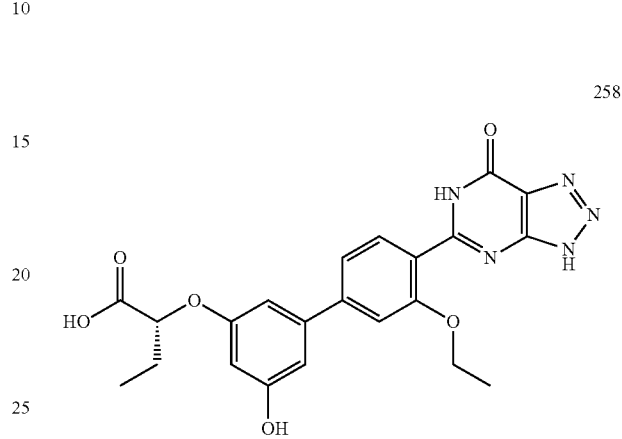

258

(R)-2-((3'-Ethoxy-5-hydroxy-4'-(7-oxo-6,7-dihydro-3H-[1,2,3]triazolo[4,5-d]pyrimidin-5-yl)-[1,1'-biphenyl]-3-yl)oxy)butanoic acid was prepared from methyl (S)-2-hydroxybutanoate and 5-bromobenzene-1,3-diol using the procedures in Examples 93, 42, and 9. LCMS (ESI)=452.1 [M+H]⁺. ¹H NMR (300 MHz, DMSO-$d_6$) δ 9.72 (s, 1H), 7.91 (d, J=8.4 Hz, 1H), 7.33-7.24 (m, 2H), 6.70 (dt, J=9.6, 1.7 Hz, 2H), 6.34 (t, J=2.1 Hz, 1H), 4.61 (t, J=6.2 Hz, 1H), 4.29 (q, J=6.9 Hz, 2H), 1.97-1.77 (m, 2H), 1.40 (t, J=6.9 Hz, 3H), 1.02 (t, J=7.4 Hz, 3H). Analytical chiral HPLC: CHIRALPAK ID-3 (50*4.6 mm, 3 um, 1 mL/min; A: hexanes/DCM, 5/1; B: EtOH w/0.1% TFA; 50% B). $t_R$=1.57 min (Peak 1).

Example 99: Synthesis of (S)-2-((3'-ethoxy-5-hydroxy-4'-(7-oxo-6,7-dihydro-3H-[1,2,3]triazolo[4,5-d]pyrimidin-5-yl)-[1,1'-biphenyl]-3-yl)oxy)butanoic Acid (Compound 259)

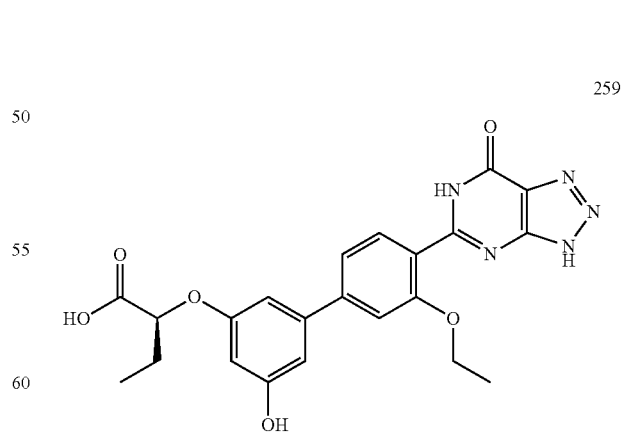

259

(S)-2-((3'-Ethoxy-5-hydroxy-4'-(7-oxo-6,7-dihydro-3H-[1,2,3]triazolo[4,5-d]pyrimidin-5-yl)-[1,1'-biphenyl]-3-yl)oxy)butanoic acid was prepared by preparative chiral HPLC with a CHIRALPAK IC-3 column using the procedure in Example 95. LCMS (ESI)=452.1 [M+H]+. Analytical chiral HPLC: CHIRALPAK ID-3 (50*4.6 mm, 3 um, 1 mL/min); A: hexanes/DCM, 5/1; B: EtOH w/0.1% TFA; 50% B. $t_R$=2.43 min (Peak 2).

Example 100: Synthesis of (R)-2-((3'-ethoxy-4,5-difluoro-4'-(7-oxo-6,7-dihydro-3H-[1,2,3]triazolo[4,5-d]pyrimidin-5-yl)-[1,1'-biphenyl]-3-yl)oxy)propanoic Acid (Compound 260)

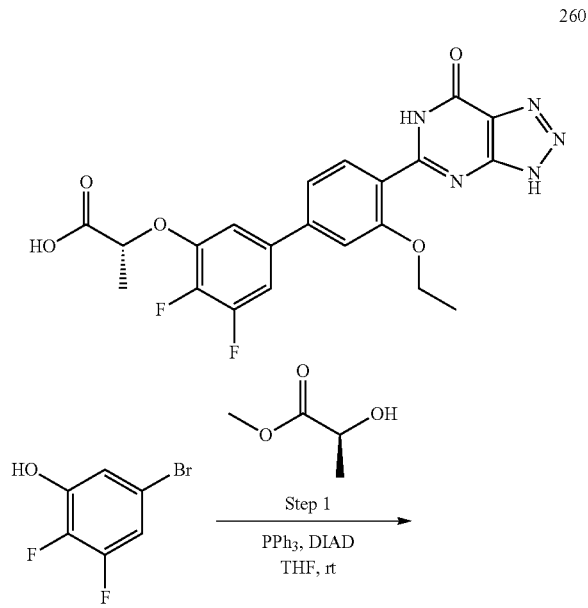

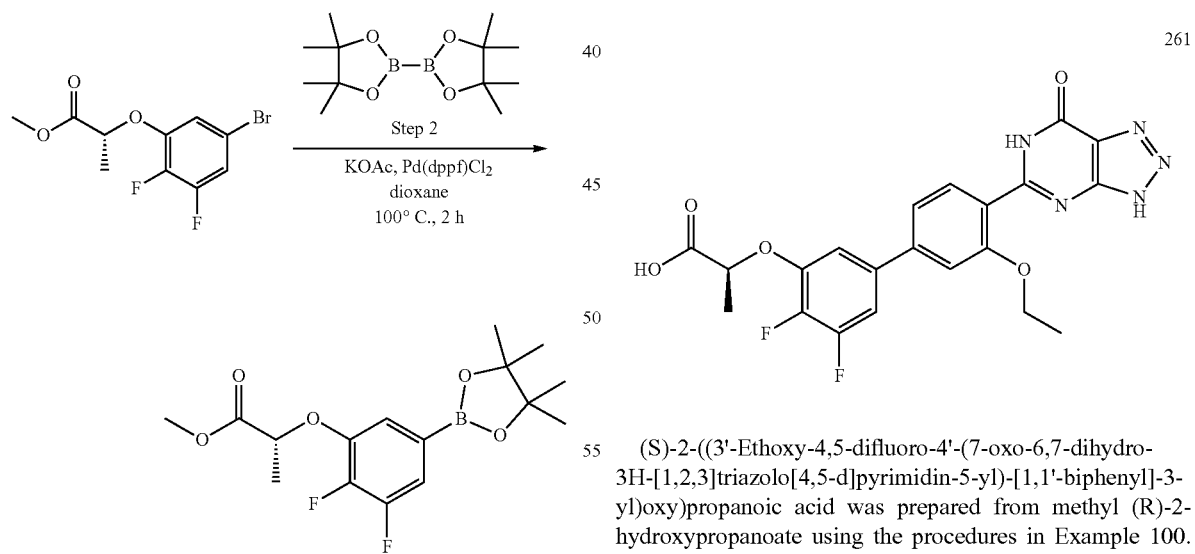

Step 1: Into a 50 ml round-bottom flask was added 5-bromo-2,3-difluorophenol (500 mg, 2.32 mmol, 1.00 equiv), methyl (S)-2-hydroxypropanoate (479 mg, 2.87 mmol, 1.2 equiv), PPh₃ (816 mg, 3.11 mmol, 1.3 equiv), and THF (10 mL). To the above mixture was added DIAD (629 mg, 3.11 mmol, 1.3 equiv) dropwise over 15 min at 0° C. The resulting mixture was stirred for additional 12 hr at rt, then the resulting mixture was concentrated under reduced pressure. The residue was purified by silica gel column chromatography to afford methyl (R)-2-(5-bromo-2,3-difluorophenoxy)propanoate (450 mg, 58%) as a yellow oil. ¹H NMR (300 MHz, DMSO-d₆) δ 7.37 (ddd, J=9.7, 6.3, 2.3 Hz, 1H), 7.23 (dt, J=6.7, 2.2 Hz, 1H), 5.33-5.11 (m, 1H), 3.70 (s, 3H), 1.54 (d, J=6.8 Hz, 3H).

Step 2: Into a 40 ml vial was added methyl (R)-2-(5-bromo-2,3-difluorophenoxy)propanoate (300 mg, 1.02 mmol, 1.00 equiv) and bis(pinacolato)diboron (310 mg, 1.22 mmol, 1.2 equiv), KOAc (299 mg, 3.05 mmol, 3.0 equiv), dioxane (6.0 mL), Pd(dppf)Cl₂ (74.4 mg, 0.102 mmol, 0.10 equiv), the resulting mixture was stirred for 2 hr at 100° C. The mixture was purified by silica gel column chromatography to afford methyl (R)-2-(2,3-difluoro-5-(4,4,5,5-tetramethyl-1,3,2-dioxaborolan-2-yl)phenoxy)propanoate (350 mg, 92%) as a yellow oil.

(R)-2-((3'-Ethoxy-4,5-difluoro-4'-(7-oxo-6,7-dihydro-3H-[1,2,3]triazolo[4,5-d]pyrimidin-5-yl)-[1,1'-biphenyl]-3-yl)oxy)propanoic acid was prepared using the procedures in Example 89. LCMS (ESI)=458.0 [M+H]+. ¹H NMR (300 MHz, DMSO-d₆) δ 7.89 (d, J=7.9 Hz, 1H), 7.42 (ddd, J=11.6, 6.7, 2.0 Hz, 1H), 7.39-7.29 (m, 2H), 7.20 (d, J=6.9 Hz, 1H), 5.02 (d, J=7.0 Hz, 1H), 4.28 (tt, J=7.0, 3.9 Hz, 2H), 1.52 (d, J=6.7 Hz, 3H), 1.39 (t, J=6.9 Hz, 3H). Analytical chiral HPLC: CHIRALPAK IC-3 (50*4.6 mm, 3 μm, 1 mL/min; A: n-hexane/DCM, 5/1; B: EtOH w/0.1% TFA), 15% B. $t_R$=1.72 min (Peak 1).

Example 101: Synthesis of (S)-2-((3'-ethoxy-4,5-difluoro-4'-(7-oxo-6,7-dihydro-3H-[1,2,3]triazolo[4,5-d]pyrimidin-5-yl)-[1,1'-biphenyl]-3-yl)oxy)propanoic Acid (Compound 261)

(S)-2-((3'-Ethoxy-4,5-difluoro-4'-(7-oxo-6,7-dihydro-3H-[1,2,3]triazolo[4,5-d]pyrimidin-5-yl)-[1,1'-biphenyl]-3-yl)oxy)propanoic acid was prepared from methyl (R)-2-hydroxypropanoate using the procedures in Example 100. LCMS (ESI)=458.0 [M+H]+. ¹H NMR (300 MHz, DMSO-d₆) δ 7.88 (d, J=8.0 Hz, 1H), 7.42 (ddd, J=11.5, 6.6, 1.9 Hz, 1H), 7.39-7.29 (m, 2H), 7.20 (d, J=6.9 Hz, 1H), 5.01 (q, J=6.7 Hz, 1H), 4.28 (qd, J=7.0, 1.8 Hz, 2H), 1.52 (d, J=6.7 Hz, 3H), 1.38 (t, J=6.9 Hz, 3H). Analytical chiral HPLC: CHIRALPAK IC-3 (50*4.6 mm, 3 μm, 1 mL/min; A: n-hexane/DCM, 5/1; B: EtOH w/0.1% TFA); 15% B). $t_R$=3.79 min (Peak 2).

Example 102: Synthesis of (R)-2-((3'-ethoxy-5-fluoro-4'-(7-oxo-6,7-dihydro-3H-[1,2,3]triazolo[4,5-d]pyrimidin-5-yl)-[1,1'-biphenyl]-3-yl)oxy)propanoic Acid (Compound 262)

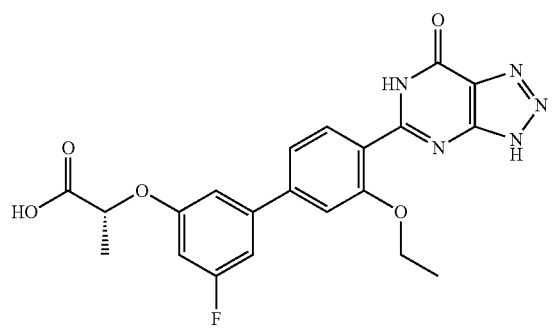

262

(R)-2-((3'-Ethoxy-5-fluoro-4'-(7-oxo-6,7-dihydro-3H-[1,2,3]triazolo[4,5-d]pyrimidin-5-yl)-[1,1'-biphenyl]-3-yl)oxy)propanoic acid was prepared using the procedures in Example 100. LCMS (ESI)=440.0 [M+H]$^+$. $^1$H NMR (300 MHz, DMSO-d$_6$) δ 7.93 (d, J=8.5 Hz, 1H), 7.43-7.35 (m, 2H), 7.21 (dt, J=9.9, 1.9 Hz, 1H), 7.12 (t, J=1.9 Hz, 1H), 6.77 (dt, J=11.0, 2.2 Hz, 1H), 4.89 (d, J=7.0 Hz, 1H), 4.32 (q, J=6.9 Hz, 2H), 1.51 (d, J=6.7 Hz, 3H), 1.40 (t, J=6.9 Hz, 3H). Analytical chiral HPLC: CHIRALPAK IA-3 (50*4.6 mm, 3 um, 1 mL/min); A: n-hexane/DCM, 5/1; B: EtOH w/0.1% TFA, 50% B). t$_R$=0.923 min (Peak 1).

Example 103: Synthesis of (S)-2-((3'-ethoxy-5-fluoro-4'-(7-oxo-6,7-dihydro-3H-[1,2,3]triazolo[4,5-d]pyrimidin-5-yl)-[1,1'-biphenyl]-3-yl)oxy)propanoic Acid (Compound 263)

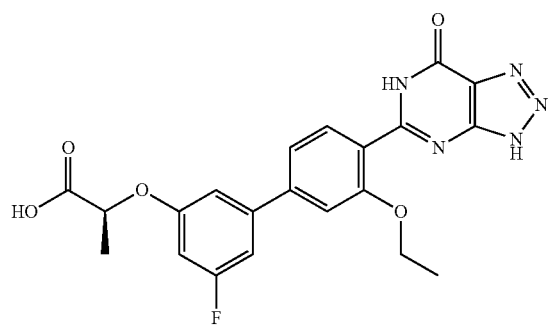

263

(S)-2-((3'-Ethoxy-5-fluoro-4'-(7-oxo-6,7-dihydro-3H-[1,2,3]triazolo[4,5-d]pyrimidin-5-yl)-[1,1'-biphenyl]-3-yl)oxy)propanoic acid was prepared using the procedures in Example 100. LCMS (ESI)=440.2 [M+H]$^+$. $^1$H NMR (300 MHz, DMSO-d$_6$) δ 7.93 (d, J=8.5 Hz, 1H), 7.43-7.35 (m, 2H), 7.21 (dt, J=9.9, 1.9 Hz, 1H), 7.12 (t, J=1.9 Hz, 1H), 6.77 (dt, J=11.0, 2.2 Hz, 1H), 4.89 (d, J=7.0 Hz, 1H), 4.32 (q, J=6.9 Hz, 2H), 1.51 (d, J=6.7 Hz, 3H), 1.40 (t, J=6.9 Hz, 3H). Analytical chiral HPLC: CHIRALPAK IA-3 (50*4.6 mm, 3 um, 1 mL/min; A: n-hexane/DCM, 5/1; B: EtOH w/0.1% TFA, 50% B). t$_R$=1.23 min (Peak 2).

Example 104: Synthesis of (R)-2-((3'-ethoxy-4-fluoro-4'-(7-oxo-6,7-dihydro-3H-[1,2,3]triazolo[4,5-d]pyrimidin-5-yl)-[1,1'-biphenyl]-3-yl)oxy)propanoic Acid (Compound 264)

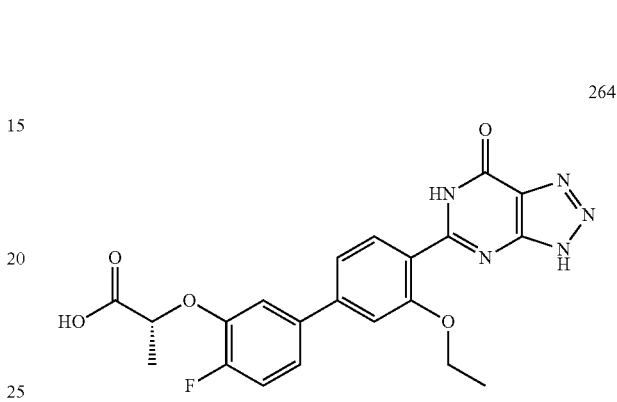

264

(R)-2-((3'-Ethoxy-4-fluoro-4'-(7-oxo-6,7-dihydro-3H-[1,2,3]triazolo[4,5-d]pyrimidin-5-yl)-[1,1'-biphenyl]-3-yl)oxy)propanoic acid was prepared using the procedures in Example 100. LCMS (ESI)=440.2 [M+H]$^+$. $^1$H NMR (300 MHz, DMSO-d$_6$) δ 7.94 (d, J=8.0 Hz, 1H), 7.29 (ddd, J=10.1, 5.1, 3.1 Hz, 5H), 4.80 (q, J=6.7 Hz, 1H), 4.35-4.20 (m, 2H), 1.49 (d, J=6.7 Hz, 3H), 1.40 (t, J=6.9 Hz, 3H).

Example 105: Synthesis of (S)-2-((3'-ethoxy-4-fluoro-4'-(7-oxo-6,7-dihydro-3H-[1,2,3]triazolo[4,5-d]pyrimidin-5-yl)-[1,1'-biphenyl]-3-yl)oxy)propanoic Acid (Compound 265)

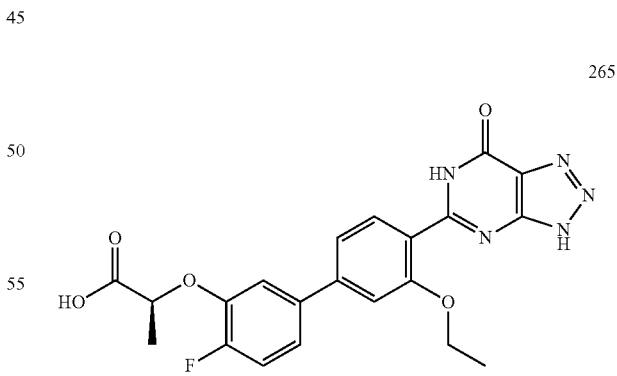

265

(S)-2-((3'-Ethoxy-4-fluoro-4'-(7-oxo-6,7-dihydro-3H-[1,2,3]triazolo[4,5-d]pyrimidin-5-yl)-[1,1'-biphenyl]-3-yl)oxy)propanoic acid was prepared using the procedures in Example 100. LCMS (ESI)=440.2 [M+H]$^+$. $^1$H NMR (300 MHz, DMSO-d$_6$) δ 7.91 (d, J=7.9 Hz, 1H), 7.38-7.25 (m, 5H), 4.94 (q, J=6.6 Hz, 1H), 4.27 (qd, J=6.8, 2.2 Hz, 2H), 1.51 (d, J=6.6 Hz, 3H), 1.39 (t, J=6.9 Hz, 2H).

Example 106: Synthesis of (R)-2-((3'-ethoxy-5-methyl-4'-(7-oxo-6,7-dihydro-3H-[1,2,3]triazolo[4,5-d]pyrimidin-5-yl)-[1,1'-biphenyl]-3-yl)oxy)propanoic Acid (Compound 266)

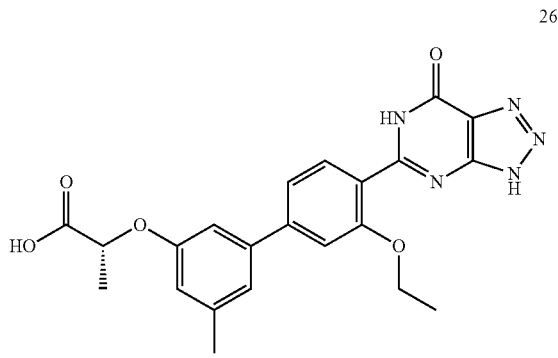

(R)-2-((3'-ethoxy-5-methyl-4'-(7-oxo-6,7-dihydro-3H-[1,2,3]triazolo[4,5-d]pyrimidin-5-yl)-[1,1'-biphenyl]-3-yl)oxy)propanoic acid was prepared from methyl (S)-2-hydroxypropanoate using the procedures in Example 100. LCMS (ESI)=436.1 [M+H]$^+$. $^1$H NMR (300 MHz, DMSO-d$_6$) δ 7.96 (d, J=8.2 Hz, 1H), 7.38-7.30 (m, 2H), 7.15 (s, 1H), 7.02 (s, 1H), 6.73 (s, 1H), 4.83 (s, 1H), 4.31 (q, J=6.8 Hz, 2H), 2.35 (s, 3H), 1.50 (d, J=6.6 Hz, 3H), 1.42 (t, J=6.9 Hz, 3H).

Example 107: Synthesis of (S)-2-((3'-ethoxy-5-methyl-4'-(7-oxo-6,7-dihydro-3H-[1,2,3]triazolo[4,5-d]pyrimidin-5-yl)-[1,1'-biphenyl]-3-yl)oxy)propanoic Acid (Compound 267)

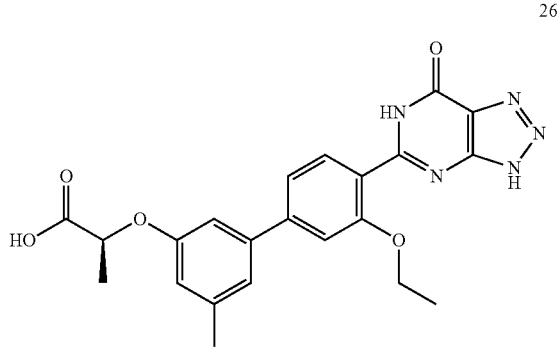

(S)-2-((3'-Ethoxy-5-methyl-4'-(7-oxo-6,7-dihydro-3H-[1,2,3]triazolo[4,5-d]pyrimidin-5-yl)-[1,1'-biphenyl]-3-yl)oxy)propanoic acid was prepared from methyl (R)-2-hydroxypropanoate using the procedures in Example 100. LCMS (ESI)=436.1 [M+H]$^+$. $^1$H NMR (300 MHz, DMSO-d$_6$) δ 7.96 (d, J=8.2 Hz, 1H), 7.38-7.30 (m, 2H), 7.15 (s, 1H), 7.02 (s, 1H), 6.73 (s, 1H), 4.83 (s, 1H), 4.31 (q, J=6.8 Hz, 2H), 2.35 (s, 3H), 1.50 (d, J=6.6 Hz, 3H), 1.42 (t, J=6.9 Hz, 3H).

Example 108: Synthesis of ethyl 2-((3'-ethoxy-4'-(7-oxo-6,7-dihydro-3H-[1,2,3]triazolo[4,5-d]pyrimidin-5-yl)-[1,1'-biphenyl]-3-yl)oxy)-3-methylbutanoate (Compound 268)

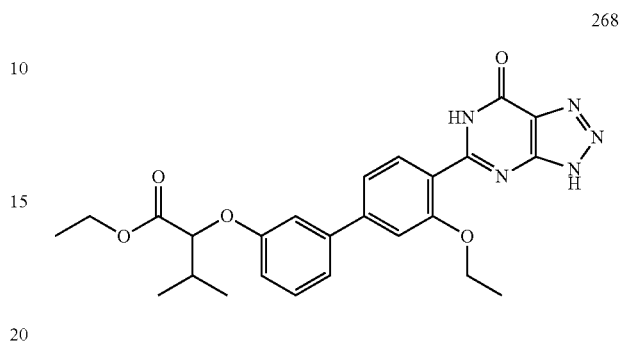

Ethyl 2-((3'-ethoxy-4'-(7-oxo-6,7-dihydro-3H-[1,2,3]triazolo[4,5-d]pyrimidin-5-yl)-[1,1'-biphenyl]-3-yl)oxy)-3-methylbutanoate was prepared using the procedures in Example 56. LCMS (ESI)=478.3 [M+H]$^+$. $^1$H NMR (300 MHz, DMSO-d$_6$) δ 12.22 (s, 1H), 7.86 (d, J=8.5 Hz, 1H), 7.48-7.33 (m, 4H), 7.29-7.22 (m, 1H), 6.94 (ddd, J=7.9, 2.6, 1.4 Hz, 1H), 4.77 (d, J=5.2 Hz, 1H), 4.31 (q, J=6.9 Hz, 2H), 4.17 (q, J=7.0 Hz, 2H), 2.24 (dt, J=11.9, 6.7 Hz, 1H), 1.39 (t, J=6.9 Hz, 3H), 1.18 (t, J=7.1 Hz, 3H), 1.05 (dd, J=6.8, 2.9 Hz, 6H).

Example 109: Synthesis of 2-((3'-ethoxy-4'-(7-oxo-6,7-dihydro-3H-[1,2,3]triazolo[4,5-d]pyrimidin-5-yl)-[1,1'-biphenyl]-3-yl)oxy)-3-methylbutanoic Acid (Compound 269)

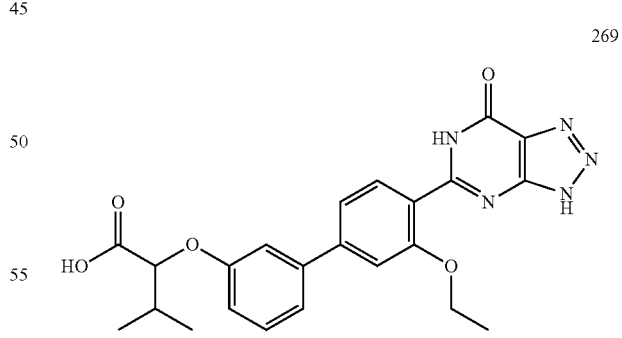

2-((3'-ethoxy-4'-(7-oxo-6,7-dihydro-3H-[1,2,3]triazolo[4,5-d]pyrimidin-5-yl)-[1,1'-biphenyl]-3-yl)oxy)-3-methylbutanoic acid was prepared using the procedures in Example 56. LCMS (ESI)=450.2 [M+H]$^+$. $^1$H NMR (300 MHz, DMSO-d$_6$) δ 7.98 (d, J=7.9 Hz, 1H), 7.34 (q, J=4.8 Hz, 3H), 7.26 (d, J=7.7 Hz, 1H), 7.19 (s, 1H), 6.92-6.83 (m, 1H), 4.32 (t, J=7.0 Hz, 1H), 4.26 (s, 2H), 2.17 (s, 1H), 1.41 (t, J=6.9 Hz, 3H), 1.01 (dd, J=6.8, 2.6 Hz, 6H).

Example 110: Synthesis of ethyl 2-((3'-(cyclopentyloxy)-4'-(7-oxo-6,7-dihydro-3H-[1,2,3]triazolo[4,5-d]pyrimidin-5-yl)-[1,1'-biphenyl]-3-yl)oxy)acetate (Compound 270)

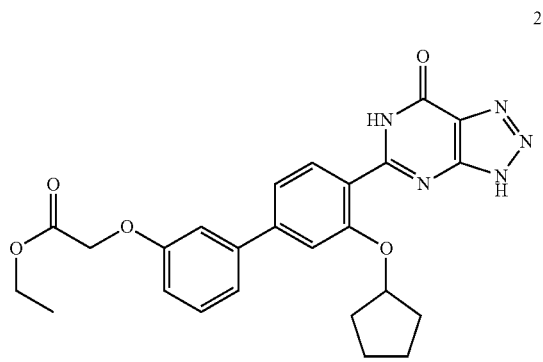

Ethyl 2-((3'-(cyclopentyloxy)-4'-(7-oxo-6,7-dihydro-3H-[1,2,3]triazolo[4,5-d]pyrimidin-5-yl)-[1,1'-biphenyl]-3-yl)oxy)acetate was prepared using the procedures in Example 56. LCMS (ESI)=476.2 [M+H]$^+$. $^1$H NMR (300 MHz, DMSO-d$_6$) δ 12.06 (s, 1H), 7.93 (d, J=8.4 Hz, 1H), 7.49-7.33 (m, 4H), 7.29 (t, J=2.1 Hz, 1H), 7.01 (ddd, J=8.0, 2.5, 1.2 Hz, 1H), 5.21 (tt, J=5.6, 2.6 Hz, 1H), 4.91 (s, 2H), 4.19 (q, J=7.1 Hz, 2H), 2.55-2.46 (m, 1H), 1.96 (tt, J=9.2, 4.6 Hz, 2H), 1.91-1.78 (m, 2H), 1.66 (ddt, J=21.5, 11.0, 3.7 Hz, 4H), 1.23 (t, J=7.1 Hz, 3H).

Example 111: Synthesis of isopropyl 2-((3'-(cyclopentyloxy)-4'-(7-oxo-6,7-dihydro-3H-[1,2,3]triazolo[4,5-d]pyrimidin-5-yl)-[1,1'-biphenyl]-3-yl)oxy)acetate (Compound 271)

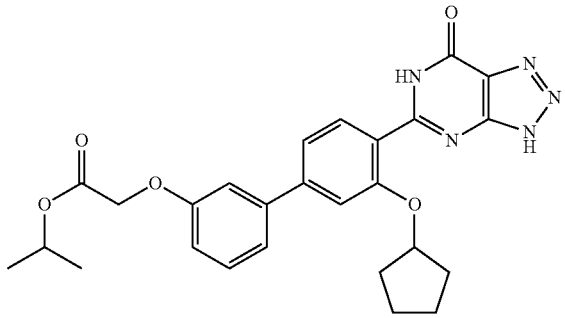

Isopropyl 2-((3'-(cyclopentyloxy)-4'-(7-oxo-6,7-dihydro-3H-[1,2,3]triazolo[4,5-d]pyrimidin-5-yl)-[1,1'-biphenyl]-3-yl)oxy)acetate was prepared using the procedures in Example 56. LCMS (ESI)=490.3 [M+H]$^+$. $^1$H NMR (300 MHz, DMSO-d$_6$) δ 12.07 (s, 1H), 7.92 (d, J=8.4 Hz, 1H), 7.49-7.33 (m, 4H), 7.28 (t, J=2.0 Hz, 1H), 7.00 (ddd, J=8.0, 2.6, 1.2 Hz, 1H), 5.21 (dt, J=5.6, 2.9 Hz, 1H), 5.02 (hept, J=6.2 Hz, 1H), 4.87 (s, 2H), 2.03-1.89 (m, 2H), 1.89-1.78 (m, 2H), 1.76-1.55 (m, 2H), 1.23 (d, J=6.3 Hz, 6H).

Example 112: Synthesis of 2-((3'-ethoxy-4-methyl-4'-(7-oxo-6,7-dihydro-3H-[1,2,3]triazolo[4,5-d]pyrimidin-5-yl)-[1,1'-biphenyl]-3-yl)oxy)butanoic Acid (Compound 272)

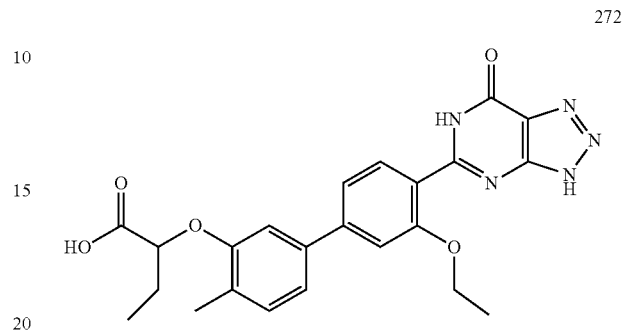

2-((3'-Ethoxy-4-methyl-4'-(7-oxo-6,7-dihydro-3H-[1,2,3]triazolo[4,5-d]pyrimidin-5-yl)-[1,1'-biphenyl]-3-yl)oxy)butanoic acid was prepared using the procedures in Example 42 and 9 from 5-bromo-2-methylphenol and ethyl 2-bromobutanoate. LCMS (ESI)=450.2 [M+H]$^+$. $^1$H NMR (300 MHz, DMSO-d$_6$) δ 7.91 (d, J=8.4 Hz, 1H), 7.36-7.19 (m, 4H), 7.10 (s, 1H), 4.84 (s, 1H), 4.34-4.20 (m, 2H), 2.25 (s, 3H), 2.03-1.84 (m, 2H), 1.40 (t, J=6.9 Hz, 3H), 1.06 (t, J=7.4 Hz, 3H).

Example 113: Synthesis of 5-(3-(cyclopentyloxy)-4'-(1H-tetrazol-5-yl)-[1,1'-biphenyl]-4-yl)-3,6-dihydro-7H-[1,2,3]triazolo[4,5-d]pyrimidin-7-one (Compound 273)

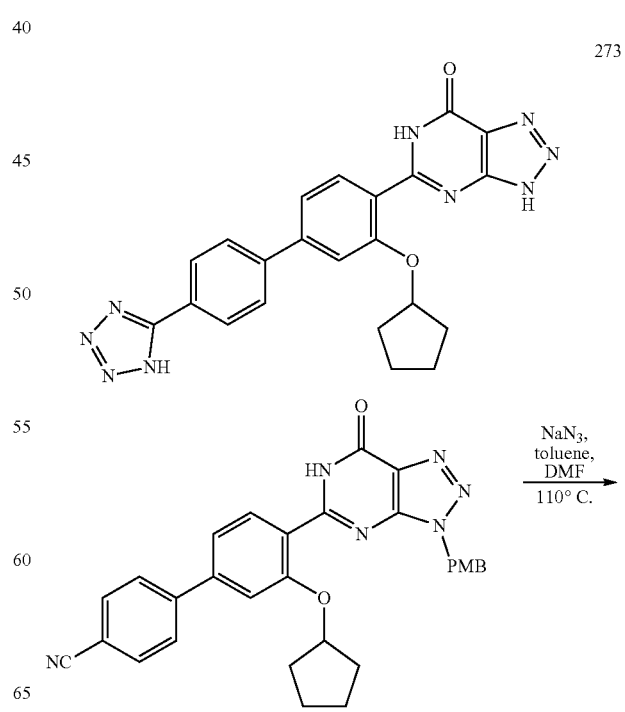

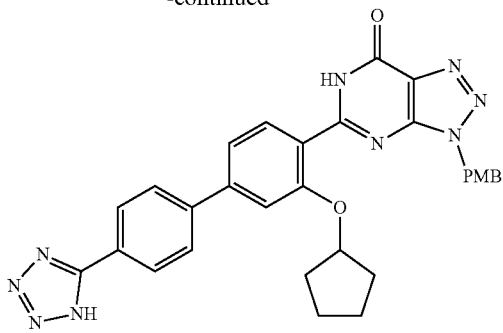

3'-(Cyclopentyloxy)-4'-(3-(4-methoxybenzyl)-7-oxo-6,7-dihydro-3H-[1,2,3]triazolo[4,5-d]pyrimidin-5-yl)-[1,1'-biphenyl]-4-carbonitrile was prepared using the procedures in Example 6 from 4-(4,4,5,5-tetramethyl-1,3,2-dioxaborolan-2-yl)benzonitrile. Into an 8-mL vial was placed 3'-(cyclopentyloxy)-4'-(3-(4-methoxybenzyl)-7-oxo-6,7-dihydro-3H-[1,2,3]triazolo[4,5-d]pyrimidin-5-yl)-[1,1'-biphenyl]-4-carbonitrile (139 mg, 0.268 mmol, 1.00 equiv) in DMF (1.0 mL) and toluene (1.0 mL). Triethylamine hydrochloride (92.2 mg, 0.670 mmol, 2.50 equiv) and sodium azide (43.6 mg, 0.670 mmol, 2.50 equiv) were added, and the resulting solution was stirred for 17 hr at 110° C. The reaction was quenched by the addition of 5 mL of water, and the pH value of the solution was adjusted to 6 with 1M HCl. The solids were collected by filtration and were dried under a heat lamp to afford 50 mg (33%) of 5-(3-(cyclopentyloxy)-4'-(1H-tetrazol-5-yl)-[1,1'-biphenyl]-4-yl)-3-(4-methoxybenzyl)-3,6-dihydro-7H-[1,2,3]triazolo[4,5-d]pyrimidin-7-one as a gray solid. LCMS (ESI)=562.3 [M+H]$^+$.

5-(3-(Cyclopentyloxy)-4'-(1H-tetrazol-5-yl)-[1,1'-biphenyl]-4-yl)-3,6-dihydro-7H-[1,2,3]triazolo[4,5-d]pyrimidin-7-one was prepared using the procedures in Example 6. LCMS (ESI)=442.2 [M+H]$^+$. $^1$H NMR (300 MHz, DMSO-d$_6$) δ 12.00 (s, 1H), 8.13 (d, J=8.4 Hz, 2H), 7.98 (d, J=8.4 Hz, 1H), 8.13 (d, J=8.7 Hz, 2H), 7.49 (d, J=7.8 Hz, 2H), 5.25-5.23 (m, 1H), 2.02-1.97 (m, 2H), 1.93-1.84 (m, 2H), 1.79-1.65 (m, 4H).

Example 114: Synthesis of (S)-2-amino-3-(3'-ethoxy-4'-(7-oxo-6,7-dihydro-3H-[1,2,3]triazolo[4,5-d]pyrimidin-5-yl)-[1,1'-biphenyl]-3-yl)propanoic Acid (Compound 274)

274

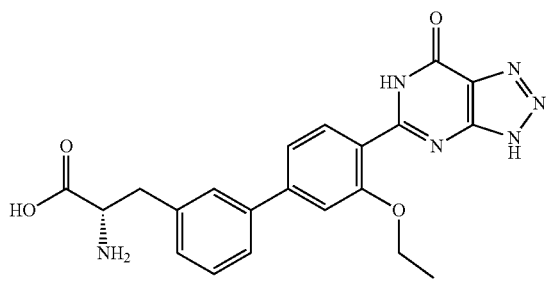

(S)-2-Amino-3-(3'-ethoxy-4'-(7-oxo-6,7-dihydro-3H-[1,2,3]triazolo[4,5-d]pyrimidin-5-yl)-[1,1'-biphenyl]-3-yl)propanoic acid was prepared using similar methods as describe in the previous examples from (S)-3-(3-bromophenyl)-2-((tert-butoxycarbonyl)amino)propanoic acid and 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one. LCMS (ESI)=421.2 [M+H]$^+$. $^1$H NMR (300 MHz, DMSO-d$_6$) δ 7.99 (d, J=8.4 Hz, 1H), 7.70-7.59 (m, 2H), 7.48-7.37 (m, 3H), 7.33 (s, 1H), 4.32 (d, J=7.1 Hz, 2H), 1.43 (t, J=6.8 Hz, 3H).

Example 115: Synthesis of (R)-2-amino-3-(3'-ethoxy-4'-(7-oxo-6,7-dihydro-3H-[1,2,3]triazolo[4,5-d]pyrimidin-5-yl)-[1,1'-biphenyl]-3-yl)propanoic Acid (Compound 275)

275

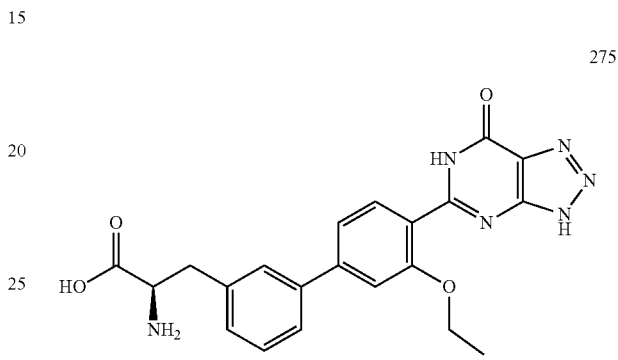

(R)-2-Amino-3-(3'-ethoxy-4'-(7-oxo-6,7-dihydro-3H-[1,2,3]triazolo[4,5-d]pyrimidin-5-yl)-[1,1'-biphenyl]-3-yl)propanoic acid was prepared using similar methods as describe in the previous examples from (R)-3-(3-bromophenyl)-2-((tert-butoxycarbonyl)amino)propanoic acid and 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one. LCMS (ESI)=421.2 [M+H]$^+$.

Example 116: Synthesis of 2-((3'-ethoxy-5-hydroxy-4'-(7-oxo-6,7-dihydro-3H-[1,2,3]triazolo[4,5-d]pyrimidin-5-yl)-[1,1'-biphenyl]-3-yl)oxy)propanoic Acid (Compound 276)

276

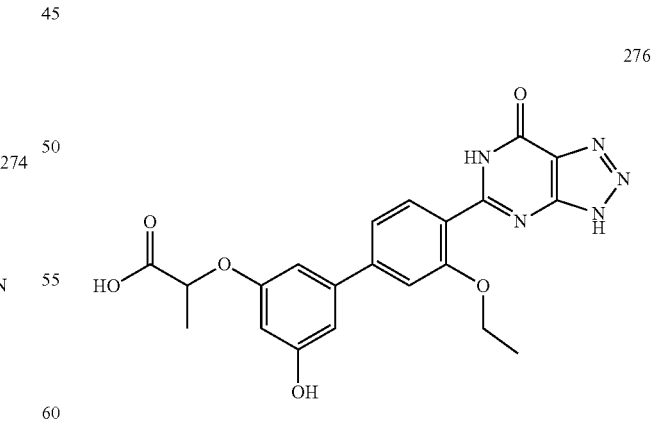

2-((3'-Ethoxy-5-hydroxy-4'-(7-oxo-6,7-dihydro-3H-[1,2,3]triazolo[4,5-d]pyrimidin-5-yl)-[1,1'-biphenyl]-3-yl)oxy)propanoic acid was prepared using the procedures in Example 96A from racemic methyl 2-(3-bromo-5-hydroxyphenoxy)propanoate. LCMS (ESI)=438.1 [M+H]$^+$. $^1$H NMR (300 MHz, DMSO-d$_6$) δ 7.95 (d, J=8.2 Hz, 1H), 7.28

(dd, J=4.5, 2.7 Hz, 2H), 6.69 (d, J=7.2 Hz, 2H), 6.33 (s, 1H), 4.76 (s, 1H), 4.29 (q, J=6.9 Hz, 2H), 1.49 (d, J=6.7 Hz, 3H), 1.42 (t, J=6.9 Hz, 3H).

Example 117: Synthesis of rac-trans-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic Acid (Compound 277)

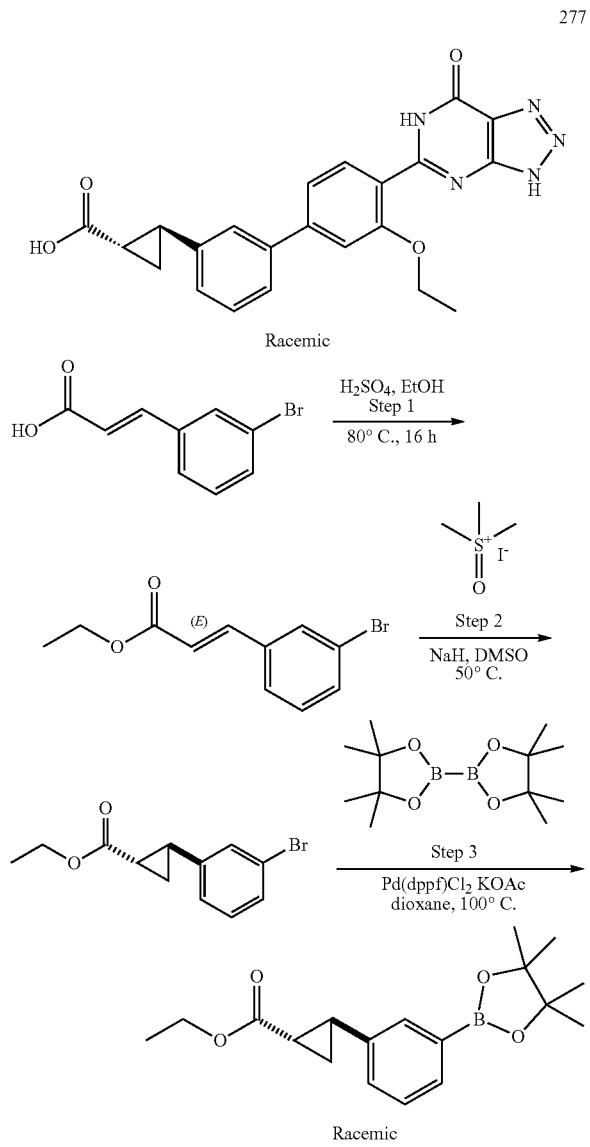

Step 1: To a stirred solution of (E)-3-(3-bromophenyl)acrylic acid (2.00 g, 8.81 mmol, 1.00 equiv) in EtOH (20 mL) was added H2SO4 (0.50 mL, 9.38 mmol, 1.06 equiv) dropwise at room temperature. The resulting mixture was stirred for 16 h at 80° C. then was concentrated under reduced pressure. The mixture was diluted with water (50 mL) and extracted with EA (2×20 mL). The combined organic layers were washed with brine (30 mL), dried over anhydrous Na2SO4, filtered and concentrated under reduced pressure. The residue was purified by silica gel column chromatography to afford ethyl (E)-3-(3-bromophenyl)acrylate (2.2 g, 98%) as a white solid. $^1$H NMR (300 MHz, CDCl$_3$) δ 7.69 (t, J=1.8 Hz, 1H), 7.62 (d, J=16.0 Hz, 1H), 7.52 (ddd, J=7.9, 2.0, 1.1 Hz, 1H), 7.46 (dt, J=7.8, 1.5 Hz, 1H), 7.28 (t, J=7.8 Hz, 1H), 6.45 (d, J=16.0 Hz, 1H), 4.47-4.23 (m, 2H), 1.36 (t, J=7.2 Hz, 3H).

Step 2: To a stirred solution of trimethylsulfoxonium iodide (1.12 g, 5.09 mmol, 1.30 equiv) in DMSO (10 mL) was added NaH (0.20 g, 5.10 mmol, 1.3 equiv, 60%) in portions at room temperature under N$_2$ atmosphere. The resulting mixture was stirred for 1 h. To the above mixture was added ethyl (E)-3-(3-bromophenyl)acrylate (1.00 g, 3.920 mmol, 1.00 equiv) at rt. The resulting mixture was stirred for 16 h at 50° C., then was quenched by the addition of ammonium chloride solution (30 mL) at rt. The resulting mixture was extracted with EA (2×30 mL). The combined organic layers were washed with brine (30 mL), dried over anhydrous Na$_2$SO$_4$, filtered, and concentrated under reduced pressure. The residue was purified by silica gel column chromatography to afford rac-ethyl trans-2-(3-bromophenyl)cyclopropane-1-carboxylate (600 mg, 57%) as a colorless oil. $^1$H NMR (300 MHz, CDCl$_3$) δ 7.35 (ddd, J=7.9, 2.0, 1.1 Hz, 1H), 7.26 (t, J=1.9 Hz, 1H), 7.17 (t, J=7.8 Hz, 1H), 7.06 (dt, J=7.8, 1.5 Hz, 1H), 4.20 (q, J=7.2 Hz, 2H), 2.50 (ddd, J=9.2, 6.5, 4.2 Hz, 1H), 1.92 (ddd, J=8.5, 5.4, 4.2 Hz, 1H), 1.63 (ddd, J=9.2, 5.4, 4.7 Hz, 1H), 1.35-1.25 (m, 4H).

Step 3: To a solution of rac-ethyl trans-2-(3-bromophenyl)cyclopropane-1-carboxylate (300 mg, 1.12 mmol, 1.00 equiv) and bis(pinacolato)diboron (340 mg, 1.34 mmol, 1.20 equiv) in dioxane (3.0 mL) was added KOAc (219 mg, 2.23 mmol, 2.00 equiv) and Pd(dppf)Cl$_2$ CH$_2$Cl$_2$ (45.5 mg, 0.056 mmol, 0.05 equiv). After stirring for 2 h at 100° C. under a nitrogen atmosphere, the resulting mixture was allowed to cool down to room temperature. The mixture was purified by silica gel column chromatography to afford rac-ethyl trans-2-(3-(4,4,5,5-tetramethyl-1,3,2-dioxaborolan-2-yl)phenyl)cyclopropane-1-carboxylate (250 mg, 71%) as a light yellow oil.

Rac-trans-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic acid was prepared using the procedures in Examples 1 and 9. LCMS (ESI)=418.2 [M+H]$^+$. $^1$H NMR (300 MHz, DMSO-d$_6$) δ 11.64 (s, 13H), 8.36 (d, J=8.4 Hz, 1H), 7.77-7.65 (m, 3H), 7.64 (s, 1H), 7.58 (t, J=7.7 Hz, 1H), 7.37 (d, J=7.7 Hz, 1H), 4.75 (q, J=6.9 Hz, 2H), 2.99 (t, J=10.2 Hz, 1H), 2.19 (dt, J=8.6, 4.5 Hz, 1H), 2.01 (dt, J=9.7, 5.1 Hz, 1H), 1.79 (t, J=7.0 Hz, 4H).

Example 118: Separation of the enantiomers of rac-trans-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic Acid (Compound 278, Peak 1 and Compound 279, Peak 2)

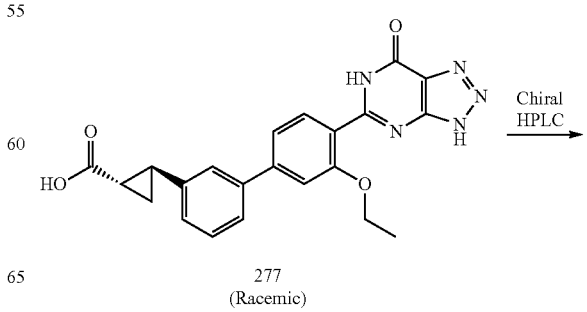

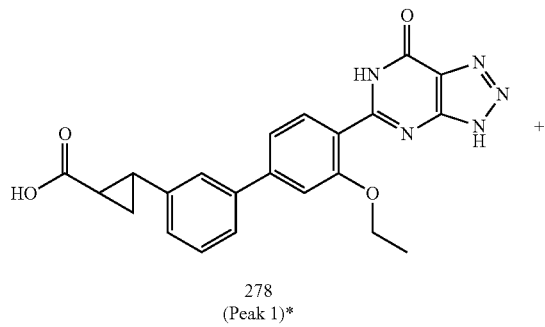

278
(Peak 1)*

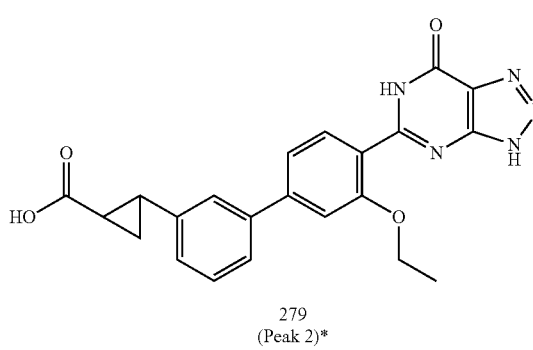

279
(Peak 2)*

Rac-trans-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic acid (50 mg) was separated into the individual enantiomers by chiral preparative HPLC with a CHIRALPAK IA-3 column, 20*250 mm, 5 um, 9 mL/min. Phase A: DCM, Phase B: Ethanol (0.1% TFA); 0% Phase B up to 30% in 25 minutes to afford 9 mg of trans-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic acid, Peak 1, and 10 mg of trans-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic acid, Peak 2.

Data for Compound 278 (Peak 1): LCMS (ESI)=418.2 [M+H]$^+$. Analytical chiral HPLC: CHIRALPAK IA-3, 4.6*50 mm, 3 μm, 1.0 mL/min; A: DCM; B: EtOH w/0.1% TFA; 80% B: $t_R$=1.16 min (99.3% ee). *Absolute stereochemistry for isolated single enantiomer not determined.

Data for Compound 279 (Peak 2): LCMS (ESI)=418.2 [M+H]$^+$. Analytical chiral HPLC: CHIRALPAK IA-3, 4.6*50 mm, 3 μm, 1.0 mL/min; A: DCM; B: EtOH w/0.1% TFA; 80% B: $t_R$=2.03 min (99.7% ee). *Absolute stereochemistry for isolated single enantiomer not determined.

Example 119: Synthesis of 2-((3'-ethoxy-4-hydroxy-4'-(7-oxo-6,7-dihydro-3H-[1,2,3]triazolo[4,5-d]pyrimidin-5-yl)-[1,1'-biphenyl]-3-yl)oxy)propanoic Acid (Compound 280)

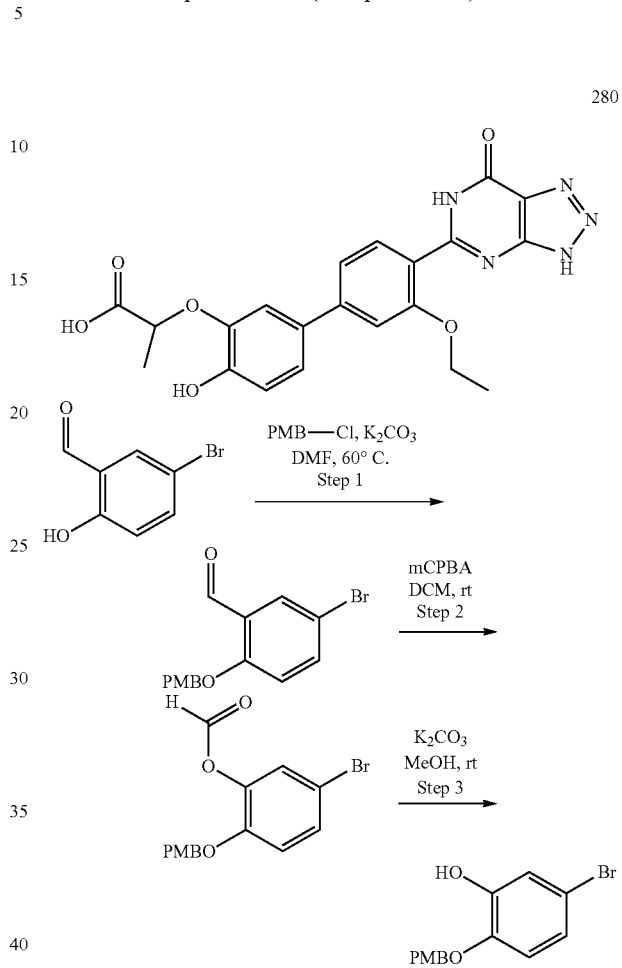

Step 1: Into a 100-mL round-bottom flask, was placed 5-bromo-2-hydroxybenzaldehyde (3.00 g, 14.9 mmol, 1.00 equiv) in DMF (30 mL), $K_2CO_3$ (6188 mg, 44.8 mmol, 3.00 equiv), and 4-methoxybenzyl chloride (2804 mg, 17.9 mmol, 1.20 equiv). The resulting solution was stirred for 4 hr at 60° C., then quenched by the addition of 10 mL of water at rt. The resulting solution was extracted with 3×10 mL of ethyl acetate and the organic layers combined and dried over anhydrous sodium sulfate, filtered and concentrated. The residue was purified by silica gel column chromatography to afford 5-bromo-2-((4-methoxybenzyl)oxy)benzaldehyde (4.0 g, 83%) as a white solid. $^1$H NMR (300 MHz, DMSO-d$_6$) δ 10.28 (s, 1H), 8.01-7.62 (m, 2H), 7.44 (d, J=8.7 Hz, 2H), 7.33 (d, J=8.9 Hz, 1H), 6.96 (d, J=8.6 Hz, 2H), 5.21 (s, 2H), 3.76 (s, 3H).

Step 2: Into a 50-mL round-bottom flask, was placed 5-bromo-2-((4-methoxybenzyl)oxy)benzaldehyde (1.00 g, 3.11 mmol, 1.00 equiv) in DCM (10 mL), m-CPBA (1075 mg, 6.23 mmol, 2.00 equiv) was added. The resulting solution was stirred for 14 hr at room temperature. The resulting mixture was concentrated. The residue was purified by silica gel column chromatography to afford 5-bromo-2-((4-methoxybenzyl)oxy)phenyl formate (900 mg, 86%) as a light yellow oil. $^1$H NMR (300 MHz, DMSO-d$_6$) δ 8.51 (s, 1H), 7.57-7.41 (m, 2H), 7.33 (d, J=8.6 Hz, 2H), 7.23 (d, J=8.6 Hz, 1H), 7.06-6.85 (m, 2H), 5.07 (s, 2H), 3.76 (s, 3H).

Step 3: Into a 50-mL round-bottom flask, was placed 5-bromo-2-((4-methoxybenzyl)oxy)phenyl formate (900 mg, 2.67 mmol, 1.00 equiv), MeOH (5.0 mL), a solution of $K_2CO_3$ (553 mg, 4.00 mmol, 1.50 equiv) in $H_2O$ (5 mL). The resulting solution was stirred for 4 hr at room temperature. The pH value of the solution was adjusted to 6 with 1M HCl. The solids were collected by filtration to afford 5-bromo-2-((4-methoxybenzyl)oxy)phenol (750 mg, 91%) as a light brown solid. $^1$H NMR (300 MHz, DMSO-$d_6$) δ 7.37 (d, J=8.6 Hz, 1H), 7.01-6.84 (m, 2H), 6.78 (dd, J=8.5, 2.4 Hz, 1H), 4.99 (s, 1H), 3.75 (s, 3H).

2-((3'-Ethoxy-4-hydroxy-4'-(7-oxo-6,7-dihydro-3H-[1,2,3]triazolo[4,5-d]pyrimidin-5-yl)-[1,1'-biphenyl]-3-yl)oxy) propanoic acid was prepared from 5-(4-bromo-2-ethoxyphenyl)-3,6-dihydro-7H-[1,2,3]triazolo[4,5-d]pyrimidin-7-one using similar methods as described in the previous examples. LCMS (ESI)=438.1 [M+H]$^+$. $^1$H NMR (300 MHz, DMSO-$d_6$) δ 7.91 (d, J=8.1 Hz, 1H), 7.33-7.31 (m, 4H), 6.81 (d, J=8.1 Hz, 1H), 4.35-4.20 (m, 3H), 1.50-1.40 (m, 6H).

Example 120: Synthesis of 2-((3'-ethoxy-4-hydroxy-4'-(7-oxo-6,7-dihydro-3H-[1,2,3]triazolo[4,5-d]pyrimidin-5-yl)-[1,1'-biphenyl]-3-yl)oxy)acetic Acid (Compound 281)

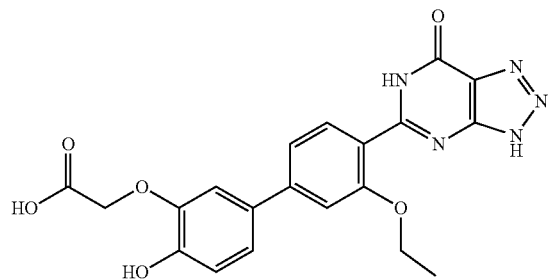

2-((3'-Ethoxy-4-hydroxy-4'-(7-oxo-6,7-dihydro-3H-[1,2,3]triazolo[4,5-d]pyrimidin-5-yl)-[1,1'-biphenyl]-3-yl)oxy) acetic acid was prepared using the procedures in Example 119. LCMS (ESI)=424.1 [M+H]$^+$. $^1$H NMR (300 MHz, DMSO-$d_6$) δ 7.95 (d, J=8.4 Hz, 1H), 7.34-7.31 (m, 4H), 6.81 (brs, 1H), 4.32 (q, J=6.9 Hz, 2H), 4.21 (s, 2H), 1.43 (t, J=6.9 Hz, 3H).

Example 121: Synthesis of (S)-3-(3'-ethoxy-4'-(7-oxo-6,7-dihydro-3H-[1,2,3]triazolo[4,5-d]pyrimidin-5-yl)-[1,1'-biphenyl]-3-yl)-2-hydroxypropanoic Acid (Compound 282)

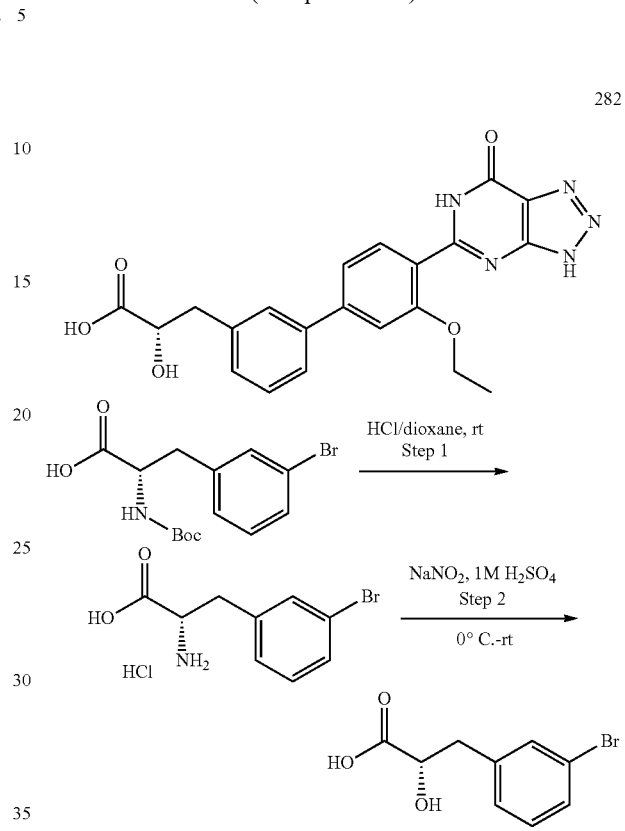

Step 1: A solution of (S)-3-(3-bromophenyl)-2-((tert-butoxycarbonyl)amino)propanoic acid (1.00 g, 2.90 mmol, 1.00 equiv) in HCl (gas) in 1,4-dioxane (15 mL) was stirred for 16 h at rt. The resulting mixture was diluted with ether (15 mL). The precipitated solids were collected by filtration and washed with ether (3×5 mL). The resulting solid was dried under a heat lamp to afford (S)-2-amino-3-(3-bromophenyl)propanoic acid hydrochloride (750 mg) as a white solid. LCMS (ESI)=244.0, 246.0 [M+H]$^+$.

Step 2: To a stirred solution of (S)-2-amino-3-(3-bromophenyl)propanoic acid hydrochloride (700 mg, 2.50 mmol, 1.00 equiv) in $H_2SO_4$ (1 M in H2O) (10 mL) was added $NaNO_2$ (861 mg, 12.5 mmol, 5.00 equiv) in H2O (2.0 mL) dropwise at 0° C. under $N_2$ atmosphere. The resulting mixture was stirred for 16 h at rt. The resulting mixture was purified by reverse flash chromatography with the following conditions to afford (S)-3-(3-bromophenyl)-2-hydroxypropanoic acid (170 mg, 28%) as an off-white solid. LCMS (ESI)=242.9, 245.0 [M−H]$^-$.

(S)-3-(3'-ethoxy-4'-(7-oxo-6,7-dihydro-3H-[1,2,3]triazolo[4,5-d]pyrimidin-5-yl)-[1,1'-biphenyl]-3-yl)-2-hydroxypropanoic acid was prepared from 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one using the procedures in Example 42. LCMS (ESI)=422.1 [M+H]$^+$. $^1$H NMR (300 MHz, DMSO-$d_6$) δ 7.98 (d, J=7.7 Hz, 1H), 7.67-7.56 (m, 2H), 7.39 (d, J=4.3 Hz, 3H), 7.29 (d, J=7.4 Hz, 1H), 4.31 (q, J=7.0 Hz, 2H), 4.12 (s, 1H), 3.14-3.07 (m, 1H), 2.91-2.82 (m, 1H), 1.43 (t, J=6.9 Hz, 3H).

Example 122: Synthesis of (S)-3-(3'-ethoxy-4'-(7-oxo-6,7-dihydro-3H-[1,2,3]triazolo[4,5-d]pyrimidin-5-yl)-[1,1'-biphenyl]-3-yl)-2-methoxypropanoic Acid (Compound 283)

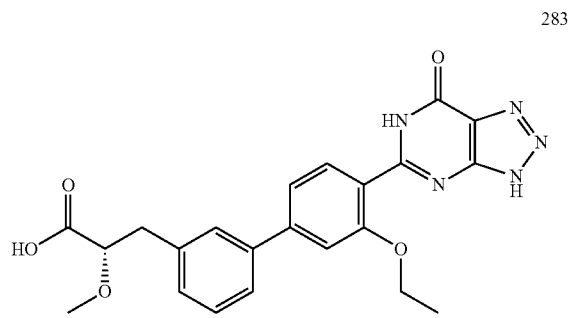 [SMILES: CCCC(Oc1cccc(-c2ccc(-c3nc4[nH]nnc4c(=O)[nH]3)c(OCC)c2)c1)C(=O)O]

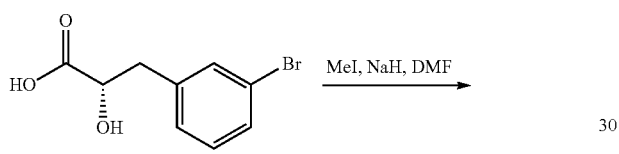

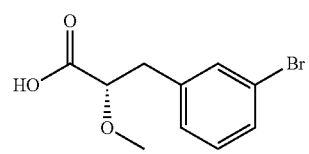

To a stirred solution of (S)-2-hydroxy-3-(3-methylphenyl)propanoic acid (100 mg, 0.555 mmol, 1.00 equiv) in DMF (1.0 mL) was added NaH (33.3 mg, 0.832 mmol, 1.50 equiv, 60%) in portions at rt. The resulting mixture was stirred for 20 min, then MeI (158 mg, 1.11 mmol, 2.00 equiv) was added. The resulting mixture was stirred for additional 5 h at rt. The mixture was purified by reverse-phase flash chromatography to afford (S)-2-methoxy-3-(3-methylphenyl)propanoic acid (70 mg, 65%) as a yellow solid. $^1$H NMR (300 MHz, DMSO-$d_6$) δ 12.78 (s, 1H), 7.47-7.35 (m, 2H), 7.31-7.19 (m, 2H), 3.97 (dd, J=7.8, 4.9 Hz, 1H), 2.99 (dd, J=14.1, 4.7 Hz, 1H), 2.88 (dd, J=14.1, 7.8 Hz, 1H).

(S)-3-(3'-Ethoxy-4'-(7-oxo-6,7-dihydro-3H-[1,2,3]triazolo[4,5-d]pyrimidin-5-yl)-[1,1'-biphenyl]-3-yl)-2-methoxypropanoic acid was prepared from 5-(2-ethoxy-4-(4,4,5,5-tetramethyl-1,3,2-dioxaborolan-2-yl)phenyl)-3-(4-methoxybenzyl)-3,6-dihydro-7H-[1,2,3]triazolo[4,5-d]pyrimidin-7-one using the procedures in Example 42. LCMS (ESI)=436.1 [M+H]$^+$. $^1$H NMR (300 MHz, DMSO-$d_6$) δ 8.04-7.95 (m, 1H), 7.61 (d, J=8.0 Hz, 2H), 7.46-7.33 (m, 3H), 7.28 (d, J=7.6 Hz, 1H), 4.32 (q, J=6.9 Hz, 2H), 4.00 (s, 1H), 3.25 (s, 3H), 3.10 (dd, J=14.0, 4.6 Hz, 1H), 2.97 (dd, J=14.2, 8.1 Hz, 1H), 1.43 (t, J=6.9 Hz, 3H).

Example 123: Synthesis of (R)-3-(3'-ethoxy-4'-(7-oxo-6,7-dihydro-3H-[1,2,3]triazolo[4,5-d]pyrimidin-5-yl)-[1,1'-biphenyl]-3-yl)-2-hydroxypropanoic Acid (Compound 284)

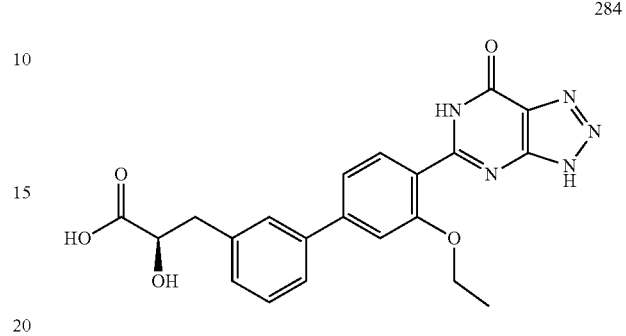

(R)-3-(3'-Ethoxy-4'-(7-oxo-6,7-dihydro-3H-[1,2,3]triazolo[4,5-d]pyrimidin-5-yl)-[1,1'-biphenyl]-3-yl)-2-hydroxypropanoic acid was prepared from (R)-3-(3-bromophenyl)-2-((tert-butoxycarbonyl)amino)propanoic acid using the procedures in Example 121.

Example 124: Synthesis of (R)-3-(3'-ethoxy-4'-(7-oxo-6,7-dihydro-3H-[1,2,3]triazolo[4,5-d]pyrimidin-5-yl)-[1,1'-biphenyl]-3-yl)-2-methoxypropanoic Acid (Compound 285)

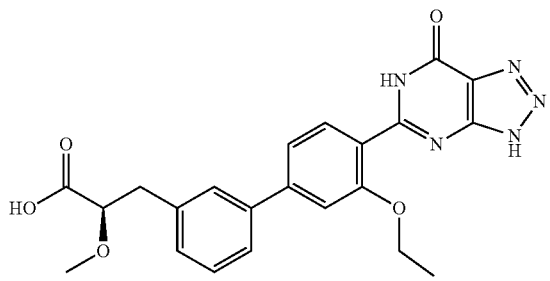

(R)-3-(3'-ethoxy-4'-(7-oxo-6,7-dihydro-3H-[1,2,3]triazolo[4,5-d]pyrimidin-5-yl)-[1,1'-biphenyl]-3-yl)-2-methoxypropanoic acid was prepared from (R)-2-hydroxy-3-(3-methylphenyl)propanoic acid using the procedures Example 122. LCMS (ESI)=436.1 [M+H]$^+$. $^1$H NMR (300 MHz, DMSO-$d_6$) δ 8.01 (d, J=8.1 Hz, 1H), 7.61 (d, J=9.2 Hz, 2H), 7.46-7.34 (m, 3H), 7.28 (d, J=7.5 Hz, 1H), 4.32 (q, J=6.9 Hz, 2H), 3.97 (s, 1H), 3.25 (s, 3H), 3.11 (d, J=14.1 Hz, 1H), 3.04-2.91 (m, 1H), 1.43 (t, J=6.9 Hz, 3H).

Example 125: Synthesis of 2'-nitro-4'-(7-oxo-6,7-dihydro-3H-[1,2,3]triazolo[4,5-d]pyrimidin-5-yl)-[1,1'-biphenyl]-4-carboxylic Acid (Compound 286)

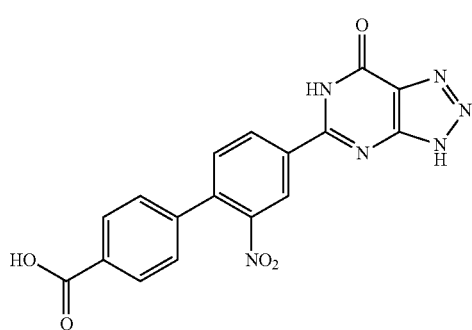

2'-Nitro-4'-(7-oxo-6,7-dihydro-3H-[1,2,3]triazolo[4,5-d]pyrimidin-5-yl)-[1,1'-biphenyl]-4-carboxylic acid was prepared from 4-bromo-3-nitrobenzaldehyde using the procedures in Examples 6 and 9. LCMS (ESI)=377.0 [M–H]⁻. ¹H NMR (300 MHz, DMSO-d₆) δ 8.77 (s, 1H), 8.53 (d, J=8.1 Hz, 1H), 8.02 (d, J=7.8 Hz, 2H), 7.71 (d, J=7.8 Hz, 1H), 7.48 (d, J=7.5 Hz, 2H), 1.24 (s, 1H).

Example 126: Synthesis of 2'-amino-4'-(7-oxo-6,7-dihydro-3H-[1,2,3]triazolo[4,5-d]pyrimidin-5-yl)-[1,1'-biphenyl]-4-carboxylic Acid (Compound 287)

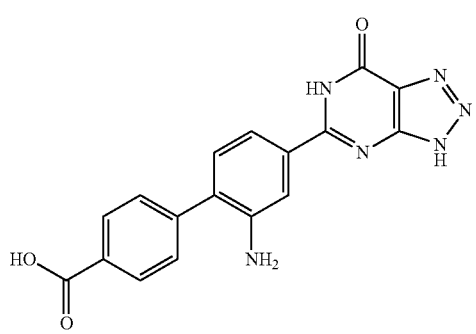

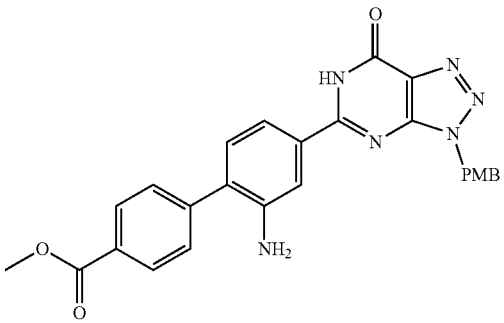

To a solution of methyl 4'-(3-(4-methoxybenzyl)-7-oxo-6,7-dihydro-3H-[1,2,3]triazolo[4,5-d]pyrimidin-5-yl)-2'-nitro-[1,1'-biphenyl]-4-carboxylate (800 mg, 1.56 mmol, 1.00 equiv) in MeOH (8 mL) and EA (8 mL) was added Pd/C (80.0 mg). H2 (g) was introduced in and the solution was stirred for 6 hr at rt under an H2 atmosphere. The solids were filtered and the resulting mixture was concentrated under reduced pressure to afford methyl 2'-amino-4'-(3-(4-methoxybenzyl)-7-oxo-6,7-dihydro-3H-[1,2,3]triazolo[4,5-d]pyrimidin-5-yl)-[1,1'-biphenyl]-4-carboxylate (500 mg, 66%) as a brown solid. LCMS (ESI)=483.2 [M+H]⁺.

2'-Amino-4'-(7-oxo-6,7-dihydro-3H-[1,2,3]triazolo[4,5-d]pyrimidin-5-yl)-[1,1'-biphenyl]-4-carboxylic acid was prepared using the procedures in Examples 6 and 9. LCMS (ESI)=349.0 [M+H]⁺. ¹H NMR (300 MHz, DMSO-d₆) δ 8.03 (d, J=8.4 Hz, 2H), 7.62-7.56 (m, 3H), 7.37 (dd, J=8.1, 1.8 Hz, 1H), 7.14 (d, J=8.1 Hz, 1H), 5.11 (s, 2H).

Example 127: Synthesis of 2'-(dimethylamino)-4'-(7-oxo-6,7-dihydro-3H-[1,2,3]triazolo[4,5-d]pyrimidin-5-yl)-[1,1'-biphenyl]-4-carboxylic Acid (Compound 288)

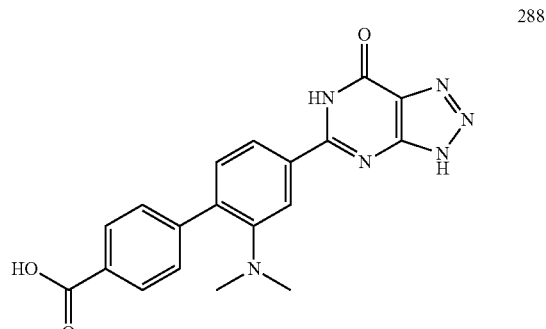

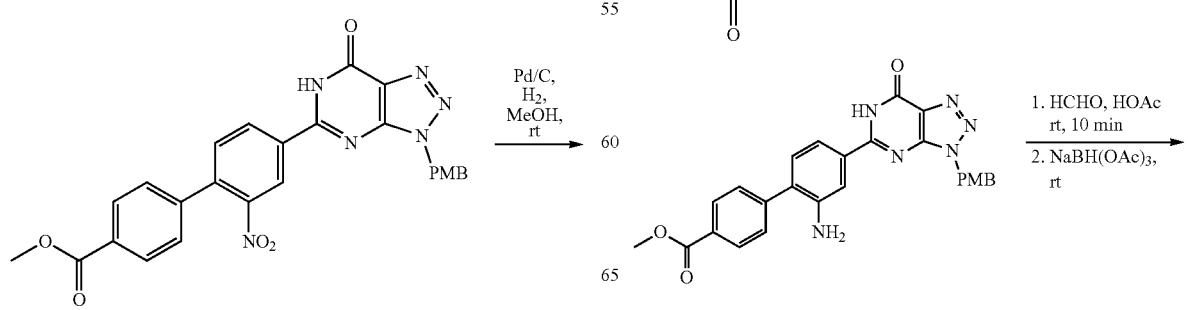

-continued

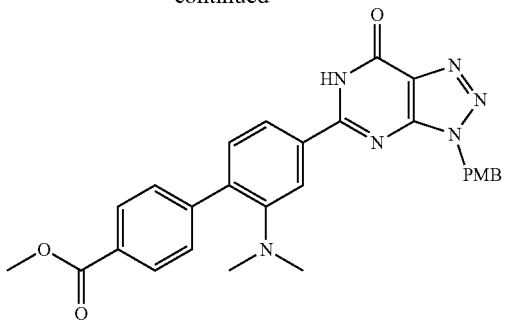

Into an 8-mL vial was placed methyl 2'-amino-4'-(3-(4-methoxybenzyl)-7-oxo-6,7-dihydro-3H-[1,2,3]triazolo[4,5-d]pyrimidin-5-yl)-[1,1'-biphenyl]-4-carboxylate (80 mg, 0.166 mmol, 1.00 equiv) and HCHO (0.30 ml, 37%) in HOAc (0.30 mL). The resulting solution was stirred for 10 min at room temperature. NaBH(OAc)₃ (13.3 mg, 1.66 mmol, 10.0 equiv) was added. The resulting solution was allowed to react, with stirring, for an additional 30 min at room temperature. The reaction was then quenched by the addition of 1 mL of water. The resulting solution was extracted with 3×5 mL of dichloromethane and the combined organic layer was dried over anhydrous sodium sulfate and concentrated to afford methyl 2'-(dimethylamino)-4'-(3-(4-methoxybenzyl)-7-oxo-6,7-dihydro-3H-[1,2,3]triazolo[4,5-d]pyrimidin-5-yl)-[1,1'-biphenyl]-4-carboxylate (50 mg) as a yellow solid. LCMS (ESI)=511.3 [M+H]⁺.

2'-(Dimethylamino)-4'-(7-oxo-6,7-dihydro-3H-[1,2,3]triazolo[4,5-d]pyrimidin-5-yl)-[1,1'-biphenyl]-4-carboxylic acid was prepared using the procedures in Examples 6 and 9. LCMS (ESI)=377.1 [M+H]⁺. ¹H NMR (300 MHz, DMSO-d₆) δ 8.02 (d, J=8.4 Hz, 2H), 7.80-7.78 (m, 2H), 7.73 (d, J=8.4 Hz, 2H), 7.34 (d, J=8.4 Hz, 1H), 2.58 (s, 6H).

Example 128: Synthesis of 2'-(cyclohexylamino)-4'-(7-oxo-6,7-dihydro-3H-[1,2,3]triazolo[4,5-d]pyrimidin-5-yl)-[1,1'-biphenyl]-4-carboxylic Acid (Compound 289)

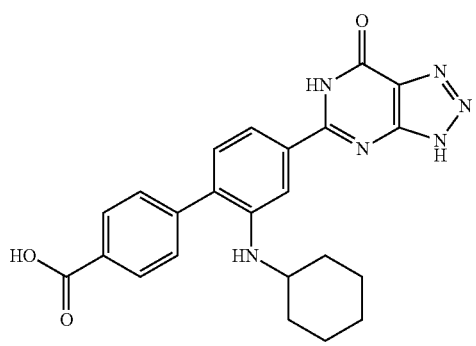

289

2'-(Cyclohexylamino)-4'-(7-oxo-6,7-dihydro-3H-[1,2,3]triazolo[4,5-d]pyrimidin-5-yl)-[1,1'-biphenyl]-4-carboxylic acid was prepared using the procedures in Example 127. LCMS (ESI)=431.2 [M+H]⁺. ¹H NMR (300 MHz, DMSO-d₆) δ 8.05 (d, J=8.4 Hz, 1H), 7.56 (d, J=8.1 Hz, 1H), 7.45 (dd, J=3.3, 1.5 Hz, 1H), 7.13 (d, J=8.4 Hz, 1H), 3.52-3.34 (m, 2H), 1.95-1.91 (m, 2H), 1.65-1.61 (m, 3H), 1.43-1.32 (m, 2H), 1.24-1.05 (m, 4H).

Example 129: Synthesis of 2'-(benzylamino)-4'-(7-oxo-6,7-dihydro-3H-[1,2,3]triazolo[4,5-d]pyrimidin-5-yl)-[1,1'-biphenyl]-4-carboxylic Acid (Compound 290)

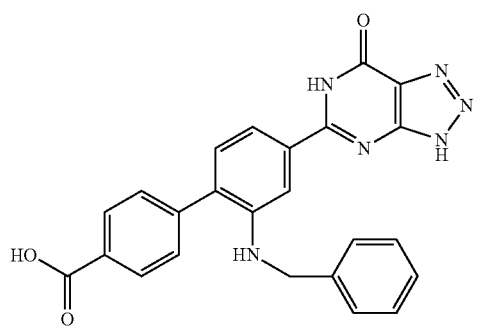

290

2'-(Benzylamino)-4'-(7-oxo-6,7-dihydro-3H-[1,2,3]triazolo[4,5-d]pyrimidin-5-yl)-[1,1'-biphenyl]-4-carboxylic acid was prepared using the procedures in Example 127. 8.06 (d, J=8.1 Hz, 2H), 7.62 (d, J=8.1 Hz, 2H), 7.43 (d, J=8.1 Hz, 1H), 7.38-7.29 (m, 5H), 7.17 (dd, J=19.8, 7.2 Hz, 1H), 5.51 (s, 1H), 4.47 (d, J=5.4 Hz, 1H).

Example 130: Synthesis of 4'-(7-oxo-6,7-dihydro-3H-[1,2,3]triazolo[4,5-d]pyrimidin-5-yl)-2'-(propylamino)-[1,1'-biphenyl]-4-carboxylic Acid (Compound 291)

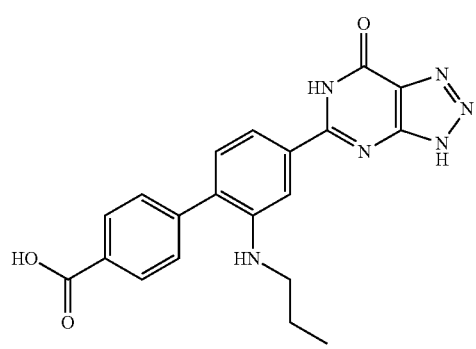

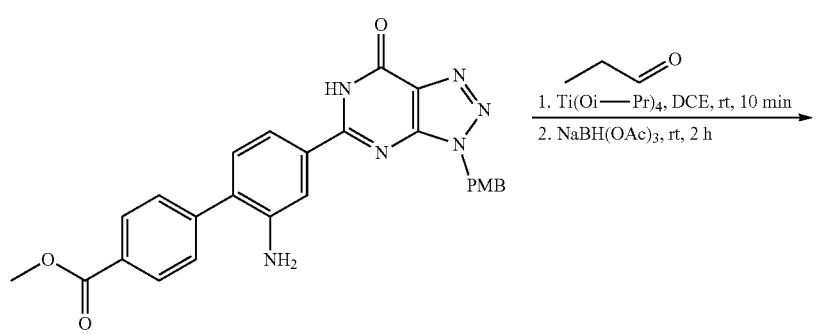

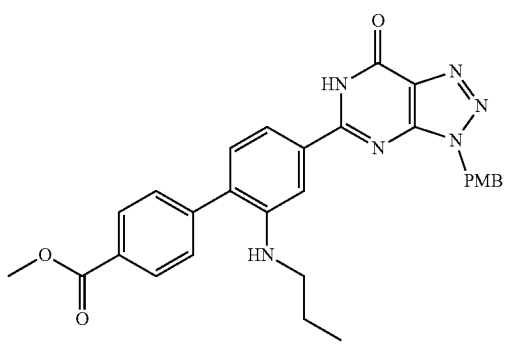

To a solution of methyl 2'-amino-4'-(3-(4-methoxybenzyl)-7-oxo-6,7-dihydro-3H-[1,2,3]triazolo[4,5-d]pyrimidin-5-yl)-[1,1'-biphenyl]-4-carboxylate (80.0 mg, 0.166 mmol, 1.00 equiv) and propionaldehyde (9.63 mg, 0.166 mmol, 1.00 equiv) in DCE (1.0 mL) was added Ti(OiPr)$_4$ (75.6 mg, 0.332 mmol, 2.00 equiv). The resulting solution was stirred for 10 min at rt. NaBH(OAc)$_3$ (87.8 mg, 0.415 mmol, 2.50 equiv) was added, and the mixture was stirred at rt for 2 h. The reaction was quenched with 5 mL of water and the solids removed by filtration. The filtrate was extracted with 3×5 mL of dichloromethane. The organic layers combined, dried over anhydrous sodium sulfate, and concentrated under reduced pressure This resulted in methyl 4'-(3-(4-methoxybenzyl)-7-oxo-6,7-dihydro-3H-[1,2,3]triazolo[4,5-d]pyrimidin-5-yl)-2'-(propylamino)-[1,1'-biphenyl]-4-carboxylate (90 mg) as a yellow solid. LCMS (ESI)=525.4 [M+H]$^+$.

4'-(7-Oxo-6,7-dihydro-3H-[1,2,3]triazolo[4,5-d]pyrimidin-5-yl)-2'-(propylamino)-[1,1'-biphenyl]-4-carboxylic acid was prepared using the procedures in Examples 6 and 9. LCMS (ESI)=391.1 [M+H]$^+$. $^1$H NMR (300 MHz, DMSO-d$_6$) δ 8.06-8.03 (m, 2H), 7.56 (d, J=8.1 Hz, 2H), 7.47-7.43 (m, 2H), 7.12 (d, J=8.1 Hz, 1H), 4.72 (s, 1H), 3.20-3.15 (m, 2H), 1.58 (q, J=7.2 Hz, 2H), 0.91 (t, J=7.2 Hz, 3H).

Example 131: Synthesis of 2'-(ethylamino)-4'-(7-oxo-6,7-dihydro-3H-[1,2,3]triazolo[4,5-d]pyrimidin-5-yl)-[1,1'-biphenyl]-4-carboxylic Acid (Compound 292)

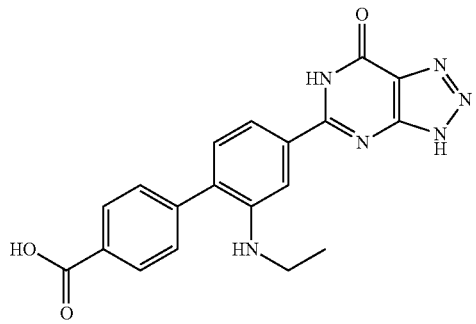

2'-(Ethylamino)-4'-(7-oxo-6,7-dihydro-3H-[1,2,3]triazolo[4,5-d]pyrimidin-5-yl)-[1,1'-biphenyl]-4-carboxylic acid was prepared using the procedures in Example 130. LCMS (ESI)=377.1 [M+H]$^+$. $^1$H NMR (300 MHz, DMSO-d$_6$) δ 8.01 (d, J=9 Hz, 2H), 7.51-7.43 (m, 4H), 7.10 (d, J=7.8 Hz, 1H), 4.70-4.60 (m, 1H), 3.23 (d, J=6.9 Hz, 2H), 1.15 (t, J=7.2 Hz, 3H).

Example 132: Synthesis of (S)-2-acetamido-3-(3'-ethoxy-4'-(7-oxo-6,7-dihydro-3H-[1,2,3]triazolo[4,5-d]pyrimidin-5-yl)-[1,1'-biphenyl]-3-yl)propanoic Acid (Compound 293)

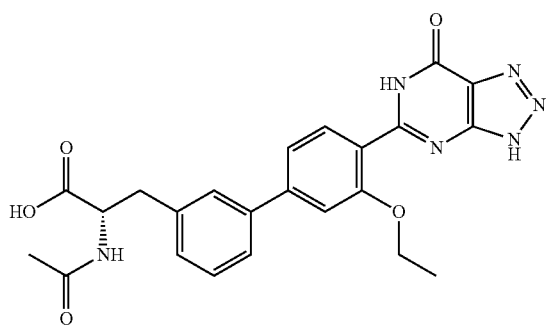

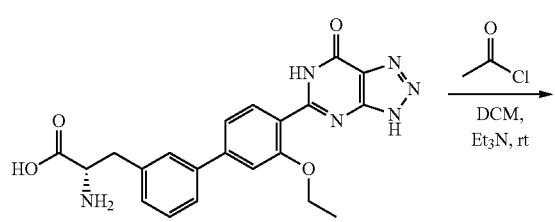

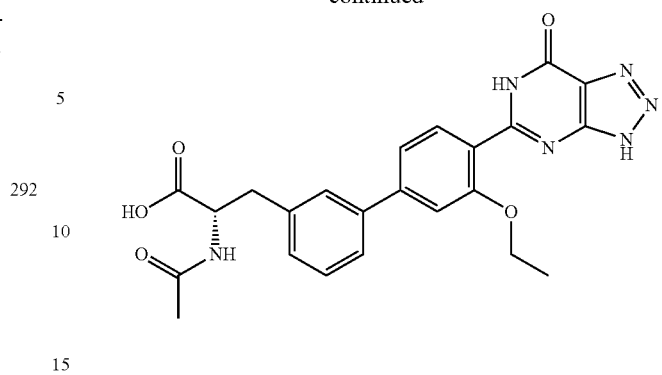

Into an 8-mL vial, was placed (S)-2-amino-3-(3'-ethoxy-4'-(7-oxo-6,7-dihydro-3H-[1,2,3]triazolo[4,5-d]pyrimidin-5-yl)-[1,1'-biphenyl]-3-yl)propanoic acid (15.0 mg, 0.036 mmol, 1.00 equiv) in DCM (1 mL). Et$_3$N (10.8 mg, 0.107 mmol, 3.00 equiv) was added, followed by the addition of acetyl chloride (2.8 mg, 0.036 mmol, 1.00 equiv) at 0° C. The resulting solution was stirred for 3 hr at rt. The resulting mixture was concentrated, and the crude product was purified by preparative HPLC to afford (S)-2-acetamido-3-(3'-ethoxy-4'-(7-oxo-6,7-dihydro-3H-[1,2,3]triazolo[4,5-d]pyrimidin-5-yl)-[1,1'-biphenyl]-3-yl)propanoic acid (3.5 mg, 21%). LCMS (ESI)=463.1 [M+H]$^+$. $^1$H NMR (300 MHz, DMSO-d$_6$) δ 11.46 (brs, 1H), 8.21 (d, J=7.5 Hz, 1H), 7.96 (d, J=8.1 Hz, 1H), 7.62 (d, J=9.0 Hz, 2H), 7.44-7.39 (m, 3H), 7.28 (d, J=7.5 Hz, 1H), 4.48-4.46 (m, 1H), 4.35-4.28 (m, 2H), 3.15-2.90 (m, 2H), 1.80 (s, 3H), 1.42 (t, J=6.6 Hz, 3H).

Example 133: Synthesis of ethyl 2-(3'-ethoxy-4'-(7-oxo-6,7-dihydro-3H-[1,2,3]triazolo[4,5-d]pyrimidin-5-yl)-[1,1'-biphenyl]-3-yl)acetate (Compound 294)

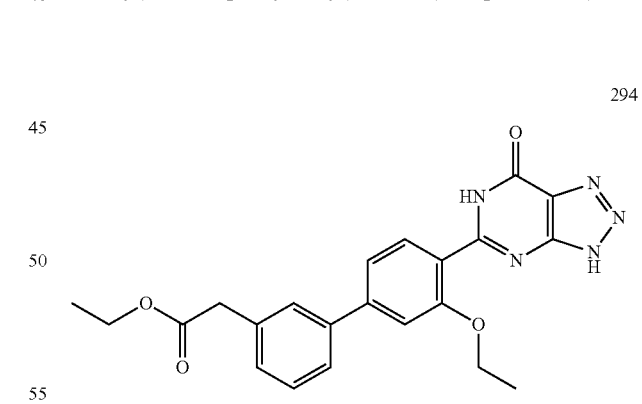

Ethyl 2-(3'-ethoxy-4'-(7-oxo-6,7-dihydro-3H-[1,2,3]triazolo[4,5-d]pyrimidin-5-yl)-[1,1'-biphenyl]-3-yl)acetate was prepared from 2-(3-bromophenyl)acetic acid using the procedures in Example 42. LCMS (ESI)=420.2 [M+H]$^+$. $^1$H NMR (300 MHz, DMSO-d$_6$) δ 7.94 (d, J=8.0 Hz, 1H), 7.64 (d, J=8.4 Hz, 2H), 7.45 (t, J=7.6 Hz, 1H), 7.41-7.33 (m, 2H), 7.29 (d, J=7.6 Hz, 1H), 4.27 (q, J=6.9 Hz, 2H), 4.07 (q, J=7.1 Hz, 2H), 3.73 (s, 2H), 1.38 (t, J=6.9 Hz, 3H), 1.17 (t, J=7.1 Hz, 3H).

Example 134: Synthesis of 2-(3'-ethoxy-4'-(7-oxo-6,7-dihydro-3H-[1,2,3]triazolo[4,5-d]pyrimidin-5-yl)-[1,1'-biphenyl]-3-yl)acetic Acid (Compound 295)

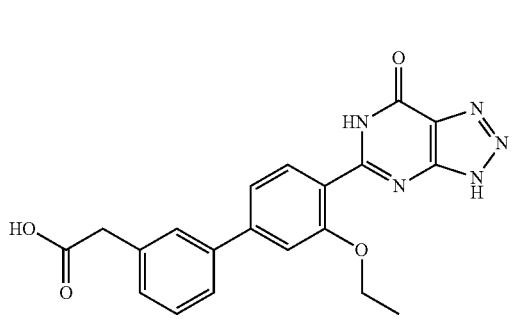

295

2-(3'-Ethoxy-4'-(7-oxo-6,7-dihydro-3H-[1,2,3]triazolo[4,5-d]pyrimidin-5-yl)-[1,1'-biphenyl]-3-yl)acetic acid was prepared using the procedures in Examples 42 and 9. LCMS (ESI)=392.1 [M+H]+. 1H NMR (300 MHz, DMSO-d6) δ 8.00 (d, J=8.5 Hz, 1H), 7.71-7.61 (m, 2H), 7.44 (t, J=7.6 Hz, 1H), 7.42-7.35 (m, 2H), 7.32 (d, J=7.7 Hz, 1H), 4.32 (q, J=6.9 Hz, 2H), 1.43 (t, J=6.9 Hz, 3H).

Example 135: Synthesis of ethyl 2-(3'-ethoxy-4'-(7-oxo-6,7-dihydro-3H-[1,2,3]triazolo[4,5-d]pyrimidin-5-yl)-[1,1'-biphenyl]-3-yl)propanoate (Compound 296)

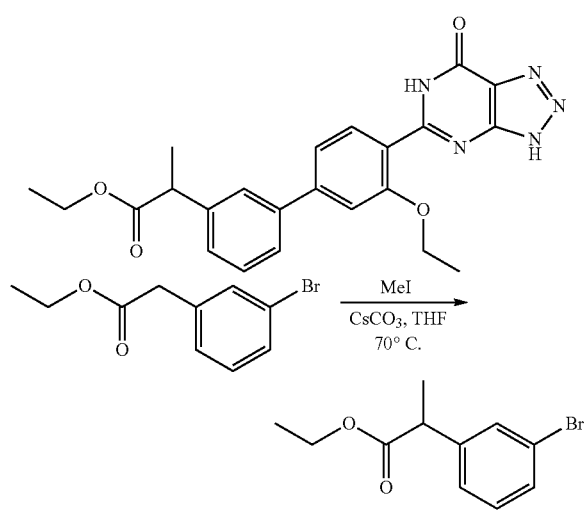

296

Into a 40 mL vial was added ethyl 2-(3-bromophenyl)acetate (500 mg, 2.06 mmol, 1.00 equiv), THF (10 ml), MeI (1.46 mg, 10.3 mmol, 5.00 equiv), and Cs2CO3 (3.35 g, 10.3 mmol, 5.0 eq) at rt. The mixture was stirred for 3 hr at 60° C. The resulting mixture was diluted with water (40 ml) and then extracted with Et2O (3×40 ml). The combined organic layers were washed with brine (2×40 ml), dried over anhydrous Na2SO4, filtered and concentrated under reduced pressure to afford ethyl 2-(3-bromophenyl)propanoate (400 mg, 68%) as a yellow oil. 1H NMR (300 MHz, DMSO-d6) δ 7.53-7.40 (m, 1H), 7.38 (s, 1H), 7.36-7.24 (m, 2H), 4.06 (qq, J=7.2, 3.8 Hz, 2H), 3.82 (q, J=7.1 Hz, 1H), 1.38 (d, J=7.2 Hz, 3H), 1.13 (t, J=7.1 Hz, 3H).

Ethyl 2-(3'-ethoxy-4'-(7-oxo-6,7-dihydro-3H-[1,2,3]triazolo[4,5-d]pyrimidin-5-yl)-[1,1'-biphenyl]-3-yl)propanoate was prepared using the procedures in Example 42.

Example 136: Synthesis of 2-(3'-ethoxy-4'-(7-oxo-6,7-dihydro-3H-[1,2,3]triazolo[4,5-d]pyrimidin-5-yl)-[1,1'-biphenyl]-3-yl)propanoic Acid (Compound 297)

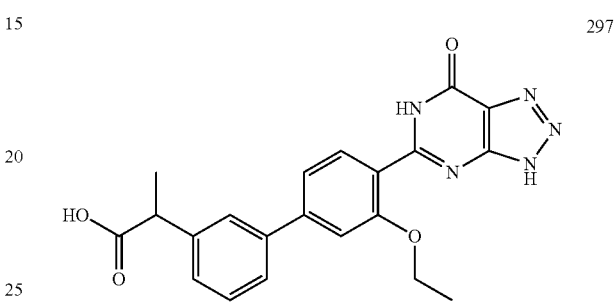

297

2-(3'-Ethoxy-4'-(7-oxo-6,7-dihydro-3H-[1,2,3]triazolo[4,5-d]pyrimidin-5-yl)-[1,1'-biphenyl]-3-yl)propanoic acid was prepared from ethyl 2-(3-bromophenyl)propanoate using the procedures in Example 42 and 9. LCMS (ESI)=406.2 [M+H]+. 1H NMR (300 MHz, DMSO-d6) δ 11.42 (s, 1H), 7.97 (d, J=8.5 Hz, 1H), 7.70-7.61 (m, 2H), 7.46 (t, J=7.6 Hz, 1H), 7.41-7.31 (m, 3H), 4.32 (q, J=6.9 Hz, 2H), 3.79 (q, J=7.1 Hz, 1H), 1.49-1.37 (m, 6H).

Example 137: Synthesis of 2-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoic Acid (Compound 298)

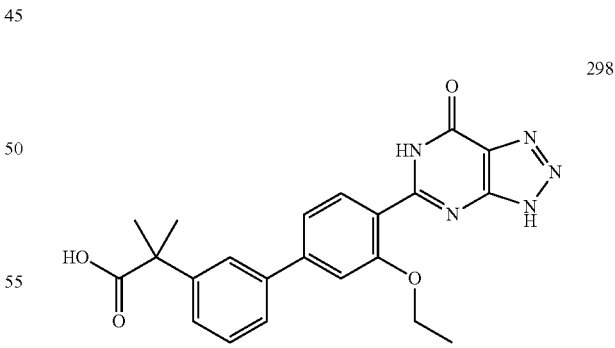

298

2-(3'-Ethoxy-4'-(7-oxo-6,7-dihydro-3H-[1,2,3]triazolo[4,5-d]pyrimidin-5-yl)-[1,1'-biphenyl]-3-yl)-2-methylpropanoic acid was prepared from methyl 2-(3-bromophenyl)-2-methylpropanoate using the procedures in Examples 42 and 9. LCMS (ESI)=420.2 [M+H]+. 1H NMR (300 MHz, DMSO-d6) δ 7.98 (d, J=8.4 Hz, 1H), 7.69-7.59 (m, 2H), 7.47 (t, J=7.5 Hz, 1H), 7.45-7.32 (m, 3H), 4.31 (q, J=6.9 Hz, 2H), 1.56 (s, 6H), 1.42 (t, J=6.9 Hz, 3H).

Example 138: Synthesis of (E)-3-(3'-ethoxy-4'-(7-oxo-6,7-dihydro-3H-[1,2,3]triazolo[4,5-d]pyrimidin-5-yl)-4-(2-(pyrrolidin-1-yl)ethoxy)-[1,1'-biphenyl]-3-yl)-2-methylacrylic Acid (Compound 299)

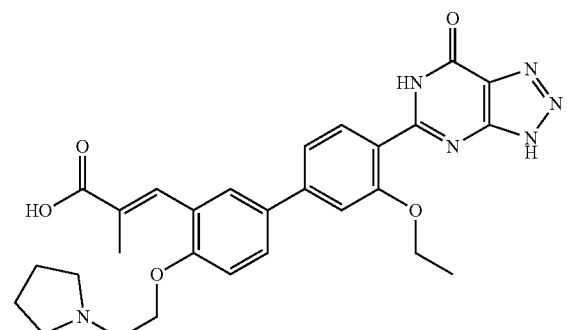

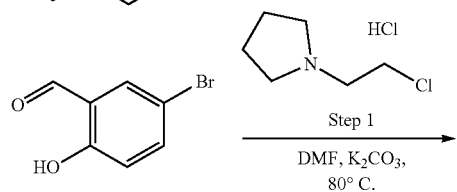

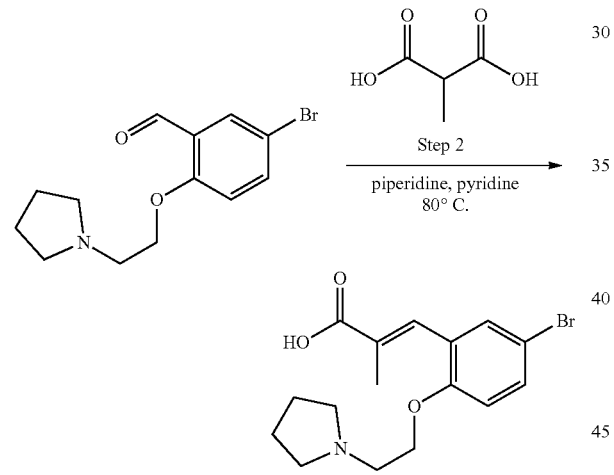

Step 1: Into a 40 mL vial were added 5-bromo-2-hydroxybenzaldehyde (2.00 g, 9.95 mmol, 1.00 equiv), 1-(2-chloroethyl)pyrrolidine hydrochloride (1.33 g, 9.95 mmol, 1.0 equiv), $K_2CO_3$ (2.75 g, 19.9 mmol, 2.00 equiv), and DMF (20 mL) at rt. The resulting mixture was stirred for 2 hr at 80° C. The mixture was allowed to cool down to rt, then the resulting mixture was diluted with water (40 mL). The mixture was extracted with $Et_2O$ (3×30 mL). The combined organic layers were washed with dried over anhydrous $Na_2SO_4$, filtered and concentrated under reduced pressure. The residue was purified by silica gel column chromatography to afford 5-bromo-2-(2-(pyrrolidin-1-yl)ethoxy)benzaldehyde (700 mg, 22%) as a yellow oil. $^1H$ NMR (300 MHz, DMSO-$d_6$) δ 10.41 (s, 1H), 7.91 (d, J=2.6 Hz, 1H), 7.61 (dd, J=8.8, 2.7 Hz, 1H), 6.90 (d, J=8.9 Hz, 1H), 4.22 (t, J=5.8 Hz, 2H), 3.01-2.93 (m, 2H), 2.91 (s, 1H), 2.73-2.55 (m, J=3.4, 2.2 Hz, 4H), 1.90-1.72 (m, J=3.8, 3.2 Hz, 4H).

Step 2: Into a 40 mL vial were added 5-bromo-2-(pyrrolidin-1-yl)ethoxy)benzaldehyde (700 mg, 2.35 mmol, 1.00 equiv), methylmalonic acid (333 mg, 2.82 mmol, 1.2 equiv), piperidine (399 mg, 4.69 mmol, 2.0 equiv), and pyridine (15 mL) at rt. The resulting mixture was stirred for 10 hr at 80° C. The residue was purified by reverse-phase flash chromatography to afford (E)-3-(5-bromo-2-(2-(pyrrolidin-1-yl)ethoxy)phenyl)-2-methylacrylic acid (400 mg, 46%) as a yellow solid. $^1H$ NMR (300 MHz, DMSO-d6) δ 7.63-7.56 (m, 1H), 7.53-7.35 (m, 2H), 7.05 (d, J=8.8 Hz, 1H), 4.12 (t, J=5.8 Hz, 2H), 2.82 (t, J=5.8 Hz, 2H), 2.55 (t, J=5.8 Hz, 4H), 1.92 (d, J=1.5 Hz, 3H), 1.67 (h, J=3.1 Hz, 4H).

(E)-3-(3'-Ethoxy-4'-(7-oxo-6,7-dihydro-3H-[1,2,3]triazolo[4,5-d]pyrimidin-5-yl)-[1,1'-biphenyl]-3-yl)-2-methylacrylic acid was prepared using the procedures in Example 42. LCMS (ESI)=531.4 [M+H]$^+$. $^1H$ NMR (300 MHz, DMSO-d6) δ 11.53 (s, 1H), 7.94 (d, J=8.4 Hz, 1H), 7.80-7.67 (m, 3H), 7.36 (d, J=6.8 Hz, 2H), 7.21 (d, J=8.7 Hz, 1H), 4.34 (d, J=6.8 Hz, 1H), 4.26 (dd, J=13.7, 8.0 Hz, 3H), 2.99 (t, J=5.7 Hz, 2H), 2.72 (d, J=6.0 Hz, 4H), 2.01 (d, J=1.5 Hz, 3H), 1.74 (p, J=3.0 Hz, 4H), 1.41 (t, J=6.9 Hz, 3H

Example 139: Synthesis of 3-(3'-ethoxy-4'-(7-oxo-6,7-dihydro-3H-[1,2,3]triazolo[4,5-d]pyrimidin-5-yl)-4-(2-(pyrrolidin-1-yl)ethoxy)-[1,1'-biphenyl]-3-yl)-2-methylpropanoic Acid (Compound 300)

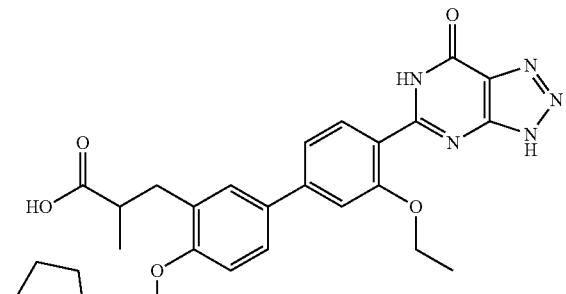

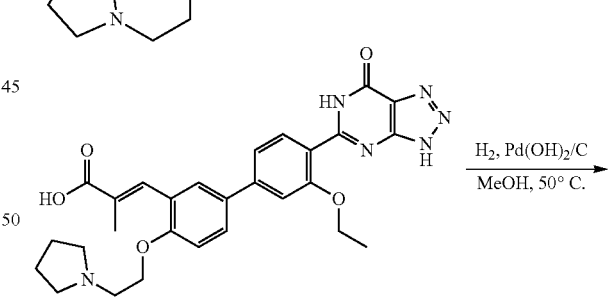

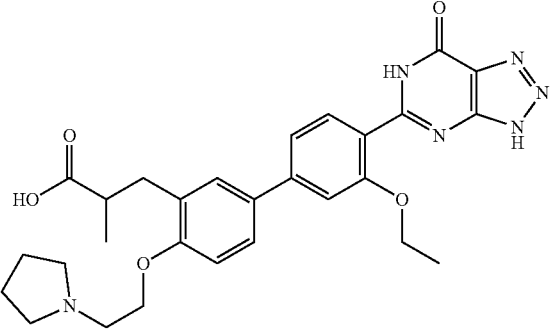

Into a 100 mL round bottom flask were added (E)-3-(3'-ethoxy-4'-(7-oxo-6,7-dihydro-3H-[1,2,3]triazolo[4,5-d]pyrimidin-5-yl)-4-(2-(pyrrolidin-1-yl)ethoxy)-[1,1'-biphenyl]-3-yl)-2-methylacrylic acid (200 mg, 0.377 mmol, 1.00 equiv), Pd(OH)$_2$/C (80.0 mg, 0.752 mmol, 1.99 equiv), and MeOH (20 mL) at rt. The gas was replaced with H2 three times. The resulting mixture was stirred for 2 hr at 50° C. under H2. The resulting mixture was filtered and the filter cake was washed with MeOH (3×10 mL). The filtrate was concentrated under reduced pressure. The crude product was purified by preparative HPLC to afford 3-(3'-ethoxy-4'-(7-oxo-6,7-dihydro-3H-[1,2,3]triazolo[4,5-d]pyrimidin-5-yl)-4-(2-(pyrrolidin-1-yl)ethoxy)-[1,1'-biphenyl]-3-yl)-2-methylpropanoic acid (24.8 mg, 12.0%) as a white solid. LCMS (ESI)=533.3 [M+H]$^+$. $^1$H NMR (300 MHz, DMSO-d6) δ 11.32 (s, 1H), 7.97 (d, J=8.5 Hz, 1H), 7.65-7.51 (m, 2H), 7.34 (dt, J=4.3, 2.1 Hz, 2H), 7.05 (d, J=8.6 Hz, 1H), 4.32 (q, J=6.9 Hz, 2H), 4.16 (t, J=5.4 Hz, 2H), 2.96 (dt, J=14.0, 6.1 Hz, 3H), 2.72 (h, J=6.9 Hz, 6H), 1.77 (s, 4H), 1.82-1.71 (m, 1H), 1.43 (t, J=6.9 Hz, 3H), 1.05 (d, J=6.6 Hz, 3H).

Example 140: Synthesis of (E)-3-(3'-ethoxy-4-isopropoxy-4'-(7-oxo-6,7-dihydro-3H-[1,2,3]triazolo[4,5-d]pyrimidin-5-yl)-[1,1'-biphenyl]-3-yl)-2-methylacrylic Acid (Compound 301)

Example 141: Synthesis of 3-(3'-ethoxy-4-isopropoxy-4'-(7-oxo-6,7-dihydro-3H-[1,2,3]triazolo[4,5-d]pyrimidin-5-yl)-[1,1'-biphenyl]-3-yl)-2-methylpropanoic Acid (Compound 302)

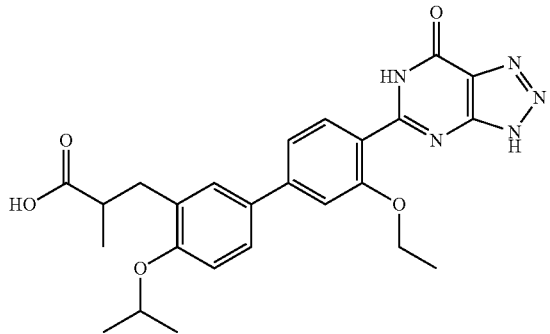

3-(3'-Ethoxy-4-isopropoxy-4'-(7-oxo-6,7-dihydro-3H-[1,2,3]triazolo[4,5-d]pyrimidin-5-yl)-[1,1'-biphenyl]-3-yl)-2-methylpropanoic acid was prepared using the procedures in Example 139. LCMS (ESI)=478.2 [M+H]$^+$.

Example 142: Synthesis of 3-(3'-ethoxy-4'-(7-oxo-6,7-dihydro-3H-[1,2,3]triazolo[4,5-d]pyrimidin-5-yl)-[1,1'-biphenyl]-3-yl)-3-methylbutanoic Acid (Compound 303) and 3-(3'-ethoxy-4'-(7-oxo-6,7-dihydro-3H-[1,2,3]triazolo[4,5-d]pyrimidin-5-yl)-[1,1'-biphenyl]-4-yl)-3-methylbutanoic Acid (Compound 304)

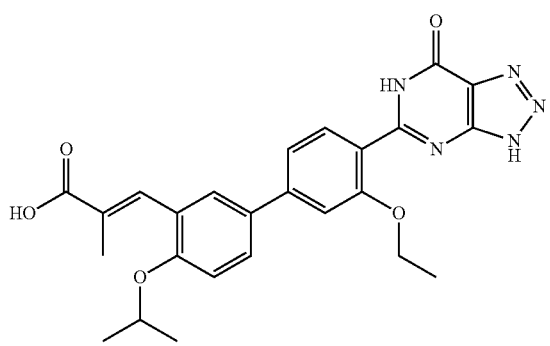

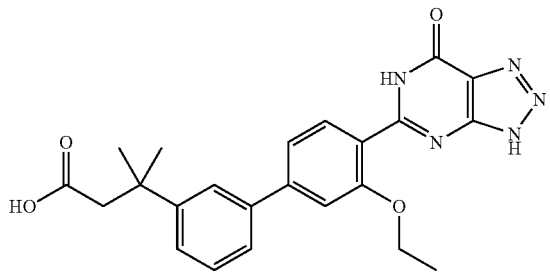

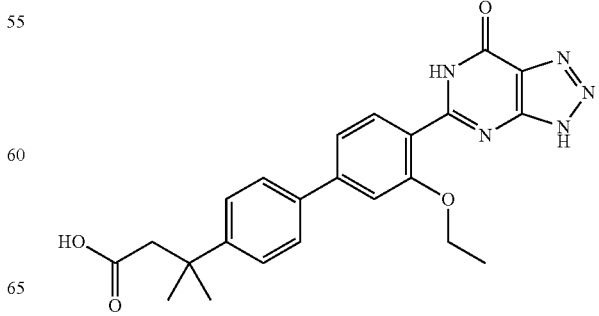

(E)-3-(3'-Ethoxy-4-isopropoxy-4'-(7-oxo-6,7-dihydro-3H-[1,2,3]triazolo[4,5-d]pyrimidin-5-yl)-[1,1'-biphenyl]-3-yl)-2-methylacrylic acid was prepared from iodopropane using the procedures in Example 138. LCMS (ESI)=476.1 [M+H]$^+$.

Example 143: Synthesis of 5-(4-(3,3-dimethyl-2-oxochroman-6-yl)-2-ethoxyphenyl)-3,6-dihydro-7H-[1,2,3]triazolo[4,5-d]pyrimidin-7-one (Compound 305)

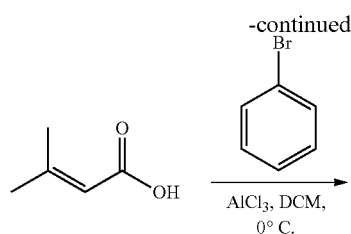

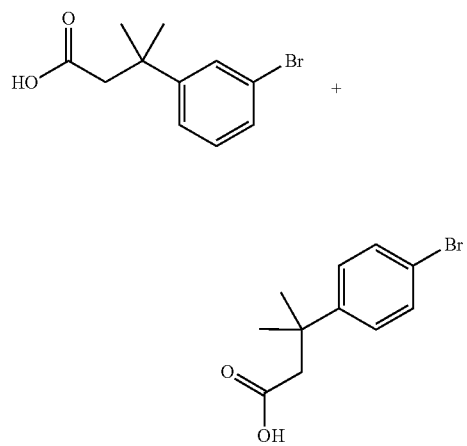

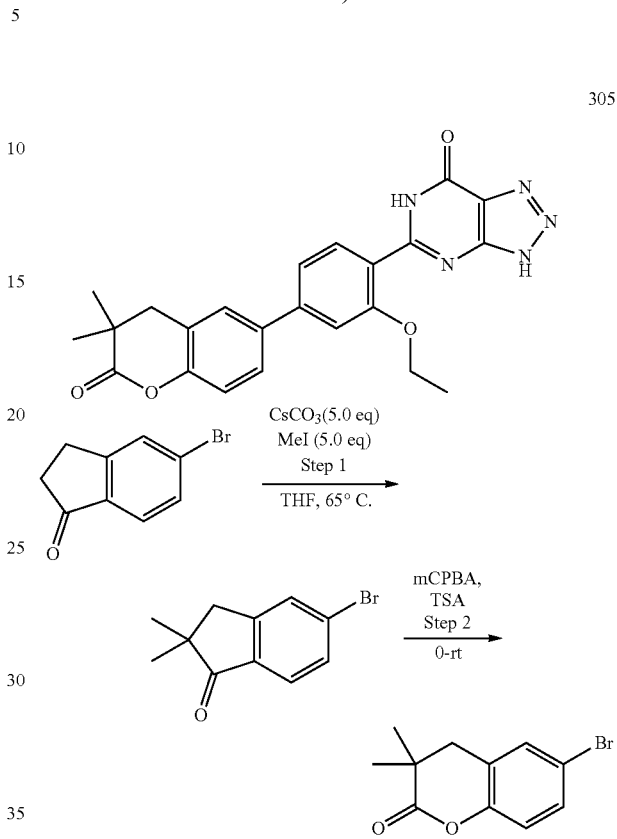

Into an 8 mL vial was added 3-methylbut-2-enoic acid (200 mg, 2.00 mmol, 1.00 equiv), bromobenzene (627 mg, 4.00 mmol, 2.0 equiv) and DCM (2.0 mL). To the mixture was added AlCl$_3$ (799 mg, 5.99 mmol, 3.0 equiv) in portions over 2 min at 0° C. The resulting mixture was stirred for additional 1 hr at 0° C. The reaction was quenched by the addition of water (40 mL) and conc. HCl (4 mL) at 0° C. The mixture was extracted with DCM (3×40 mL). The combined organic layers were dried over anhydrous Na$_2$SO$_4$, filtered, and concentrated under reduced pressure. The residue was purified by reverse flash chromatography to afford a mixture (280 mg) of 3-(3-bromophenyl)-3-methylbutanoic acid and 3-(4-bromophenyl)-3-methylbutanoic acid as a white oil.

3-(3'-Ethoxy-4'-(7-oxo-6,7-dihydro-3H-[1,2,3]triazolo[4,5-d]pyrimidin-5-yl)-[1,1'-biphenyl]-3-yl)-3-methylbutanoic acid and 3-(3'-ethoxy-4'-(7-oxo-6,7-dihydro-3H-[1,2,3]triazolo[4,5-d]pyrimidin-5-yl)-[1,1'-biphenyl]-4-yl)-3-methylbutanoic acid were prepared using the procedures in Example 42 by carrying on the mixture of compounds and purifying the two final compounds after the final step.

Data for 3-(3'-ethoxy-4'-(7-oxo-6,7-dihydro-3H-[1,2,3]triazolo[4,5-d]pyrimidin-5-yl)-[1,1'-biphenyl]-3-yl)-3-methylbutanoic acid: LCMS (ESI)=434.3 [M+H]$^+$. $^1$H NMR (300 MHz, DMSO-d$_6$) δ 8.03 (d, J=7.9 Hz, 1H), 7.72 (s, 1H), 7.56 (d, J=6.3 Hz, 1H), 7.47-7.34 (m, 4H), 4.33 (q, J=7.0 Hz, 2H), 3.30 (s, 1H), 2.67 (s, 2H), 1.46 (s, 6H), 1.43 (d, J=6.9 Hz, 2H).

Data for 3-(3'-ethoxy-4'-(7-oxo-6,7-dihydro-3H-[1,2,3]triazolo[4,5-d]pyrimidin-5-yl)-[1,1'-biphenyl]-4-yl)-3-methylbutanoic acid: LCMS (ESI)=434.3 [M+H]$^+$. $^1$H NMR (300 MHz, DMSO-d$_6$) δ 8.00 (d, J=8.5 Hz, 1H), 7.70 (d, J=8.4 Hz, 2H), 7.51 (d, J=8.4 Hz, 2H), 7.39 (dt, J=4.3, 2.1 Hz, 2H), 4.32 (q, J=6.9 Hz, 2H), 2.64 (s, 2H), 1.51-1.37 (m, 9H).

Step 1: Into an 8 mL vial was added 5-bromo-2,3-dihydroinden-1-one (1.00 g, 4.73 mmol, 1.00 equiv) and THF (15 mL), Cs$_2$CO$_3$ (7.72 g, 23.7 mmol, 5.0 equiv), MeI (3.36 g, 23.7 mmol, 5.0 equiv) at rt. The resulting mixture was stirred for 12 hr at 65° C. The mixture was allowed to cool down to rt. The resulting mixture was filtered and the filter cake was washed with THF (3×40 ml). The filtrate was concentrated under reduced pressure to afford 5-bromo-2,2-dimethyl-3H-inden-1-one (1.0 g, 77.0%) as a yellow oil. $^1$H NMR (300 MHz, DMSO-d$_6$) δ 7.62 (dd, J=6.1, 0.7 Hz, 1H), 7.60 (s, 1H), 7.51 (ddt, J=8.1, 1.7, 0.8 Hz, 1H), 2.98 (d, J=1.2 Hz, 2H), 1.23 (s, 6H).

Step 2: To a stirred solution of 5-bromo-2,2-dimethyl-3H-inden-1-one (1.00 g, 4 mmol, 1.00 equiv) and mCPBA (1.44 g, 8 mmol, 2.0 equiv) in DCM (25 mL) were added CF$_3$SO$_3$H (1.26 g, 8 mmol, 2.01 equiv) in portions at 0° C. The resulting mixture was stirred for 12 hr at rt and the mixture was concentrated under reduced pressure. The residue was purified by silica gel column chromatography to afford 6-bromo-3,3-dimethyl-4H-1-benzopyran-2-one (250 mg, 22.2%) as a yellow solid. $^1$H NMR (300 MHz, DMSO-d$_6$) δ 7.57-7.41 (m, 2H), 7.03 (d, J=8.5 Hz, 1H), 2.94 (s, 2H), 1.18 (s, 6H).

5-(4-(3,3-Dimethyl-2-oxochroman-6-yl)-2-ethoxyphenyl)-3,6-dihydro-7H-[1,2,3]triazolo[4,5-d]pyrimidin-7-one was prepared using the procedures in Example 42. LCMS (ESI)=432.1 [M+H]$^+$. $^1$H NMR (300 MHz, DMSO-d6) δ 12.23 (s, 1H), 7.88 (dd, J=7.9, 4.1 Hz, 1H), 7.77-7.68 (m, 2H), 7.44 (s, 2H), 7.41 (d, J=1.6 Hz, 0H), 7.24-7.15 (m, 1H), 4.32 (q, J=6.9 Hz, 2H), 3.04 (s, 2H), 1.40 (t, J=6.9 Hz, 3H), 1.24 (s, 6H).

Example 144: Synthesis of rac-cis-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic Acid (Compound 306)

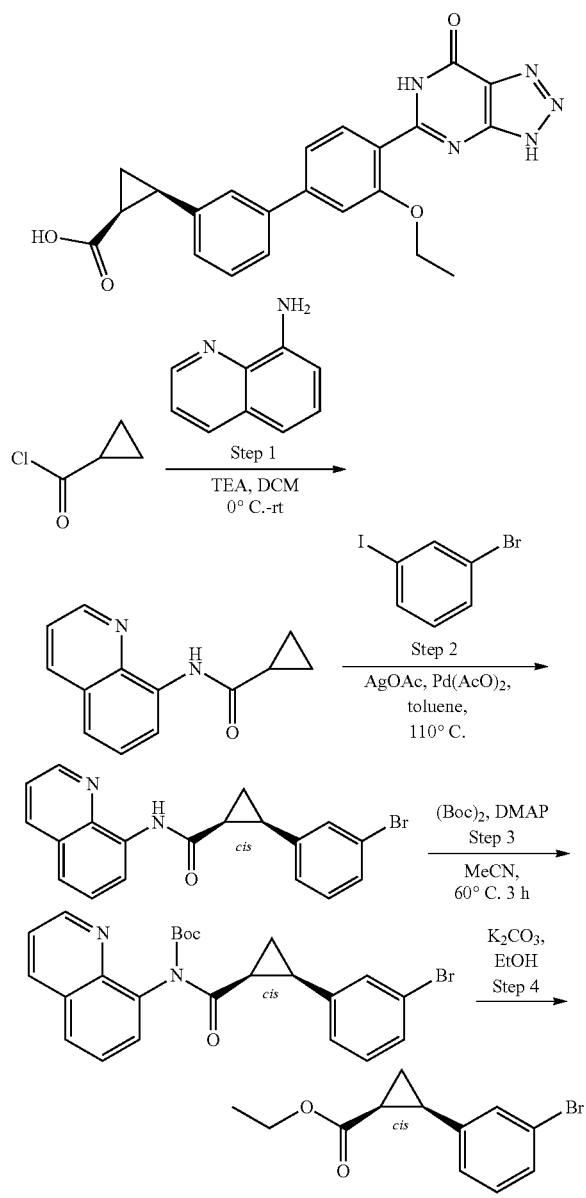

Step 1: To a stirred solution of 8-aminoquinoline (3.00 g, 20.8 mmol, 1.00 equiv) and TEA (3.16 g, 31.2 mmol, 1.50 equiv) in DCM (30 mL) was added cyclopropanecarbonyl chloride (2.39 g, 22.9 mmol, 1.10 equiv) dropwise at 0° C. under $N_2$. The mixture was stirred for 2 hr at rt, then the reaction was quenched by the addition of water (100 mL). The resulting mixture was extracted with DCM (3×30 mL). The combined organic layers were washed with brine (50 mL), dried over anhydrous $Na_2SO_4$, and concentrated under reduced pressure. The residue was purified by silica gel column chromatography to afford N-(quinolin-8-yl)cyclopropanecarboxamide (4.2 g, 95%) as a yellow oil. $^1$H NMR (300 MHz, CDCl$_3$) δ 10.04 (s, 1H), 8.84 (dd, J=4.2, 1.7 Hz, 1H), 8.77 (dd, J=7.1, 1.9 Hz, 1H), 8.19 (dd, J=8.3, 1.7 Hz, 1H), 7.61-7.43 (m, 3H), 1.84 (tt, J=7.8, 4.5 Hz, 1H), 1.27-1.14 (m, 2H), 0.94 (dt, J=7.9, 3.4 Hz, 2H).

Step 2: To a stirred solution of N-(quinolin-8-yl)cyclopropanecarboxamide (1.00 g, 4.71 mmol, 1.00 equiv) and 1-bromo-3-iodobenzene (1.33 g, 4.71 mmol, 1.00 equiv) in toluene (10 mL) was added silver acetate (865 mg, 5.18 mmol, 1.10 equiv) and Pd(OAc)$_2$ (0.05 g, 0.24 mmol, 0.05 equiv) at rt under $N_2$ atmosphere. The resulting mixture was stirred for 16 hr at 110° C. After cooling to rt, the mixture was filtered and the filter cake was washed with EA (3×10 mL). The filtrate was concentrated under reduced pressure. The residue was purified by silica gel column chromatography to afford rac-2-(3-bromophenyl)-N-(quinolin-8-yl)cyclopropane-1-carboxamide (900 mg, 52%) as a yellow oil. $^1$H NMR (300 MHz, CDCl$_3$) δ 9.94 (s, 1H), 8.84 (dd, J=4.3, 1.7 Hz, 1H), 8.67-8.50 (m, 1H), 8.17 (dd, J=8.3, 1.7 Hz, 1H), 7.54 (d, J=2.0 Hz, 1H), 7.54-7.39 (m, 3H), 7.37-7.23 (m, 2H), 7.16-7.02 (m, 1H), 2.62 (q, J=8.4 Hz, 1H), 2.36 (td, J=8.5, 5.6 Hz, 1H), 1.90 (dt, J=7.5, 5.4 Hz, 1H), 1.47 (ddd, J=8.7, 7.9, 5.1 Hz, 1H).

Step 3: To a stirred solution of rac-cis-2-(3-bromophenyl)-N-(quinolin-8-yl)cyclopropane-1-carboxamide (900 mg, 2.45 mmol, 1.00 equiv) and di-tert-butyl dicarbonate (1281 mg, 7.35 mmol, 3.00 equiv) in MeCN (10 mL) was added DMAP (29.9 mg, 0.245 mmol, 0.10 equiv) at rt. The resulting mixture was stirred for 3 h at 60° C. After cooling, the resulting mixture was concentrated under reduced pressure. The residue was purified by silica gel column chromatography to afford rac-tert-butyl cis-2-(3-bromophenyl)cyclopropane-1-carbonyl)(quinolin-8-yl)carbamate (1.2 g) as a yellow oil. LCMS (ESI)=467.1, 469.1 [M+H]$^+$.

Step 4: A solution of rac-tert-butyl cis-2-(3-bromophenyl)cyclopropane-1-carbonyl)(quinolin-8-yl)carbamate (1.00 g, 2.14 mmol, 1.00 equiv) and $K_2CO_3$ (0.59 g, 4.28 mmol, 2.00 equiv) in EtOH (10 mL) was stirred for 16 h at 80° C. The mixture was allowed to cool down to room temperature. The resulting mixture was filtered, the filter cake was washed with DCM (2×10 mL). The filtrate was concentrated under reduced pressure. The residue was purified by silica gel column chromatography to afford rac-ethyl cis-2-(3-bromophenyl)cyclopropane-1-carboxylate (500 mg, 87%) as a light yellow oil. $^1$H NMR (300 MHz, CDCl$_3$) δ 7.44 (d, J=2.1 Hz, 1H), 7.35 (dt, J=7.6, 1.8 Hz, 1H), 7.26-7.10 (m, 2H), 3.94 (q, J=7.1 Hz, 2H), 2.56 (q, J=8.7 Hz, 1H), 2.11 (ddd, J=9.3, 7.9, 5.7 Hz, 1H), 1.71 (dt, J=7.4, 5.4 Hz, 1H), 1.43-1.28 (m, 1H), 1.04 (t, J=7.1 Hz, 3H).

Rac-cis-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic acid was prepared using the procedures in Examples 58 and 9. LCMS (ESI)=418.2 [M+H]$^+$. $^1$H NMR (300 MHz, DMSO-d$_6$) δ 8.01 (d, J=8.4 Hz, 1H), 7.59 (d, J=9.1 Hz, 2H), 7.44-7.33 (m, 3H), 7.30 (d, J=7.5 Hz, 1H), 4.32 (q, J=6.9 Hz, 2H), 2.72-2.60 (m, 1H), 2.18-2.01 (m, 1H), 1.67-1.55 (m, 1H), 1.49-1.29 (m, 4H).

Example 145: Separation of the enantiomers of rac-cis-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic Acid (Compound 307, Peak 1 and Compound 308, Peak 2)

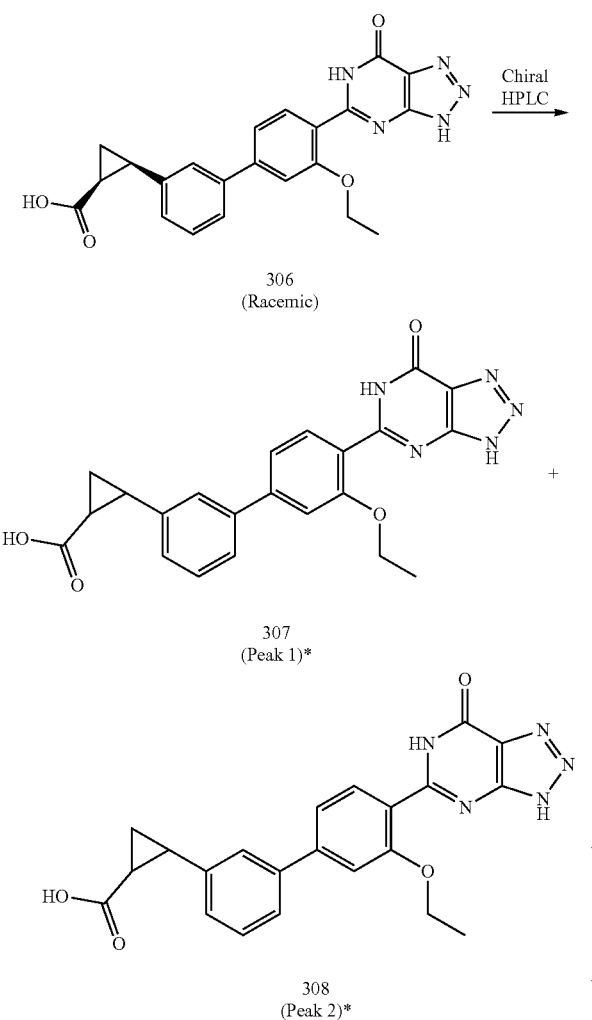

Cis-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic acid, Peak 1, and cis-2-(3'-ethoxy-4'-(7-oxo-6,7-dihydro-3H-[1,2,3]triazolo[4,5-d]pyrimidin-5-yl)-[1,1'-biphenyl]-3-yl)cyclopropane-1-carboxylic acid, Peak 2, were separated into their individual enantiomers using the procedures in Example 118

Data for Compound 307 (Peak 1) LCMS (ESI)=418.1 [M+H]$^+$. Analytical chiral HPLC: CHIRALPAK ID-3, 4.6*50 mm, 3 μm, 1.0 mL/min; A: n-hexane/DCM, 3/1; B: EtOH (0.5% FA); 15% B: $t_R$=1.74 min (100% ee). *Absolute stereochemistry for isolated single enantiomer not determined.

Data for Compound 308 (Peak 2): LCMS (ESI)=418.1 [M+H]$^+$. CHIRALPAK ID-3, 4.6*50 mm, 3 μm, 1.0 mL/min; A: n-hexane/DCM, 3/1; B: EtOH (0.5% FA); 15% B: $t_R$=2.57 min (98.9% ee). *Absolute stereochemistry for isolated single enantiomer not determined.

Example 146: Synthesis of 3-(3'-ethoxy-4-hydroxy-4'-(7-oxo-6,7-dihydro-3H-[1,2,3]triazolo[4,5-d]pyrimidin-5-yl)-[1,1'-biphenyl]-3-yl)propanoic Acid (Compound 309)

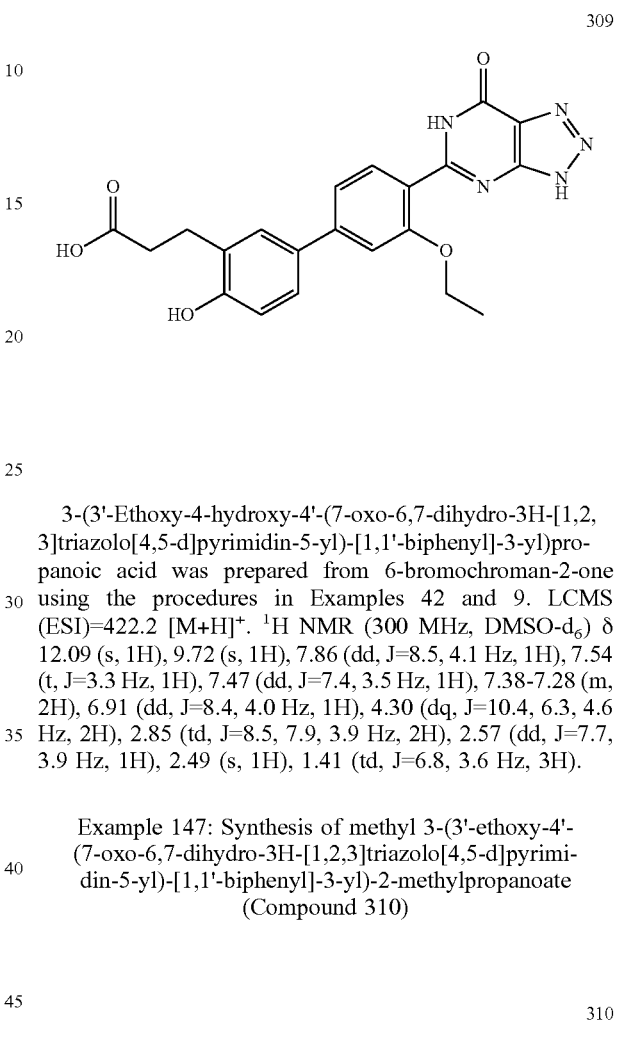

3-(3'-Ethoxy-4-hydroxy-4'-(7-oxo-6,7-dihydro-3H-[1,2,3]triazolo[4,5-d]pyrimidin-5-yl)-[1,1'-biphenyl]-3-yl)propanoic acid was prepared from 6-bromochroman-2-one using the procedures in Examples 42 and 9. LCMS (ESI)=422.2 [M+H]$^+$. $^1$H NMR (300 MHz, DMSO-$d_6$) δ 12.09 (s, 1H), 9.72 (s, 1H), 7.86 (dd, J=8.5, 4.1 Hz, 1H), 7.54 (t, J=3.3 Hz, 1H), 7.47 (dd, J=7.4, 3.5 Hz, 1H), 7.38-7.28 (m, 2H), 6.91 (dd, J=8.4, 4.0 Hz, 1H), 4.30 (dq, J=10.4, 6.3, 4.6 Hz, 2H), 2.85 (td, J=8.5, 7.9, 3.9 Hz, 2H), 2.57 (dd, J=7.7, 3.9 Hz, 1H), 2.49 (s, 1H), 1.41 (td, J=6.8, 3.6 Hz, 3H).

Example 147: Synthesis of methyl 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoate (Compound 310)

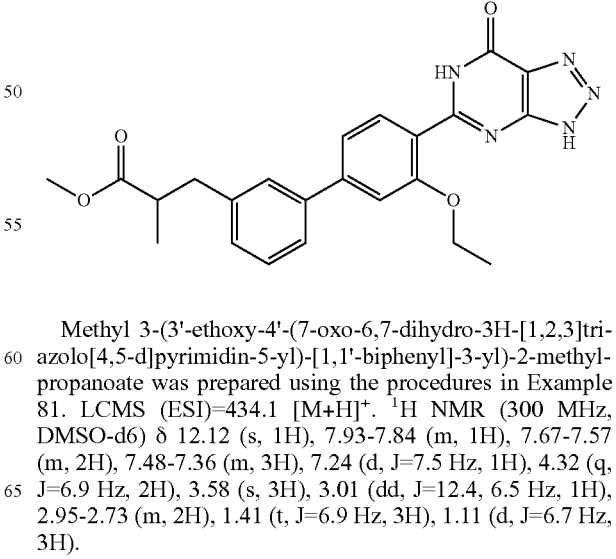

Methyl 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoate was prepared using the procedures in Example 81. LCMS (ESI)=434.1 [M+H]$^+$. $^1$H NMR (300 MHz, DMSO-d6) δ 12.12 (s, 1H), 7.93-7.84 (m, 1H), 7.67-7.57 (m, 2H), 7.48-7.36 (m, 3H), 7.24 (d, J=7.5 Hz, 1H), 4.32 (q, J=6.9 Hz, 2H), 3.58 (s, 3H), 3.01 (dd, J=12.4, 6.5 Hz, 1H), 2.95-2.73 (m, 2H), 1.41 (t, J=6.9 Hz, 3H), 1.11 (d, J=6.7 Hz, 3H).

Example 148: Synthesis of the Enantiomers of 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoic Acid (Compound 311, Peak 1 and Compound 312, Peak 2)

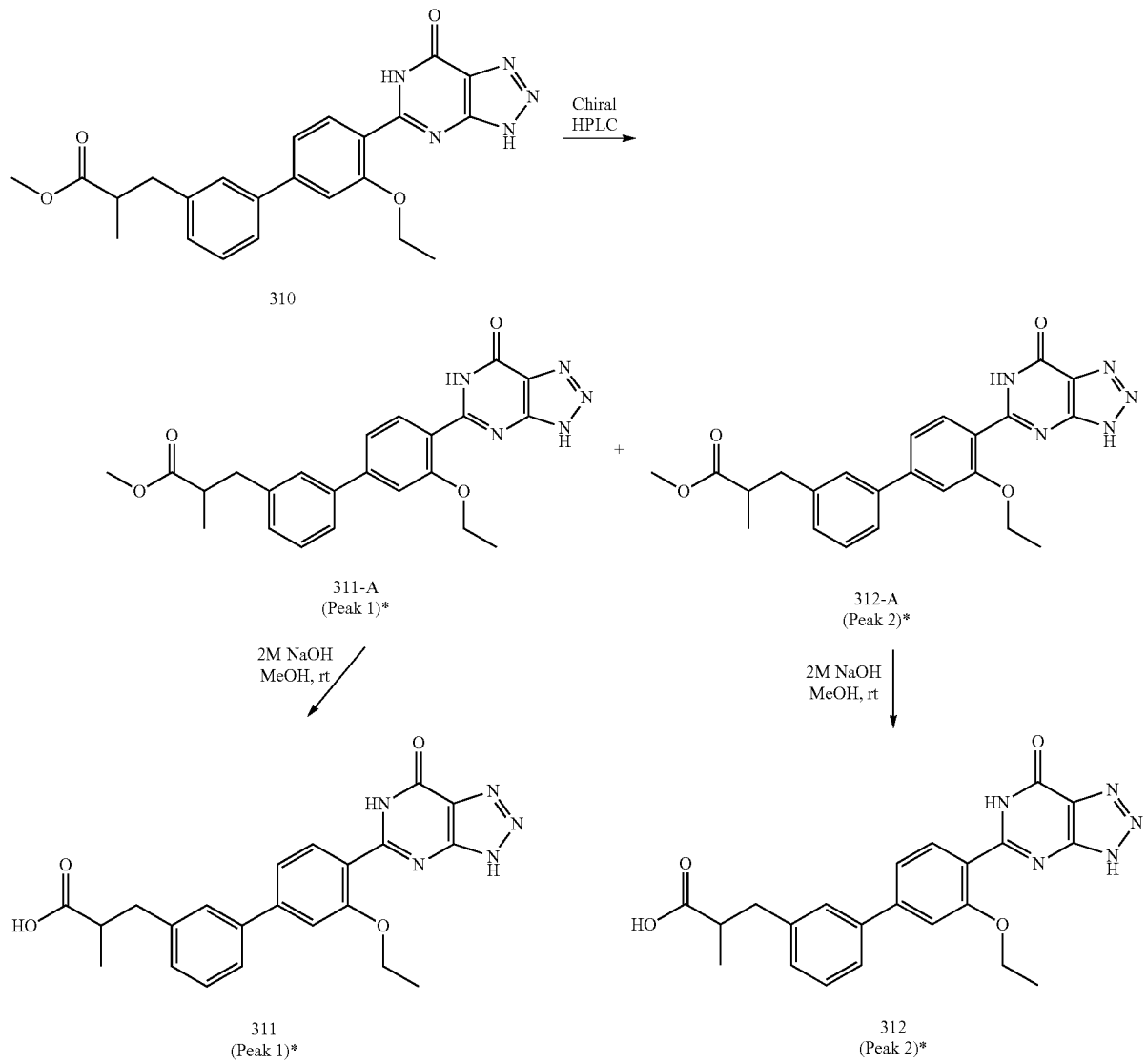

Methyl 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoate (74.0 mg) was separated by chiral preparative HPLC: CHIRALPAK IF-3, 20*250 mm, 5 um; Phase A: EtOH (0.2% TFA); Phase B: THF; 15% B, 8 min; 20 ml/min. This afforded methyl 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoate, Peak 1 (Compound 311-A), 15 mg, as a white solid, and Peak 2 (Compound 312-A), 13 mg, as a white solid.

Data for Compound 311-A (Peak 1): Chiral HPLC (CHIRALPAK IF-3, 100×4.6 mm, 3 μm, 0.8 mL/min, 20% B). A: Ethanol (0.1% TFA); B: THF: $t_R$=2.87 min. *Absolute stereochemistry for isolated single enantiomer not determined.

Data for Compound 312-A (Peak 2): Chiral HPLC (CHIRALPAK IF-3, 100×4.6 mm, 3 μm, 0.8 mL/min, 20% B). A: Ethanol (0.1% TFA); B: THF: $t_R$=3.48 min. *Absolute stereochemistry for isolated single enantiomer not determined.

A solution of methyl 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoate, Peak 1 (Compound 311-A) (15.0 mg, 0.035 mmol, 1.00 equiv) and 2M NaOH (0.30 mL) in MeOH (1.0 mL) was stirred for 2 hr at rt. The mixture was acidified to pH 5-6 with FA. The mixture was purified by preparative HPLC to afford 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoic acid (4.0 mg, 26%) as a white solid.

Data for Compound 311: LCMS (ESI)=420.1 [M+H]$^+$. $^1$H NMR (300 MHz, DMSO-d$_6$) δ 8.02 (d, J=8.5 Hz, 1H), 7.64-7.56 (m, 2H), 7.46-7.33 (m, 3H), 7.25 (d, J=7.5 Hz, 1H), 4.32 (q, J=6.9 Hz, 2H), 3.08-2.94 (m, 1H), 2.70 (s, 1H), 2.53 (s, 1H), 1.43 (t, J=6.9 Hz, 3H), 1.09 (d, J=6.2 Hz, 3H). Chiral HPLC (CHIRALPAK IC-3, 4.6*50 mm, 3 μm, 1 mL/min, 12.5 min, 10% B). A: Ethanol (0.5% TFA); B: n-Hexane/DCM, 3/1: t$_R$=6.45 min. *Absolute stereochemistry for isolated single enantiomer not determined.

3-(3'-Ethoxy-4'-(7-oxo-6,7-dihydro-3H-[1,2,3]triazolo[4,5-d]pyrimidin-5-yl)-[1,1'-biphenyl]-3-yl)-2-methylpropanoic acid, Peak 2 (Compound 312) was prepared with the same procedure used for Compound 311 to afford 3-(3'-ethoxy-4'-(7-oxo-6,7-dihydro-3H-[1,2,3]triazolo[4,5-d]pyrimidin-5-yl)-[1,1'-biphenyl]-3-yl)-2-methylpropanoic acid, Peak 2 (Compound 312).

Data for Compound 312: Chiral HPLC (CHIRALPAK IC-3, 4.6*50 mm, 3 μm, 1 mL/min, 12.5 min, 10% B). A: Ethanol (0.5% TFA); B: n-Hexane/DCM, 3/1: t$_R$=7.50 min. *Absolute stereochemistry for isolated single enantiomer not determined.

Example 149: Separation of the enantiomers of 3-(3'-ethoxy-4-isopropoxy-4'-(7-oxo-6,7-dihydro-3H-[1,2,3]triazolo[4,5-d]pyrimidin-5-yl)-[1,1'-biphenyl]-3-yl)-2-methylpropanoic acid (Compound 313, Peak 1, and Compound 314, Peak 2)

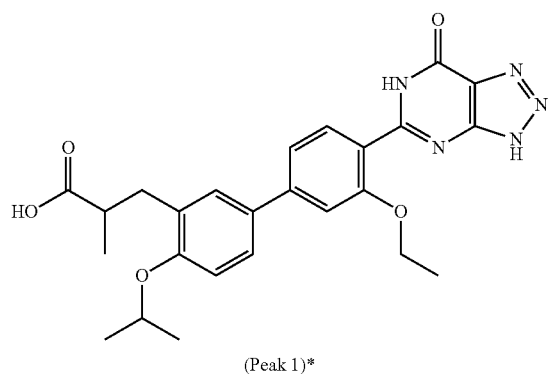

(Peak 1)*

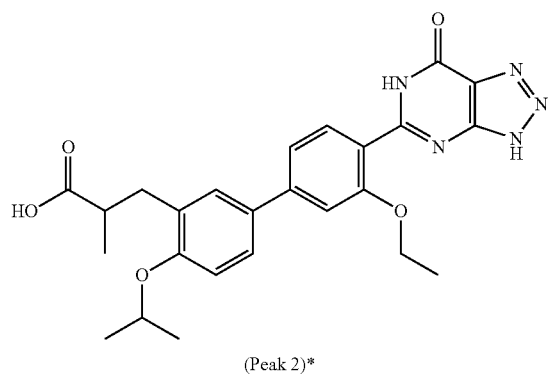

(Peak 2)*

3-(3'-Ethoxy-4-isopropoxy-4'-(7-oxo-6,7-dihydro-3H-[1,2,3]triazolo[4,5-d]pyrimidin-5-yl)-[1,1'-biphenyl]-3-yl)-2-methylpropanoic acid was separated into the individual enantiomers using the procedure in Example 83 except a preparative CHIRALPAK IG-3 column was used in the separation.

Data for Compound 313 (Peak 1): LCMS (ESI)=478.2 [M+H]$^+$. Chiral HPLC (CHIRALPAK IG-3, 100*4.6 mm, 3 μm, 1 mL/min, 20% B). A: n-Hexane/DCM, 4/1; B: Ethanol (0.5% FA): t$_R$=3.09 min. *Absolute stereochemistry for isolated single enantiomer not determined.

Data for Compound 314 (Peak 2): LCMS (ESI)=478.2 [M+H]$^+$. Chiral HPLC: t$_R$=3.79 min. *Absolute stereochemistry for isolated single enantiomer not determined.

Example 150: Synthesis of (E)-3-(3'-ethoxy-4-methoxy-4'-(7-oxo-6,7-dihydro-3H-[1,2,3]triazolo[4,5-d]pyrimidin-5-yl)-[1,1'-biphenyl]-3-yl)-2-methylacrylic Acid (Compound 315)

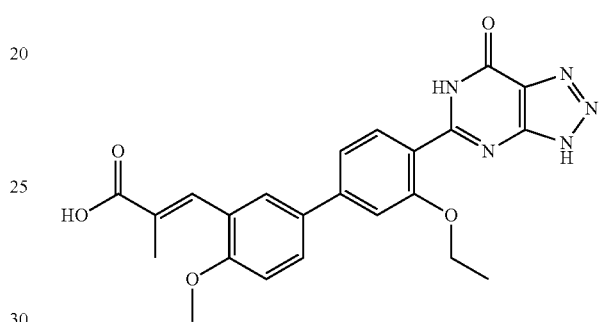

(E)-3-(3'-Ethoxy-4-methoxy-4'-(7-oxo-6,7-dihydro-3H-[1,2,3]triazolo[4,5-d]pyrimidin-5-yl)-[1,1'-biphenyl]-3-yl)-2-methylacrylic acid was prepared using the procedures in Example 138. LCMS (ESI)=448.1 [M+H]$^+$. $^1$H NMR (300 MHz, DMSO-d$_6$) δ 12.13 (s, 1H), 7.87 (d, J=8.5 Hz, 1H), 7.84-7.76 (m, 1H), 7.72 (dd, J=4.6, 2.1 Hz, 2H), 7.44-7.35 (m, 2H), 7.20 (d, J=8.7 Hz, 1H), 4.31 (q, J=7.0 Hz, 2H), 3.89 (s, 3H), 2.00 (d, J=1.5 Hz, 3H), 1.40 (t, J=6.9 Hz, 3H).

Example 151: Synthesis of 3-(3'-ethoxy-4-methoxy-4'-(7-oxo-6,7-dihydro-3H-[1,2,3]triazolo[4,5-d]pyrimidin-5-yl)-[1,1'-biphenyl]-3-yl)-2-methylpropanoic Acid (Compound 316)

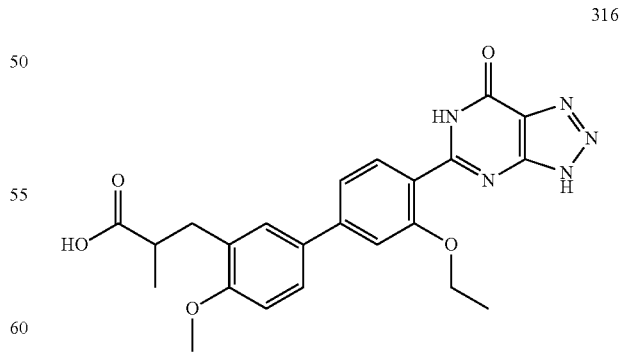

3-(3'-Ethoxy-4-methoxy-4'-(7-oxo-6,7-dihydro-3H-[1,2,3]triazolo[4,5-d]pyrimidin-5-yl)-[1,1'-biphenyl]-3-yl)-2-methylpropanoic acid was prepared using the procedure in Example 139. LCMS (ESI)=450.2 [M+H]$^+$. $^1$H NMR (300 MHz, DMSO-d$_6$) δ 7.93 (d, J=8.4 Hz, 1H), 7.64 (dd, J=8.9, 2.5 Hz, 1H), 7.55 (d, J=2.4 Hz, 1H), 7.39-7.30 (m, 2H), 7.08 (d, J=8.6 Hz, 1H), 4.31 (q, J=6.8 Hz, 2H), 3.85 (s, 3H), 2.94 (s, 1H), 2.80-2.64 (m, 2H), 1.42 (t, J=6.9 Hz, 3H), 1.07 (d, J=6.2 Hz, 3H).

Example 152: Synthesis of (E)-3-(3'-ethoxy-4'-(7-oxo-6,7-dihydro-3H-[1,2,3]triazolo[4,5-d]pyrimidin-5-yl)-4-(2-(pyrrolidin-1-yl)ethoxy)-[1,1'-biphenyl]-3-yl)acrylic Acid (Compound 317)

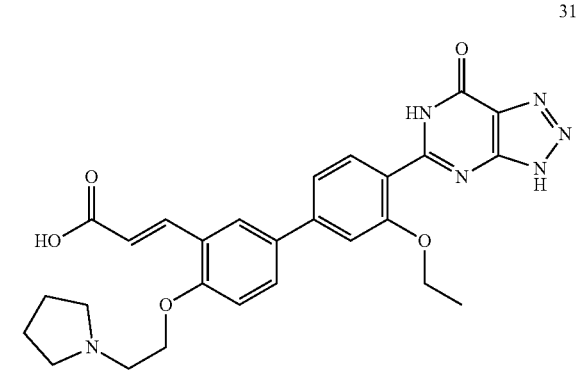

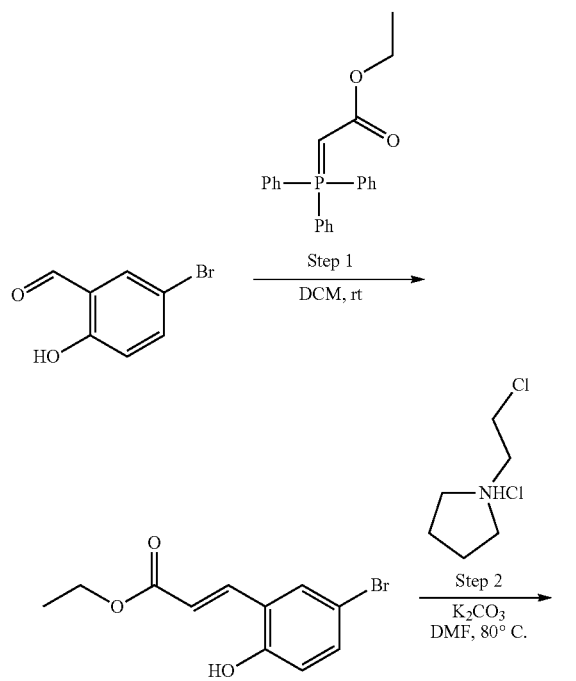

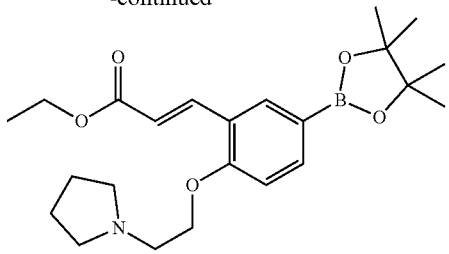

Step 1: A solution of 5-bromo-2-hydroxybenzaldehyde (3.50 g, 17.4 mmol, 1.00 equiv) and ethyl 2-(triphenyl-$\lambda^5$-phosphanylidene)acetate (9.10 g, 26.5 mmol, 1.5 equiv) in DCM (40 mL) was stirred for 2 hr at rt. The resulting mixture was concentrated under reduced pressure. The residue was purified by silica gel column chromatography, eluted with EA/PE (0-30%) to afford ethyl (E)-3-(5-bromo-2-hydroxyphenyl)acrylate (4.0 g, 76.3%) as a yellow solid. $^1$H NMR (300 MHz, DMSO-$d_6$) δ 10.55 (s, 1H), 7.85-7.72 (m, 2H), 7.69-7.46 (m, 1H), 7.34 (dd, J=8.7, 2.5 Hz, 1H), 6.88 (d, J=8.7 Hz, 1H), 6.65 (d, J=16.2 Hz, 1H), 4.16 (q, J=7.1 Hz, 2H), 1.23 (t, J=7.1 Hz, 3H).

Step 2: A solution of ethyl (E)-3-(5-bromo-2-hydroxyphenyl)acrylate (500 mg, 1.84 mmol, 1.00 equiv) and 1-(2-chloroethyl)pyrrolidine (271 mg, 2.03 mmol, 1.1 equiv) in DMF (10 mL) and $K_2CO_3$ (510 mg, 3.69 mmol, 2.00 equiv) was stirred for 3 hr at 80° C. The resulting mixture was diluted with water (40 mL). The resulting mixture was extracted with EA (3×40 mL). The combined organic layers were washed with brine (2×40 mL), dried over anhydrous $Na_2SO_4$. After filtration, the filtrate was concentrated under reduced pressure. The residue was purified by silica gel column chromatography, eluted with MeOH/DCM (0-20%) to afford ethyl (E)-3-(5-bromo-2-(2-(pyrrolidin-1-yl)ethoxy)phenyl)acrylate (500 mg, 66.3%) as a yellow solid. $^1$H NMR (300 MHz, CDCl$_3$) δ 7.92 (d, J=16.2 Hz, 1H), 7.63 (d, J=2.5 Hz, 1H), 7.42 (dd, J=8.8, 2.5 Hz, 1H), 6.81 (d, J=8.8 Hz, 1H), 6.51 (d, J=16.2 Hz, 1H), 4.27 (q, J=7.2 Hz, 2H), 4.17 (t, J=6.0 Hz, 2H), 2.99 (t, J=6.0 Hz, 2H), 2.75-2.62 (m, 4H), 1.93-1.76 (m, 4H), 1.34 (t, J=7.2 Hz, 3H).

Step 3: To a stirred solution of ethyl (E)-3-(5-bromo-2-(2-(pyrrolidin-1-yl)ethoxy)phenyl)acrylate (500 mg, 1.36 mmol, 1.00 equiv) and bis(pinacolato)diboron (414 mg, 1.63 mmol, 1.2 equiv) in dioxane (5.00 mL) were added KOAc (266 mg, 2.72 mmol, 2.0 equiv) and Pd(dppf)Cl$_2$ (99.3 mg, 0.136 mmol, 0.1 equiv) in portions at rt. The resulting mixture was stirred for 2 hr at 100° C. The mixture was purified by silica gel column chromatography, eluted with MeOH/DCM (0-20%) to afford ethyl (E)-3-(2-(2-(pyrrolidin-1-yl)ethoxy)-5-(4,4,5,5-tetramethyl-1,3,2-dioxaborolan-2-yl)phenyl)acrylate (400 mg, 66.1%) as a grey oil. (E)-3-(3'-Ethoxy-4'-(7-oxo-6,7-dihydro-3H-[1,2,3]triazolo[4,5-d]pyrimidin-5-yl)-4-(2-(pyrrolidin-1-yl)ethoxy)-[1,1'-biphenyl]-3-yl)acrylic acid was prepared using the procedures in Examples 1 and 9. LCMS (ESI)=517.3 [M+H]$^+$. $^1$H NMR (300 MHz, DMSO-d6) δ 11.70 (s, 1H), 8.10 (d, J=2.4 Hz, 1H), 7.97-7.86 (m, 2H), 7.81 (dd, J=8.7, 2.3 Hz, 1H), 7.46 (s, 1H), 7.24 (d, J=8.8 Hz, 1H), 6.81 (d, J=16.1 Hz, 1H), 4.36 (d, J=6.8 Hz, 1H), 4.30 (t, J=7.2 Hz, 3H), 3.05 (t, J=5.6 Hz, 2H), 2.74 (d, J=12.2 Hz, 1H), 2.74 (s, 3H), 1.84-1.71 (m, 4H), 1.42 (t, J=6.9 Hz, 3H.

Example 153: Synthesis of 3-(3'-ethoxy-4'-(7-oxo-6,7-dihydro-3H-[1,2,3]triazolo[4,5-d]pyrimidin-5-yl)-4-(2-(pyrrolidin-1-yl)ethoxy)-[1,1'-biphenyl]-3-yl)propanoic Acid (Compound 318)

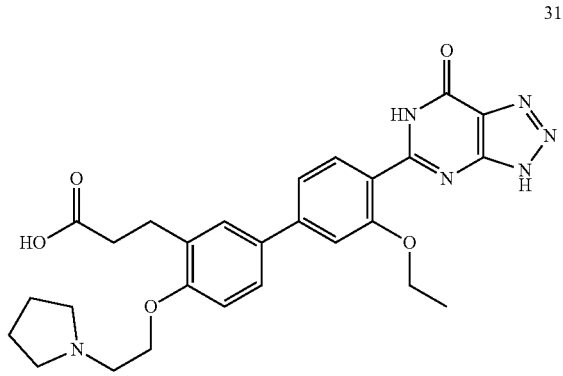

318

3-(3'-Ethoxy-4'-(7-oxo-6,7-dihydro-3H-[1,2,3]triazolo[4,5-d]pyrimidin-5-yl)-4-(2-(pyrrolidin-1-yl)ethoxy)-[1,1'-biphenyl]-3-yl)propanoic acid was prepared using the procedure in Example 139. LCMS (ESI)=519.2 [M+H]$^+$. $^1$H NMR (300 MHz, DMSO-d$_6$) δ 11.49 (s, 1H), 7.94 (d, J=8.5 Hz, 1H), 7.64-7.55 (m, 2H), 7.35 (d, J=6.5 Hz, 2H), 7.08 (d, J=9.2 Hz, 1H), 4.31 (q, J=6.9 Hz, 2H), 4.19 (t, J=5.6 Hz, 2H), 2.99 (t, J=5.5 Hz, 2H), 2.90 (t, J=7.6 Hz, 2H), 2.76-2.67 (m, 4H), 2.56 (d, J=7.5 Hz, 2H), 1.75 (p, J=3.2 Hz, 4H), 1.42 (t, J=6.9 Hz, 3H).

Example 154: Synthesis of (E)-3-(4-(2-(dimethylamino)ethoxy)-3'-ethoxy-4'-(7-oxo-6,7-dihydro-3H-[1,2,3]triazolo[4,5-d]pyrimidin-5-yl)-[1,1'-biphenyl]-3-yl)acrylic Acid (Compound 319)

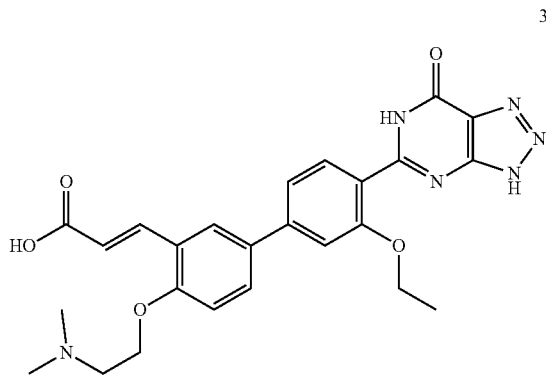

319

(E)-3-(4-(2-(Dimethylamino)ethoxy)-3'-ethoxy-4'-(7-oxo-6,7-dihydro-3H-[1,2,3]triazolo[4,5-d]pyrimidin-5-yl)-[1,1'-biphenyl]-3-yl)acrylic acid was prepared using the procedures in Example 152. LCMS (ESI)=491.3 [M+H]$^+$. $^1$H NMR (300 MHz, DMSO-d6) δ 11.67 (s, 1H), 8.10 (d, J=2.3 Hz, 1H), 7.98-7.84 (m, 2H), 7.83 (dd, J=8.7, 2.4 Hz, 1H), 7.46 (dd, J=4.5, 2.9 Hz, 2H), 7.24 (d, J=8.8 Hz, 1H), 6.81 (d, J=16.1 Hz, 1H), 4.35 (q, J=6.9 Hz, 2H), 4.25 (t, J=5.6 Hz, 2H), 2.80 (t, J=5.6 Hz, 2H), 2.32 (s, 6H), 1.42 (t, J=6.9 Hz, 3H).

Example 155: Synthesis of 3-(4-(2-(dimethylamino)ethoxy)-3'-ethoxy-4'-(7-oxo-6,7-dihydro-3H-[1,2,3]triazolo[4,5-d]pyrimidin-5-yl)-[1,1'-biphenyl]-3-yl)propanoic Acid (Compound 320)

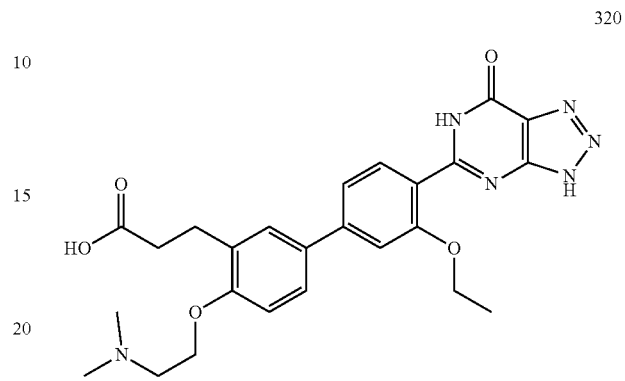

320

3-(4-(2-(Dimethylamino)ethoxy)-3'-ethoxy-4'-(7-oxo-6,7-dihydro-3H-[1,2,3]triazolo[4,5-d]pyrimidin-5-yl)-[1,1'-biphenyl]-3-yl)propanoic acid was prepared using the procedure in Example 139. LCMS (ESI)=493.2 [M+H]$^+$. $^1$H NMR (300 MHz, DMSO-d6) δ 7.93 (d, J=8.0 Hz, 1H), 7.55 (dq, J=3.9, 2.4 Hz, 2H), 7.32 (d, J=1.6 Hz, 1H), 7.29 (s, 1H), 7.03 (d, J=9.2 Hz, 1H), 3.10 (s, 2H), 2.88 (s, 2H), 2.55 (s, 6H), 2.44 (t, J=7.2 Hz, 2H), 1.39 (t, J=6.9 Hz, 3H).

Example 156: Synthesis of 3-(3'-ethoxy-4-methyl-4'-(7-oxo-6,7-dihydro-3H-[1,2,3]triazolo[4,5-d]pyrimidin-5-yl)-[1,1'-biphenyl]-3-yl)propanoic Acid (Compound 321)

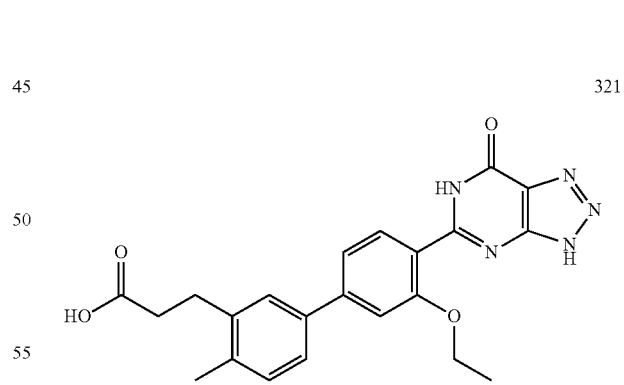

321

3-(3'-Ethoxy-4-methyl-4'-(7-oxo-6,7-dihydro-3H-[1,2,3]triazolo[4,5-d]pyrimidin-5-yl)-[1,1'-biphenyl]-3-yl)propanoic acid was prepared using methods described in the previous examples. LCMS (ESI)=420.1 [M+H]$^+$. $^1$H NMR (300 MHz, DMSO-d6) δ 7.95 (d, J=8.4 Hz, 1H), 7.58 (d, J=2.0 Hz, 1H), 7.52 (dd, J=7.8, 2.0 Hz, 1H), 7.38 (dt, J=4.5, 2.2 Hz, 2H), 7.27 (d, J=7.9 Hz, 1H), 4.31 (q, J=6.8 Hz, 2H), 2.91 (t, J=7.8 Hz, 2H), 2.58 (dd, J=8.6, 7.0 Hz, 2H), 2.34 (s, 3H), 1.42 (t, J=6.9 Hz, 3H).

Example 157: Synthesis of (E)-3-(3'-ethoxy-4'-(7-oxo-6,7-dihydro-3H-[1,2,3]triazolo[4,5-d]pyrimidin-5-yl)-6-(2-(pyrrolidin-1-yl)ethoxy)-[1,1'-biphenyl]-3-yl)acrylic Acid (Compound 322)

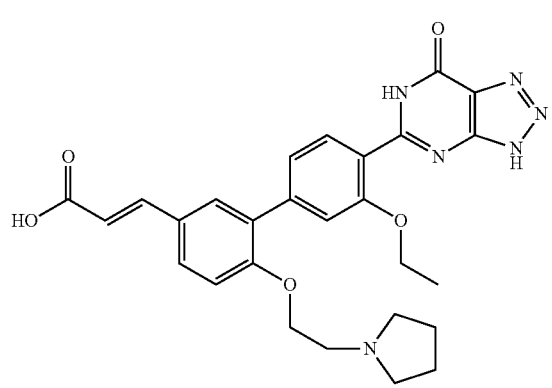

322

(E)-3-(3'-Ethoxy-4'-(7-oxo-6,7-dihydro-3H-[1,2,3]triazolo[4,5-d]pyrimidin-5-yl)-6-(2-(pyrrolidin-1-yl)ethoxy)-[1,1'-biphenyl]-3-yl)acrylic acid was prepared from 3-bromo-4-hydroxybenzaldehyde using methods described in the previous examples. LCMS (ESI)=517.2 [M+H]$^+$. $^1$H NMR (300 MHz, DMSO-d6) δ 12.04 (s, 1H), 7.86 (d, J=8.0 Hz, 1H), 7.75 (d, J=6.9 Hz, 2H), 7.64 (d, J=15.9 Hz, 1H), 7.40-7.30 (m, 2H), 7.24 (d, J=9.1 Hz, 1H), 6.51 (d, J=16.0 Hz, 1H), 4.32-4.19 (m, 4H), 3.05 (s, 2H), 2.76-2.70 (m, 4H), 1.76-1.70 (m, 4H), 1.40 (t, J=6.9 Hz, 3H).

Example 158: Synthesis of 3-(3'-ethoxy-4'-(7-oxo-6,7-dihydro-3H-[1,2,3]triazolo[4,5-d]pyrimidin-5-yl)-6-(2-(pyrrolidin-1-yl)ethoxy)-[1,1'-biphenyl]-3-yl) propanoic Acid (Compound 323)

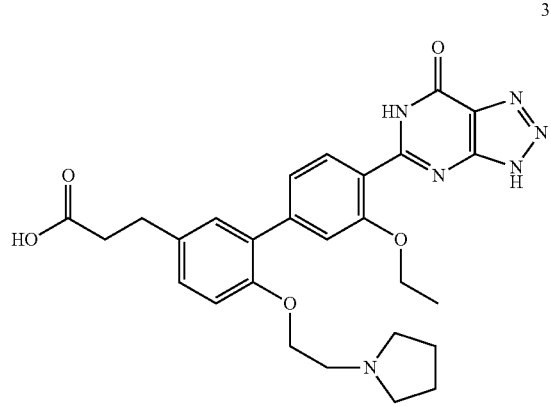

323

3-(3'-Ethoxy-4'-(7-oxo-6,7-dihydro-3H-[1,2,3]triazolo[4,5-d]pyrimidin-5-yl)-6-(2-(pyrrolidin-1-yl)ethoxy)-[1,1'-biphenyl]-3-yl)propanoic acid was prepared using methods described in the previous examples. LCMS (ESI)=519.2 [M+H]$^+$. $^1$H NMR (300 MHz, DMSO-d$_6$) δ 11.89 (s, 1H), 7.86 (d, J=8.1 Hz, 1H), 7.36-7.20 (m, 4H), 7.09 (d, J=8.4 Hz, 1H), 4.30-4.13 (m, 4H), 3.01-2.95 (m, 2H), 2.84 (t, J=7.5 Hz, 2H), 2.72-2.66 (m, 4H), 2.62-2.51 (m, 2H), 1.75-1.69 (m, 4H), 1.40 (t, J=6.9 Hz, 3H).

Example 159: Synthesis of (E)-3-(3'-ethoxy-4'-(7-oxo-6,7-dihydro-3H-[1,2,3]triazolo[4,5-d]pyrimidin-5-yl)-5-(2-(pyrrolidin-1-yl)ethoxy)-[1,1'-biphenyl]-3-yl)acrylic Acid (Compound 324)

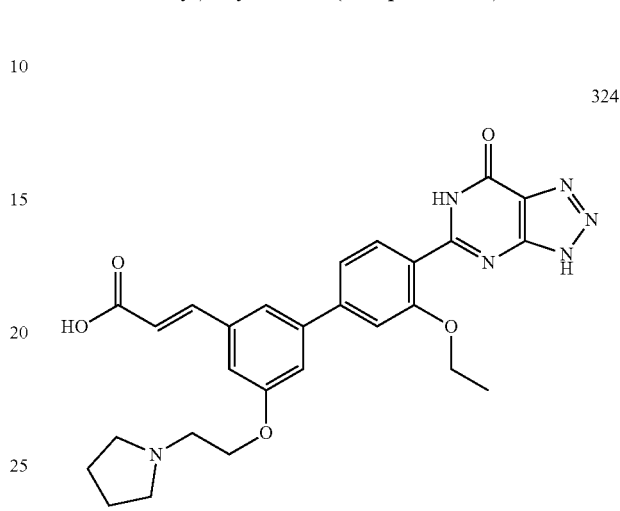

324

(E)-3-(3'-Ethoxy-4'-(7-oxo-6,7-dihydro-3H-[1,2,3]triazolo[4,5-d]pyrimidin-5-yl)-5-(2-(pyrrolidin-1-yl)ethoxy)-[1,1'-biphenyl]-3-yl)acrylic acid was prepared from 3-bromo-5-hydroxybenzaldehyde using methods described in the previous examples. LCMS (ESI)=517.4 [M+H]$^+$. $^1$H NMR (300 MHz, DMSO-d6) δ 11.84 (broad s, 1H), 7.92 (d, J=8.4 Hz, 1H), 7.74-7.62 (m, 2H), 7.49 (dd, J=4.5, 2.9 Hz, 2H), 7.38 (s, 2H), 6.74 (d, J=16.0 Hz, 1H), 4.40-4.26 (m, 4H), 3.10 (d, J=5.5 Hz, 2H), 2.83 (s, 4H), 1.79 (t, J=3.7 Hz, 4H), 1.41 (t, J=6.9 Hz, 3H).

Example 160: Synthesis of 3-(3'-ethoxy-4'-(7-oxo-6,7-dihydro-3H-[1,2,3]triazolo[4,5-d]pyrimidin-5-yl)-5-(2-(pyrrolidin-1-yl)ethoxy)-[1,1'-biphenyl]-3-yl) propanoic Acid (Compound 325)

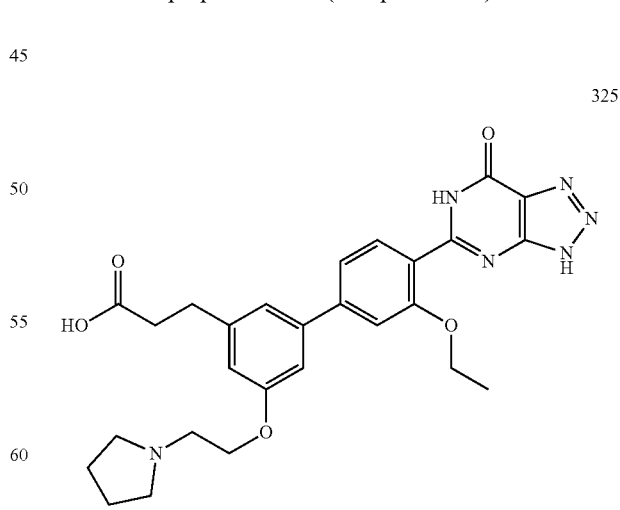

325

3-(3'-Ethoxy-4'-(7-oxo-6,7-dihydro-3H-[1,2,3]triazolo[4,5-d]pyrimidin-5-yl)-5-(2-(pyrrolidin-1-yl)ethoxy)-[1,1'-biphenyl]-3-yl)propanoic acid was prepared using methods described in the previous examples. LCMS (ESI)=519.4

[M+H]+. 1H NMR (300 MHz, DMSO-d6) δ 11.92 (s, 1H), 8.15 (s, OH), 7.90 (d, J=8.4 Hz, 1H), 7.44-7.35 (m, 2H), 7.26 (s, 1H), 7.15 (d, J=2.2 Hz, 1H), 6.92 (s, 1H), 4.38-4.22 (m, 4H), 3.19 (t, J=5.4 Hz, 2H), 2.96-2.84 (m, 6H), 2.62 (t, J=7.7 Hz, 2H), 1.88-1.78 (m, 4H), 1.41 (t, J=6.9 Hz, 3H).

Example 161: Synthesis of (E)-3-(6-(2-(dimethyl-amino)ethoxy)-3'-ethoxy-4'-(7-oxo-6,7-dihydro-3H-[1,2,3]triazolo[4,5-d]pyrimidin-5-yl)-[1,1'-biphenyl]-3-yl)acrylic Acid (Compound 326)

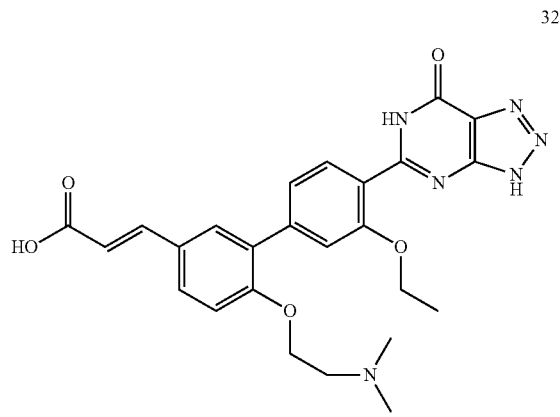

326

(E)-3-(6-(2-(dimethylamino)ethoxy)-3'-ethoxy-4'-(7-oxo-6,7-dihydro-3H-[1,2,3]triazolo[4,5-d]pyrimidin-5-yl)-[1,1'-biphenyl]-3-yl)acrylic acid was prepared using methods described in the previous examples. LCMS (ESI)=491.2 [M+H]+. 1H NMR (300 MHz, DMSO-d6) δ 12.04 (s, 1H), 7.86 (d, J=8.0 Hz, 1H), 7.75 (d, J=8.3 Hz, 2H), 7.63 (d, J=16.0 Hz, 1H), 7.41 (d, J=1.5 Hz, 1H), 7.35 (dd, J=8.1, 1.5 Hz, 1H), 7.24 (d, J=8.4 Hz, 1H), 6.51 (d, J=16.0 Hz, 1H), 4.33-4.18 (m, 4H), 2.79 (t, J=5.5 Hz, 2H), 2.30 (s, 6H), 1.40 (t, J=6.9 Hz, 3H).

Example 162: Synthesis of 3-(6-(2-(dimethylamino) ethoxy)-3'-ethoxy-4'-(7-oxo-6,7-dihydro-3H-[1,2,3] triazolo[4,5-d]pyrimidin-5-yl)-[1,1'-biphenyl]-3-yl) propanoic Acid (Compound 327)

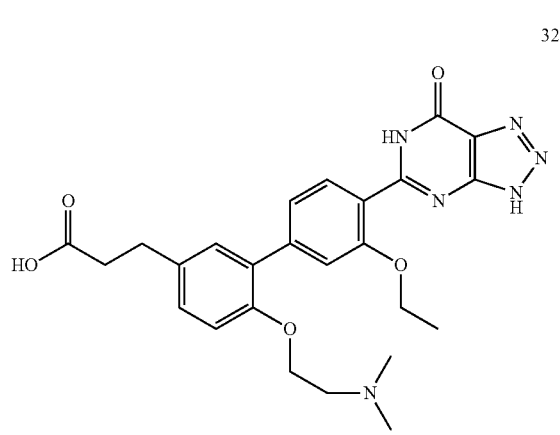

327

3-(6-(2-(Dimethylamino)ethoxy)-3'-ethoxy-4'-(7-oxo-6,7-dihydro-3H-[1,2,3]triazolo[4,5-d]pyrimidin-5-yl)-[1,1'-biphenyl]-3-yl)propanoic acid was prepared using methods described in the previous examples. LCMS (ESI)=493.2 [M+H]+. 1H NMR (300 MHz, DMSO-d6) δ 11.97 (s, 1H), 7.86 (d, J=8.1 Hz, 1H), 7.37 (d, J=1.5 Hz, 1H), 7.32-7.19 (m, 3H), 7.09 (d, J=8.4 Hz, 1H), 4.24 (q, J=6.9 Hz, 2H), 4.14 (t, J=5.6 Hz, 2H), 2.82 (dt, J=8.2, 6.5 Hz, 4H), 2.56 (t, J=7.5 Hz, 2H), 2.32 (s, 6H), 1.40 (t, J=6.9 Hz, 3H).

Example 163: Synthesis of (E)-3-(5-(2-(dimethyl-amino)ethoxy)-3'-ethoxy-4'-(7-oxo-6,7-dihydro-3H-[1,2,3]triazolo[4,5-d]pyrimidin-5-yl)-[1,1'-biphenyl]-3-yl)acrylic Acid (Compound 328)

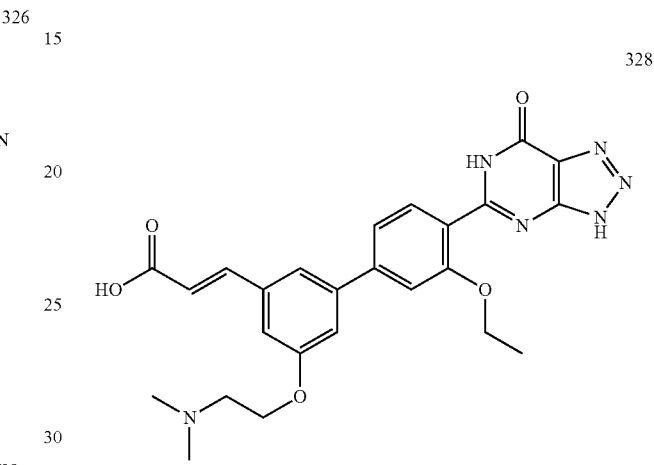

328

(E)-3-(5-(2-(dimethylamino)ethoxy)-3'-ethoxy-4'-(7-oxo-6,7-dihydro-3H-[1,2,3]triazolo[4,5-d]pyrimidin-5-yl)-[1,1'-biphenyl]-3-yl)acrylic acid was prepared using methods described in the previous examples. LCMS (ESI)=491.4 [M+H]+.

Example 164: Synthesis of 3-(5-(2-(dimethylamino) ethoxy)-3'-ethoxy-4'-(7-oxo-6,7-dihydro-3H-[1,2,3] triazolo[4,5-d]pyrimidin-5-yl)-[1,1'-biphenyl]-3-yl) propanoic Acid (Compound 329)

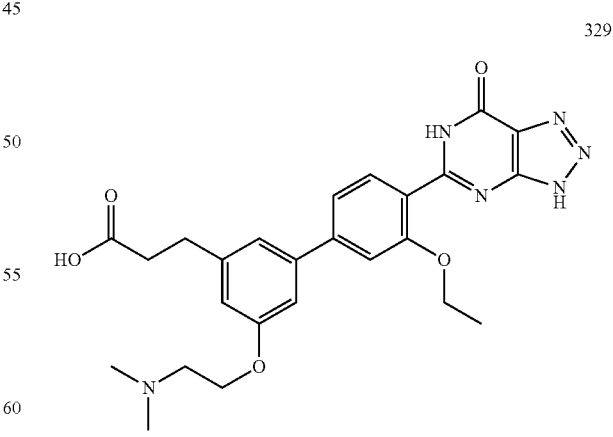

329

3-(5-(2-(dimethylamino)ethoxy)-3'-ethoxy-4'-(7-oxo-6,7-dihydro-3H-[1,2,3]triazolo[4,5-d]pyrimidin-5-yl)-[1,1'-biphenyl]-3-yl)propanoic acid was prepared using methods described in the previous examples. LCMS (ESI)=493.3 [M+H]+. 1H NMR (300 MHz, DMSO-d6) δ 11.94 (s, 1H), 7.89 (d, J=8.4 Hz, 1H), 7.40 (dq, J=3.1, 1.6 Hz, 2H), 7.24 (d, J=1.5 Hz, 1H), 7.14 (t, J=2.0 Hz, 1H), 6.94-6.87 (m, 1H), 4.31 (q, J=6.9 Hz, 2H), 4.22 (t, J=5.5 Hz, 2H), 2.90 (q, J=7.9, 6.6 Hz, 4H), 2.62 (t, J=7.6 Hz, 2H), 2.43 (s, 6H), 1.41 (t, J=6.9 Hz, 3H).

Example 165: Beta-Arrestin Assay

Human GPR35 expressing Tango U2OS cells were plated in 384-well format in clear bottom plates at a cell density of 10,000 cells/well and allowed to grow overnight. The next day, cells were treated with serially diluted test compounds for 5 hours. LiveBLAzer-FRET B/G (CCF4-AM) detection reagents were then added and cells were allowed to incubate for 2 hours before reading plates on a BioTek Cytation 5 plate reader. Zaprinast was used as a positive control for dose-response curves. In order to determine EC50 values, data were fit to a four-parameter dose-response curve. EC50 values are shown, in Table 1.

TABLE 1

| Compound | $EC_{50}$ |
| --- | --- |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | B |
| 140 | A |
| 141 | A |
| 142 | A |
| 143 | A |
| 144 | A |
| 145 | A |
| 146 | A |
| 148 | B |
| 149 | A |
| 150 | A |
| 151 | A |
| 152 | A |
| 153 | A |
| 154 | A |
| 155 | A |

TABLE 1-continued

| Compound | $EC_{50}$ |
| --- | --- |
| 156 | A |
| 157 | A |
| 158 | B |
| 159 | B |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | B |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |

A: $EC_{50}$ of less than or equal to 10 μM;
B: $EC_{50}$ of greater than 10 μM.

Example 166: Alternative Beta-Arrestin Assay

Human GPR35 expressing JumpIn (Thermo Fisher) 294R Tango U2OS cells were plated in 384-well format in clear bottom plates at a cell density of 10,000 cells/well and allowed to grow overnight. The next day, cells were treated with serially diluted test compounds for 5 hours. Live-BLAzer-FRET B/G (CCF4-AM) detection reagents were then added and cells were allowed to incubate for 2 hours before reading plates on a BioTek Cytation 5 plate reader. Zaprinast was used as a positive control for dose-response curves. In order to determine EC50 values, data were fit to a four-parameter dose-response curves. EC50 values are shown in Table 2.

TABLE 2

| Compound | $EC_{50}$ |
| --- | --- |
| 101 | A |
| 102 | A |
| 103 | A |
| 104 | A |
| 105 | A |
| 106 | A |
| 107 | A |
| 108 | A |
| 109 | B |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |

TABLE 2-continued

| Compound | EC$_{50}$ |
|---|---|
| 123 | A |
| 124 | A |
| 125 | A |
| 126 | A |
| 127 | A |
| 128 | A |
| 129 | B |
| 130 | A |
| 131 | A |
| 132 | A |
| 133 | B |
| 134 | A |
| 135 | A |
| 136 | B |
| 137 | A |
| 138 | B |
| 139 | 35% inhibition at 50 μM |
| 140 | A |
| 141 | A |
| 142 | A |
| 143 | A |
| 144 | A |
| 145 | A |
| 146 | A |
| 147 | A |
| 148 | C |
| 149 | A |
| 150 | A |
| 151 | A |
| 152 | A |
| 153 | A |
| 154 | A |
| 155 | A |
| 156 | A |
| 157 | A |
| 158 | 48% inhibition at 50 μM |
| 159 | B |
| 160 | A |
| 161 | A |
| 162 | B |
| 163 | A |
| 164 | A |
| 165 | 66% inhibition at 50 μM |
| 166 | A |
| 167 | A |
| 168 | A |
| 169 | A |
| 170 | A |
| 171 | B |
| 172 | B |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | A |
| 221 | 57% inhibition at 50 μM |
| 222 | A |
| 223 | A |
| 224 | A |
| 225 | A |
| 226 | A |
| 227 | 66% inhibition at 50 μM |
| 228 | 16% inhibition at 50 μM |
| 229 | B |
| 230 | B |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | 30% inhibition at 5.6 μM |
| 243 | A |
| 244 | A |
| 245 | 12% inhibition at 50 μM |
| 246 | A |
| 247 | A |
| 248 | A |
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | A |
| 270 | A |

TABLE 2-continued

| Compound | EC$_{50}$ |
|---|---|
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |
| 283 | A |
| 284 | A |
| 285 | A |
| 286 | A |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 305 | A |
| 306 | A |
| 307 | A |
| 308 | A |
| 309 | A |
| 310 | A |
| 311 | A |
| 312 | A |
| 313 | A |
| 314 | A |
| 315 | A |
| 316 | A |
| 317 | A |
| 318 | A |
| 319 | A |
| 320 | A |
| 321 | A |

A: EC$_{50}$ of less than or equal to 10 μM;
B: EC$_{50}$ of greater than 10 μM and less than 50 μM;
C: EC$_{50}$ of greater than 50 μM.

Example 167. Phase I/II Clinical Trial for Mild to Moderate Ulcerative Colitis

A double blind, randomized, placebo controlled, clinical study to evaluate the safety, tolerability and pilot therapeutic activity of Compound Formula (I), (I'), or (I") (hereinafter, "Compound"), was performed. Subjects with mild to moderate Ulcerative Colitis are administered the Compound as capsules by mouth, for 6 weeks.

Eligible subjects will be randomly assigned to either Compound or placebo, respectively. Sigmoidoscopies with biopsies will be performed at the first treatment visit and week 6. Subjects are treated for 12 weeks, with clinical evaluation on weeks 2, 4, 6 and between weeks 10-12.

Inclusion Criteria:

1. Subject has a documented diagnosis of mild to moderate Ulcerative Colitis, as demonstrated clinically and by endoscopy at Visit 2.
2. Baron score greater than or equal to 2 at baseline.
3. Truelove-Witt (modified) score of 14 or less.
4. At least 6 months duration of disease
5. At baseline the subject should have either stable disease or stable disease requiring 5-ASA treatment
6. If on a 5-ASA treatment, subject must have been on stable dose for at least two weeks prior to screening and is expected to continue on that dose until the study is completed
7. Subject has normally functioning major organ systems (aside from gastrointestinal tract) as indicated by medical history, vital signs, physical exam and clinical laboratories (including hematology, coagulation, chemistries and urinalysis).
8. Male or female subjects 18-70 years old
9. Subject has provided voluntary written informed consent to participate in this study.
10. Subject may be of child-bearing potential, but is not pregnant, nursing, or planning a pregnancy for the duration of the study and has a negative pregnancy test prior to enrollment.
11. Subject agrees to use a medically-acceptable form of contraception from screening through 30 days after the final dose of study drug. Female partners of male subjects enrolled into this study are also recommended to use an acceptable method of birth control. Males must agree to not donate sperm during the entire study and for 90 days after the last dose of study drug.

Exclusion Criteria

1. A clinically significant medical history, medical finding or an ongoing medical or psychiatric condition which, in the opinion of the Investigator, could jeopardize the safety of the subject, impact the validity of the study results, or interfere with the completion of treatment according to this protocol.
2. Subject has an ALT or serum creatinine greater than 1.5 times the upper limit of normal range for the reference lab at screening.
3. Subject who, in the opinion of the investigator, is febrile at screening.
4. Subject had used the following treatments for IBD: steroids or any or biologic immunomodulators or any topical treatments (e.g. enemas) within the last 4 weeks prior to baseline, immunosuppressants or antimetabolites within the preceding 6 weeks, antibiotic use within the previous 7 days or chronic use of any anti-inflammatory drugs (except aminosalicylates) within 7 days.
5. History of illicit drug abuse or positive urine screen for drugs of abuse or history of alcohol abuse if acknowledged at the screening visit or noted in the subject's medical record at screening.
6. Subject has a positive blood screen for HIV, Hepatitis B (HBsAg), or Hepatitis C.
7. Subject has evidence of infectious colitis, e.g., *Clostridium difficile*, Amoebiasis, *Giardia lamblia* by stool examination of at screening.
8. Subject has evidence for gastrointestinal parasites as per stool ova and parasites testing at screening.
9. Subject has evidence of tuberculosis by blood interferon gamma release assay at screening.
10. Any uncontrolled, intercurrent illness (e.g., active infection).
11. History of gastrointestinal cancer.
12. Abdominal surgery or any major surgery within the preceding 28 days of the screening visit.

Primary Outcome Measure:

The safety and tolerability of Compound in subjects with ulcerative colitis as demonstrated by the frequency and severity of adverse events [Time Frame: 6 Week].

Secondary Outcome Measure:
1. Change in the modified Baron Score from Baseline to Week 6 [Time Frame: 6 Week]
2. Change in the Ulcerative Colitis Clinical Score from Baseline [Time Frame: 6 Week]
3. Change in the partial Mayo Score from baseline [Time Frame: 6 week]
4. Calprotectin concentrations [Time Frame: 6 week]
5. Riley Acute Inflammation Scale (histology) [Time Frame: 6 week]
6. Clinical remission [Time Frame: Week 6]

Example 168. Treating a Subject with Ulcerative Colitis

A subject diagnosed with mild to moderate Ulcerative Colitis (UC), as demonstrated clinically and by endoscopy at visit 2, is treated with Compound Formula (I), (I'), or (I") (hereinafter, "Compound"). The Compound is administered to the subject intravenously or orally at least once, but in some cases, multiple times per week. After a period of time (e.g., six weeks) the subject may show reduced symptoms associated with UC, including ectal bleeding, bloody diarrhea, abdominal cramps, or pain. Additionally, the subject may show a reduced modified Baron Score, Ulcerative Colitis Clinical Score, parial Mayo Score (endoscopic), or Rily Acute Inflammation Scale (histology). In some cases, the subject shows clinical remission. In some cases, biomarkers such as Calprotectin concentrations are reduced, as measured in a fecal sample collected from the subject following treatment as compared to baseline (collected prior to treatment).

The examples and embodiments described herein are for illustrative purposes only and in some embodiments, various modifications or changes are to be included within the purview of disclosure and scope of the appended claims.

What is claimed is:

1. A method of treating an inflammatory bowel disease in a patient in need thereof, comprising administering to the patient a therapeutically effective amount of a compound or a pharmaceutically acceptable salt or solvate thereof, wherein the compound has the structure of Formula (I"):

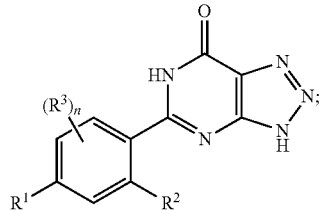

Formula (I")

wherein:

$R^1$ is —$CH_2R^4$, —CN, —$B(OH)_2$, —$N(R^{10})_2$, —$NR^{10}C(O)R^9$, —C(O)OH, —$CH_2C(O)OH$, —$C(O)N(R^{10})_2$, —$C(O)NHS(O)_2N(R^{10})_2$, —$C_{1-6}$alkyl-OH, $C_{3-8}$cycloalkyl,

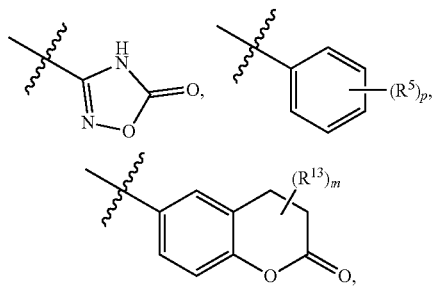

or a 5- or 6-membered heteroaryl optionally substituted with one, two, or three $R^8$ groups;

$R^2$ is H, —OH, —$N(R^{10})_2$, —$NHS(O)_2R^9$, —$S(O)_2N(R^{10})_2$, —$C(O)N(R^{10})_2$, —$OC(O)N(R^{10})_2$, —O—$C_{1-6}$alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$ haloalkyl, $C_{3-8}$cycloalkyl;

each $R^3$ is independently selected from halogen, —CN, —OH, —$OR^9$, —$SR^9$, —$N(R^{10})_2$, —$NO_2$, —$S(O)R^9$, —$S(O)_2R^9$, —$NHS(O)_2R^9$, —$S(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$ alkyl, —$C_{1-6}$alkyl-OH, —$C_{1-6}$alkyl-$OR^9$, —$C_{1-6}$alkyl-$N(R^{10})_2$, $C_{2-6}$alkenyl, $C_{2-6}$alkynyl, $C_{1-6}$ haloalkyl, $C_{3-8}$cycloalkyl, and —$C_{1-6}$alkyl-$C_{3-8}$cycloalkyl;

$R^4$ is

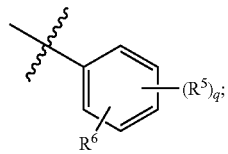

each R5 is independently selected from halogen, —CN, —OH, —$OR^9$, —$SR^9$, —$N(R^{10})_2$, —$S(O)R^9$, —$S(O)_2R^9$, —$NHS(O)_2R^9$, —$S(O)_2N(R^{10})_2$, —$C(O)NHS(O)_2N(R^{10})_2$, —$C(O)R^9$, —$C(O)OR^{10}$, —$OC(O)R^9$, —$C(O)N(R^{10})_2$, —$OC(O)N(R^{10})_2$, —$NR^{10}C(O)N(R^{10})_2$, —$NR^{10}C(O)R^9$, —$NR^{10}C(O)OR^9$, $C_{1-6}$alkyl, —$C_{1-6}$alkyl-$R^9$, —$C_{1-6}$alkyl-OH, —$C_{1-6}$alkyl-$OR^9$, —$C_{1-6}$alkyl-$N(R^{10})_2$, —$C_{1-6}$alkyl-$C(O)OR^{10}$, $C_{2-6}$alkenyl, —$C_{2-6}$alkenyl-$C(O)OR^{10}$, $C_{2-6}$alkynyl, $C_{1-6}$ haloalkyl, $C_{1-6}$haloalkyl-OH, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, and $C_{1-9}$ heteroaryl; wherein $C_{3-8}$cycloalkyl, —$C_{1-6}$alkyl-$C_{3-8}$cycloalkyl, phenyl, —$C_{1-6}$alkyl-phenyl, and $C_{1-9}$heteroaryl are optionally substituted with one, two, or three groups independently selected from halogen, —$C(O)OR^{10}$, $C_{1-6}$alkyl, $C_{1-6}$haloalkyl, $C_{3-8}$ cycloalkyl, and $C_{2-9}$heterocycloalkyl; and wherein $C_{2-9}$heterocycloalkyl and —$C_{1-6}$ alkyl-$C_{2-9}$heterocycloalkyl are optionally substituted with one, two, or three groups independently selected from halogen, —$C(O)OR^{10}$, $C_{1-6}$alkyl, $C_{1-6}$haloalkyl, and oxo;

$R^6$ is —C(O)OR$^7$, —C(O)NHS(O)$_2$N(R$^{10}$)$_2$,

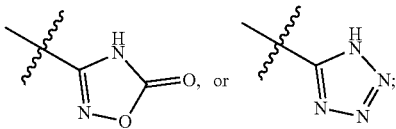 [SMILES: *c1noc(=O)[nH]1 ; *c1nnn[nH]1]

$R^7$ is independently selected from H and C$_{1-6}$alkyl;
each $R^8$ is independently selected from halogen, —OH, —OR$^9$, —N(R$^{10}$)$_2$, —S(O)R$^9$, —S(O)$_2$R$^9$, —NHS(O)$_2$R$^9$, —S(O)$_2$N(R$^{10}$)$_2$, —C(O)NHS(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$), —NR$^{10}$C(O)N(R$^{10}$)$_2$, —NR$^{10}$C(O)R$^9$, —NR$^{10}$C(O)OR$^9$, C$_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{1-6}$haloalkyl, C$_{1-6}$haloalkyl-OH, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, and C$_{1-9}$heteroaryl; wherein phenyl, —C$_{1-6}$alkyl-phenyl, and C$_{1-9}$heteroaryl are optionally substituted with one, two, or three groups independently selected from halogen, C$_{1-6}$alkyl, C$_{1-6}$haloalkyl, C$_{3-8}$cycloalkyl, and C$_{2-9}$heterocycloalkyl; and wherein C$_{2-9}$heterocycloalkyl is optionally substituted with one, two, or three groups independently selected from halogen, C$_{1-6}$alkyl, C$_{1-6}$ haloalkyl, and oxo;
each $R^9$ is independently selected from C$_{1-6}$alkyl, C$_{1-6}$haloalkyl, C$_{3-8}$cycloalkyl, —C$_{1-6}$alkyl-C$_{3-8}$cycloalkyl, phenyl, —C$_{1-6}$alkyl-phenyl, C$_{2-9}$heterocycloalkyl, —C$_{1-6}$alkyl-C$_{2-9}$heterocycloalkyl, C$_{2-9}$heteroaryl, and —C$_{1-6}$alkyl-C$_{2-9}$heteroaryl, wherein C$_{1-6}$alkyl, phenyl, —C$_{1-6}$alkyl-phenyl, —C$_{1-6}$alkyl-C$_{2-9}$heterocycloalkyl, C$_{2-9}$heteroaryl, and —C$_{1-6}$ alkyl-C$_{2-9}$heteroaryl are optionally substituted with one or two groups independently selected from C$_{1-6}$alkyl, —OR$^{11}$, —N(R$^{11}$)$_2$, C$_{1-6}$alkyl, C$_{3-8}$cycloalkyl, —N(R$^{11}$)C(O)R$^{12}$, —C(O)R$^{12}$, and —C(O)OR$^{12}$;
each $R^{10}$ is independently selected from H, C$_{1-6}$alkyl, C$_{1-6}$haloalkyl, C$_{3-8}$cycloalkyl, —C$_{1-6}$ alkyl-C$_{3-8}$cycloalkyl, phenyl, —C$_{1-6}$alkyl-phenyl, and C$_{2-9}$heteroaryl, wherein C$_{1-6}$ alkyl, phenyl, —C$_{1-6}$alkyl-phenyl, and C$_{2-9}$heteroaryl are optionally substituted with one or two groups independently selected from halogen, C$_{1-6}$alkyl, —N(R$^{11}$)$_2$, and —C(O)OR$^{12}$; or two $R^{10}$ and the nitrogen atom to which they are attached are combined to form a 5- or 6-membered heterocycloalkyl ring optionally substituted with one, two, or three groups independently selected from C$_{1-6}$alkyl, oxo, and —C(O)OH;
each $R^{11}$ is independently selected from H and C$_{1-6}$alkyl;
each $R^{12}$ is independently selected from H and C$_{1-6}$alkyl;
each $R^{13}$ is independently selected from C$_{1-6}$alkyl;
m is 1, 2, 3, or 4;
n is 0, 1, 2, or 3;
p is 0, 1, 2, 3, 4, or 5; and
q is 0, 1, 2, 3, or 4;
or a pharmaceutically acceptable salt or solvate thereof.

2. The method of claim 1, wherein $R^1$ is

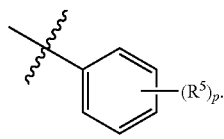

3. The method of claim 2, wherein p is 0, 1, or 2.

4. The method of claim 3, wherein each $R^5$ is independently selected from halogen, —OH, —OR$^9$, —N(R$^{10}$)$_2$, —S(O)$_2$R$^9$, —NHS(O)$_2$R$^9$, —S(O)$_2$N(R$^{10}$)$_2$, —C(O)NHS(O)$_2$N(R$^{10}$)$_2$, —C(O)R$^9$, —C(O)OR$^{10}$, —OC(O)R$^9$, —C(O)N(R$^{10}$)$_2$, —OC(O)N(R$^{10}$), —NR$^{10}$C(O)N(R$^{10}$)$_2$, —NR$^{10}$C(O)R$^9$, C$_{1-6}$alkyl, —C$_{1-6}$alkyl-OH, —C$_{1-6}$alkyl-OR$^9$, —C$_{1-6}$alkyl-N(R$^{10}$)$_2$, —C$_{1-6}$alkyl-C(O)OR$^{10}$, C$_{1-6}$haloalkyl, C$_{1-6}$haloalkyl-OH, C$_{3-8}$cycloalkyl, C$_{2-9}$heterocycloalkyl, and C$_{1-9}$heteroaryl.

5. The method of claim 4, wherein each $R^5$ is independently selected from halogen, —OH, —OR$^9$, —N(R$^{10}$)$_2$, —C(O)NHS(O)$_2$N(R$^{10}$)$_2$, —C(O)OR$^{10}$, —C(O)N(R$^{10}$)$_2$, —NR$^{10}$C(O)R$^9$, C$_{1-6}$alkyl, —C$_{1-6}$alkyl-C(O)OR$^{10}$, and C$_{1-9}$heteroaryl.

6. The method of claim 5, wherein each $R^5$ is independently selected from halogen, —OH, —OR$^9$, —C(O)OR$^{10}$, —C(O)N(R$^{10}$)$_2$, C$_{1-6}$alkyl, —C$_{1-6}$alkyl-C(O)OR$^{10}$, and

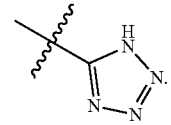 [SMILES: *c1nnn[nH]1]

7. The method of claim 6, wherein each $R^5$ is independently selected from halogen, —OH, and —C(O)OR$^{10}$.

8. The method of claim 4, wherein each $R^5$ is independently selected from halogen, —OH, —OR$^9$ and —C$_{1-6}$alkyl-C(O)OR$^{10}$.

9. The method of claim 8, wherein $R^9$ is C$_{1-6}$alkyl optionally substituted with —C(O)OR$^{12}$.

10. The method of claim 4, wherein each $R^{10}$ is independently selected from H and C$_{1-6}$alkyl.

11. The method of claim 1, wherein $R^1$ is a 5- or 6-membered heteroaryl optionally substituted with one, two, or three $R^8$ groups.

12. The method of claim 11, wherein $R^1$ is a 5-membered heteroaryl optionally substituted with one or two $R^8$ groups, wherein the 5-membered heteroaryl is selected from oxazolyl, thiazolyl, pyrazolyl, furanyl, thienyl, pyrrolyl, tetrazolyl, and isoxazolyl.

13. The method of claim 11, wherein $R^1$ is a 6-membered heteroaryl optionally substituted with one or two $R^8$ groups, wherein the 6-membered heteroaryl is selected from pyridinyl and pyrimidinyl.

14. The method of claim 11, wherein each $R^8$ is independently selected from halogen, —C(O)OR$^{10}$, C$_{1-6}$alkyl, and —C$_{1-6}$alkyl-C(O)OR$^{10}$.

15. The method of claim 1, wherein $R^2$ is H, —OH, —N(R$^{10}$)$_2$, or —O—C$_{1-6}$alkyl.

16. The method of claim 15, wherein $R^2$ is —OCH$_2$CH$_3$.

17. The method of claim 1, wherein n is 0.

18. A method of treating an inflammatory bowel disease in a patient in need thereof, comprising administering to the patient a therapeutically effective amount of a compound or a pharmaceutically acceptable salt or solvate thereof, wherein the compound is selected from:

275
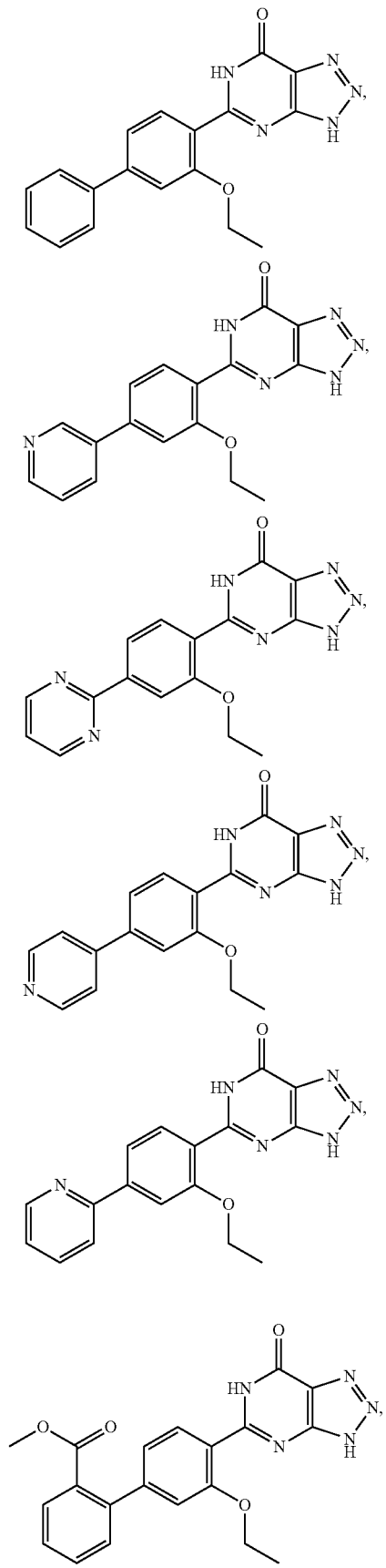
276
-continued
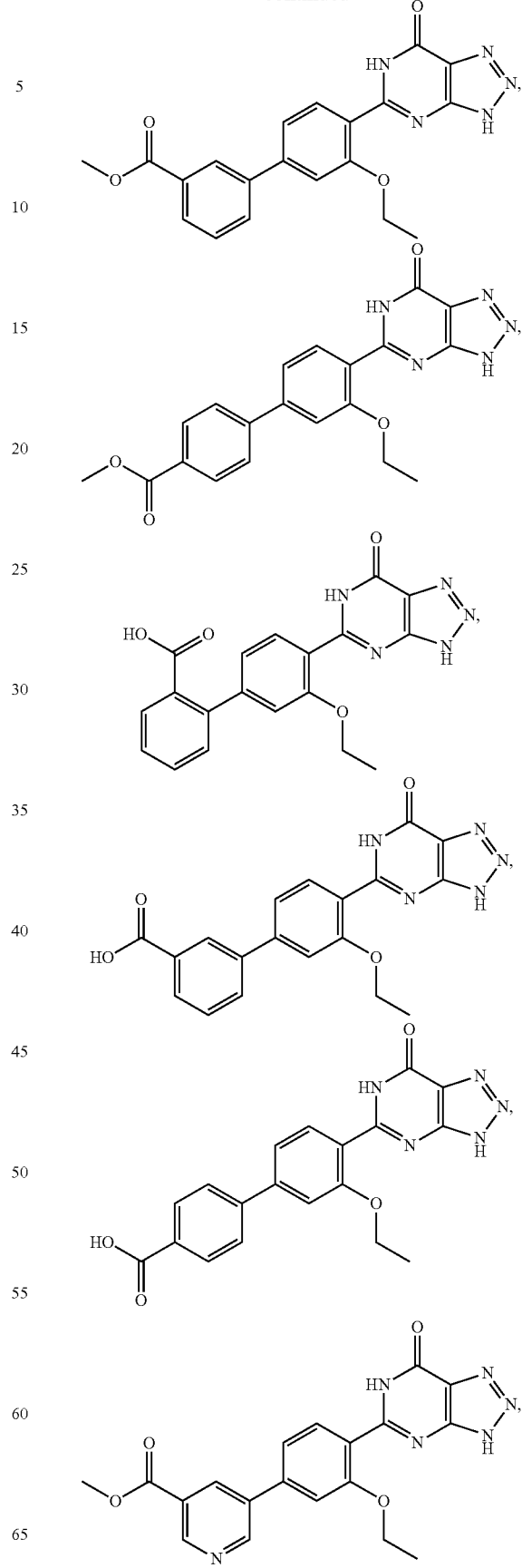

277
-continued
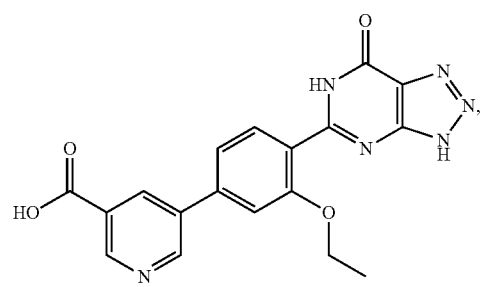
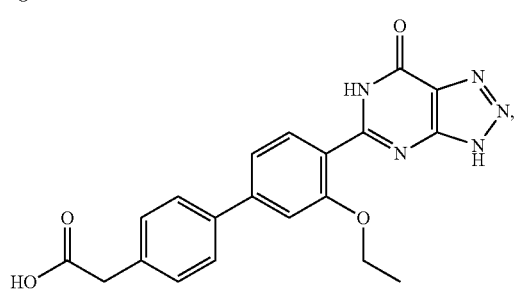
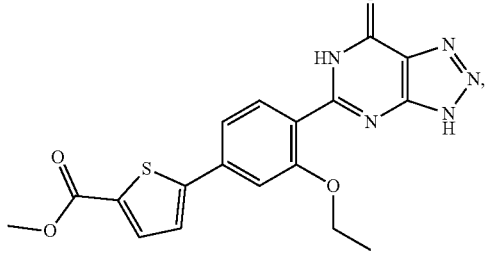
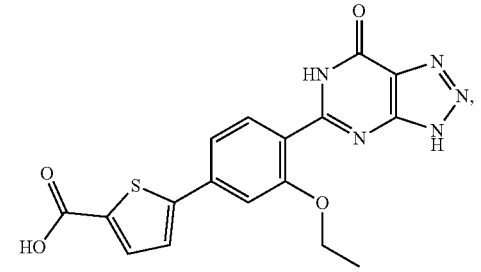
278
-continued
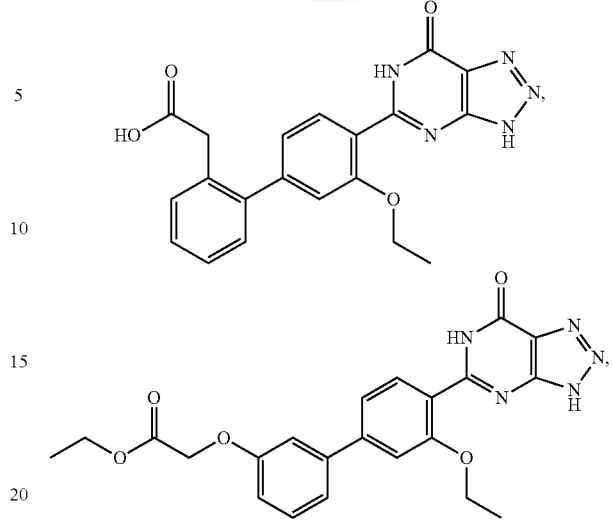
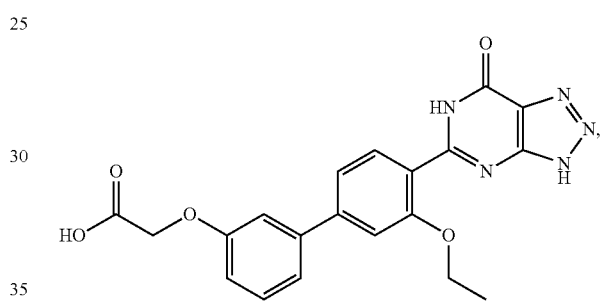
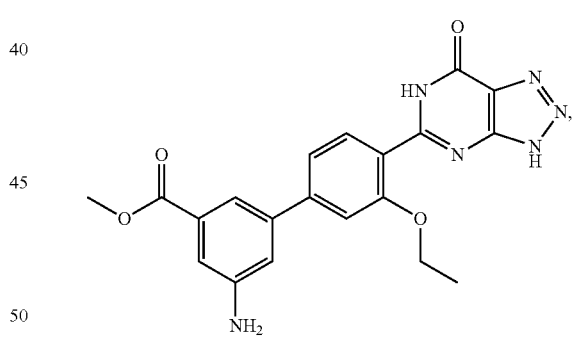
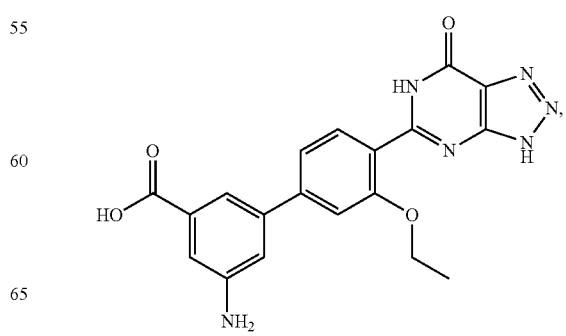

279
-continued
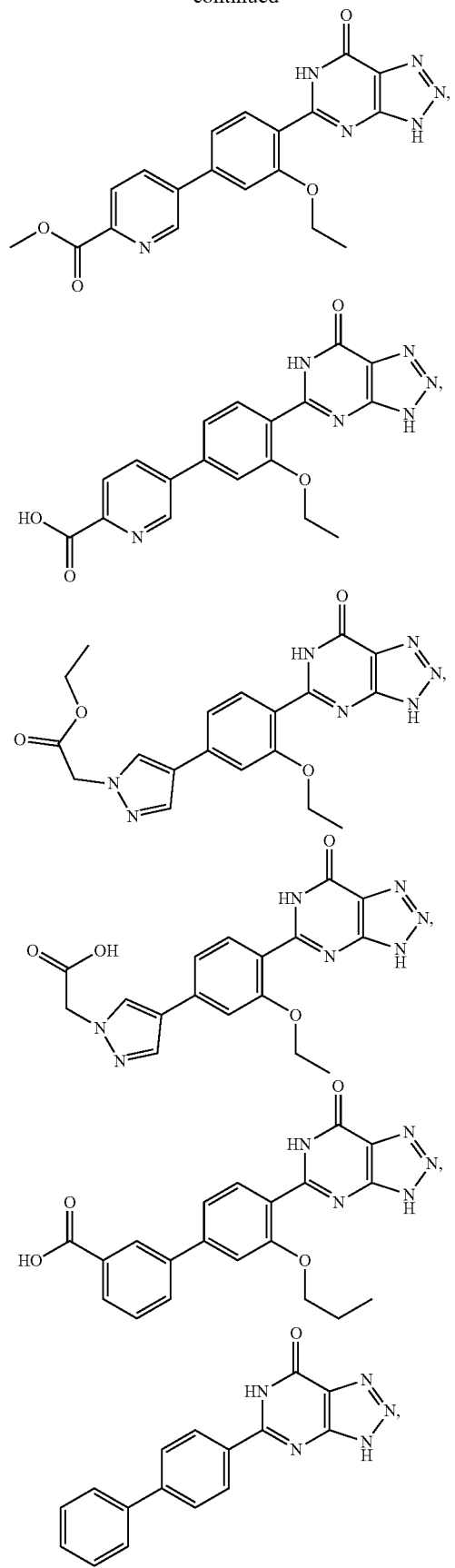
280
-continued
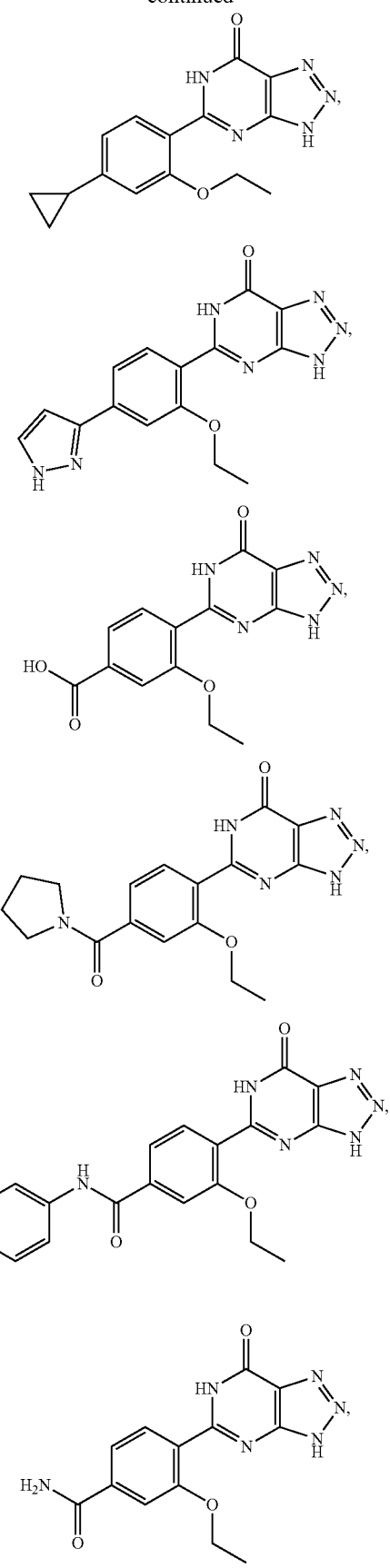

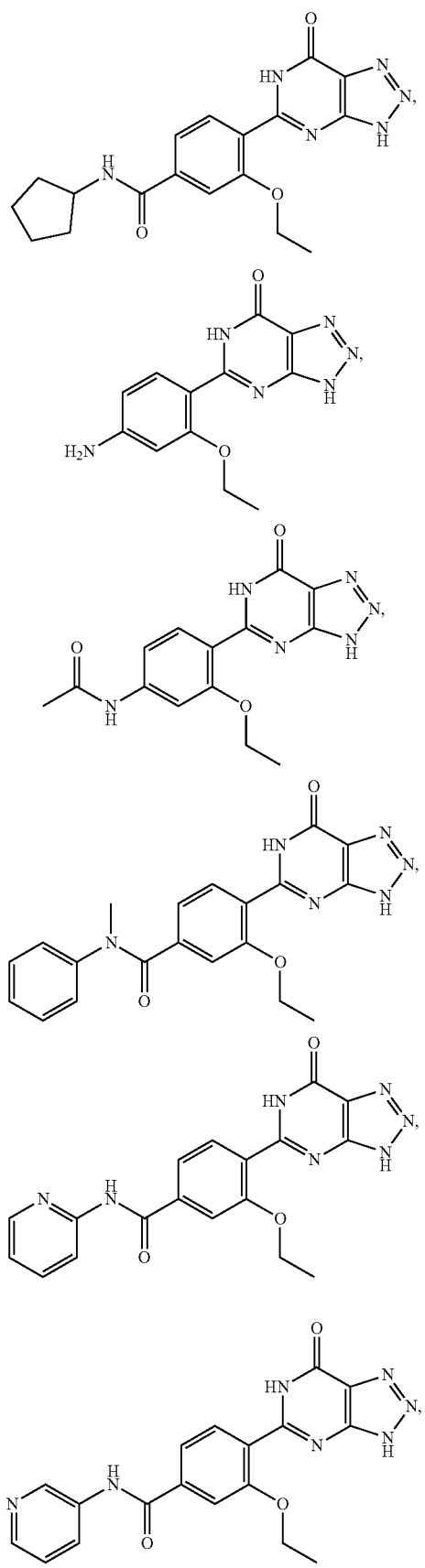
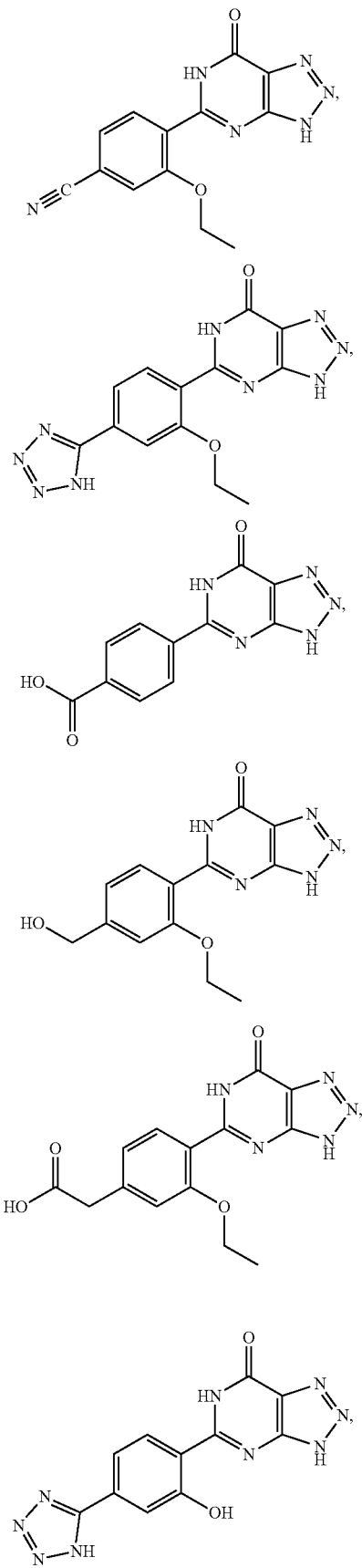

283
-continued
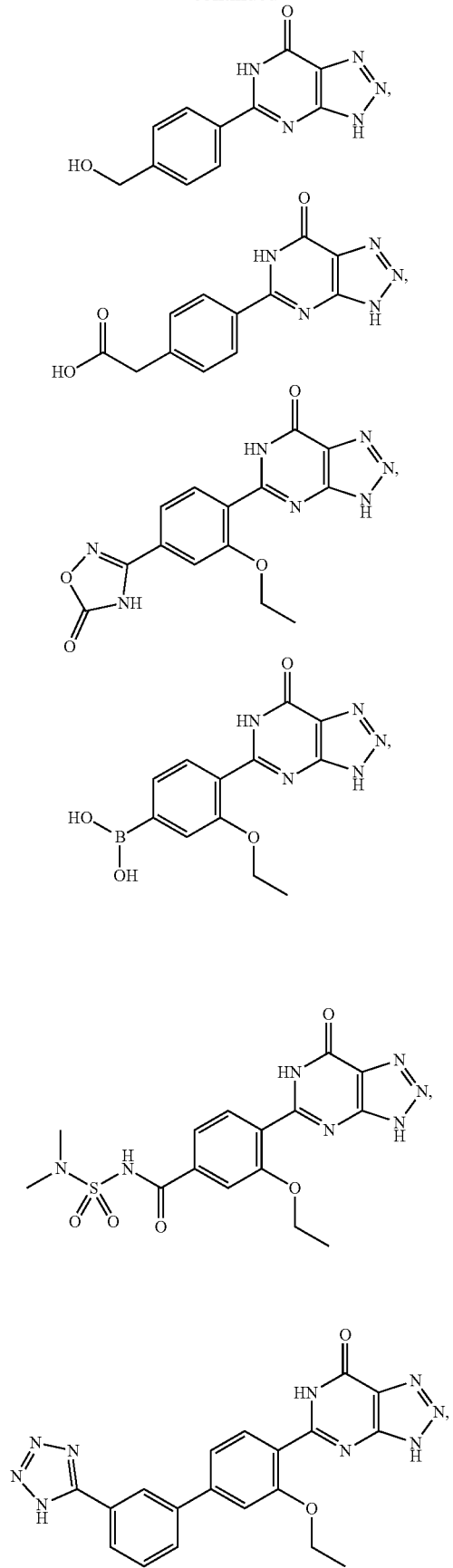
284
-continued
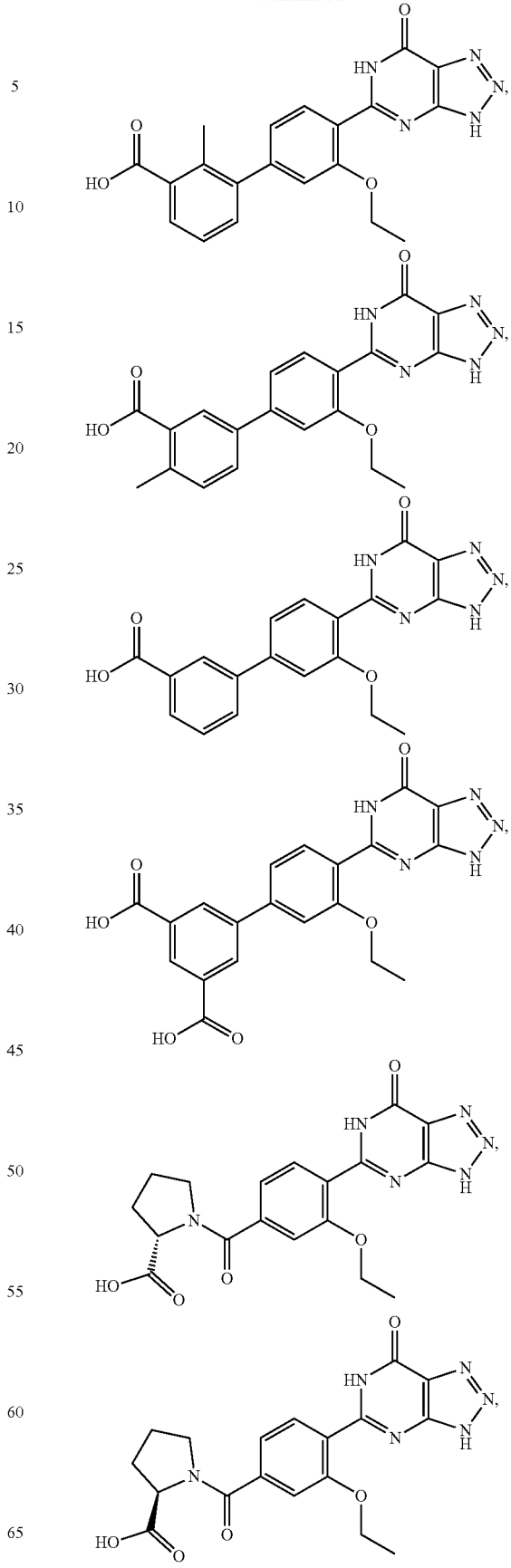

285
-continued
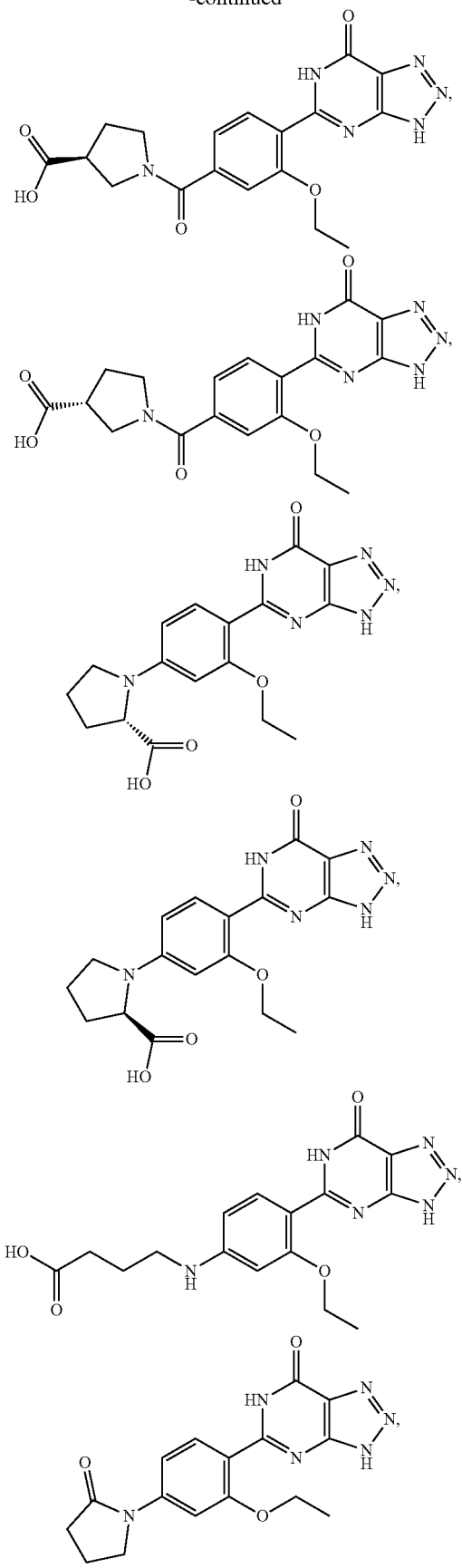
286
-continued
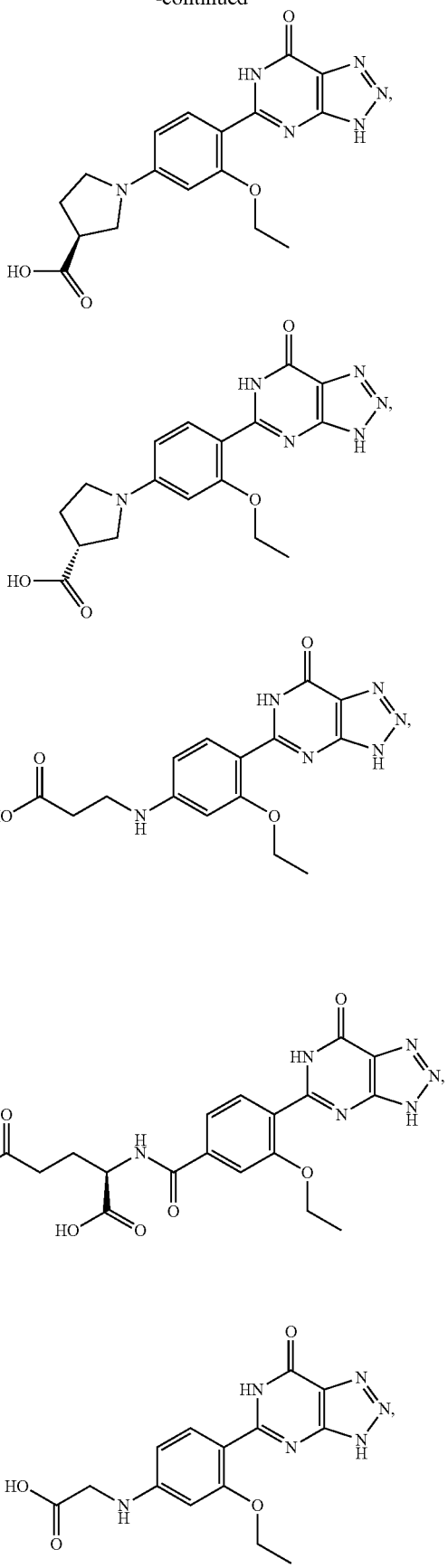

287
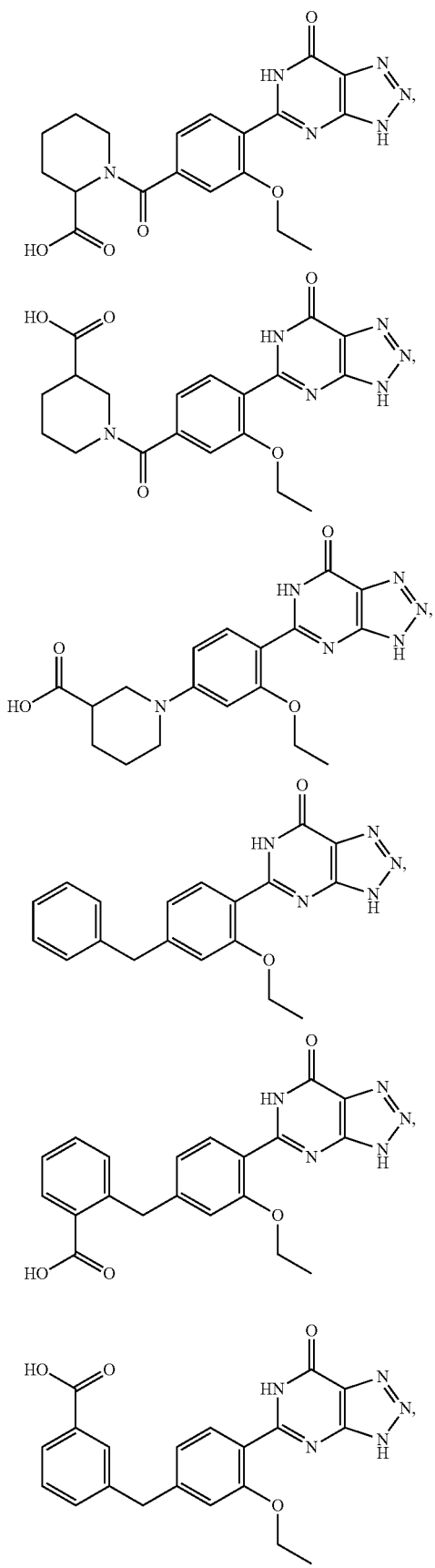
288
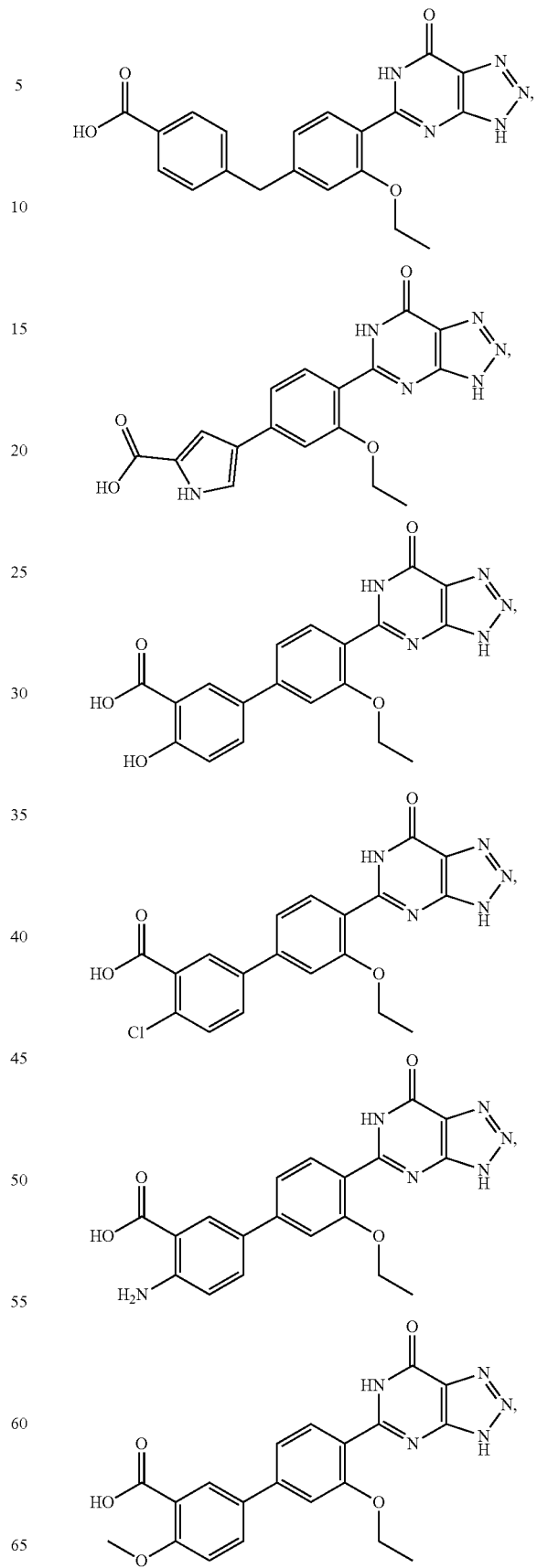

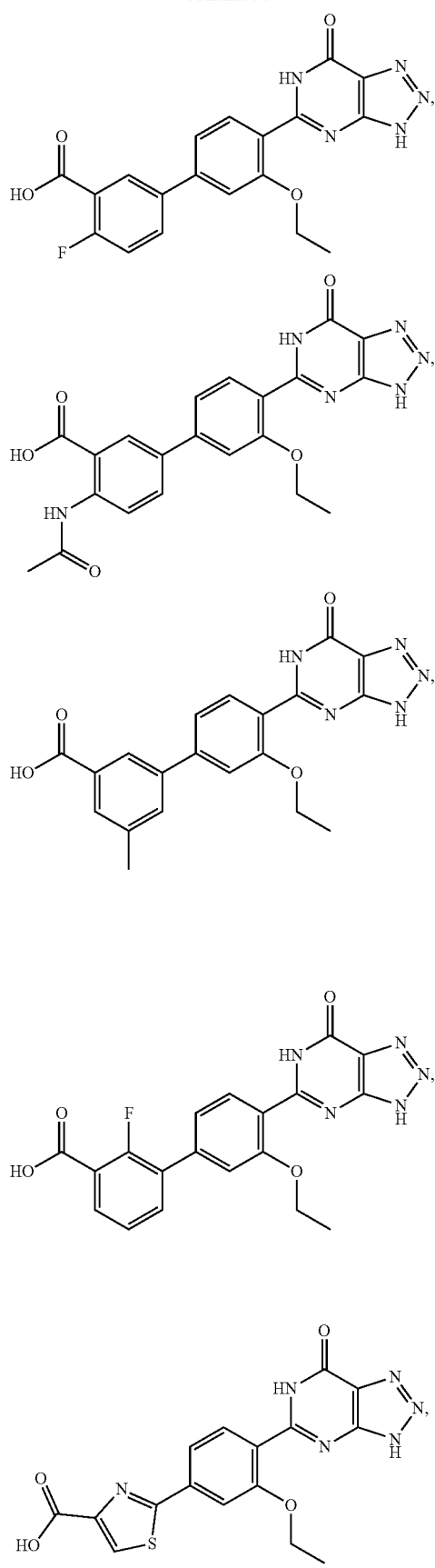
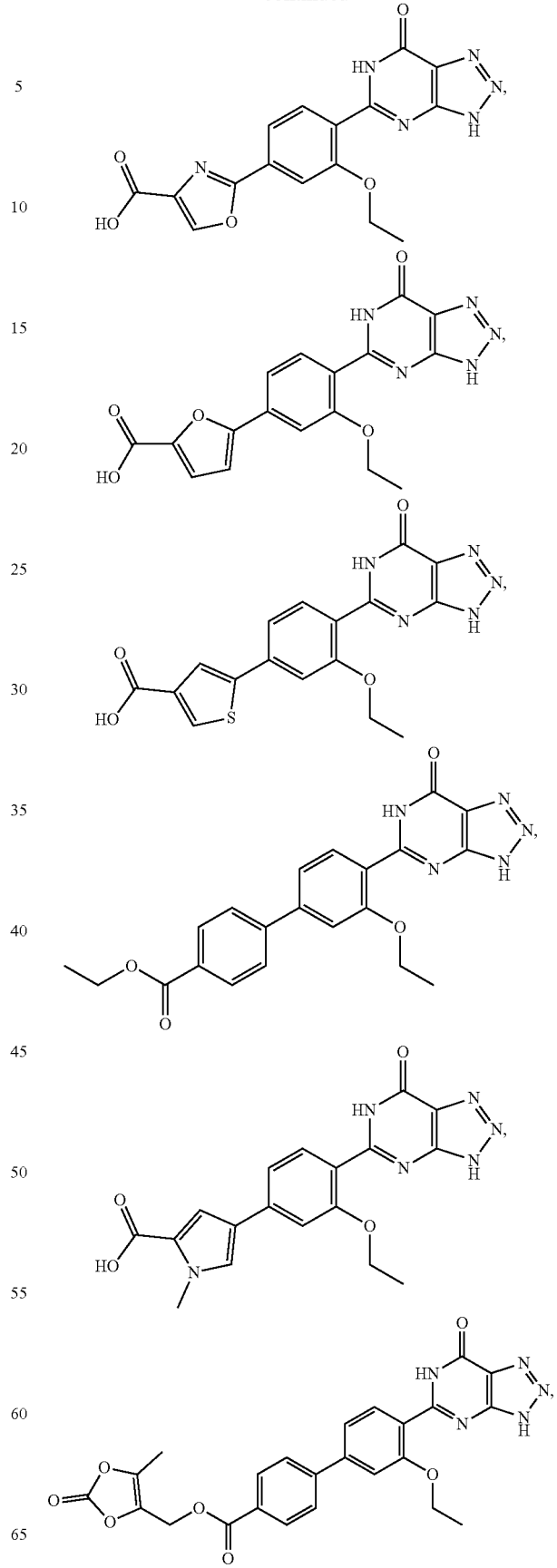

291
-continued
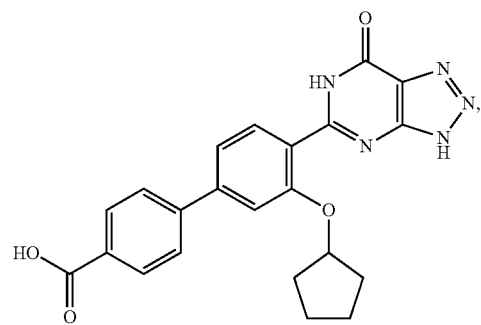
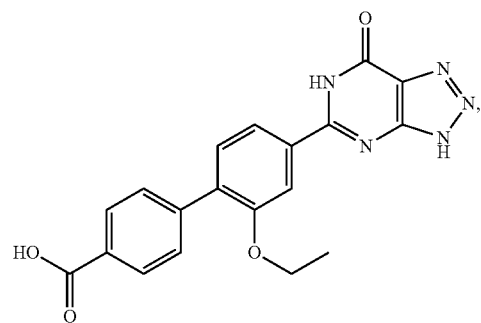
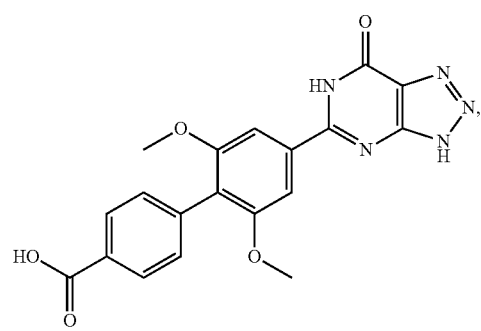
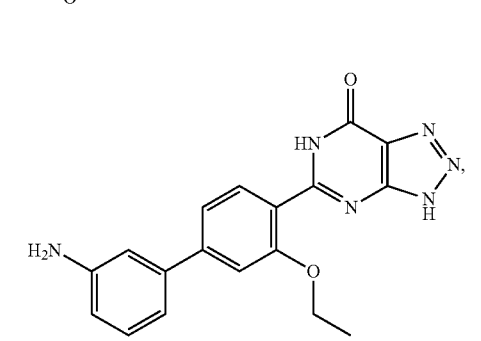
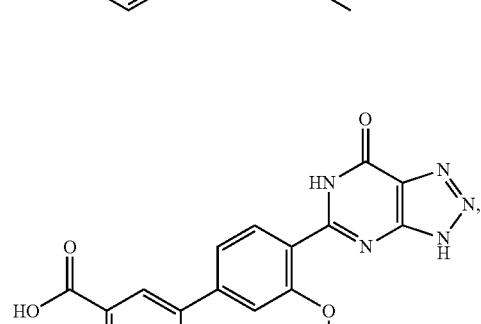
292
-continued
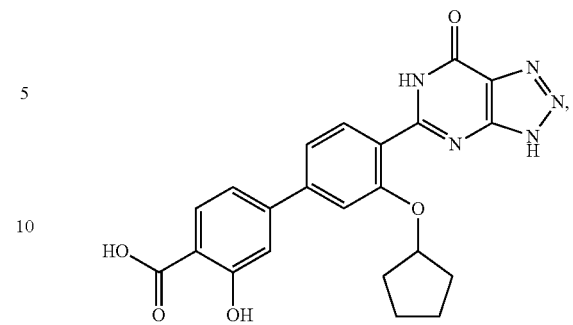
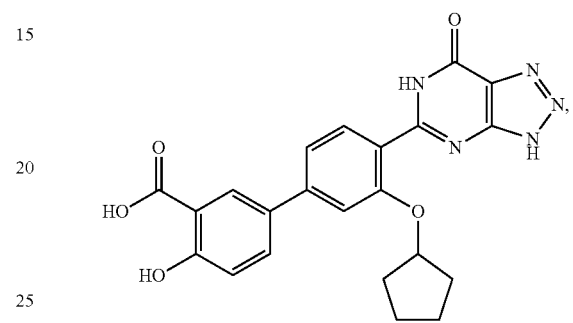
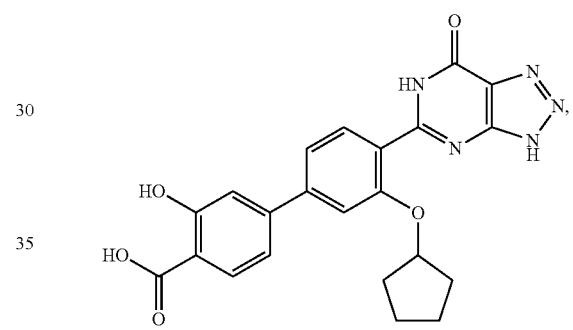
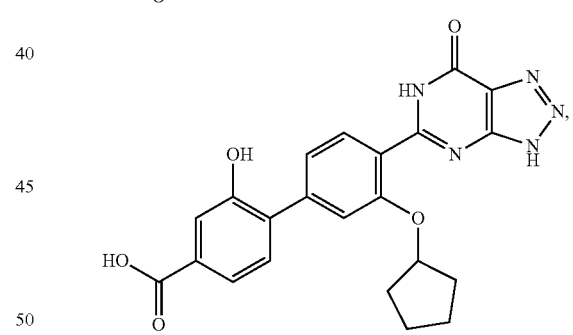
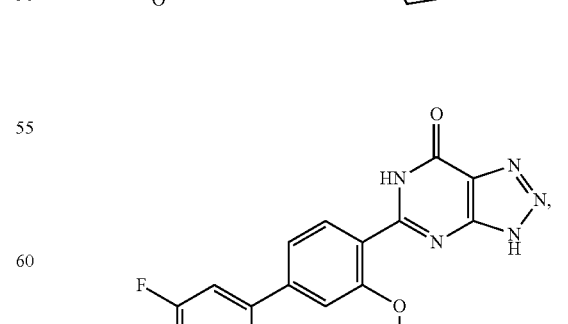

293
-continued
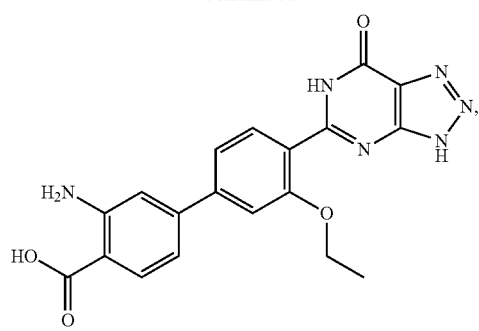
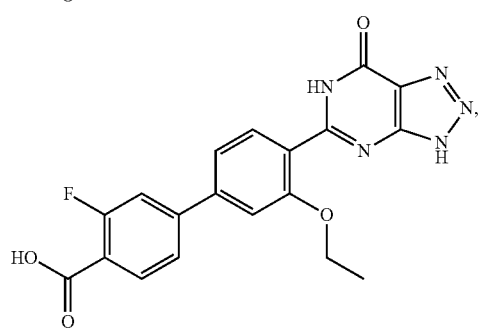
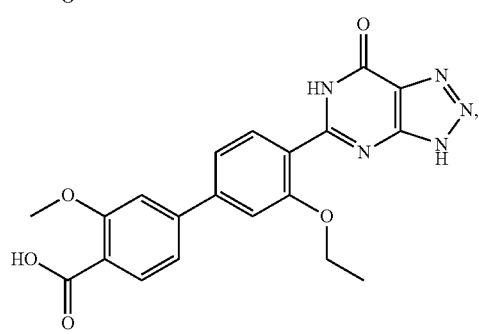
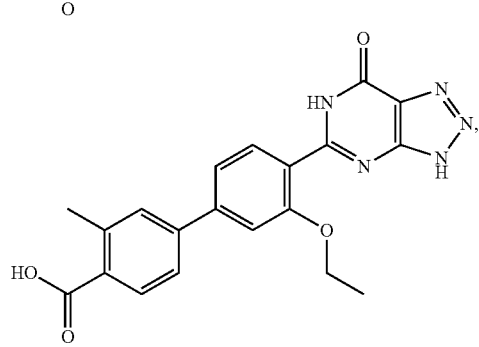
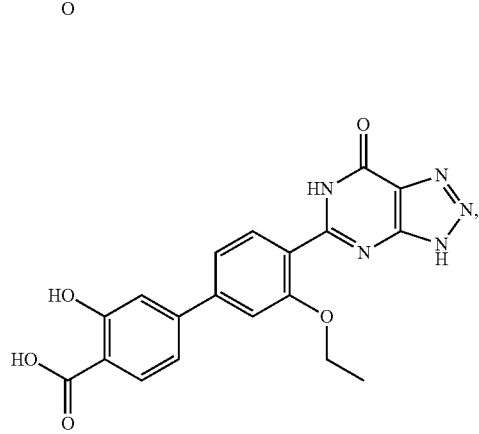
294
-continued
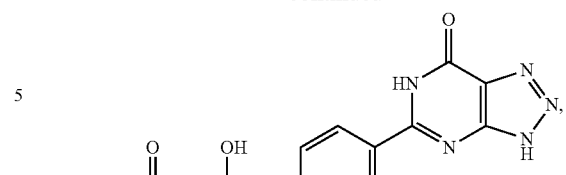
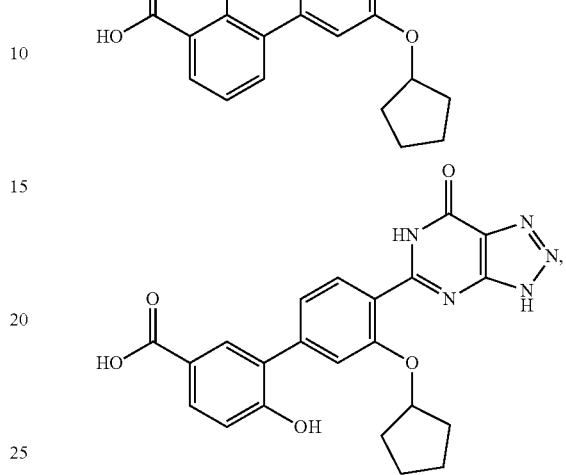
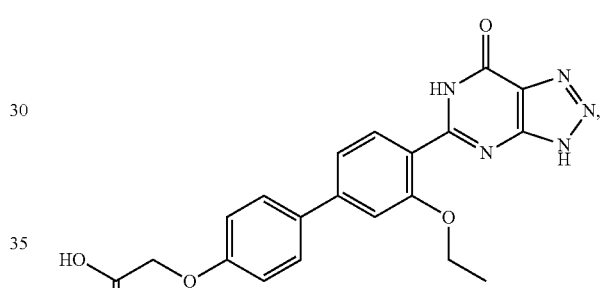
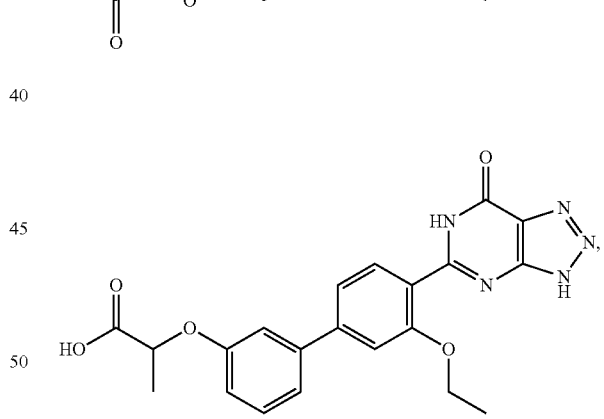
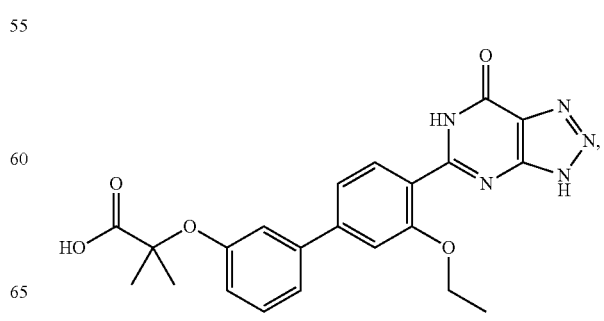

295
-continued
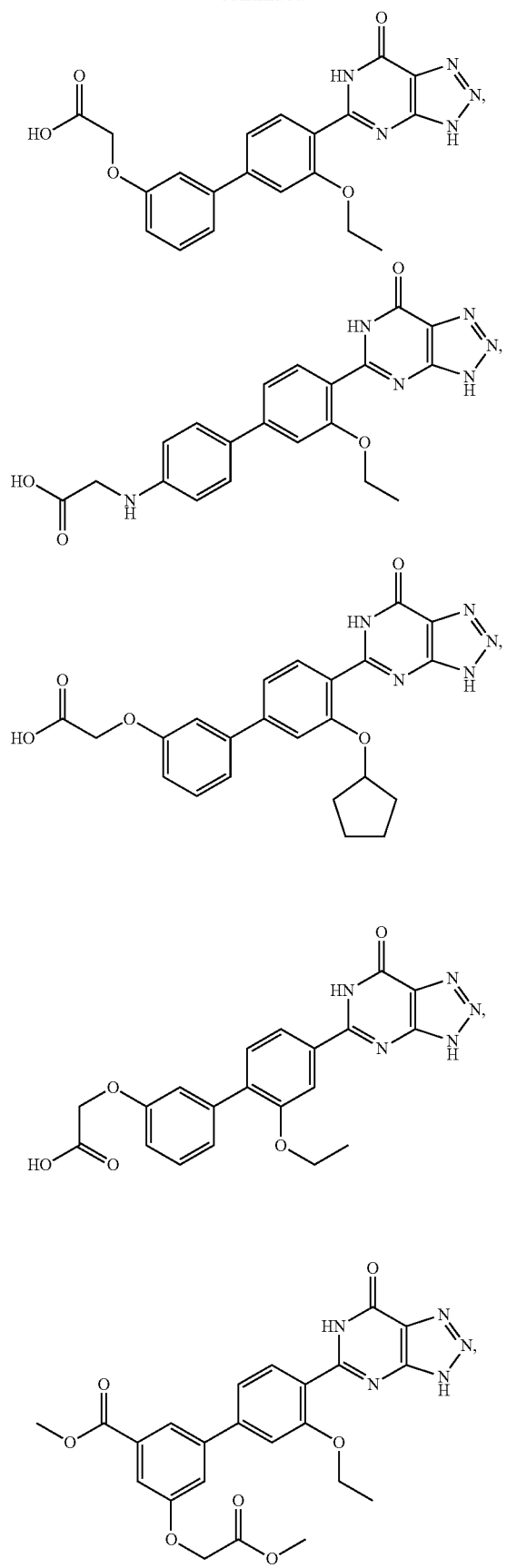
296
-continued
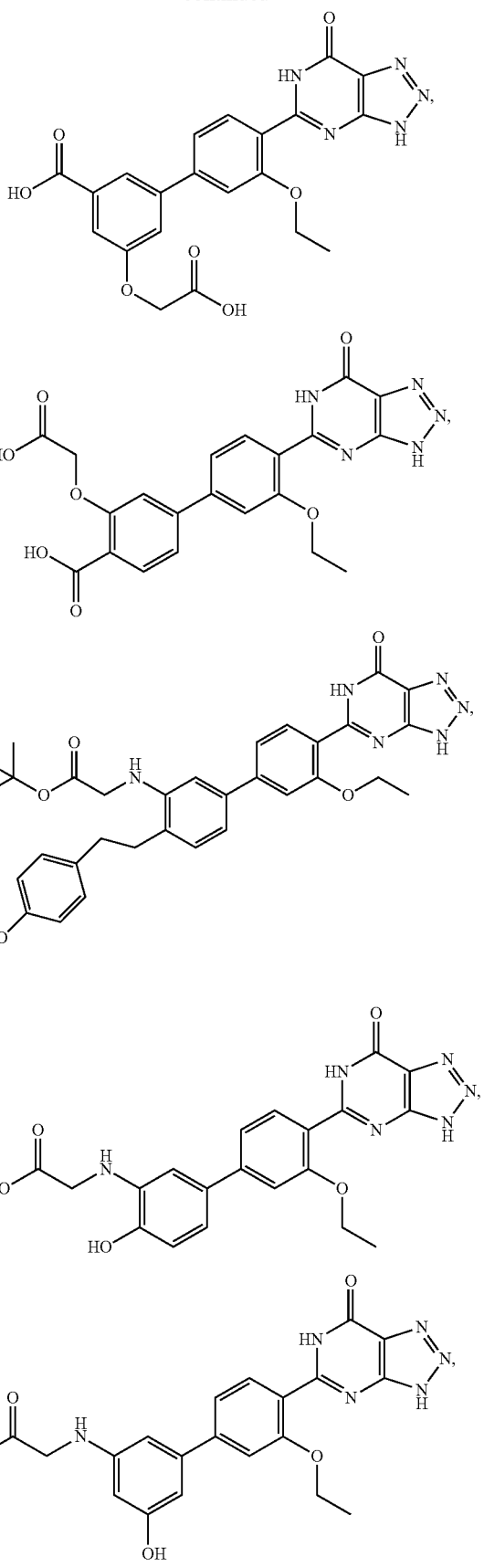

297
-continued
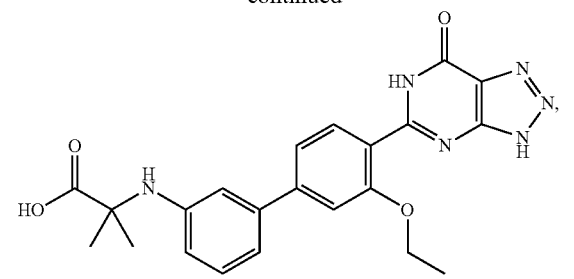
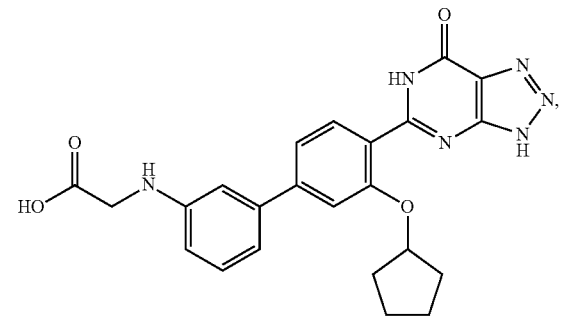
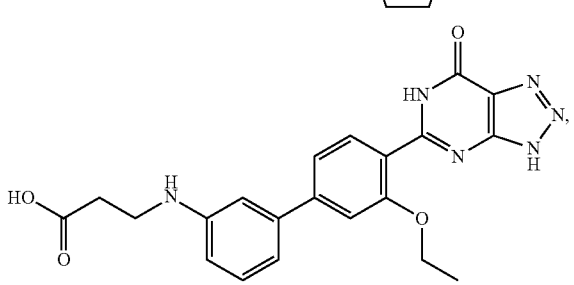
298
-continued
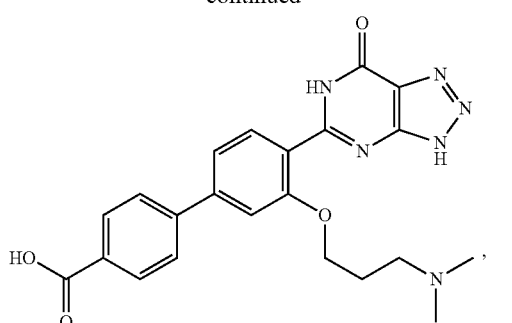

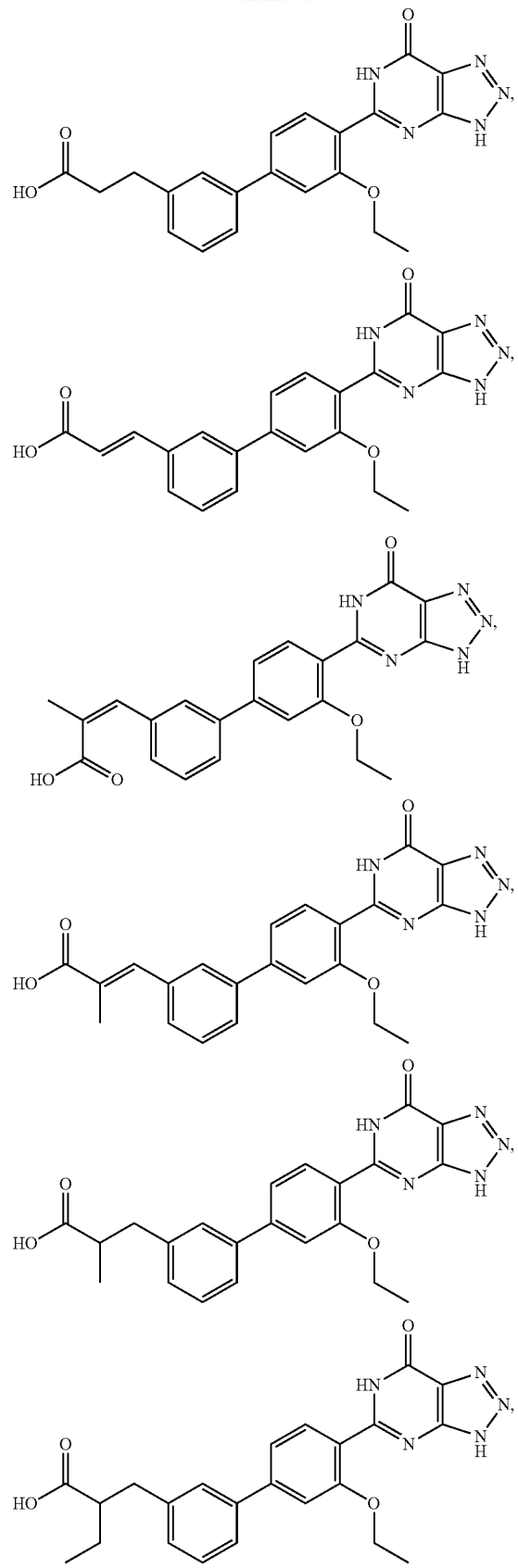
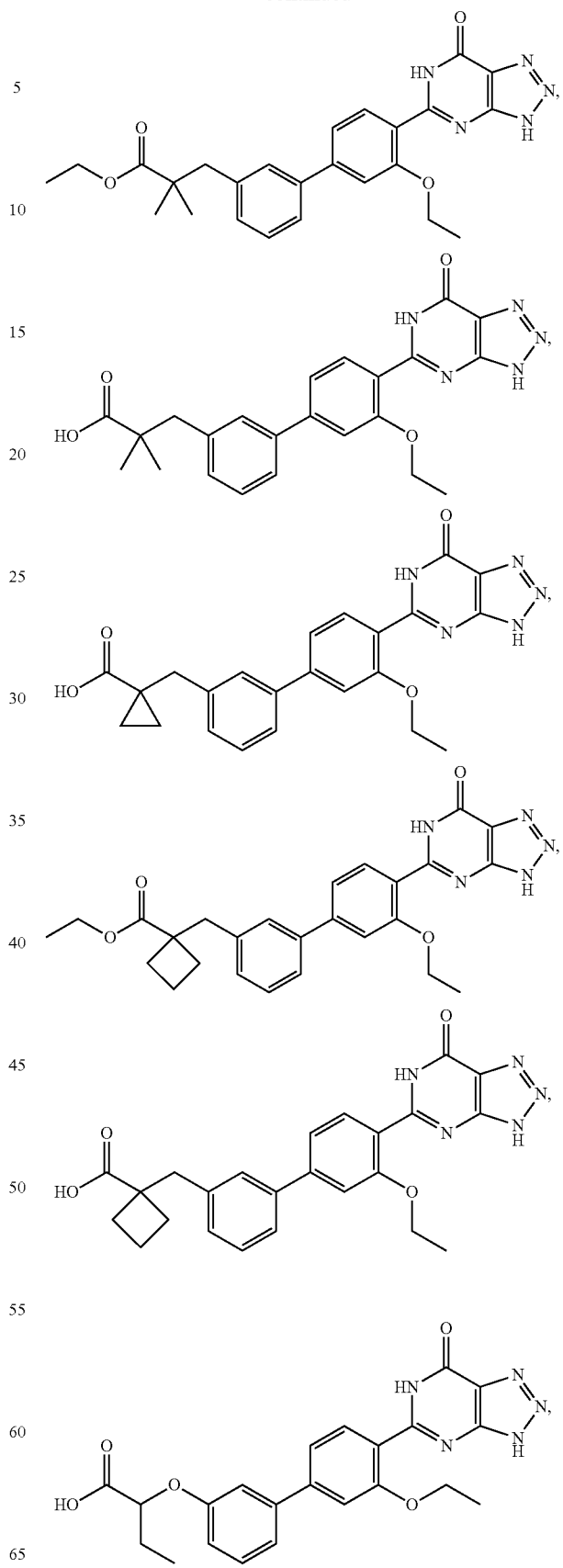

301
-continued
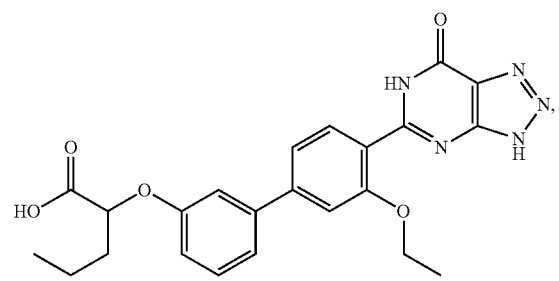
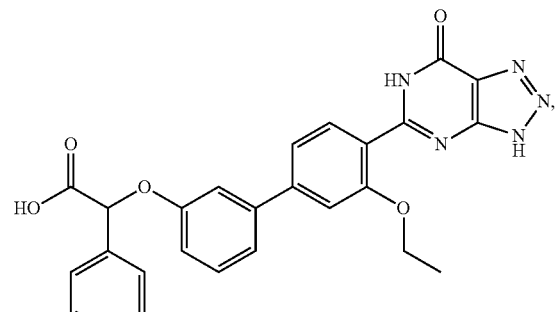
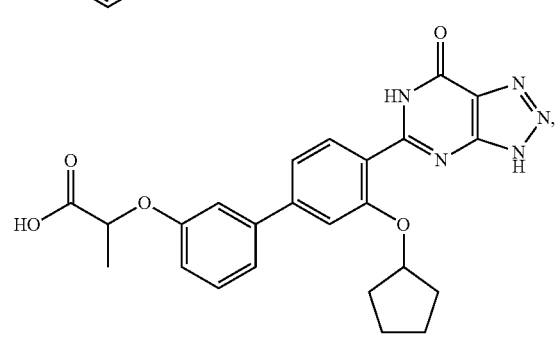
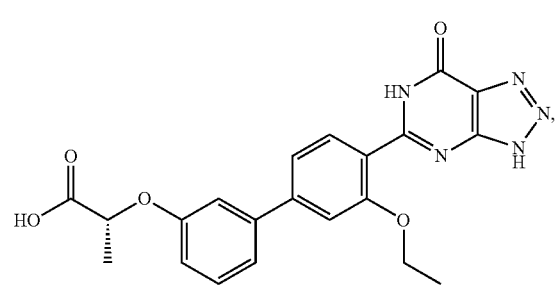
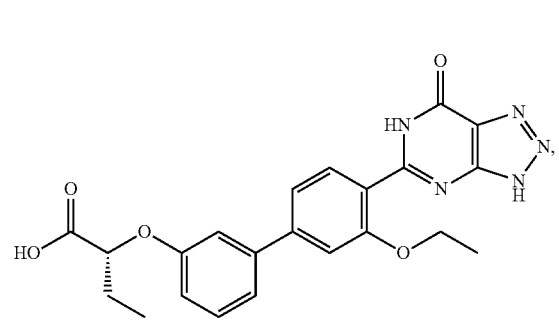
302
-continued
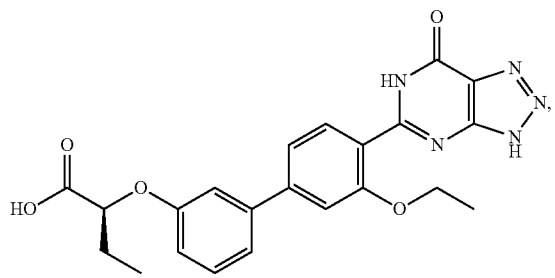
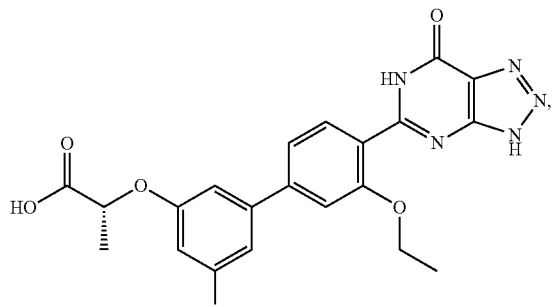
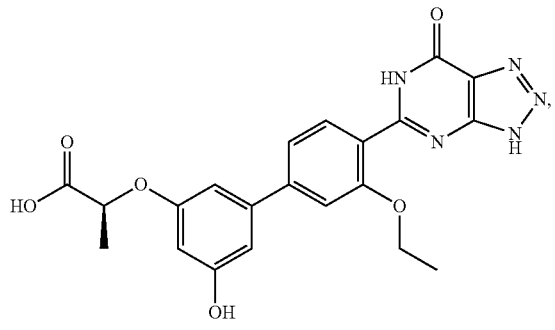
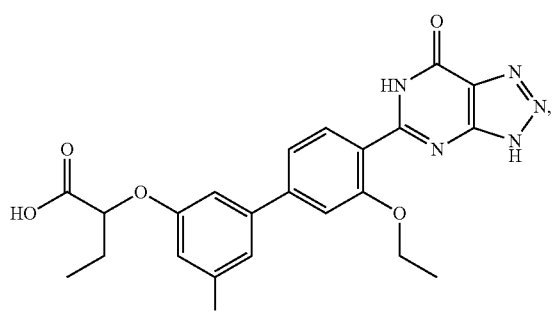
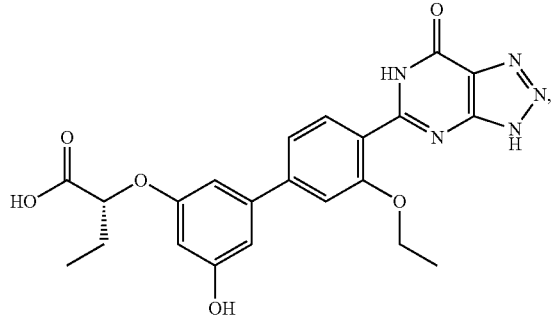

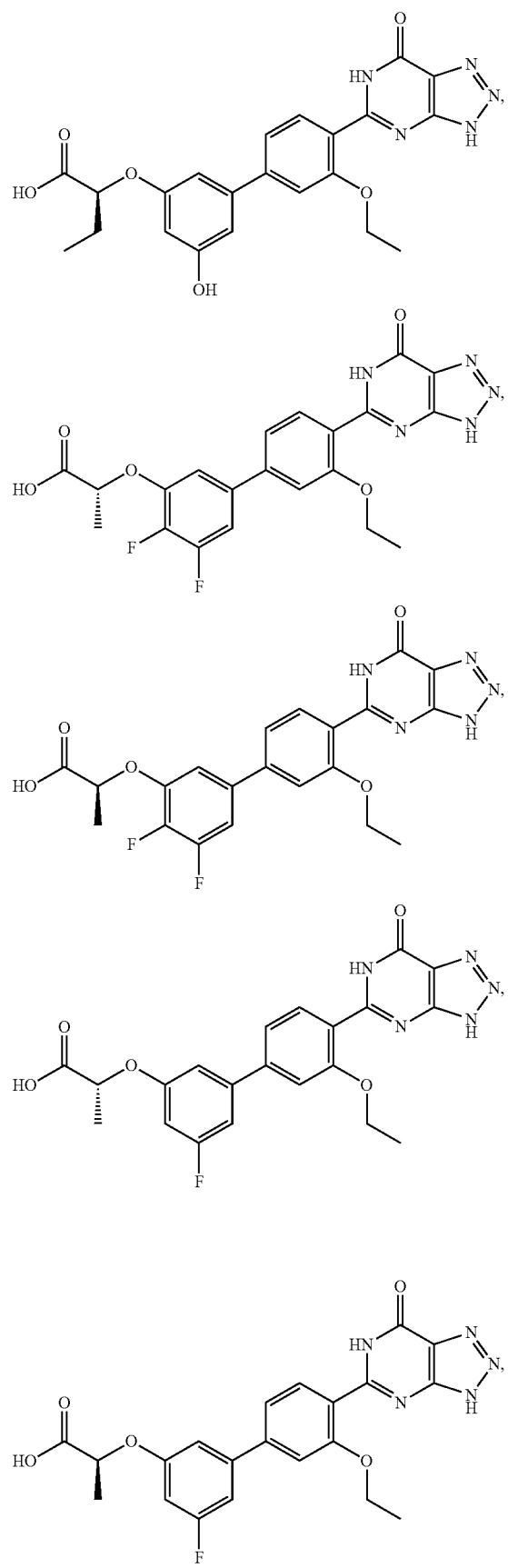
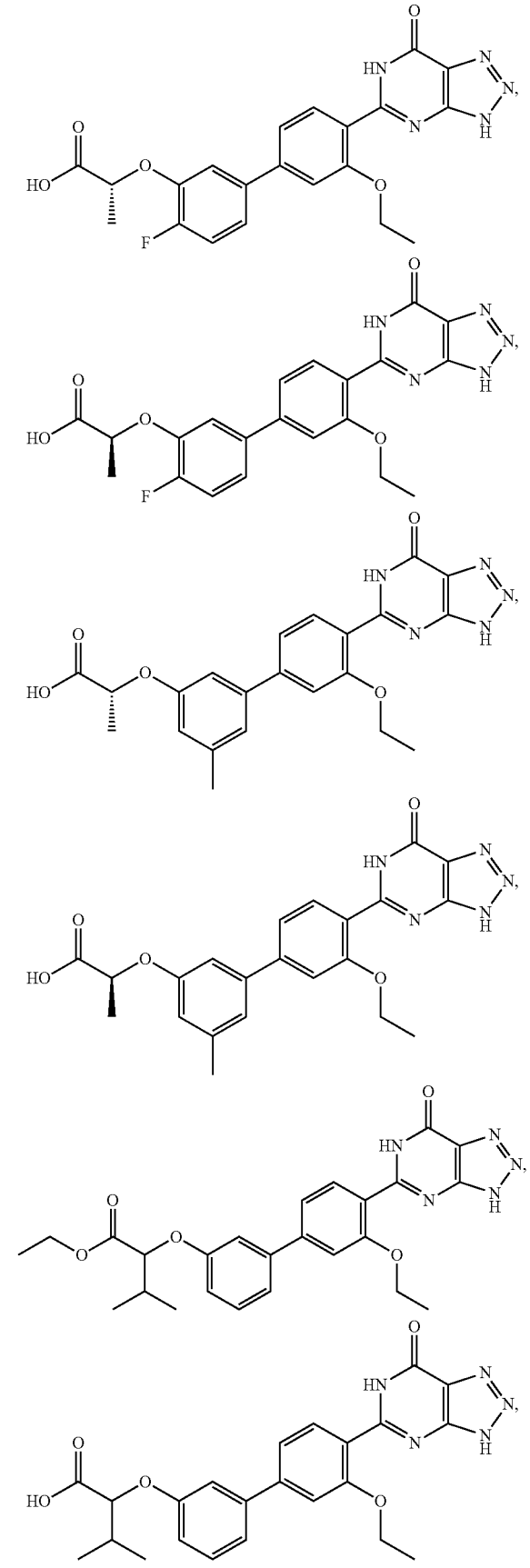

305
-continued
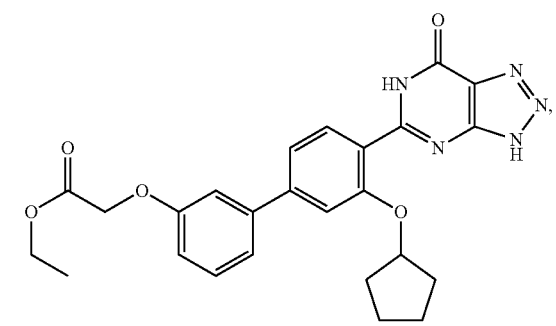
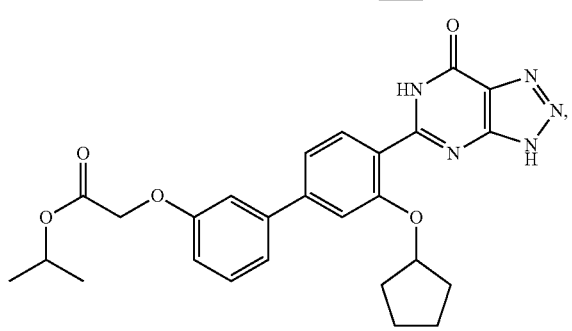
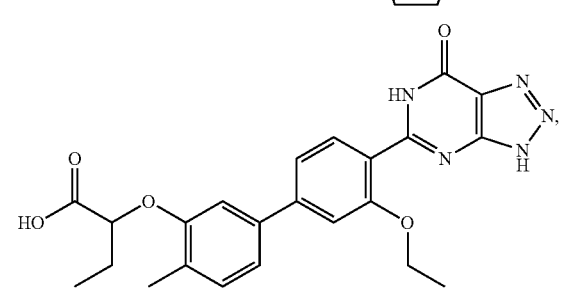
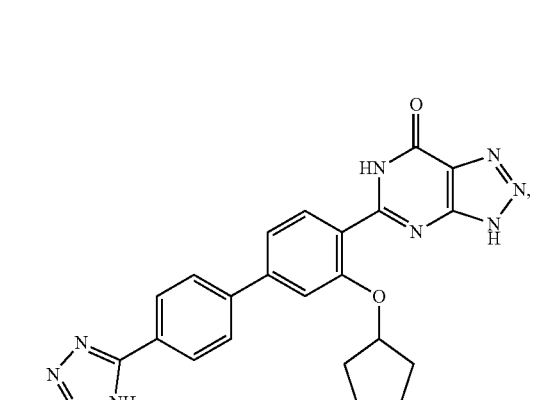
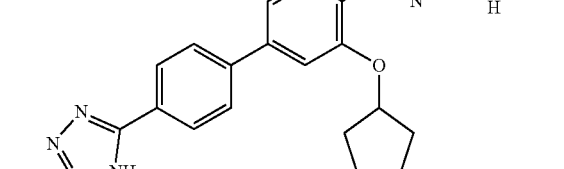
306
-continued
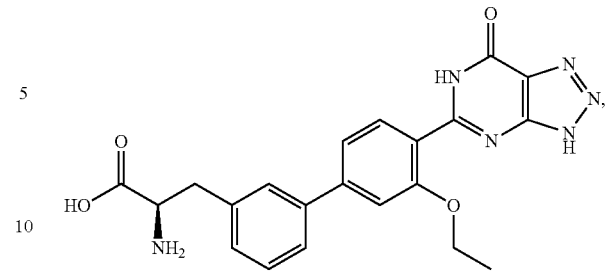
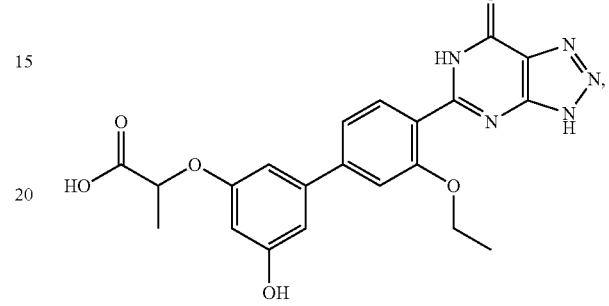
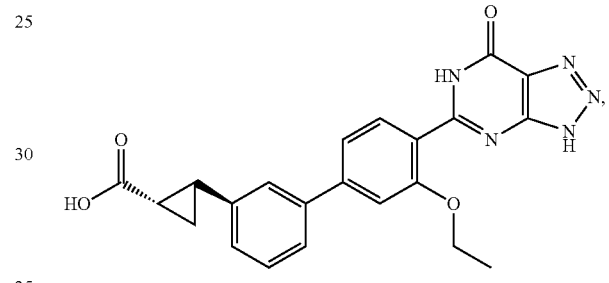
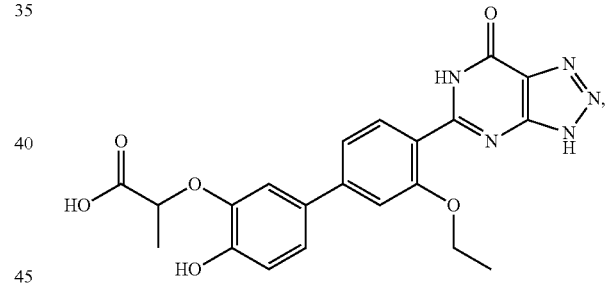
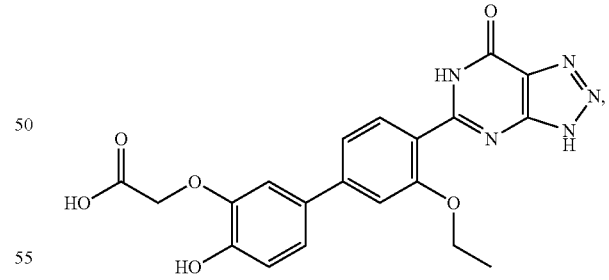
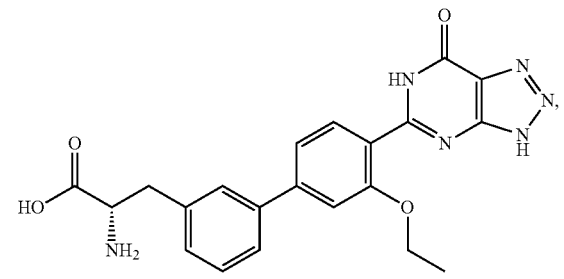
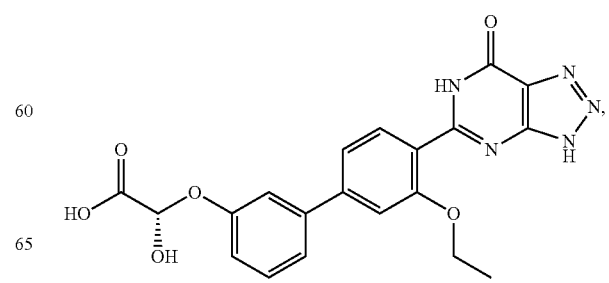

307
-continued
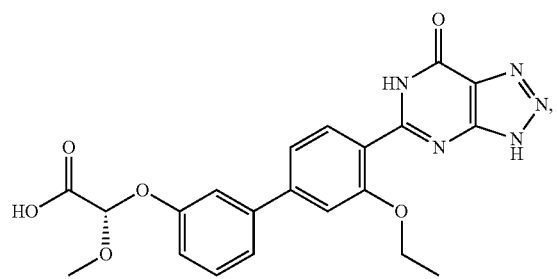
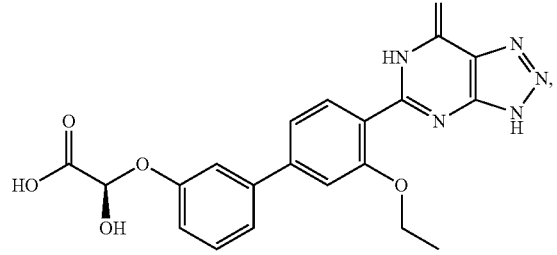
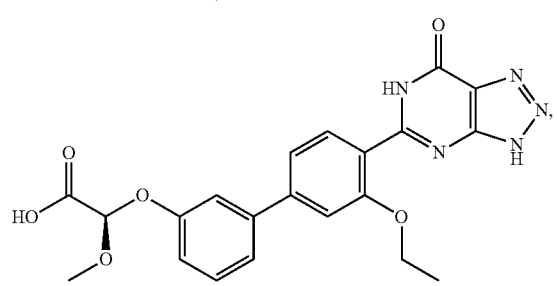
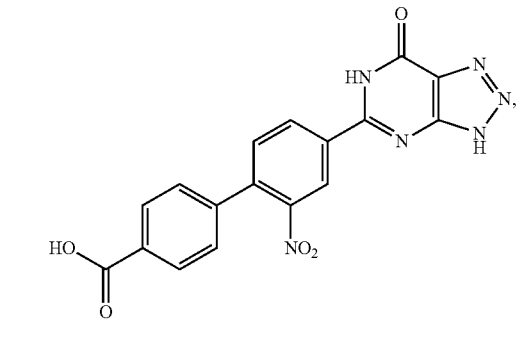
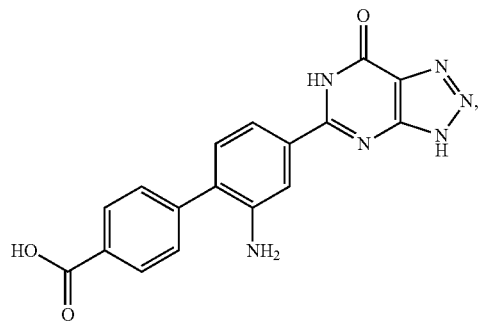
308
-continued
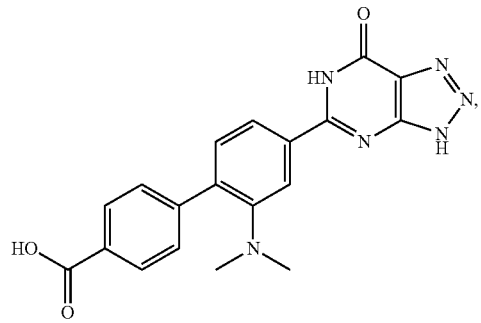
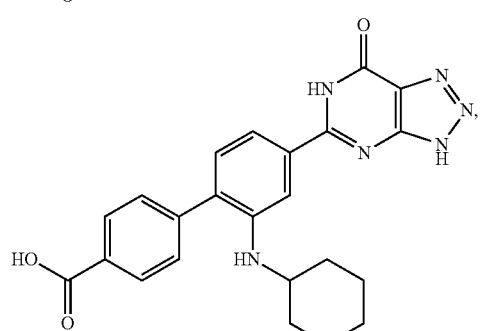
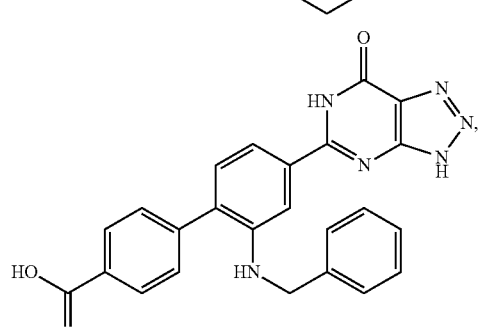
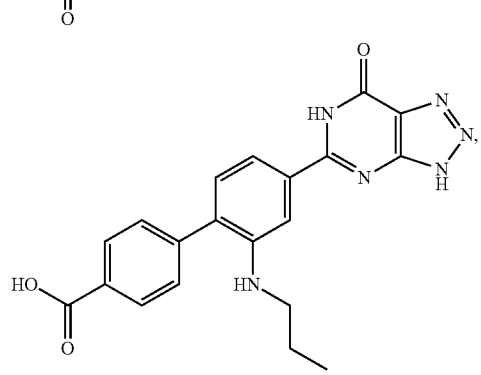
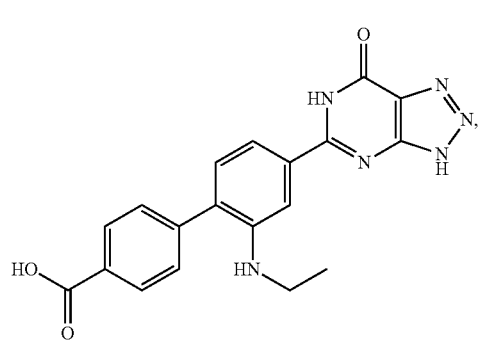

309
-continued
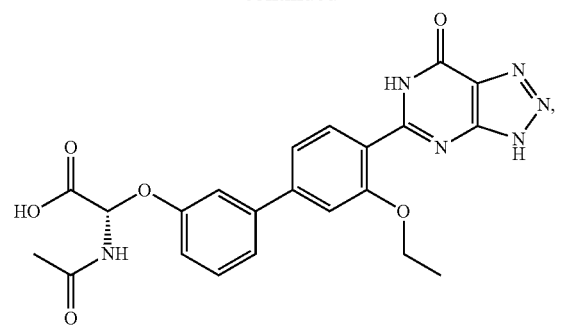
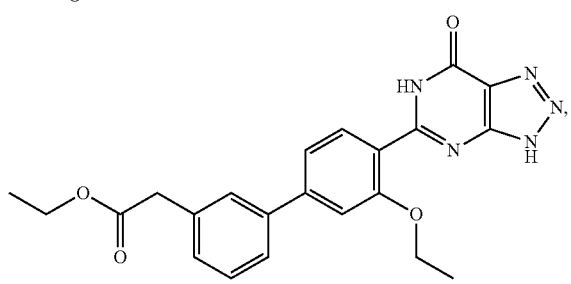
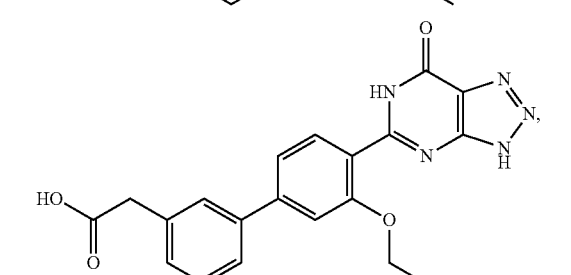
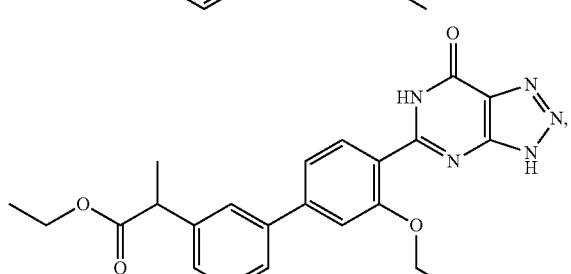
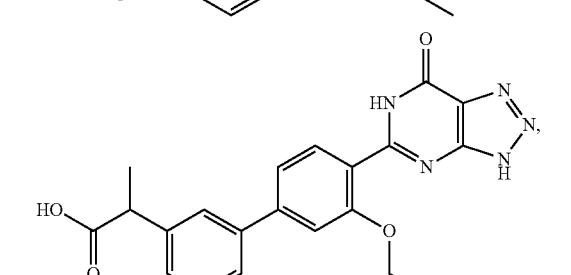
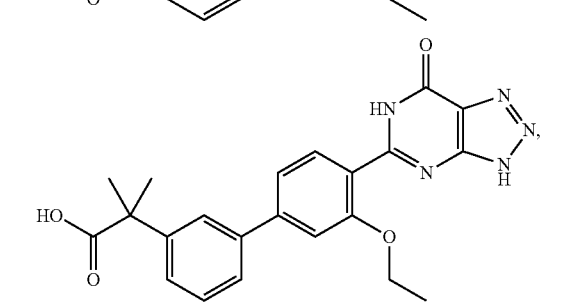
310
-continued
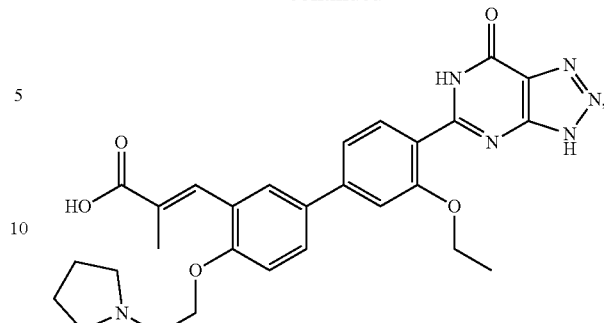
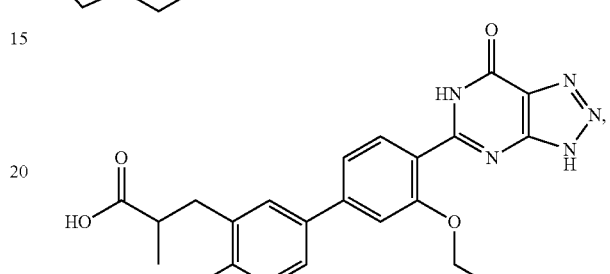
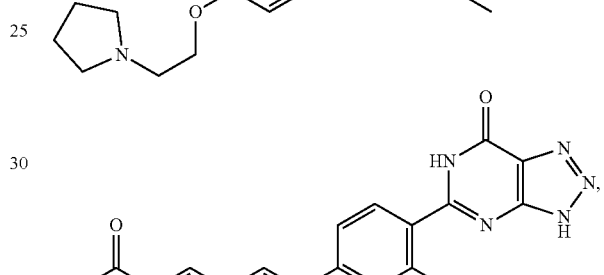
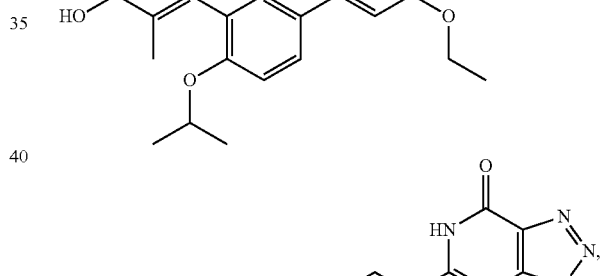
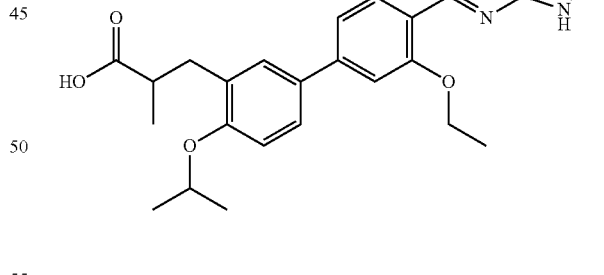
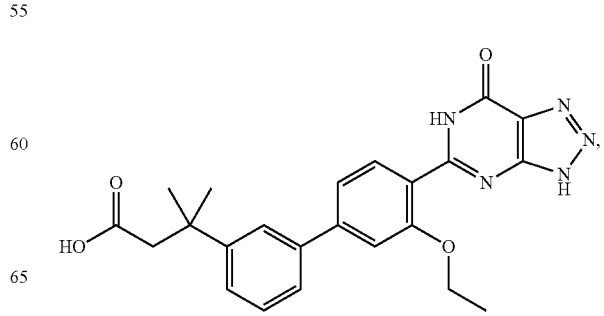

311
-continued
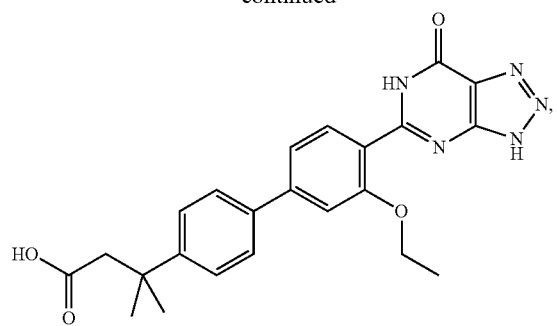
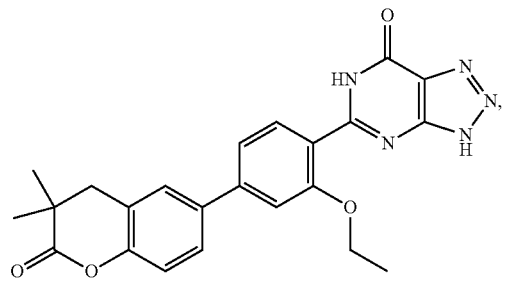
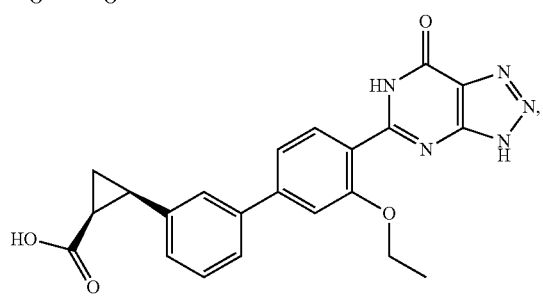
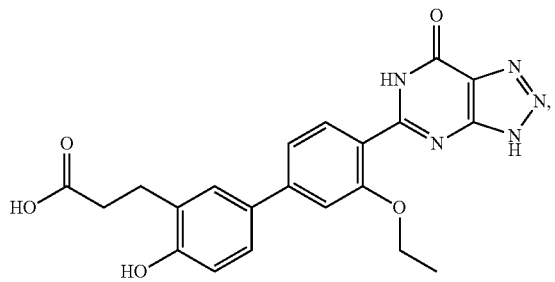
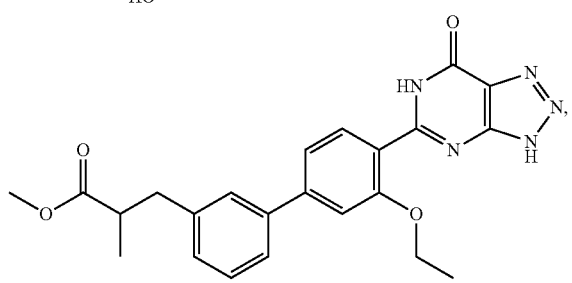
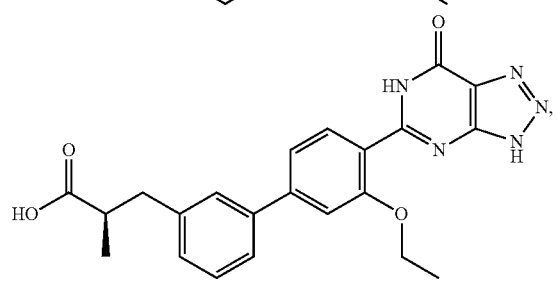
312
-continued
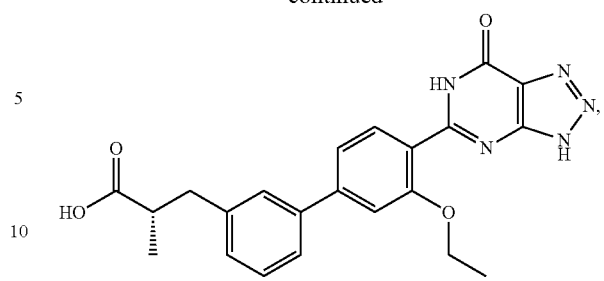
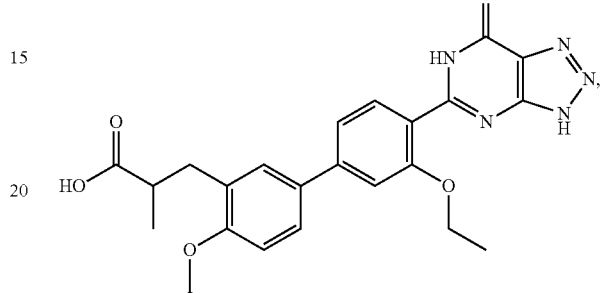
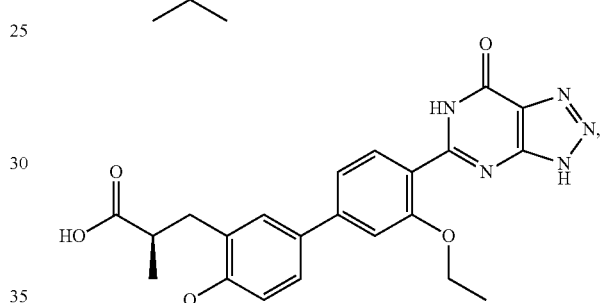
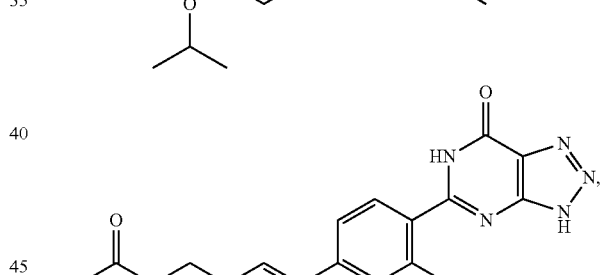
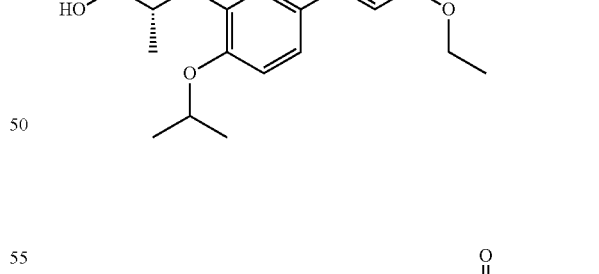
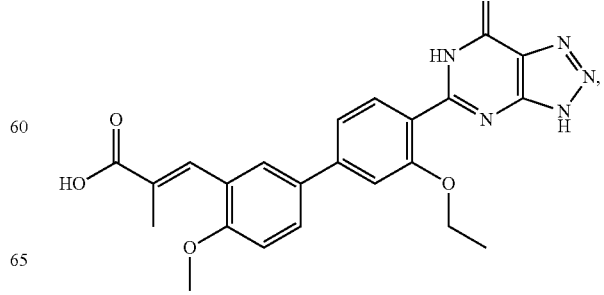

313
-continued
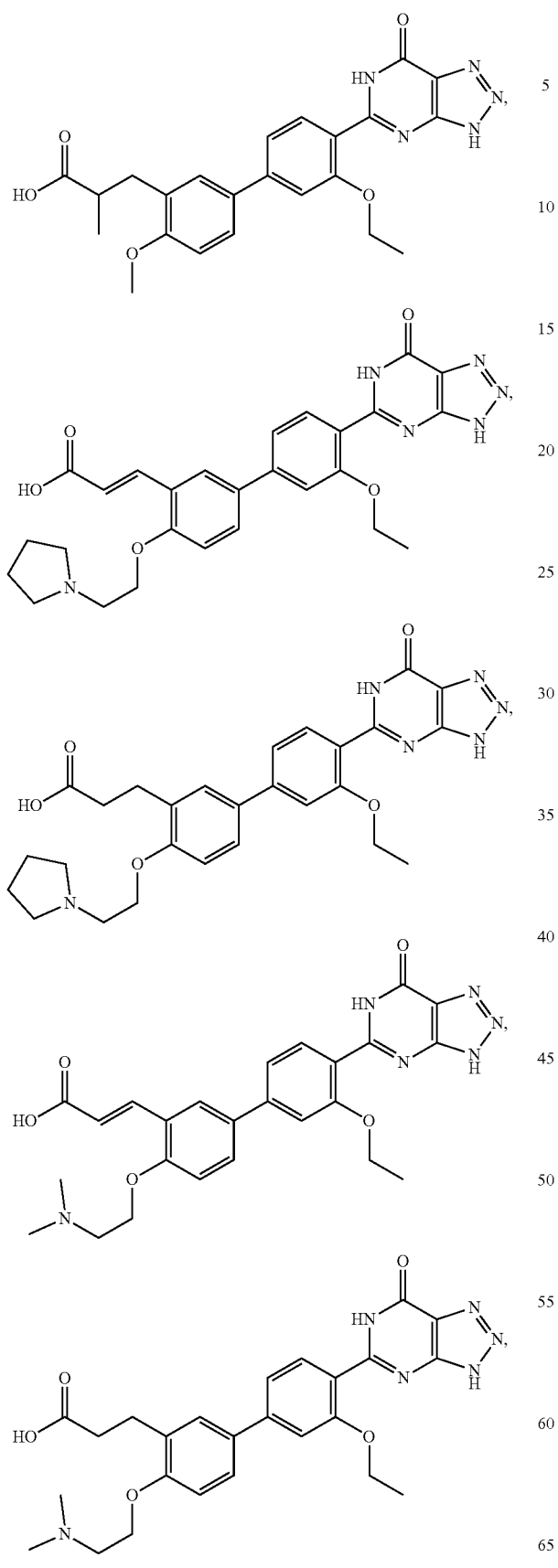
314
-continued
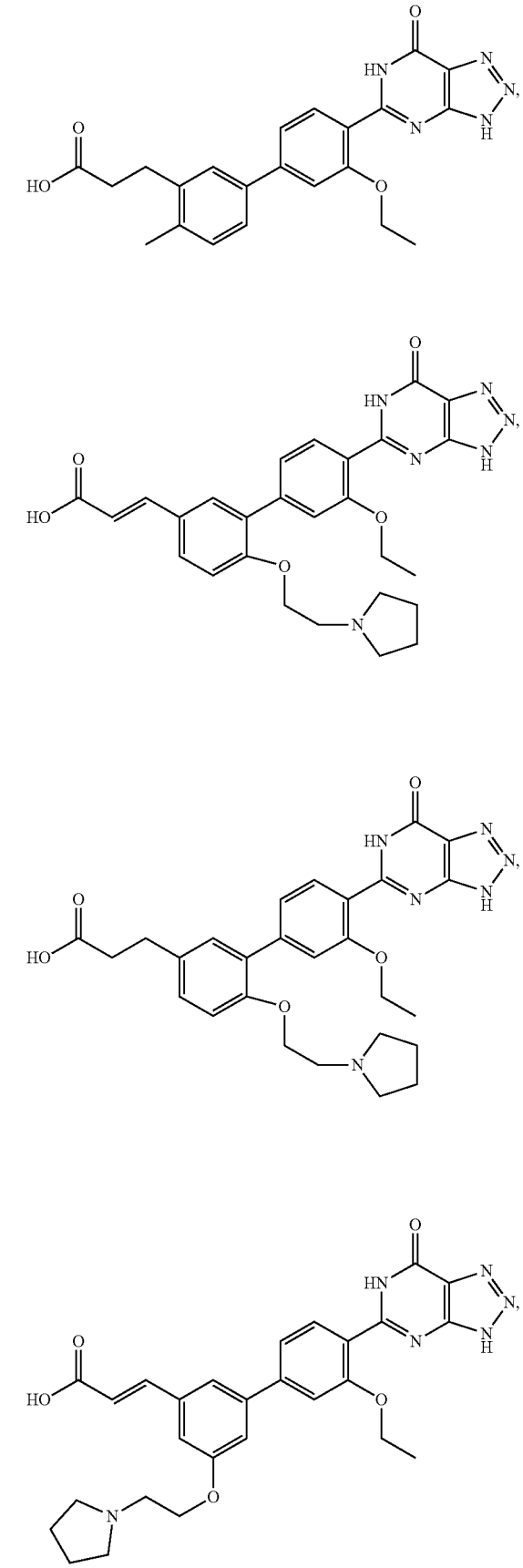

315
-continued
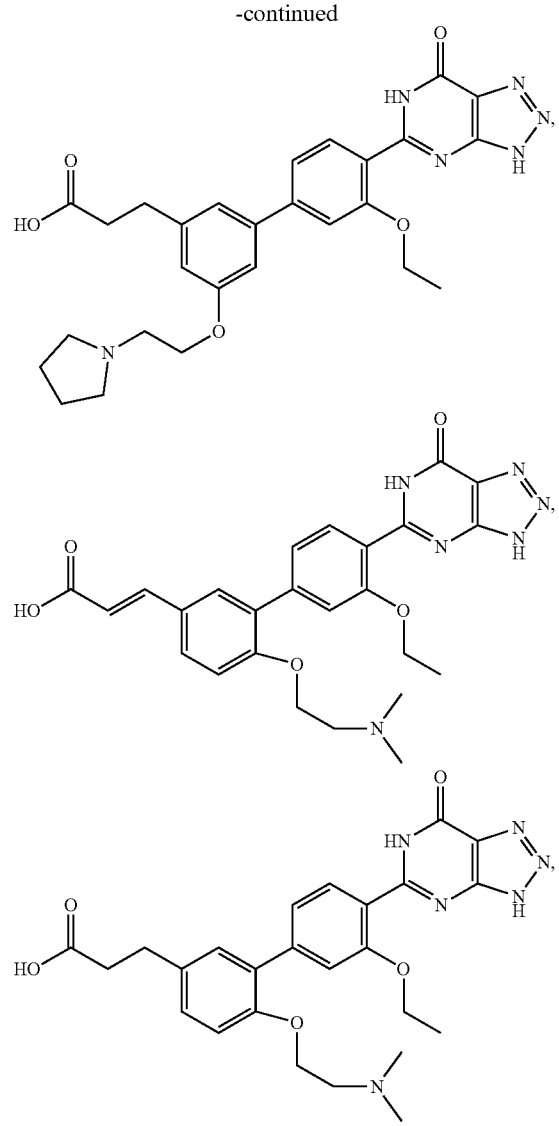
316
-continued
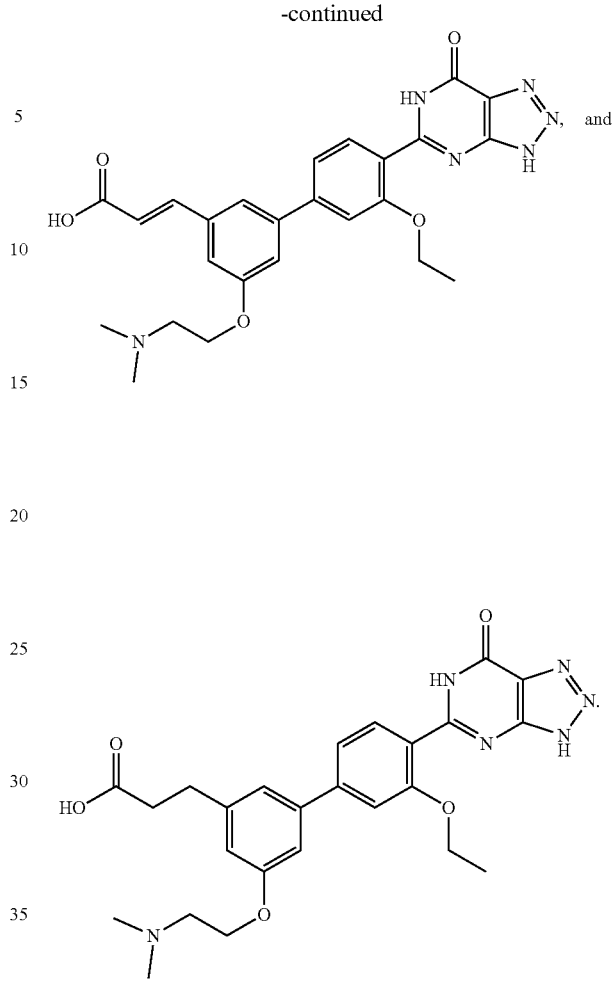
19. The method of claim 1, wherein the inflammatory bowel disease is selected from Crohn's disease, ulcerative colitis, and perianal Crohn's disease.
* * * * *